(12) United States Patent
Isabella et al.

(10) Patent No.: US 11,273,184 B2
(45) Date of Patent: Mar. 15, 2022

(54) BACTERIA ENGINEERED TO TREAT DISORDERS IN WHICH OXALATE IS DETRIMENTAL

(71) Applicant: Synlogic Operating Company, Inc., Cambridge, MA (US)

(72) Inventors: Vincent Isabella, Medford, MA (US); Dean Falb, Sherborn, MA (US); Cami Leigh Anderson, Cambridge, MA (US); Paul Miller, Salem, CT (US); Yves Millet, Newton, MA (US); Jonathan Kotula, Berkeley, CA (US)

(73) Assignee: Synlogic Operating Company, Inc., Cambridge, MA (US)

( * ) Notice: Subject to any disclaimer, the term of this patent is extended or adjusted under 35 U.S.C. 154(b) by 1053 days.

(21) Appl. No.: 15/755,836

(22) PCT Filed: Aug. 31, 2016

(86) PCT No.: PCT/US2016/049781
§ 371 (c)(1),
(2) Date: Feb. 27, 2018

(87) PCT Pub. No.: WO2017/040719
PCT Pub. Date: Mar. 9, 2017

(65) Prior Publication Data
US 2018/0325963 A1 Nov. 15, 2018

Related U.S. Application Data

(63) Continuation-in-part of application No. PCT/US2016/032565, filed on May 13, 2016.

(60) Provisional application No. 62/341,315, filed on May 25, 2016, provisional application No. 62/212,223, filed on Aug. 31, 2015.

(51) Int. Cl.
| | |
|---|---|
| *A61K 35/74* | (2015.01) |
| *C07K 14/195* | (2006.01) |
| *C12N 1/00* | (2006.01) |
| *A61P 3/00* | (2006.01) |
| *C12N 15/52* | (2006.01) |
| *C12N 15/70* | (2006.01) |

(52) U.S. Cl.
CPC ............ *A61K 35/74* (2013.01); *A61P 3/00* (2018.01); *C07K 14/195* (2013.01); *C12N 1/00* (2013.01); *C12N 15/52* (2013.01); *C12N 15/70* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 6,162,632 A | 12/2000 | Maloney et al. | |
| 6,699,469 B2 | 3/2004 | Allison et al. | |

FOREIGN PATENT DOCUMENTS

| | | |
|---|---|---|
| EP | 2270138 A1 | 1/2011 |
| EP | 2338976 A1 | 6/2011 |
| WO | 2006/047680 A2 | 5/2006 |

OTHER PUBLICATIONS

Levanon, S. et al., Biotech. Bioeng., 2005, pp. 556-564.*
Ashida et al., Nature Chem. Biol., 2012, pp. 36-45.*
Steidler et al., Nature Biotech., 2003, pp. 785-789.*
Amalaradjou, M. et al., Bioengineered; 2013, vol. 4, pp. 379-387.*
Abe et al., Cloning, sequencing, and expression in *Escherichia coli* of OxlT, the oxalate:formate exchange protein of Oxalobacter formigenes. J Biol Chem. Mar. 22, 1996;271(12):6789-93.
Abratt et al.. Oxalate-degrading bacteria of the human gut as probiotics in the management of kidney stone disease. Adv Appl Microbiol. 2010;72:63-87.
Duong et al., Construction of vectors for inducible and constitutive gene expression in Lactobacillus. Microb Biotechnol. May 2011;4(3):357-67.
Federici et al., Characterization and heterologous expression of the oxalyl coenzyme A decarboxylase gene from Bifidobacterium lactis. Appl Environ Microbiol. Sep. 2004;70(9):5066-73.
Fontenot et al., YfdW and YfdU are required for oxalate-induced acid tolerance in *Escherichia coli* K-12. J Bacteriol. Apr. 2013;195(7):1446-55.
Foster et al., An oxalyl-CoA synthetase is important for oxalate metabolism in *Saccharomyces cerevisiae*. FEBS Lett. Jan. 3, 2014;588(1):160-6.
Gnanandarajah, Role of Oxalate Metabolizing Bacteria in Calcium Oxalate Urolithiasis in Dogs. A Dissertation submitted to the faculty of the Graduate School of the University of Minnesota in partial fulfillment of the requirements for the degree of Doctor of Philosophy. 156 pages, Aug. 2011.
Hoppe et al., Oxalobacter formigenes: a potential tool for the treatment of primary hyperoxaluria type 1. Kidney Int. Oct. 2006;70(7):1305-11.
Mullins et al., Function and X-ray crystal structure of *Escherichia coli* YfdE. PLoS One. Jul. 23, 2013;8(7):e67901. 10 pages.
Sidhu et al., DNA sequencing and expression of the formyl coenzyme A transferase gene, frc, from Oxalobacter formigenes. J Bacteriol. May 1997;179(10):3378-81.

(Continued)

*Primary Examiner* — Michael D Burkhart
(74) *Attorney, Agent, or Firm* — McCarter & English, LLP; Marcie B. Clarke

(57) ABSTRACT

The present invention provides recombinant bacterial cells comprising at least one heterologous gene encoding at least one oxalate catabolism enzyme. In another aspect, the recombinant bacterial cells further comprise at least one heterologous gene encoding an importer of oxalate. The invention further provides pharmaceutical compositions comprising the recombinant bacteria, and methods for treating disorders in which oxalate is detrimental, such as hyperoxaluria, using the pharmaceutical compositions of the invention.

20 Claims, 43 Drawing Sheets

Specification includes a Sequence Listing.

(56) References Cited

OTHER PUBLICATIONS

International Search Report and Written Opinion for Application No. PCT/US2016/049781, dated Jan. 19, 2017, 15 pages.

* cited by examiner

TetR-ScAAE3-oxc-frc construct (5416 bp)

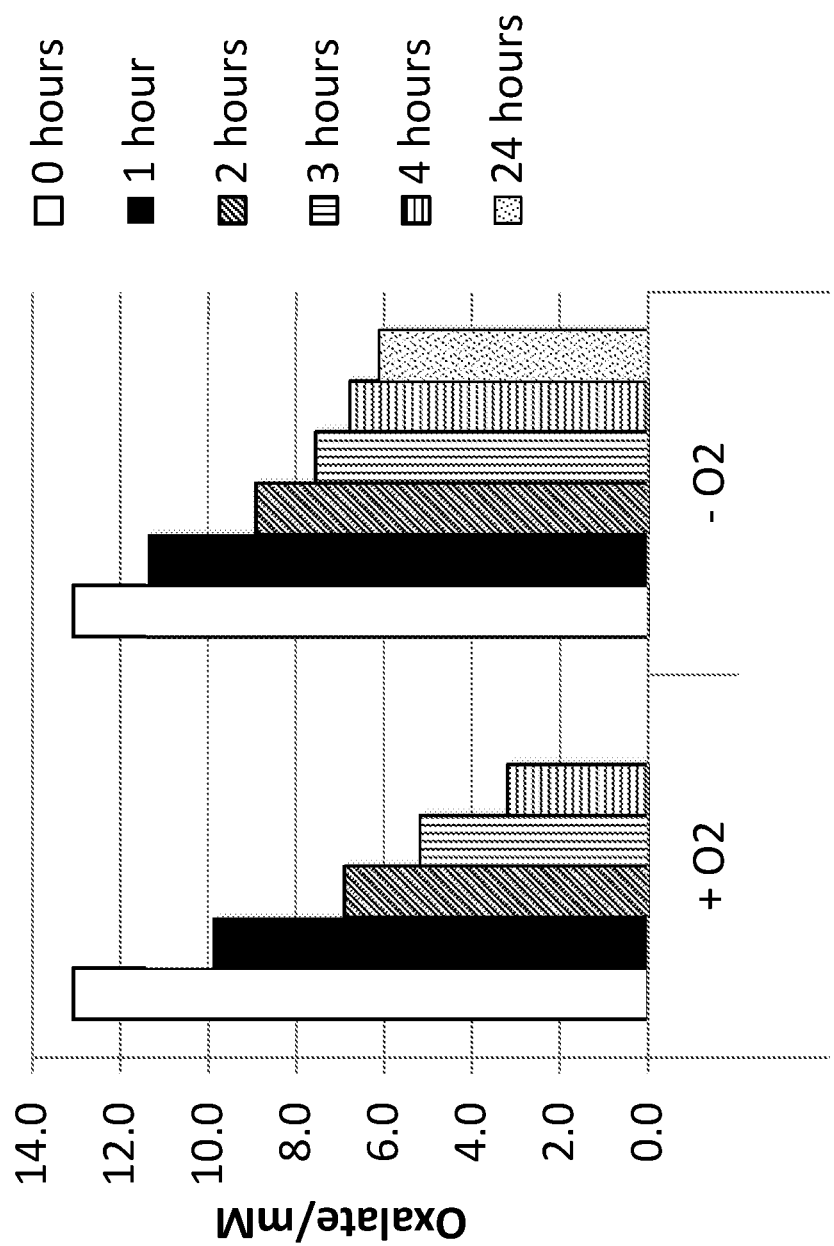

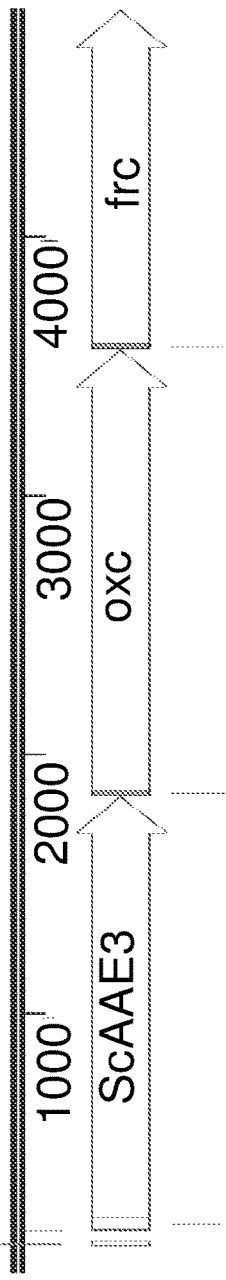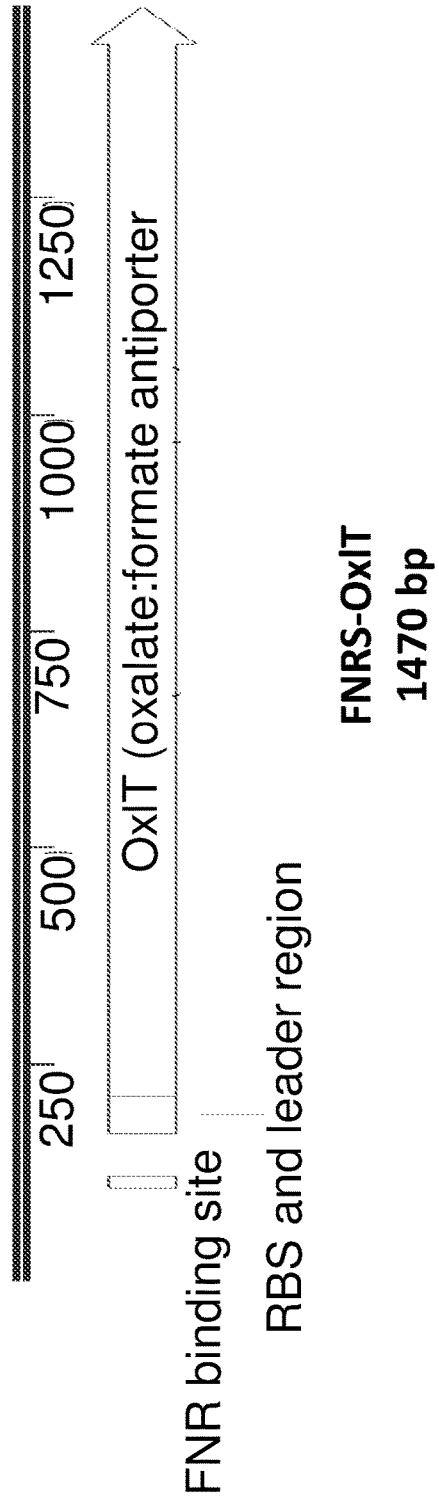

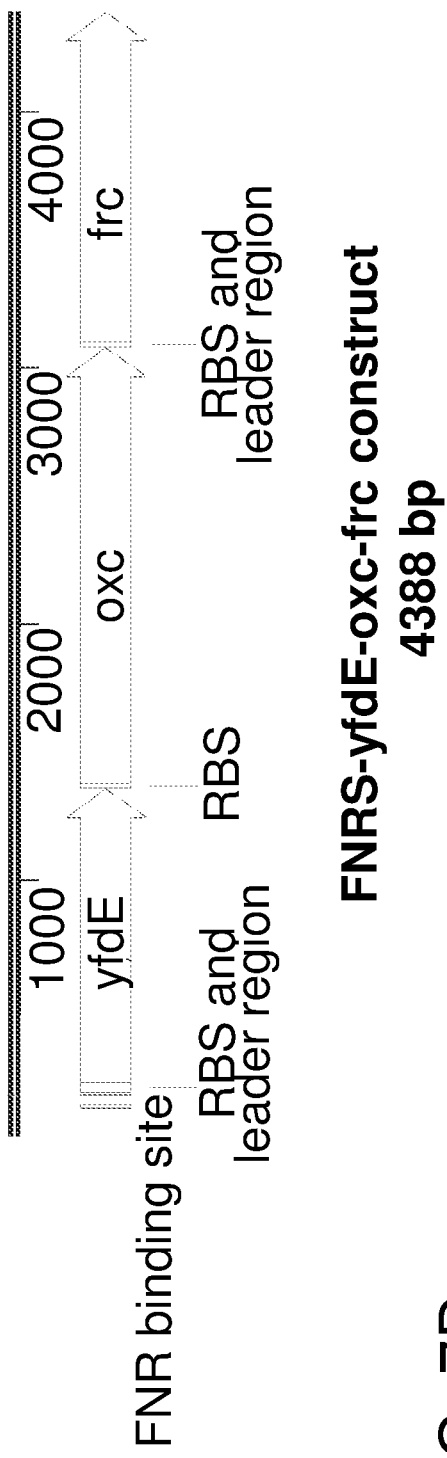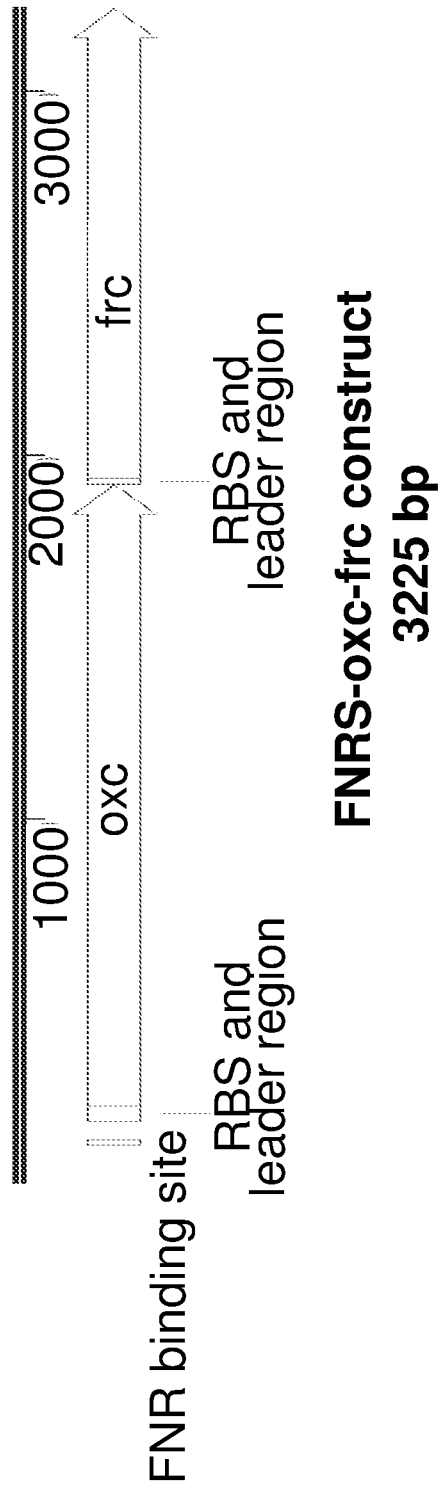

Brightness of constitutive RFP integrated in three locations:
1. AraB/C
2. MalE/K
3. MetY/ArgG
4. Nissle (non-fluorescent)

FIG. 19
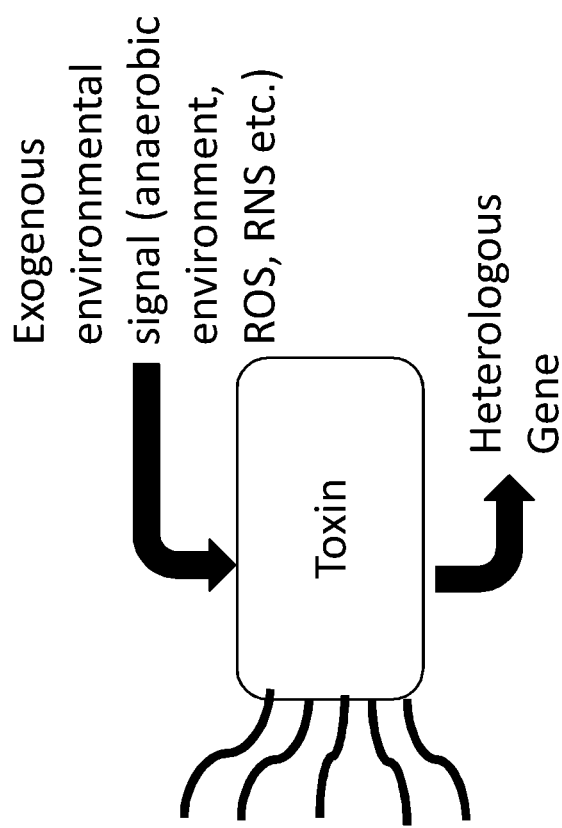
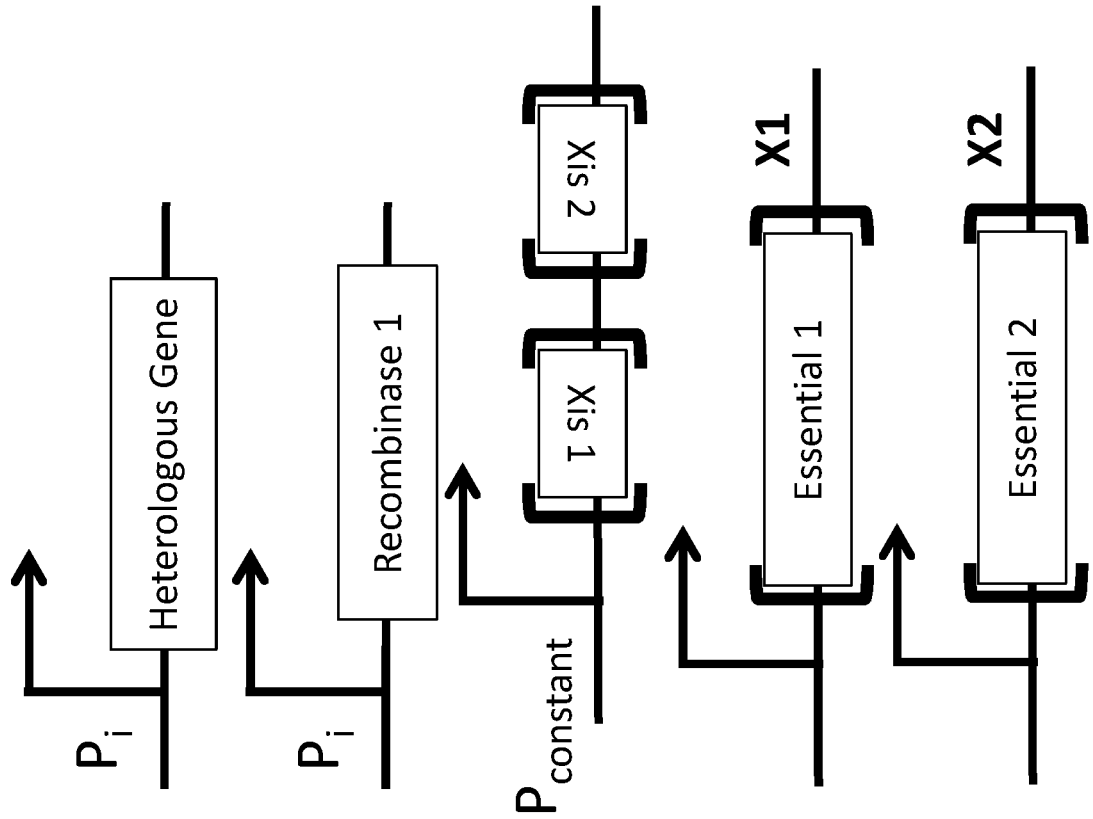

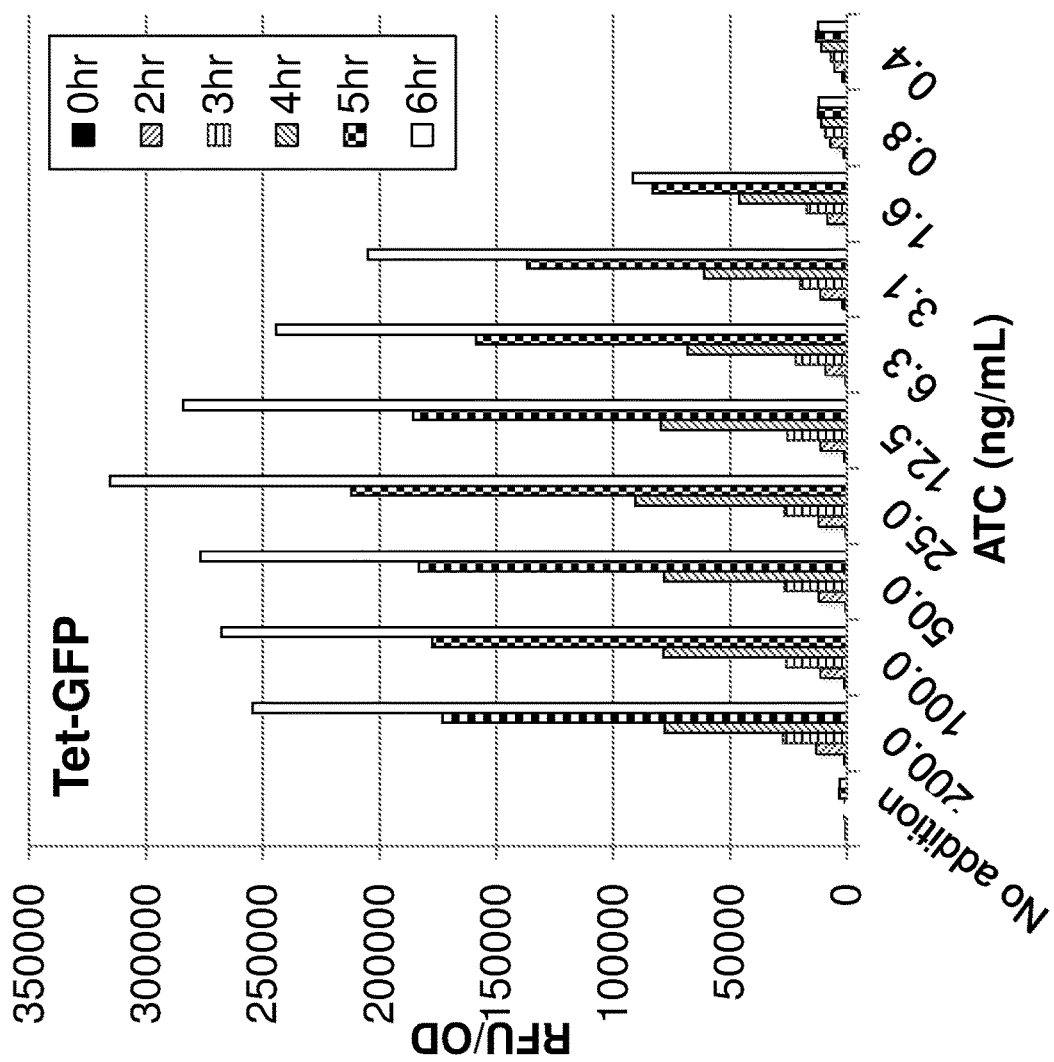

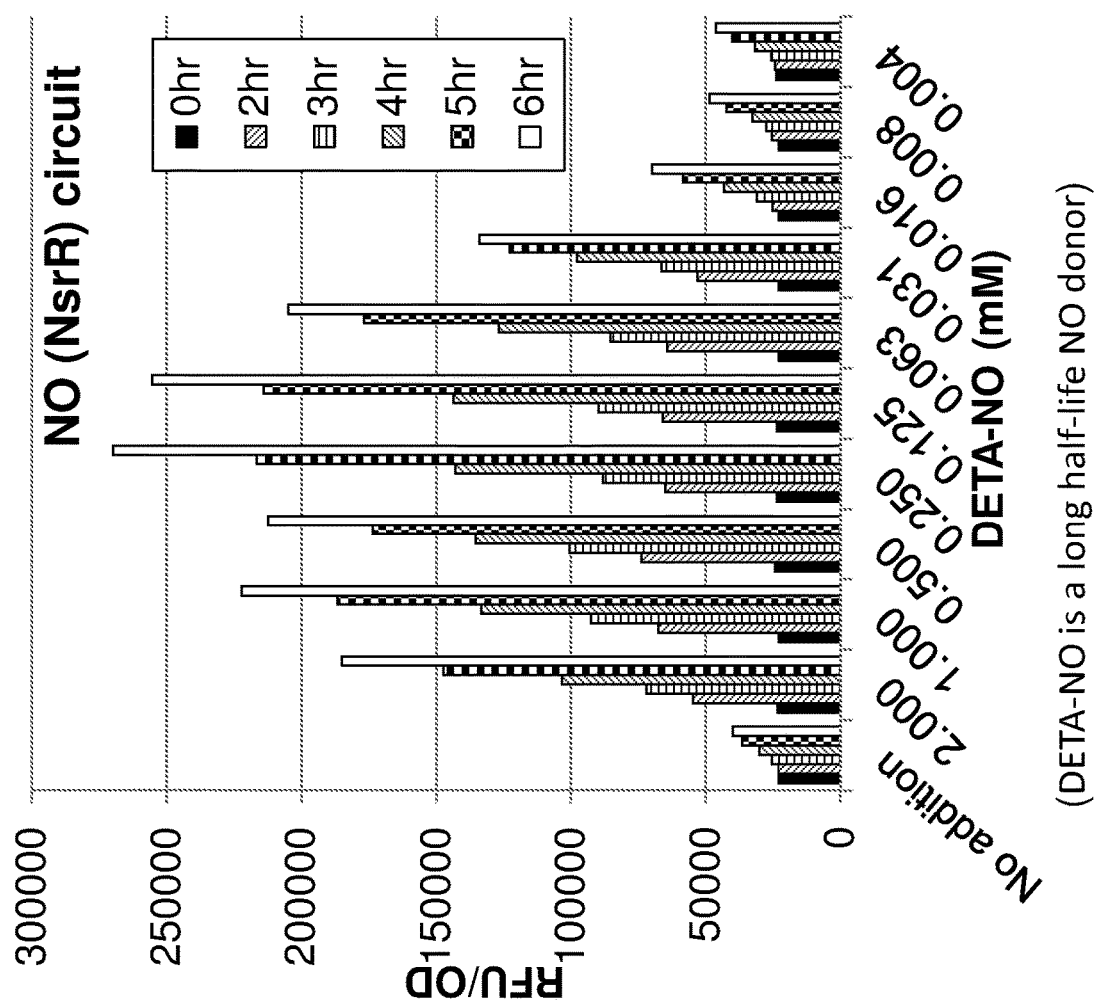

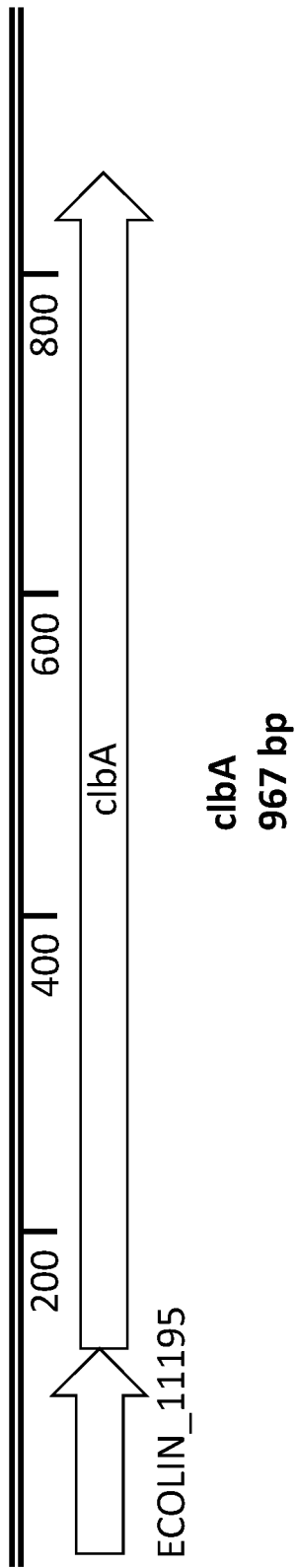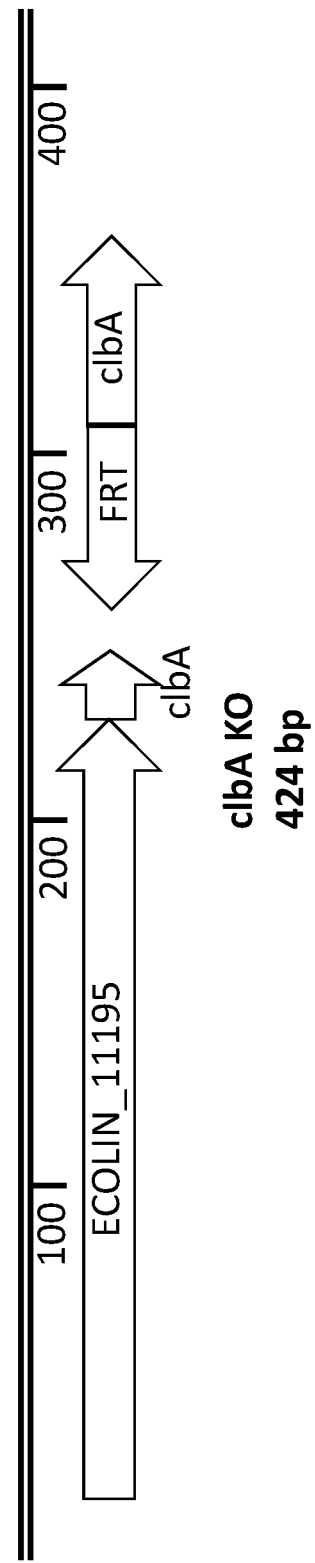

SEQUENCE LISTING

<160> NUMBER OF SEQ ID NOS: 63

<210> SEQ ID NO 1
<211> LENGTH: 1287
<212> TYPE: DNA
<213> ORGANISM: O. formigenes
<220> FEATURE:
<221> NAME/KEY: misc_feature
<222> LOCATION: (1)..(1287)
<223> OTHER INFORMATION: frc (formyl-CoA transferase from O. formigenes)

<400> SEQUENCE: 1

| atgactaaac cattagatgg aattaatgtg cttgacttta cccacgtcca ggcaggtcct | 60 |
|---|---|
| gcctgtacac agatgatggg tttcttgggc gcaaacgtca tcaagattga agacgtggt | 120 |
| tccggagata tgactcgtgg atggctgcag gacaaaccaa atgttgattc cctgtatttc | 180 |
| acgatgttca actgtaacaa acgttcgatt gaactggaca tgaaaacccc ggaaggcaaa | 240 |
| gagcttctgg aacagatgat caagaaagcc gacgtcatgg tcgaaaactt cggaccaggc | 300 |
| gcactggacc gtatgggctt tacttgggaa tacattcagg aactgaatcc acgcgtcatt | 360 |
| ctggcttccg ttaaaggcta tgcagaaggc cacgccaacg aacacctgaa agtttatgaa | 420 |
| aacgttgcac agtgttccgg cggtgctgca gctaccaccg gtttctggga tggtcctcca | 480 |
| accgtttccg gcgctgctct gggtgactcc aactccggta tgcacctgat gatcggtatt | 540 |
| ctggccgctc tggaaatgcg tcacaaaacc ggccgtggtc agaaagttgc cgtcgctatg | 600 |
| caggacgctg ttctgaatct ggttcgtatc aaactgcgtg accagcaacg tctggaaaga | 660 |
| accggcattc tggctgaata cccacaggct cagcctaact ttgccttcga cagagacggt | 720 |
| aacccactgt ccttcgacaa catcacttcc gttccacgtg gtgtaacgc aggtggcggc | 780 |
| ggccagccag gctggatgct gaaatgtaaa ggttgggaaa ccgatgcgga ctcctacgtt | 840 |
| tacttcacca tcgctgcaaa catgtggcca cagatctgcg acatgatcga caagccagaa | 900 |
| tggaaagacg acccagccta caacacattc gaaggtcgtg ttgacaagct gatggacatc | 960 |
| ttctcccttca tcgaaccaa gttcgctgac aaggacaaat tcgaagttac cgaatgggct | 1020 |
| gcccagtacg gcattccttg cggtccggtc atgtccatga agaactggc tcacgatcct | 1080 |
| tccctgcaga agttggtac cgtcgttgaa gttgtcgacg aaattcgtgg taaccacctg | 1140 |
| accgttggcg caccgttcaa attctccgga ttccagccgg aaattacccg tgctccgctg | 1200 |

```
ttgggcgaac ataccgacga agttctgaaa gaactgggtc ttgacgatgc caagatcaag    1260
gaactgcatg caaaacaggt agtttga                                         1287

<210> SEQ ID NO 2
<211> LENGTH: 1707
<212> TYPE: DNA
<213> ORGANISM: O. formigenes
<220> FEATURE:
<221> NAME/KEY: misc_feature
<222> LOCATION: (1)..(1707)
<223> OTHER INFORMATION: oxc (oxalylCoA decarboxylase from O.
      formigenes)

<400> SEQUENCE: 2
atgagtaacg acgacaatgt agagttgact gatggctttc atgttttgat cgatgccctg      60
aaaatgaatg acatcgatac catgtatggt gttgtcggca ttcctatcac gaacctggct     120
cgtatgtggc aagatgacgg tcagcgtttt tacagcttcc gtcacgaaca cacgcaggt     180 tatgcagctt ctatcgccgg ttacatcgaa ggaaaacctg gcgtttgctt gaccgtttcc    240
gcccctggct tcctgaacgg cgtgacttcc ctggctcatg caaccaccaa ctgcttccca    300
atgatcctgt gagcggttc cagtgaacgt gaaatcgtcg atttgcaaca gggcgattac    360
gaagaaatgg atcagatgaa tgttgcacgt ccacactgca agcttctttt ccgtatcaac    420
agcatcaaag acattccaat cggtatcgct cgtgcagttc gcaccgctgt atccggacgt    480
ccaggtggtg tttacgttga cttgccagca aaactgttcg gtcagaccat ttctgtagaa    540
gaagctaaca actgctcttt caaaccaatc gatccagctc cggcacagat tcctgctgaa    600
gacgctatcg ctcgcgctgc tgacctgatc aagaacgcca acgtccagt tatcatgctg    660 ggtaaaggcg ctgcatacgc acaatgcgac gacgaaatcc gcgcactggt tgaagaaacc    720
ggcatcccat tcctgccaat gggtatggct aaaggcctgc tgcctgacaa ccatccacaa    780
tccgctgctg caacccgtgc tttcgcactg gcacagtgtg acgtttgcgt actgatcggc    840
gctcgtctga actggctgat gcagcacggt aaaggcaaaa cctggggcga cgaactgaag    900
aaatacgttc agatcgacat ccaggctaac gaaatggaca gcaaccagcc tatcgctgca    960
ccagttgttg gtgacatcaa gtccgccgtt tccctgctcc gcaaagcact gaaaggcgct   1020
ccaaaagctg acgctgaatg gaccggcgct ctgaaagcca agttgacgg caacaaagcc    1080 aaactggctg gcaagatgac tgccgaaacc ccatccggaa tgatgaacta ctccaattcc    1140
ctgggcgttg ttcgtgactt catgctggca aatccggata tttccctggt taacgaaggc    1200
gctaatgcac tcgacaacac tcgtatgatt gttgacatgc tgaaaccacg caacgtctt    1260 gactccggta cctggggtgt tatgggtatt ggtatgggct actgcgttgc tgcagctgct    1320
gttaccggca aaccggttat cgctgttgaa ggcgatagcg cattcggttt ctccggtatg    1380
gaactggaaa ccatctgccg ttacaacctg ccagttaccg ttatcatcat gaacaatggt    1440
ggtatctata aggtaacga agcagatcca caaccaggcg ttatctcctg tacccgtctg    1500
acccgtggtc gttacgacat gatgatggaa gcatttggcg gtaaaggtta tgttgccaat    1560
actccagcag aactgaaagc tgctctggaa gaagctgttg cttccggcaa accatgcctg    1620
atcaacgcga tgatcgatcc agacgctggt gtcgaatctg ccgtatcaa gagcctgaac    1680 gttgtaagta agttggcaa gaaataa                                         1707

<210> SEQ ID NO 3
<211> LENGTH: 1632
<212> TYPE: DNA
```

<213> ORGANISM: S. cerevisiae
<220> FEATURE:
<221> NAME/KEY: misc_feature
<222> LOCATION: (1)..(1632)
<223> OTHER INFORMATION: ScAAE3 (oxalate-CoA ligase from S. cerevisiae)

<400> SEQUENCE: 3

```
atgaccagtg cagctacggt gaccgcgagc tttaatgaca cttttctgt gagcgataat      60
gtcgcggtaa tcgtaccgga aaccgatacg caggtcacct accgtgatct ttcccacatg    120
gtaggacact ttcaaacaat gttcacgaac ccgaatagtc ctctgtacgg ggcggtcttt    180
cgtcaagaca cggtagcgat tagcatgcgt aacggccttg aatttattgt ggctttcctt    240
ggagccacga tggatgcgaa aattggtgcg ccactgaatc ccaattataa agagaaggag    300
tttaattttt acctgaatga cttaaagtcc aaagccatct gcgtgccgaa aggcaccacc    360
aaactgcaaa gttcagaaat tcttaagagt gcgtccacgt tcgggtgctt tattgtggaa    420
ctggcgtttg acgccacccg ttttcgtgtt gaatatgaca tttactcccc ggaggacaat    480
tataaacgtg tgatctaccg cagccttaac aatgctaagt ttgtcaacac aaaccctgtc    540
aagttcccgg tttcgcccg cagctcggat gttgcactta ttttgcatac ctcaggcacc    600
actagtaccc caaagaccgt acccctcttg catctgaata ttgtccgttc aaccctgaat    660
atcgccaaca cttacaaact taccccgctg gatcgctcct atgttgtaat gccgctgttt    720
catgtacatg gattaatcgg cgtcttactg agtacgttcc gcacccaggg cagtgtagtc    780
gtcccggacg gctttcatcc gaagctcttc tgggatcagt ttgttaaata aactgcaat    840
tggtttagtt gcgtcccaac gatctctatg attatgttga atatgcccaa accgaatccg    900
tttccgcaca ttcgctttat ccgctcatgt agcagcgcgc tggcgccagc aacgtttcac    960
aagctggaaa agaatttaa tgccccagtt ctggaagcgt acgcgatgac agaagcatct   1020
catcagatga ccagtaacaa tctgcctccc ggtaaacgta accggggac cgtgggccaa   1080
cctcaaggtg taaccgtagt aatcctggat gacaacgata cgttctgcc gcccggcaaa   1140
gttggcgagg tgtcgatccg tggggagaac gtcaccctgg gctacgctaa taccccgaaa   1200
gctaacaaag aaaacttcac taaacgtgaa aactatttcc gtaccgggga tcagggctac   1260
ttcgacccgg agggctttct cgtgctgacc ggccgcatta agaattgat caatcgcggt   1320
ggtgaaaaaa ttagtcctat tgaactggac ggaatcatgc tctcgcatcc taaaatcgac   1380
gaggcggtgg cgttcggcgt tccagatgat atgtatggcc aagtcgttca ggcggcaatc   1440
gtgttgaaaa aggggggaaaa gatgacctat gaagaattag tgaatttcct gaaaaagcat   1500
ttagcaagct ttaaaatccc aaccaaagtc tactttgtgg ataagctgcc taaaacggcc   1560
accgggaaga ttcaacgtcg cgtaatcgcc gaaaccttcg cgaaatctag tcgcaacaaa   1620
agcaaacttt aa                                                      1632
```

<210> SEQ ID NO 4
<211> LENGTH: 1146
<212> TYPE: DNA
<213> ORGANISM: E. coli
<220> FEATURE:
<221> NAME/KEY: misc_feature
<222> LOCATION: (1)..(1146)
<223> OTHER INFORMATION: yfdE (Acetyl-CoA:oxalate CoA-transferase from E coli)

<400> SEQUENCE: 4

```
atgacaaata tgaaagcaa agggccgttt gaaggcttat tagttatcga tatgacacat      60
```

```
gtccttaatg gacctttcgg aactcaactt ctttgtaata tgggcgcaag ggtaattaaa    120
gttgagccgc cgggtcatgg tgatgatacc cgcacatttg gtccctatgt ggatggacag    180
tcactctatt acagttttat taatcatggc aaagagagtg tggttcttga tttaaagaat    240
gatcacgata aaagtatatt tataaatatg ctcaaacaag ctgatgtatt agctgagaat    300
tttcgcccag gtacaatgga aaaactgggg ttttcatggg aaacgcttca agaaatcaac    360
ccgcgcctca tatatgcttc atcgtcaggt ttcggacata ccggtccgct aaaagatgct    420
cctgcctacg ataccatcat tcaggcaatg agcgggataa tgatggaaac aggatatcct    480
gatgctccgc cagtgcgcgt tggtacatct cttgcggatc tatgcggcgg tgtctattta    540
ttcagcggaa tagtgagtgc actttatggc cgcgaaaaga gccagagagg ggcgcatgtc    600
gatatagcga tgtttgatgc cacgctgagt tttctggagc atggtctgat ggcatatatc    660
gcaactggga agtcaccaca acgtctggga aatcgccatc cctacatggc acctttgat    720 gttttcaata ctcaggataa gccgattacg atttgttgtg gtaatgacaa gcttttttct    780
gcgttatgcc aggcactgga gcttacgaa ctggttaata tccccgatt tagcagcaat    840 attttacgcg tacaaaacca ggctattctt aaacaatata ttgagcggac gttaaaaacg    900
caggcagctg aagtttggtt agccagaata catgaagttg gtgtacccgt cgcgccgtta    960
ttaagtgtgg ctgaggccat taaattgcca caaactcagg cgagaaatat gttgattgaa   1020 gccggggaa taatgatgcc gggtaatccg ataaaaatca gcggctgcgc ggacccgcat   1080
gttatgccgg agcggcaac gctcgaccag catggggaac aaattcgcca ggagttctca   1140
tcataa                                                              1146

<210> SEQ ID NO 5
<211> LENGTH: 428
<212> TYPE: PRT
<213> ORGANISM: O. formigenes
<220> FEATURE:
<221> NAME/KEY: misc_feature
<222> LOCATION: (1)..(428)
<223> OTHER INFORMATION: Frc (Formyl-CoA transferase from O. formigenes)

<400> SEQUENCE: 5

Met Thr Lys Pro Leu Asp Gly Ile Asn Val Leu Asp Phe Thr His Val
1               5                   10                  15

Gln Ala Gly Pro Ala Cys Thr Gln Met Met Gly Phe Leu Gly Ala Asn
            20                  25                  30

Val Ile Lys Ile Glu Arg Arg Gly Ser Gly Asp Met Thr Arg Gly Trp
        35                  40                  45

Leu Gln Asp Lys Pro Asn Val Asp Ser Leu Tyr Phe Thr Met Phe Asn
    50                  55                  60

Cys Asn Lys Arg Ser Ile Glu Leu Asp Met Lys Thr Pro Glu Gly Lys
65                  70                  75                  80

Glu Leu Leu Glu Gln Met Ile Lys Lys Ala Asp Val Met Val Glu Asn
                85                  90                  95

Phe Gly Pro Gly Ala Leu Asp Arg Met Gly Phe Thr Trp Glu Tyr Ile
            100                 105                 110

Gln Glu Leu Asn Pro Arg Val Ile Leu Ala Ser Val Lys Gly Tyr Ala
        115                 120                 125

Glu Gly His Ala Asn Glu His Leu Lys Val Tyr Glu Asn Val Ala Gln
    130                 135                 140

Cys Ser Gly Gly Ala Ala Ala Thr Thr Gly Phe Trp Asp Gly Pro Pro
145                 150                 155                 160
```

```
Thr Val Ser Gly Ala Ala Leu Gly Asp Ser Asn Ser Gly Met His Leu
            165                 170                 175

Met Ile Gly Ile Leu Ala Ala Leu Glu Met Arg His Lys Thr Gly Arg
        180                 185                 190

Gly Gln Lys Val Ala Val Ala Met Gln Asp Ala Val Leu Asn Leu Val
            195                 200                 205

Arg Ile Lys Leu Arg Asp Gln Gln Arg Leu Glu Arg Thr Gly Ile Leu
210                 215                 220

Ala Glu Tyr Pro Gln Ala Gln Pro Asn Phe Ala Phe Asp Arg Asp Gly
225                 230                 235                 240

Asn Pro Leu Ser Phe Asp Asn Ile Thr Ser Val Pro Arg Gly Gly Asn
            245                 250                 255

Ala Gly Gly Gly Gln Pro Gly Trp Met Leu Lys Cys Lys Gly Trp
            260                 265                 270

Glu Thr Asp Ala Asp Ser Tyr Val Tyr Phe Thr Ile Ala Ala Asn Met
            275                 280                 285

Trp Pro Gln Ile Cys Asp Met Ile Asp Lys Pro Glu Trp Lys Asp Asp
            290                 295                 300

Pro Ala Tyr Asn Thr Phe Glu Gly Arg Val Asp Lys Leu Met Asp Ile
305                 310                 315                 320

Phe Ser Phe Ile Glu Thr Lys Phe Ala Asp Lys Asp Lys Phe Glu Val
            325                 330                 335

Thr Glu Trp Ala Ala Gln Tyr Gly Ile Pro Cys Gly Pro Val Met Ser
            340                 345                 350

Met Lys Glu Leu Ala His Asp Pro Ser Leu Gln Lys Val Gly Thr Val
            355                 360                 365

Val Glu Val Val Asp Glu Ile Arg Gly Asn His Leu Thr Val Gly Ala
            370                 375                 380

Pro Phe Lys Phe Ser Gly Phe Gln Pro Glu Ile Thr Arg Ala Pro Leu
385                 390                 395                 400

Leu Gly Glu His Thr Asp Glu Val Leu Lys Glu Leu Gly Leu Asp Asp
                405                 410                 415

Ala Lys Ile Lys Glu Leu His Ala Lys Gln Val Val
            420                 425

<210> SEQ ID NO 6
<211> LENGTH: 568
<212> TYPE: PRT
<213> ORGANISM: O. formigenes
<220> FEATURE:
<221> NAME/KEY: misc_feature
<222> LOCATION: (1)..(568)
<223> OTHER INFORMATION: Oxc (oxalylCoA decarboxylase from O.
      formigenes)

<400> SEQUENCE: 6

Met Ser Asn Asp Asp Asn Val Glu Leu Thr Asp Gly Phe His Val Leu
1               5                   10                  15

Ile Asp Ala Leu Lys Met Asn Asp Ile Asp Thr Met Tyr Gly Val Val
            20                  25                  30

Gly Ile Pro Ile Thr Asn Leu Ala Arg Met Trp Gln Asp Asp Gly Gln
        35                  40                  45

Arg Phe Tyr Ser Phe Arg His Glu Gln His Ala Gly Tyr Ala Ala Ser
    50                  55                  60

Ile Ala Gly Tyr Ile Glu Gly Lys Pro Gly Val Cys Leu Thr Val Ser
65                  70                  75                  80
```

```
Ala Pro Gly Phe Leu Asn Gly Val Thr Ser Leu Ala His Ala Thr Thr
                85                  90                  95

Asn Cys Phe Pro Met Ile Leu Leu Ser Gly Ser Ser Glu Arg Glu Ile
            100                 105                 110

Val Asp Leu Gln Gln Gly Asp Tyr Glu Glu Met Asp Gln Met Asn Val
        115                 120                 125

Ala Arg Pro His Cys Lys Ala Ser Phe Arg Ile Asn Ser Ile Lys Asp
    130                 135                 140

Ile Pro Ile Gly Ile Ala Arg Ala Val Arg Thr Ala Val Ser Gly Arg
145                 150                 155                 160

Pro Gly Gly Val Tyr Val Asp Leu Pro Ala Lys Leu Phe Gly Gln Thr
                165                 170                 175

Ile Ser Val Glu Glu Ala Asn Lys Leu Leu Phe Lys Pro Ile Asp Pro
            180                 185                 190

Ala Pro Ala Gln Ile Pro Ala Glu Asp Ala Ile Ala Arg Ala Ala Asp
        195                 200                 205

Leu Ile Lys Asn Ala Lys Arg Pro Val Ile Met Leu Gly Lys Gly Ala
    210                 215                 220

Ala Tyr Ala Gln Cys Asp Asp Glu Ile Arg Ala Leu Val Glu Glu Thr
225                 230                 235                 240

Gly Ile Pro Phe Leu Pro Met Gly Met Ala Lys Gly Leu Leu Pro Asp
                245                 250                 255

Asn His Pro Gln Ser Ala Ala Thr Arg Ala Phe Ala Leu Ala Gln
            260                 265                 270

Cys Asp Val Cys Val Leu Ile Gly Ala Arg Leu Asn Trp Leu Met Gln
    275                 280                 285

His Gly Lys Gly Lys Thr Trp Gly Asp Glu Leu Lys Lys Tyr Val Gln
290                 295                 300

Ile Asp Ile Gln Ala Asn Glu Met Asp Ser Asn Gln Pro Ile Ala Ala
305                 310                 315                 320

Pro Val Val Gly Asp Ile Lys Ser Ala Val Ser Leu Leu Arg Lys Ala
                325                 330                 335

Leu Lys Gly Ala Pro Lys Ala Asp Ala Glu Trp Thr Gly Ala Leu Lys
            340                 345                 350

Ala Lys Val Asp Gly Asn Lys Ala Lys Leu Ala Gly Lys Met Thr Ala
        355                 360                 365

Glu Thr Pro Ser Gly Met Met Asn Tyr Ser Asn Ser Leu Gly Val Val
    370                 375                 380

Arg Asp Phe Met Leu Ala Asn Pro Asp Ile Ser Leu Val Asn Glu Gly
385                 390                 395                 400

Ala Asn Ala Leu Asp Asn Thr Arg Met Ile Val Asp Met Leu Lys Pro
                405                 410                 415

Arg Lys Arg Leu Asp Ser Gly Thr Trp Gly Val Met Gly Ile Gly Met
            420                 425                 430

Gly Tyr Cys Val Ala Ala Ala Val Thr Gly Lys Pro Val Ile Ala
        435                 440                 445

Val Glu Gly Asp Ser Ala Phe Gly Phe Ser Gly Met Glu Leu Glu Thr
    450                 455                 460

Ile Cys Arg Tyr Asn Leu Pro Val Thr Val Ile Met Asn Asn Gly
465                 470                 475                 480

Gly Ile Tyr Lys Gly Asn Glu Ala Asp Pro Gln Pro Gly Val Ile Ser
                485                 490                 495
```

```
Cys Thr Arg Leu Thr Arg Gly Arg Tyr Asp Met Met Glu Ala Phe
            500                 505                 510

Gly Gly Lys Gly Tyr Val Ala Asn Thr Pro Ala Glu Leu Lys Ala Ala
        515                 520                 525

Leu Glu Glu Ala Val Ala Ser Gly Lys Pro Cys Leu Ile Asn Ala Met
    530                 535                 540

Ile Asp Pro Asp Ala Gly Val Glu Ser Gly Arg Ile Lys Ser Leu Asn
545                 550                 555                 560

Val Val Ser Lys Val Gly Lys Lys
                565

<210> SEQ ID NO 7
<211> LENGTH: 543
<212> TYPE: PRT
<213> ORGANISM: S. cerevisiae
<220> FEATURE:
<221> NAME/KEY: misc_feature
<222> LOCATION: (1)..(543)
<223> OTHER INFORMATION: ScAAE3 (Oxalate-CoA ligase from S. cerevisiae)

<400> SEQUENCE: 7

Met Thr Ser Ala Ala Thr Val Thr Ala Ser Phe Asn Asp Thr Phe Ser
1               5                   10                  15

Val Ser Asp Asn Val Ala Val Ile Val Pro Glu Thr Asp Thr Gln Val
            20                  25                  30

Thr Tyr Arg Asp Leu Ser His Met Val Gly His Phe Gln Thr Met Phe
        35                  40                  45

Thr Asn Pro Asn Ser Pro Leu Tyr Gly Ala Val Phe Arg Gln Asp Thr
    50                  55                  60

Val Ala Ile Ser Met Arg Asn Gly Leu Glu Phe Ile Val Ala Phe Leu
65                  70                  75                  80

Gly Ala Thr Met Asp Ala Lys Ile Gly Ala Pro Leu Asn Pro Asn Tyr
                85                  90                  95

Lys Glu Lys Glu Phe Asn Phe Tyr Leu Asn Asp Leu Lys Ser Lys Ala
            100                 105                 110

Ile Cys Val Pro Lys Gly Thr Thr Lys Leu Gln Ser Ser Glu Ile Leu
        115                 120                 125

Lys Ser Ala Ser Thr Phe Gly Cys Phe Ile Val Glu Leu Ala Phe Asp
130                 135                 140

Ala Thr Arg Phe Arg Val Glu Tyr Asp Ile Tyr Ser Pro Glu Asp Asn
145                 150                 155                 160

Tyr Lys Arg Val Ile Tyr Arg Ser Leu Asn Asn Ala Lys Phe Val Asn
                165                 170                 175

Thr Asn Pro Val Lys Phe Pro Gly Phe Ala Arg Ser Ser Asp Val Ala
            180                 185                 190

Leu Ile Leu His Thr Ser Gly Thr Thr Ser Thr Pro Lys Thr Val Pro
        195                 200                 205

Leu Leu His Leu Asn Ile Val Arg Ser Thr Leu Asn Ile Ala Asn Thr
    210                 215                 220

Tyr Lys Leu Thr Pro Leu Asp Arg Ser Tyr Val Val Met Pro Leu Phe
225                 230                 235                 240

His Val His Gly Leu Ile Gly Val Leu Leu Ser Thr Phe Arg Thr Gln
                245                 250                 255

Gly Ser Val Val Val Pro Asp Gly Phe His Pro Lys Leu Phe Trp Asp
            260                 265                 270

Gln Phe Val Lys Tyr Asn Cys Asn Trp Phe Ser Cys Val Pro Thr Ile
```

```
            275                 280                 285
Ser Met Ile Met Leu Asn Met Pro Lys Pro Asn Pro Phe Pro His Ile
        290                 295                 300
Arg Phe Ile Arg Ser Cys Ser Ser Ala Leu Ala Pro Ala Thr Phe His
305                 310                 315                 320
Lys Leu Glu Lys Glu Phe Asn Ala Pro Val Leu Glu Ala Tyr Ala Met
                325                 330                 335
Thr Glu Ala Ser His Gln Met Thr Ser Asn Asn Leu Pro Pro Gly Lys
            340                 345                 350
Arg Lys Pro Gly Thr Val Gly Gln Pro Gln Gly Val Thr Val Val Ile
        355                 360                 365
Leu Asp Asp Asn Asp Asn Val Leu Pro Pro Gly Lys Val Gly Glu Val
        370                 375                 380
Ser Ile Arg Gly Glu Asn Val Thr Leu Gly Tyr Ala Asn Asn Pro Lys
385                 390                 395                 400
Ala Asn Lys Glu Asn Phe Thr Lys Arg Glu Asn Tyr Phe Arg Thr Gly
                405                 410                 415
Asp Gln Gly Tyr Phe Asp Pro Glu Gly Phe Leu Val Leu Thr Gly Arg
            420                 425                 430
Ile Lys Glu Leu Ile Asn Arg Gly Glu Lys Ile Ser Pro Ile Glu
        435                 440                 445
Leu Asp Gly Ile Met Leu Ser His Pro Lys Ile Asp Glu Ala Val Ala
        450                 455                 460
Phe Gly Val Pro Asp Asp Met Tyr Gly Gln Val Val Gln Ala Ala Ile
465                 470                 475                 480
Val Leu Lys Lys Gly Glu Lys Met Thr Tyr Glu Glu Leu Val Asn Phe
                485                 490                 495
Leu Lys Lys His Leu Ala Ser Phe Lys Ile Pro Thr Lys Val Tyr Phe
            500                 505                 510
Val Asp Lys Leu Pro Lys Thr Ala Thr Gly Lys Ile Gln Arg Arg Val
        515                 520                 525
Ile Ala Glu Thr Phe Ala Lys Ser Ser Arg Asn Lys Ser Lys Leu
        530                 535                 540

<210> SEQ ID NO 8
<211> LENGTH: 381
<212> TYPE: PRT
<213> ORGANISM: E. coli
<220> FEATURE:
<221> NAME/KEY: misc_feature
<222> LOCATION: (1)..(381)
<223> OTHER INFORMATION: yfdE (Acetyl-CoA:oxalate CoA-transferase from
      E. coli)

<400> SEQUENCE: 8

Met Thr Asn Asn Glu Ser Lys Gly Pro Phe Glu Gly Leu Leu Val Ile
1               5                   10                  15
Asp Met Thr His Val Leu Asn Gly Pro Phe Gly Thr Gln Leu Leu Cys
            20                  25                  30
Asn Met Gly Ala Arg Val Ile Lys Val Glu Pro Pro Gly His Gly Asp
        35                  40                  45
Asp Thr Arg Thr Phe Gly Pro Tyr Val Asp Gly Gln Ser Leu Tyr Tyr
    50                  55                  60
Ser Phe Ile Asn His Gly Lys Glu Ser Val Val Leu Asp Leu Lys Asn
65                  70                  75                  80
Asp His Asp Lys Ser Ile Phe Ile Asn Met Leu Lys Gln Ala Asp Val
```

85                  90                  95
Leu Ala Glu Asn Phe Arg Pro Gly Thr Met Glu Lys Leu Gly Phe Ser
                100                 105                 110

Trp Glu Thr Leu Gln Glu Ile Asn Pro Arg Leu Ile Tyr Ala Ser Ser
                115                 120                 125

Ser Gly Phe Gly His Thr Gly Pro Leu Lys Asp Ala Pro Ala Tyr Asp
            130                 135                 140

Thr Ile Ile Gln Ala Met Ser Gly Ile Met Met Glu Thr Gly Tyr Pro
145                 150                 155                 160

Asp Ala Pro Pro Val Arg Val Gly Thr Ser Leu Ala Asp Leu Cys Gly
                165                 170                 175

Gly Val Tyr Leu Phe Ser Gly Ile Val Ser Ala Leu Tyr Gly Arg Glu
                180                 185                 190

Lys Ser Gln Arg Gly Ala His Val Asp Ile Ala Met Phe Asp Ala Thr
            195                 200                 205

Leu Ser Phe Leu Glu His Gly Leu Met Ala Tyr Ile Ala Thr Gly Lys
        210                 215                 220

Ser Pro Gln Arg Leu Gly Asn Arg His Pro Tyr Met Ala Pro Phe Asp
225                 230                 235                 240

Val Phe Asn Thr Gln Asp Lys Pro Ile Thr Ile Cys Cys Gly Asn Asp
                245                 250                 255

Lys Leu Phe Ser Ala Leu Cys Gln Ala Leu Glu Leu Thr Glu Leu Val
                260                 265                 270

Asn Asp Pro Arg Phe Ser Ser Asn Ile Leu Arg Val Gln Asn Gln Ala
            275                 280                 285

Ile Leu Lys Gln Tyr Ile Glu Arg Thr Leu Lys Thr Gln Ala Ala Glu
        290                 295                 300

Val Trp Leu Ala Arg Ile His Glu Val Gly Val Pro Val Ala Pro Leu
305                 310                 315                 320

Leu Ser Val Ala Glu Ala Ile Lys Leu Pro Gln Thr Gln Ala Arg Asn
                325                 330                 335

Met Leu Ile Glu Ala Gly Gly Ile Met Met Pro Gly Asn Pro Ile Lys
            340                 345                 350

Ile Ser Gly Cys Ala Asp Pro His Val Met Pro Gly Ala Ala Thr Leu
        355                 360                 365

Asp Gln His Gly Glu Gln Ile Arg Gln Glu Phe Ser Ser
            370                 375                 380

<210> SEQ ID NO 9
<211> LENGTH: 437
<212> TYPE: PRT
<213> ORGANISM: E. coli
<220> FEATURE:
<221> NAME/KEY: misc_feature
<222> LOCATION: (1)..(437)
<223> OTHER INFORMATION: yfdW (formyl CoA transferase from E. coli)

<400> SEQUENCE: 9

Ser Tyr Tyr His His His His His His Leu Glu Ser Thr Ser Leu Tyr
1               5                   10                  15

Lys Lys Ala Gly Leu Met Ser Thr Pro Leu Gln Gly Ile Lys Val Leu
            20                  25                  30

Asp Phe Thr Gly Val Gln Ser Gly Pro Ser Cys Thr Gln Met Leu Ala
        35                  40                  45

Trp Phe Gly Ala Asp Val Ile Lys Ile Glu Arg Pro Gly Val Gly Asp
    50                  55                  60

Val Thr Arg His Gln Leu Arg Asp Ile Pro Asp Ile Asp Ala Leu Tyr
 65                  70                  75                  80

Phe Thr Met Leu Asn Ser Asn Lys Arg Ser Ile Glu Leu Asn Thr Lys
             85                  90                  95

Thr Ala Glu Gly Lys Glu Val Met Glu Lys Leu Ile Arg Glu Ala Asp
            100                 105                 110

Ile Leu Val Glu Asn Phe His Pro Gly Ala Ile Asp His Met Gly Phe
        115                 120                 125

Thr Trp Glu His Ile Gln Glu Ile Asn Pro Arg Leu Ile Phe Gly Ser
130                 135                 140

Ile Lys Gly Phe Asp Glu Cys Ser Pro Tyr Val Asn Val Lys Ala Tyr
145                 150                 155                 160

Glu Asn Val Ala Gln Ala Ala Gly Gly Ala Ser Thr Thr Gly Phe
                165                 170                 175

Trp Asp Gly Pro Pro Leu Val Ser Ala Ala Leu Gly Asp Ser Asn
                180                 185                 190

Thr Gly Met His Leu Leu Ile Gly Leu Leu Ala Ala Leu Leu His Arg
            195                 200                 205

Glu Lys Thr Gly Arg Gly Gln Arg Val Thr Met Ser Met Gln Asp Ala
210                 215                 220

Val Leu Asn Leu Cys Arg Val Lys Leu Arg Asp Gln Gln Arg Leu Asp
225                 230                 235                 240

Lys Leu Gly Tyr Leu Glu Glu Tyr Pro Gln Tyr Pro Asn Gly Thr Phe
                245                 250                 255

Gly Asp Ala Val Pro Arg Gly Gly Asn Ala Gly Gly Gly Gln Pro
                260                 265                 270

Gly Trp Ile Leu Lys Cys Lys Gly Trp Glu Thr Asp Pro Asn Ala Tyr
            275                 280                 285

Ile Tyr Phe Thr Ile Gln Glu Gln Asn Trp Glu Asn Thr Cys Lys Ala
        290                 295                 300

Ile Gly Lys Pro Glu Trp Ile Thr Asp Pro Ala Tyr Ser Thr Ala His
305                 310                 315                 320

Ala Arg Gln Pro His Ile Phe Asp Ile Phe Ala Glu Ile Glu Lys Tyr
                325                 330                 335

Thr Val Thr Ile Asp Lys His Glu Ala Val Ala Tyr Leu Thr Gln Phe
            340                 345                 350

Asp Ile Pro Cys Ala Pro Val Leu Ser Met Lys Glu Ile Ser Leu Asp
        355                 360                 365

Pro Ser Leu Arg Gln Ser Gly Ser Val Val Glu Val Glu Gln Pro Leu
370                 375                 380

Arg Gly Lys Tyr Leu Thr Val Gly Cys Pro Met Lys Phe Ser Ala Phe
385                 390                 395                 400

Thr Pro Asp Ile Lys Ala Ala Pro Leu Leu Gly Glu His Thr Ala Ala
                405                 410                 415

Val Leu Gln Glu Leu Gly Tyr Ser Asp Asp Glu Ile Ala Ala Met Lys
                420                 425                 430

Gln Asn His Ala Ile
            435

<210> SEQ ID NO 10
<211> LENGTH: 564
<212> TYPE: PRT
<213> ORGANISM: E. coli
<220> FEATURE:

<221> NAME/KEY: misc_feature
<222> LOCATION: (1)..(564)
<223> OTHER INFORMATION: yfdU (oxalyl-CoA decarboxylase E. coli)

<400> SEQUENCE: 10

```
Met Ser Asp Gln Leu Gln Met Thr Asp Gly Met His Ile Ile Val Glu
1               5                   10                  15

Ala Leu Lys Gln Asn Asn Ile Asp Thr Ile Tyr Gly Val Val Gly Ile
            20                  25                  30

Pro Val Thr Asp Met Ala Arg His Ala Gln Ala Glu Gly Ile Arg Tyr
        35                  40                  45

Ile Gly Phe Arg His Glu Gln Ser Ala Gly Tyr Ala Ala Ala Ala Ser
    50                  55                  60

Gly Phe Leu Thr Gln Lys Pro Gly Ile Cys Leu Thr Val Ser Ala Pro
65                  70                  75                  80

Gly Phe Leu Asn Gly Leu Thr Ala Leu Ala Asn Ala Thr Val Asn Gly
                85                  90                  95

Phe Pro Met Ile Met Ile Ser Gly Ser Ser Asp Arg Ala Ile Val Asp
            100                 105                 110

Leu Gln Gln Gly Asp Tyr Glu Glu Leu Asp Gln Met Asn Ala Ala Lys
        115                 120                 125

Pro Tyr Ala Lys Ala Ala Phe Arg Val Asn Gln Pro Gln Asp Leu Gly
    130                 135                 140

Ile Ala Leu Ala Arg Ala Ile Arg Val Ser Val Ser Gly Arg Pro Gly
145                 150                 155                 160

Gly Val Tyr Leu Asp Leu Pro Ala Asn Val Leu Ala Ala Thr Met Glu
                165                 170                 175

Lys Asp Glu Ala Leu Thr Thr Ile Val Lys Val Glu Asn Pro Ser Pro
            180                 185                 190

Ala Leu Leu Pro Cys Pro Lys Ser Val Thr Ser Ala Ile Ser Leu Leu
        195                 200                 205

Ala Lys Ala Glu Arg Pro Leu Ile Ile Leu Gly Lys Gly Ala Ala Tyr
    210                 215                 220

Ser Gln Ala Asp Glu Gln Leu Arg Glu Phe Ile Glu Ser Ala Gln Ile
225                 230                 235                 240

Pro Phe Leu Pro Met Ser Met Ala Lys Gly Ile Leu Glu Asp Thr His
                245                 250                 255

Pro Leu Ser Ala Ala Ala Ala Arg Ser Phe Ala Leu Ala Asn Ala Asp
            260                 265                 270

Val Val Met Leu Val Gly Ala Arg Leu Asn Trp Leu Leu Ala His Gly
        275                 280                 285

Lys Lys Gly Trp Ala Ala Asp Thr Gln Phe Ile Gln Leu Asp Ile Glu
    290                 295                 300

Pro Gln Glu Ile Asp Ser Asn Arg Pro Ile Ala Val Pro Val Val Gly
305                 310                 315                 320

Asp Ile Ala Ser Ser Met Gln Gly Met Leu Ala Glu Leu Lys Gln Asn
                325                 330                 335

Thr Phe Thr Thr Pro Leu Val Trp Arg Asp Ile Leu Asn Ile His Lys
            340                 345                 350

Gln Gln Asn Ala Gln Lys Met His Glu Lys Leu Ser Thr Asp Thr Gln
        355                 360                 365

Pro Leu Asn Tyr Phe Asn Ala Leu Ser Ala Val Arg Asp Val Leu Arg
    370                 375                 380

Glu Asn Gln Asp Ile Tyr Leu Val Asn Glu Gly Ala Asn Thr Leu Asp
```

```
                385                 390                 395                 400
        Asn Ala Arg Asn Ile Ile Asp Met Tyr Lys Pro Arg Arg Leu Asp
                        405                 410                 415

Cys Gly Thr Trp Gly Val Met Gly Ile Gly Met Gly Tyr Ala Ile Gly
                    420                 425                 430

Ala Ser Val Thr Ser Gly Ser Pro Val Val Ala Ile Glu Gly Asp Ser
                        435                 440                 445

Ala Phe Gly Phe Ser Gly Met Glu Ile Glu Thr Ile Cys Arg Tyr Asn
                    450                 455                 460

Leu Pro Val Thr Ile Val Ile Phe Asn Asn Gly Gly Ile Tyr Arg Gly
        465                 470                 475                 480

Asp Gly Val Asp Leu Ser Gly Ala Gly Ala Pro Ser Pro Thr Asp Leu
                        485                 490                 495

Leu His His Ala Arg Tyr Asp Lys Leu Met Asp Ala Phe Arg Gly Val
                    500                 505                 510

Gly Tyr Asn Val Thr Thr Thr Asp Glu Leu Arg His Ala Leu Thr Thr
                    515                 520                 525

Gly Ile Gln Ser Arg Lys Pro Thr Ile Ile Asn Val Val Ile Asp Pro
                    530                 535                 540

Ala Ala Gly Thr Glu Ser Gly His Ile Thr Lys Leu Asn Pro Lys Gln
        545                 550                 555                 560

Val Ala Gly Asn

<210> SEQ ID NO 11
<211> LENGTH: 1257
<212> TYPE: DNA
<213> ORGANISM: O. formigenes
<220> FEATURE:
<221> NAME/KEY: misc_feature
<222> LOCATION: (1)..(1257)
<223> OTHER INFORMATION: OxlT coding region (oxalate:formate antiporter
      from O. formigenes)

<400> SEQUENCE: 11
atgaataatc cacaaacagg acaatcaaca ggcctcttgg gcaatcgttg gttctacttg    60
gtattagcag ttttgctgat gtgtatgatc tcgggtgtcc aatattcctg gacactgtac   120
gctaacccgg ttaaagacaa ccttggcgtt tctttggctg cggttcagac ggctttcaca   180
ctctctcagg tcattcaagc tggttctcag cctggtggtg gttacttcgt tgataaattc   240
ggtccaagaa ttccattgat gttcggtggt gcgatggttc tcgctggctg gaccttcatg   300
ggtatggttg acagtgttcc tgctctgtat gctctttata ctctggccgg tgcaggtgtt   360
ggtatcgttt acggtatcgc gatgaacacg gctaacagat ggttcccgga caaacgcggt   420
ctggcttccg gtttcaccgc tgccggttac ggtctgggtg ttctgccgtt cctgccactg   480
atcagctccg ttctgaaagt tgaaggtgtt ggcgcagcat tcatgtacac cggtttgatc   540
atgggtatcc tgattatcct gatcgctttc gttatccgtt ccctggcca  gcaaggcgcc   600 aaaaaacaaa tcgttgttac cgacaaggat ttcaattctg gcgaaatgct gagaacacca   660
caattctggg ttctgtggac cgcattcttt ccgttaact  ttggtggttt gctgctggtt   720
gccaacagcg tcccttacgg tcgcagcctc ggtcttgccg caggtgtgct gacgatcggt   780
gtttcgatcc agaacctgtt caatggtggt tgccgtcctt tctggggttt cgtttccgat   840
aaaatcggcc gttacaaaac catgtccgtc gttttcggta tcaatgctgt tgttctcgca   900
cttttcccga cgattgctgc cttgggcgat gtagccttta tcgccatgtt ggcaatcgca   960
```

-continued

```
ttcttcacat ggggtggtag ctacgctctg ttcccatcga ccaacagcga tattttcggt    1020
acggcatact ctgccagaaa ctatggtttc ttctgggctg caaaagcaac tgcctcgatc    1080
ttcggtggtg gtctgggtgc tgcaattgca accaacttcg gatggaatac cgctttcctg    1140
attactgcga ttacttcttt catcgcattt gctctggcta ccttcgttat tccaagaatg    1200
ggccgtccag tcaagaaaat ggtcaaattg tctccagaag aaaaagctgt acattaa      1257
```

<210> SEQ ID NO 12
<211> LENGTH: 418
<212> TYPE: PRT
<213> ORGANISM: O. formigenes
<220> FEATURE:
<221> NAME/KEY: misc_feature
<222> LOCATION: (1)..(418)
<223> OTHER INFORMATION: OxlT (oxalate:formate antiporter from O. formigenes)

<400> SEQUENCE: 12

```
Met Asn Asn Pro Gln Thr Gly Gln Ser Thr Gly Leu Leu Gly Asn Arg
  1               5                  10                  15

Trp Phe Tyr Leu Val Leu Ala Val Leu Leu Met Cys Met Ile Ser Gly
                 20                  25                  30

Val Gln Tyr Ser Trp Thr Leu Tyr Ala Asn Pro Val Lys Asp Asn Leu
             35                  40                  45

Gly Val Ser Leu Ala Ala Val Gln Thr Ala Phe Thr Leu Ser Gln Val
         50                  55                  60

Ile Gln Ala Gly Ser Gln Pro Gly Gly Tyr Phe Val Asp Lys Phe
 65                  70                  75                  80

Gly Pro Arg Ile Pro Leu Met Phe Gly Ala Met Val Leu Ala Gly
                 85                  90                  95

Trp Thr Phe Met Gly Met Val Asp Ser Val Pro Ala Leu Tyr Ala Leu
            100                 105                 110

Tyr Thr Leu Ala Gly Ala Gly Val Gly Ile Val Tyr Gly Ile Ala Met
            115                 120                 125

Asn Thr Ala Asn Arg Trp Phe Pro Asp Lys Arg Gly Leu Ala Ser Gly
        130                 135                 140

Phe Thr Ala Ala Gly Tyr Gly Leu Gly Val Leu Pro Phe Leu Pro Leu
145                 150                 155                 160

Ile Ser Ser Val Leu Lys Val Glu Gly Val Gly Ala Ala Phe Met Tyr
                165                 170                 175

Thr Gly Leu Ile Met Gly Ile Leu Ile Ile Leu Ile Ala Phe Val Ile
            180                 185                 190

Arg Phe Pro Gly Gln Gln Gly Ala Lys Lys Gln Ile Val Val Thr Asp
        195                 200                 205

Lys Asp Phe Asn Ser Gly Glu Met Leu Arg Thr Pro Gln Phe Trp Val
    210                 215                 220

Leu Trp Thr Ala Phe Phe Ser Val Asn Phe Gly Gly Leu Leu Leu Val
225                 230                 235                 240

Ala Asn Ser Val Pro Tyr Gly Arg Ser Leu Gly Leu Ala Ala Gly Val
                245                 250                 255

Leu Thr Ile Gly Val Ser Ile Gln Asn Leu Phe Asn Gly Gly Cys Arg
            260                 265                 270

Pro Phe Trp Gly Phe Val Ser Asp Lys Ile Gly Arg Tyr Lys Thr Met
        275                 280                 285

Ser Val Val Phe Gly Ile Asn Ala Val Val Leu Ala Leu Phe Pro Thr
    290                 295                 300
```

```
Ile Ala Ala Leu Gly Asp Val Ala Phe Ile Ala Met Leu Ala Ile Ala
305                 310                 315                 320

Phe Phe Thr Trp Gly Gly Ser Tyr Ala Leu Phe Pro Ser Thr Asn Ser
            325                 330                 335

Asp Ile Phe Gly Thr Ala Tyr Ser Ala Arg Asn Tyr Gly Phe Phe Trp
            340                 345                 350

Ala Ala Lys Ala Thr Ala Ser Ile Phe Gly Gly Leu Gly Ala Ala
            355                 360                 365

Ile Ala Thr Asn Phe Gly Trp Asn Thr Ala Phe Leu Ile Thr Ala Ile
370                 375                 380

Thr Ser Phe Ile Ala Phe Ala Leu Ala Thr Phe Val Ile Pro Arg Met
385                 390                 395                 400

Gly Arg Pro Val Lys Lys Met Val Lys Leu Ser Pro Glu Glu Lys Ala
                405                 410                 415

Val His

<210> SEQ ID NO 13
<211> LENGTH: 290
<212> TYPE: DNA
<213> ORGANISM: Artificial Sequence
<220> FEATURE:
<223> OTHER INFORMATION: Synthetic: FNR Responsive Promoter

<400> SEQUENCE: 13
gtcagcataa caccctgacc tctcattaat tgttcatgcc gggcggcact atcgtcgtcc      60
ggccttttcc tctcttactc tgctacgtac atctatttct ataaatccgt tcaatttgtc     120
tgttttttgc acaaacatga aatatcagac aattccgtga cttaagaaaa tttatacaaa     180
tcagcaatat accccttaag gagtatataa aggtgaattt gatttacatc aataagcggg     240
gttgctgaat cgttaaggta ggcggtaata gaaagaaat cgaggcaaaa                  290

<210> SEQ ID NO 14
<211> LENGTH: 173
<212> TYPE: DNA
<213> ORGANISM: Artificial Sequence
<220> FEATURE:
<223> OTHER INFORMATION: Synthetic: FNR Responsive Promoter

<400> SEQUENCE: 14
atttcctctc atcccatccg gggtgagagt cttttccccc gacttatggc tcatgcatgc      60
atcaaaaaag atgtgagctt gatcaaaaac aaaaaatatt tcactcgaca ggagtattta     120
tattgcgccc gttacgtggg cttcgactgt aaatcagaaa ggagaaaaca cct            173

<210> SEQ ID NO 15
<211> LENGTH: 305
<212> TYPE: DNA
<213> ORGANISM: Artificial Sequence
<220> FEATURE:
<223> OTHER INFORMATION: Synthetic: FNR Responsive Promoter

<400> SEQUENCE: 15
gtcagcataa caccctgacc tctcattaat tgttcatgcc gggcggcact atcgtcgtcc      60
ggccttttcc tctcttactc tgctacgtac atctatttct ataaatccgt tcaatttgtc     120
tgttttttgc acaaacatga aatatcagac aattccgtga cttaagaaaa tttatacaaa     180
tcagcaatat accccttaag gagtatataa aggtgaattt gatttacatc aataagcggg     240
gttgctgaat cgttaaggat ccctctagaa ataatttgt ttaactttaa gaaggagata     300
```

```
<210> SEQ ID NO 16
<211> LENGTH: 180
<212> TYPE: DNA
<213> ORGANISM: Artificial Sequence
<220> FEATURE:
<223> OTHER INFORMATION: Synthetic: FNR Responsive Promoter

<400> SEQUENCE: 16
catttcctct catcccatcc ggggtgagag tcttttcccc cgacttatgg ctcatgcatg      60
catcaaaaaa gatgtgagct tgatcaaaaa caaaaaatat ttcactcgac aggagtattt     120
atattgcgcc cggatccctc tagaaataat tttgtttaac tttaagaagg agatatacat     180

<210> SEQ ID NO 17
<211> LENGTH: 199
<212> TYPE: DNA
<213> ORGANISM: Artificial Sequence
<220> FEATURE:
<223> OTHER INFORMATION: Synthetic: FNR Responsive Promoter

<400> SEQUENCE: 17
agttgttctt attggtggtg ttgctttatg gttgcatcgt agtaaatggt tgtaacaaaa      60 gcaattttc cggctgtctg tatacaaaaa cgccgtaaag tttgagcgaa gtcaataaac      120
tctctaccca ttcagggcaa tatctctctt ggatccctct agaaataatt ttgtttaact     180
ttaagaagga gatatacat                                                  199

<210> SEQ ID NO 18
<211> LENGTH: 117
<212> TYPE: DNA
<213> ORGANISM: Artificial Sequence
<220> FEATURE:
<223> OTHER INFORMATION: Synthetic: FNR-responsive regulatory region
      Sequence

<400> SEQUENCE: 18
atccccatca ctcttgatgg agatcaattc cccaagctgc tagagcgtta ccttgccctt      60
aaacattagc aatgtcgatt tatcagaggg ccgacaggct cccacaggag aaaaccg       117

<210> SEQ ID NO 19
<211> LENGTH: 108
<212> TYPE: DNA
<213> ORGANISM: Artificial Sequence
<220> FEATURE:
<223> OTHER INFORMATION: Synthetic: FNR-responsive regulatory region
      Sequence

<400> SEQUENCE: 19
ctcttgatcg ttatcaattc ccacgctgtt tcagagcgtt accttgccct taaacattag      60
caatgtcgat ttatcagagg gccgacaggc tcccacagga gaaaaccg                 108

<210> SEQ ID NO 20
<211> LENGTH: 290
<212> TYPE: DNA
<213> ORGANISM: Artificial Sequence
<220> FEATURE:
<223> OTHER INFORMATION: Synthetic: FNR-responsive regulatory region
      Sequence: nirB1

<400> SEQUENCE: 20
gtcagcataa caccctgacc tctcattaat tgttcatgcc gggcggcact atcgtcgtcc      60
```

```
ggccttttcc tctcttactc tgctacgtac atctatttct ataaatccgt tcaatttgtc    120
tgttttttgc acaaacatga aatatcagac aattccgtga cttaagaaaa tttatacaaa    180
tcagcaatat accccttaag gagtatataa aggtgaattt gatttacatc aataagcggg    240
gttgctgaat cgttaaggta ggcggtaata gaaaagaaat cgaggcaaaa               290

<210> SEQ ID NO 21
<211> LENGTH: 433
<212> TYPE: DNA
<213> ORGANISM: Artificial Sequence
<220> FEATURE:
<223> OTHER INFORMATION: Synthetic: FNR-responsive regulatory region
      Sequence: nirB2

<400> SEQUENCE: 21
cggcccgatc gttgaacata gcggtccgca ggcggcactg cttacagcaa acggtctgta     60
cgctgtcgtc tttgtgatgt gcttcctgtt aggtttcgtc agccgtcacc gtcagcataa    120
caccctgacc tctcattaat tgctcatgcc ggacggcact atcgtcgtcc ggccttttcc    180
tctcttcccc cgctacgtgc atctatttct ataaacccgc tcattttgtc tattttttgc    240
acaaacatga aatatcagac aattccgtga cttaagaaaa tttatacaaa tcagcaatat    300
acccattaag gagtatataa aggtgaattt gatttacatc aataagcggg gttgctgaat    360
cgttaaggta ggcggtaata gaaaagaaat cgaggcaaaa atgtttgttt aactttaaga    420
aggagatata cat                                                       433

<210> SEQ ID NO 22
<211> LENGTH: 290
<212> TYPE: DNA
<213> ORGANISM: Artificial Sequence
<220> FEATURE:
<223> OTHER INFORMATION: Synthetic: FNR-responsive regulatory region
      Sequence: nirB3

<400> SEQUENCE: 22
gtcagcataa caccctgacc tctcattaat tgctcatgcc ggacggcact atcgtcgtcc     60
ggccttttcc tctcttcccc cgctacgtgc atctatttct ataaacccgc tcattttgtc    120
tattttttgc acaaacatga aatatcagac aattccgtga cttaagaaaa tttatacaaa    180
tcagcaatat acccattaag gagtatataa aggtgaattt gatttacatc aataagcggg    240
gttgctgaat cgttaaggta ggcggtaata gaaaagaaat cgaggcaaaa               290

<210> SEQ ID NO 23
<211> LENGTH: 173
<212> TYPE: DNA
<213> ORGANISM: Artificial Sequence
<220> FEATURE:
<223> OTHER INFORMATION: Synthetic: FNR-responsive regulatory region
      Sequence: ydfZ

<400> SEQUENCE: 23
atttcctctc atcccatccg gggtgagagt cttttccccc gacttatggc tcatgcatgc     60
atcaaaaaag atgtgagctt gatcaaaaac aaaaaatatt tcactcgaca ggagtattta    120
tattgcgccc gttacgtggg cttcgactgt aaatcagaaa ggagaaaaca cct           173

<210> SEQ ID NO 24
<211> LENGTH: 305
<212> TYPE: DNA
<213> ORGANISM: Artificial Sequence
```

```
<220> FEATURE:
<223> OTHER INFORMATION: Synthetic: FNR-responsive regulatory region
      Sequence: nirB+RBS

<400> SEQUENCE: 24
gtcagcataa caccctgacc tctcattaat tgttcatgcc gggcggcact atcgtcgtcc      60
ggccttttcc tctcttactc tgctacgtac atctatttct ataaatccgt tcaatttgtc     120
tgttttttgc acaaacatga aatatcagac aattccgtga cttaagaaaa tttatacaaa     180
tcagcaatat accccttaag gagtatataa aggtgaattt gatttacatc aataagcggg     240
gttgctgaat cgttaaggat ccctctagaa ataattttgt ttaactttaa gaaggagata     300
tacat                                                                 305

<210> SEQ ID NO 25
<211> LENGTH: 180
<212> TYPE: DNA
<213> ORGANISM: Artificial Sequence
<220> FEATURE:
<223> OTHER INFORMATION: Synthetic: FNR-responsive regulatory region
      Sequence: ydfZ+RBS

<400> SEQUENCE: 25
catttcctct catcccatcc ggggtgagag tcttttcccc cgacttatgg ctcatgcatg      60
catcaaaaaa gatgtgagct tgatcaaaaa caaaaaatat ttcactcgac aggagtattt     120
atattgcgcc cggatccctc tagaaataat tttgtttaac tttaagaagg agatatacat     180

<210> SEQ ID NO 26
<211> LENGTH: 199
<212> TYPE: DNA
<213> ORGANISM: Artificial Sequence
<220> FEATURE:
<223> OTHER INFORMATION: Synthetic: FNR-responsive regulatory region
      Sequence: fnrS1

<400> SEQUENCE: 26
agttgttctt attggtggtg ttgctttatg gttgcatcgt agtaaatggt tgtaacaaaa      60 gcaattttc cggctgtctg tatacaaaaa cgccgtaaag tttgagcgaa gtcaataaac      120
tctctaccca ttcagggcaa tatctctctt ggatccctct agaaataatt ttgtttaact     180
ttaagaagga gatatacat                                                  199

<210> SEQ ID NO 27
<211> LENGTH: 207
<212> TYPE: DNA
<213> ORGANISM: Artificial Sequence
<220> FEATURE:
<223> OTHER INFORMATION: Synthetic: FNR-responsive regulatory region
      Sequence: fnrS2

<400> SEQUENCE: 27
agttgttctt attggtggtg ttgctttatg gttgcatcgt agtaaatggt tgtaacaaaa      60 gcaattttc cggctgtctg tatacaaaaa cgccgcaaag tttgagcgaa gtcaataaac      120
tctctaccca ttcagggcaa tatctctctt ggatccaaag tgaactctag aaataatttt     180 gtttaactt aagaaggaga tatacat                                          207

<210> SEQ ID NO 28
<211> LENGTH: 390
<212> TYPE: DNA
<213> ORGANISM: Artificial Sequence
<220> FEATURE:
```

<223> OTHER INFORMATION: Synthetic: FNR-responsive regulatory region
       Sequence: nirB+crp

<400> SEQUENCE: 28

```
tcgtctttgt gatgtgcttc ctgttaggtt tcgtcagccg tcaccgtcag cataacaccc     60
tgacctctca ttaattgctc atgccggacg gcactatcgt cgtccggcct tttcctctct   120
tcccccgcta cgtgcatcta tttctataaa cccgctcatt ttgtctattt tttgcacaaa   180
catgaaatat cagacaattc cgtgacttaa gaaaatttat acaaatcagc aatatacccca  240
ttaaggagta tataaaggtg aatttgattt acatcaataa gcggggttgc tgaatcgtta  300
aggtagaaat gtgatctagt tcacatttgc ggtaatagaa agaaatcga ggcaaaaatg   360
tttgtttaac tttaagaagg agatatacat                                    390
```

<210> SEQ ID NO 29
<211> LENGTH: 200
<212> TYPE: DNA
<213> ORGANISM: Artificial Sequence
<220> FEATURE:
<223> OTHER INFORMATION: Synthetic: FNR-responsive regulatory region
       Sequence: fnrS+crp

<400> SEQUENCE: 29

```
agttgttctt attggtggtg ttgctttatg gttgcatcgt agtaaatggt tgtaacaaaa    60
gcaattttc cggctgtctg tatacaaaaa cgccgcaaag tttgagcgaa gtcaataaac   120
tctctaccca ttcagggcaa tatctctcaa atgtgatcta gttcacattt tttgtttaac   180
tttaagaagg agatatacat                                               200
```

<210> SEQ ID NO 30
<211> LENGTH: 355
<212> TYPE: DNA
<213> ORGANISM: Artificial Sequence
<220> FEATURE:
<223> OTHER INFORMATION: Synthetic: Regulatory sequence: katG

<400> SEQUENCE: 30

```
tgtggctttt atgaaaatca cacagtgatc acaaattta aacagagcac aaaatgctgc     60
ctcgaaatga gggcgggaaa ataaggttat cagccttgtt ttctccctca ttacttgaag  120
gatatgaagc taaaacccctt ttttataaag catttgtccg aattcggaca taatcaaaaa 180
agcttaatta agatcaattt gatctacatc tctttaacca acaatatgta agatctcaac  240
tatcgcatcc gtggattaat tcaattataa cttctctcta acgctgtgta tcgtaacggt  300
aacactgtag aggggagcac attgatgcga attcattaaa gaggagaaag gtacc        355
```

<210> SEQ ID NO 31
<211> LENGTH: 228
<212> TYPE: DNA
<213> ORGANISM: Artificial Sequence
<220> FEATURE:
<223> OTHER INFORMATION: Synthetic: Regulatory sequence: dps

<400> SEQUENCE: 31

```
ttccgaaaat tcctggcgag cagataaata agaattgttc ttatcaatat atctaactca    60
ttgaatcttt attagttttg tttttcacgc ttgttaccac tattagtgtg ataggaacag  120
ccagaatagc ggaacacata gccggtgcta tacttaatct cgttaattac tgggacataa  180
catcaagagg atatgaaatt cgaattcatt aaagaggaga aggtacc                 228
```

```
<210> SEQ ID NO 32
<211> LENGTH: 334
<212> TYPE: DNA
<213> ORGANISM: Artificial Sequence
<220> FEATURE:
<223> OTHER INFORMATION: Synthetic: Regulatory sequence: ahpC

<400> SEQUENCE: 32
gcttagatca ggtgattgcc ctttgtttat gagggtgttg taatccatgt cgttgttgca      60
tttgtaaggg caacacctca gcctgcaggc aggcactgaa gataccaaag ggtagttcag     120
attacacggt cacctggaaa gggggccatt ttacttttta tcgccgctgg cggtgcaaag     180
ttcacaaagt tgtcttacga aggttgtaag gtaaaactta tcgatttgat aatggaaacg     240
cattagccga atcggcaaaa attggttacc ttacatctca tcgaaaacac ggaggaagta     300
tagatgcgaa ttcattaaag aggagaaagg tacc                                  334

<210> SEQ ID NO 33
<211> LENGTH: 134
<212> TYPE: DNA
<213> ORGANISM: Artificial Sequence
<220> FEATURE:
<223> OTHER INFORMATION: Synthetic: Regulatory sequence: oxyS

<400> SEQUENCE: 33
ctcgagttca ttatccatcc tccatcgcca cgatagttca tggcgatagg tagaatagca      60
atgaacgatt atccctatca agcattctga ctgataattg ctcacacgaa ttcattaaag     120
aggagaaagg tacc                                                        134

<210> SEQ ID NO 34
<211> LENGTH: 5409
<212> TYPE: DNA
<213> ORGANISM: Artificial Sequence
<220> FEATURE:
<223> OTHER INFORMATION: Synthetic construct: TetR in reverse
      orientation, TetR/TetA promoter, and oxalate catabolism cassette
      comprising ScAAE3, oxy, oxylyl-coA decarboxylase from O.
      formigenes, and formyl-coA transferase from O. formigenes,
      separated by ribosome binding

<400> SEQUENCE: 34
ttaagaccca ctttcacatt taagttgttt ttctaatccg catatgatca attcaaggcc      60
gaataagaag gctggctctg caccttggtg atcaaataat tcgatagctt gtcgtaataa     120
tggcggcata ctatcagtag taggtgtttc cctttcttct ttagcgactt gatgctcttg     180
atcttccaat acgcaaccta agtaaaatg ccccacagcg ctgagtgcat ataatgcatt     240
ctctagtgaa aaaccttgtt ggcataaaaa ggctaattga ttttcgagag tttcatactg     300
tttttctgta ggccgtgtac ctaaatgtac ttttgctcca tcgcgatgac ttagtaaagc     360
acatctaaaa cttttagcgt tattacgtaa aaaatcttgc cagctttccc cttctaaagg     420
gcaaaagtga gtatggtgcc tatctaacat ctcaatggct aaggcgtcga gcaaagcccg     480
cttatttttt acatgccaat acaatgtagg ctgctctaca cctagcttct gggcgagttt     540
acgggttgtt aaaccttcga ttccgacctc attaagcagc tctaatgcgc tgttaatcac     600 tttacttta tctaatctag acatcattaa ttcctaattt tgttgacac tctatcattg     660 atagagttat tttaccactc cctatcagtg atagagaaaa gtgaactcta gaaataattt     720
tgtttaactt taagaaggag atatacatat gaccagtgca gctacggtga ccgcgagctt     780
taatgacact ttttctgtga gcgataatgt cgcggtaatc gtaccggaaa ccgatacgca     840
```

```
ggtcacctac cgtgatcttt cccacatggt aggacacttt caaacaatgt tcacgaaccc    900
gaatagtcct ctgtacgggg cggtctttcg tcaagacacg gtagcgatta gcatgcgtaa    960
cggccttgaa tttattgtgg ctttccttgg agccacgatg gatgcgaaaa ttggtgcgcc   1020
actgaatccc aattataaag agaaggagtt taattttac ctgaatgact aaagtccaa     1080
agccatctgc gtgccgaaag gcaccaccaa actgcaaagt tcagaaattc ttaagagtgc   1140
gtccacgttc gggtgcttta ttgtggaact ggcgtttgac gccacccgtt ttcgtgttga   1200
atatgacatt tactccccgg aggacaatta taaacgtgtg atctaccgca gccttaacaa   1260
tgctaagttt gtcaacacaa accctgtcaa gttcccgggt ttcgcccgca gctcggatgt   1320
tgcacttatt ttgcatacct caggcaccac tagtacccca aagaccgtac ccctcttgca   1380
tctgaatatt gtccgttcaa ccctgaatat cgccaacact tacaaactta ccccgctgga   1440
tcgctcctat gttgtaatgc cgctgtttca tgtacatgga ttaatcggcg tcttactgag   1500
tacgttccgc acccagggca gtgtagtcgt cccggacggc tttcatccga agctcttctg   1560
ggatcagttt gttaaatata actgcaattg gtttagttgc gtcccaacga tctctatgat   1620
tatgttgaat atgcccaaac cgaatccgtt tccgcacatt cgctttatcc gctcatgtag   1680
cagcgcgctg gcgccagcaa cgtttcacaa gctggaaaaa gaatttaatg ccccagttct   1740
ggaagcgtac gcgatgacag aagcatctca tcagatgacc agtaacaatc tgcctcccgg   1800
taaacgtaaa ccggggaccg tgggccaacc tcaaggtgta accgtagtaa tcctggatga   1860
caacgataac gttctgccgc ccggcaaagt tggcgaggtg tcgatccgtg gggagaacgt   1920
cacccctgggc tacgctaata acccgaaagc taacaaagaa aacttcacta aacgtgaaaa   1980
ctatttccgt accggggatc agggctactt cgacccggag ggctttctcg tgctgaccgg   2040
ccgcattaaa gaattgatca atcgcggtgg tgaaaaaatt agtcctattg aactggacgg   2100
aatcatgctc tcgcatccta aaatcgacga ggcggtggcg ttcggcgttc cagatgatat   2160
gtatggccaa gtcgttcagg cggcaatcgt gttgaaaaag ggggaaaaga tgacctatga   2220
agaattagtg aatttcctga aaaagcattt agcaagcttt aaaatcccaa ccaaagtcta   2280
ctttgtggat aagctgccta aaacggccac cgggaagatt caacgtcgcg taatcgccga   2340
aaccttcgcg aaatctagtc gcaacaaaag caaactttaa agaaggaga tatacatatg   2400
agtaacgacg acaatgtaga gttgactgat ggctttcatg ttttgatcga tgccctgaaa   2460
atgaatgaca tcgataccat gtatggtgtt gtcggcattc ctatcacgaa cctggctcgt   2520
atgtggcaag atgacggtca gcgtttttac agcttccgtc acgaacaaca cgcaggttat   2580
gcagcttcta tcgccggtta catcgaagga aaacctggcg tttgcttgac cgtttccgcc   2640
cctggcttcc tgaacggcgt gacttccctg gctcatgcaa ccaccaactg cttcccaatg   2700
atcctgttga gcggttccag tgaacgtgaa atcgtcgatt tgcaacaggg cgattacgaa   2760
gaaatggatc agatgaatgt tgcacgtcca cactgcaaag cttctttccg tatcaacagc   2820
atcaaagaca ttccaatcgg tatcgctcgt gcagttcgca ccgctgtatc cggacgtcca   2880
ggtggtgttt acgttgactt gccagcaaaa ctgttcggtc agaccatttc tgtagaagaa   2940
gctaacaaac tgctcttcaa accaatcgat ccagctccgg cacagattcc tgctgaagac   3000
gctatcgctc gcgctgctga cctgatcaag aacgccaaac gtccagttat catgctgggt   3060
aaaggcgctg catacgcaca atgcgacgac gaaatccgcg cactggttga agaaaccggc   3120
atcccattcc tgccaatggg tatggctaaa ggctgctgc ctgacaacca tccacaatcc   3180
gctgctgcaa cccgtgcttt cgcactggca cagtgtgacg tttgcgtact gatcggcgct   3240
```

```
cgtctgaact ggctgatgca gcacggtaaa ggcaaaacct ggggcgacga actgaagaaa    3300
tacgttcaga tcgacatcca ggctaacgaa atggacagca accagcctat cgctgcacca    3360
gttgttggtg acatcaagtc cgccgtttcc ctgctccgca agcactgaa aggcgctcca     3420 aaagctgacg ctgaatggac cggcgctctg aaagccaaag ttgacggcaa caaagccaaa    3480
ctggctggca agatgactgc cgaaacccca tccggaatga tgaactactc caattccctg    3540
ggcgttgttc gtgacttcat gctggcaaat ccggatattt ccctggttaa cgaaggcgct    3600
aatgcactcg acaacactcg tatgattgtt gacatgctga aaccacgcaa acgtcttgac    3660
tccggtacct ggggtgttat gggtattggt atgggctact gcgttgctgc agctgctgtt    3720
accggcaaac cggttatcgc tgttgaaggc gatagcgcat tcggtttctc cggtatggaa    3780
ctggaaacca tctgccgtta caacctgcca gttaccgtta tcatcatgaa caatggtggt    3840
atctataaag gtaacgaagc agatccacaa ccaggcgtta tctcctgtac ccgtctgacc    3900
cgtggtcgtt acgacatgat gatggaagca tttggcggta aggttatgt tgccaatact    3960 ccagcagaac tgaaagctgc tctggaagaa gctgttgctt ccggcaaacc atgcctgatc    4020
aacgcgatga tcgatccaga cgctggtgtc gaatctggcc gtatcaagag cctgaacgtt    4080
gtaagtaaag ttggcaagaa ataataagaa ggagatatac atatgactaa accattagat    4140
ggaattaatg tgcttgactt tacccacgtc caggcaggtc ctgcctgtac acagatgatg    4200
ggtttcttgg gcgcaaacgt catcaagatt gaaagacgtg gttccggaga tatgactcgt    4260
ggatggctgc aggacaaacc aaatgttgat tccctgtatt tcacgatgtt caactgtaac    4320
aaacgttcga ttgaactgga catgaaaacc ccggaaggca aagagcttct ggaacagatg    4380
atcaagaaag ccgacgtcat ggtcgaaaac ttcggaccag cgcactgga ccgtatgggc    4440 tttacttggg aatacattca ggaactgaat ccacgcgtca ttctggcttc cgttaaaggc    4500
tatgcagaag gccacgccaa cgaacacctg aaagtttatg aaaacgttgc acagtgttcc    4560
ggcggtgctg cagctaccac cggtttctgg gatggtcctc caaccgtttc cggcgctgct    4620
ctgggtgact ccaactccgg tatgcacctg atgatcggta ttctggccgc tctggaaatg    4680
cgtcacaaaa ccggccgtgg tcagaaagtt gccgtcgcta tgcaggacgc tgttctgaat    4740
ctggttcgta tcaaactgcg tgaccagcaa cgtctggaaa gaaccggcat tctggctgaa    4800
tacccacagg ctcagcctaa ctttgccttc gacagagacg taacccact gtccttcgac     4860 aacatcactt ccgttccacg tggtggtaac gcaggtggcg gcggccagcc aggctggatg    4920
ctgaaatgta aggttgggga accgatgcg gactcctacg tttacttcac catcgctgca    4980
aacatgtggc cacagatctg cgacatgatc gacaagccag aatggaaaga cgacccagcc    5040
tacaacacat tcgaaggtcg tgttgacaag ctgatggaca tcttctcctt catcgaaacc    5100
aagttcgctg acaaggacaa attcgaagtt accgaatggg ctgcccagta cggcattcct    5160
tgcggtccgg tcatgtccat gaagaactg gctcacgatc cttccctgca gaaagttggt    5220
accgtcgttg aagttgtcga cgaaattcgt ggtaaccacc tgaccgttgg cgcaccgttc    5280
aaattctccg gattccagcc ggaaattacc cgtgctccgc tgttgggcga acataccgac    5340
gaagttctga agaactggg tcttgacgat gccaagatca ggaactgca tgcaaaacag    5400 gtagtttga                                                            5409
```

<210> SEQ ID NO 35
<211> LENGTH: 4785
<212> TYPE: DNA

<213> ORGANISM: Artificial Sequence
<220> FEATURE:
<223> OTHER INFORMATION: Synthetic construct: TetR/TetA promoter, and oxalate catabolism cassette comprising ScAAE3, oxc, oxylyl-coA decarboxylase from O. formigenes, and frc, formyl-coA transferase from O. formigenes, separated by ribosome binding sites

<400> SEQUENCE: 35

```
cattaattcc taatttttgt tgacactcta tcattgatag agttatttta ccactcccta      60
tcagtgatag agaaaagtga actctagaaa taattttgtt taactttaag aaggagatat     120
acatatgacc agtgcagcta cggtgaccgc gagctttaat gacactttt ctgtgagcga      180
taatgtcgcg gtaatcgtac cggaaaccga tacgcaggtc acctaccgtg atctttccca     240
catggtagga cactttcaaa caatgttcac gaacccgaat agtcctctgt acggggcggt     300
ctttcgtcaa gacacggtag cgattagcat gcgtaacggc cttgaattta ttgtggcttt    360
ccttggagcc acgatggatg cgaaaattgg tgcgccactg aatcccaatt ataaagagaa    420
ggagtttaat ttttacctga atgacttaaa gtccaaagcc atctgcgtgc cgaaaggcac    480
caccaaactg caaagttcag aaattcttaa gagtgcgtcc acgttcgggt gctttattgt    540
ggaactggcg tttgacgcca cccgttttcg tgttgaatat gacatttact ccccggagga    600
caattataaa cgtgtgatct accgcagcct taacaatgct aagtttgtca acacaaaccc    660
tgtcaagttc ccgggtttcg cccgcagctc ggatgttgca cttattttgc atacctcagg    720
caccactagt accccaaaga ccgtaccct cttgcatctg aatattgtcc gttcaaccct    780
gaatatcgcc aacacttaca aacttacccc gctggatcgc tcctatgttg taatgccgct    840
gtttcatgta catggattaa tcggcgtctt actgagtacg ttccgcaccc agggcagtgt    900
agtcgtcccg gacggctttc atccgaagct cttctgggat cagtttgtta aatataactg    960
caattggttt agttgcgtcc caacgatctc tatgattatg ttgaatatgc ccaaaccgaa   1020
tccgttttccg cacattcgct ttatccgctc atgtagcagc gcgctggcgc cagcaacgtt   1080
tcacaagctg gaaaaagaat ttaatgcccc agttctggaa gcgtacgcga tgacagaagc   1140
atctcatcag atgaccagta acaatctgcc tcccggtaaa cgtaaaccgg ggaccgtggg   1200
ccaacctcaa ggtgtaaccg tagtaatcct ggatgacaac gataacgttc tgccgcccgg   1260
caaagttggc gaggtgtcga tccgtgggga aacgtcacc ctgggctacg ctaataaccc    1320
gaaagctaac aaagaaaact tcactaaacg tgaaaactat ttccgtaccg gggatcaggg   1380
ctacttcgac ccggagggct ttctcgtgct gaccggccgc attaaagaat tgatcaatcg   1440
cggtggtgaa aaaattagtc ctattgaact ggacggaatc atgctctcgc atcctaaaat   1500
cgacgaggcg gtggcgttcg gcgttccaga tgatatgtat ggccaagtcg ttcaggcggc   1560
aatcgtgttg aaaagggggg aaaagatgac ctatgaagaa ttagtgaatt tcctgaaaaa   1620
gcatttagca agctttaaaa tcccaaccaa agtctacttt gtggataagc tgcctaaaac   1680
ggccaccggg aagattcaac gtcgcgtaat cgccgaaacc ttcgcgaaat ctagtcgcaa   1740
caaaagcaaa ctttaaaaga aggagatata catatgagta acgacgacaa tgtagagttg   1800
actgatggct ttcatgtttt gatcgatgcc ctgaaaatga atgacatcga taccatgtat   1860
ggtgttgtcg gcattcctat cacgaacctg gctcgtatgt ggcaagatga cggtcagcgt   1920
ttttacagct ccgtcacga acaacacgca ggttatgcag cttctatcgc cggttacatc    1980
gaaggaaaac ctggcgtttg cttgaccgtt tccgccctg gcttcctgaa cggcgtgact   2040
tccctggctc atgcaaccac caactgcttc ccaatgatcc tgttgagcgg ttccagtgaa   2100
```

-continued

```
cgtgaaatcg tcgatttgca acagggcgat tacgaagaaa tggatcagat gaatgttgca    2160
cgtccacact gcaaagcttc tttccgtatc aacagcatca aagacattcc aatcggtatc    2220
gctcgtgcag ttcgcaccgc tgtatccgga cgtccaggtg gtgtttacgt tgacttgcca    2280
gcaaaactgt tcggtcagac catttctgta gaagaagcta acaaactgct cttcaaacca    2340
atcgatccag ctccggcaca gattcctgct gaagacgcta tcgctcgcgc tgctgacctg    2400
atcaagaacg ccaaacgtcc agttatcatg ctgggtaaag cgctgcata cgcacaatgc    2460 gacgacgaaa tccgcgcact ggttgaagaa accggcatcc cattcctgcc aatgggtatg    2520
gctaaaggcc tgctgcctga caaccatcca caatccgctg ctgcaacccg tgctttcgca    2580
ctggcacagt gtgacgtttg cgtactgatc ggcgctcgtc tgaactggct gatgcagcac    2640
ggtaaaggca aaacctgggg cgacgaactg aagaaatacg ttcagatcga catccaggct    2700
aacgaaatgg acagcaacca gcctatcgct gcaccagttg ttggtgacat caagtccgcc    2760
gtttccctgc tccgcaaagc actgaaaggc gctccaaaag ctgacgctga atggaccggc    2820
gctctgaaag ccaaagttga cggcaacaaa gccaaactgg ctggcaagat gactgccgaa    2880
accccatccg gaatgatgaa ctactccaat tccctgggcg ttgttcgtga cttcatgctg    2940
gcaaatccgg atatttccct ggttaacgaa ggcgctaatg cactcgacaa cactcgtatg    3000
attgttgaca tgctgaaacc acgcaaacgt cttgactccg gtacctgggg tgttatgggt    3060
attggtatgg gctactgcgt tgctgcagct gctgttaccg gcaaaccggt tatcgctgtt    3120
gaaggcgata gcgcattcgg tttctccggt atggaactgg aaaccatctg ccgttacaac    3180
ctgccagtta ccgttatcat catgaacaat ggtggtatct ataaaggtaa cgaagcagat    3240
ccacaaccag gcgttatctc ctgtacccgt ctgacccgtg tcgttacga catgatgatg    3300 gaagcatttg gcggtaaagg ttatgttgcc aatactccag cagaactgaa agctgctctg    3360
gaagaagctg ttgcttccgg caaaccatgc ctgatcaacg cgatgatcga tccagacgct    3420
ggtgtcgaat ctgccgtat caagagcctg aacgttgtaa gtaaagttgg caagaaataa    3480
taagaaggag atatacatat gactaaacca ttagatggaa ttaatgtgct tgactttacc    3540
cacgtccagg caggtcctgc ctgtacacag atgatgggtt tcttgggcgc aaacgtcatc    3600
aagattgaaa gacgtggttc cggagatatg actcgtggat ggctgcagga caaaccaaat    3660
gttgattccc tgtatttcac gatgttcaac tgtaacaaac gttcgattga actggacatg    3720
aaaaccccgg aaggcaaaga gcttctggaa cagatgatca agaaagccga cgtcatggtc    3780
gaaaacttcg gaccaggcgc actggaccgt atgggcttta cttgggaata cattcaggaa    3840
ctgaatccac gcgtcattct ggcttccgtt aaaggctatg cagaaggcca cgccaacgaa    3900
cacctgaaag tttatgaaaa cgttgcacag tgttccggcg tgctgcagc taccaccggt    3960 ttctgggatg gtcctccaac cgtttccggc gctgctctgg gtgactccaa ctccggtatg    4020
cacctgatga tcggtattct ggccgctctg gaaatgcgtc acaaaaccgg ccgtggtcag    4080
aaagttgccg tcgctatgca ggacgctgtt ctgaatctgg ttcgtatcaa actgcgtgac    4140
cagcaacgtc tggaaagaac cggcattctg gctgaatacc cacaggctca gcctaacttt    4200
gccttcgaca gagacggtaa cccactgtcc ttcgacaaca tcacttccgt tccacgtggt    4260
ggtaacgcag gtggcggcgg ccagccaggc tggatgctga atgtaaagg ttgggaaacc    4320 gatgcggact cctacgttta cttcaccatc gctgcaaaca tgtggccaca gatctgcgac    4380
atgatcgaca agccagaatg gaaagacgac ccagcctaca acacattcga aggtcgtgtt    4440
gacaagctga tggacatctt ctccttcatc gaaaccaagt tcgctgacaa ggacaaattc    4500
```

```
gaagttaccg aatgggctgc ccagtacggc attccttgcg gtccggtcat gtccatgaaa    4560
gaactggctc acgatccttc cctgcagaaa gttggtaccg tcgttgaagt tgtcgacgaa    4620
attcgtggta accacctgac cgttggcgca ccgttcaaat tctccggatt ccagccggaa    4680
attacccgtg ctccgctgtt gggcgaacat accgacgaag ttctgaaaga actgggtctt    4740
gacgatgcca agatcaagga actgcatgca aaacaggtag tttga                   4785
```

<210> SEQ ID NO 36
<211> LENGTH: 4661
<212> TYPE: DNA
<213> ORGANISM: Artificial Sequence
<220> FEATURE:
<223> OTHER INFORMATION: Synthetic: Construct comprising oxalate catabolism cassette comprising ScAAE3 (oxalate-CoA ligase from S. cerevisiae), oxy, oxylyl-coA decarboxylase from O. formigenes, and formyl-coA transferase from O. formigenes, separated by ribosome binding

<400> SEQUENCE: 36

```
atgaccagtg cagctacggt gaccgcgagc tttaatgaca cttttctgt gagcgataat      60 gtcgcggtaa tcgtaccgga aaccgatacg caggtcacct accgtgatct ttcccacatg    120
gtaggacact ttcaaacaat gttcacgaac ccgaatagtc ctctgtacgg ggcggtcttt    180
cgtcaagaca cggtagcgat tagcatgcgt aacggccttg aatttattgt ggctttcctt    240
ggagccacga tggatgcgaa aattggtgcg ccactgaatc ccaattataa agagaaggag    300 tttaatttt acctgaatga cttaaagtcc aaagccatct gcgtgccgaa aggcaccacc    360
aaactgcaaa gttcagaaat tcttaagagt gcgtccacgt tcgggtgctt tattgtggaa    420
ctggcgtttg acgccacccg ttttcgtgtt gaatatgaca tttactcccc ggaggacaat    480
tataaacgtg tgatctaccg cagccttaac aatgctaagt ttgtcaacac aaaccctgtc    540
aagttcccgg gtttcgcccg cagctcggat gttgcactta ttttgcatac ctcaggcacc    600
actagtaccc caaagaccgt accctcttg catctgaata ttgtccgttc aaccctgaat    660
atcgccaaca cttacaaact taccccgctg atcgctcct atgttgtaat gccgctgttt    720
catgtacatg gattaatcgg cgtcttactg agtacgttcc gcacccaggg cagtgtagtc    780
gtcccggacg gctttcatcc gaagctcttc tgggatcagt ttgttaaata aactgcaat    840 tggtttagtt gcgtcccaac gatctctatg attatgttga atatgcccaa accgaatccg    900
tttccgcaca ttcgctttat ccgctcatgt agcagcgcgc tggcgccagc aacgtttcac    960
aagctggaaa agaatttaa tgccccagtt ctggaagcgt acgcgatgac agaagcatct   1020
catcagatga ccagtaacaa tctgcctccc ggtaaacgta accggggac cgtgggccaa   1080 cctcaaggtg taaccgtagt aatcctggat gacaacgata cgttctgcc gcccggcaaa   1140 gttggcgagg tgtcgatccg tggggagaac gtcaccctgg gctacgctaa taacccgaaa   1200
gctaacaaag aaaacttcac taaacgtgaa aactatttcc gtaccgggga tcagggctac   1260
ttcgacccgg agggctttct cgtgctgacc ggccgcatta agaattgat caatcgcggt   1320 ggtgaaaaaa ttagtcctat tgaactggac ggaatcatgc tctcgcatcc taaaatcgac   1380
gaggcggtgg cgttcggcgt tccagatgat atgtatggcc aagtcgttca ggcggcaatc   1440
gtgttgaaaa agggggaaaa gatgaccat gaagaattag tgaatttcct gaaaaagcat   1500
ttagcaagct ttaaaatccc aaccaaagtc tactttgtgg ataagctgcc taaaacggcc   1560
accgggaaga ttcaacgtcg cgtaatcgcc gaaaccttcg cgaaatctag tcgcaacaaa   1620
```

-continued

```
agcaaacttt aaaagaagga gatatacata tgagtaacga cgacaatgta gagttgactg    1680
atggctttca tgttttgatc gatgccctga aaatgaatga catcgatacc atgtatggtg    1740
ttgtcggcat tcctatcacg aacctggctc gtatgtggca agatgacggt cagcgttttt    1800
acagcttccg tcacgaacaa cacgcaggtt atgcagcttc tatcgccggt tacatcgaag    1860
gaaaacctgg cgtttgcttg accgtttccg cccctggctt cctgaacggc gtgacttccc    1920
tggctcatgc aaccaccaac tgcttcccaa tgatcctgtt gagcggttcc agtgaacgtg    1980
aaatcgtcga tttgcaacag ggcgattacg aagaaatgga tcagatgaat gttgcacgtc    2040
cacactgcaa agcttctttc cgtatcaaca gcatcaaaga cattccaatc ggtatcgctc    2100
gtgcagttcg caccgctgta tccggacgtc caggtggtgt ttacgttgac ttgccagcaa    2160
aactgttcgg tcagaccatt tctgtagaag aagctaacaa actgctcttc aaaccaatcg    2220
atccagctcc ggcacagatt cctgctgaag acgctatcgc tcgcgctgct gacctgatca    2280
agaacgccaa acgtccagtt atcatgctgg gtaaaggcgc tgcatacgca caatgcgacg    2340
acgaaatccg cgcactggtt gaagaaaccg gcatcccatt cctgccaatg ggtatggcta    2400
aaggcctgct gcctgacaac catccacaat ccgctgctgc aacccgtgct ttcgcactgg    2460
cacagtgtga cgtttgcgta ctgatcggcg ctcgtctgaa ctggctgatg cagcacggta    2520
aaggcaaaac ctggggcgac gaactgaaga atacgttca gatcgacatc caggctaacg    2580
aaatggacag caaccagcct atcgctgcac cagttgttgg tgacatcaag tccgccgttt    2640
ccctgctccg caaagcactg aaaggcgctc caaaagctga cgctgaatgg accggcgctc    2700
tgaaagccaa agttgacggc aacaaagcca actggctgg caagatgact gccgaaaccc    2760
catccggaat gatgaactac tccaattccc tgggcgttgt tcgtgacttc atgctggcaa    2820
atccggatat ttccctggtt aacgaaggcg ctaatgcact cgacaacact cgtatgattg    2880
ttgacatgct gaaaccacgc aaacgtcttg actccggtac ctggggtgtt atgggtattg    2940
gtatgggcta ctgcgttgct gcagctgctg ttaccggcaa accggttatc gctgttgaag    3000
gcgatagcgc attcggtttc tccggtatgg aactggaaac catctgccgt tacaacctgc    3060
cagttaccgt tatcatcatg aacaatggtg gtatctataa aggtaacgaa gcagatccac    3120
aaccaggcgt tatctcctgt acccgtctga cccgtggtcg ttacgacatg atgatggaag    3180
catttggcgg taaaggttat gttgccaata ctccagcaga actgaaagct gctctggaag    3240
aagctgttgc ttccggcaaa ccatgcctga tcaacgcgat gatcgatcca gacgctggtg    3300
tcgaatctgg ccgtatcaag agcctgaacg ttgtaagtaa agttggcaag aaataataag    3360
aaggagatat acatatgact aaaccattag atggaattaa tgtgcttgac tttacccacg    3420
tccaggcagg tcctgcctgt acacagatga tgggtttctt gggcgcaaac gtcatcaaga    3480
ttgaaagacg tggttccgga gatatgactc gtggatggc gcaggacaaa ccaaatgttg    3540
attccctgta tttcacgatg ttcaactgta caaacgttc gattgaactg acatgaaaa    3600 cccccggaagg caaagagctt ctggaacaga tgatcaagaa agccgacgtc atggtcgaaa    3660
acttcggacc aggcgcactg gaccgtatgg gctttacttg gaatacatt caggaactga    3720 atccacgcgt cattctggct tccgttaaag gctatgcaga aggccacgcc aacgaacacc    3780
tgaaagttta tgaaaacgtt gcacagtgtt ccggcggtgc tgcagctacc accggtttct    3840
gggatggtcc tccaaccgtt tccggcgctg ctctgggtga ctccaactcc ggtatgcacc    3900
tgatgatcgt tattctggcc gctctggaaa tgcgtcacaa aaccgccgt ggtcagaaag    3960 ttgccgtcgc tatgcaggac gctgttctga atctggttcg tatcaaactg cgtgaccagc    4020
```

```
aacgtctgga agaaccggc attctggctg aataccccaca ggctcagcct aactttgcct    4080
tcgacagaga cggtaaccca ctgtccttcg acaacatcac ttccgttcca cgtggtggta    4140
acgcaggtgg cggcggccag ccaggctgga tgctgaaatg taaaggttgg gaaaccgatg    4200
cggactccta cgtttacttc accatcgctg caaacatgtg gccacagatc tgcgacatga    4260
tcgacaagcc agaatggaaa gacgacccag cctacaacac attcgaaggt cgtgttgaca    4320
agctgatgga catcttctcc ttcatcgaaa ccaagttcgc tgacaaggac aaattcgaag    4380
ttaccgaatg ggctgcccag tacggcattc cttgcggtcc ggtcatgtcc atgaaagaac    4440
tggctcacga tccttccctg cagaaagttg gtaccgtcgt tgaagttgtc gacgaaattc    4500
gtggtaacca cctgaccgtt ggcgcaccgt tcaaattctc cggattccag ccggaaatta    4560
cccgtgctcc gctgttgggc gaacataccg acgaagttct gaaagaactg ggtcttgacg    4620
atgccaagat caaggaactg catgcaaaac aggtagtttg a                       4661
```

<210> SEQ ID NO 37
<211> LENGTH: 2005
<212> TYPE: DNA
<213> ORGANISM: Artificial Sequence
<220> FEATURE:
<223> OTHER INFORMATION: Synthetic: Construct comprising TetR in reverse
      orientation, TetR/TetA promoter, driving OxlT (oxalate:formate
      antiporter from O. formigenes)

<400> SEQUENCE: 37

```
ttaagaccca ctttcacatt taagttgttt ttctaatccg catatgatca attcaaggcc      60
gaataagaag gctggctctg caccttggtg atcaaataat tcgatagctt gtcgtaataa     120
tggcggcata ctatcagtag taggtgtttc cctttcttct ttagcgactt gatgctcttg     180
atcttccaat acgcaaccta agtaaaatg ccccacagcg ctgagtgcat ataatgcatt      240
ctctagtgaa aaaccttgtt ggcataaaaa ggctaattga ttttcgagag tttcatactg     300
tttttctgta ggccgtgtac ctaaatgtac ttttgctcca tcgcgatgac ttagtaaagc     360
acatctaaaa cttttagcgt tattacgtaa aaaatcttgc cagctttccc cttctaaagg     420
gcaaaagtga gtatggtgcc tatctaacat ctcaatggct aaggcgtcga gcaaagcccg     480
cttatttttt acatgccaat acaatgtagg ctgctctaca cctagcttct gggcgagttt     540
acgggttgtt aaaccttcga ttccgacctc attaagcagc tctaatgcgc tgttaatcac     600
tttactttta tctaatctag acatcattaa ttcctaattt tgttgacac tctatcattg      660 atagagttat tttaccactc cctatcagtg atagagaaaa gtgaactcta gaaataaattt    720 tgtttaactt taagaaggag atatacatat gaataatcca caaacaggac aatcaacagg     780
cctcttgggc aatcgttggt tctacttggt attagcagtt ttgctgatgt gtatgatctc     840
gggtgtccaa tattcctgga cactgtacgc taacccggtt aaagacaacc ttggcgtttc     900
tttggctgcg gttcagacgg cttttcacact ctctcaggtc attcaagctg ttctcagcc    960 tggtggtggt tacttcgttg ataaattcgg tccaagaatt ccattgatgt tcggtggtgc    1020
gatggttctc gctggctgga ccttcatggg tatggttgac agtgttcctg ctctgtatgc    1080
tctttatact ctggccggtg caggtgttgg tatcgtttac ggtatcgcga tgaacacggc    1140
taacagatgg ttcccggaca aacgcgtct ggcttccggt ttcaccgctg ccggttacgg     1200
tctgggtgtt ctgccgttcc tgccactgat cagctccgtt ctgaaagttg aaggtgttgg    1260
cgcagcattc atgtacaccg gtttgatcat gggtatcctg attatcctga tcgctttcgt    1320
```

| | |
|---|---|
| tatccgttc cctggccagc aaggcgccaa aaaacaaatc gttgttaccg acaaggattt | 1380 |
| caattctggc gaaatgctga gaacaccaca attctgggtt ctgtggaccg cattcttttc | 1440 |
| cgttaacttt ggtggtttgc tgctggttgc caacagcgtc ccttacggtc gcagcctcgg | 1500 |
| tcttgccgca ggtgtgctga cgatcggtgt ttcgatccag aacctgttca atggtggttg | 1560 |
| ccgtcctttc tggggtttcg tttccgataa aatcggccgt tacaaaacca tgtccgtcgt | 1620 |
| tttcggtatc aatgctgttg ttctcgcact tttcccgacg attgctgcct gggcgatgt | 1680 |
| agcctttatc gccatgttgg caatcgcatt cttcacatgg ggtggtagct acgctctgtt | 1740 |
| cccatcgacc aacagcgata ttttcggtac ggcatactct gccagaaact atggtttctt | 1800 |
| ctgggctgca aaagcaactg cctcgatctt cggtggtggt ctgggtgctg caattgcaac | 1860 |
| caacttcgga tggaataccg ctttcctgat tactgcgatt acttctttca tcgcatttgc | 1920 |
| tctggctacc ttcgttattc caagaatggg ccgtccagtc aagaaaatgg tcaaattgtc | 1980 |
| tccagaagaa aaagctgtac attaa | 2005 |

<210> SEQ ID NO 38
<211> LENGTH: 1381
<212> TYPE: DNA
<213> ORGANISM: Artificial Sequence
<220> FEATURE:
<223> OTHER INFORMATION: Synthetic: Construct comprising TetR/TetA promoter, driving OxlT (oxalate:formate antiporter from O. formigenes)

<400> SEQUENCE: 38

| | |
|---|---|
| cattaattcc taattttgt tgacactcta tcattgatag agttatttta ccactcccta | 60 |
| tcagtgatag agaaaagtga actctagaaa taattttgtt taactttaag aaggagatat | 120 |
| acatatgaat aatccacaaa caggacaatc aacaggcctc ttgggcaatc gttggttcta | 180 |
| cttggtatta gcagttttgc tgatgtgtat gatctcgggt gtccaatatt cctggacact | 240 |
| gtacgctaac ccggttaaag acaaccttgg cgtttctttg gctgcggttc agacggcttt | 300 |
| cacactctct caggtcattc aagctggttc tcagcctggt ggtggttact tcgttgataa | 360 |
| attcggtcca agaattccat tgatgttcgg tggtgcgatg gttctcgctg ctgaccttt | 420 |
| catgggtatg gttgacagtg ttcctgctct gtatgctctt tatactctgg ccggtgcagg | 480 |
| tgttggtatc gtttacggta tcgcgatgaa cacggctaac agatggttcc cggacaaacg | 540 |
| cggtctggct tccggtttca ccgctgccgg ttacggtctg ggtgttctgc cgttcctgcc | 600 |
| actgatcagc tccgttctga agttgaaggt gttggcgca gcattcatgt acaccggttt | 660 |
| gatcatgggt atcctgatta tcctgatcgc tttcgttatc cgtttccctg ccagcaagg | 720 |
| cgccaaaaaa caaatcgttg ttaccgacaa ggatttcaat tctggcgaaa tgctgagaac | 780 |
| accacaattc tgggttctgt ggaccgcatt cttttccgtt aactttggtg gtttgctgct | 840 |
| ggttgccaac agcgtccctt acggtcgcag cctcggtctt gccgcaggtg tgctgacgat | 900 |
| cggtgtttcg atccagaacc tgttcaatgg tggttgccgt cctttctggg gtttcgtttc | 960 |
| cgataaaatc ggccgttaca aaaccatgtc cgtcgttttc ggtatcaatg ctgttgttct | 1020 |
| cgcacttttc ccgacgattg ctgccttggg cgatgtagcc tttatcgcca tgttggcaat | 1080 |
| cgcattcttc acatggggtg gtagctacgc tctgttccca tcgaccaaca gcgatatttt | 1140 |
| cggtacggca tactctgcca gaaactatgg tttcttctgg gctgcaaaag caactgcctc | 1200 |
| gatcttcggt ggtggtctgg gtgctgcaat tgcaaccaac ttcggatgga ataccgcttt | 1260 |
| cctgattact gcgattactt ctttcatcgc atttgctctg ctaccttcg ttattccaag | 1320 |

```
aatgggccgt ccagtcaaga aaatggtcaa attgtctcca gaagaaaaag ctgtacatta    1380
a                                                                   1381
```

<210> SEQ ID NO 39
<211> LENGTH: 1300
<212> TYPE: DNA
<213> ORGANISM: Artificial Sequence
<220> FEATURE:
<223> OTHER INFORMATION: Synthetic: Construct comprising RBS and leader
      region driving OxlT (oxalate:formate antiporter from O.
      formigenes)

<400> SEQUENCE: 39

```
ctctagaaat aattttgttt aactttaaga aggagatata catatgaata atccacaaac      60
aggacaatca acaggcctct tgggcaatcg ttggttctac ttggtattag cagttttgct    120
gatgtgtatg atctcgggtg tccaatattc ctggacactg tacgctaacc cggttaaaga    180
caaccttggc gtttctttgg ctgcggttca gacggctttc acactctctc aggtcattca    240
agctggttct cagcctggtg gtggttactt cgttgataaa ttcggtccaa gaattccatt    300
gatgttcggt ggtgcgatgg ttctcgctgg ctggaccttc atgggtatgg ttgacagtgt    360
tcctgctctg tatgctcttt atactctggc cggtgcaggt gttggtatcg tttacggtat    420
cgcgatgaac acggctaaca gatggttccc ggacaaacgc ggtctggctt ccggtttcac    480
cgctgccggt tacggtctgg tgttctgcc gttcctgcca ctgatcagct ccgttctgaa    540
agttgaaggt gttggcgcag cattcatgta caccggtttg atcatgggta tcctgattat    600
cctgatcgct ttcgttatcc gtttccctgg ccagcaaggc gccaaaaaac aaatcgttgt    660
taccgacaag gatttcaatt ctggcgaaat gctgagaaca ccacaattct gggttctgtg    720
gaccgcattc ttttccgtta actttggtgg tttgctgctg gttgccaaca gcgtccctta    780
cggtcgcagc ctcggtcttg ccgcaggtgt gctgacgatc ggtgtttcga tccagaacct    840
gttcaatggt ggttgccgtc ctttctgggg tttcgtttcc gataaaatcg gccgttacaa    900
aaccatgtcc gtcgttttcg gtatcaatgc tgttgttctc gcactttcc cgacgattgc    960 tgccttgggc gatgtagcct ttatcgccat gttggcaatc gcattcttca catggggtgg   1020
tagctacgct ctgttcccat cgaccaacag cgatatttc ggtacggcat actctgccag   1080
aaactatggt ttcttctggg ctgcaaaagc aactgcctcg atcttcggtg gtggtctggg   1140
tgctgcaatt gcaaccaact tcggatggaa taccgctttc ctgattactg cgattacttc   1200
tttcatcgca tttgctctgg ctaccttcgt tattccaaga atgggccgtc cagtcaagaa   1260
aatggtcaaa ttgtctccag aagaaaaagc tgtacattaa                          1300
```

<210> SEQ ID NO 40
<211> LENGTH: 4874
<212> TYPE: DNA
<213> ORGANISM: Artificial Sequence
<220> FEATURE:
<223> OTHER INFORMATION: Synthetic construct: promoter with FNR binding
      site driving expression of cassette comprising ScAAE3, oxy,
      oxylyl-coA decarboxylase from O. formigenes, and formyl-coA
      transferase from O. formigenes, separated by ribosome binding
      sites

<400> SEQUENCE: 40

```
ggtaccagtt gttcttattg gtggtgttgc tttatggttg catcgtagta aatggttgta      60
acaaaagcaa ttttccggc tgtctgtata caaaaacgcc gtaaagtttg agcgaagtca    120
```

```
ataaactctc tacccattca gggcaatatc tctcttggat ccaaagtgaa ctctagaaat    180
aattttgttt aactttaaga aggagatata catatgacca gtgcagctac ggtgaccgcg    240
agctttaatg acactttttc tgtgagcgat aatgtcgcgg taatcgtacc ggaaaccgat    300
acgcaggtca cctaccgtga tctttcccac atggtaggac actttcaaac aatgttcacg    360
aacccgaata gtcctctgta cggggcggtc tttcgtcaag acacggtagc gattagcatg    420
cgtaacggcc ttgaatttat tgtggctttc cttggagcca cgatggatgc gaaaattggt    480
gcgccactga atcccaatta taaagagaag gagtttaatt tttacctgaa tgacttaaag    540
tccaaagcca tctgcgtgcc gaaaggcacc accaaactgc aaagttcaga aattcttaag    600
agtgcgtcca cgttcgggtg ctttattgtg gaactggcgt ttgacgccac ccgttttcgt    660
gttgaatatg acatttactc cccggaggac aattataaac gtgtgatcta ccgcagcctt    720
aacaatgcta agtttgtcaa cacaaaccct gtcaagttcc cgggtttcgc ccgcagctcg    780
gatgttgcac ttattttgca tacctcaggc accactagta ccccaaagac cgtacccctc    840
ttgcatctga atattgtccg ttcaaccctg aatatcgcca cacttacaa acttaccccg     900 ctggatcgct cctatgttgt aatgccgctg tttcatgtac atggattaat cggcgtctta    960
ctgagtacgt tccgcaccca gggcagtgta gtcgtcccgg acggctttca tccgaagctc   1020
ttctgggatc agtttgttaa atataactgc aattggttta gttgcgtccc aacgatctct   1080
atgattatgt tgaatatgcc caaaccgaat ccgtttccgc acattcgctt tatccgctca   1140
tgtagcagcg cgctggcgcc agcaacgttt cacaagctgg aaaaagaatt taatgcccca   1200
gttctggaag cgtacgcgat gacagaagca tctcatcaga tgaccagtaa caatctgcct   1260
cccggtaaac gtaaaccggg gaccgtgggc caacctcaag gtgtaaccgt agtaatcctg   1320
gatgacaacg ataacgttct gccgcccggc aaagttggcg aggtgtcgat ccgtggggag   1380
aacgtcaccc tgggctacgc taataacccg aaagctaaca agaaaaactt cactaaacgt   1440
gaaaactatt ccgtaccggg ggatcagggc tacttcgacc cggagggctt tctcgtgctg   1500
accggccgca ttaaagaatt gatcaatcgc ggtggtgaaa aaattagtcc tattgaactg   1560
gacggaatca tgctctcgca tcctaaaatc gacgaggcgg tggcgttcgg cgttccagat   1620
gatatgtatg gccaagtcgt tcaggcggca atcgtgttga aaaagggggga aaagatgacc   1680 tatgaagaat tagtgaattt cctgaaaaag catttagcaa gctttaaaat cccaaccaaa   1740
gtctactttg tggataagct gcctaaaacg gccaccggga agattcaacg tcgcgtaatc   1800
gccgaaacct tcgcgaaatc tagtcgcaac aaaagcaaac tttaaaagaa ggagatatac   1860
atatgagtaa cgacgacaat gtagagttga ctgatggctt tcatgttttg atcgatgccc   1920
tgaaaatgaa tgcatcgat accatgtatg gtgttgtcgg cattcctatc acgaacctgg   1980
ctcgtatgtg gcaagatgac ggtcagcgtt tttacagctt ccgtcacgaa caacacgcag   2040
gttatgcagc ttctatcgcc ggttacatcg aaggaaaacc tggcgtttgc ttgaccgttt   2100
ccgcccctgg cttcctgaac ggcgtgactt ccctggctca tgcaaccacc aactgcttcc   2160
caatgatcct gttgagcggt tccagtgaac gtgaaatcgt cgatttgcaa cagggcgatt   2220
acgaagaaat ggatcagatg aatgttgcac gtccacactg caaagcttct ttccgtatca   2280
acagcatcaa agacattcca atcggtatcg ctcgtgcagt tcgcaccgct gtatccggac   2340
gtccaggtgg tgtttacgtt gacttgccag caaaactgtt cggtcagacc atttctgtag   2400
aagaagctaa caaactgctc ttcaaaccaa tcgatccagc tccggcacag attcctgctg   2460
aagacgctat cgctcgcgct gctgacctga tcaagaacgc caaacgtcca gttatcatgc   2520
```

```
tgggtaaagg cgctgcatac gcacaatgcg acgacgaaat ccgcgcactg gttgaagaaa    2580
ccggcatccc attcctgcca atgggtatgg ctaaaggcct gctgcctgac aaccatccac    2640
aatccgctgc tgcaacccgt gctttcgcac tggcacagtg tgacgtttgc gtactgatcg    2700
gcgctcgtct gaactggctg atgcagcacg gtaaaggcaa aacctggggc gacgaactga    2760
agaaatacgt tcagatcgac atccaggcta acgaaatgga cagcaaccag cctatcgctg    2820
caccagttgt tggtgacatc aagtccgccg tttccctgct ccgcaaagca ctgaaaggcg    2880
ctccaaaagc tgacgctgaa tggaccggcg ctctgaaagc caaagttgac ggcaacaaag    2940
ccaaactggc tggcaagatg actgccgaaa ccccatccgg aatgatgaac tactccaatt    3000
ccctgggcgt tgttcgtgac ttcatgctgg caaatccgga tatttccctg gttaacgaag    3060
gcgctaatgc actcgacaac actcgtatga ttgttgacat gctgaaacca cgcaaacgtc    3120
ttgactccgg tacctggggt gttatgggta ttggtatggg ctactgcgtt gctgcagctg    3180
ctgttaccgg caaaccggtt atcgctgttg aaggcgatag cgcattcggt ttctccggta    3240
tggaactgga aaccatctgc cgttacaacc tgccagttac cgttatcatc atgaacaatg    3300
gtggtatcta taaggtaac gaagcagatc cacaaccagg cgttatctcc tgtacccgtc    3360
tgacccgtgg tcgttacgac atgatgatgg aagcatttgg cggtaaaggt tatgttgcca    3420
atactccagc agaactgaaa gctgctctgg aagaagctgt tgcttccggc aaaccatgcc    3480
tgatcaacgc gatgatcgat ccagacgctg gtgtcgaatc tggccgtatc aagagcctga    3540
acgttgtaag taaagttggc aagaaataat aagaaggaga tatacatatg actaaaccat    3600
tagatggaat taatgtgctt gactttaccc acgtccaggc aggtcctgcc tgtacacaga    3660
tgatgggttt cttgggcgca aacgtcatca agattgaaag acgtggttcc ggagatatga    3720
ctcgtggatg gctgcaggac aaaccaaatg ttgattccct gtatttcacg atgttcaact    3780
gtaacaaacg ttcgattgaa ctggacatga aacccccgga aggcaaagag cttctggaac    3840
agatgatcaa gaaagccgac gtcatggtcg aaaacttcgg accaggcgca ctggaccgta    3900
tgggctttac ttgggaatac attcaggaac tgaatccacg cgtcattctg gcttccgtta    3960
aaggctatgc agaaggccac gccaacgaac acctgaaagt ttatgaaaac gttgcacagt    4020
gttccggcgg tgctgcagct accaccggtt tctgggatgg tcctccaacc gtttccggcg    4080
ctgctctggg tgactccaac tccggtatgc acctgatgat cggtattctg gccgctctgg    4140
aaatgcgtca aaaccggcc gtggtcaga agttgccgt cgctatgcag gacgctgttc    4200
tgaatctggt tcgtatcaaa ctgcgtgacc agcaacgtct ggaaagaacc ggcattctgg    4260
ctgaataccc acaggctcag cctaactttg ccttcgacag agacggtaac ccactgtcct    4320
tcgacaacat cacttccgtt ccacgtggtg gtaacgcagg tggcggcggc cagccaggct    4380
ggatgctgaa atgtaaaggt tgggaaaccg atgcggactc ctacgtttac ttcaccatcg    4440
ctgcaaacat gtgccacag atctgcgaca tgatcgacaa gccagaatgg aaagacgacc    4500
cagcctacaa cacattcgaa ggtcgtgttg acaagctgat ggacatcttc tccttcatcg    4560
aaaccaagtt cgctgacaag acaaattcg aagttaccga atgggctgcc cagtacggca    4620
ttccttgcgg tccggtcatg tccatgaaag aactggctca cgatccttcc ctgcagaaag    4680
ttggtaccgt cgttgaagtt gtcgacgaaa ttcgtggtaa ccacctgacc gttggcgcac    4740
cgttcaaatt ctccggattc cagccggaaa ttacccgtgc tccgctgttg ggcgaacata    4800
ccgacgaagt tctgaaagaa ctgggtcttg acgatgccaa gatcaaggaa ctgcatgcaa    4860
```
aacaggtagt ttga                                                       4874

<210> SEQ ID NO 41
<211> LENGTH: 213
<212> TYPE: DNA
<213> ORGANISM: Artificial Sequence
<220> FEATURE:
<223> OTHER INFORMATION: Synthetic: FNR promoter with RBS and leader
      region

<400> SEQUENCE: 41
ggtaccagtt gttcttattg gtggtgttgc tttatggttg catcgtagta aatggttgta     60
acaaaagcaa ttttccggc tgtctgtata caaaaacgcc gtaaagtttg agcgaagtca    120
ataaactctc tacccattca gggcaatatc tctcttggat ccaaagtgaa ctctagaaat    180
aattttgttt aactttaaga aggagatata cat                                 213

<210> SEQ ID NO 42
<211> LENGTH: 1470
<212> TYPE: DNA
<213> ORGANISM: Artificial Sequence
<220> FEATURE:
<223> OTHER INFORMATION: Synthetic: Construct comprising FNR promoter,
      driving OxlT (oxalate:formate antiporter from O. formigenes)

<400> SEQUENCE: 42
ggtaccagtt gttcttattg gtggtgttgc tttatggttg catcgtagta aatggttgta     60
acaaaagcaa ttttccggc tgtctgtata caaaaacgcc gtaaagtttg agcgaagtca    120
ataaactctc tacccattca gggcaatatc tctcttggat ccaaagtgaa ctctagaaat    180
aattttgttt aactttaaga aggagatata catatgaata atccacaaac aggacaatca    240
acaggcctct tgggcaatcg ttggttctac ttggtattag cagttttgct gatgtgtatg    300
atctcgggtg tccaatattc ctggacactg tacgctaacc cggttaaaga caaccttggc    360
gtttctttgg ctgcggttca gacggctttc acactctctc aggtcattca agctggttct    420
cagcctggtg gtggttactt cgttgataaa ttcggtccaa gaattccatt gatgttcggt    480
ggtgcgatgt tctcgctgg ctggaccttc atgggtatgg ttgacagtgt tcctgctctg    540 tatgctctt atactctggc cggtgcaggt gttggtatcg tttacggtat cgcgatgaac    600
acggctaaca gatggttccc ggacaaaacgc ggtctggctt ccggtttcac cgctgccggt    660
tacggtctgg gtgttctgcc gttcctgcca ctgatcagct ccgttctgaa agttgaaggt    720
gttggcgcag cattcatgta caccggtttg atcatgggta tcctgattat cctgatcgct    780
ttcgttatcc gtttccctgg ccagcaaggc gccaaaaaac aaatcgttgt taccgacaag    840
gatttcaatt ctggcgaaat gctgagaaca ccacaattct gggttctgtg gaccgcattc    900
ttttccgtta actttggtgg tttgctgctg gttgccaaca gcgtccctta cggtcgcagc    960
ctcggtcttg ccgcaggtgt gctgacgatc ggtgttttcga tccagaacct gttcaatggt   1020
ggttgccgtc ctttctgggg tttcgtttcc gataaaatcg gccgttacaa accatgtcc   1080 gtcgttttcg gtatcaatgc tgttgttctc gcactttttcc cgacgattgc tgccttgggc   1140
gatgtagcct ttatcgccat gttggcaatc gcattcttca catggggtgg tagctacgct   1200
ctgttcccat cgaccaacag cgatattttc ggtacggcat actctgccag aaactatggt   1260
ttcttctggg ctgcaaaagc aactgcctcg atcttcggtg gtggtctggg tgctgcaatt   1320
gcaaccaact tcggatggaa taccgctttc ctgattactg cgattacttc tttcatcgca   1380
tttgctctgg ctaccttcgt tattccaaga atgggccgtc cagtcaagaa aatggtcaaa   1440
ttgtctccag aagaaaaagc tgtacattaa                                     1470

<210> SEQ ID NO 43
<211> LENGTH: 3225
<212> TYPE: DNA
<213> ORGANISM: Artificial Sequence
<220> FEATURE:
<223> OTHER INFORMATION: Synthetic: Construct comprising FNR promoter,
      driving a oxalate catabolism cassette comprising oxc-frc.

<400> SEQUENCE: 43
ggtaccagtt gttcttattg gtggtgttgc tttatggttg catcgtagta aatggttgta      60
acaaaagcaa ttttccggc tgtctgtata caaaaacgcc gtaaagtttg agcgaagtca     120
ataaactctc tacccattca gggcaatatc tctcttggat ccaaagtgaa ctctagaaat    180
aattttgttt aactttaaga aggagatata catatgagta cgacgacaa tgtagagttg    240 actgatggct ttcatgtttt gatcgatgcc ctgaaaatga atgacatcga taccatgtat    300
ggtgttgtcg gcattcctat cacgaacctg gctcgtatgt ggcaagatga cggtcagcgt    360
ttttacagct ccgtcacga acaacacgca ggttatgcag cttctatcgc cggttacatc     420
gaaggaaaac ctggcgtttg cttgaccgtt ccgccctg gcttcctgaa cggcgtgact      480
tccctggctc atgcaaccac caactgcttc ccaatgatcc tgttgagcgg ttccagtgaa    540
cgtgaaatcg tcgatttgca cagggcgat tacgaagaaa tggatcagat gaatgttgca     600
cgtccacact gcaaagcttc tttccgtatc aacagcatca agacattcc aatcggtatc     660 gctcgtgcag ttcgcaccgc tgtatccgga cgtccaggtg tgtttacgt tgacttgcca     720 gcaaaactgt tcggtcagac catttctgta gaagaagcta acaaactgct cttcaaacca    780
atcgatccac tccggcaca gattcctgct gaagacgcta tcgctcgcgc tgctgacctg    840
atcaagaacg ccaaacgtcc agttatcatg ctgggtaaag gcgctgcata cgcacaatgc    900
gacgacgaaa tccgcgcact ggttgaagaa accggcatcc cattcctgcc aatgggtatg    960
gctaaaggcc tgctgcctga caaccatcca caatccgctg ctgcaacccg tgctttcgca   1020
ctggcacagt gtgacgtttg cgtactgatc ggcgctcgtc tgaactggct gatgcagcac   1080
ggtaaaggca aacctgggg cgacgaactg aagaaatacg ttcagatcga catccaggct    1140
aacgaaatgg acagcaacca gcctatcgct gcaccagttg ttggtgacat caagtccgcc   1200
gtttccctgc tccgcaaagc actgaaaggc gctccaaaag ctgacgctga atggaccggc   1260
gctctgaaag ccaaagttga cggcaacaaa gccaaactgg ctggcaagat gactgccgaa   1320 acccatccg gaatgatgaa ctactccaat tccctgggcg ttgttcgtga cttcatgctg    1380
gcaaatccgg atatttccct ggttaacgaa ggcgctaatg cactcgacaa cactcgtatg   1440
attgttgaca tgctgaaacc acgcaaacgt cttgactccg gtacctgggg tgttatgggt    1500
attggtatgg gctactgcgt tgctgcagct gctgttaccg gcaaaccggt tatcgctgtt   1560
gaaggcgata gcgcattcgg tttctccggt atggaactgg aaaccatctg ccgttacaac   1620
ctgccagtta ccgttatcat catgaacaat ggtggtatct ataaaggtaa cgaagcagat   1680
ccacaaccag gcgttatctc ctgtacccgt ctgacccgtg tcgttacga catgatgatg    1740 gaagcatttg gcggtaaagg ttatgttgcc aatactccag cagaactgaa agctgctctg   1800
gaagaagctg ttgcttccgg caaaccatgc ctgatcaacg cgatgatcga tccagacgct   1860
ggtgtcgaat ctgccgtat caagagcctg aacgttgtaa gtaaagttgg caagaaataa    1920
taagaaggag atatacatat gactaaacca ttagatggaa ttaatgtgct tgactttacc   1980

```
cacgtccagg caggtcctgc ctgtacacag atgatgggtt tcttgggcgc aaacgtcatc    2040
aagattgaaa gacgtggttc cggagatatg actcgtggat ggctgcagga caaaccaaat    2100
gttgattccc tgtatttcac gatgttcaac tgtaacaaac gttcgattga actggacatg    2160 aaaacccgg aaggcaaaga gcttctggaa cagatgatca agaaagccga cgtcatggtc     2220
gaaaacttcg gaccaggcgc actggaccgt atgggctta cttgggaata cattcaggaa     2280
ctgaatccac gcgtcattct ggcttccgtt aaaggctatg cagaaggcca cgccaacgaa    2340
cacctgaaag tttatgaaaa cgttgcacag tgttccggcg gtgctgcagc taccaccggt    2400
ttctgggatg tcctccaac cgtttccggc gctgctctgg gtgactccaa ctccggtatg     2460
cacctgatga tcggtattct ggccgctctg gaaatgcgtc acaaaaccgg ccgtggtcag    2520
aaagttgccg tcgctatgca ggacgctgtt ctgaatctgg ttcgtatcaa actgcgtgac    2580
cagcaacgtc tggaaagaac cggcattctg gctgaatacc cacaggctca gcctaacttt    2640
gccttcgaca gagacggtaa cccactgtcc ttcgacaaca tcacttccgt tccacgtggt    2700
ggtaacgcag gtggcggcgg ccagccaggc tggatgctga atgtaaagg ttgggaaacc     2760 gatgcggact cctacgttta cttcaccatc gctgcaaaca tgtggccaca gatctgcgac    2820
atgatcgaca agccagaatg gaaagacgac ccagcctaca acacattcga aggtcgtgtt    2880
gacaagctga tggacatctt ctccttcatc gaaaccaagt cgctgacaa ggacaaattc     2940 gaagttaccg aatgggctgc ccagtacggc attccttgcg gtccggtcat gtccatgaaa    3000
gaactggctc acgatccttc cctgcagaaa gttggtaccg tcgttgaagt tgtcgacgaa    3060
attcgtggta ccacctgac cgttggcgca ccgttcaaat tctccggatt ccagccggaa     3120
attacccgtg ctccgctgtt gggcgaacat accgacgaag ttctgaaaga actgggtctt    3180
gacgatgcca agatcaagga actgcatgca aaacaggtag tttga                    3225
```

<210> SEQ ID NO 44
<211> LENGTH: 3055
<212> TYPE: DNA
<213> ORGANISM: Artificial Sequence
<220> FEATURE:
<223> OTHER INFORMATION: Synthetic: Construct comprising oxalate
   catabolism cassette comprising oxc-frc with RBS and leader region

<400> SEQUENCE: 44

```
ctctagaaat aattttgttt aactttaaga aggagatata catatgagta acgacgacaa     60
tgtagagttg actgatggct ttcatgtttt gatcgatgcc ctgaaaatga atgacatcga    120
taccatgtat ggtgttgtcg gcattccat cacgaacctg gctcgtatgt ggcaagatga    180
cggtcagcgt ttttacagct tccgtcacga acaacacgca ggttatgcag cttctatcgc    240
cggttacatc gaaggaaaac ctggcgtttg cttgaccgtt tccgcccctg gcttcctgaa    300
cggcgtgact ccctggctc atgcaaccac caactgcttc ccaatgatcc tgttgagcgg    360
ttccagtgaa cgtgaaatcg tcgatttgca acagggcgat tacgaagaaa tggatcagat    420
gaatgttgca cgtccacact gcaaagcttc tttccgtatc aacagcatca agacattcc     480 aatcggtatc gctcgtgcag ttcgcaccgc tgtatccgga cgtccaggtg tgtttacgt     540 tgacttgcca gcaaaactgt tcggtcagac catttctgta gaagaagcta acaaactgct    600
cttcaaacca atcgatccag ctccggcaca gattcctgct gaagacgcta tcgctcgcgc    660
tgctgaccta atcaagaacg ccaaacgtcc agttatcatg ctgggtaaag cgctgcata    720 cgcacaatgc gacgacgaaa tccgcgcact ggttgaagaa accggcatcc cattcctgcc    780
```

```
aatgggtatg gctaaaggcc tgctgcctga caaccatcca caatccgctg ctgcaacccg      840
tgctttcgca ctggcacagt gtgacgtttg cgtactgatc ggcgctcgtc tgaactggct      900
gatgcagcac ggtaaaggca aaacctgggg cgacgaactg aagaaatacg ttcagatcga      960
catccaggct aacgaaatgg acagcaacca gcctatcgct gcaccagttg ttggtgacat     1020
caagtccgcc gtttccctgc tccgcaaagc actgaaaggc gctccaaaag ctgacgctga     1080
atggaccggc gctctgaaag ccaaagttga cggcaacaaa gccaaactgg ctggcaagat     1140
gactgccgaa accccatccg gaatgatgaa ctactccaat tccctgggcg ttgttcgtga     1200
cttcatgctg gcaaatccgg atatttccct ggttaacgaa ggcgctaatg cactcgacaa     1260
cactcgtatg attgttgaca tgctgaaacc acgcaaacgt cttgactccg gtacctgggg     1320
tgttatgggt attggtatgg ctactgcgt tgctgcagct gctgttaccg gcaaaccggt      1380
tatcgctgtt gaaggcgata gcgcattcgg tttctccggt atggaactgg aaaccatctg     1440
ccgttacaac ctgccagtta ccgttatcat catgaacaat ggtggtatct ataaaggtaa     1500
cgaagcagat ccacaaccag gcgttatctc ctgtacccgt ctgacccgtg gtcgttacga     1560
catgatgatg aagcatttg gcggtaaagg ttatgttgcc aatactccag cagaactgaa      1620
agctgctctg aagaagctg ttgcttccgg caaaccatgc ctgatcaacg cgatgatcga      1680
tccagacgct ggtgtcgaat ctggccgtat caagagcctg aacgttgtaa gtaaagttgg     1740
caagaaataa taagaaggag atatacatat gactaaacca ttagatggaa ttaatgtgct     1800
tgactttacc cacgtccagg caggtcctgc ctgtacacag atgatgggtt tcttgggcgc     1860
aaacgtcatc aagattgaaa gacgtggttc cggagatatg actcgtggat ggctgcagga     1920
caaaccaaat gttgattccc tgtatttcac gatgttcaac tgtaacaaac gttcgattga     1980
actggacatg aaaaccccgg aaggcaaaga gcttctggaa cagatgatca agaaagccga     2040
cgtcatggtc gaaaacttcg gaccaggcgc actggaccgt atgggcttta cttgggaata     2100
cattcaggaa ctgaatccac gcgtcattct ggcttccgtt aaaggctatg cagaaggcca     2160
cgccaacgaa cacctgaaag tttatgaaaa cgttgcacag tgttccggcg gtgctgcagc     2220
taccaccggt ttctgggatg gtcctccaac cgtttccggc gctgctctgg gtgactccaa     2280
ctccggtatg cacctgatga tcggtattct ggccgctctg gaaatgcgtc acaaaaccgg     2340
ccgtggtcag aaagttgccg tcgctatgca ggacgctgtt ctgaatctgg ttcgtatcaa     2400
actgcgtgac cagcaacgtc tggaaagaac cggcattctg gctgaatacc cacaggctca     2460
gcctaacttt gccttcgaca gagacggtaa cccactgtcc ttcgacaaca tcacttccgt     2520
tccacgtggt ggtaacgcag gtggcggcgg ccagccaggc tggatgctga atgtaaagg      2580
ttgggaaacc gatgcggact cctacgtta cttcaccatc gctgcaaaca tgtggccaca      2640
gatctgcgac atgatcgaca agccagaatg gaaagacgac ccagcctaca acacattcga     2700
aggtcgtgtt gacaagctga tggacatctt ctccttcatc gaaaccaagt cgctgacaa      2760
ggacaaattc gaagttaccg aatgggctgc ccagtacggc attccttgcg gtccggtcat     2820
gtccatgaaa gaactggctc acgatccttc cctgcagaaa gttggtaccg tcgttgaagt     2880
tgtcgacgaa attcgtggta accacctgac cgttggcgca ccgttcaaat ctccggatt      2940
ccagccggaa attacccgtg ctccgctgtt gggcgaacat accgacgaag ttctgaaaga     3000
actgggtctt gacgatgcca agatcaagga actgcatgca aaacaggtag tttga          3055
```

<210> SEQ ID NO 45

<211> LENGTH: 4388
<212> TYPE: DNA
<213> ORGANISM: Artificial Sequence
<220> FEATURE:
<223> OTHER INFORMATION: Synthetic: Construct comprising FNR promoter,
      driving a oxalate catabolism cassette comprising yfdE-oxc-frc.

<400> SEQUENCE: 45

| | | | | | |
|---|---|---|---|---|---|
| ggtaccagtt | gttcttattg | gtggtgttgc | tttatggttg | catcgtagta | aatggttgta | 60 |
| acaaaagcaa | tttttccggc | tgtctgtata | caaaaacgcc | gtaaagtttg | agcgaagtca | 120 |
| ataaactctc | tacccattca | gggcaatatc | tctcttggat | ccaaagtgaa | ctctagaaat | 180 |
| aattttgttt | aactttaaga | aggagatata | catatgacaa | ataatgaaag | caaagggccg | 240 |
| tttgaaggct | tattagttat | cgatatgaca | catgtcctta | atggaccttt | cggaactcaa | 300 |
| cttctttgta | atatgggcgc | aagggtaatt | aaagttgagc | cgccgggtca | tggtgatgat | 360 |
| acccgcacat | ttggtcccta | tgtggatgga | cagtcactct | attacagttt | tattaatcat | 420 |
| ggcaaagaga | gtgtggttct | tgatttaaag | aatgatcacg | ataaaagtat | atttataaat | 480 |
| atgctcaaac | aagctgatgt | attagctgag | aattttcgcc | caggtacaat | ggaaaaactg | 540 |
| gggttttcat | gggaaacgct | tcaagaaatc | aacccgcgcc | tcatatatgc | ttcatcgtca | 600 |
| ggtttcggac | ataccggtcc | gctaaaagat | gctcctgcct | acgataccat | cattcaggca | 660 |
| atgagcggga | taatgatgga | aacaggatat | cctgatgctc | cgccagtgcg | cgttggtaca | 720 |
| tctcttgcgg | atctatgcgg | cggtgtctat | ttattcagcg | gaatagtgag | tgcactttat | 780 |
| ggccgcgaaa | agagccagag | aggggcgcat | gtcgatatag | cgatgtttga | tgccacgctg | 840 |
| agttttctgg | agcatggtct | gatggcatat | atcgcaactg | ggaagtcacc | acaacgtctg | 900 |
| ggaaatcgcc | atccctacat | ggcacctttt | gatgttttca | atactcagga | taagccgatt | 960 |
| acgatttgtt | gtggtaatga | caagcttttt | tctgcgttat | gccaggcact | ggagcttacg | 1020 |
| gaactggtta | tgatccccg | atttagcagc | aatattttac | gcgtacaaaa | ccaggctatt | 1080 |
| cttaaacaat | atattgagcg | gacgttaaaa | acgcaggcag | ctgaagtttg | gttagccaga | 1140 |
| atacatgaag | ttggtgtacc | cgtcgcgccg | ttattaagtg | tggctgaggc | cattaaattg | 1200 |
| ccacaaactc | aggcgagaaa | tatgttgatt | gaagccgggg | gaataatgat | gccgggtaat | 1260 |
| ccgataaaaa | tcagcggctg | cgcggacccg | catgttatgc | cgggagcggc | aacgctcgac | 1320 |
| cagcatgggg | aacaaattcg | ccaggagttc | tcatcataaa | agaaggagat | atacatatga | 1380 |
| gtaacgacga | caatgtagag | ttgactgatg | gctttcatgt | tttgatcgat | gccctgaaaa | 1440 |
| tgaatgacat | cgataccatg | tatggtgttg | tcggcattcc | tatcacgaac | ctggctcgta | 1500 |
| tgtggcaaga | tgacggtcag | cgttttttaca | gcttccgtca | cgaacaacac | gcaggttatg | 1560 |
| cagcttctat | cgccggttac | atcgaaggaa | aacctggcgt | tgcttgacc | gtttccgccc | 1620 |
| ctggcttcct | gaacggcgtg | acttccctgg | ctcatgcaac | caccaactgc | ttcccaatga | 1680 |
| tcctgttgag | cggttccagt | gaacgtgaaa | tcgtcgattt | gcaacagggc | gattacgaag | 1740 |
| aaatggatca | gatgaatgtt | gcacgtccac | actgcaaagc | ttctttccgt | atcaacagca | 1800 |
| tcaaagacat | tccaatcggt | atcgctcgtg | cagttcgcac | cgctgtatcc | ggacgtccag | 1860 |
| gtggtgttta | cgttgacttg | ccagcaaaac | tgttcggtca | gaccatttct | gtagaagaag | 1920 |
| ctaacaaact | gctcttcaaa | ccaatcgatc | cagctccggc | acagattcct | gctgaagacg | 1980 |
| ctatcgctcg | cgctgctgac | ctgatcaaga | acgccaaacg | tccagttatc | atgctgggta | 2040 |
| aaggcgctgc | atacgcacaa | tgcgacgacg | aaatccgcgc | actggttgaa | gaaaccggca | 2100 |

```
tcccattcct gccaatgggt atggctaaag gcctgctgcc tgacaaccat ccacaatccg    2160
ctgctgcaac ccgtgctttc gcactggcac agtgtgacgt ttgcgtactg atcggcgctc    2220
gtctgaactg gctgatgcag cacggtaaag gcaaaacctg gggcgacgaa ctgaagaaat    2280
acgttcagat cgacatccag gctaacgaaa tggacagcaa ccagcctatc gctgcaccag    2340
ttgttggtga catcaagtcc gccgtttccc tgctccgcaa agcactgaaa ggcgctccaa    2400
aagctgacgc tgaatggacc ggcgctctga agccaaagt tgacggcaac aaagccaaac    2460
tggctggcaa gatgactgcc gaaaccccat ccggaatgat gaactactcc aattccctgg    2520
gcgttgttcg tgacttcatg ctggcaaatc cggatatttc cctggttaac gaaggcgcta    2580
atgcactcga caacactcgt atgattgttg acatgctgaa accacgcaaa cgtcttgact    2640
ccggtacctg gggtgttatg ggtattggta tgggctactg cgttgctgca gctgctgtta    2700
ccggcaaacc ggttatcgct gttgaaggcg atagcgcatt cggtttctcc ggtatggaac    2760
tggaaaccat ctgccgttac aacctgccag ttaccgttat catcatgaac aatggtggta    2820
tctataaagg taacgaagca gatccacaac caggcgttat ctcctgtacc cgtctgaccc    2880
gtggtcgtta cgacatgatg atggaagcat ttggcggtaa aggttatgtt gccaatactc    2940
cagcagaact gaaagctgct ctggaagaag ctgttgcttc cggcaaacca tgcctgatca    3000
acgcgatgat cgatccagac gctggtgtcg aatctggccg tatcaagagc ctgaacgttg    3060
taagtaaagt tggcaagaaa taataagaag gagatataca tatgactaaa ccattagatg    3120
gaattaatgt gcttgacttt acccacgtcc aggcaggtcc tgcctgtaca cagatgatgg    3180
gtttcttggg cgcaaacgtc atcaagattg aaagacgtgg ttccggagat atgactcgtg    3240
gatggctgca ggacaaacca aatgttgatt ccctgtattt cacgatgttc aactgtaaca    3300
aacgttcgat tgaactggac atgaaaaccc cggaaggcaa agagcttctg gaacagatga    3360
tcaagaaagc cgacgtcatg gtcgaaaact tcggaccagg cgcactggac cgtatgggct    3420
ttacttggga atacattcag gaactgaatc cacgcgtcat tctggcttcc gttaaaggct    3480
atgcagaagg ccacgccaac gaacacctga agtttatga aaacgttgca cagtgttccg    3540
gcggtgctgc agctaccacc ggtttctggg atggtcctcc aaccgtttcc ggcgctgctc    3600
tgggtgactc caactccggt atgcacctga tgatcggtat tctggccgct ctggaaatgc    3660
gtcacaaaac cggccgtggt cagaaagttg ccgtcgctat gcaggacgct gttctgaatc    3720
tggttcgtat caaactgcgt gaccagcaac gtctggaaag aaccggcatt ctggctgaat    3780
acccacaggc tcagcctaac tttgccttcg acagagacgg taacccactg tccttcgaca    3840
acatcacttc cgttccacgt ggtggtaacg caggtggcgg cggccagcca ggctggatgc    3900
tgaaatgtaa aggttgggaa accgatgcgg actcctacgt ttacttcacc atcgctgcaa    3960
acatgtggcc acagatctgc gacatgatcg acaagccaga atggaaagac gacccagcct    4020
acaacacatt cgaaggtcgt gttgacaagc tgatggacat cttctccttc atcgaaacca    4080
agttcgctga caaggacaaa ttcgaagtta ccgaatgggc tgcccagtac ggcattcctt    4140
gcggtccggt catgtccatg aaagaactgg ctcacgatcc ttccctgcag aaagttggta    4200
ccgtcgttga agttgtcgac gaaattcgtg taaccacct gaccgttggc gcaccgttca    4260
aattctccgg attccagccg gaaattaccc gtgctccgct gttgggcgaa cataccgacg    4320
aagttctgaa agaactgggt cttgacgatg ccaagatcaa ggaactgcat gcaaaacagg    4380
tagtttga                                                            4388
```

<210> SEQ ID NO 46
<211> LENGTH: 4388
<212> TYPE: DNA
<213> ORGANISM: Artificial Sequence
<220> FEATURE:
<223> OTHER INFORMATION: Synthetic: Construct comprising oxalate
catabolism cassette comprising yfdE-oxc-frc with RBS and leader
region

<400> SEQUENCE: 46

| | | | | |
|---|---|---|---|---|
| ggtaccagtt | gttcttattg | gtggtgttgc | tttatggttg | catcgtagta aatggttgta | 60 |
| acaaaagcaa | ttttccggc | tgtctgtata | caaaaacgcc | gtaaagtttg agcgaagtca | 120 |
| ataaactctc | tacccattca | ggcaatatc | tctcttggat | ccaaagtgaa ctctagaaat | 180 |
| aattttgttt | aactttaaga | aggagatata | catatgacaa | ataatgaaag caaagggccg | 240 |
| tttgaaggct | tattagttat | cgatatgaca | catgtcctta | atggacctttt cggaactcaa | 300 |
| cttctttgta | atatgggcgc | aagggtaatt | aaagttgagc | cgccgggtca tggtgatgat | 360 |
| acccgcacat | ttggtcccta | tgtggatgga | cagtcactct | attacagttt tattaatcat | 420 |
| ggcaaagaga | gtgtggttct | tgatttaaag | aatgatcacg | ataaaagtat atttataaat | 480 |
| atgctcaaac | aagctgatgt | attagctgag | aattttcgcc | caggtacaat ggaaaaactg | 540 |
| gggttttcat | gggaaacgct | tcaagaaatc | aacccgcgcc | tcatatatgc ttcatcgtca | 600 |
| ggtttcggac | ataccggtcc | gctaaaagat | gctcctgcct | acgataccat cattcaggca | 660 |
| atgagcggga | taatgatgga | aacaggatat | cctgatgctc | cgccagtgcg cgttggtaca | 720 |
| tctcttgcgg | atctatgcgg | cggtgtctat | ttattcagcg | gaatagtgag tgcactttat | 780 |
| ggccgcgaaa | agagccagag | aggggcgcat | gtcgatatag | cgatgtttga tgccacgctg | 840 |
| agttttctgg | agcatggtct | gatggcatat | atcgcaactg | gaagtcacc acaacgtctg | 900 |
| ggaaatcgcc | atccctacat | ggcacctttt | gatgttttca | atactcagga taagccgatt | 960 |
| acgatttgtt | gtggtaatga | caagcttttt | tctgcgttat | gccaggcact ggagcttacg | 1020 |
| gaactggtta | atgatccccg | atttagcagc | aatattttac | gcgtacaaaa ccaggctatt | 1080 |
| cttaaacaat | atattgagcg | gacgttaaaa | acgcaggcag | ctgaagtttg gttagccaga | 1140 |
| atacatgaag | ttggtgtacc | cgtcgcgccg | ttattaagtg | tggctgaggc cattaaattg | 1200 |
| ccacaaactc | aggcgagaaa | tatgttgatt | gaagccgggg | gaataatgat gccgggtaat | 1260 |
| ccgataaaaa | tcagcggctg | cgcggacccg | catgttatgc | cggagcggc aacgctcgac | 1320 |
| cagcatgggg | aacaaattcg | ccaggagttc | tcatcataaa | agaaggagat atacatatga | 1380 |
| gtaacgacga | caatgtagag | ttgactgatg | gctttcatgt | tttgatcgat gccctgaaaa | 1440 |
| tgaatgacat | cgataccatg | tatggtgttg | tcggcattcc | tatcacgaac ctggctcgta | 1500 |
| tgtggcaaga | tgacggtcag | cgtttttaca | gcttccgtca | cgaacaacac gcaggttatg | 1560 |
| cagcttctat | cgccggttac | atcgaaggaa | aacctggcgt | ttgcttgacc gtttccgccc | 1620 |
| ctggcttcct | gaacgcgtg | acttccctgg | ctcatgcaac | caccaactgc ttcccaatga | 1680 |
| tcctgttgag | cggttccagt | gaacgtgaaa | tcgtcgattt | gcaacagggc gattacgaag | 1740 |
| aaatggatca | gatgaatgtt | gcacgtccac | actgcaaagc | ttctttccgt atcaacagca | 1800 |
| tcaaagacat | tccaatcggt | atcgctcgtg | cagttcgcac | cgctgtatcc ggacgtccag | 1860 |
| gtggtgttta | cgttgacttg | ccagcaaaaac | tgttcggtca | gaccattctc gtagaagaag | 1920 |
| ctaacaaact | gctcttcaaa | ccaatcgatc | cagctccggc | acagattcct gctgaagacg | 1980 |
| ctatcgctcg | cgctgctgac | ctgatcaaga | acgccaaacg | tccagttatc atgctgggta | 2040 |

```
aaggcgctgc atacgcacaa tgcgacgacg aaatccgcgc actggttgaa gaaaccggca    2100
tcccattcct gccaatgggt atggctaaag gcctgctgcc tgacaaccat ccacaatccg    2160
ctgctgcaac ccgtgctttc gcactggcac agtgtgacgt ttgcgtactg atcggcgctc    2220
gtctgaactg gctgatgcag cacggtaaag gcaaaacctg gggcgacgaa ctgaagaaat    2280
acgttcagat cgacatccag gctaacgaaa tggacagcaa ccagcctatc gctgcaccag    2340
ttgttggtga catcaagtcc gccgtttccc tgctccgcaa agcactgaaa ggcgctccaa    2400
aagctgacgc tgaatggacc ggcgctctga agccaaagt tgacggcaac aaagccaaac    2460
tggctggcaa gatgactgcc gaaaccccat ccggaatgat gaactactcc aattccctgg    2520
gcgttgttcg tgacttcatg ctggcaaatc cggatatttc cctggttaac gaaggcgcta    2580
atgcactcga caacactcgt atgattgttg acatgctgaa accacgcaaa cgtcttgact    2640
ccggtacctg gggtgttatg ggtattggta tgggctactg cgttgctgca gctgctgtta    2700
ccggcaaacc ggttatcgct gttgaaggcg atagcgcatt cggtttctcc ggtatggaac    2760
tggaaaccat ctgccgttac aacctgccag ttaccgttat catcatgaac aatggtggta    2820
tctataaagg taacgaagca gatccacaac caggcgttat ctcctgtacc cgtctgaccc    2880
gtggtcgtta cgacatgatg atggaagcat ttggcggtaa aggttatgtt gccaatactc    2940
cagcagaact gaaagctgct ctggaagaag ctgttgcttc cggcaaacca tgcctgatca    3000
acgcgatgat cgatccagac gctggtgtcg aatctggccg tatcaagagc ctgaacgttg    3060
taagtaaagt tggcaagaaa taataagaag gagatataca tatgactaaa ccattagatg    3120
gaattaatgt gcttgacttt acccacgtcc aggcaggtcc tgcctgtaca cagatgatgg    3180
gtttcttggg cgcaaacgtc atcaagattg aaagacgtgg ttccggagat atgactcgtg    3240
gatggctgca ggacaaacca aatgttgatt ccctgtattt cacgatgttc aactgtaaca    3300
aacgttcgat tgaactggac atgaaaaccc cggaaggcaa agagcttctg gaacagatga    3360
tcaagaaagc cgacgtcatg gtcgaaaact tcggaccagg cgcactggac cgtatgggct    3420
ttacttggga atacattcag gaactgaatc cacgcgtcat tctggcttcc gttaaaggct    3480
atgcagaagg ccacgccaac gaacacctga agtttatga aaacgttgca cagtgttccg    3540
gcggtgctgc agctaccacc ggtttctggg atggtcctcc aaccgtttcc ggcgctgctc    3600
tgggtgactc caactccggt atgcacctga tgatcggtat tctggccgct ctggaaatgc    3660
gtcacaaaac cggccgtggt cagaaagttg ccgtcgctat gcaggacgct gttctgaatc    3720
tggttcgtat caaactgcgt gaccagcaac gtctggaaag aaccggcatt ctggctgaat    3780
acccacaggc tcagcctaac tttgccttcg acagagacgg taacccactg tccttcgaca    3840
acatcacttc cgttccacgt ggtggtaacg caggtggcgg cggccagcca ggctggatgc    3900
tgaaatgtaa aggttgggaa accgatgcgg actcctacgt ttacttcacc atcgctgcaa    3960
acatgtggcc acagatctgc gacatgatcg acaagccaga atggaaagac gacccagcct    4020
acaacacatt cgaaggtcgt gttgacaagc tgatggacat cttctccttc atcgaaacca    4080
agttcgctga caaggacaaa ttcgaagtta ccgaatgggc tgcccagtac ggcattcctt    4140
gcggtccggt catgtccatg aaagaactgg ctcacgatcc ttccctgcag aaagttggta    4200
ccgtcgttga agttgtcgac gaaattcgtg gtaaccacct gaccgttggc gcaccgttca    4260
aattctccgg attccagccg gaaattaccc gtgctccgct gttgggcgaa cataccgacg    4320
aagttctgaa agaactgggt cttgacgatg ccaagatcaa ggaactgcat gcaaaacagg    4380
tagtttga                                                             4388
```

<210> SEQ ID NO 47
<211> LENGTH: 60
<212> TYPE: DNA
<213> ORGANISM: Artificial Sequence
<220> FEATURE:
<223> OTHER INFORMATION: Synthetic: primer SR36

<400> SEQUENCE: 47
tagaactgat gcaaaaagtg ctcgacgaag gcacacagat gtgtaggctg gagctgcttc    60

<210> SEQ ID NO 48
<211> LENGTH: 60
<212> TYPE: DNA
<213> ORGANISM: Artificial Sequence
<220> FEATURE:
<223> OTHER INFORMATION: Synthetic: primer SR38

<400> SEQUENCE: 48
gtttcgtaat tagatagcca ccggcgcttt aatgcccgga catatgaata tcctccttag    60

<210> SEQ ID NO 49
<211> LENGTH: 52
<212> TYPE: DNA
<213> ORGANISM: Artificial Sequence
<220> FEATURE:
<223> OTHER INFORMATION: Synthetic: primer SR33

<400> SEQUENCE: 49
caacacgttt cctgaggaac catgaaacag tatttagaac tgatgcaaaa ag    52

<210> SEQ ID NO 50
<211> LENGTH: 46
<212> TYPE: DNA
<213> ORGANISM: Artificial Sequence
<220> FEATURE:
<223> OTHER INFORMATION: Synthetic: primer SR34

<400> SEQUENCE: 50
cgcacactgg cgtcggctct ggcaggatgt ttcgtaatta gatagc    46

<210> SEQ ID NO 51
<211> LENGTH: 36
<212> TYPE: DNA
<213> ORGANISM: Artificial Sequence
<220> FEATURE:
<223> OTHER INFORMATION: Synthetic: primer SR43

<400> SEQUENCE: 51
atatcgtcgc agcccacagc aacacgtttc ctgagg    36

<210> SEQ ID NO 52
<211> LENGTH: 47
<212> TYPE: DNA
<213> ORGANISM: Artificial Sequence
<220> FEATURE:
<223> OTHER INFORMATION: Synthetic: primer SR44

<400> SEQUENCE: 52
aagaatttaa cggagggcaa aaaaaaccga cgcacactgg cgtcggc    47

<210> SEQ ID NO 53
<211> LENGTH: 3383
<212> TYPE: DNA
<213> ORGANISM: Artificial Sequence
<220> FEATURE:

<223> OTHER INFORMATION: Synthetic: Nucleotide sequences of Pfnr1-lacZ
construct, low-copy

<400> SEQUENCE: 53

| | | | | | |
|---|---|---|---|---|---|
| ggtaccgtca | gcataacacc | ctgacctctc | attaattgtt | catgccgggc | ggcactatcg | 60 |
| tcgtccggcc | ttttcctctc | ttactctgct | acgtacatct | atttctataa | atccgttcaa | 120 |
| tttgtctgtt | ttttgcacaa | acatgaaata | tcagacaatt | ccgtgactta | agaaaattta | 180 |
| tacaaatcag | caatataccc | cttaaggagt | atataaggt | gaatttgatt | tacatcaata | 240 |
| agcggggttg | ctgaatcgtt | aaggtaggcg | gtaatagaaa | agaaatcgag | gcaaaaatga | 300 |
| gcaaagtcag | actcgcaatt | atggatcctc | tggccgtcgt | attacaacgt | cgtgactggg | 360 |
| aaaaccctgg | cgttacccaa | cttaatcgcc | ttgcggcaca | tccccctttc | gccagctggc | 420 |
| gtaatagcga | agaggcccgc | accgatcgcc | cttcccaaca | gttgcgcagc | ctgaatggcg | 480 |
| aatggcgctt | tgcctggttt | ccggcaccag | aagcggtgcc | ggaaagctgg | ctggagtgcg | 540 |
| atcttcctga | cgccgatact | gtcgtcgtcc | cctcaaactg | gcagatgcac | ggttacgatg | 600 |
| cgcctatcta | caccaacgtg | acctatccca | ttacggtcaa | tccgccgttt | gttcccgcgg | 660 |
| agaatccgac | aggttgttac | tcgctcacat | ttaatattga | tgaaagctgg | ctacaggaag | 720 |
| gccagacgcg | aattatttt | gatggcgtta | actcggcgtt | tcatctgtgg | tgcaacgggc | 780 |
| gctgggtcgg | ttacggccag | gacagccgtt | tgccgtctga | atttgacctg | agcgcatttt | 840 |
| tacgcgccgg | agaaaaccgc | ctcgcggtga | tggtgctgcg | ctggagtgac | ggcagttatc | 900 |
| tggaagatca | ggatatgtgg | cggatgagcg | gcattttccg | tgacgtctcg | ttgctgcata | 960 |
| aaccgaccac | gcaaatcagc | gatttccaag | ttaccactct | ctttaatgat | gatttcagcc | 1020 |
| gcgcggtact | ggaggcagaa | gttcagatgt | acggcgagct | gcgcgatgaa | ctgcgggtga | 1080 |
| cggtttcttt | gtggcagggt | gaaacgcagg | tcgccagcgg | caccgcgcct | tcggcggtg | 1140 |
| aaattatcga | tgagcgtggc | ggttatgccg | atcgcgtcac | actacgcctg | aacgttgaaa | 1200 |
| atccggaact | gtggagcgcc | gaaatcccga | atctctatcg | tgcagtggtt | gaactgcaca | 1260 |
| ccgccgacgg | cacgctgatt | gaagcagaag | cctgcgacgt | cggtttccgc | gaggtgcgga | 1320 |
| ttgaaaatgg | tctgctgctg | ctgaacggca | agccgttgct | gattcgcggc | gttaaccgtc | 1380 |
| acgagcatca | tcctctgcat | ggtcaggtca | tggatgagca | gacgatggtg | caggatatcc | 1440 |
| tgctgatgaa | gcagaacaac | tttaacgccg | tgcgctgttc | gcattatccg | aaccatccgc | 1500 |
| tgtggtacac | gctgtgcgac | cgctacggcc | tgtatgtggt | ggatgaagcc | aatattgaaa | 1560 |
| cccacggcat | ggtgccaatg | aatcgtctga | ccgatgatcc | gcgctggcta | cccgcgatga | 1620 |
| gcgaacgcgt | aacgcggatg | gtgcagcgcg | atcgtaatca | cccgagtgtg | atcatctggt | 1680 |
| cgctggggaa | tgaatcaggc | cacggcgcta | atcacgacgc | gctgtatcgc | tggatcaaat | 1740 |
| ctgtcgatcc | ttcccgcccg | gtacagtatg | aaggcggcgg | agccgacacc | acggccaccg | 1800 |
| atattatttg | cccgatgtac | gcgcgcgtgg | atgaagacca | gcccttcccg | gcggtgccga | 1860 |
| aatggtccat | caaaaaatgg | ctttcgctgc | ctggagaaat | gcgcccgctg | atcctttgcg | 1920 |
| aatatgccca | cgcgatgggt | aacagtcttg | gcggcttcgc | taaatactgg | caggcgtttc | 1980 |
| gtcagtaccc | ccgtttacag | gcggcttcg | tctgggactg | ggtggatcag | tcgctgatta | 2040 |
| aatatgatga | aaacggcaac | ccgtggtcgg | cttacggcgg | tgattttggc | gatacgccga | 2100 |
| acgatcgcca | gttctgtatg | aacggtctgg | tctttgccga | ccgcacgccg | catccggcgc | 2160 |
| tgacggaagc | aaaacaccaa | cagcagtatt | tccagttccg | tttatccggg | cgaaccatcg | 2220 |

| | | | | |
|---|---|---|---|---|
| aagtgaccag | cgaatacctg | ttccgtcata | gcgataacga | gttcctgcac tggatggtgg | 2280 |
| cactggatgg | caagccgctg | gcaagcggtg | aagtgcctct | ggatgttggc ccgcaaggta | 2340 |
| agcagttgat | tgaactgcct | gaactgccgc | agccggagag | cgccggacaa ctctggctaa | 2400 |
| cggtacgcgt | agtgcaacca | aacgcgaccg | catggtcaga | agccggacac atcagcgcct | 2460 |
| ggcagcaatg | gcgtctggcg | gaaaacctca | gcgtgacact | cccctccgcg tcccacgcca | 2520 |
| tccctcaact | gaccaccagc | ggaacggatt | tttgcatcga | gctgggtaat aagcgttggc | 2580 |
| aatttaaccg | ccagtcaggc | tttctttcac | agatgtggat | tggcgatgaa aaacaactgc | 2640 |
| tgaccccgct | gcgcgatcag | ttcacccgtg | cgccgctgga | taacgacatt ggcgtaagtg | 2700 |
| aagcgacccg | cattgaccct | aacgcctggg | tcgaacgctg | gaaggcggcg ggccattacc | 2760 |
| aggccgaagc | ggcgttgttg | cagtgcacgg | cagatacact | tgccgacgcg gtgctgatta | 2820 |
| caaccgccca | cgcgtggcag | catcagggga | aaaccttatt | tatcagccgg aaaacctacc | 2880 |
| ggattgatgg | gcacggtgag | atggtcatca | atgtggatgt | tgcggtggca agcgatacac | 2940 |
| cgcatccggc | gcggattggc | ctgacctgcc | agctggcgca | ggtctcagag cgggtaaact | 3000 |
| ggctcggcct | ggggccgcaa | gaaaactatc | ccgaccgcct | tactgcagcc tgttttgacc | 3060 |
| gctgggatct | gccattgtca | gacatgtata | ccccgtacgt | cttcccgagc gaaaacggtc | 3120 |
| tgcgctgcgg | gacgcgcgaa | ttgaattatg | cccacacca | gtggcgcggc gacttccagt | 3180 |
| tcaacatcag | ccgctacagc | caacaacaac | tgatggaaac | cagccatcgc catctgctgc | 3240 |
| acgcggaaga | aggcacatgg | ctgaatatcg | acggtttcca | tatggggatt ggtggcgacg | 3300 |
| actcctggag | cccgtcagta | tcggcggaat | tccagctgag | cgccggtcgc taccattacc | 3360 |
| agttggtctg | gtgtcaaaaa | taa | | | 3383 |

<210> SEQ ID NO 54
<211> LENGTH: 3258
<212> TYPE: DNA
<213> ORGANISM: Artificial Sequence
<220> FEATURE:
<223> OTHER INFORMATION: Synthetic: Nucleotide sequences of Pfnr2-lacZ construct, low-copy

<400> SEQUENCE: 54

| | | | | |
|---|---|---|---|---|
| ggtacccatt | tcctctcatc | ccatccgggg | tgagagtctt | tccccccgac ttatggctca | 60 |
| tgcatgcatc | aaaaaagatg | tgagcttgat | caaaaacaaa | aatatttca ctcgacagga | 120 |
| gtatttatat | tgcgcccgtt | acgtgggctt | cgactgtaaa | tcagaaagga gaaaacacct | 180 |
| atgacgacct | acgatcggga | tcctctggcc | gtcgtattac | aacgtcgtga ctgggaaaac | 240 |
| cctggcgtta | cccaacttaa | tcgccttgcg | gcacatcccc | ctttcgccag ctggcgtaat | 300 |
| agcgaagagg | cccgcaccga | tcgcccttcc | caacagttgc | gcagcctgaa tggcgaatgg | 360 |
| cgctttgcct | ggtttccggc | accagaagcg | gtgccggaaa | gctggctgga gtgcgatctt | 420 |
| cctgacgccg | atactgtcgt | cgtccctca | aactggcaga | tgcacggtta cgatgcgcct | 480 |
| atctacacca | acgtgaccta | tcccattacg | gtcaatccgc | cgtttgttcc cgcggagaat | 540 |
| ccgacaggtt | gttactcgct | cacatttaat | attgatgaaa | gctggctaca ggaaggccag | 600 |
| acgcgaatta | ttttttgatgg | cgttaactcg | gcgtttcatc | tgtggtgcaa cgggcgctgg | 660 |
| gtcggttacg | gccaggacag | ccgtttgccg | tctgaatttg | acctgagcgc atttttacgc | 720 |
| gccggagaaa | accgcctcgc | ggtgatggtg | ctgcgctgga | gtgacggcag ttatctggaa | 780 |
| gatcaggata | tgtggcggat | gagcggcatt | ttccgtgacg | tctcgttgct gcataaaccg | 840 |

```
accacgcaaa tcagcgattt ccaagttacc actctcttta atgatgattt cagccgcgcg    900
gtactggagg cagaagttca gatgtacggc gagctgcgcg atgaactgcg ggtgacggtt    960
tctttgtggc agggtgaaac gcaggtcgcc agcggcaccg cgcctttcgg cggtgaaatt   1020
atcgatgagc gtggcggtta tgccgatcgc gtcacactac gcctgaacgt tgaaaatccg   1080
gaactgtgga gcgccgaaat cccgaatctc tatcgtgcag tggttgaact gcacaccgcc   1140
gacggcacgc tgattgaagc agaagcctgc gacgtcggtt ccgcgaggt gcggattgaa    1200 aatggtctgc tgctgctgaa cggcaagccg ttgctgattc gcggcgttaa ccgtcacgag   1260
catcatcctc tgcatggtca ggtcatggat gagcagacga tggtgcagga tatcctgctg   1320
atgaagcaga acaactttaa cgccgtgcgc tgttcgcatt atccgaacca tccgctgtgg   1380
tacacgctgt gcgaccgcta cggcctgtat gtggtggatg aagccaatat tgaaacccac   1440
ggcatggtgc caatgaatcg tctgaccgat gatccgcgct ggctaccgc gatgagcgaa    1500 cgcgtaacgc ggatggtgca gcgcgatcgt aatcacccga gtgtgatcat ctggtcgctg   1560
gggaatgaat caggccacgg cgctaatcac gacgcgctgt atcgctggat caaatctgtc   1620
gatccttccc gcccggtaca gtatgaaggc ggcggagccg acaccacggc caccgatatt   1680
atttgcccga tgtacgcgcg cgtggatgaa gaccagcccg tcccggcggt gccgaaatgg   1740
tccatcaaaa aatggctttc gctgcctgga gaaatgcgcc cgctgatcct ttgcgaatat   1800
gcccacgcga tgggtaacag tcttggcggc ttcgctaaat actggcaggc gtttcgtcag   1860
tacccccgtt tacagggcgg cttcgtctgg gactgggtgg atcagtcgct gattaaatat   1920
gatgaaaacg gcaacccgtg gtcggcttac ggcggtgatt ttggcgatac gccgaacgat   1980
cgccagttct gtatgaacgg tctggtcttt gccgaccgca cgccgcatcc ggcgctgacg   2040
gaagcaaaac accaacagca gtatttccag ttccgtttat ccgggcgaac catcgaagtg   2100
accagcgaat acctgttccg tcatagcgat aacgagttcc tgcactggat ggtggcactg   2160
gatggcaagc cgctggcaag cggtgaagtg cctctggatg ttggcccgca aggtaagcag   2220
ttgattgaac tgcctgaact gccgcagccg gagagcgccg gacaactctg gctaacggta   2280
cgcgtagtgc aaccaaacgc gaccgcatgg tcagaagccg gacacatcag cgcctggcag   2340
caatggcgtc tggcggaaaa cctcagcgtg acactcccct ccgcgtccca cgccatccct   2400
caactgacca ccagcggaac ggattttgc atcgagctgg gtaataagcg ttggcaattt   2460
aaccgccagt caggctttct ttcacagatg tggattggcg atgaaaaaca actgctgacc   2520
ccgctgcgcg atcagttcac ccgtgcgccg ctggataacg acattggcgt aagtgaagcg   2580
acccgcattg accctaacgc ctgggtcgaa cgctggaagg cggcgggcca ttaccaggcc   2640
gaagcggcgt tgttgcagtg cacggcagat acacttgccg acgcggtgct gattacaacc   2700
gcccacgcgt ggcagcatca ggggaaaacc ttatttatca gccggaaaac ctaccggatt   2760
gatgggcacg tgagatggt catcaatgtg gatgttgcgg tggcaagcga tacaccgcat   2820
ccggcgcgga ttggcctgac ctgccagctg gcgcaggtct cagagcgggt aaactggctc   2880
ggcctggggc cgcaagaaaa ctatcccgac cgccttactg cagcctgttt tgaccgctgg   2940
gatctgccat tgtcagacat gtatacccg tacgtcttcc cgagcgaaaa cggtctgcgc    3000
tgcgggacgc gcgaattgaa ttatggccca caccagtggc gcggcgactt ccagttcaac   3060
atcagccgct acagccaaca acaactgatg gaaaccagcc atcgccatct gctgcacgcg   3120
gaagaaggca catggctgaa tatcgacggt ttccatatgg ggattggtgg cgacgactcc   3180
tggagcccgt cagtatcggc ggaattccag ctgagcgccg gtcgctacca ttaccagttg   3240
```

| | |
|---|---|
| gtctggtgtc aaaaataa | 3258 |

<210> SEQ ID NO 55
<211> LENGTH: 3386
<212> TYPE: DNA
<213> ORGANISM: Artificial Sequence
<220> FEATURE:
<223> OTHER INFORMATION: Synthetic: Nucleotide sequences of Pfnr3-lacZ construct, low-copy

<400> SEQUENCE: 55

| | |
|---|---|
| ggtaccgtca gcataacacc ctgacctctc attaattgtt catgccgggc ggcactatcg | 60 |
| tcgtccggcc ttttcctctc ttactctgct acgtacatct atttctataa atccgttcaa | 120 |
| tttgtctgtt ttttgcacaa acatgaaata tcagacaatt ccgtgactta agaaaattta | 180 |
| tacaaatcag caatataccc cttaaggagt atataaaggt gaatttgatt tacatcaata | 240 |
| agcggggttg ctgaatcgtt aaggatccct ctagaaataa ttttgtttaa ctttaagaag | 300 |
| gagatataca tatgactatg attacggatt ctctggccgt cgtattacaa cgtcgtgact | 360 |
| gggaaaaccc tggcgttacc caacttaatc gccttgcggc acatccccct ttcgccagct | 420 |
| ggcgtaatag cgaagaggcc cgcaccgatc gcccttccca acagttgcgc agcctgaatg | 480 |
| gcgaatggcg ctttgcctgg tttccggcac cagaagcggt gccggaaagc tggctggagt | 540 |
| gcgatcttcc tgacgccgat actgtcgtcg tcccctcaaa ctggcagatg cacggttacg | 600 |
| atgcgcctat ctacaccaac gtgacctatc ccattacggt caatccgccg tttgttcccg | 660 |
| cggagaatcc gacaggttgt tactcgctca catttaatat tgatgaaagc tggctacagg | 720 |
| aaggccagac gcgaattatt tttgatggcg ttaactcggc gtttcatctg tggtgcaacg | 780 |
| ggcgctgggt cggttacggc caggacagcc gtttgccgtc tgaatttgac ctgagcgcat | 840 |
| ttttacgcgc cggagaaaac cgcctcgcgg tgatggtgct gcgctggagt gacggcagtt | 900 |
| atctggaaga tcaggatatg tggcggatga gcggcatttt ccgtgacgtc tcgttgctgc | 960 |
| ataaaccgac cacgcaaatc agcgatttcc aagttaccac tctctttaat gatgatttca | 1020 |
| gccgcgcggt actggaggca gaagttcaga tgtacggcga gctgcgcgat gaactgcggg | 1080 |
| tgacggtttc tttgtggcag ggtgaaacgc aggtcgccag cggcaccgcg cctttcggcg | 1140 |
| gtgaaattat cgatgagcgt ggcggttatg ccgatcgcgt cacactacgc ctgaacgttg | 1200 |
| aaaatccgga actgtggagc gccgaaatcc cgaatctcta tcgtgcagtg gttgaactgc | 1260 |
| acaccgccga cggcacgctg attgaagcag aagcctgcga cgtcggtttc cgcgaggtgc | 1320 |
| ggattgaaaa tggtctgctg ctgctgaacg gcaagccgtt gctgattcgc ggcgttaacc | 1380 |
| gtcacgagca tcatcctctg catggtcagg tcatggatga gcagacgatg gtgcaggata | 1440 |
| tcctgctgat gaagcagaac aactttaacg ccgtgcgctg ttcgcattat ccgaaccatc | 1500 |
| cgctgtggta cacgctgtgc gaccgctacg gcctgtatgt ggtggatgaa gccaatattg | 1560 |
| aaacccacgg catggtgcca atgaatcgtc tgaccgatga tccgcgctgg ctaccgcgcga | 1620 |
| tgagcgaacg cgtaacgcgg atggtgcagc gcgatcgtaa tcacccgagt gtgatcatct | 1680 |
| ggtcgctggg gaatgaatca ggccacgcgc taatcacga cgcgctgtat cgctggatca | 1740 |
| aatctgtcga tccttcccgc ccggtacagt atgaaggcgg cggagccgac accacggcca | 1800 |
| ccgatattat tgcccgatg tacgcgcgcg tggatgaaga ccagcccttc ccggcggtgc | 1860 |
| cgaaatggtc catcaaaaaa tggctttcgc tgcctggaga aatgcgcccg ctgatccttt | 1920 |
| gcgaatatgc ccacgcgatg ggtaacagtc ttggcggctt cgctaaatac tggcaggcgt | 1980 |

```
ttcgtcagta cccccgttta cagggcggct tcgtctggga ctgggtggat cagtcgctga    2040
ttaaatatga tgaaaacggc aacccgtggt cggcttacgg cggtgatttt ggcgatacgc    2100
cgaacgatcg ccagttctgt atgaacggtc tggtctttgc cgaccgcacg ccgcatccgg    2160
cgctgacgga agcaaaacac caacagcagt atttccagtt ccgtttatcc gggcgaacca    2220
tcgaagtgac cagcgaatac ctgttccgtc atagcgataa cgagttcctg cactggatgg    2280
tggcactgga tggcaagccg ctggcaagcg gtgaagtgcc tctggatgtt ggcccgcaag    2340
gtaagcagtt gattgaactg cctgaactgc cgcagccgga gagcgccgga caactctggc    2400
taacggtacg cgtagtgcaa ccaaacgcga ccgcatggtc agaagccgga cacatcagcg    2460
cctggcagca atggcgtctg gcggaaaacc tcagcgtgac actcccctcc gcgtcccacg    2520
ccatccctca actgaccacc agcggaacgg attttgcat cgagctgggt aataagcgtt    2580
ggcaatttaa ccgccagtca ggctttcttt cacagatgtg gattggcgat gaaaaacaac    2640
tgctgacccc gctgcgcgat cagttcaccc gtgcgccgct ggataacgac attggcgtaa    2700
gtgaagcgac ccgcattgac cctaacgcct gggtcgaacg ctggaaggcg gcgggccatt    2760
accaggccga agcggcgttg ttgcagtgca cggcagatac acttgccgac gcggtgctga    2820
ttacaaccgc ccacgcgtgg cagcatcagg ggaaaacctt atttatcagc cggaaaacct    2880
accggattga tgggcacggt gagatggtca tcaatgtgga tgttgcggtg gcaagcgata    2940
caccgcatcc ggcgcggatt ggcctgacct gccagctggc gcaggtctca gagcgggtaa    3000
actggctcgg cctggggccg caagaaaact atcccgaccg ccttactgca gcctgttttg    3060
accgctggga tctgccattg tcagacatgt ataccccgta cgtcttcccg agcgaaaacg    3120
gtctgcgctg cgggacgcgc gaattgaatt atgcccaca ccagtggcgc ggcgacttcc    3180
agttcaacat cagccgctac agccaacaac aactgatgga aaccagccat cgccatctgc    3240
tgcacgcgga agaaggcaca tggctgaata tcgacggttt ccatatgggg attggtggcg    3300
acgactcctg gagcccgtca gtatcggcgg aattccagct gagcgccggt cgctaccatt    3360
accagttggt ctggtgtcaa aaataa                                         3386
```

<210> SEQ ID NO 56  
<211> LENGTH: 3261  
<212> TYPE: DNA  
<213> ORGANISM: Artificial Sequence  
<220> FEATURE:  
<223> OTHER INFORMATION: Synthetic: Nucleotide sequences of Pfnr4-lacZ construct, low-copy

<400> SEQUENCE: 56

```
ggtacccatt tcctctcatc ccatccgggg tgagagtctt ttcccccgac ttatggctca      60
tgcatgcatc aaaaaagatg tgagcttgat caaaaacaaa aaatatttca ctcgacagga    120
gtatttatat tgcgcccgga tccctctaga aataattttg tttaacttta agaaggagat    180
atacatatga ctatgattac ggattctctg gccgtcgtat tacaacgtcg tgactgggaa    240
aaccctggcg ttacccaact taatcgcctt gcggcacatc cccctttcgc cagctggcgt    300
aatagcgaag aggcccgcac cgatcgccct tcccaacagt tgcgcagcct gaatggcgaa    360
tggcgctttg cctggtttcc ggcaccagaa gcggtgccgg aaagctggct ggagtgcgat    420
cttcctgacg ccgatactgt cgtcgtcccc tcaaactggc agatgcacgg ttacgatgcg    480
cctatctaca ccaacgtgac ctatcccatt acggtcaatc cgccgtttgt tcccgcggag    540
aatccgacag gttgttactc gctcacattt aatattgatg aaagctggct acaggaaggc    600
```

```
cagacgcgaa ttattttga tggcgttaac tcggcgtttc atctgtggtg caacgggcgc    660
tgggtcggtt acggccagga cagccgtttg ccgtctgaat ttgacctgag cgcattttta    720
cgcgccggag aaaaccgcct cgcggtgatg gtgctgcgct ggagtgacgg cagttatctg    780
gaagatcagg atatgtggcg gatgagcggc attttccgtg acgtctcgtt gctgcataaa    840
ccgaccacgc aaatcagcga tttccaagtt accactctct ttaatgatga tttcagccgc    900
gcggtactgg aggcagaagt tcagatgtac ggcgagctgc gcgatgaact gcgggtgacg    960
gtttctttgt ggcagggtga aacgcaggtc gccagcggca ccgcgccttt cggcggtgaa   1020
attatcgatg agcgtggcgg ttatgccgat cgcgtcacac tacgcctgaa cgttgaaaat   1080
ccggaactgt ggagcgccga atcccgaat ctctatcgtg cagtggttga actgcacacc   1140
gccgacggca cgctgattga agcagaagcc tgcgacgtcg gttccgcga ggtgcggatt   1200 gaaaatggtc tgctgctgct gaacggcaag ccgttgctga ttcgcggcgt taaccgtcac   1260
gagcatcatc ctctgcatgg tcaggtcatg gatgagcaga cgatggtgca ggatatcctg   1320
ctgatgaagc agaacaactt taacgccgtg cgctgttcgc attatccgaa ccatccgctg   1380
tggtacacgc tgtgcgaccg ctacggcctg tatgtggtgg atgaagccaa tattgaaacc   1440
cacggcatgg tgccaatgaa tcgtctgacc gatgatccgc gctggctacc cgcgatgagc   1500
gaacgcgtaa cgcggatggt gcagcgcgat cgtaatcacc cgagtgtgat catctggtcg   1560
ctggggaatg aatcaggcca cggcgctaat cacgacgcgc tgtatcgctg gatcaaatct   1620
gtcgatcctt cccgcccggt acagtatgaa ggcggcggag ccgacaccac ggccaccgat   1680
attatttgcc cgatgtacgc gcgcgtggat gaagaccagc ccttcccggc ggtgccgaaa   1740
tggtccatca aaaaatggct ttcgctgcct ggagaaatgc gcccgctgat cctttgcgaa   1800
tatgcccacg cgatgggtaa cagtcttggc ggcttcgcta atactggca ggcgtttcgt   1860 cagtaccccc gtttacaggg cggcttcgtc tgggactggg tggatcagtc gctgattaaa   1920
tatgatgaaa acggcaaccc gtggtcggct tacggcggtg attttggcga tacgccgaac   1980
gatcgccagt tctgtatgaa cggtctggtc tttgccgacc gcacgccgca tccgcgctg   2040 acggaagcaa acaccaaca gcagtatttc cagttccgtt tatccgggcg aaccatcgaa   2100
gtgaccagcg aatacctgtt ccgtcatagc gataacgagt tcctgcactg gatggtggca   2160
ctggatggca agccgctggc aagcggtgaa gtgcctctgg atgttggccc gcaaggtaag   2220
cagttgattg aactgcctga actgccgcag ccggagagcg ccggacaact ctggctaacg   2280
gtacgcgtag tgcaaccaaa cgcgaccgca tggtcagaag ccggacacat cagcgcctgg   2340
cagcaatggc gtctggcgga aaacctcagc gtgacactcc cctccgcgtc ccacgccatc   2400
cctcaactga ccaccagcgg aacggatttt tgcatcgagc tgggtaataa cgcttggcaa   2460
tttaaccgcc agtcaggctt tctttcacag atgtggattg gcgatgaaaa acaactgctg   2520
accccgctgc gcgatcagtt cacccgtgcg ccgctggata cgacattgg cgtaagtgaa   2580 gcgacccgca ttgaccctaa cgcctgggtc gaacgctgga aggcggcggg ccattaccag   2640
gccgaagcgg cgttgttgca gtgcacggca gatacacttg ccgacgcggt gctgattaca   2700
accgcccacg cgtggcagca tcaggggaaa accttatta tcagccggaa aacctaccgg   2760
attgatgggc acggtgagat ggtcatcaat gtggatgttg cggtggcaag cgatacaccg   2820
catccggcgc ggattggcct gacctgccag ctggcgcagg tctcagagcg ggtaaactgg   2880
ctcggcctgg ggccgcaaga aaactatccc gaccgcctta ctgcagcctg ttttgaccgc   2940
```

-continued

| | |
|---|---|
| tgggatctgc cattgtcaga catgtatacc ccgtacgtct tcccgagcga aaacggtctg | 3000 |
| cgctgcggga cgcgcgaatt gaattatggc ccacaccagt ggcgcggcga cttccagttc | 3060 |
| aacatcagcc gctacagcca acaacaactg atggaaacca gccatcgcca tctgctgcac | 3120 |
| gcggaagaag gcacatggct gaatatcgac ggttttccata tggggattgg tggcgacgac | 3180 |
| tcctggagcc cgtcagtatc ggcggaattc cagctgagcg ccggtcgcta ccattaccag | 3240 |
| ttggtctggt gtcaaaaata a | 3261 |

<210> SEQ ID NO 57
<211> LENGTH: 3279
<212> TYPE: DNA
<213> ORGANISM: Artificial Sequence
<220> FEATURE:
<223> OTHER INFORMATION: Synthetic: Nucleotide sequences of Pfnrs-lacZ
      construct, low-copy

<400> SEQUENCE: 57

| | |
|---|---|
| ggtaccagtt gttcttattg gtggtgttgc tttatggttg catcgtagta aatggttgta | 60 |
| acaaaagcaa ttttccggc tgtctgtata caaaaacgcc gtaaagtttg agcgaagtca | 120 |
| ataaactctc tacccattca gggcaatatc tctcttggat ccctctagaa ataattttgt | 180 |
| ttaactttaa gaaggagata tacatatgct atgattacgg attctctggc cgtcgtatta | 240 |
| caacgtcgtg actgggaaaa ccctggcgtt acccaactta atcgccttgc ggcacatccc | 300 |
| cctttcgcca gctggcgtaa tagcgaagag gcccgcaccg atcgcccttc ccaacagttg | 360 |
| cgcagcctga atggcgaatg gcgctttgcc tggtttccgg caccagaagc ggtgccggaa | 420 |
| agctggctgg agtgcgatct tcctgacgcc gatactgtcg tcgtcccctc aaactggcag | 480 |
| atgcacggtt acgatgcgcc tatctacacc aacgtgacct atcccattac ggtcaatccg | 540 |
| ccgtttgttc ccgcggagaa tccgacaggt tgttactcgc tcacatttaa tattgatgaa | 600 |
| agctggctac aggaaggcca gacgcgaatt atttttgatg gcgttaactc ggcgtttcat | 660 |
| ctgtggtgca acgggcgctg ggtcggttac ggccaggaca gccgtttgcc gtctgaattt | 720 |
| gacctgagcg catttttacg cgccggagaa aaccgcctcg cggtgatggt gctgcgctgg | 780 |
| agtgacggca gttatctgga agatcaggat atgtggcgga tgagcggcat tttccgtgac | 840 |
| gtctcgttgc tgcataaacc gaccacgcaa atcagcgatt tccaagttac cactctcttt | 900 |
| aatgatgatt tcagccgcgc ggtactggag gcagaagttc agatgtacgg cgagctgcgc | 960 |
| gatgaactgc gggtgacggt ttcttttgtgg cagggtgaaa cgcaggtcgc cagcggcacc | 1020 |
| gcgcctttcg gcggtgaaat tatcgatgag cgtggcggtt atgccgatcg cgtcacacta | 1080 |
| cgcctgaacg ttgaaaatcc ggaactgtgg agcgccgaaa tcccgaatct ctatcgtgca | 1140 |
| gtggttgaac tgcacaccgc cgacggcacg ctgattgaag cagaagcctg cgacgtcggt | 1200 |
| ttccgcgagg tgcggattga aaatggtctg ctgctgctga acggcaagcc gttgctgatt | 1260 |
| cgcggcgtta accgtcacga gcatcatcct ctgcatggtc aggtcatgga tgagcagacg | 1320 |
| atggtgcagg atatcctgct gatgaagcag aacaacttta acgccgtgcg ctgttcgcat | 1380 |
| tatccgaacc atccgctgtg gtacacgctg tgcgaccgct acggcctgta tgtggtggat | 1440 |
| gaagccaata ttgaaaccca cggcatggtg ccaatgaatc gtctgaccga tgatccgcgc | 1500 |
| tggctacccg cgatgagcga acgcgtaacg cggatggtgc agcgcgatcg taatcacccg | 1560 |
| agtgtgatca tctggtcgct ggggaatgaa tcaggccacg gcgctaatca cgacgcgctg | 1620 |
| tatcgctgga tcaaatctgt cgatcccttcc cgcccggtac agtatgaagg cggcggagcc | 1680 |

```
gacaccacgg ccaccgatat tatttgcccg atgtacgcgc gcgtggatga agaccagccc    1740
ttcccggcgg tgccgaaatg gtccatcaaa aaatggcttt cgctgcctgg agaaatgcgc    1800
ccgctgatcc tttgcgaata tgcccacgcg atgggtaaca gtcttggcgg cttcgctaaa    1860
tactggcagg cgtttcgtca gtaccccgt ttacagggcg gcttcgtctg ggactgggtg     1920
gatcagtcgc tgattaaata tgatgaaaac ggcaacccgt ggtcggctta cggcggtgat    1980
tttggcgata cgccgaacga tcgccagttc tgtatgaacg gtctggtctt tgccgaccgc    2040
acgccgcatc cggcgctgac ggaagcaaaa caccaacagc agtatttcca gttccgttta    2100
tccgggcgaa ccatcgaagt gaccagcgaa tacctgttcc gtcatagcga taacgagttc    2160
ctgcactgga tggtggcact ggatggcaag ccgctggcaa gcggtgaagt gcctctggat    2220
gttggcccgc aaggtaagca gttgattgaa ctgcctgaac tgccgcagcc ggagagcgcc    2280
ggacaactct ggctaacggt acgcgtagtg caaccaaacg cgaccgcatg gtcagaagcc    2340
ggacacatca gcgcctggca gcaatggcgt ctggcggaaa acctcagcgt gacactcccc    2400
tccgcgtccc acgccatccc tcaactgacc accagcggaa cggatttttg catcgagctg    2460
ggtaataagc gttggcaatt taaccgccag tcaggctttc tttcacagat gtggattggc    2520
gatgaaaaac aactgctgac cccgctgcgc gatcagttca cccgtgcgcc gctggataac    2580
gacattggcg taagtgaagc gacccgcatt gaccctaacg cctgggtcga acgctggaag    2640
gcggcgggcc attaccaggc cgaagcggcg ttgttgcagt gcacggcaga tacacttgcc    2700
gacgcggtgc tgattacaac cgcccacgcg tggcagcatc aggggaaaac cttatttatc    2760
agccggaaaa cctaccggat tgatgggcac ggtgagatgg tcatcaatgt ggatgttgcg    2820
gtggcaagcg atacaccgca tccggcgcgg attggcctga cctgccagct ggcgcaggtc    2880
tcagagcggg taaactggct cggcctgggg ccgcaagaaa actatcccga ccgccttact    2940
gcagcctgtt ttgaccgctg ggatctgcca ttgtcagaca tgtataccccc gtacgtcttc    3000 ccgagcgaaa acgtctgcg ctgcgggacg cgcgaattga attatggccc acaccagtgg    3060
cgcggcgact tccagttcaa catcagccgc tacagccaac aacaactgat ggaaaccagc    3120
catcgccatc tgctgcacgc ggaagaaggc acatggctga atatcgacgg tttccatatg    3180
gggattggtg gcgacgactc ctggagcccg tcagtatcgg cggaattcca gctgagcgcc    3240
ggtcgctacc attaccagtt ggtctggtgt caaaaataa                          3279
```

<210> SEQ ID NO 58
<211> LENGTH: 1921
<212> TYPE: DNA
<213> ORGANISM: Artificial Sequence
<220> FEATURE:
<223> OTHER INFORMATION: Synthetic: Prp promoter  Highlight: prpR, lower case:Ribosome binding site,

<400> SEQUENCE: 58

```
ttacccgtct ggattttcag tacgcgcttt taaacgacgc cacagcgtgg tacggctgat     60
ccccaaataa cgtgcggcgg cgcgcttatc gccattaaag cgtgcgagca cctcctgcaa    120
tggaagcgct tctgctgacg agggcgtgat ttctgctgtg gtccccacca gttcaggtaa    180
taattgccgc ataaattgtc tgtccagtgt tggtgcggga tcgacgctta aaaaagcgc     240 caggcgttcc atcatattcc gcagttcgcg aatattaccg ggccaatgat agttcagtag    300
aagcggctga cactgcgtca gcccatgacg caccgattcg gtaaaaggga tctccatcgc    360
ggccagcgat tgttttaaaa agttttccgc cagaggcaga atatcaggct gtcgctcgcg    420
```

| | | |
|---|---|---|
| caaggggga agcggcagac gcagaatgct caaacggtaa aacagatcgg tacgaaaacg | 480 | |
| tccttgcgtt atctcccgat ccagatcgca atgcgtggcg ctgatcaccc ggacatctac | 540 | |
| cgggatcggc tgatgcccgc caacgcgggt gacggctttt tcctccagta cgcgtagaag | 600 | |
| gcgggtttgt aacggcagcg gcatttcgcc aatttcgtca agaaacagcg tgccgccgtg | 660 | |
| ggcgacctca acagccccg cacgtccacc tcgtcttgag ccggtaaacg ctccctcctc | 720 | |
| atagccaaac agttcagcct ccagcaacga ctcggtaatc gcgccgcaat taacggcgac | 780 | |
| aaagggcgga gaaggcttgt tctgacggtg gggctgacgg ttaaacaacg cctgatgaat | 840 | |
| cgcttgcgcc gccagctctt tcccggtccc tgtttccccc tgaatcagca ctgccgcgcg | 900 | |
| ggaacgggca tagagtgtaa tcgtatggcg aacctgctcc atttgtggtg aatcgccgag | 960 | |
| gatatcgctc agcgcataac gggtctgtaa tcccttgctg gaggtatgct ggctatactg | 1020 | |
| acgccgtgtc aggcgggtca tatccagcgc atcatggaaa gcctgacgta cggtggccgc | 1080 | |
| tgaataaata aagatggcgg tcattcctgc ctcttccgcc aggtcggtaa ttagtcctgc | 1140 | |
| cccaattaca gcctcaatgc cgttagcttt gagctcgtta atttgcccgc gagcatcctc | 1200 | |
| ttcagtgata tagcttcgct gttcaagacg gaggtgaaac gttttctgaa aggcgaccag | 1260 | |
| agccggaatg gtctcctgat aggtcacgat tcccattgag gaagtcagct ttcccgcttt | 1320 | |
| tgccagagcc tgtaatacat cgaatccgct gggtttgatg aggatgacag gtaccgacag | 1380 | |
| tcggcttttt aaataagcgc cgttggaacc tgccgcgata atcgcgtcgc agcgttcggt | 1440 | |
| tgccagtttt ttgcgaatgt aggctactgc cttttcaaaa ccgagctgaa taggcgtgat | 1500 | |
| cgtcgccaga tgatcaaact ccaggctgat atcccgaaat agttcgaaca ggcgcgttac | 1560 | |
| cgagaccgtc cagatcaccg gtttatcgct attatcgcgc gaagcgctat gcacagtaac | 1620 | |
| catcgtcgta gattcatgtt taaggaacga attcttgttt tatagatgtt tcgttaatgt | 1680 | |
| tgcaatgaaa cacaggcctc cgtttcatga aacgttagct gactcgtttt tcttgtgact | 1740 | |
| cgtctgtcag tattaaaaaa gattttcat ttaactgatt gttttaaat tgaatttat | 1800 | |
| ttaatggttt ctcggttttt gggtctggca tatcccttgc tttaatgagt gcatcttaat | 1860 | |
| taacaattca ataacaagag ggctgaatag taatttcaac aaaataacga gcattcgaat | 1920 | |
| g | 1921 | |

<210> SEQ ID NO 59
<211> LENGTH: 967
<212> TYPE: DNA
<213> ORGANISM: Artificial Sequence
<220> FEATURE:
<223> OTHER INFORMATION: Synthetic: Wild-type clbA

<400> SEQUENCE: 59

| | | |
|---|---|---|
| caaatatcac ataatcttaa catatcaata aacacagtaa agtttcatgt gaaaaacatc | 60 | |
| aaacataaaa tacaagctcg gaatacgaat cacgctatac acattgctaa caggaatgag | 120 | |
| attatctaaa tgaggattga tatattaatt ggacatacta gttttttca tcaaaccagt | 180 | |
| agagataact tccttcacta tctcaatgag gaagaaataa aacgctatga tcagtttcat | 240 | |
| tttgtgagtg ataaagaact ctatatttta gccgtatcc tgctcaaaac agcactaaaa | 300 | |
| agatatcaac ctgatgtctc attacaatca tggcaattta gtacgtgcaa atatggcaaa | 360 | |
| ccatttatag ttttcctca gttggcaaaa aagatttttt ttaacctttc ccatactata | 420 | |
| gatacagtag ccgttgctat tagttctcac tgcgagcttg gtgtcgatat tgaacaaata | 480 | |
| agagattag acaactctta tctgaatatc agtcagcatt tttttactcc acaggaagct | 540 | |

```
actaacatag tttcacttcc tcgttatgaa ggtcaattac ttttttggaa aatgtggacg      600
ctcaaagaag cttacatcaa atatcgaggt aaaggcctat ctttaggact ggattgtatt      660
gaatttcatt taacaaataa aaaactaact tcaaaatata gaggttcacc tgtttatttc      720
tctcaatgga aaatatgtaa ctcatttctc gcattagcct ctccactcat caccgctaaa      780
ataactattg agctatttcc tatgcagtcc caactttatc accacgacta tcagctaatt      840
cattcgtcaa atgggcagaa ttgaatcgcc acggataatc tagacacttc tgagccgtcg      900
ataatattga ttttcatatt ccgtcggtgg tgtaagtatc ccgcataatc gtgccattca      960
catttag                                                               967

<210> SEQ ID NO 60
<211> LENGTH: 424
<212> TYPE: DNA
<213> ORGANISM: Artificial Sequence
<220> FEATURE:
<223> OTHER INFORMATION: Synthetic: clbA knock-out

<400> SEQUENCE: 60
ggatgggggg aaacatggat aagttcaaag aaaaaaaccc gttatctctg cgtgaaagac       60
aagtattgcg catgctggca caaggtgatg agtactctca aatatcacat aatcttaaca      120
tatcaataaa cacagtaaag tttcatgtga aaaacatcaa acataaaata caagctcgga      180
atacgaatca cgctatacac attgctaaca ggaatgagat tatctaaatg aggattgatg      240
tgtaggctgg agctgcttcg aagttcctat actttctaga gaataggaac ttcggaatag      300
gaacttcgga ataggaacta aggaggatat tcatatgtcg tcaaatgggc agaattgaat      360
cgccacggat aatctagaca cttctgagcc gtcgataata ttgattttca tattccgtcg      420
gtgg                                                                  424

<210> SEQ ID NO 61
<211> LENGTH: 170
<212> TYPE: DNA
<213> ORGANISM: Artificial Sequence
<220> FEATURE:
<223> OTHER INFORMATION: Synthetic: FNR promoter without RBS and leader
      region

<400> SEQUENCE: 61
ggtaccagtt gttcttattg gtggtgttgc tttatggttg catcgtagta aatggttgta       60
acaaaagcaa ttttccggc tgtctgtata caaaaacgcc gtaaagtttg agcgaagtca      120
ataaactctc tacccattca gggcaatatc tctcttggat ccaaagtgaa                 170

<210> SEQ ID NO 62
<211> LENGTH: 18
<212> TYPE: DNA
<213> ORGANISM: Artificial Sequence
<220> FEATURE:
<223> OTHER INFORMATION: Synthetic: consensus sequence

<400> SEQUENCE: 62
ttgttgayry rtcaacwa                                                    18

<210> SEQ ID NO 63
<211> LENGTH: 15
<212> TYPE: DNA
<213> ORGANISM: Artificial Sequence
<220> FEATURE:
<223> OTHER INFORMATION: Synthetic: consensus sequence
```

```
<220> FEATURE:
<221> NAME/KEY: misc_feature
<222> LOCATION: (8)..(8)
<223> OTHER INFORMATION: n is a, c, g, or t

<400> SEQUENCE: 63
ttataatnat tataa                                              15
```

BACTERIA ENGINEERED TO TREAT DISORDERS IN WHICH OXALATE IS DETRIMENTAL

RELATED APPLICATIONS

This application is a 35 U.S.C. § 371 national stage filing of International Application No. PCT/US2016/049781, filed on Aug. 31, 2016, which in turn claims priority to U.S. Provisional Patent Application No. 62/212,223, filed on Aug. 31, 2015, U.S. Provisional Patent Application No. 62/341,315, filed on May 25, 2016, and to International Patent Application No. PCT/US2016/032565, filed on May 13, 2016. The entire contents of each of the foregoing applications are expressly incorporated herein by reference.

SEQUENCE LISTING

The instant application contains a Sequence Listing which has been submitted electronically in ASCII format and is hereby incorporated by reference in its entirety. Said ASCII copy, created on Dec. 16, 2016, is named 126046-00520_SL.txt and is 137,594 bytes in size.

BACKGROUND OF THE INVENTION

Oxalate, the ionic form of oxalic acid, arises in the human body from dietary intake or from endogenous synthesis. Oxalate is ubiquitous in plants and plant-derived foods, and as such, is inevitably part of the human diet. Endogenously-synthesized oxalate is primarily derived from glyoxylate in the liver where excess glyoxylate is converted to oxalate by glycolate oxidase or lactate dehydrogenase (Robijn et al., *Kidney Int.* 80: 1146-58 (2011)). Healthy individuals normally excrete urinary oxalate in ranges between 20-40 mg of oxalate per 24 hours. However, urinary oxalate excretion at concentrations exceeding 40-45 mg per 24 hours is clinically considered hyperoxaluria (Robijn et al. (2011)). Hyperoxaluria is characterized by increased urinary excretion of and elevated systemic levels of oxalate. If left untreated, hyperoxaluria can cause significant morbidity and mortality, including the development of renal stones (kidney stones), nephrocalcinosis (increased calcium in the kidney) and most significantly, End Stage Renal Disease.

Hyperoxalurias can generally be divided into two clinical categories: primary and secondary hyperoxalurias. Primary hyperoxalurias are autosomal-recessive inherited diseases resulting from mutations in one of several genes involved in oxalate metabolism (Hoppe et al., *Nephr. Dial. Transplant.* 26: 3609-15 (2011)). The primary hyperoxalurias are characterized by elevated urinary oxalate excretion which ultimately may result in recurrent urolithiasis, progressive nephrocalcinosis and early end-stage renal disease. In addition, when chronic renal insufficiency occurs in patients with primary hyperoxalurias, systemic deposition of calcium oxalate (also known as oxalosis) may occur in various organ systems which can lead to bone disease, erythropoietin refractory anemia, skin ulcers, digital gangrene, cardiac arrhythmias, and cardiomyopathy (Hoppe et al. (2011)).

Primary hyperoxaluria type I (PHI) is the most common and severe form of hyperoxaluria, and is caused by a defect in the vitamin B6-dependent hepatic peroxisomal enzyme, alanine glyoxalate aminotransferase (AGT, encoded by the AGXT gene; FIG. 3), which catalyzes the transamination of glyoxalate to glycine (Purdue et al., *J. Cell Biol.* 111: 2341-51 (1990); Hoppe et al., *Kidney Int.* 75: 1264-71 (2009)). AGT deficiency allows glyoxylate to be reduced to glycolate which is then oxidized to produce oxalate. Over 140 mutations of the human AGXT gene have been identified (Williams et al., *Hum. Mut.* 30: 910-7 (2009)). Primary hyperoxaluria type II (PHII) is caused by mutations of the enzyme glyoxylate/hydroxypyruvate reductase (GRHPR; FIG. 3), an enzyme having glyoxylate reductase (GR), hydroxypyruvate reductase (HPR), and D-glycerate dehydrogenase (DGDH) activities (see, e.g., Cramer et al., *Hum. Mol. Gen.* 8:2063-9 (1999)). More than a dozen mutation of the human GRHPR gene have been identified (Cregeen et al., *Hum. Mut.* 22: 497 (2003)). Both PHI and PHII result in severe hyperoxaluria (Robijn et al. (2011)). Primary hyperoxaluria type III (PHIII) is caused by a mutation in the HOGA1 gene (FIG. 3), which encodes a 4-hydroxy 2-oxoglutarate aldolase, a mitochondrial enzyme that breaks down 4-hydroxy 2-oxoglutarate into pyruvate and glyoxalate (Pitt et al., *JIMD Reports* 15: 1-6 (2015)). 15 mutations in the human HOGA1 gene have been identified (Bhasin et al., *World J. Nephrol.* 4: 235-44 (2015)).

Secondary hyperoxaluria typically results from conditions underlying increased absorption of oxalate, including increased dietary intake of oxalate, increased intestinal absorption of oxalate, excessive intake of oxalate precursors, gut microflora imbalances, and genetic variations of intestinal oxalate transporters (Bhasin et al., 2015; Robijn et al. (2011)). Increased oxalate absorption with consequent hyperoxaluria, often referred to as enteric hyperoxaluria, is observed in patients with a variety of intestinal disorders, including the syndrome of bacterial overgrowth, Crohn's disease, inflammatory bowel disease, as well as other malabsorptive states, such as, after jejunoileal bypass for obesity, after gastric ulcer surgery, and chronic mesenteric ischemia (Pardi et al., *Am. J. Gastroenterol.* 93: 500-14 (1998); Hylander et al., *Scand. J. Gastroent.* 15: 349-52 (1980); Canos et al., *Can. Med. Assoc. J.* 124: 729-33 (1981); Drenick et al., *Ann. Intern. Med.* 89: 594-9 (1978)). In addition, hyperoxaluria may also occur following renal transplantation (Robijn et al. (2011)). Patients with secondary hyperoxalurias and enteric hyperoxalurias are predisposed to developing calcium oxalate stones, which may lead to significant renal damage and ultimately result in End Stage Renal Disease.

Currently available treatments for hyperoxalurias are inadequate. Strategies for the treatment of primary hyperoxalurias include reducing urinary oxalate with pyridoxine, which is only effective in less than half of patients with PHI, and ineffective in patients with PHII and PHIII (Hoppe et al. (2011)). Further, treatments with citrate, orthophosphate, and magnesium to increase the urinary solubility of calcium oxalate, and thus preserve renal function, are not well characterized (Hoppe et al. (2011)). Other strategies for the treatment of secondary and enteric hyperoxalurias, which are quite arduous and often ineffective, include reducing the dietary intake of oxalate, oral calcium supplementation, and the use of bile acid sequestrants (Parivar et al, *J. Urol.* 155: 432-40 (1996); Hylander et al. (1980); McLeod and Churchill, *J. Urol.* 148: 974-8 (1992)). Generally, dietary restrictions are not entirely effective because patients cannot readily identify the food products to avoid (Parivar et al. (1996)). Therefore, there is significant unmet need for effective, reliable, and/or long-term treatment of hyperoxalurias.

SUMMARY OF THE INVENTION

The present disclosure provides engineered bacterial cells, pharmaceutical compositions thereof, and methods of modulating and treating disorders in which oxalate is detrimental. Specifically, the engineered bacteria disclosed herein have been constructed to comprise genetic circuits composed of, for example, one or more oxalate catabolism genes to treat the disease, as well as other optional circuitry designed to ensure the safety and non-colonization of a subject that is administered the engineered bacteria, such as, for example, auxotrophies, kill switches, and combinations thereof. These engineered bacteria are safe and well tolerated and augment the innate activities of the subject's microbiome to achieve a therapeutic effect.

In some embodiments, the disclosure provides a bacterial cell that has been genetically engineered to comprise one or more genes, gene cassettes, and/or synthetic circuits encoding one or more oxalate catabolism enzyme(s) or oxalate catabolism pathway, and is capable of metabolizing oxalate and/or other metabolites, such as oxalyl-CoA. Thus, the genetically engineered bacterial cells and pharmaceutical compositions comprising the bacterial cells may be used to treat and/or prevent diseases associated with disorders in which oxalate is detrimental, such as primary hyperoxalurias and secondary hyperoxalurias.

In some embodiments, the disclosure provides a bacterial cell that has been engineered to comprise gene sequence(s) encoding one or more oxalate catabolism enzyme(s). In some embodiments, the disclosure provides a bacterial cell has been engineered to comprise gene sequence(s) encoding one or more oxalate catabolism enzyme(s) and is capable of reducing the level of oxalate and/or other metabolites, for example, oxalyl-CoA. In some embodiments, the bacterial cell has been engineered to comprise gene sequence(s) encoding one or more transporter(s) (importer(s)) of oxalate. In some embodiments, the bacterial cell has been engineered to comprise gene sequence(s) encoding one or more exporter(s) of formate. In some embodiments, the engineered bacteria comprise gene sequence(s) encoding one or more polypeptide(s) which mediate both the transport (import) of oxalate and the export of formate (e.g., oxalate:formate antiporter(s)). In some embodiments, the engineered bacteria comprise gene sequence(s) encoding one or more of the following: (i) one or more transporter(s) of oxalate; (ii) one or more exporter(s) of formate; (iii) one or more polypeptide(s) which mediate both the transport (import) of oxalate and the export of formate (e.g., oxalate:formate antiporter(s)); and (iv) any combination thereof. In some embodiments, the bacterial cell has been engineered to comprise gene sequence(s) encoding one or more oxalate catabolism enzyme(s) and one or more transporter(s) (importer(s)) of oxalate. In some embodiments, the bacterial cell of the disclosure has been genetically engineered to comprise gene sequence(s) encoding one or more oxalate catabolism enzyme(s) and one or more exporter(s) of formate. In some embodiments, genetically engineered bacteria comprise gene sequence(s) encoding one or more oxalate catabolism enzyme(s) and one or more polypeptide(s), which mediate both the transport (import) of oxalate and the export of formate (e.g., oxalate:formate antiporter(s)). In some embodiments, the bacterial cell has been engineered to comprise gene sequence(s) encoding one or more oxalate catabolism enzyme(s) and gene sequence(s) encoding one or more of the following: (i) one or more transporter(s) of oxalate; (ii) one or more exporter(s) of formate; (iii) one or more polypeptide(s) which mediate both the transport (import) of oxalate and the export of formate (e.g., oxalate:formate antiporter(s)); and (iv) any combination thereof.

In some embodiments, the gene sequence(s) encoding one or more oxalate catabolism enzyme(s) is operably linked to an inducible promoter. In some embodiments, the gene sequence(s) encoding one or more oxalate transporter(s) (importer(s)) is operably linked to an inducible promoter. In some embodiments, the gene sequence(s) encoding one or more exporter(s) of formate is operably linked to an inducible promoter. In some embodiments, the gene sequence(s) encoding one or more polypeptide(s) which mediate both the transport (import) of oxalate and the export of formate (e.g., oxalate:formate antiporter(s)) is operably linked to an inducible promoter. In some embodiments, the gene sequence(s) encoding one or more oxalate catabolism enzyme(s) and the gene sequence(s) encoding one or more oxalate transporter(s) (importer(s)) are operably linked to an inducible promoter. In some embodiments, the gene sequence(s) encoding one or more oxalate catabolism enzyme(s) and the gene sequence(s) encoding one or more exporter(s) of formate are operably linked to an inducible promoter. In some embodiments, the gene sequence(s) encoding one or more oxalate catabolism enzyme(s) and the gene sequence(s) encoding one or more polypeptide(s) which mediate both the transport (import) of oxalate and the export of formate (e.g., oxalate:formate antiporter(s)) are operably linked to an inducible promoter. In some embodiments, any one or more of the following gene sequences, if present in the bacterial cell, are operably linked to an inducible promoter: (i) gene sequence(s) encoding one or more oxalate catabolism enzyme(s); (ii) gene sequence(s) encoding one or more oxalate transporter(s); (iii) gene sequence(s) encoding one or more exporter(s) of formate; and (iv) gene sequence(s) encoding one or more polypeptide(s) which mediate both the transport (import) of oxalate and the export of formate (e.g., oxalate:formate antiporter(s)).

In some embodiments, the disclosure provides a bacterial cell which has been engineered to comprise gene sequence(s) encoding one or more oxalate catabolism enzyme(s) operably linked to an inducible promoter that is induced under low oxygen and/or anaerobic conditions, e.g., such as those conditions found in the mammalian gut. In some embodiments, the disclosure provides a bacterial cell which has been engineered to comprise gene sequence(s) encoding one or more oxalate transporter(s) (importer(s)) operably linked to an inducible promoter that is induced under low oxygen and/or anaerobic conditions, e.g., such as those conditions found in the mammalian gut. In some embodiments, the disclosure provides a bacterial cell which has been engineered to comprise gene sequence(s) encoding one or more exporter(s) of formate operably linked to an inducible promoter that is induced under low oxygen and/or anaerobic conditions, e.g., such as those conditions found in the mammalian gut. In some embodiments, the disclosure provides a bacterial cell which has been engineered to comprise gene sequence(s) encoding one or more polypeptide(s) which mediate both the transport (import) of oxalate and the export of formate (e.g., oxalate:formate antiporter(s)) operably linked to an inducible promoter that is induced under low oxygen and/or anaerobic conditions, e.g., such as those conditions found in the mammalian gut. In some embodiments, the gene sequence(s) encoding one or more oxalate catabolism enzyme(s) and the gene sequence(s) encoding one or more oxalate transporter(s) (importer(s)) are operably linked to an inducible promoter that is induced under low oxygen and/or anaerobic conditions. In some embodiments, the gene sequence(s) encoding one or more oxalate catabolism enzyme(s) and the gene sequence(s) encoding one or more exporter(s) of formate are operably linked to an inducible promoter that is induced under low oxygen and/or anaerobic conditions. In some embodiments, the gene sequence(s) encoding one or more oxalate catabolism enzyme(s) and the gene sequence(s) encoding one or more polypeptide(s) which mediate both the transport (import) of oxalate and the export of formate (e.g., oxalate:formate antiporter(s)) are operably linked to an inducible promoter that is induced under low oxygen and/or anaerobic conditions. In some embodiments, any one or more of the following gene sequences, if present in the bacterial cell, are operably linked to an inducible promoter that is induced under low oxygen and/or anaerobic conditions: (i) gene sequence(s) encoding one or more oxalate catabolism enzyme(s); (ii) gene sequence(s) encoding one or more oxalate transporter(s); (iii) gene sequence(s) encoding one or more exporter(s) of formate; and (iv) gene sequence(s) encoding one or more polypeptide(s) which mediate both the transport (import) of oxalate and the export of formate (e.g., oxalate:formate antiporter(s)).

In some embodiments, the disclosure provides a bacterial cell that has been engineered to comprise gene sequence(s) encoding one or more oxalate catabolism enzyme(s) that is operably linked to an inducible promoter that is induced by environmental signals and/or conditions found in the mammalian gut (e.g., induced by metabolites (e.g., oxalate metabolites) or other biomolecules found in the mammalian gut, and/or induced by inflammatory conditions (e.g., reactive nitrogen species and/or reactive oxygen species)). The environmental signals and/or conditions found in the mammalian gut may be signals and conditions found in a healthy mammalian gut or signals and conditions found in a diseased mammalian gut, such as the gut of a subject having hyperoxaluria or other condition in which the level of oxalate and/or an oxalate metabolite is elevated, and/or the gut of a subject having an inflammatory condition, such as irritable bowel disease, an autoimmune disease, and any other condition that results in inflammation in the gut. In some embodiments, the disclosure provides a bacterial cell which has been engineered to comprise gene sequence(s) encoding one or more oxalate catabolism enzyme(s) operably linked to an inducible promoter that is induced under inflammatory conditions, e.g., such as inflammatory conditions found in a mammalian gut. In some embodiments, the disclosure provides a bacterial cell which has been engineered to comprise gene sequence(s) encoding one or more oxalate transporter(s) (importer(s)) operably linked to an inducible promoter that is induced under inflammatory conditions, e.g., such as inflammatory conditions found in a mammalian gut. In some embodiments, the disclosure provides a bacterial cell which has been engineered to comprise gene sequence(s) encoding one or more exporter(s) of formate operably linked to an inducible promoter that is induced under inflammatory conditions, e.g., such as inflammatory conditions found in a mammalian gut. In some embodiments, the disclosure provides a bacterial cell which has been engineered to comprise gene sequence(s) encoding one or more polypeptide(s) which mediate both the transport (import) of oxalate and the export of formate (e.g., oxalate:formate antiporter(s)) operably linked to an inducible promoter that is induced under inflammatory conditions, e.g., such as inflammatory conditions found in a mammalian gut. In some embodiments, the gene sequence(s) encoding one or more oxalate catabolism enzyme(s) and the gene sequence(s) encoding one or more oxalate transporter(s) (importer(s)) are operably linked to an inducible promoter that is induced under inflammatory conditions. In some embodiments, the gene sequence(s) encoding one or more oxalate catabolism enzyme(s) and the gene sequence(s) encoding one or more exporter(s) of formate are operably linked to an inducible promoter that is induced under inflammatory conditions. In some embodiments, the gene sequence(s) encoding one or more oxalate catabolism enzyme(s) and the gene sequence(s) encoding one or more polypeptide(s) which mediate both the transport (import) of oxalate and the export of formate (e.g., oxalate:formate antiporter(s)) are operably linked to an inducible promoter that is induced under inflammatory conditions. In some embodiments, any one or more of the following gene sequences, if present in the bacterial cell, are operably linked to an inducible promoter that is induced under inflammatory conditions: (i) gene sequence(s) encoding one or more oxalate catabolism enzyme(s); (ii) gene sequence(s) encoding one or more oxalate transporter(s); (iii) gene sequence(s) encoding one or more exporter(s) of formate; and (iv) gene sequence(s) encoding one or more polypeptide(s) which mediate both the transport (import) of oxalate and the export of formate (e.g., oxalate:formate antiporter(s)).

In some embodiments, the disclosure provides a bacterial cell that has been engineered to comprise gene sequence(s) encoding one or more polypeptide(s) capable of reducing the level of oxalate and/or other metabolites, for example, oxalyl-CoA, in low-oxygen environments, e.g., the gut. In some embodiments, the bacterial cell that has been engineered to comprise gene sequence(s) encoding one or more of the following: (i) one or more oxalate catabolism enzyme(s); (ii) one or more oxalate transporter(s); (ii) one or more formate exporter(s); and (iv) one or more oxalate: formate antiporter(s). In some embodiments, the bacterial cell has been genetically engineered to comprise one or more circuits encoding one or more oxalate catabolism enzyme(s) and is capable of processing and reducing levels of oxalate, and/or oxalyl-CoA e.g., in low-oxygen environments, e.g., the gut. Thus, in some embodiments, the genetically engineered bacterial cells and pharmaceutical compositions comprising the bacterial cells of the disclosure may be used to import excess oxalate and/or oxalyl-CoA into the bacterial cell in order to treat and/or prevent conditions associated with disorders in which oxalate is detrimental, such as primary hyperoxalurias and secondary hyperoxalurias. In some embodiments, the genetically engineered bacterial cells and pharmaceutical compositions comprising the bacterial cells of the disclosure may be used to convert excess oxalate and/or oxalyl-CoA into non-toxic molecules in order to treat and/or prevent conditions associated with disorders in which oxalate is detrimental, such as primary hyperoxalurias and secondary hyperoxalurias.

The present invention provides recombinant bacterial cells, pharmaceutical compositions thereof, and methods of modulating and treating disorders in which oxalate is detrimental. The genetically engineered bacterial cells and pharmaceutical compositions comprising the bacterial cells of the invention may be used to convert excess oxalate and/or oxalic acid into non-toxic molecules in order to treat and/or prevent conditions associated with disorders in which oxalate is detrimental, such as primary hyperoxalurias and secondary hyperoxalurias. In some embodiments, a bacterial cell of the invention has been engineered to comprise at least one heterologous gene encoding at least one oxalate catabolism enzyme and is capable of processing and reducing levels of oxalate, in low-oxygen environments, e.g., the gut. In some embodiments, a bacterial cell of the invention has been engineered to comprise at least one heterologous gene encoding an importer of oxalate and is capable of reducing levels of oxalate, in low-oxygen environments, e.g., the gut. In some embodiments, a bacterial cell of the invention has been engineered to comprise at least one heterologous gene encoding an exporter of formate and is capable of reducing levels of oxalate, in low-oxygen environments, e.g., the gut.

In some embodiments, a bacterial cell of the invention has been engineered to comprise at least one heterologous gene encoding an oxalate:formate antiporter and is capable of reducing levels of oxalate, in low-oxygen environments, e.g., the gut. In some embodiments, a bacterial cell of the invention has been engineered to comprise at least one heterologous gene encoding at least one oxalate catabolism enzyme and is capable of processing and reducing levels of oxalate, in inflammatory environments, such as may be present in the gut. In some embodiments, a bacterial cell of the invention has been engineered to comprise at least one heterologous gene encoding an importer of oxalate and is capable of reducing levels of oxalate, in inflammatory environments, e.g., such as may be present in the gut. In some embodiments, a bacterial cell of the invention has been engineered to comprise at least one heterologous gene encoding an exporter of formate and is capable of reducing levels of oxalate, in inflammatory environments, e.g., such as may be present in the gut. In some embodiments, a bacterial cell of the invention has been engineered to comprise at least one heterologous gene encoding an oxalate:formate antiporter and is capable of reducing levels of oxalate, in inflammatory environments, e.g., such as may be present in the gut.

In some embodiments, the at least one oxalate catabolism enzyme converts oxalate to formate or formyl CoA. In some embodiments, the at least one oxalate catabolism enzyme is selected from an oxalate-CoA ligase, (e.g., ScAAE3 from S. cerevisiae), an oxalyl-CoA decarboxylase (Oxc, e.g., from O. formigenes), and a formyl-CoA transferase (e.g., Frc, e.g., from O. formigenes). In some embodiments, the at least one heterologous gene encoding at least one oxalate catabolism enzyme is selected from a frc gene and an oxc gene In one embodiment, the at least one heterologous gene encoding an oxalate transporter is an oxlT gene. In some embodiments, the at least one heterologous gene encoding at least one oxalate catabolism enzyme is located on a plasmid in the bacterial cell. In some embodiments, the at least one heterologous gene encoding at least one oxalate catabolism enzyme is located on a chromosome in the bacterial cell. In some embodiments, the at least one heterologous gene encoding an oxalate transporter is located on a plasmid in the bacterial cell. In some embodiments, the at least one heterologous gene encoding the oxalate transporter is located on a chromosome in the bacterial cell. In some embodiments, the at least one heterologous gene encoding a formate exporter is located on a plasmid in the bacterial cell. In some embodiments, the at least one heterologous gene encoding a formate exporter is located on a chromosome in the bacterial cell. In some embodiments, the at least one heterologous gene encoding an oxalate:formate antiporter is located on a plasmid in the bacterial cell. In some embodiments, the at least one heterologous gene encoding an oxalate:formate antiporter is located on a chromosome in the bacterial cell.

In some embodiments, the engineered bacterial cell is a probiotic bacterial cell. In some embodiments, the engineered bacterial cell is a member of a genus selected from the group consisting of Bacteroides, Bifidobacterium, Clostridium, Escherichia, Lactobacillus and Lactococcus. In some embodiments, the engineered bacterial cell is of the genus Escherichia. In some embodiments, the recombinant bacterial cell is of the species Escherichia coli strain Nissle.

In some embodiments, the engineered bacterial cell is an auxotroph in a gene that is complemented when the engineered bacterial cell is present in a mammalian gut. In some embodiments, the mammalian gut is a human gut. In some embodiments, the engineered bacterial cell is an auxotroph in diaminopimelic acid or an enzyme in the thymine biosynthetic pathway. In some embodiments, the engineered bacterial cell further comprises a heterologous gene encoding a substance that is toxic to the bacterial cell that is operably linked to an inducible promoter, wherein the inducible promoter is directly or indirectly induced by an environmental condition not naturally present in the mammalian gut.

In another aspect, the invention provides a pharmaceutical composition comprising a recombinant bacterial cell comprising at least one heterologous gene encoding at least one oxalate catabolism enzyme operably linked to a first inducible promoter and a pharmaceutically acceptable carrier. In another aspect, the invention provides a pharmaceutical composition comprising a recombinant bacterial cell comprising at least one heterologous gene encoding at least one oxalate catabolism enzyme operably linked to a first inducible promoter, at least one heterologous gene encoding an oxalate transporter operably linked to a second inducible promoter, which may be the same or different promoter from the first inducible promoter, and a pharmaceutically acceptable carrier. In another aspect, the invention provides a pharmaceutical composition comprising a recombinant bacterial cell comprising at least one heterologous gene encoding at least one oxalate catabolism enzyme operably linked to a first inducible promoter, at least one heterologous gene encoding a formate exporter operably linked to a second inducible promoter, which may be the same or different promoter from the first inducible promoter, and a pharmaceutically acceptable carrier. In another aspect, the invention provides a pharmaceutical composition comprising a recombinant bacterial cell comprising at least one heterologous gene encoding at least one oxalate catabolism enzyme operably linked to a first inducible promoter, at least one heterologous gene encoding an oxalate:formate antiporter operably linked to a second inducible promoter, which may be the same or different promoter from the first inducible promoter, and a pharmaceutically acceptable carrier. In any of these embodiments, the first promoter and the second promoter may be separate copies of the same promoter. In some embodiments, the first inducible promoter, the second inducible promoter, or the first inducible promoter and the second inducible promoter, are each directly induced by environmental conditions. In some embodiments, the first inducible promoter, the second inducible promoter, or the first inducible promoter and the second inducible promoter, are each indirectly induced by environmental conditions. In some embodiments, the first inducible promoter, the second inducible promoter, or the first inducible promoter and the second inducible promoter, are each directly or indirectly induced by environmental conditions found in the gut of a mammal. In some embodiments, the first inducible promoter, the second inducible promoter, or the first inducible promoter and the second inducible promoter, are each directly or indirectly induced by low-oxygen or anaerobic conditions. In some embodiments, the first inducible promoter, the second inducible promoter, or the first inducible promoter and the second inducible promoter, are each directly or indirectly induced by inflammatory conditions. In some embodiments, the first inducible promoter, the second inducible promoter, or the first inducible promoter and the second inducible promoter, are each an FNR responsive promoter. In some embodiments, the first inducible promoter, the second inducible promoter, or the first inducible promoter and the second inducible promoter, are each an RNSresponsive promoter. In some embodiments, the first inducible promoter, the second inducible promoter, or the first inducible promoter and the second inducible promoter, are each an ROS responsive promoter. In another aspect, the invention provides a method for treating a disease or disorder in which oxalate is detrimental in a subject, the method comprising administering a an engineered bacterial cell or a pharmaceutical composition comprising an engineered bacterial cell to the subject, wherein the engineered bacterial cell comprises gene sequence encoding one or more oxalate catabolism enzyme(s). In another aspect, the invention provides a method for treating a disease or disorder in which oxalate is detrimental in a subject, the method comprising administering an engineered bacterial cell or a pharmaceutical composition comprising an engineered bacterial cell to the subject, wherein the engineered bacterial cell comprises gene sequence encoding one or more oxalate transporter(s). In another aspect, the invention provides a method for treating a disease or disorder in which oxalate is detrimental in a subject, the method comprising administering an engineered bacterial cell or a pharmaceutical composition comprising an engineered bacterial cell to the subject, wherein the engineered bacterial cell comprises gene sequence encoding one or more formate exporter(s). In another aspect, the invention provides a method for treating a disease or disorder in which oxalate is detrimental in a subject, the method comprising administering an engineered bacterial cell or a pharmaceutical composition comprising an engineered bacterial cell to the subject, wherein the engineered bacterial cell comprises gene sequence encoding one or more oxalate:formate antiporter(s). In another aspect, the invention provides a method for treating a disease or disorder in which oxalate is detrimental in a subject, the method comprising administering an engineered bacterial cell or a pharmaceutical composition comprising an engineered bacterial cell to the subject, wherein the engineered bacterial cell comprises gene sequence encoding one or more of the following: (i) oxalate catabolism enzyme(s); (ii) one or more oxalate transporter(s); (iii) one or more formate exporter(s); and (iv) one or more oxalate:formate antiporter(s).

In another aspect, the invention provides a method for treating a disease or disorder in which oxalate is detrimental in a subject, the method comprising administering an engineered bacterial cell or a pharmaceutical composition comprising an engineered bacterial cell to the subject, wherein the engineered bacterial cell expresses at least one heterologous gene encoding at least one oxalate catabolism enzyme in response to an exogenous environmental condition in the subject, thereby treating the disease or disorder in which oxalate is detrimental in the subject. In some embodiments, the engineered bacterial cell further expresses one or more of the following: (i) at least one heterologous gene encoding an importer of oxalate; (ii) at least one heterologous gene encoding an exporter of formate; and/or (iii) at least one heterologous gene encoding an oxalate:formate antiporter. In one aspect, the invention provides a method for treating a disorder in which oxalate is detrimental in a subject, the method comprising administering an engineered bacterial cell or a pharmaceutical composition of the invention to the subject, thereby treating the disorder in which oxalate is detrimental in the subject. In another aspect, the invention provides a method for decreasing a level of oxalate in plasma of a subject, the method comprising administering an engineered bacterial cell or a pharmaceutical composition of the invention to the subject, thereby decreasing the level of oxalate in the plasma of the subject. In another aspect, the invention provides a method for decreasing a level of oxalate in urine of a subject, the method comprising administering an engineered bacterial cell or a pharmaceutical composition of the invention to the subject, thereby decreasing the level of oxalate in the urine of the subject. In one embodiment, the level of oxalate is decreased in plasma of the subject after administering the engineered bacterial cell or pharmaceutical composition to the subject. In another embodiment, the level of oxalate is reduced in urine of the subject after administering the engineered bacterial cell or pharmaceutical composition to the subject. In one embodiment, the engineered bacterial cell or pharmaceutical composition is administered orally. In another embodiment, the method further comprises isolating a plasma sample from the subject or a urine sample from the subject after administering the engineered bacterial cell or pharmaceutical composition to the subject, and determining the level of oxalate in the plasma sample from the subject or the urine sample from the subject. In another embodiment, the method further comprises comparing the level of oxalate in the plasma sample from the subject or the urine sample from the subject to a control level of oxalate. In one embodiment, the control level of oxalate is the level of oxalate in the plasma of the subject or in the urine of the subject before administration of the engineered bacterial cell or pharmaceutical composition.

In one embodiment, the disorder in which oxalate is detrimental is a hyperoxaluria. In one embodiment, the hyperoxaluria is primary hyperoxaluria type I. In another embodiment, the hyperoxaluria is primary hyperoxaluria type II. In another embodiment, the hyperoxaluria is primary hyperoxaluria type III. In one embodiment, the hyperoxaluria is enteric hyperoxaluria. In another embodiment, the hyperoxaluria is dietary hyperoxaluria. In another embodiment, the hyperoxaluria is idiopathic hyperoxaluria.

In one embodiment, the subject is fed a meal within one hour of administering the pharmaceutical composition. In another embodiment, the subject is fed a meal concurrently with administering the pharmaceutical composition.

BRIEF DESCRIPTION OF THE DRAWINGS

FIG. 4A depicts a schematic of the reaction catalyzed by formyl-CoA:oxalate CoA-transferase (FCOCT; also called formyl-CoA transferase), which converts formyl-CoA and oxalate to oxalyl-CoA and formate. In a non-limiting example, the formyl-CoA:oxalate CoA-transferase is Frc from *O. formigenes*. FIG. 4B depicts a schematic of the reaction catalyzed acetyl-CoA:oxalate CoA-transferase (ACOCT), which converts acetyl-CoA and oxalate to oxalyl-CoA and acetate. In a non-limiting example, the acetyl-CoA:oxalate CoA-transferase is YfdE from *E. coli*. FIG. 4C depicts a schematic of the reaction catalyzed by oxalyl-CoA synthetase (OCL; also called oxalate-CoA ligase), which converts oxalate and CoA and ATP to oxalyl-CoA and AMP and di-phosphate. In a non-limiting example, the oxalate-CoA ligase is Saccharomyces cerevisiae acyl-activating enzyme 3 (ScAAE3). FIG. 4D depicts a schematic of the reaction catalyzed by Oxalyl-CoA Decarboxylase, which converts OxalylCoA to formyl-CoA and $CO_2$. In a non-limiting example, Oxalyl-CoA Decarboxylase is oxc from *O. formigenes*.

In FIG. 5A, the genetically engineered bacteria comprise one or more circuit(s) encoding an oxalate importer and/or oxalate importer/formate exporter and/or formate exporter, e.g., OxlT (oxalate:formate antiporter, e.g., from *O. formigenes*). In FIG. 5B, the genetically engineered bacteria comprise one or more oxalate catabolism circuit(s) encoding Oxalate-CoA ligase, (e.g., ScAAE3 from *S. cerevisiae*), an oxalyl-CoA decarboxylase (Oxc, e.g., from *O. formigenes*), and formyl-CoA transferase (e.g., Frc, e.g., from *O. formigenes*) and, optionally, one or more circuit(s) encoding an oxalate importer and/or oxalate importer/formate exporter and/or formate exporter, e.g., OxlT (oxalate:formate antiporter, e.g., from *O. formigenes*). In FIG. 5C, the genetically engineered bacteria comprise one or more oxalate catabolism circuit(s) encoding oxalyl-CoA decarboxylase (e.g., Oxc, e.g., from *O. formigenes*), and formyl-CoA transferase (e.g., Frc, e.g., from *O. formigenes*), and, optionally, one or more circuit(s) encoding an oxalate importer and/or oxalate importer/formate exporter and/or formate exporter, e.g., OxlT (oxalate:formate antiporter, e.g., from *O. formigenes*). In FIG. 5D, the genetically engineered bacteria comprise one or more oxalate catabolism circuit(s) encoding oxalate-CoA ligase (e.g., ScAAE3 from *S. cerevisiae*) and formyl-CoA transferase (e.g., frc, e.g., from *O. formigenes*), and, optionally, one or more circuit(s) encoding an oxalate importer and/or oxalate importer/formate exporter and/or formate exporter, e.g., OxlT (oxalate:formate antiporter, e.g., from *O. formigenes*). In FIG. 5E, the genetically engineered bacteria comprise one or more of three oxalate catabolism circuits, a first circuit encoding oxalate-CoA ligase (e.g., ScAAE3 from *S. cerevisiae*), a second circuit encoding oxalyl-CoA decarboxylase (e.g., oxc, e.g., from *O. formigenes*), and a third circuit encoding formyl-CoA transferase (e.g., Frc, e.g., from *O. formigenes*). In addition, the genetically engineered bacteria may optionally comprise one or more circuit(s) encoding an oxalate importer and/or oxalate importer/formate exporter and/or formate exporter, e.g., OxlT (oxalate:formate antiporter, e.g., from *O. formigenes*). In FIG. 5F, the genetically engineered bacteria comprise one or more of two oxalate catabolism circuits, a first circuit encoding oxalyl-CoA decarboxylase (e.g., Oxc, e.g., from *O. formigenes*), and a second circuit encoding formyl-CoA transferase. (Frc, e.g., from *O. formigenes*). In addition, the genetically engineered bacteria may optionally comprise one or more circuit(s) encoding an oxalate importer and/or oxalate importer/formate exporter and/or formate exporter, e.g., OxlT (oxalate:formate antiporter, e.g., from *O. formigenes*). In FIG. 5G, the genetically engineered bacteria comprise one or more oxalate catabolism circuit(s) encoding acetyl-CoA:oxalate CoA-transferase (e.g., yfdE from *E. coli*), oxalyl-CoA decarboxylase (Oxc, e.g., from *O. formigenes*), and formyl-CoA transferase (e.g., Frc, e.g., from *O. formigenes*) and optionally one or more circuit(s) encoding an oxalate importer and/or oxalate importer/formate exporter and/or formate exporter, e.g., OxlT (oxalate:formate antiporter, e.g., from *O. formigenes*).

FIG. 6A, FIG. 6B, FIG. 6C, and FIG. 6D depict schematics of oxalate degradation cassettes (FIG. 6A), oxalate degradation constructs (FIGS. 6B and 6C), and a bar graph showing the results of in vitro oxalate degradation assay (FIG. 6D). FIG. 6A depicts a schematic of the catabolic reactions occurring in a cassette comprising ScAAE3 (oxalate-CoA ligase, e.g., from *S. cerevisiae*), oxc (oxalyl-CoA decarboxylase, e.g., from *O. formigenes*), and frc (formyl-CoA transferase, e.g., from *O. formigenes*). FIGS. 6B and 6C depict schematics of the constructs used in the in vitro oxalate assay shown in FIG. 6D. FIG. 6B depicts a schematic of a gene cassette comprising ScAAE3 from *S. cerevisiae*, oxc from *O. formigenes*, and frc from *O. formigenes*, under the control of a tetracycline inducible promoter. FIG. 6C depicts a schematic of a gene cassette comprising OxlT from *O. formigenes*, under the control of a tetracycline inducible promoter. FIG. 6D depicts a bar graph showing the results of an in vitro oxalate degradation assay under high oxygen and low oxygen conditions, using a recombinant *E. coli* strain engineered to comprise a gene cassette encoding an oxalate:formate antiporter (OxlT) from *O. formigenes*, and a gene cassette encoding a formyl-CoA transferase (FRC) from *O. formigenes*, an oxalyl-CoA decarboxylase (OXC) from *O. formigenes*, and an oxalate-CoA ligase (ScAAE3) from *C. cerevisiae*. The expression of both gene cassettes is under the control of a tetracycline inducible promoter (see constructs in FIGS. 6B and 6C).

FIG. 7A, FIG. 7B, FIG. 7C, and FIG. 7D depicts schematics of circuits of the disclosure, under the control of an inducible promoter, e.g., a low oxygen inducible promoter, e.g., a FNR promoter. FIG. 7A depicts a schematic of a gene cassette encoding ScAAE3 from *S. cerevisiae*, Oxc from *Oxalobacter formigenes*, and Frc from *O. formigenes*, under the control of an inducible promoter, e.g., a low oxygen inducible promoter, e.g., a FNR promoter. FIG. 7B depicts a schematic of a gene cassette encoding OxlT (oxalate:formate antiporter from *O. formigenes*), under the control of an inducible promoter, e.g., a low oxygen inducible promoter, e.g., a FNR promoter. FIG. 7C depicts a schematic of a gene cassette encoding yfdE (acetyl-CoA:oxalate CoA-transferase from *E. coli*), Oxc from *Oxalobacter formigenes*, and Frc from *O. formigenes*, under the control of an inducible promoter, e.g., a low oxygen inducible promoter, e.g., a FNR promoter. FIG. 7D depicts a schematic of a gene cassette encoding Oxc from *Oxalobacter formigenes*, and Frc from *O. formigenes*, under the control of an inducible promoter, e.g., a low oxygen inducible promoter, e.g., a FNR promoter.

FIG. 16A depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the ParaBAD promoter ($P_{araBAD}$), which induces expression of the Tet repressor (TetR) and an anti-toxin. The anti-toxin builds up in the recombinant bacterial cell, while TetR prevents expression of a toxin (which is under the control of a promoter having a TetR binding site). However, when arabinose is not present, both the anti-toxin and TetR are not expressed. Since TetR is not present to repress expression of the toxin, the toxin is expressed and kills the cell. FIG. 16A also depicts another non-limiting embodiment of the disclosure, wherein the expression of an essential gene not found in the recombinant bacteria is activated by an exogenous environmental signal. In the absence of arabinose, the AraC transcription factor adopts a conformation that represses transcription of the essential gene under the control of the araBAD promoter and the bacterial cell cannot survive. In the presence of arabinose, the AraC transcription factor undergoes a conformational change that allows it to bind to and activate the araBAD promoter, which induces expression of the essential gene and maintains viability of the bacterial cell. FIG. 16B depicts a non-limiting embodiment of the disclosure, where an anti-toxin is expressed from a constitutive promoter, and expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the araBAD promoter, which induces expression of TetR, thus preventing expression of a toxin. However, when arabinose is not present, TetR is not expressed, and the toxin is expressed, eventually overcoming the anti-toxin and killing the cell. The constitutive promoter regulating expression of the anti-toxin should be a weaker promoter than the promoter driving expression of the toxin. The araC gene is under the control of a constitutive promoter in this circuit. FIG. 16C depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the araBAD promoter, which induces expression of the Tet repressor (TetR) and an anti-toxin. The anti-toxin builds up in the recombinant bacterial cell, while TetR prevents expression of a toxin (which is under the control of a promoter having a TetR binding site). However, when arabinose is not present, both the anti-toxin and TetR are not expressed. Since TetR is not present to repress expression of the toxin, the toxin is expressed and kills the cell. The araC gene is either under the control of a constitutive promoter or an inducible promoter (e.g., AraC promoter) in this circuit.

FIG. 19 depicts another non-limiting embodiment of the disclosure, where an exogenous environmental condition or one or more environmental signals activates expression of a heterologous gene and at least one recombinase from an inducible promoter or inducible promoters. The recombinase then flips at least one excision enzyme into an activated conformation. The at least one excision enzyme then excises one or more essential genes, leading to senescence, and eventual cell death. The natural kinetics of the recombinase and excision genes cause a time delay, the kinetics of which can be altered and optimized depending on the number and choice of essential genes to be excised, allowing cell death to occur within a matter of hours or days. The presence of multiple nested recombinases can be used to further control the timing of cell death.

FIG. 23B depicts a bar graph of FNRS promoter activity as a function of β-galactosidase activity. The engineered bacterial strain harboring a low-copy fnrS-lacZ fusion gene was grown in under aerobic and anaerobic conditions. Values for standard β-galactosidase colorimetric assays are expressed in Miller units (Miller, 1972). These data suggest that the fnrS promoter begins to drive high-level gene expression within 1 hr. under anaerobic conditions. FIG. 23C depicts a line graph of the growth of bacterial cell cultures expressing lacZ driven by the FNRS promoter over time, both in the presence and absence of oxygen.

FIG. 24A, FIG. 24B, FIG. 24C, FIG. 24D relate to ATC- and nitric oxide-inducible reporter constructs. FIG. 24A shows the activity of an ATC-inducible reporter construct. FIG. 24B shows the activity of a nitric oxide-inducible reporter construct. These constructs, when induced by their cognate inducer, lead to expression of GFP. Nissle cells harboring plasmids with either the control, ATC-inducible $P_{tet}$-GFP reporter construct or the nitric oxide inducible $P_{nsrR}$-GFP reporter construct induced across a range of concentrations. Promoter activity is expressed as relative florescence units. FIG. 24C depicts a schematic of the constructs. FIG. 24D depicts a dot blot of bacteria harboring a plasmid expressing NsrR under control of a constitutive promoter and the reporter gene gfp (green fluorescent protein) under control of an NsrR-inducible promoter. DSS-treated mice serve as exemplary models for HE. As in HE subjects, the guts of mice are damaged by supplementing drinking water with 2-3% dextran sodium sulfate (DSS). Chemiluminescent is shown for NsrR-regulated promoters induced in DSS-treated mice.

FIG. 26 depicts a bar graph of residence over time for streptomycin resistant Nissle.

FIG. 27A and FIG. 27B depicts a schematic diagram of a wild-type clbA construct (FIG. 27A) and a schematic diagram of a clbA knockout construct (FIG. 27B).

DETAILED DESCRIPTION OF THE INVENTION

Figure 1:
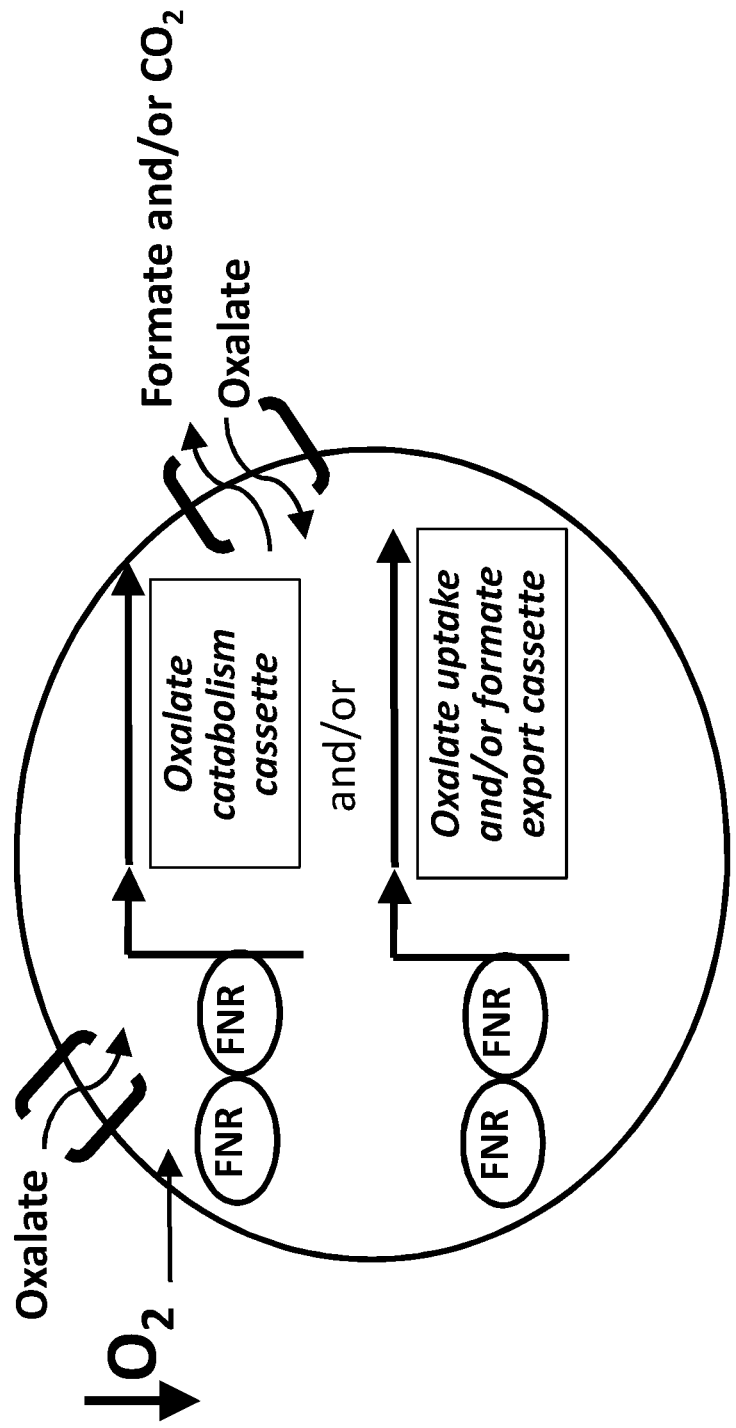
FIG. 1 depicts a schematic of an exemplary circuit described herein, which is inducible under anaerobic or low oxygen conditions and allows oxalate to be catabolized. Optionally, an additional cassette which facilitates the uptake of oxalate or the uptake of oxalate and/or export of formate, which is inducible under anaerobic or low oxygen conditions, is also provided. In other embodiments, a cassette which facilitates the uptake of oxalate or the uptake of oxalate and/or the export of formate is provided in the absence of one or more oxalate catabolism circuit.
Figure 2:
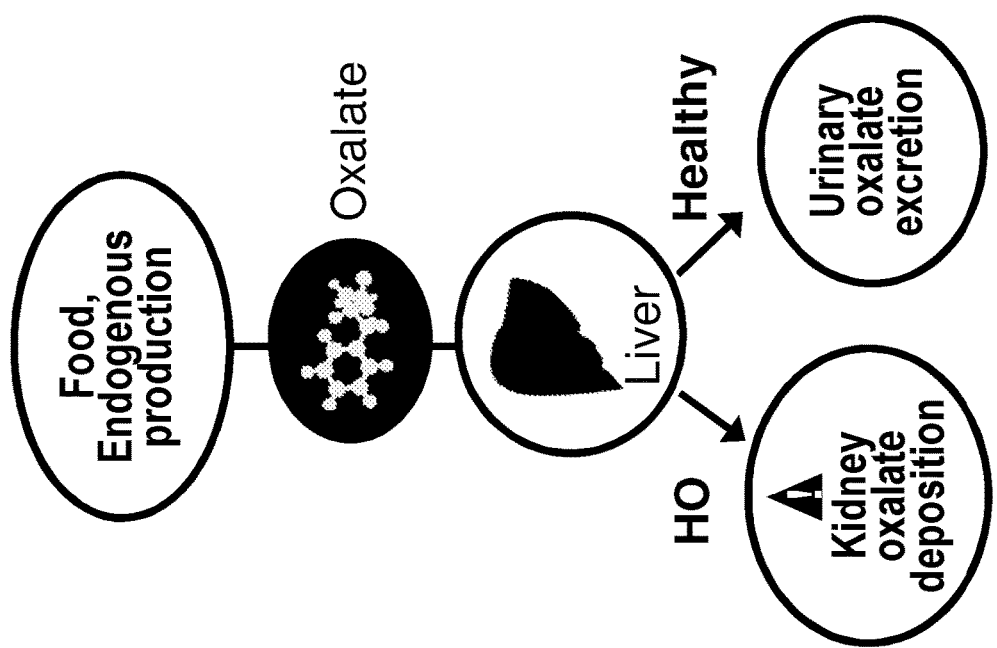
FIG. 2 depicts a schematic of the fate of oxalate taken up through food or produced endogenously in a healthy and a hypoxaluric state.

The disclosure includes engineered and programmed microorganisms, e.g., bacteria, yeast, viruses etc, pharmaceutical compositions thereof, and methods of modulating and treating disorders in which oxalate is detrimental. In some embodiments, the microorganism, e.g., bacterium, yeast, or virus, has been genetically engineered to comprise heterologous gene sequence(s) encoding one or more oxalate catabolism enzyme(s). In some embodiments, the microorganism, e.g., bacterium, yeast, or virus, has been genetically engineered to comprise heterologous gene sequence(s) encoding one or more oxalate catabolism enzyme(s) and is capable of processing and reducing oxalate and/or oxalic acid in low-oxygen environments, e.g., the gut. In some embodiments, the engineered microorganism comprises heterologous gene sequence(s) encoding one or more oxalate catabolism enzyme(s) and is capable of transporting oxalic acid and/or oxalate and/or another related metabolite(s) into the bacterium. Thus, the recombinant microorganism and pharmaceutical compositions comprising the microorganism of the invention may be used to catabolize oxalate or oxalic acid to treat and/or prevent conditions associated with disorders in which oxalate is detrimental. In one embodiment, the disorder in which oxalate is detrimental is a disorder involving the abnormal levels of oxalate, such as primary hyperoxalurias (i.e., PHI, PHII, and PHIII), secondary hyperoxaluria, enteric hyperoxaluria, dietary hyperoxaluria, or idiopathic hyperoxaluria.

In some embodiments, the engineered microorganism comprise gene sequence(s) encoding one or more of the following: (i) one or more transporter(s) of oxalate; (ii) one or more exporter(s) of formate; (iii) one or more polypeptide(s) which mediate both the transport (import) of oxalate and the export of formate (e.g., oxalate:formate antiporter(s)); and (iv) any combination thereof. In some embodiments, the microorganism has been engineered to comprise gene sequence(s) encoding one or more oxalate catabolism enzyme(s) and one or more of the following: (i) one or more transporter(s) of oxalate; (ii) one or more exporter(s) of formate; (iii) one or more polypeptide(s) which mediate both the transport (import) of oxalate and the export of formate (e.g., oxalate:formate antiporter(s)); and (iv) any combination thereof.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, the term "microorganism" or "recombinant microorganism" refers to a microorganism, e.g., bacterial or viral cell, or bacteria or virus, that has been genetically modified from its native state. Thus, a "recombinant bacterial cell" or "recombinant bacteria" refers to a bacterial cell or bacteria that have been genetically modified from their native state. For instance, a recombinant bacterial cell may have nucleotide insertions, nucleotide deletions, nucleotide rearrangements, and nucleotide modifications introduced into their DNA. These genetic modifications may be present in the chromosome of the bacteria or bacterial cell, or on a plasmid in the bacteria or bacterial cell. Recombinant bacterial cells disclosed herein may comprise exogenous nucleotide sequences on plasmids. Alternatively, recombinant bacterial cells may comprise exogenous nucleotide sequences stably incorporated into their chromosome.

A "programmed or engineered microorganism" refers to a microorganism, e.g., bacterial or viral cell, or bacteria or virus, that has been genetically modified from its native state to perform a specific function. Thus, a "programmed or engineered bacterial cell" or "programmed or engineered bacteria" or "genetically engineered bacterial cell or bacteria" refers to a bacterial cell or bacteria that has been genetically modified from its native state to perform a specific function, e.g., to metabolize a metabolite, e.g., oxalate. In certain embodiments, the programmed or engineered bacterial cell has been modified to express one or more proteins, for example, one or more proteins that have a therapeutic activity or serve a therapeutic purpose. The programmed or engineered bacterial cell may additionally have the ability to stop growing or to destroy itself once the protein(s) of interest have been expressed.

As used herein, the term "gene" refers to a nucleic acid fragment that encodes a protein or fragment thereof, optionally including regulatory sequences preceding (5' non-coding sequences) and following (3' non-coding sequences) the coding sequence. In one embodiment, a "gene" does not include regulatory sequences preceding and following the coding sequence. A "native gene" refers to a gene as found in nature, optionally with its own regulatory sequences preceding and following the coding sequence. A "chimeric gene" refers to any gene that is not a native gene, optionally comprising regulatory sequences preceding and following the coding sequence, wherein the coding sequences and/or the regulatory sequences, in whole or in part, are not found together in nature. Thus, a chimeric gene may comprise regulatory sequences and coding sequences that are derived from different sources, or regulatory and coding sequences that are derived from the same source, but arranged differently than is found in nature.

As used herein, the term "gene sequence" is meant to refer to a genetic sequence, e.g., a nucleic acid sequence. The gene sequence or genetic sequence is meant to include a complete gene sequence or a partial gene sequence. The gene sequence or genetic sequence is meant to include sequence that encodes a protein or polypeptide and is also meant to include genetic sequence that does not encode a protein or polypeptide, e.g., a regulatory sequence, leader sequence, signal sequence, or other non-protein coding sequence.

As used herein, a "heterologous" gene or "heterologous sequence" refers to a nucleotide sequence that is not normally found in a given cell in nature. As used herein, a heterologous sequence encompasses a nucleic acid sequence that is exogenously introduced into a given cell and can be a native sequence (naturally found or expressed in the cell) or non-native sequence (not naturally found or expressed in the cell) and can be a natural or wild-type sequence or a variant, non-natural, or synthetic sequence. "Heterologous gene" includes a native gene, or fragment thereof, that has been introduced into the host cell in a form that is different from the corresponding native gene. For example, a heterologous gene may include a native coding sequence that is a portion of a chimeric gene to include non-native regulatory regions that is reintroduced into the host cell. A heterologous gene may also include a native gene, or fragment thereof, introduced into a non-native host cell. Thus, a heterologous gene may be foreign or native to the recipient cell; a nucleic acid sequence that is naturally found in a given cell but expresses an unnatural amount of the nucleic acid and/or the polypeptide which it encodes; and/or two or more nucleic acid sequences that are not found in the same relationship to each other in nature. As used herein, the term "endogenous gene" refers to a native gene in its natural location in the genome of an organism. As used herein, the term "transgene" refers to a gene that has been introduced into the host organism, e.g., host bacterial cell, genome.

As used herein, a "non-native" nucleic acid sequence refers to a nucleic acid sequence not normally present in a microorganism, e.g., an extra copy of an endogenous sequence, or a heterologous sequence such as a sequence from a different species, strain, or substrain of bacteria or virus, or a sequence that is modified and/or mutated as compared to the unmodified sequence from bacteria or virus of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in gene cassette. In some embodiments, "non-native" refers to two or more nucleic acid sequences that are not found in the same relationship to each other in nature. The non-native nucleic acid sequence may be present on a plasmid or chromosome. In some embodiments, the genetically engineered microorganism of the disclosure comprises a gene and/or gene cassette that is operably linked to a promoter that is not associated with said gene in nature. For example, in some embodiments, the genetically engineered bacteria disclosed herein comprise a gene or gene cassette encoding one or more oxalate-metabolizing enzyme(s) described herein and/or one or more oxalate transporter(s), one or more exporter(s) (e.g., of formate) and/or one or more antiporter(s)(e.g., oxalate:formate antiporter(s)) that is operably linked to a directly or indirectly inducible promoter that is not associated with said gene in nature, e.g., an FNR responsive one or more oxalate-metabolizing enzyme(s) described herein and/or one or more oxalate transporter(s), one or more exporter(s) (e.g., of formate) and/or one or more antiporter(s)(e.g., oxalate:formate antiporter(s)) (or other promoter disclosed herein) operably linked to a gene encoding a one or more oxalate-metabolizing enzyme(s) described herein and/or one or more oxalate transporter(s), one or more exporter(s) (e.g., of formate) and/or one or more antiporter(s)(e.g., oxalate:formate antiporter(s)). In some embodiments, the genetically engineered virus of the disclosure comprises a gene or gene cassette that is operably linked to a directly or indirectly inducible promoter that is not associated with said gene or gene cassette in nature, e.g., a promoter operably linked to a gene and/or gene cassette encoding one or more oxalate-metabolizing enzyme(s) and/or one or more oxalate transporter(s) and/or one or more exporter(s) (e.g., of formate) and/or one or more antiporter(s)(e.g., oxalate:formate antiporter(s)).

As used herein, the term "coding region" refers to a nucleotide sequence that codes for a specific amino acid sequence. The term "regulatory sequence" refers to a nucleotide sequence located upstream (5' non-coding sequences), within, or downstream (3' non-coding sequences) of a coding sequence, and which influences the transcription, RNA processing, RNA stability, or translation of the associated coding sequence. Examples of regulatory sequences include, but are not limited to, promoters, translation leader sequences, effector binding sites, signal sequences, and stem-loop structures. In one embodiment, the regulatory sequence comprises a promoter, e.g., an FNR responsive promoter or other promoter disclosed herein.

"Operably linked" refers to the association of nucleic acid sequences on a single nucleic acid fragment so that the function of one is affected by the other. A regulatory element is operably linked with a coding sequence when it is capable of affecting the expression of the gene coding sequence, regardless of the distance between the regulatory element and the coding sequence. More specifically, operably linked refers to a nucleic acid sequence, e.g., a gene or gene cassette encoding one or more an oxalate catabolism enzyme, that is joined to a regulatory sequence in a manner which allows expression of the nucleic acid sequence, e.g., the gene(s) or gene cassettes encoding one or more oxalate catabolism enzyme(s) and/or one or more oxalate transporter(s), one or more exporter(s) (e.g., of formate) and/or one or more antiporter(s)(e.g., oxalate:formate antiporter(s)). In other words, the regulatory sequence acts in cis. In one embodiment, a gene may be "directly linked" to a regulatory sequence in a manner which allows expression of the gene. In another embodiment, a gene may be "indirectly linked" to a regulatory sequence in a manner which allows expression of the gene. In one embodiment, two or more genes may be directly or indirectly linked to a regulatory sequence in a manner which allows expression of the two or more genes. A regulatory region or sequence is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

A "promoter" as used herein, refers to a nucleotide sequence that is capable of controlling the expression of a coding sequence or gene. Promoters are generally located 5' of the sequence that they regulate. Promoters may be derived in their entirety from a native gene, or be composed of different elements derived from promoters found in nature, and/or comprise synthetic nucleotide segments. Those skilled in the art will readily ascertain that different promoters may regulate expression of a coding sequence or gene in response to a particular stimulus, e.g., in a cell- or tissue-specific manner, in response to different environmental or physiological conditions, or in response to specific compounds. Prokaryotic promoters are typically classified into two classes: inducible and constitutive. A "constitutive promoter" refers to a promoter that allows for continual transcription of the coding sequence or gene under its control.

"Constitutive promoter" refers to a promoter that is capable of facilitating continuous transcription of a coding sequence or gene under its control and/or to which it is operably linked. Constitutive promoters and variants are well known in the art and include, but are not limited to, Ptac promoter, BBa_J23100, a constitutive *Escherichia coli* $\sigma^S$ promoter (e.g., an osmY promoter (International Genetically Engineered Machine (iGEM) Registry of Standard Biological Parts Name BBa_J45992; BBa_J45993)), a constitutive *Escherichia coli* $\sigma^{32}$ promoter (e.g., htpG heat shock promoter (BBa_J45504)), a constitutive *Escherichia coli* $\sigma^{70}$ promoter (e.g., lacq promoter (BBa_J54200; BBa_J56015), *E. coli* CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive *Bacillus subtilis* $\sigma^A$ promoter (e.g., promoter veg (BBa_K143013), promoter 43 (BBa_K143013), $P_{liaG}$ (BBa_K823000), $P_{lepA}$ (BBa_K823002), $P_{veg}$ (BBa_K823003)), a constitutive *Bacillus subtilis* $\sigma^B$ promoter (e.g., promoter ctc (BBa_K143010), promoter gsiB (BBa_K143011)), a *Salmonella* promoter (e.g., Pspv2 from *Salmonella* (BBa_K112706), Pspv from *Salmonella* (BBa_K112707)), a bacteriophage T7 promoter (e.g., T7 promoter (BBa_I712074; BBa_I719005; BBa_J34814; BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), and a bacteriophage SP6 promoter (e.g., SP6 promoter (BBa_J64998)).

An "inducible promoter" refers to a regulatory region that is operably linked to one or more genes, wherein expression of the gene(s) is increased in the presence of an inducer of said regulatory region. An "inducible promoter" refers to a promoter that initiates increased levels of transcription of the coding sequence or gene under its control in response to a stimulus or an exogenous environmental condition. A "directly inducible promoter" refers to a regulatory region, wherein the regulatory region is operably linked to a gene and/or gene cassette encoding one or more oxalate-metabolizing enzyme(s) and/or one or more oxalate transporter(s) and/or one or more exporter(s) (e.g., of formate) and/or one or more antiporter(s) (e.g., oxalate:formate antiporter(s)), where, in the presence of an inducer of said regulatory region, the protein or polypeptide is expressed. An "indirectly inducible promoter" refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by "inducible promoter." Exemplary inducible promoters described herein include oxygen level-dependent promoters (e.g., FNR-inducible promoter), promoters induced by inflammation or an inflammatory response (RNS, ROS promoters), and promoters induced by a metabolite that may or may not be naturally present (e.g., can be exogenously added) in the gut, e.g., arabinose and tetracycline. Examples of inducible promoters include, but are not limited to, an FNR responsive promoter, a $P_{araC}$ promoter, a $P_{araBAD}$ promoter, and a $P_{TetR}$ promoter, each of which are described in more detail herein. Examples of other inducible promoters are provided herein below.

As used herein, "stably maintained" or "stable" bacterium is used to refer to a bacterial host cell carrying non-native genetic material, e.g., a gene and/or gene cassette encoding one or more oxalate-metabolizing enzyme(s) and/or one or more oxalate transporter(s) and/or one or more exporter(s) (e.g., of formate) and/or one or more antiporter(s)(e.g., oxalate:formate antiporter(s)), which is incorporated into the host genome or propagated on a self-replicating extrachromosomal plasmid, such that the non-native genetic material is retained, expressed, and propagated. The stable bacterium is capable of survival and/or growth in vitro, e.g., in medium, and/or in vivo, e.g., in the gut. For example, the stable bacterium may be a genetically engineered bacterium comprising a gene and/or gene cassette encoding one or more oxalate-metabolizing enzyme(s) and/or one or more oxalate transporter(s) and/or one or more exporter(s) (e.g., of formate) and/or one or more antiporter(s)(e.g., oxalate: formate antiporter(s)), in which the plasmid or chromosome carrying the gene is stably maintained in the bacterium, such that the one or more oxalate-metabolizing enzyme(s) and/or one or more oxalate transporter(s) and/or one or more exporter(s) (e.g., of formate) and/or one or more antiporter(s)(e.g., oxalate:formate antiporter(s)) can be expressed in the bacterium, and the bacterium is capable of survival and/or growth in vitro and/or in vivo. In some embodiments, copy number affects the stability of expression of the non-native genetic material. In some embodiments, copy number affects the level of expression of the non-native genetic material.

As used herein, the term "expression" refers to the transcription and stable accumulation of sense (mRNA) or anti-sense RNA derived from a nucleic acid, and/or to translation of an mRNA into a polypeptide.

As used herein, the term "plasmid" or "vector" refers to an extrachromosomal nucleic acid, e.g., DNA, construct that is not integrated into a bacterial cell's genome. Plasmids are usually circular and capable of autonomous replication. Plasmids may be low-copy, medium-copy, or high-copy, as is well known in the art. Plasmids may optionally comprise a selectable marker, such as an antibiotic resistance gene, which helps select for bacterial cells containing the plasmid and which ensures that the plasmid is retained in the bacterial cell. A plasmid disclosed herein may comprise a nucleic acid sequence encoding a heterologous gene, e.g., a gene and/or gene cassette encoding one or more oxalate-metabolizing enzyme(s) and/or one or more oxalate transporter(s) and/or one or more exporter(s) (e.g., of formate) and/or one or more antiporter(s) (e.g., oxalate:formate antiporter(s)).

As used herein, the term "transform" or "transformation" refers to the transfer of a nucleic acid fragment into a host bacterial cell, resulting in genetically-stable inheritance. Host bacterial cells comprising the transformed nucleic acid fragment are referred to as "recombinant" or "transgenic" or "transformed" organisms.

The term "genetic modification," as used herein, refers to any genetic change. Exemplary genetic modifications include those that increase, decrease, or abolish the expression of a gene, including, for example, modifications of native chromosomal or extrachromosomal genetic material. Exemplary genetic modifications also include the introduction of at least one plasmid, modification, mutation, base deletion, base addition, base substitution, and/or codon modification of chromosomal or extrachromosomal genetic sequence(s), gene over-expression, gene amplification, gene suppression, promoter modification or substitution, gene addition (either single or multi-copy), antisense expression or suppression, or any other change to the genetic elements of a host cell, whether the change produces a change in phenotype or not. Genetic modification can include the introduction of a plasmid, e.g., a plasmid comprising a gene and/or gene cassette encoding one or more oxalate-metabolizing enzyme(s) and/or one or more oxalate transporter(s) and/or one or more exporter(s) (e.g., of formate) and/or one or more antiporter(s) (e.g., oxalate:formate antiporter(s)) operably linked to a promoter, into a bacterial cell. Genetic modification can also involve a targeted replacement in the chromosome, e.g., to replace a native gene promoter with an inducible promoter, regulated promoter, strong promoter, or constitutive promoter. Genetic modification can also involve gene amplification, e.g., introduction of at least one additional copy of a native gene into the chromosome of the cell. Alternatively, chromosomal genetic modification can involve a genetic mutation.

As used herein, the term "genetic mutation" refers to a change or changes in a nucleotide sequence of a gene or related regulatory region that alters the nucleotide sequence as compared to its native or wild-type sequence. Mutations include, for example, substitutions, additions, and deletions, in whole or in part, within the wild-type sequence. Such substitutions, additions, or deletions can be single nucleotide changes (e.g., one or more point mutations), or can be two or more nucleotide changes, which may result in substantial changes to the sequence. Mutations can occur within the coding region of the gene as well as within the non-coding and regulatory sequence of the gene. The term "genetic mutation" is intended to include silent and conservative mutations within a coding region as well as changes which alter the amino acid sequence of the polypeptide encoded by the gene. A genetic mutation in a gene coding sequence may, for example, increase, decrease, or otherwise alter the activity (e.g., enzymatic activity) of the gene's polypeptide product. A genetic mutation in a regulatory sequence may increase, decrease, or otherwise alter the expression of sequences operably linked to the altered regulatory sequence.

Specifically, the term "genetic modification that reduces export of oxalate from the bacterial cell" refers to a genetic modification that reduces the rate of export or quantity of export of an oxalate from the bacterial cell, as compared to the rate of export or quantity of export of oxalate from a bacterial cell not having said modification, e.g., a wild-type bacterial cell. In one embodiment, a recombinant bacterial cell having a genetic modification that reduces export of oxalate from the bacterial cell comprises a genetic mutation in a native gene. In another embodiment, a recombinant bacterial cell having a genetic modification that reduces export of oxalate from the bacterial cell comprises a genetic mutation in a native promoter, which reduces or inhibits transcription of a gene encoding an oxalate exporter. In another embodiment, a recombinant bacterial cell having a genetic modification that reduces export of oxalate from the bacterial cell comprises a genetic mutation leading to overexpression of a repressor of an exporter of oxalate. In another embodiment, a recombinant bacterial cell having a genetic modification that reduces export of oxalate from the bacterial cell comprises a genetic mutation which reduces or inhibits translation of the gene encoding the oxalate exporter.

Moreover, the term "genetic modification that increases import of oxalate into the bacterial cell" refers to a genetic modification that increases the uptake rate or increases the uptake quantity of oxalate into the cytosol of the bacterial cell, as compared to the uptake rate or uptake quantity of the oxalate into the cytosol of a bacterial cell not having said modification, e.g., a wild-type bacterial cell. In some embodiments, an engineered bacterial cell having a genetic modification that increases import of oxalate into the bacterial cell refers to a bacterial cell comprising a heterologous gene sequence (native or non-native) encoding one or more importer/transporter(s) of oxalate. In some embodiments, the genetically engineered bacteria comprising genetic modification that increases import of oxalate into the bacterial cell comprise gene sequence(s) encoding an oxalate transporter or other metabolite transporter or an antiporter, e.g. an oxalate:formate antiporter, that transports oxalate into the bacterial cell. The transporter can be any transporter that assists or allows import of oxalate into the cell. In certain embodiments, the oxalate transporter is antiporter, e.g. an oxalate:formate antiporter, e.g., OxlT, e.g. from *O. formigenes*. In certain embodiments, the engineered bacterial cell contains gene sequence encoding OxlT, e.g. from *O. formigenes*. In some embodiments, the engineered bacteria comprise more than one copy of gene sequence encoding an oxalate transporter, e.g., an oxalate:formate antiporter, e.g., OxlT, e.g. from *O. formigenes*. In some embodiments, the engineered bacteria comprise gene sequence(s) encoding more than one oxalate transporter, e.g., two or more different oxalate transporters.

As used herein, the term "transporter" is meant to refer to a mechanism, e.g., protein, proteins, or protein complex, for importing a molecule, e.g., amino acid, peptide (di-peptide, tri-peptide, polypeptide, etc.), toxin, metabolite, substrate, as well as other biomolecules into the microorganism from the extracellular milieu. As used herein, the term "transporter" also includes antiporters, which can import and export metabolites, e.g. such as oxalate:formate antiporters described herein. As used herein, the terms "transporter" and "importer" are used equivalently.

The term "oxalate" as used herein, refers to the dianion of the formula $C_2O_4^{2-}$. Oxalate is the conjugate base of oxalic acid. The term "oxalic acid," as used herein, refers to a dicarboxylic acid with the chemical formula $H_2C_2O_4$.

As used herein, the phrase "exogenous environmental condition" or "exogenous environment signal" refers to settings, circumstances, stimuli, or biological molecules under which a promoter described herein is directly or indirectly induced. The phrase "exogenous environmental conditions" is meant to refer to the environmental conditions external to the engineered microorganism, but endogenous or native to the host subject environment. Thus, "exogenous" and "endogenous" may be used interchangeably to refer to environmental conditions in which the environmental conditions are endogenous to a mammalian body, but external or exogenous to an intact microorganism cell. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, the exogenous environmental conditions are low-oxygen, microaerobic, or anaerobic conditions, such as the environment of the mammalian gut. In some embodiments, exogenous environmental conditions are molecules or metabolites that are specific to the mammalian gut, e.g., propionate. In some embodiments, the exogenous environmental condition is a tissue-specific or disease-specific metabolite or molecule(s). In some embodiments, the exogenous environmental condition is specific to a disease, e.g., hyperoxaluria. In some embodiments, the exogenous environmental condition is a low-pH environment. In some embodiments, the genetically engineered microorganism of the disclosure comprises a pH-dependent promoter. In some embodiments, the genetically engineered microorganism of the disclosure comprise an oxygen level-dependent promoter. In some aspects, bacteria have evolved transcription factors that are capable of sensing oxygen levels. Different signaling pathways may be triggered by different oxygen levels and occur with different kinetics. An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR (fumarate and nitrate reductase), ANR, and DNR. Corresponding FNR-responsive promoters, ANR (anaerobic nitrate respiration)—responsive promoters, and DNR (dissimilatory nitrate respiration regulator)—responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003), and non-limiting examples are shown in Table 1.

In a non-limiting example, a promoter (PfnrS) was derived from the *E. coli* Nissle fumarate and nitrate reductase gene S (fnrS) that is known to be highly expressed under conditions of low or no environmental oxygen (Durand and Storz, 2010; Boysen et al, 2010). The PfnrS promoter is activated under anaerobic conditions by the global transcriptional regulator FNR that is naturally found in Nissle. Under anaerobic conditions, FNR forms a dimer and binds to specific sequences in the promoters of specific genes under its control, thereby activating their expression. However, under aerobic conditions, oxygen reacts with iron-sulfur clusters in FNR dimers and converts them to an inactive form. In this way, the PfnrS inducible promoter is adopted to modulate the expression of proteins or RNA. PfnrS is used interchangeably in this application as FNRS, fnrs, FNR, P-FNRS promoter and other such related designations to indicate the promoter PfnrS.

TABLE 1

Examples of transcription factors and responsive genes and regulatory regions

| Transcription Factor | Examples of responsive genes, promoters, and/or regulatory regions: |
|---|---|
| FNR | nirB, ydfZ, pdhR, focA, ndH, hlyE, narK, narX, narG, yfiD, tdcD |
| ANR | arcDABC |
| DNR | norb, norC | presence or absence of reactive oxygen species (ROS). In other embodiments, the exogenous environmental conditions are the presence or absence of reactive nitrogen species (RNS). In some embodiments, exogenous environmental conditions are biological molecules that are involved in the inflammatory response, for example, molecules present in an inflammatory disorder of the gut. In some embodiments, the exogenous environmental conditions or signals exist naturally or are naturally absent in the environment in which the recombinant bacterial cell resides. In some embodiments, the exogenous environmental conditions or signals are artificially created, for example, by the creation or removal of biological conditions and/or the administration or removal of biological molecules.

In some embodiments, the exogenous environmental condition(s) and/or signal(s) stimulates the activity of an inducible promoter. In some embodiments, the exogenous environmental condition(s) and/or signal(s) that serves to activate the inducible promoter is not naturally present within the gut of a mammal. In some embodiments, the inducible promoter is stimulated by a molecule or metabolite that is administered in combination with the pharmaceutical composition of the disclosure, for example, tetracycline, arabinose, or any biological molecule that serves to activate an inducible promoter. In some embodiments, the exogenous environmental condition(s) and/or signal(s) is added to culture media comprising a recombinant bacterial cell of the disclosure. In some embodiments, the exogenous environmental condition that serves to activate the inducible promoter is naturally present within the gut of a mammal (for example, low oxygen or anaerobic conditions, or biological molecules involved in an inflammatory response). In some embodiments, the loss of exposure to an exogenous environmental condition (for example, in vivo) inhibits the activity of an inducible promoter, as the exogenous environmental condition is not present to induce the promoter (for example, an aerobic environment outside the gut). "Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

"Microorganism" refers to an organism or microbe of microscopic, submicroscopic, or ultramicroscopic size that typically consists of a single cell. Examples of microorganisms include bacteria, viruses, parasites, fungi, certain algae, and protozoa. In some aspects, the microorganism is engineered ("engineered microorganism") to produce one or more therapeutic molecules, e.g., oxalate catabolism enzyme(s). In certain embodiments, the engineered microorganism is an engineered bacterium. In certain embodiments, the engineered microorganism is an engineered virus.

"Non-pathogenic bacteria" refer to bacteria that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria do not contain lipopolysaccharides (LPS). In some embodiments, non-pathogenic bacteria are commensal bacteria. Examples of non-pathogenic bacteria include, but are not limited to certain strains belonging to the genus *Bacillus, Bacteroides, Bifidobacterium, Brevibacte-* ria, *Clostridium, Enterococcus, Escherichia coli, Lactobacillus, Lactococcus, Saccharomyces,* and *Staphylococcus,* e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Escherichia coli Nissle, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis* and *Saccharomyces boulardii* (Sonnenborn et al., 2009; Dinleyici et al., 2014; U.S. Pat. Nos. 6,835,376; 6,203,797; 5,589,168; 7,731,976). Non-pathogenic bacteria also include commensal bacteria, which are present in the indigenous microbiota of the gut. In one embodiment, the disclosure further includes non-pathogenic Saccharomyces, such as *Saccharomyces boulardii.* Naturally pathogenic bacteria may be genetically engineered to reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. In some embodiments, the probiotic bacteria are Gram-negative bacteria. In some embodiments, the probiotic bacteria are Gram-positive bacteria. Some species, strains, and/or subtypes of non-pathogenic bacteria are currently recognized as probiotic bacteria. Examples of probiotic bacteria include, but are not limited to, certain strains belonging to the genus *Bifidobacteria, Escherichia coli, Lactobacillus,* and *Saccharomyces* e.g., *Bifidobacterium bifidum, Enterococcus faecium, Escherichia coli* strain *Nissle, Lactobacillus acidophilus, Lactobacillus bulgaricus, Lactobacillus paracasei, and Lactobacillus plantarum,* and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, the term "auxotroph" or "auxotrophic" refers to an organism that requires a specific factor, e.g., an amino acid, a sugar, or other nutrient) to support its growth. An "auxotrophic modification" is a genetic modification that causes the organism to die in the absence of an exogenously added nutrient essential for survival or growth because it is unable to produce said nutrient. As used herein, the term "essential gene" refers to a gene which is necessary to for cell growth and/or survival. Essential genes are described in more detail infra and include, but are not limited to, DNA synthesis genes (such as thyA), cell wall synthesis genes (such as dapA), and amino acid genes (such as serA and metA).

As used herein, the terms "modulate" and "treat" and their cognates refer to an amelioration of a disease, disorder, and/or condition, or at least one discernible symptom thereof. In another embodiment, "modulate" and "treat" refer to an amelioration of at least one measurable physical parameter, not necessarily discernible by the patient. In another embodiment, "modulate" and "treat" refer to inhibiting the progression of a disease, disorder, and/or condition, either physically (e.g., stabilization of a discernible symptom), physiologically (e.g., stabilization of a physical parameter), or both. In another embodiment, "modulate" and "treat" refer to slowing the progression or reversing the progression of a disease, disorder, and/or condition. As used herein, "prevent" and its cognates refer to delaying the onset or reducing the risk of acquiring a given disease, disorder and/or condition or a symptom associated with such disease, disorder, and/or condition.

Those in need of treatment may include individuals already having a particular medical disease, as well as those at risk of having, or who may ultimately acquire the disease. The need for treatment is assessed, for example, by the presence of one or more risk factors associated with the development of a disease, the presence or progression of a disease, or likely receptiveness to treatment of a subject having the disease. Disorders in which oxalate is detrimental, e.g., a hyperoxaluria, may be caused by inborn genetic mutations for which there are no known cures. Diseases can also be secondary to other conditions, e.g., an intestinal disorder. Treating diseases in which oxalate is detrimental, such as a primary hyperoxaluria or secondary hyperoxaluria, may encompass reducing normal levels of oxalate and/or oxalic acid, reducing excess levels of oxalate and/or oxalic acid, or eliminating oxalate, and/or oxalic acid, and does not necessarily encompass the elimination of the underlying disease.

As used herein, the term "catabolism" refers to the cellular uptake of oxalate, and/or degradation of oxalate into its corresponding oxalyl CoA, and/or the degradation of oxalyl CoA formate and carbon dioxide. In one embodiment, the cellular uptake of oxalate occurs in the kidney. In one embodiment, the cellular uptake occurs in the liver. In one embodiment, the cellular uptake of oxalate occurs in the intestinal tract. In one embodiment, the cellular uptake of oxalate occurs in the stomach. In one embodiment, the cellular uptake is mediated by a SLC26 transporting protein (see Robijn et al. (2011)). In one embodiment, the cellular uptake is mediated by the transport protein SLC26A1. In one embodiment, the cellular uptake is mediated by the transport protein SLC26A6. In one embodiment, the cellular uptake of oxalate is mediated by a paracellular transport system. In one embodiment, the cellular uptake of oxalate is mediated by a transcellular transport system.

In one embodiment, "abnormal catabolism" refers to a decrease in the rate of cellular uptake of oxalate. In one embodiment, "abnormal catabolism" refers to any condition(s), disorder(s), disease(s), predisposition(s), and/or genetic mutations(s) that result in daily urinary oxalate excretion over 40 mg per 24 hours. In one embodiment, "abnormal catabolism" refers to an inability and/or decreased capacity of an organ and/or system to process and/or mediate the cellular uptake of oxalate. In one embodiment, said inability or decreased capacity of an organ and/or system to process and/or mediate the cellular uptake of oxalate is caused by the increased endogenous production of oxalate. In one embodiment, increased endogenous production of oxalate results from the absence of, or a deficiency in, the peroxisomal liver enzyme AGT. In one embodiment, increased endogenous production of oxalate results from the absence of, or a deficiency in the enzyme GRHPR. In one embodiment, increased endogenous production of oxalate results from the absence of, or a deficiency in the enzyme 4-hydroxy-2-oxoglutarate aldolase. In one embodiment, said inability or decreased capacity of an organ and/or system to process and/or mediate the cellular uptake of oxalate is caused by increased absorption of oxalate. In one embodiment, said increased absorption of oxalate results from an increased dietary intake of oxalate. In one embodiment, said increased absorption of oxalate results from increased intestinal absorption of oxalate. In one embodiment, said increased absorption of oxalate results from excessive intake of oxalate precursors. In one embodiment, said increased absorption of oxalate results from a decrease in intestinal oxalate-degrading microorganisms. In one embodiment, said increased absorption of oxalate results from genetic variations of intestinal oxalate transporters.

In one embodiment, a "disorder in which oxalate is detrimental" is a disease or disorder involving the abnormal, e.g., increased, levels of oxalate and/or oxalic acid or molecules directly upstream, such as glyoxylate. In one embodiment, the disorder in which oxalate is detrimental is a disorder or disease in which hyperoxaluria is observed in the subject. In one embodiment the disorder in which oxalate is detrimental refers to any condition(s), disorder(s), disease(s), predisposition(s), and/or genetic mutations(s) that result in daily urinary oxalate excretion over 40 mg per 24 hours. In one embodiment the disorder in which oxalate is detrimental is a disorder or disease selected from the group consisting of: PHI, PHII, PHII, secondary hyperoxaluria, enteric hyperoxaluria, syndrome of bacterial overgrowth, Crohn's disease, inflammatory bowel disease, hyperoxaluria following renal transplantation, hyperoxaluria after a jejunoileal bypass for obesity, hyperoxaluria after gastric ulcer surgery, and chronic mesenteric ischemia.

As used herein a "pharmaceutical composition" refers to a preparation of genetically engineered microorganism of the disclosure, e.g., genetically engineered bacteria or virus, with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial or viral compound. An adjuvant is included under these phrases.

The term "excipient" refers to an inert substance added to a pharmaceutical composition to further facilitate administration of an active ingredient. Examples include, but are not limited to, calcium bicarbonate, sodium bicarbonate calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., a disorder in which oxalate is detrimental. A therapeutically effective amount may, for example, be sufficient to treat, prevent, reduce the severity, delay the onset, and/or reduce the risk of occurrence of one or more symptoms of a disease or condition associated with daily urinary oxalate excretion over 40 mg per 24 hours. A therapeutically effective amount, as well as a therapeutically effective frequency of administration, can be determined by methods known in the art and discussed below.

As used herein, the term "bacteriostatic" or "cytostatic" refers to a molecule or protein which is capable of arresting, retarding, or inhibiting the growth, division, multiplication or replication of recombinant bacterial cell of the disclosure.

As used herein, the term "bactericidal" refers to a molecule or protein which is capable of killing the recombinant bacterial cell of the disclosure.

As used herein, the term "toxin" refers to a protein, enzyme, or polypeptide fragment thereof, or other molecule which is capable of arresting, retarding, or inhibiting the growth, division, multiplication or replication of the recombinant bacterial cell of the disclosure, or which is capable of killing the recombinant bacterial cell of the disclosure. The term "toxin" is intended to include bacteriostatic proteins and bactericidal proteins. The term "toxin" is intended to include, but not limited to, lytic proteins, bacteriocins (e.g., microcins and colicins), gyrase inhibitors, polymerase inhibitors, transcription inhibitors, translation inhibitors, DNases, and RNases. The term "anti-toxin" or "antitoxin," as used herein, refers to a protein or enzyme which is capable of inhibiting the activity of a toxin. The term anti-toxin is intended to include, but not limited to, immunity modulators, and inhibitors of toxin expression. Examples of toxins and antitoxins are known in the art and described in more detail infra.

As used herein, the term "oxalate catabolic or catabolism enzyme" or "oxalate catabolic or catabolism enzyme" or "oxalate metabolic enzyme" refers to any enzyme that is capable of metabolizing oxalate or capable of reducing accumulated oxalate or that can lessen, ameliorate, or prevent one or more diseases, or disease symptoms in which oxalate is detrimental. Examples of oxalate enzymes include, but are not limited to, formyl-CoA:oxalate CoA-transferase (also called formyl-CoA transferase), e.g., Frc from O. formigenes, oxalyl-CoA synthetase (also called oxalate-CoA ligase), e.g., Saccharomyces cerevisiae acyl-activating enzyme 3(ScAAE3) from Saccharomyces cerevisiae, Oxalyl-CoA Decarboxylase, e.g., Oxc from O. formigenes, acetyl-CoA:oxalate CoA-transferase (ACOCT), e.g., YfdE from E. coli and any other enzymes that catabolizes oxalate, oxalyl-CoA or any other metabolite thereof. Catabolism enzymes also include alanine glyoxalate aminotransferase (AGT, encoded by the AGXT gene, e.g. the human form), glyoxylate/hydroxypyruvate reductase (GRHPR; an enzyme having glyoxylate reductase (GR), hydroxypyruvate reductase (HPR), and D-glycerate dehydrogenase (DGDH) activities, e.g., the human form), and 4-hydroxy 2-oxoglutarate aldolase (encoded by the HOGA1 gene, e.g. in humans, and which breaks down 4-hydroxy 2-oxoglutarate into pyruvate and glyoxalate). Functional deficiencies in these proteins result in the accumulation of oxalate or its corresponding α-keto acid in cells and tissues. Oxalate metabolic enzymes of the present disclosure include both wild-type or modified oxalate metabolic enzymes and can be produced using recombinant and synthetic methods or purified from nature sources. Oxalate metabolic enzymes include full-length polypeptides and functional fragments thereof, as well as homologs and variants thereof. oxalate metabolic enzymes include polypeptides that have been modified from the wild-type sequence, including, for example, polypeptides having one or more amino acid deletions, insertions, and/or substitutions and may include, for example, fusion polypeptides and polypeptides having additional sequence, e.g., regulatory peptide sequence, linker peptide sequence, and other peptide sequence.

As used herein, "payload" refers to one or more molecules of interest to be produced by a genetically engineered microorganism, such as a bacteria or a virus. In some embodiments, the payload is a therapeutic payload, e.g., an oxalate catabolic enzyme or an oxalate transporter polypeptide. In some embodiments, the payload is a regulatory molecule, e.g., a transcriptional regulator such as FNR. In some embodiments, the payload comprises a regulatory element, such as a promoter or a repressor. In some embodiments, the payload comprises an inducible promoter, such as from FNRS. In some embodiments the payload comprises a repressor element, such as a kill switch. In some embodiments the payload comprises an antibiotic resistance gene or gene cassette. In some embodiments, the payload is encoded by a gene, multiple genes, gene cassette, or an operon. In alternate embodiments, the payload is produced by a biosynthetic or biochemical pathway, wherein the biosynthetic or biochemical pathway may optionally be endogenous to the microorganism. In alternate embodiments, the payload is produced by a biosynthetic or biochemical pathway, wherein the biosynthetic or biochemical pathway is not endogenous to the microorganism. In some embodiments, the genetically engineered microorganism comprises two or more payloads.

As used herein, the term "conventional hyperoxaluria treatment" or "conventional hyperoxaluria therapy" refers to treatment or therapy that is currently accepted, considered current standard of care, and/or used by most healthcare professionals for treating a disease or disorders in which oxalate is detrimental. It is different from alternative or complementary therapies, which are not as widely used.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length of the product. Thus, "peptides," "dipeptides," "tripeptides, "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the genetically engineered bacteria or virus of the current invention. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides, which do not possess a defined three-dimensional structure, but rather can adopt a large number of different conformations, are referred to as unfolded. The term "peptide" or "polypeptide" may refer to an amino acid sequence that corresponds to a protein or a portion of a protein or may refer to an amino acid sequence that corresponds with non-protein sequence, e.g., a sequence selected from a regulatory peptide sequence, leader peptide sequence, signal peptide sequence, linker peptide sequence, and other peptide sequence.

An "isolated" polypeptide or a fragment, variant, or derivative thereof refers to a polypeptide that is not in its natural milieu. No particular level of purification is required. Recombinantly produced polypeptides and proteins expressed in host cells, including but not limited to bacterial or mammalian cells, are considered isolated for purposed of the invention, as are native or recombinant polypeptides which have been separated, fractionated, or partially or substantially purified by any suitable technique. Recombinant peptides, polypeptides or proteins refer to peptides, polypeptides or proteins produced by recombinant DNA techniques, i.e. produced from cells, microbial or mammalian, transformed by an exogenous recombinant DNA expression construct encoding the polypeptide. Proteins or peptides expressed in most bacterial cultures will typically be free of glycan. Fragments, derivatives, analogs or variants of the foregoing polypeptides, and any combination thereof are also included as polypeptides. The terms "fragment," "variant," "derivative" and "analog" include polypeptides having an amino acid sequence sufficiently similar to the amino acid sequence of the original peptide and include any polypeptides, which retain at least one or more properties of the corresponding original polypeptide. Fragments of polypeptides of the present invention include proteolytic fragments, as well as deletion fragments. Fragments also include specific antibody or bioactive fragments or immunologically active fragments derived from any polypeptides described herein. Variants may occur naturally or be non-naturally occurring. Non-naturally occurring variants may be produced using mutagenesis methods known in the art. Variant polypeptides may comprise conservative or non-conservative amino acid substitutions, deletions or additions.

Polypeptides also include fusion proteins. As used herein, the term "variant" includes a fusion protein, which comprises a sequence of the original peptide or sufficiently similar to the original peptide. As used herein, the term "fusion protein" refers to a chimeric protein comprising amino acid sequences of two or more different proteins. Typically, fusion proteins result from well known in vitro recombination techniques. Fusion proteins may have a similar structural function (but not necessarily to the same extent), and/or similar regulatory function (but not necessarily to the same extent), and/or similar biochemical function (but not necessarily to the same extent) and/or immunological activity (but not necessarily to the same extent) as the individual original proteins which are the components of the fusion proteins. "Derivatives" include but are not limited to peptides, which contain one or more naturally occurring amino acid derivatives of the twenty standard amino acids. "Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; -Val, Ile, Leu, Met, Ala, Phe; -Lys, Arg, His; -Phe, Tyr, Trp, His; and -Asp, Glu.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar Preferably, variants will be sufficiently similar to the amino acid sequence of the peptides of the invention. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

As used herein the term "linker", "linker peptide" or "peptide linkers" or "linker" refers to synthetic or non-native or non-naturally-occurring amino acid sequences that connect or link two polypeptide sequences, e.g., that link two polypeptide domains. As used herein the term "synthetic" refers to amino acid sequences that are not naturally occurring. Exemplary linkers are described herein. Additional exemplary linkers are provided in US 20140079701, the contents of which are herein incorporated by reference in its entirety.

As used herein the term "codon-optimized" refers to the modification of codons in the gene or coding regions of a nucleic acid molecule to reflect the typical codon usage of the host organism without altering the polypeptide encoded by the nucleic acid molecule. Such optimization includes replacing at least one, or more than one, or a significant number, of codons with one or more codons that are more frequently used in the genes of the host organism. A "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. Many organisms display a bias or preference for use of particular codons to code for insertion of a particular amino acid in a growing polypeptide chain. Codon preference or codon bias, differences in codon usage between organisms, is allowed by the degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

As used herein, the terms "secretion system" or "secretion protein" refers to a native or non-native secretion mechanism capable of secreting or exporting a biomolecule, e.g., polypeptide from the microbial, e.g., bacterial cytoplasm. The secretion system may comprise a single protein or may comprise two or more proteins assembled in a complex e.g. HlyBD. Non-limiting examples of secretion systems for gram negative bacteria include the modified type III flagellar, type I (e.g., hemolysin secretion system), type II, type IV, type V, type VI, and type VII secretion systems, resistance-nodulation-division (RND) multi-drug efflux pumps, various single membrane secretion systems. Non-liming examples of secretion systems for gram positive bacteria include Sec and TAT secretion systems. In some embodiments, the polypeptide to be secreted include a "secretion tag" of either RNA or peptide origin to direct the polypeptide to specific secretion systems. In some embodiments, the secretion system is able to remove this tag before secreting the polypeptide from the engineered bacteria. For example, in Type V auto-secretion-mediated secretion the N-terminal peptide secretion tag is removed upon translocation of the "passenger" peptide from the cytoplasm into the periplasmic compartment by the native Sec system. Further, once the auto-secretor is translocated across the outer membrane the C-terminal secretion tag can be removed by either an autocatalytic or protease-catalyzed e.g., OmpT cleavage thereby releasing the therapeutic polypeptide into the extracellular milieu. In some embodiments, the secretion system involves the generation of a "leaky" or de-stabilized outer membrane, which may be accomplished by deleting or mutagenizing genes responsible for tethering the outer membrane to the rigid peptidoglycan skeleton, including for example, lpp, ompC, ompA, ompF, tolA, tolB, pal, degS, degP, and nlpI. Lpp functions as the primary 'staple' of the bacterial cell wall to the peptidoglycan. TolA-PAL and OmpA complexes function similarly to Lpp and are other deletion targets to generate a leaky phenotype. Additionally, leaky phenotypes have been observed when periplasmic proteases, such as degS, degP or nlpI, are deactivated. Thus, in some embodiments, the engineered bacteria have one or more deleted or mutated membrane genes, e.g., selected from lpp, ompA, ompA, ompF, tolA, tolB, and pal genes. In some embodiments, the engineered bacteria have one or more deleted or mutated periplasmic protease genes, e.g., selected from degS, degP, and nlpI. In some embodiments, the engineered bacteria have one or more deleted or mutated gene(s), selected from lpp, ompA, ompA, ompF, tolA, tolB, pal, degS, degP, and nlpI genes.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Bacteria of the Invention

The genetically engineered microorganisms, or programmed microorganisms, such as genetically engineered bacteria of the disclosure are capable of producing one or more enzymes for metabolizing an oxalate and/or a metabolite thereof. In some aspects, the disclosure provides a bacterial cell that comprises one or more heterologous gene sequence(s) encoding an oxalate catabolism enzyme or other protein that results in a decrease in oxalate levels.

In certain embodiments, the genetically engineered bacteria are obligate anaerobic bacteria. In certain embodiments, the genetically engineered bacteria are facultative anaerobic bacteria. In certain embodiments, the genetically engineered bacteria are aerobic bacteria. In some embodiments, the genetically engineered bacteria are Gram-positive bacteria. In some embodiments, the genetically engineered bacteria are Gram-positive bacteria and lack LPS. In some embodiments, the genetically engineered bacteria are Gram-negative bacteria. In some embodiments, the genetically engineered bacteria are Gram-positive and obligate anaerobic bacteria. In some embodiments, the genetically engineered bacteria are Gram-positive and facultative anaerobic bacteria. In some embodiments, the genetically engineered bacteria are non-pathogenic bacteria. In some embodiments, the genetically engineered bacteria are commensal bacteria. In some embodiments, the genetically engineered bacteria are probiotic bacteria. In some embodiments, the genetically engineered bacteria are naturally pathogenic bacteria that are modified or mutated to reduce or eliminate pathogenicity. Exemplary bacteria include, but are not limited to, *Bacillus, Bacteroides, Bifidobacterium, Brevibacteria, Caulobacter, Clostridium, Enterococcus, Escherichia coli, Lactobacillus, Lactococcus, Listeria, Mycobacterium, Saccharomyces, Salmonella, Staphylococcus, Streptococcus, Vibrio, Bacillus coagulans, Bacillus subtilis, Bacteroides fragilis, Bacteroides subtilis, Bacteroides thetaiotaomicron, Bifidobacterium adolescentis, Bifidobacterium bifidum, Bifidobacterium breve* UCC2003, *Bifidobacterium infantis, Bifidobacterium lactis, Bifidobacterium longum, Clostridium acetobutylicum, Clostridium butyricum, Clostridium butyricum* M-55, *Clostridium cochlearum, Clostridium felsineum, Clostridium histolyticum, Clostridium multifermentans, Clostridium novyi*-NT, *Clostridium paraputrificum, Clostridium pasteureanum, Clostridium pectinovorum, Clostridium perfringens, Clostridium roseum, Clostridium sporogenes, Clostridium tertium, Clostridium tetani, Clostridium tyrobutyricum, Corynebacterium parvum, Escherichia coli* MG1655, *Escherichia coli Nissle* 1917, *Listeria monocytogenes, Mycobacterium bovis, Salmonella choleraesuis, Salmonella typhimurium,* and *Vibrio cholera*. In certain embodiments, the genetically engineered bacteria are selected from the group consisting of *Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis,* and *Oxalobacter formigenes* bacterial cell. *Saccharomyces boulardii*. In certain embodiments, the genetically engineered bacteria are selected from *Bacteroides fragilis, Bacteroides thetaiotaomicron, Bacteroides subtilis, Bifidobacterium bifidum, Bifidobacterium infantis, Bifidobacterium lactis, Clostridium butyricum, Escherichia coli, Escherichia coli Nissle, Lactobacillus acidophilus, Lactobacillus plantarum, Lactobacillus reuteri,* and *Lactococcus lactis* bacterial cell. In one embodiment, the bacterial cell is a *Bacteroides fragilis* bacterial cell. In one embodiment, the bacterial cell is a *Bacteroides thetaiotaomicron* bacterial cell. In one embodiment, the bacterial cell is a *Bacteroides subtilis* bacterial cell. In one embodiment, the bacterial cell is a *Bifidobacterium bifidum* bacterial cell. In one embodiment, the bacterial cell is a *Bifidobacterium infantis* bacterial cell. In one embodiment, the bacterial cell is a *Bifidobacterium lactis* or *B. infantis* bacterial cell. In one embodiment, the bacterial cell is a *Clostridium butyricum* bacterial cell. In one embodiment, the bacterial cell is an *Escherichia coli* bacterial cell. In one embodiment, the bacterial cell is a *Lactobacillus acidophilus* bacterial cell. In one embodiment, the bacterial cell is a *Lactobacillus plantarum* bacterial cell. In one embodiment the bacterial cell is a *Bifidobacterium lactis* bacterial cell. In one embodiment, the bacterial cell is a *Clostridium butyricum* bacterial cell. In one embodiment, the bacterial cell is an *Escherichia coli* bacterial cell. In one embodiment, the bacterial cell is a *Lactobacillus acidophilus* bacterial cell. In one embodiment, the bacterial cell is a *Lactobacillus plantarum* bacterial cell. In one embodiment, the bacterial cell is a *Lactobacillus reuteri* bacterial cell. In one embodiment, the bacterial cell is a *Lactococcus lactis* bacterial cell. In one embodiment, the bacterial cell is a *Oxalobacter formigenes* bacterial cell. In another embodiment, the bacterial cell does not include *Oxalobacter formigenes*.

In some embodiments, the genetically engineered bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reister et al., 2014, emphasis added). Genomic sequencing confirmed that *E. coli* Nissle lacks prominent virulence factors (e.g., *E. coli* α-hemolysin, P-fimbrial adhesins) (Schultz, 2008). In addition, it has been shown that *E. coli* Nissle does not carry pathogenic adhesion factors, does not produce any enterotoxins or cytotoxins, is not invasive, and not uropathogenic (Sonnenborn et al., 2009). As early as in 1917, *E. coli* Nissle was packaged into medicinal capsules, called Mutaflor, for therapeutic use. *E. coli* Nissle has since been used to treat ulcerative colitis in humans in vivo (Rembacken et al., 1999), to treat inflammatory bowel disease, Crohn's disease, and pouchitis in humans in vivo (Schultz, 2008), and to inhibit enteroinvasive *Salmonella, Legionella, Yersinia,* and *Shigella* in vitro (Altenhoefer et al., 2004). It is commonly accepted that *E. coli* Nissle's therapeutic efficacy and safety have convincingly been proven (Ukena et al., 2007).

In one embodiment, the recombinant bacterial cell of the invention does not colonize the subject having the disorder in which oxalate is detrimental.

One of ordinary skill in the art would appreciate that the genetic modifications disclosed herein may be adapted for other species, strains, and subtypes of bacteria. Furthermore, genes from one or more different species can be introduced into one another, e.g., an oxalate catabolism gene from *Lactococcus lactis* can be expressed in *Escherichia coli*. Unmodified *E. coli* Nissle and the genetically engineered bacteria of the invention may be destroyed, e.g., by defense factors in the gut or blood serum (Sonnenborn et al., 2009). In some embodiments, the residence time is calculated for a human subject. In some embodiments, residence time in vivo is calculated for the genetically engineered bacteria of the invention.

In some embodiments, the bacterial cell is a genetically engineered bacterial cell. In another embodiment, the bacterial cell is a recombinant bacterial cell. In some embodiments, the disclosure comprises a colony of bacterial cells disclosed herein.

In another aspect, the disclosure provides a recombinant bacterial culture which comprises bacterial cells disclosed herein. In one aspect, the disclosure provides a recombinant bacterial culture which reduces levels of oxalate or oxalic acid in the media of the culture. In one embodiment, the levels of the oxalate or oxalic acid are reduced by about 50%, about 75%, or about 100% in the media of the cell culture. In another embodiment, the levels of the oxalate or oxalic acid are reduced by about two-fold, three-fold, four-fold, five-fold, six-fold, seven-fold, eight-fold, nine-fold, or ten-fold in the media of the cell culture. In one embodiment, the levels of the oxalate or oxalic acid are reduced below the limit of detection in the media of the cell culture.

In some embodiments of the above described genetically engineered bacteria, the gene and/or gene cassette encoding one or more oxalate catabolism enzyme(s) is present on a plasmid in the bacterium. In some embodiments of the above described genetically engineered bacteria, the gene and/or gene cassette encoding one or more oxalate catabolism enzyme(s) is present on a plasmid in the bacterium and operatively linked on the plasmid to a promoter that is induced under low-oxygen or anaerobic conditions, such as any of the promoters disclosed herein. In other embodiments, the gene and/or gene cassette encoding one or more oxalate catabolism enzyme(s) is present in the bacterial chromosome. In other embodiments, the gene and/or gene cassette encoding one or more oxalate catabolism enzyme(s) is present in the bacterial chromosome and is operatively linked in the chromosome to the promoter that is induced under low-oxygen or anaerobic conditions, such as any of the promoters disclosed herein. In some embodiments of the above described genetically engineered bacteria, the gene and/or gene cassette encoding one or more oxalate catabolism enzyme(s) is present on a plasmid in the bacterium and operatively linked on the plasmid to the promoter that is induced under inflammatory conditions, such as any of the promoters disclosed herein. In other embodiments, the gene and/or gene cassette encoding one or more oxalate catabolism enzyme(s) is present in the bacterial chromosome and is operatively linked in the chromosome to the promoter that is induced under inflammatory conditions, such as any of the promoters disclosed herein.

In some embodiments, the genetically engineered bacteria comprising the gene and/or gene cassette encoding one or more oxalate catabolism enzyme(s) further comprise gene sequence(s) encoding an oxalate transporter. In some embodiments, the genetically engineered bacteria comprising the gene and/or gene cassette encoding one or more oxalate catabolism enzyme(s) further comprise gene sequence(s) encoding a formate exporter. In some embodiments, the genetically engineered bacteria comprising the gene and/or gene cassette encoding one or more oxalate catabolism enzyme(s) further comprise gene sequence(s) encoding an oxalate:formate antiporter. In some embodiments, the genetically engineered bacteria comprising the gene and/or gene cassette encoding one or more oxalate catabolism enzyme(s) further comprise gene sequence(s) encoding one or more of the following: an oxalate transporter, a formate exporter, and/or an oxalate:formate antiporter.

In some embodiments, the genetically engineered bacteria comprising the gene and/or gene cassette encoding one or more oxalate catabolism enzyme(s) and/or oxalate transporter, and/or formate exporter, and/or oxalate:formate antiporter is an auxotroph. In one embodiment, the genetically engineered bacteria is an auxotroph selected from a cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thiI auxotroph. In some embodiments, the engineered bacteria have more than one auxotrophy, for example, they may be a ΔthyA and ΔdapA auxotroph.

In some embodiments, the genetically engineered bacteria comprising the gene and/or gene cassette encoding one or more oxalate catabolism enzyme(s) and/or oxalate transporter, and/or formate exporter, and/or oxalate:formate antiporter further comprise gene sequence(s) encoding a secretion protein or protein complex for secreting a biomolecule, such as any of the secretion systems disclosed herein.

In some embodiments, the genetically engineered bacteria comprising the gene and/or gene cassette encoding one or more oxalate catabolism enzyme(s) and/or oxalate transporter, and/or formate exporter, and/or oxalate:formate antiporter further comprise gene sequence(s) encoding one or more antibiotic gene(s), such as any of the antibiotic genes disclosed herein.

In some embodiments, the genetically engineered bacteria comprising a gene and/or gene cassette encoding one or more oxalate catabolism enzyme(s) and/or oxalate transporter, and/or formate exporter, and/or oxalate:formate antiporter further comprise a kill-switch circuit, such as any of the kill-switch circuits provided herein. For example, in some embodiments, the genetically engineered bacteria further comprise one or more genes encoding one or more recombinase(s) under the control of an inducible promoter, and an inverted toxin sequence. In some embodiments, the genetically engineered bacteria further comprise one or more genes encoding an antitoxin. In some embodiments, the engineered bacteria further comprise one or more genes encoding one or more recombinase(s) under the control of an inducible promoter and one or more inverted excision genes, wherein the excision gene(s) encode an enzyme that deletes an essential gene. In some embodiments, the genetically engineered bacteria further comprise one or more genes encoding an antitoxin. In some embodiments, the engineered bacteria further comprise one or more genes encoding a toxin under the control of a promoter having a TetR repressor binding site and a gene encoding the TetR under the control of an inducible promoter that is induced by arabinose, such as $P_{araBAD}$. In some embodiments, the genetically engineered bacteria further comprise one or more genes encoding an antitoxin.

In some embodiments, the genetically engineered bacteria is an auxotroph comprising the gene and/or gene cassette encoding one or more oxalate catabolism enzyme(s) and further comprises a kill-switch circuit, such as any of the kill-switch circuits described herein.

In some embodiments of the above described genetically engineered bacteria, the gene and/or gene cassette encoding one or more oxalate catabolism enzyme(s) is present on a plasmid in the bacterium. In some embodiments, the gene and/or gene cassette encoding one or more oxalate catabolism enzyme(s) is present in the bacterial chromosome. In some embodiments, the genetically engineered bacteria comprise one or more gene and/or gene cassette(s) encoding one or more oxalate transporter(s) that transports oxalate into the bacterial cell. In some embodiments, the gene sequence(s) encoding an oxalate transporter is present on a plasmid in the bacterium. In some embodiments, the gene sequence(s) encoding an oxalate transporter is present in the bacterial chromosome. In some embodiments, the gene sequence encoding a secretion protein or protein complex for secreting a biomolecule, such as any of the secretion systems disclosed herein, is present on a plasmid in the bacterium. In some embodiments, the gene sequence encoding a secretion protein or protein complex for secreting a biomolecule, such as any of the secretion systems disclosed herein, is present in the bacterial chromosome. In some embodiments, the gene sequence(s) encoding an antibiotic resistance gene is present on a plasmid in the bacterium. In some embodiments, the gene sequence(s) encoding an antibiotic resistance gene is present in the bacterial chromosome.

Oxalate Catabolism Enzymes

*O. formigenes* was the first oxalate-degrading obligate anaerobe to be described in humans and has served as the paradigm organism in which anaerobic oxalate degradation has been studied. *O. formigenes* has three enzymes involved in the catabolism of oxalic acid. First extracellular oxalate is taken up by the membrane-associated oxalate—formate antiporter, OxlT, encoded by the oxlT gene. The frc gene encodes formyl-CoA transferase, Frc, which activates the intracellular oxalate to form oxalyl-CoA. This is decarboxylated in a thiamine PPi-dependent reaction by the oxalyl-CoA decarboxylase, Oxc, enzyme, expressed from the oxc gene. Formate and carbon dioxide are the end products, and the oxalate—formate antiporter, OxlT, catalyzes the export of the intracellular formate out of the cells. In *O. formigenes*, the generation of energy is coupled to oxalate transport, mediated by the oxalate transport membrane protein OxlT, (as described in Abratt and Reid Oxalate-Degrading Bacteria of the Human Gut as Probiotics in the Management of Kidney Stone Disease, the contents of which is herein incorporated by reference in its entirety, and references therein).

As used herein, the term "oxalate catabolism enzyme" refers to an enzyme involved in the catabolism of oxalate to its corresponding oxalyl-CoA molecule, the catabolism of oxalyl-CoA to formate and carbon dioxide, or the catabolism of oxalate to another metabolite. Enzymes involved in the catabolism of oxalate are well known to those of skill in the art. For example, in the obligate anaerobe *Oxalobacter formigenes*, the formyl coenzyme A transferase FRC (encoded by the frc gene) transfers a coenzyme A moiety to oxalic acid, forming oxalyl-CoA (see, e.g., Sidhu et al., *J. Bacteriol.* 179: 3378-81 (1997), the entire contents of which are expressly incorporated herein by reference). Subsequently, the oxalyl-CoA is subject to a reaction mediated by the oxalyl-CoA decarboxylase OXC (encoded by the oxc gene), which leads to the formation of formate and carbon dioxide (see, e.g., Lung et al., *J. Bacteriol.* 176: 2468-72 (1994), the entire contents of which are expressly incorporated herein by reference). Further, the *E. coli* protein YfdW (Protein Data Bank Accession No. 1pt5) and YfdU (Protein Data Bank Accession No. EOSNC8) are a formyl-CoA transferase and an oxalyl-CoA decarboxylase that have been shown to be functional homologs of the *O. formigenes* FRC and OXC enzymes (see, e.g., Toyota et al., *J. Bact.* 190: 2256-64 (2008); Werther et al., *FEBS J.* 277: 2628-40 (2010); Fontenot et al., *J. Bact.* 195: 1446-55 (2013)).

Another oxalate catabolism enzyme, acetyl-CoA:oxalate CoA-transferase, converts acetyl-CoA and oxalate to oxalyl-CoA and acetate. In a non-limiting example, the acetyl-CoA: oxalate CoA-transferase is YfdE from *E. coli* (e.g., described in Function and X-ray crystal structure of *Escherichia coli* YfdE; PLoS One. 2013 Jul. 23; 8(7):e67901). Acetyl-CoA substrate a very ubiquitous metabolite in bacteria, such as *E. coli*, and acetate produced can for example diffuse into the extracellular space without the need of a transporter. In one example, acetyl-CoA:oxalate CoA-transferase reaction can be followed by oxalyl-CoA decarboxylase OXC (encoded by the oxc gene), which leads to the formation of formate and carbon dioxide. Formate can exit the cell, for example through a formate exporter, including but not limited to, OxlT from *O. formigenes*.

Another exemplary oxalate catabolism enzyme oxalyl-CoA synthetase (OCL; also called oxalate-CoA ligase), which converts oxalate and CoA and ATP to oxalyl-CoA and AMP and di-phosphate. In a non-limiting example, the oxalate-CoA ligase is *Saccharomyces cerevisiae* acyl-activating enzyme 3 (ScAAE3) (e.g., described in Foster and Nakata, An oxalyl-CoA synthetase is important for oxalate metabolism in Saccharomyces cerevisiae. FEBS Lett. 2014 Jan. 3; 588(1):160-6). In one example, oxalate-CoA ligase can be followed by oxalyl-CoA decarboxylase OXC (encoded by the oxc gene), which leads to the formation of formate and carbon dioxide. Formate can exit the cell, for example through a formate exporter, including but not limited to, OxlT from *O. formigenes*.

In some embodiments, the genetically engineered bacteria of the disclosure comprise one or more gene(s) and/or gene cassette(s) encoding at least one oxalate catabolism enzyme. In some embodiments, the engineered bacteria comprise one or more gene(s) and/or gene cassette(s) encoding at least one oxalate catabolism enzyme and are capable of converting oxalate into oxalyl-CoA. In some embodiments, the engineered bacteria comprise one or more gene(s) and/or gene cassette(s) encoding at least one oxalate catabolism enzyme and are capable of converting oxalyl-CoA into formate and carbon dioxide. In some embodiments, the engineered bacteria comprise one or more gene(s) and/or gene cassette(s) encoding at least one oxalate catabolism enzyme and are capable of converting oxalate into oxalyl-CoA, and oxalyl-CoA into formate and carbon dioxide. In some embodiments, the engineered bacteria of the disclosure comprise one or more gene(s) and or gene cassette encoding one or more oxalate catabolism enzyme(s) which convert oxalate and formyl CoA into oxalyl-CoA and formate. In some embodiments, the engineered bacteria of the disclosure comprise one or more gene(s) and/or gene cassette(s) encoding one or more oxalate catabolism enzyme(s) which convert oxalate and acetyl-coA into oxalyl-CoA and acetate. In some embodiments, the engineered bacteria of the disclosure comprise one or more gene(s) and/or gene cassette(s) encoding one or more oxalate catabolism enzyme(s) which convert oxalate and CoA into oxalyl-CoA (e.g., by converting one ATP to AMP plus diphosphate). In some embodiments, the engineered bacteria of the disclosure comprise one or more gene(s) and/or gene cassette(s) encoding one or more oxalate catabolism enzyme(s) which convert oxalyl-CoA to carbon dioxide and formyl-CoA. In some embodiments, the engineered bacteria produce formate as a result of oxalate catabolism. In some embodiments, the engineered bacteria produce formate and carbon dioxide as a result of oxalate catabolism. In some embodiments, the engineered bacteria produce acetate as a result of oxalate catabolism. In some embodiments, the engineered bacteria produce acetate and carbon dioxide as a result of oxalate catabolism. In some embodiments, the engineered bacteria produce formate, acetate, and carbon dioxide as a result of oxalate catabolism.

In some embodiments, the genetically engineered bacteria comprise gene sequence(s) encoding one or more oxalate catabolism enzyme (s). In some embodiments, the one or more oxalate catabolism enzyme(s) increases the rate of oxalate and/or oxalyl-CoA catabolism in the cell. In some embodiments, the one or more oxalate catabolism enzyme(s) decreases the level of oxalate in the cell. In some embodiments, the one or more oxalate catabolism enzyme(s) decreases the level of oxalyl-CoA in the cell. In some embodiments, the one or more oxalate catabolism enzyme(s) decreases the level of oxalic acid in the cell.

In some embodiments, the one or more oxalate catabolism enzyme(s) increases the level of oxalyl-CoA in the cell as compared to the level of its corresponding oxalate in the cell. In some embodiments, the one or more oxalate catabolism enzyme(s) increases the level of formate and carbon dioxide in the cell as compared to the level of its corresponding oxalyl-CoA in the cell. In some embodiments, the one or more oxalate catabolism enzyme(s) decreases the level of the oxalate and/or oxalyl CoA as compared to the level of oxalate in the cell.

Enzymes involved in the catabolism of oxalate may be expressed or modified in the bacteria of the invention in order to enhance catabolism of oxalate. Specifically, when at least one oxalate catabolism enzyme is expressed in the engineered bacterial cells of the invention, the engineered bacterial cells convert more oxalate into oxalyl-CoA, or convert more oxalyl-CoA into formate and carbon dioxide when the catabolism enzyme is expressed than unmodified bacteria of the same bacterial subtype under the same conditions. Thus, the genetically engineered bacteria comprising a heterologous gene encoding an oxalate catabolism enzyme can catabolize oxalate and/or oxalyl-CoA to treat disorders in which oxalate is detrimental, such as PHI, PHII, PHIII, and secondary hyperoxaluria, enteric hyperoxaluria, and idiopathic hyperoxaluria.

In one embodiment, the bacterial cell of the invention comprises at least one heterologous gene encoding at least one oxalate catabolism enzyme. In one embodiment, the bacterial cell of the invention comprises at least one heterologous gene encoding an importer of oxalate and at least one heterologous gene encoding at least one oxalate catabolism enzyme. In one embodiment, the bacterial cell of the invention comprises at least one heterologous gene encoding an exporter of formate and at least one heterologous gene encoding at least one oxalate catabolism enzyme. In one embodiment, the bacterial cell of the invention comprises at least one heterologous gene encoding an oxalate:formate antiporter and at least one heterologous gene encoding at least one oxalate catabolism enzyme.

In some embodiments, the invention provides a bacterial cell that comprises at least one heterologous gene encoding at least one oxalate catabolism enzyme operably linked to a first promoter. In one embodiment, the bacterial cell comprises at least one gene encoding at least one oxalate catabolism enzyme from a different organism, e.g., a different species of bacteria. In another embodiment, the bacterial cell comprises more than one copy of a native gene encoding an oxalate catabolism enzyme. In yet another embodiment, the bacterial cell comprises at least one native gene encoding at least one oxalate catabolism enzyme, as well as at least one copy of at least one gene encoding an oxalate catabolism enzyme from a different organism, e.g., a different species of bacteria. In one embodiment, the bacterial cell comprises at least one, two, three, four, five, or six copies of a gene encoding an oxalate catabolism enzyme. In one embodiment, the bacterial cell comprises multiple copies of a gene encoding an oxalate catabolism enzyme.

Oxalate catabolism enzymes are known in the art. In some embodiments, AN oxalate catabolism enzyme is encoded by at least one gene encoding at least one oxalate catabolism enzyme derived from a bacterial species. In some embodiments, an oxalate catabolism enzyme is encoded by a gene encoding an oxalate catabolism enzyme derived from a non-bacterial species. In some embodiments, an oxalate catabolism enzyme is encoded by a gene derived from a eukaryotic species, e.g., a yeast species or a plant species. In one embodiment, an oxalate catabolism enzyme is encoded by a gene derived from a human. In one embodiment, the gene sequence(s) encoding the one or more oxalate catabolism enzyme(s) is derived from an organism of the genus or species that includes, but is not limited to, *Bifidobacterium, Bordetella, Bradyrhizobium, Burkholderia, Clostridium, Enterococcus, Escherichia, Eubacterium, Lactobacillus, Magnetospirillium, Mycobacterium, Neurospora, Oxalobacter*, e.g., *Oxalobacter formigenes, Ralstonia, Rhodopseudomonas, Shigella, Thermoplasma,* and *Thauera,* e.g., *Bifidobacterium animalis, Bifidobacterium bifidum, Bifidobacterium infantis, Bifidobacterium lactis, Bifidobacterium longum, Bordatella bronchiseptica, Bordatella parapertussis, Burkholderia fungorum, Burkholderia xenovorans, Bradyrhizobium japonicum, Clostridium acetobutylicum, Clostridium difficile, Clostridium scindens, Clostridium sporogenes, Clostridium tentani, Enterococcus faecalis, Escherichia coli, Eubacterium lentum, Lactobacillus acidophilus, Lactobacillus bulgaricus, Lactobacillus casei, Lactobacillus gasseri, Lactobacillus plantarum, Lactobacillus rhamnosus, Lactococcus lactis, Magnetospirillium magentotaticum, Mycobacterium avium, Mycobacterium intracellulare, Mycobacterium kansasii, Mycobacterium leprae, Mycobacterium smegmatis, Mycobacterium tuberculosis, Mycobacterium ulcerans, Neurospora crassa, Oxalobacter formigenes, Providencia rettgeri, Eubacterium lentum, Ralstonia eutropha, Ralstonia metallidurans, Rhodopseudomonas palustris, Shigella flexneri, Thermoplasma volcanium,* and *Thauera aromatica.*

In one embodiment, one or more oxalate catabolism enzyme(s) encoded by the genetically engineered bacteria are derived from *O. formigenes*, e.g., oxc and frc described above.

In one embodiment, one or more oxalate catabolism enzyme(s) encoded by the engineered bacteria are derived from *Enteroccoccus faecalis*. An inducible oxalate catabolism system has been described in *Enterococcus faecalis*, which comprised homologs to *O. formigenes* Frc and Oxc (Hokama et al., Oxalate-degrading *Enterococcus faecalis*. Microbiol. Immunol. 44, 235-240).

In one embodiment, one or more oxalate catabolism enzyme(s) encoded by the engineered bacteria are derived from are from *Eubacterium lentum*. The oxalate-degrading proteins oxalyl-CoA decarboxylase and formyl-CoA transferase were reportedly isolated from this strain (Ito, H., Kotake, T., and Masai, M. (1996). In vitro degradation of oxalic acid by human feces. Int. J. Urol. 3, 207-211).

In one embodiment, one or more oxalate catabolism enzyme(s) encoded by the engineered bacteria are derived from *Providencia rettgeri*, which have shown to have homologs to *O. formigenes* Frc and Oxc (e.g., as described in Abratt and Reid, Oxalate-degrading bacteria of the human gut as probiotics in the management of kidney stone disease; Adv Appl Microbiol. 2010; 72:63-87, and references therein).

In one embodiment, one or more oxalate catabolism enzyme(s) encoded by the engineered bacteria are derived from *E. coli*, e.g. from the yfdXWUVE operon. For example, the ydfU is thought to be a oxc homolog. In one embodiment, one or more oxalate catabolism enzyme(s) encoded by the engineered bacteria are derived from *Lactobacillus* and/or *Bifidobacterium* species. In a non-limiting example one or more oxalate catabolism enzyme(s) are derived from oxc and frc homologs *Lactobacillus* and/or *Bifidobacterium* species. Non-limiting examples of such *Lactobacillus* species include *Lactobacillus, plantarum, Lactobacillus brevis, Lactobacillus acidophilus, Lactobacillus casei, Lactobacillus gasseri, Lactobacillus rhamnosus,* and *Lactobacillus salivarius*. Non-limiting examples of such *Bifidobacterium* species include *Bifidobacterium infantis, Bifidobacterium animalis, Bifidobacterium breve, Bifidobacterium longum, Bifidobacterium lactis,* and *Bifidobacterium adolescentis.*

In one embodiment, the gene sequence(s) encoding the one or more oxalate catabolism enzyme(s) has been codon-optimized for use in the recombinant bacterial cell of the invention. In one embodiment, the gene sequence(s) encoding the one or more oxalate catabolism enzyme(s) has been codon-optimized for use in *Escherichia coli*. In one embodiment, the gene sequence(s) encoding the one or more oxalate catabolism enzyme(s) has not been codon-optimized for use in *Escherichia coli*. In another embodiment, the gene sequence(s) encoding the one or more oxalate catabolism enzyme(s) has been codon-optimized for use in *Lactococcus*. When the gene sequence(s) encoding the one or more oxalate catabolism enzyme(s) is expressed in the recombinant bacterial cells of the invention, the bacterial cells catabolize more oxalate or oxalyl-CoA than unmodified bacteria of the same bacterial subtype under the same conditions (e.g., culture or environmental conditions). Thus, the genetically engineered bacteria comprising at least one heterologous gene encoding at least one oxalate catabolism enzyme may be used to catabolize excess oxalate, oxalic acid, and/or oxalyl-CoA to treat a disorder in which oxalate is detrimental, such as PHI, PHII, PHIII, and secondary hyperoxaluria, enteric hyperoxaluria, and idiopathic hyperoxaluria.

The present invention further comprises genes encoding functional fragments of an oxalate catabolism enzyme or functional variants of an oxalate catabolism enzyme. As used herein, the term "functional fragment thereof" or "functional variant thereof" of an oxalate catabolism enzyme relates to an element having qualitative biological activity in common with the wild-type oxalate catabolism enzyme from which the fragment or variant was derived. For example, a functional fragment or a functional variant of a mutated oxalate catabolism enzyme is one which retains essentially the same ability to catabolize oxalyl-CoA as the oxalate catabolism enzyme from which the functional fragment or functional variant was derived. For example, a polypeptide having oxalate catabolism enzyme activity may be truncated at the N-terminus or C-terminus and the retention of oxalate catabolism enzyme activity assessed using assays known to those of skill in the art, including the exemplary assays provided herein. In one embodiment, the recombinant bacterial cell of the invention comprises a heterologous gene encoding an oxalate catabolism enzyme functional variant. In another embodiment, the recombinant bacterial cell of the invention comprises a heterologous gene encoding an oxalate catabolism enzyme functional fragment.

Assays for testing the activity of an oxalate catabolism enzyme, an oxalate catabolism enzyme functional variant, or an oxalate catabolism enzyme functional fragment are well known to one of ordinary skill in the art. For example, oxalate catabolism can be assessed by expressing the protein, functional variant, or fragment thereof, in a recombinant bacterial cell that lacks endogenous oxalate catabolism enzyme activity. Oxalate catabolism activity can be assessed by quantifying oxalate degradation in the culture media as described by Federici et al., *Appl. Environ. Microbiol.* 70: 5066-73 (2004), the entire contents of which are expressly incorporated herein by reference. Formyl-CoA transferase and oxalyl-CoA decarboxylase activities can be measured by capillary electrophoresis as described in Turroni et al., *J. Appl. Microbiol.* 103: 1600-9 (2007).

As used herein, the term "percent (%) sequence identity" or "percent (%) identity," also including "homology," is defined as the percentage of amino acid residues or nucleotides in a candidate sequence that are identical with the amino acid residues or nucleotides in the reference sequences after aligning the sequences and introducing gaps, if necessary, to achieve the maximum percent sequence identity, and not considering any conservative substitutions as part of the sequence identity. Optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl. Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The present invention encompasses genes encoding an oxalate catabolism enzyme comprising amino acids in its sequence that are substantially the same as an amino acid sequence described herein. Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T. Similarly, contemplated is replacing a basic amino acid with another basic amino acid (e.g., replacement among Lys, Arg, His), replacing an acidic amino acid with another acidic amino acid (e.g., replacement among Asp and Glu), replacing a neutral amino acid with another neutral amino acid (e.g., replacement among Ala, Gly, Ser, Met, Thr, Leu, Ile, Asn, Gln, Phe, Cys, Pro, Trp, Tyr, Val).

In some embodiments, the gene encoding an oxalate catabolism enzyme is mutagenized; mutants exhibiting increased activity are selected; and the mutagenized gene encoding the oxalate catabolism enzyme is isolated and inserted into the bacterial cell of the invention. In one embodiment, spontaneous mutants that arise that allow bacteria to grow on oxalate as the sole carbon source can be screened for and selected. The gene comprising the modifications described herein may be present on a plasmid or chromosome. Non-limiting examples of oxalate catabolism enzymes of the disclosure are listed in Table 2.

TABLE 2

Oxalate Catabolism Enzyme Polynucleotide Sequences

| Description | Sequence | SEQ ID NO |
|---|---|---|
| frc (formyl-CoA transferase from *O. formigenes*) | ATGACTAAACCATTAGATGGAATTAATGTGCTTGACTTT ACCCACGTCCAGGCAGGTCCTGCCTGTACACAGATGAT GGGTTTCTTGGGCGCAAACGTCATCAAGATTGAAAGAC GTGGTTCCGGAGATATGACTCGTGGATGGCTGCAGGAC AAACCAAATGTTGATTCCCTGTATTTCACGATGTTCAAC | SEQ ID NO: 1 |

TABLE 2-continued

Oxalate Catabolism Enzyme Polynucleotide Sequences

| Description | Sequence | SEQ ID NO |
|---|---|---|
| | TGTAACAAACGTTCGATTGAACTGGACATGAAAACCCC<br>GGAAGGCAAAGAGCTTCTGGAACAGATGATCAAGAAA<br>GCCGACGTCATGGTCGAAAACTTCGGACCAGGCGCACT<br>GGACCGTATGGGCTTTACTTGGGAATACATTCAGGAAC<br>TGAATCCACGCGTCATTCTGGCTTCCGTTAAAGGCTATG<br>CAGAAGGCCACGCCAACGAACACCTGAAAGTTTATGAA<br>AACGTTGCACAGTGTTCCGGCGGTGCTGCAGCTACCAC<br>CGGTTTCTGGGATGGTCCTCCAACCGTTTCCGGCGCTGC<br>TCTGGGTGACTCCAACTCCGGTATGCACCTGATGATCG<br>GTATTCTGGCCGCTCTGGAAATGCGTCACAAAACCGGC<br>CGTGGTCAGAAAGTTGCCGTCGCTATGCAGGACGCTGT<br>TCTGAATCTGGTTCGTATCAAACTGCGTGACCAGCAAC<br>GTCTGGAAAGAACCGGCATTCTGGCTGAATACCCACAG<br>GCTCAGCCTAACTTTGCCTTCGACAGAGACGGTAACCC<br>ACTGTCCTTCGACAACATCACTTCCGTTCCACGTGGTGG<br>TAACGCAGGTGGCGGCGGCCAGCCAGGCTGGATGCTGA<br>AATGTAAAGGTTGGGAAACCGATGCGGACTCCTACGTT<br>TACTTCACCATCGCTGCAAACATGTGGCCACAGATCTG<br>CGACATGATCGACAAGCCAGAATGGAAAGACGACCCA<br>GCCTACAACACATTCGAAGGTCGTGTTGACAAGCTGAT<br>GGACATCTTCTCCTTCATCGAAACCAAGTTCGCTGACAA<br>GGACAAATTCGAAGTTACCGAATGGGCTGCCCAGTACG<br>GCATTCCTTGCGGTCCGGTCATGTCCATGAAAGAACTG<br>GCTCACGATCCTTCCCTGCAGAAAGTTGGTACCGTCGTT<br>GAAGTTGTCGACGAAATTCGTGGTAACCACCTGACCGT<br>TGGCGCACCGTTCAAATTCTCCGGATTCCAGCCGGAAA<br>TTACCCGTGCTCCGCTGTTGGGCGAACATACCGACGAA<br>GTTCTGAAAGAACTGGGTCTTGACGATGCCAAGATCAA<br>GGAACTGCATGCAAAACAGGTAGTTTGA | |
| oxc<br>(oxalylCoA<br>decarboxylase<br>from *O. formigenes*) | ATGAGTAACGACGACAATGTAGAGTTGACTGATGGCTT<br>TCATGTTTTGATCGATGCCCTGAAAATGAATGACATCG<br>ATACCATGTATGGTGTTGTCGGCATTCCTATCACGAACC<br>TGGCTCGTATGTGGCAAGATGACGGTCAGCGTTTTTAC<br>AGCTTCCGTCACGAACAACACGCAGGTTATGCAGCTTC<br>TATCGCCGGTTACATCGAAGGAAAACCTGGCGTTTGCT<br>TGACCGTTTCCGCCCCTGGCTTCCTGAACGGCGTGACTT<br>CCCTGGCTCATGCAACCACCAACTGCTTCCCAATGATCC<br>TGTTGAGCGGTTCCAGTGAACGTGAAATCGTCGATTTG<br>CAACAGGGCGATTACGAAGAAATGGATCAGATGAATGT<br>TGCACGTCCACACTGCAAAGCTTCTTTCCGTATCAACAG<br>CATCAAAGACATTCCAATCGGTATCGCTCGTGCAGTTC<br>GCACCGCTGTATCCGGACGTCCAGGTGGTGTTTACGTTG<br>ACTTGCCAGCAAAACTGTTCGGTCAGACCATTTCTGTAG<br>AAGAAGCTAACAAACTGCTCTTCAAACCAATCGATCCA<br>GCTCCGGCACAGATTCCTGCTGAAGACGCTATCGCTCG<br>CGCTGCTGACCTGATCAAGAACGCCAAACGTCCAGTTA<br>TCATGCTGGGTAAAGGCGCTGCATACGCACAATGCGAC<br>GACGAAATCCGCGCACTGGTTGAAGAAACCGGCATCCC<br>ATTCCTGCCAATGGGTATGGCTAAAGGCCTGCTGCCTG<br>ACAACCATCCACAATCCGCTGCTGCAACCCGTGCTTTCG<br>CACTGGCACAGTGTGACGTTTGCGTACTGATCGGCGCT<br>CGTCTGAACTGGCTGATGCAGCACGGTAAAGGCAAAAC<br>CTGGGGCGACGAACTGAAGAAATACGTTCAGATCGACA<br>TCCAGGCTAACGAAATGGACAGCAACCAGCCTATCGCT<br>GCACCAGTTGTTGGTGACATCAAGTCCGCCGTTTCCCTG<br>CTCCGCAAAGCACTGAAAGGCGCTCCAAAAGCTGACGC<br>TGAATGGACCGGCGCTCTGAAAGCCAAAGTTGACGGCA<br>ACAAAGCCAAACTGGCTGGCAAGATGACTGCCGAAACC<br>CCATCCGGAATGATGAACTACTCCAATTCCCTGGGCGTT<br>GTTCGTGACTTCATGCTGGCAAATCCGGATATTTCCCTG<br>GTTAACGAAGGCGCTAATGCACTCGACAACACTCGTAT<br>GATTGTTGACATGCTGAAACCACGCAAACGTCTTGACT<br>CCGGTACCTGGGGTGTTATGGGTATTGGTATGGGCTACT<br>GCGTTGCTGCAGCTGCTGTTACCGGCAAACCGGTTATC<br>GCTGTTGAAGGCGATAGCGCATTCGGTTTCTCCGGTATG<br>GAACTGGAAACCATCTGCCGTTACAACCTGCCAGTTAC<br>CGTTATCATCATGAACAATGGTGGTATCTATAAAGGTA<br>ACGAAGCAGATCCACAACCAGGCGTTATCTCCTGTACC<br>CGTCTGACCCGTGGTCGTTACGACATGATGATGGAAGC<br>ATTTGGCGGTAAAGGTTATGTTGCCAATACTCCAGCAG<br>AACTGAAAGCTGCTCTGGAAGAAGCTGTTGCTTCCGGC<br>AAACCATGCCTGATCAACGCGATGATCGATCCAGACGC<br>TGGTGTCGAATCTGGCCGTATCAAGAGCCTGAACGTTG<br>TAAGTAAAGTTGGCAAGAAATAA | SEQ ID NO: 2 |

TABLE 2-continued

Oxalate Catabolism Enzyme Polynucleotide Sequences

| Description | Sequence | SEQ ID NO |
|---|---|---|
| ScAAE3 (oxalate-CoA ligase from *S. cerevisiae*) | ATGACCAGTGCAGCTACGGTGACCGCGAGCTTTAATGA CACTTTTTCTGTGAGCGATAATGTCGCGGTAATCGTACC GGAAACCGATACGCAGGTCACCTACCGTGATCTTTCCC ACATGGTAGGACACTTTCAAACAATGTTCACGAACCCG AATAGTCCTCTGTACGGGGCGGTCTTTCGTCAAGACAC GGTAGCGATTAGCATGCGTAACGGCCTTGAATTTATTGT GGCTTTCCTTGGAGCCACGATGGATGCGAAAATTGGTG CGCCACTGAATCCCAATTATAAAGAGAAGGAGTTTAAT TTTTACCTGAATGACTTAAAGTCCAAAGCCATCTGCGTG CCGAAAGGCACCACCAAACTGCAAAGTTCAGAAATTCT TAAGAGTGCGTCCACGTTCGGGTGCTTTATTGTGGAACT GGCGTTTGACGCCACCCGTTTTCGTGTTGAATATGACAT TTACTCCCCGGAGGACAATTATAAACGTGTGATCTACC GCAGCCTTAACAATGCTAAGTTTGTCAACACAAACCCT GTCAAGTTCCCGGGTTTCGCCCGCAGCTCGGATGTTGCA CTTATTTTGCATACCTCAGGCACCACTAGTACCCCAAAG ACCGTACCCCTCTTGCATCTGAATATTGTCCGTTCAACC CTGAATATCGCCAACACTTACAAACTTACCCCGCTGGA TCGCTCCTATGTTGTAATGCCGCTGTTTCATGTACATGG ATTAATCGGCGTCTTACTGAGTACGTTCCGCACCCAGG GCAGTGTAGTCGTCCCGGACGGCTTTCATCCGAAGCTCT TCTGGGATCAGTTTGTTAAATATAACTGCAATTGGTTTA GTTGCGTCCCAACGATCTCTATGATTATGTTGAATATGC CCAAACCGAATCCGTTTCCGCACATTCGCTTTATCCGCT CATGTAGCAGCGCGCTGGCGCCAGCAACGTTTCACAAG CTGGAAAAAGAATTTAATGCCCCAGTTCTGGAAGCGTA CGCGATGACAGAAGCATCTCATCAGATGACCAGTAACA ATCTGCCTCCCGGTAAACGTAAACCGGGGACCGTGGGC CAACCTCAAGGTGTAACCGTAGTAATCCTGGATGACAA CGATAACGTTCTGCCGCCCGGCAAAGTTGGCGAGGTGT CGATCCGTGGGGAGAACGTCACCCTGGGCTACGCTAAT AACCCGAAAGCTAACAAAGAAAACTTCACTAAACGTGA AAACTATTTCCGTACCGGGGATCAGGGCTACTTCGACC CGGAGGGCTTTCTCGTGCTGACCGGCCGCATTAAAGAA TTGATCAATCGCGGTGGTGAAAAAATTAGTCCTATTGA ACTGGACGGAATCATGCTCTCGCATCCTAAAATCGACG AGGCGGTGGCGTTCGGCGTTCCAGATGATATGTATGGC CAAGTCGTTCAGGCGGCAATCGTGTTGAAAAAGGGGGA AAAGATGACCTATGAAGAATTAGTGAATTTCCTGAAAA AGCATTTAGCAAGCTTTAAAATCCCAACCAAAGTCTAC TTTGTGGATAAGCTGCCTAAAACGGCCACCGGGAAGAT TCAACGTCGCGTAATCGCCGAAACCTTCGCGAAATCTA GTCGCAACAAAAGCAAACTTtaa | SEQ ID NO: 3 |
| yfdE (Acetyl-CoA:oxalate CoA-transferase from *E coli*) | atgACAAATAATGAAAGCAAAGGGCCGTTTGAAGGCTTA TTAGTTATCGATATGACACATGTCCTTAATGGACCTTTC GGAACTCAACTTCTTTGTAATATGGGCGCAAGGGTAAT TAAAGTTGAGCCGCCGGGTCATGGTGATGATACCCGCA CATTTGGTCCCTATGTGGATGGACAGTCACTCTATTACA GTTTTATTAATCATGGCAAAGAGAGTGTGGTTCTTGATT TAAAGAATGATCACGATAAAAGTATATTTATAAATATG CTCAAACAAGCTGATGTATTAGCTGAGAATTTTCGCCC AGGTACAATGGAAAAACTGGGGTTTTCATGGGAAACGC TTCAAGAAATCAACCCGCGCCTCATATATGCTTCATCGT CAGGTTTCGGACATACCGGTCCGCTAAAAGATGCTCCT GCCTACGATACCATCATTCAGGCAATGAGCGGGATAAT GATGGAAACAGGATATCCTGATGCTCCGCCAGTGCGCG TTGGTACATCTCTTGCGGATCTATGCGGCGGTGTCTATT TATTCAGCGGAATAGTGAGTGCACTTTATGGCCGCGAA AAGAGCCAGAGAGGGCGCATGTCGATATAGCGATGTT TGATGCCACGCTGAGTTTTCTGGAGCATGGTCTGATGGC ATATATCGCAACTGGGAAGTCACCACAACGTCTGGGAA ATCGCCATCCCTACATGGCACCTTTTGATGTTTTCAATA CTCAGGATAAGCCGATTACGATTTGTTGTGGTAATGAC AAGCTTTTTTCTCGTTATGCCAGGCACTGGAGCTTACG GAACTGGTTAATGATCCCCGATTTAGCAGCAATATTTTA CGCGTACAAAACCAGGCTATTCTTAAACAATATATTGA GCGGACGTTAAAAACGCAGGCAGCTGAAGTTTGGTTAG CCAGAATACATGAAGTTGGTGTACCCGTCGCGCCGTTA TTAAGTGTGGCTGAGGCCATTAAATTGCCACAAACTCA GGCGAGAAATATGTTGATTGAAGCCGGGGGAATAATGA TGCCGGGTAATCCGATAAAAATCAGCGGCTGCGCGGAC CCGCATGTTATGCCGGGAGCGGCAACGCTCGACCAGCA TGGGGAACAAATTCGCCAGGAGTTCTCATCAtaa | SEQ ID NO: 4 |

In one embodiment, the gene sequence(s) encoding the one or more oxalate catabolism enzyme(s) comprises a formyl-CoA:oxalate CoA-transferase sequence. In one embodiment, the formyl-CoA:oxalate CoA-transferase is frc, e.g., from *O. formigenes*. Accordingly, in one embodiment, the frc gene has at least about 80% identity with the entire sequence of SEQ ID NO: 1. Accordingly, in one embodiment, the frc gene has at least about 90% identity with the entire sequence of SEQ ID NO: 1. Accordingly, in one embodiment, the frc gene has at least about 95% identity with the entire sequence of SEQ ID NO: 1. Accordingly, in one embodiment, the frc gene has at least about 85%, 86%, 87%, 88%, 89%, 90%, 91%, 92%, 93%, 94%, 95%, 96%, 97%, 98%, or 99% identity with the entire sequence of SEQ ID NO: 1. In another embodiment, the frc gene comprises the sequence of SEQ ID NO: 1. In yet another embodiment the frc gene consists of the sequence of SEQ ID NO:1.

In one embodiment, the gene sequence(s) encoding the one or more oxalate catabolism enzyme(s) comprises a oxalyl-CoA decarboxylase sequence. In one embodiment, the oxalyl-CoA decarboxylase is oxc, e.g., from *O. formigenes*. Accordingly, in one embodiment, the oxc gene has at least about 80% identity with the entire sequence of SEQ ID NO: 2. Accordingly, in one embodiment, the oxc gene has at least about 90% identity with the entire sequence of SEQ ID NO: 2. Accordingly, in one embodiment, the oxc gene has at least about 95% identity with the entire sequence of SEQ ID NO: 2. Accordingly, in one embodiment, the oxc gene has at least about 85%, 86%, 87%, 88%, 89%, 90%, 91%, 92%, 93%, 94%, 95%, 96%, 97%, 98%, or 99% identity with the entire sequence of SEQ ID NO: 2. In another embodiment, the oxc gene comprises the sequence of SEQ ID NO: 2. In yet another embodiment the oxc gene consists of the sequence of SEQ ID NO: 2. In another embodiment, the oxc gene consists of the sequence of SEQ ID NO: 2.

In one embodiment, the at least one gene encoding the at least one oxalate catabolism enzyme comprises an oxalate-CoA ligase sequence. In one embodiment, the oxalate-CoA ligase is ScAAE3 from *S. cerevisiae*. Accordingly, in one embodiment, the ScAAE3 gene has at least about 80% identity with the entire sequence of SEQ ID NO: 3. Accordingly, in one embodiment, the ScAAE3 gene has at least about 90% identity with the entire sequence of SEQ ID NO: 3. Accordingly, in one embodiment, the ScAAE3 gene has at least about 95% identity with the entire sequence of SEQ ID NO: 3. Accordingly, in one embodiment, the ScAAE3 gene has at least about 85%, 86%, 87%, 88%, 89%, 90%, 91%, 92%, 93%, 94%, 95%, 96%, 97%, 98%, or 99% identity with the entire sequence of SEQ ID NO: 3. In another embodiment, the ScAAE3 gene comprises the sequence of SEQ ID NO: 3. In yet another embodiment the ScAAE3 gene consists of the sequence of SEQ ID NO: 3.

In one embodiment, the at least one gene encoding the at least one oxalate catabolism enzyme comprises an acetyl-CoA:oxalate CoA-transferase sequence. In one embodiment, the acetyl-CoA:oxalate CoA-transferase is YfdE from *E. coli* from *S. cerevisiae*. Accordingly, in one embodiment, the YfdE gene has at least about 80% identity with the entire sequence of SEQ ID NO: 4. Accordingly, in one embodiment, the YfdE gene has at least about 90% identity with the entire sequence of SEQ ID NO: 4. Accordingly, in one embodiment, the YfdE gene has at least about 95% identity with the entire sequence of SEQ ID NO: 4. Accordingly, in one embodiment, the YfdE gene has at least about 85%, 86%, 87%, 88%, 89%, 90%, 91%, 92%, 93%, 94%, 95%, 96%, 97%, 98%, or 99% identity with the entire sequence of SEQ ID NO: 4. In another embodiment, the YfdE gene comprises the sequence of SEQ ID NO: 4. In yet another embodiment the YfdE gene consists of the sequence of SEQ ID NO: 4.

Table 3 lists non-limiting examples of oxalate catabolism enzyme polypeptide sequences.

TABLE 3

Polypeptide Sequences of Oxalate Catabolism Enzymes

| Description | Sequence | SEQ ID NO |
|---|---|---|
| Frc (Formyl-CoA transferase from *O. formigenes*) | MTKPLDGINVLDFTHVQAGPACTQMMGFLGANVIKIERRGSGDMT RGWLQDKPNVDSLYFTMFNCNKRSIELDMKTPEGKELLEQMIKKA DVMVENFGPGALDRMGFTWEYIQELNPRVILASVKGYAEGHANE HLKVYENVAQCSGGAAATTGFWDGPPTVSGAALGDSNSGMHLMI GILAALEMRHKTGRGQKVAVAMQDAVLNLVRIKLRDQQRLERTG ILAEYPQAQPNFAFDRDGNPLSFDNITSVPRGGNAGGGGQPGWML KCKGWETDADSYVYFTIAANMWPQICDMIDKPEWKDDPAYNTFE GRVDKLMDIFSFIETKFADKDKFEVTEWAAQYGIPCGPVMSMKEL AHDPSLQKVGTVVEVVDEIRGNHLTVGAPFKFSGFQPEITRAPLLG EHTDEVLKELGLDDAKIKELHAKQVV* | SEQ ID NO: 5 |
| Oxc (oxalylCoA decarboxylase from *O. formigenes*) | MSNDDNVELTDGFHVLIDALKMNDIDTMYGVVGIPITNLARMWQ DDGQRFYSFRHEQHAGYAASIAGYIEGKPGVCLTVSAPGFLNGVTS LAHATTNCFPMILLSGSSEREIVDLQQGDYEEMDQMNVARPHCKA SFRINSIKDIPIGIARAVRTAVSGRPGGVYVDLPAKLFGQTISVEEAN KLLFKPIDPAPAQIPAEDAIARAADLIKNAKRPVIMLGKGAAYAQC DDEIRALVEETGIPFLPMGMAKGLLPDNHPQSAAATRAFALAQCD VCVLIGARLNWLMQHGKGKTWGDELKKYVQIDIQANEMDSNQPI AAPVVGDIKSAVSLLRKALKGAPKADAEWTGALKAKVDGNKAKL AGKMTAETPSGMMNYSNSLGVVRDFMLANPDISLVNEGANALDN TRMIVDMLKPRKRLDSGTWGVMGIGMGYCVAAAAVTGKPVIAVE GDSAFGFSGMELETICRYNLPVTVIIMNNGGIYKGNEADPQPGVISC TRLTRGRYDMMMEAFGGKGYVANTPAELKAALEEAVASGKPCLI NAMIDPDAGVESGRIKSLNVVSKVGKK* | SEQ ID NO: 6 |
| ScAAE3 (Oxalate-CoA ligase from *S. cerevisiae*) | MTSAATVTASFNDTFSVSDNVAVIVPETDTQVTYRDLSHMVGHFQ TMFTNPNSPLYGAVFRQDTVAISMRNGLEFIVAFLGATMDAKIGAP LNPNYKEKEFNFYLNDLKSKAICVPKGTTKLQSSEILKSASTFGCFI VELAFDATRFRVEYDIYSPEDNYKRVIYRSLNNAKFVNTNPVKFPG FARSSDVALILHTSGTTSTPKTVPLLHLNIVRSTLNIANTYKLTPLDR | SEQ ID NO: 7 |

TABLE 3-continued

Polypeptide Sequences of Oxalate Catabolism Enzymes

| Description | Sequence | SEQ ID NO |
|---|---|---|
| | SYVVMPLFHVHGLIGVLLSTFRTQGSVVVPDGFHPKLFWDQFVKY<br>NCNWFSCVPTISMIMLNMPKPNPFPHIRFIRSCSSALAPATFHKLEK<br>EFNAPVLEAYAMTEASHQMTSNNLPPGKRKPGTVGQPQGVTVVIL<br>DDNDNVLPPGKVGEVSIRGENVTLGYANNPKANKENFTKRENYFR<br>TGDQGYFDPEGFLVLTGRIKELINRGGEKISPIELDGIMLSHPKIDEA<br>VAFGVPDDMYGQVVQAAIVLKKGEKMTYEELVNFLKKHLASFKI<br>PTKVYFVDKLPKTATGKIQRRVIAETFAKSSRNKSKL* | |
| yfdE<br>(Acetyl-<br>CoA:oxalate<br>CoA-<br>transferase<br>from E. coli) | MTNNESKGPFEGLLVIDMTHVLNGPFGTQLLCNMGARVIKVEPPG<br>HGDDTRTFGPYVDGQSLYYSFINHGKESVVLDLKNDHDKSIFINML<br>KQADVLAENFRPGTMEKLGFSWETLQEINPRLIYASSSGFGHTGPL<br>KDAPAYDTIIQAMSGIMMETGYPDAPPVRVGTSLADLCGGVYLFS<br>GIVSALYGREKSQRGAHVDIAMFDATLSFLEHGLMAYIATGKSPQ<br>RLGNRHPYMAPFDVFNTQDKPITICCGNDKLFSALCQALELTELVN<br>DPRFSSNILRVQNQAILKQYIERTLKTQAAEVWLARIHEVGVPVAP<br>LLSVAEAIKLPQTQARNMLIEAGGIMMPGNPIKISGCADPHVMPGA<br>ATLDQHGEQIRQEFSS* | SEQ ID NO: 8 |
| yfdW (formyl<br>CoA<br>transferase<br>from E. coli) | SYYHHHHHHLESTSLYKKAGLMSTPLQGIKVLDFTGVQSGPSCT<br>QMLAWFGADVIKIERPGVGDVTRHQLRDIPDIDALYFTMLNSNK<br>RSIELNTKTAEGKEVMEKLIREADILVENFHPGAIDHMGFTWEHI<br>QEINPRLIFGSIKGFDECSPYVNVKAYENVAQAAGGAASTTGFW<br>DGPPLVSAAALGDSNTGMHLLIGLLAALLHREKTGRGQRVTMS<br>MQDAVLNLCRVKLRDQQRLDKLGYLEEYPQYPNGTFGDAVPRG<br>GNAGGGGQPGWILKCKGWETDPNAYIYFTIQEQNWENTCKAIG<br>KPEWITDPAYSTAHARQPHIFDIFAEIEKYTVTIDKHEAVAYLTQF<br>DIPCAPVLSMKEISLDPSLRQSGSVVEVEQPLRGKYLTVGCPMKF<br>SAFTPDIKAAPLLGEHTAAVLQELGYSDDEIAAMKQNHAI | SEQ ID NO: 9 |
| yfdU (oxalyl-<br>CoA<br>decarboxylase<br>E. coli) | MSDQLQMTDGMHIIVEALKQNNIDTIYGVVGIPVTDMARHAQAE<br>GIRYIGFRHEQSAGYAAAASGFLTQKPGICLTVSAPGFLNGLTAL<br>ANATVNGFPMIMISGSSDRAIVDLQQGDYEELDQMNAAKPYAK<br>AAFRVNQPQDLGIALARAIRVSVSGRPGGVYLDLPANVLAATME<br>KDEALTTIVKVENPSPALLPCPKSVTSAISLLAKAERPLIILGKGAA<br>YSQADEQLREFIESAQIPFLPMSMAKGILEDTHPLSAAAARSFALA<br>NADVVMLVGARLNWLLAHGKKGWAADTQFIQLDIEPQEIDSNR<br>PIAVPVVGDIASSMQGMLAELKQNTFTTPLVWRDILNIHKQQNA<br>QKMHEKLSTDTQPLNYFNALSAVRDVLRENQDIYLVNEGANTL<br>DNARNIIDMYKPRRRLDCGTWGVMGIGMGYAIGASVTSGSPVV<br>AIEGDSAFGFSGMEIETICRYNLPVTIVIFNNGGIYRGDGVDLSGA<br>GAPSPTDLLHHARYDKLMDAFRGVGYNVTTTDELRHALTTGIQS<br>RKPTIINVVIDPAAGTESGHITKLNPKQVAGN | SEQ ID NO: 10 |

In one embodiment, one or more polypeptide(s) encoded by the oxalate catabolism cassette(s) and expressed by the genetically engineered bacteria comprises a formyl-CoA transferase, e.g. frc from O. formigenes. In one embodiment the polypeptide(s) have at least about 80% identity with SEQ ID NO: 5. In another embodiment, one or more polypeptide(s) encoded by the oxalate catabolism gene(s) or gene cassette(s) and expressed by the genetically engineered bacteria have at least about 85% identity with SEQ ID NO: 5. In one embodiment, one or more polypeptide(s) encoded by the oxalate catabolism gene(s) or gene cassette(s) and expressed by the genetically engineered bacteria have at least about 90% identity with SEQ ID NO: 5. In one embodiment, one or more polypeptide(s) encoded by the oxalate catabolism gene(s) or gene cassette(s) and expressed by the genetically engineered bacteria have at least about 95% identity with SEQ ID NO: 5. In another embodiment, one or more polypeptide(s) encoded by the oxalate catabolism gene(s) or gene cassette(s) and expressed by the genetically engineered bacteria have at least about 96%, 97%, 98%, or 99% identity with SEQ ID NO: 5. Accordingly, in one embodiment, one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 5. In another embodiment, one or more polypeptide(s) encoded by the oxalate catabolism gene(s) or gene cassette(s) and expressed by the genetically engineered bacteria comprise the sequence of SEQ ID NO: 5. In yet another embodiment one or more polypeptide(s) encoded by the oxalate catabolism gene(s) or gene cassette(s) and expressed by the genetically engineered bacteria consist of the sequence of SEQ ID NO: 5.

In one embodiment, one or more polypeptide(s) encoded by the oxalate catabolism cassette(s) and expressed by the engineered bacteria comprises a oxalyl-CoA decarboxylase, e.g. oxc from O. formigenes. In one embodiment the polypeptide(s) have at least about 80% identity with SEQ ID NO: 6. In another embodiment, one or more polypeptide(s) encoded by the oxalate catabolism gene(s) or gene cassette(s and expressed by the engineered bacteria have at least about 85% identity with SEQ ID NO: 6. In one embodiment, one or more polypeptide(s) encoded by the oxalate catabolism gene(s) or gene cassette(s) and expressed by the engineered bacteria have at least about 90% identity with SEQ ID NO: 6. In one embodiment, one or more polypeptide(s) encoded by the oxalate catabolism gene(s) or gene cassette(s) and expressed by the engineered bacteria have at least about 95% identity with SEQ ID NO: 6. In another embodiment, one or more polypeptide(s) encoded by the oxalate catabolism gene(s) or gene cassette(s) and expressed by the engineered bacteria have at least about 96%, 97%, 98%, or 99% identity with SEQ ID NO: 6. Accordingly, in one embodiment, one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 6. In another embodiment, one or more polypeptide(s) encoded by the oxalate catabolism gene(s) or gene cassette(s) and expressed by the engineered bacteria comprise the sequence of SEQ ID NO: 6. In yet another embodiment one or more polypeptide(s) encoded by the oxalate catabolism gene(s) or gene cassette(s) and expressed by the genetically engineered bacteria consist of the sequence of SEQ ID NO: 6.

In one embodiment, one or more polypeptide(s) encoded by the oxalate catabolism gene(s) or gene cassette(s) and expressed by the engineered bacteria comprises an oxalate-CoA ligase, e.g. ScAAE3 from *S. cerevisiae*. In one embodiment the polypeptide(s) have at least about 80% identity with SEQ ID NO: 7. In another embodiment, one or more polypeptide(s) encoded by the oxalate catabolism gene(s) or gene cassette(s and expressed by the engineered bacteria have at least about 85% identity with SEQ ID NO: 7. In one embodiment, one or more polypeptide(s) encoded by the oxalate catabolism gene(s) or gene cassette(s) and expressed by the engineered bacteria have at least about 90% identity with SEQ ID NO: 7. In one embodiment, one or more polypeptide(s) encoded by the oxalate catabolism gene(s) or gene cassette(s) and expressed by the engineered bacteria have at least about 95% identity with SEQ ID NO: 7. In another embodiment, one or more polypeptide(s) encoded by the oxalate catabolism gene(s) or gene cassette(s) and expressed by the engineered bacteria have at least about 96%, 97%, 98%, or 99% identity with SEQ ID NO: 7. Accordingly, in one embodiment, one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 7. In another embodiment, one or more polypeptide(s) encoded by the oxalate catabolism gene(s) or gene cassette(s) and expressed by the engineered bacteria comprise the sequence of SEQ ID NO: 7. In yet another embodiment one or more polypeptide(s) encoded by the oxalate catabolism cassette(s) and expressed by the genetically engineered bacteria consist of the sequence of SEQ ID NO: 7.

In one embodiment, one or more polypeptide(s) encoded by the oxalate catabolism cassette(s) and expressed by the engineered bacteria comprises an Acetyl-CoA:oxalate CoA-transferase from, e.g. YfdE from *E. coli*. In one embodiment the polypeptide(s) have at least about 80% identity with SEQ ID NO: 8. In another embodiment, one or more polypeptide(s) encoded by the oxalate catabolism gene(s) or gene cassette(s and expressed by the engineered bacteria have at least about 85% identity with SEQ ID NO: 8. In one embodiment, one or more polypeptide(s) encoded by the oxalate catabolism gene(s) or gene cassette(s) and expressed by the engineered bacteria have at least about 90% identity with SEQ ID NO: 8. In one embodiment, one or more polypeptide(s) encoded by the oxalate catabolism gene(s) or gene cassette(s) and expressed by the engineered bacteria have at least about 95% identity with SEQ ID NO: 8. In another embodiment, one or more polypeptide(s) encoded by the oxalate catabolism gene(s) or gene cassette(s) and expressed by the engineered bacteria have at least about 96%, 97%, 98%, or 99% identity with SEQ ID NO: 8. Accordingly, in one embodiment, one or more polypeptide(s) encoded by the oxalate catabolism gene(s) or gene cassette(s) and expressed by the genetically engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 8. In another embodiment, one or more polypeptide(s) encoded by the oxalate catabolism gene(s) or gene cassette(s) and expressed by the engineered bacteria comprise the sequence of SEQ ID NO: 8. In yet another embodiment one or more polypeptide(s) encoded by the oxalate catabolism gene(s) or gene cassette(s) and expressed by the engineered bacteria consist of the sequence of with SEQ ID NO: 8.

In one embodiment, one or more polypeptide(s) encoded by the oxalate catabolism gene(s) or gene cassette(s) and expressed by the genetically engineered bacteria comprises a formyl CoA transferase, e.g., yfdW from *E. coli*. In one embodiment the polypeptide(s) have at least about 80% identity with SEQ ID NO: 9. In another embodiment, one or more polypeptide(s) encoded by the oxalate catabolism gene(s) or gene cassette(s and expressed by the engineered bacteria have at least about 85% identity with SEQ ID NO: 9. In one embodiment, one or more polypeptide(s) encoded by the oxalate catabolism gene(s) or gene cassette(s) and expressed by the engineered bacteria have at least about 90% identity with SEQ ID NO: 9. In one embodiment, one or more polypeptide(s) encoded by the oxalate catabolism gene(s) or gene cassette(s) and expressed by the engineered bacteria have at least about 95% identity with SEQ ID NO: 9. In another embodiment, one or more polypeptide(s) encoded by the oxalate catabolism gene(s) or gene cassette(s) and expressed by the engineered bacteria have at least about 96%, 97%, 98%, or 99% identity with SEQ ID NO: 9. Accordingly, in one embodiment, one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 9. In another embodiment, one or more polypeptide(s) encoded by the oxalate catabolism gene(s) or gene cassette(s) and expressed by the engineered comprise the sequence of SEQ ID NO: 9. In yet another embodiment one or more polypeptide(s) encoded by the oxalate catabolism gene(s) or gene cassette(s) and expressed by the engineered bacteria consist of the sequence of SEQ ID NO: 9.

In one embodiment, one or more polypeptide(s) encoded by the oxalate catabolism gene(s) or gene cassette(s) and expressed by the engineered bacteria comprises a oxalyl-CoA decarboxylase, e.g., yfdU from *E. coli*. In one embodiment the polypeptide(s) have at least about 80% identity with SEQ ID NO: 10. In another embodiment, one or more polypeptide(s) encoded by the oxalate catabolism gene(s) or gene cassette(s and expressed by the engineered bacteria have at least about 85% identity with SEQ ID NO: 10. In one embodiment, one or more polypeptide(s) encoded by the oxalate catabolism gene(s) or gene cassette(s) and expressed by the engineered bacteria have at least about 90% identity with SEQ ID NO: 10. In one embodiment, one or more polypeptide(s) encoded by the oxalate catabolism gene(s) or gene cassette(s) and expressed by the engineered bacteria have at least about 95% identity with SEQ ID NO: 10. In another embodiment, one or more polypeptide(s) encoded by the oxalate catabolism gene(s) or gene cassette(s) and expressed by the engineered bacteria have at least about 96%, 97%, 98%, or 99% identity with SEQ ID NO: 10.

Accordingly, in one embodiment, one or more polypeptide(s) encoded by the oxalate catabolism gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 10. In another embodiment, one or more polypeptide(s) encoded by the oxalate catabolism gene(s) or gene cassette(s) and expressed by the engineered bacteria comprise the sequence of SEQ ID NO: 10. In yet another embodiment one or more polypeptide(s) encoded by the oxalate catabolism gene(s) or gene cassette(s) and expressed by the engineered bacteria consist of the sequence of SEQ ID NO: 10.

In one embodiment, the gene sequence(s) encoding the one or more oxalate catabolism enzyme(s) is directly operably linked to a first promoter. In another embodiment, the gene sequence(s) encoding the one or more oxalate catabolism enzyme(s) is indirectly operably linked to a first promoter. In one embodiment, the promoter is not operably linked with the at least one gene encoding the oxalate catabolism enzyme in nature.

In some embodiments, the gene sequence(s) encoding the one or more oxalate catabolism enzyme(s) is expressed under the control of a constitutive promoter. In another embodiment, the gene sequence(s) encoding the one or more oxalate catabolism enzyme(s) is expressed under the control of an inducible promoter. In some embodiments, the gene sequence(s) encoding the one or more oxalate catabolism enzyme(s) is expressed under the control of a promoter that is directly or indirectly induced by exogenous environmental conditions. In one embodiment, the gene sequence(s) encoding the one or more oxalate catabolism enzyme(s) is expressed under the control of a promoter that is directly or indirectly induced by low-oxygen or anaerobic conditions, such as the environmental conditions of a mammalian gut, wherein expression of the gene sequence(s) encoding the one or more oxalate catabolism enzyme(s) is activated under low-oxygen or anaerobic environments, such as the environment of a mammalian gut. In some embodiments, the gene sequence(s) encoding the one or more oxalate catabolism enzyme(s) is expressed under the control of a promoter that is directly or indirectly induced by inflammatory conditions. Exemplary inducible promoters described herein include oxygen level-dependent promoters (e.g., FNR-inducible promoter), promoters induced by inflammation or an inflammatory response (RNS, ROS promoters), and promoters induced by a metabolite that may or may not be naturally present (e.g., can be exogenously added) in the gut, e.g., arabinose and tetracycline. Examples of inducible promoters include, but are not limited to, an FNR responsive promoter, a $P_{araC}$ promoter, a $P_{araBAD}$ promoter, and a $P_{TetR}$ promoter, each of which are described in more detail herein. Inducible promoters are described in more detail infra.

The at least one gene encoding the at least one oxalate catabolism enzyme may be present on a plasmid or chromosome in the bacterial cell. In one embodiment, the gene sequence(s) encoding the one or more oxalate catabolism enzyme(s) is located on a plasmid in the bacterial cell. In another embodiment, the gene sequence(s) encoding the one or more oxalate catabolism enzyme(s) is located in the chromosome of the bacterial cell. In yet another embodiment, a native copy of the gene sequence(s) encoding the one or more oxalate catabolism enzyme(s) is located in the chromosome of the bacterial cell, and at least one gene encoding at least one oxalate catabolism enzyme from a different species of bacteria is located on a plasmid in the bacterial cell. In yet another embodiment, a native copy of the gene sequence(s) encoding the one or more oxalate catabolism enzyme(s) is located on a plasmid in the bacterial cell, and at least one gene encoding the at least one oxalate catabolism enzyme from a different species of bacteria is located on a plasmid in the bacterial cell. In yet another embodiment, a native copy of the gene sequence(s) encoding the one or more oxalate catabolism enzyme(s) is located in the chromosome of the bacterial cell, and at least one gene encoding the at least one oxalate catabolism enzyme from a different species of bacteria is located in the chromosome of the bacterial cell.

In some embodiments, the gene sequence(s) encoding the one or more oxalate catabolism enzyme(s) is expressed on a low-copy plasmid. In some embodiments, the gene sequence(s) encoding the one or more oxalate catabolism enzyme(s) is expressed on a high-copy plasmid. In some embodiments, the high-copy plasmid may be useful for increasing expression of the at least one oxalate catabolism enzyme, thereby increasing the catabolism of oxalate, oxalic acid, and/or oxalyl-CoA.

In some embodiments, a recombinant bacterial cell of the invention comprising at least one gene encoding at least one oxalate catabolism enzyme expressed on a high-copy plasmid does not increase oxalate catabolism or decrease oxalate and/or oxalic acid levels as compared to a recombinant bacterial cell comprising the same gene expressed on a low-copy plasmid in the absence of a heterologous importer of oxalate and additional copies of a native importer of oxalate. Furthermore, in some embodiments that incorporate an importer of oxalate into the recombinant bacterial cell, there may be additional advantages to using a low-copy plasmid comprising the gene sequence(s) encoding the one or more oxalate catabolism enzyme(s) in conjunction in order to enhance the stability of expression of the oxalate catabolism enzyme, while maintaining high oxalate catabolism and to reduce negative selection pressure on the transformed bacterium. In alternate embodiments, the importer of oxalate is used in conjunction with a high-copy plasmid.

Transporter (Importer) of Oxalate

The uptake of oxalate into the anaerobic bacterium, *Oxalobacter formigenes*, has been found to occur via the oxalate transporter OxlT (see, e.g., Ruan et al., *J. Biol. Chem.* 267: 10537-43 (1992), the entire contents of which are expressly incorporated herein by reference). OxlT catalyzes the exchange of extracellular oxalate, a divalent anion, for intracellular formate, a monovalent cation that is derived from the decarboxylation of oxalate, thus generating a proton-motive force. Other proteins that mediate the import of oxalate are well known to those of skill in the art.

Oxalate transporters, e.g., oxalate importers, may be expressed or modified in the bacteria of the invention in order to enhance oxalate transport into the cell. Specifically, when the importer of oxalate is expressed in the recombinant bacterial cells of the invention, the bacterial cells import more oxalate into the cell when the importer is expressed than unmodified bacteria of the same bacterial subtype under the same conditions. Thus, the genetically engineered bacteria comprising one or more heterologous gene sequence(s) encoding an importer of oxalate may be used to import oxalate into the bacteria so that any gene sequence(s) encoding an oxalate catabolism enzyme(s) expressed in the organism can be used to treat disorders in which oxalate is detrimental, such as PHI, PHII, PHIII, and secondary hyperoxaluria, enteric hyperoxaluria, and idiopathic hyperoxaluria. In one embodiment, the bacterial cell of the invention comprises a heterologous gene sequence(s) encoding a transporter (importer) of oxalate. In one embodiment, the bacterial cell of the invention comprises a heterologous gene sequence(s) encoding transporter of oxalate and one or more heterologous gene sequence(s) encoding one or more oxalate catabolism enzyme(s). In one embodiment, the bacterial cell of the invention comprises a heterologous gene sequence(s) encoding transporter of oxalate and one or more heterologous gene sequence(s) encoding one or more polypeptides selected from a formate exporter, an oxalate:formate antiporter, and combinations thereof. In one embodiment, the bacterial cell of the invention comprises a heterologous gene sequence(s) encoding a transporter of oxalate, one or more heterologous gene sequence(s) encoding one or more oxalate catabolism enzyme(s), and one or more heterologous gene sequence(s) encoding one or more polypeptides selected from a formate exporter, an oxalate:formate antiporter, and combinations thereof.

Thus, in some embodiments, the invention provides a bacterial cell that comprises one or more heterologous gene sequence(s) encoding an oxalate catabolism enzyme operably linked to a first promoter and one or more heterologous gene sequence(s) encoding an transporter (importer) of oxalate. In some embodiments, the invention provides a bacterial cell that comprises one or more heterologous gene sequence(s) encoding an transporter (importer) of oxalate operably linked to the first promoter. In another embodiment, the invention provides a bacterial cell that comprises one or more heterologous gene sequence(s) encoding one or more oxalate catabolism enzyme(s) operably linked to a first promoter and one or more heterologous gene sequence(s) encoding an transporter (importer) of oxalate operably linked to a second promoter. In one embodiment, the first promoter and the second promoter are separate copies of the same promoter. In another embodiment, the first promoter and the second promoter are different promoters.

In one embodiment, the bacterial cell comprises one or more gene sequence(s) encoding an transporter (importer) of oxalate from a different organism, e.g., a different species of bacteria. In one embodiment, the bacterial cell comprises one or more native gene sequence(s) encoding an transporter (importer) of oxalate. In some embodiments, the one or more native gene sequence(s) encoding an transporter (importer) of oxalate is not modified. In another embodiment, the bacterial cell comprises more than one copy of one or more native gene sequence(s) encoding an transporter (importer) of oxalate. In yet another embodiment, the bacterial cell comprises a copy of one or more gene sequence(s) encoding a native transporter (importer) of oxalate, as well as one or more copy of one or more heterologous gene sequence(s) encoding an transporter of oxalate from a different bacterial species. In one embodiment, the bacterial cell comprises one or more, two, three, four, five, or six copies of the one or more heterologous gene sequence(s) encoding an transporter of oxalate. In one embodiment, the bacterial cell comprises multiple copies of the one or more heterologous gene sequence(s) encoding an transporter of oxalate.

In some embodiments, the transporter of oxalate is encoded by an transporter of oxalate gene derived from a bacterial genus or species, including but not limited to, *Oxalobacter*. In some embodiments, the transporter of oxalate gene is derived from a bacteria of the species *Oxalobacter formigenes*. In some embodiments, the transporter is the OxlT Oxalate:Formate Antiporter from *Oxalobacter formigenes*

In other embodiments, transporter of oxalate is encoded by a gene selected from the oxalate:formate antiporter (OFA) family. The OFA family members belong to the major facilitator superfamily and are widely distributed in nature, being present in the bacterial, archaeal, and eukaryotic kingdoms (see., e.g., Pao et al., Major Facilitator Superfamily Microbiol. Mol. Biol. Rev. March 1998 vol. 62 no. 1 1-34). In a non-limiting example, the transporter is a homolog and/or ortholog of the *Oxalobacter formigenes* oxalate:formate antiporter. In another non-limiting example, the transporter is a bacterially derived homolog and/or ortholog of the *Oxalobacter formigenes* oxalate:formate antiporter (OxlT). The present invention further comprises genes encoding functional fragments of an transporter of oxalate or functional variants of an transporter of oxalate. As used herein, the term "functional fragment thereof" or "functional variant thereof" of an transporter of oxalate relates to an element having qualitative biological activity in common with the wild-type transporter of oxalate from which the fragment or variant was derived. For example, a functional fragment or a functional variant of a mutated transporter of oxalate protein is one which retains essentially the same ability to import oxalate into the bacterial cell as does the transporter protein from which the functional fragment or functional variant was derived. In one embodiment, the recombinant bacterial cell of the invention comprises one or more heterologous gene sequence(s) encoding a functional fragment of an transporter of oxalate. In another embodiment, the recombinant bacterial cell of the invention comprises one or more heterologous gene sequence(s) encoding a functional variant of an transporter of oxalate.

Assays for testing the activity of an transporter of oxalate, an transporter of oxalate functional variant, or an transporter of oxalate functional fragment are well known to one of ordinary skill in the art. For example, oxalate import can be assessed by preparing detergent-extracted proteoliposomes from recombinant bacterial cells expressing the protein, functional variant, or fragment thereof, and determining [$^{14}$C]oxalate uptake as described in Abe et al., *J. Biol. Chem.* 271: 6789-93 (1996), the entire contents of which are expressly incorporated herein by reference.

In one embodiment the genes encoding the transporter of oxalate have been codon-optimized for use in the host organism. In one embodiment, the genes encoding the transporter of oxalate have been codon-optimized for use in *Escherichia coli*.

The present invention also encompasses genes encoding an transporter of oxalate comprising amino acids in its sequence that are substantially the same as an amino acid sequence described herein. Amino acid sequences that are substantially the same as the sequences described herein include sequences comprising conservative amino acid substitutions, as well as amino acid deletions and/or insertions.

In some embodiments, the one or more gene sequence(s) encoding an transporter of oxalate is mutagenized; mutants exhibiting increased oxalate transport are selected; and the mutagenized one or more gene sequence(s) encoding an transporter of oxalate is isolated and inserted into the bacterial cell of the invention. In some embodiments, the one or more gene sequence(s) encoding an transporter of oxalate is mutagenized; mutants exhibiting decreased oxalate transport are selected; and the mutagenized one or more gene sequence(s) encoding an transporter of oxalate is isolated and inserted into the bacterial cell of the invention. The transporter modifications described herein may be present on a plasmid or chromosome.

Table 4 lists polypeptide and polynucleotide sequences for a non-limiting example of an Oxalate:formate antiporter.

TABLE 4

OxlT sequences

| Description | Sequence | SEQ ID NO |
|---|---|---|
| OxlT coding region (oxalate:formate antiporter from *O. formigenes*) | ATGAATAATCCACAAACAGGACAATCAACAGGCCTCTTGGG<br>CAATCGTTGGTTCTACTTGGTATTAGCAGTTTTGCTGATGTG<br>TATGATCTCGGGTGTCCAATATTCCTGGACACTGTACGCTAA<br>CCCGGTTAAAGACAACCTTGGCGTTTCTTTGGCTGCGGTTCA<br>GACGGCTTTCACACTCTCTCAGGTCATTCAAGCTGGTTCTCA<br>GCCTGGTGGTGGTTACTTCGTTGATAAATTCGGTCCAAGAAT<br>TCCATTGATGTTCGGTGGTGCGATGGTTCTCGCTGGCTGGAC<br>CTTCATGGGTATGGTTGACAGTGTTCCTGCTCTGTATGCTCT<br>TTATACTCTGGCCGGTGCAGGTGTTGGTATCGTTTACGGTAT<br>CGCGATGAACACGGCTAACAGATGGTTCCCGGACAAACGCG<br>GTCTGGCTTCCGGTTTCACCGCTGCCGGTTACGGTCTGGGTG<br>TTCTGCCGTTCCTGCCACTGATCAGCTCCGTTCTGAAAGTTG<br>AAGGTGTTGGCGCAGCATTCATGTACACCGGTTTGATCATG<br>GGTATCCTGATTATCCTGATCGCTTTCGTTATCCGTTTCCCTG<br>GCCAGCAAGGCGCCAAAAAACAAATCGTTGTTACCGACAAG<br>GATTTCAATTCTGGCGAAATGCTGAGAACACCACAATTCTG<br>GGTTCTGTGGACCGCATTCTTTTCCGTTAACTTTGGTGGTTT<br>GCTGCTGGTTGCCAACAGCGTCCCTTACGGTCGCAGCCTCG<br>GTCTTGCCGCAGGTGTGCTGACGATCGGTGTTTCGATCCAGA<br>ACCTGTTCAATGGTGGTTGCCGTCCTTTCTGGGGTTTCGTTT<br>CCGATAAAATCGGCCGTTACAAAACCATGTCCGTCGTTTTCG<br>GTATCAATGCTGTTGTTCTCGCACTTTTCCCGACGATTGCTG<br>CCTTGGGCGATGTAGCCTTTATCGCCATGTTGGCAATCGCAT<br>TCTTCACATGGGGTGGTAGCTACGCTCTGTTCCCATCGACCA<br>ACAGCGATATTTTCGGTACGGCATACTCTGCCAGAAACTAT<br>GGTTTCTTCTGGGCTGCAAAAGCAACTGCCTCGATCTTCGGT<br>GGTGGTCTGGGTGCTGCAATTGCAACCAACTTCGGATGGAA<br>TACCGCTTTCCTGATTACTGCGATTACTTCTTTCATCGCATTT<br>GCTCTGGCTACCTTCGTTATTCCAAGAATGGGCCGTCCAGTC<br>AAGAAAATGGTCAAATTGTCTCCAGAAGAAAAAGCTGTACA<br>TTAA | SEQ ID NO: 11 |
| OxlT (oxalate:formate antiporter from *O. formigenes*) | MNNPQTGQSTGLLGNRWFYLVLAVLLMCMISGVQYSWTLYA<br>NPVKDNLGVSLAAVQTAFTLSQVIQAGSQPGGGYFVDKFGPRI<br>PLMFGGAMVLAGWTFMGMVDSVPALYALYTLAGAGVGIVY<br>GIAMNTANRWFPDKRGLASGFTAAGYGLGVLPFLPLISSVLKV<br>EGVGAAFMYTGLIMGILIILIAFVIRFPGQQGAKKQIVVTDKDF<br>NSGEMLRTPQFWVLWTAFFSVNFGGLLLVANSVPYGRSLGLA<br>AGVLTIGVSIQNLFNGGCRPFWGFVSDKIGRYKTMSVVFGINA<br>VVLALFPTIAALGDVAFIAMLAIAFFTWGGSYALFPSTNSDIFG<br>TAYSARNYGFFWAAKATASIFGGGLGAAIATNFGWNTAFLITA<br>ITSFIAFALATFVIPRMGRPVKKMVKLSPEEKAVH* | SEQ ID NO: 12 |

In one embodiment, the oxalate importer is the oxalate:formate antiporter OxlT. In one embodiment, the OxlT gene has at least about 80% identity to SEQ ID NO: 11. Accordingly, in one embodiment, the OxlT gene has at least about 90% identity to SEQ ID NO: 11. Accordingly, in one embodiment, the OxlT gene has at least about 95% identity to SEQ ID NO: 11. Accordingly, in one embodiment, the OxlT gene has at least about 85%, 86%, 87%, 88%, 89%, 90%, 91%, 92%, 93%, 94%, 95%, 96%, 97%, 98%, or 99% identity to SEQ ID NO: 11. In another embodiment, the OxlT gene comprises the sequence of SEQ ID NO: 11. In yet another embodiment the OxlT gene consists of the sequence of SEQ ID NO: 11.

In one embodiment, one or more polypeptide(s) encoded by one or more gene(s) or gene cassette(s) and expressed by the genetically engineered bacteria is the oxalate:formate antiporter OxlT. In one embodiment the polypeptide(s) have at least about 80% identity with SEQ ID NO: 12. In another embodiment, one or more polypeptide(s) encoded by one or more gene(s) or gene cassette(s) and expressed by the engineered bacteria have at least about 85% identity with SEQ ID NO: 12. In one embodiment, one or more polypeptide(s) encoded by one or more gene(s) or gene cassette(s) and expressed by the engineered bacteria have at least about 90% identity with SEQ ID NO: 12. In one embodiment, one or more polypeptide(s) encoded by one or more gene(s) or gene cassette(s) and expressed by the engineered bacteria have at least about 95% identity with SEQ ID NO: 12. In another embodiment, one or more polypeptide(s) encoded by one or more gene(s) or gene cassette(s) and expressed by the engineered bacteria have at least about 96%, 97%, 98%, or 99% identity with SEQ ID NO: 12. Accordingly, in one embodiment, one or more polypeptide(s) encoded by one or more gene(s) or gene cassette(s) and expressed by the engineered bacteria have at least about 80%, 81%, 82%, 83%, 84%, 85%, 86%, 87%, 88%, 89%, 90%, 91%, 92%, 93%, 94%, 95%, 96%, 97%, 98%, or 99% identity with SEQ ID NO: 12. In another embodiment, one or more polypeptide(s) encoded by one or more gene(s) or gene cassette(s) and expressed by the engineered bacteria comprise the sequence of SEQ ID NO: 12. In yet another embodiment one or more polypeptide(s) encoded by one or more gene(s) or gene cassette(s) and expressed by the engineered bacteria consist of the sequence of SEQ ID NO: 12.

In some embodiments, the bacterial cell comprises one or more heterologous gene sequence(s) encoding at least one oxalate catabolism enzyme(s) operably linked to a first promoter and one or more heterologous gene sequence(s) encoding an importer of oxalate. In some embodiments, the one or more heterologous gene sequence(s) encoding an importer of oxalate is operably linked to the first promoter. In other embodiments, the one or more heterologous gene sequence(s) encoding an importer of oxalate is operably linked to a second promoter. In one embodiment, the one or more gene sequence(s) encoding an importer of oxalate is directly operably linked to the second promoter. In another embodiment, the one or more gene sequence(s) encoding an importer of oxalate is indirectly operably linked to the second promoter.

In some embodiments, expression of one or more gene sequence(s) encoding an importer of oxalate is controlled by a different promoter than the promoter that controls expression of the gene sequence(s) encoding the one or more oxalate catabolism enzyme(s). In some embodiments, expression of the one or more gene sequence(s) encoding an importer of oxalate is controlled by the same promoter that controls expression of the one or more oxalate catabolism enzyme(s). In some embodiments, one or more gene sequence(s) encoding an importer of oxalate and the oxalate catabolism enzyme are divergently transcribed from a promoter region. In some embodiments, expression of each of genes encoding the gene sequence(s) encoding an importer of oxalate and the gene sequence(s) encoding the one or more oxalate catabolism enzyme(s) is controlled by different promoters.

In one embodiment, the promoter is not operably linked with the one or more gene sequence(s) encoding an importer of oxalate in nature. In some embodiments, the one or more gene sequence(s) encoding an importer of oxalate is controlled by its native promoter. In some embodiments, the one or more gene sequence(s) encoding an importer of oxalate is controlled by an inducible promoter. In some embodiments, the one or more gene sequence(s) encoding the importer of oxalate is controlled by a promoter that is stronger than its native promoter. In some embodiments, the one or more gene sequence(s) encoding an importer of oxalate is controlled by a constitutive promoter.

In another embodiment, the promoter is an inducible promoter. Inducible promoters are described in more detail infra.

In one embodiment, the one or more gene sequence(s) encoding an importer of oxalate is located on a plasmid in the bacterial cell. In another embodiment, the one or more gene sequence(s) encoding an importer of oxalate is located in the chromosome of the bacterial cell. In yet another embodiment, a native copy of the one or more gene sequence(s) encoding an importer of oxalate is located in the chromosome of the bacterial cell, and a copy of one or more gene sequence(s) encoding an importer of oxalate from a different species of bacteria is located on a plasmid in the bacterial cell. In yet another embodiment, a native copy of the one or more gene sequence(s) encoding an importer of oxalate is located on a plasmid in the bacterial cell, and a copy of one or more gene sequence(s) encoding an importer of oxalate from a different species of bacteria is located on a plasmid in the bacterial cell. In yet another embodiment, a native copy of the one or more gene sequence(s) encoding an importer of oxalate is located in the chromosome of the bacterial cell, and a copy of the one or more gene sequence(s) encoding an importer of oxalate from a different species of bacteria is located in the chromosome of the bacterial cell.

In some embodiments, the at least one native gene encoding the importer of oxalate in the bacterial cell is not modified, and one or more additional copies of the native importer of oxalate are inserted into the genome. In one embodiment, the one or more additional copies of the native importer that is inserted into the genome are under the control of the same inducible promoter that controls expression of the one or more gene sequence(s) encoding the oxalate catabolism enzyme, e.g., the FNR responsive promoter, or a different inducible promoter than the one that controls expression of the at least one oxalate catabolism enzyme, or a constitutive promoter. In alternate embodiments, the at least one native gene encoding the importer is not modified, and one or more additional copies of the importer from a different bacterial species is inserted into the genome of the bacterial cell. In one embodiment, the one or more additional copies of the importer inserted into the genome of the bacterial cell are under the control of the same inducible promoter that controls expression of the one or more gene sequence(s) encoding the oxalate catabolism enzyme, e.g., the FNR responsive promoter, or a different inducible promoter than the one that controls expression of the gene sequence(s) encoding the one or more oxalate catabolism enzyme(s), or a constitutive promoter.

In one embodiment, when the importer of oxalate is expressed in the recombinant bacterial cells of the invention, the bacterial cells import 10% more oxalate into the bacterial cell when the importer is expressed than unmodified bacteria of the same bacterial subtype under the same conditions. In another embodiment, when the importer of oxalate is expressed in the recombinant bacterial cells of the invention, the bacterial cells import 20%, 30%, 40%, 50%, 60%, 70%, 80%, 90% or 100% more oxalate into the bacterial cell when the importer is expressed than unmodified bacteria of the same bacterial subtype under the same conditions. In yet another embodiment, when the importer of oxalate is expressed in the recombinant bacterial cells of the invention, the bacterial cells import two-fold more oxalate into the cell when the importer is expressed than unmodified bacteria of the same bacterial subtype under the same conditions. In yet another embodiment, when the importer of oxalate is expressed in the recombinant bacterial cells of the invention, the bacterial cells import three-fold, four-fold, five-fold, six-fold, seven-fold, eight-fold, nine-fold, or ten-fold more oxalate into the cell when the importer is expressed than unmodified bacteria of the same bacterial subtype under the same conditions.

In some embodiments, the bacterial cell comprises a genetic mutation in one or more endogenous gene(s) encoding a transporter (importer) of formate, wherein the genetic mutation reduces influx of formate into the bacterial cell. Without wishing to be bound by theory, such mutations may decrease intracellular formate concentrations and increase the flux through oxalate catabolism pathways. FocA of *E. coli* catalyzes bidirectional formate transport and may function by a channel-type mechanism (Flake et al., Unexpected oligomeric structure of the FocA formate channel of *Escherichia coli*: a paradigm for the formate-nitrite transporter family of integral membrane proteins". FEMS microbiology letters. 303 (1): 69-75). FocA may be able to switch its mode of operation from a passive export channel at high external pH to a secondary active formate/H importer at low pH. In a non-limiting example, the genetically engineered bacteria may comprise a mutation and/or deletion in FocA, rendering it non-functional.

Exporters of Formate

Formate is a major metabolite in the anaerobic fermentation of glucose by many intestinal bacteria. Several types of formate import and export proteins are known in the art. For example, formate is translocated across cellular membranes by the pentameric ion channel/transporter FocA in *E coli* and other Enterobacteriaceae. FocA acts as a passive exporter for formate anions generated in the cytoplasm. In the periplasm, formate is subsequently reduced by formate dehydrogenase into carbon dioxide. Another form of formate dehydrogenase and/or formate lyase also exists in the cytoplasm in *E. coli*. A functional switch of transport mode occurs when the pH of the growth medium drops below 6.8. With ample protons available in the periplasm, the cell switches to active import of formate and again uses FocA for the task.

In another example, as mentioned above, the uptake of oxalate into the anaerobic bacterium, *Oxalobacter formigenes*, has been found to occur via the oxalate transporter OxlT. OxlT allows the exchange of oxalate with the intracellular formate derived from oxalate decarboxylation. The overall effect of these associated activities (exchange and decarboxylation) is generation of a proton-motive force to support membrane functions, including ATP synthesis, accumulation of growth substrates and extrusion of waste products. As such, "exporter of formate" in some embodiments also encompasses a transporter of oxalate, e.g., as in the case of OxlT, the formate:oxalate antiporter.

Formate exporters and/or formate exporters with coupled oxalate import functions may be expressed or modified in the bacteria in order to enhance formate export (and in cases when coupled to oxalate import, thereby enhance oxalate import). Specifically, in some embodiments, when the exporter of formate is expressed in the engineered bacterial cells, the bacterial cells export more formate outside of the cell when the exporter is expressed than unmodified bacteria of the same bacterial subtype under the same conditions. In one embodiment, the bacterial cell comprises one or more gene sequence(s) encoding an exporter of formate. In one embodiment, the bacterial cell comprises a heterologous gene encoding an exporter of formate and at least one heterologous gene or gene cassette encoding at least one oxalate catabolism enzyme.

Thus, in some embodiments, the disclosure provides a bacterial cell that comprises one or more gene sequence(s) encoding one or more oxalate catabolism enzyme(s) operably linked to a first promoter and one or more gene sequence(s) encoding an exporter of formate. In some embodiments, the one or more gene sequence(s) encoding an exporter of formate is operably linked to the first promoter. In another embodiment, the one or more gene sequence(s) encoding one or more oxalate catabolism enzyme(s) is operably is linked to a first promoter, and the one or more gene sequence(s) encoding an exporter of formate is operably linked to a second promoter. In one embodiment, the first promoter and the second promoter are separate copies of the same promoter. In another embodiment, the first promoter and the second promoter are different promoters.

In one embodiment, the bacterial cell comprises one or more gene sequence(s) encoding an exporter of formate from a different organism, e.g., a different species of bacteria. In one embodiment, the bacterial cell comprises at least one native gene sequence(s) encoding an exporter of formate. In some embodiments, the at least one native gene sequence(s) encoding an exporter of formate is not modified. In another embodiment, the bacterial cell comprises more than one copy of at least one gene native sequence(s) encoding an exporter of formate. In yet another embodiment, the bacterial cell comprises a copy one or more gene sequence(s) encoding a native exporter of formate, as well as at least one copy of at least one heterologous gene sequence(s) encoding an exporter of formate from a different bacterial species. In one embodiment, the bacterial cell comprises at least one, two, three, four, five, or six copies of the at least one heterologous gene sequences encoding an exporter of formate. In one embodiment, the bacterial cell comprises multiple copies of one or more heterologous gene sequence(s) encoding an exporter of formate.

In some embodiments, the exporter of formate is encoded by an exporter of formate gene derived from a bacterial genus or species, including but not limited to, *Bifidobacterium, Bordetella, Bradyrhizobium, Burkholderia, Clostridium, Enterococcus, Escherichia, Eubacterium, Lactobacillus, Magnetospirillium, Mycobacterium, Neurospora, Oxalobacter*, e.g., *Oxalobacter formigenes, Ralstonia, Rhodopseudomonas, Shigella, Thermoplasma*, and *Thauera*, e.g., *Bifidobacterium animalis, Bifidobacterium bifidum, Bifidobacterium infantis, Bifidobacterium lactis, Bifidobacterium longum, Bordatella bronchiseptica, Bordatella parapertussis, Burkholderia fungorum, Burkholderia xenovorans, Bradyrhizobium japonicum, Clostridium acetobutylicum, Clostridium difficile, Clostridium scindens, Clostridium sporogenes, Clostridium tentani, Enterococcus faecalis, Escherichia coli, Eubacterium lentum, Lactobacillus acidophilus, Lactobacillus bulgaricus, Lactobacillus casei, Lactobacillus gasseri, Lactobacillus plantarum, Lactobacillus rhamnosus, Lactococcus lactis, Magnetospirillium magentotaticum, Mycobacterium avium, Mycobacterium intracellulare, Mycobacterium kansasii, Mycobacterium leprae, Mycobacterium smegmatis, Mycobacterium tuberculosis, Mycobacterium ulcerans, Neurospora crassa, Oxalobacter formigenes, Providencia rettgeri, Eubacterium lentum, Ralstonia eutropha, Ralstonia metallidurans, Rhodopseudomonas palustris, Shigella flexneri, Thermoplasma volcanium*, and *Thauera aromatica*.

The present disclosure further comprises genes encoding functional fragments of an exporter of formate or functional variants of an exporter of formate. As used herein, the term "functional fragment thereof" or "functional variant thereof" of an exporter of formate relates to an element having qualitative biological activity in common with the wild-type exporter of formate from which the fragment or variant was derived. For example, a functional fragment or a functional variant of a mutated exporter of formate protein is one which retains essentially the same ability to import formate into the bacterial cell as does the exporter protein from which the functional fragment or functional variant was derived. In one embodiment, the engineered bacterial cell comprises at least one heterologous gene encoding a functional fragment of an exporter of formate. In another embodiment, the engineered bacterial cell comprises at least one heterologous gene encoding a functional variant of an exporter of formate.

Assays for testing the activity of an exporter of formate, an exporter of formate functional variant, or an exporter of formate functional fragment are well known to one of ordinary skill in the art. For example, formate export can be assessed by expressing the protein, functional variant, or fragment thereof, in an engineered bacterial cell that lacks an endogenous formate exporter and assessing formate levels in the media after expression of the protein. Methods for measuring formate export are well known to one of ordinary skill in the art (see, e.g., Wraight et al., Structure and mechanism of a pentameric formate channel Nat Struct Mol Biol. 2010 January; 17(1): 31-37).

In one embodiment the genes encoding the exporter of formate have been codon-optimized for use in the host organism. In one embodiment, the genes encoding the exporter of formate have been codon-optimized for use in *Escherichia coli*.

The present disclosure also encompasses genes encoding an exporter of formate comprising amino acids in its sequence that are substantially the same as an amino acid sequence described herein. Amino acid sequences that are substantially the same as the sequences described herein include sequences comprising conservative amino acid substitutions, as well as amino acid deletions and/or insertions.

In some embodiments, the at least one gene encoding an exporter of formate is mutagenized; mutants exhibiting increased formate transport are selected; and the mutagenized at least one gene encoding an exporter of formate is isolated and inserted into the bacterial cell. In a non-limiting example, increasing export of formate may also allow increased oxalate import. In some embodiments, the at least one gene encoding an exporter of formate is mutagenized; mutants exhibiting decreased formate transport are selected; and the mutagenized at least one gene encoding an exporter of formate is isolated and inserted into the bacterial cell. The exporter modifications described herein may be present on a plasmid or chromosome.

In one embodiment, the formate exporter is OxlT. In one embodiment, the OxlT gene has at least about 80% identity to SEQ ID NO: 11. Accordingly, in one embodiment, the OxlT gene has at least about 90% identity to SEQ ID NO: 11. Accordingly, in one embodiment, the OxlT gene has at least about 95% identity to SEQ ID NO: 11. Accordingly, in one embodiment, the OxlT gene has at least about 85%, 86%, 87%, 88%, 89%, 90%, 91%, 92%, 93%, 94%, 95%, 96%, 97%, 98%, or 99% identity to SEQ ID NO: 11. In another embodiment, the OxlT gene comprises the sequence of SEQ ID NO: 11. In yet another embodiment the OxlT gene consists of the sequence of SEQ ID NO: 11.

In one embodiment, the OxlT gene encodes a polypeptide which has at least about 80% identity to SEQ ID NO: 12. Accordingly, in one embodiment, the OxlT gene encodes a polypeptide which has at least about 90% identity to SEQ ID NO: 12. Accordingly, in one embodiment, the OxlT gene encodes a polypeptide which has at least about 95% identity to SEQ ID NO: 12. Accordingly, in one embodiment, the OxlT gene encodes a polypeptide which has at least about 85%, 86%, 87%, 88%, 89%, 90%, 91%, 92%, 93%, 94%, 95%, 96%, 97%, 98%, or 99% identity to SEQ ID NO: 12. In another embodiment, the OxlT gene encodes a polypeptide which comprises the sequence of SEQ ID NO: 12. In yet another embodiment the OxlT gene encodes a polypeptide which consists of the sequence of SEQ ID NO: 12.

In some embodiments, the bacterial cell comprises one or more heterologous gene sequence(s) encoding at least one oxalate catabolism enzyme operably linked to a first promoter and one or more heterologous gene sequence(s) encoding an exporter of formate. In some embodiments, the one or more heterologous gene sequence(s) encoding an exporter of formate are operably linked to the first promoter. In other embodiments, the one or more heterologous gene sequence(s) encoding an exporter of formate are operably linked to a second promoter. In one embodiment, one or more heterologous gene sequence(s) encoding an exporter of formate are directly operably linked to the second promoter. In another embodiment, the one or more heterologous gene sequence(s) encoding an exporter of formate are indirectly operably linked to the second promoter.

In some embodiments, expression one or more gene sequence(s) encoding an exporter of formate is controlled by a different promoter than the promoter that controls expression of the at least one gene encoding the at least one oxalate catabolism enzyme. In some embodiments, expression of the one or more gene sequence(s) encoding an exporter of formate is controlled by the same promoter that controls expression of the at least one oxalate catabolism enzyme. In some embodiments, the one or more gene sequence(s) encoding an exporter of formate and the oxalate catabolism enzyme are divergently transcribed from a promoter region. In some embodiments, expression of each of genes encoding the one or more gene sequence(s) encoding an exporter of formate and the one or more gene sequence(s) encoding the at least one oxalate catabolism enzyme is controlled by different promoters.

In one embodiment, the promoter is not operably linked with the one or more gene sequence(s) encoding an exporter of formate in nature. In some embodiments, the one or more gene sequence(s) encoding the exporter of formate is controlled by its native promoter. In some embodiments, the one or more gene sequence(s) encoding the exporter of formate is controlled by an inducible promoter. In some embodiments, the one or more gene sequence(s) encoding the exporter of formate is controlled by a promoter that is stronger than its native promoter. In some embodiments, the one or more gene sequence(s) encoding the exporter of formate is controlled by a constitutive promoter.

In another embodiment, the promoter is an inducible promoter. Inducible promoters are described in more detail infra.

In one embodiment, the one or more gene sequence(s) encoding an exporter of formate is located on a plasmid in the bacterial cell. In another embodiment, the one or more gene sequence(s) encoding an exporter of formate is located in the chromosome of the bacterial cell. In yet another embodiment, a native copy of the one or more gene sequence(s) encoding an exporter of formate is located in the chromosome of the bacterial cell, and a copy of at least one gene encoding an exporter of formate from a different species of bacteria is located on a plasmid in the bacterial cell. In yet another embodiment, a native copy of the one or more gene sequence(s) encoding an exporter of a formate is located on a plasmid in the bacterial cell, and a copy of at least one gene encoding an exporter of formate from a different species of bacteria is located on a plasmid in the bacterial cell. In yet another embodiment, a native copy of the one or more gene sequence(s) encoding an exporter of formate is located in the chromosome of the bacterial cell, and a copy of the one or more gene sequence(s) encoding an exporter of formate from a different species of bacteria is located in the chromosome of the bacterial cell.

In some embodiments, the at least one native gene encoding the exporter in the bacterial cell is not modified, and one or more additional copies of the native exporter are inserted into the genome. In one embodiment, the one or more additional copies of the native exporter that is inserted into the genome are under the control of the same inducible promoter that controls expression of the at least one gene encoding the oxalate catabolism enzyme, e.g., the FNR responsive promoter, or a different inducible promoter than the one that controls expression of the at least one oxalate catabolism enzyme, or a constitutive promoter. In alternate embodiments, the at least one native gene encoding the exporter is not modified, and one or more additional copies of the exporter from a different bacterial species is inserted into the genome of the bacterial cell. In one embodiment, the one or more additional copies of the exporter inserted into the genome of the bacterial cell are under the control of the same inducible promoter that controls expression of the at least one gene encoding the oxalate catabolism enzyme, e.g., the FNR responsive promoter, or a different inducible promoter than the one that controls expression of the at least one gene encoding the at least one oxalate catabolism enzyme, or a constitutive promoter.

In one embodiment, when the exporter of formate is expressed in the engineered bacterial cells, the bacterial cells export 10% more formate out of the bacterial cell when the exporter is expressed than unmodified bacteria of the same bacterial subtype under the same conditions. In another embodiment, when the exporter of formate is expressed in the engineered bacterial cells, the bacterial cells export 20%, 30%, 40%, 50%, 60%, 70%, 80%, 90% or 100% more formate out of the bacterial cell when the exporter is expressed than unmodified bacteria of the same bacterial subtype under the same conditions. In yet another embodiment, when the exporter of formate is expressed in the engineered bacterial cells, the bacterial cells export two-fold more formate out of the cell when the exporter is expressed than unmodified bacteria of the same bacterial subtype under the same conditions. In yet another embodiment, when the exporter of formate is expressed in the engineered bacterial cells, the bacterial cells export three-fold, four-fold, five-fold, six-fold, seven-fold, eight-fold, nine-fold, or ten-fold more formate out of the cell when the exporter is expressed than unmodified bacteria of the same bacterial subtype under the same conditions.

In one embodiment, the bacterial cell comprises a mutation or deletion in an exporter of oxalate, rendering the exporter less functional or non-functional. Such a mutation may prevent intracellular oxalate from being exported and increase the catabolism of oxalate.

In some embodiments, the genetically engineered bacteria further comprise a mutation or deletion in one or more endogenous formate exporters, e.g., FocA. In a non-limiting example, such genetically engineered bacteria comprising a mutation in FocA comprise one or more gene sequence(s) encoding a formate:oxalate antiporter, e.g., OxlT. In a non-limiting example one or more endogenous formate exporter(s) are mutagenized or deleted, e.g., (e.g., FocA) to reduce or prevent the export of formate without the concurrent import of oxalate through a formate: oxalate antiporter, e.g., OxlT. Such a mutation may increase the uptake and catabolism of oxalate in the bacterial cell.

In some embodiments, formate dehydrogenase and/or formate lyase is mutated or deleted, e.g. to prevent the catabolism of formate in the bacterial cell. Without wishing to be bound by theory, such mutations may increase intracellular formate concentrations, allowing an increase in the flux through a formate oxalate antiporter, and thereby allowing increased oxalate uptake.

Inducible Promoters

In some embodiments, the bacterial cell comprises a stably maintained plasmid or chromosome carrying the gene and/or gene cassette encoding one or more oxalate catabolism enzyme(s), e.g., selected from formyl-CoA:oxalate CoA-transferase, e.g., frc (from *O. formigenes*), oxalyl-CoA synthetase, e.g., ScAAE3 (from *S. cerevisiae*), oxalyl-CoA decarboxylase, e.g., selected from oxc (from *O. formigenes*), and/or acetyl-CoA:oxalate CoA-transferase, e.g., YfdE (from *E. coli*), genes. such that the oxalate catabolism enzyme(s) can be expressed in the host cell, and the host cell is capable of survival and/or growth in vitro, e.g., in medium, and/or in vivo, e.g., in the gut. In some embodiments, bacterial cell comprises two or more distinct oxalate catabolism enzymes, e.g., formyl-CoA:oxalate CoA-transferase, e.g., frc (from *O. formigenes*), oxalyl-CoA synthetase, e.g., ScAAE3 (from *S. cerevisiae*), oxalyl-CoA decarboxylase, e.g., oxc (from *O. formigenes*), and/or acetyl-CoA:oxalate CoA-transferase, e.g., YfdE (from *E. coli*) genes In some embodiments, the genetically engineered bacteria comprise multiple copies of the same oxalate catabolism enzyme gene and/or gene cassette. In some embodiments, the genetically engineered bacteria comprise multiple copies of different oxalate catabolism enzyme genes. In some embodiments, the gene and/or gene cassette encoding one or more oxalate catabolism enzyme(s) is present on a plasmid and operably linked to a directly or indirectly inducible promoter. In some embodiments, the gene and/or gene cassette encoding one or more oxalate catabolism enzyme(s) is present on a plasmid and operably linked to a promoter that is induced under low-oxygen or anaerobic conditions. In some embodiments, the gene and/or gene cassette encoding one or more oxalate catabolism enzyme(s) is present on a chromosome and operably linked to a directly or indirectly inducible promoter. In some embodiments, the gene and/or gene cassette encoding one or more oxalate catabolism enzyme(s) is present in the chromosome and operably linked to a promoter that is induced under low-oxygen or anaerobic conditions. In some embodiments, the gene and/or gene cassette encoding one or more oxalate catabolism enzyme(s) is present on a plasmid and operably linked to a promoter that is induced by exposure to tetracycline or arabinose.

In some embodiments, the bacterial cell comprises a stably maintained plasmid or chromosome carrying the gene and/or gene cassette encoding one or more transporter(s) of oxalate, e.g., OxlT from *O. formigenes*, such that the transporter, e.g., OxlT from *O. formigenes*, can be expressed in the host cell, and the host cell is capable of survival and/or growth in vitro, e.g., in medium, and/or in vivo, e.g., in the gut. In some embodiments, bacterial cell comprises two or more distinct copies of the gene and/or gene cassette encoding one or more transporter(s) of oxalate, e.g., OxlT from *O. formigenes*. In some embodiments, the genetically engineered bacteria comprise multiple copies of the same gene and/or gene cassette encoding one or more transporter(s) of oxalate, e.g., OxlT from *O. formigenes*. In some embodiments, the at least one gene and/or gene cassette encoding one or more transporter(s) of oxalate, e.g., OxlT from *O. formigenes*, is present on a plasmid and operably linked to a directly or indirectly inducible promoter. In some embodiments, the gene and/or gene cassette encoding one or more transporter(s) of oxalate, e.g., OxlT from *O. formigenes*, is present on a plasmid and operably linked to a promoter that is induced under low-oxygen or anaerobic conditions. In some embodiments, the gene and/or gene cassette encoding one or more transporter(s) of oxalate, e.g., OxlT from *O. formigenes*, is present on a chromosome and operably linked to a directly or indirectly inducible promoter. In some embodiments, the gene and/or gene cassette encoding one or more transporter(s) of oxalate, e.g., OxlT from *O. formigenes*, is present in the chromosome and operably linked to a promoter that is induced under low-oxygen or anaerobic conditions. In some embodiments, the gene and/or gene cassette encoding one or more transporter(s) of oxalate, e.g., OxlT from *O. formigenes*, is present on a plasmid and operably linked to a promoter that is induced by exposure to tetracycline.

In some embodiments, the promoter that is operably linked to the gene and/or gene cassette encoding one or more oxalate catabolism enzyme(s) and the promoter that is operably linked to the gene and/or gene cassette encoding one or more transporter(s) of oxalate, e.g., OxlT from *O. formigenes*, is directly induced by exogenous environmental conditions. In some embodiments, the promoter that is operably linked to the gene and/or gene cassette encoding one or more oxalate catabolism enzyme(s) and the promoter that is operably linked to the gene and/or gene cassette encoding one or more transporter(s) of oxalate, e.g., OxlT from *O. formigenes*, is indirectly induced by exogenous environmental conditions. In some embodiments, the promoter is directly or indirectly induced by exogenous environmental conditions specific to the gut of a mammal. In some embodiments, the promoter is directly or indirectly induced by exogenous environmental conditions specific to the small intestine of a mammal. In some embodiments, the promoter is directly or indirectly induced by low-oxygen or anaerobic conditions such as the environment of the mammalian gut. In some embodiments, the promoter is directly or indirectly induced by molecules or metabolites that are specific to the gut of a mammal, e.g., propionate. In some embodiments, the promoter is directly or indirectly induced by a molecule that is co-administered with the bacterial cell.

Oxygen Dependent Regulation

In certain embodiments, the bacterial cell comprises a gene and/or gene cassette encoding one or more oxalate catabolism enzyme(s), e.g., selected from formyl-CoA:oxalate CoA-transferase, e.g., frc (from *O. formigenes*), oxalyl-CoA synthetase, e.g., ScAAE3 (from *S. cerevisiae*), oxalyl-CoA decarboxylase, e.g., oxc (from *O. formigenes*), and/or acetyl-CoA:oxalate CoA-transferase, e.g., YfdE (from *E. coli*), is expressed under the control of the fumarate and nitrate reductase regulator (FNR) promoter. In certain embodiments, the bacterial cell comprises gene and/or gene cassette encoding one or more transporter(s) of oxalate, e.g., OxlT from *O. formigenes*, is expressed under the control of the fumarate and nitrate reductase regulator (FNR) promoter. In *E. coli*, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive.

FNR responsive promoters include, but are not limited to, the FNR responsive promoters listed in the chart, below. Underlined sequences are predicted ribosome binding sites, and bolded sequences are restriction sites used for cloning.

TABLE 5

FNR responsive promoters

| FNR Responsive Promoter | Sequence |
|---|---|
| SEQ ID NO: 13 | GTCAGCATAACACCCTGACCTCTCATTAATTGTTCATGCCGGGCGGCACTAT<br>CGTCGTCCGGCCTTTTCCTCTCTTACTCTGCTACGTACATCTATTTCTATAAA<br>TCCGTTCAATTTGTCTGTTTTTTGCACAAACATGAAATATCAGACAATTCCG<br>TGACTTAAGAAAATTTATACAAATCAGCAATATACCCCTTAAGGAGTATAT<br>AAAGGTGAATTTGATTTACATCAATAAGCGGGGTTGCTGAATCGTTAAGGT<br>AGGCGGTAATAG<u>AAAAGAAATCGAGGCAAAA</u> |
| SEQ ID NO: 14 | ATTTCCTCTCATCCCATCCGGGGTGAGAGTCTTTTCCCCCGACTTATGGCTC<br>ATGCATGCATCAAAAAAGATGTGAGCTTGATCAAAAACAAAAAATATTTCA<br>CTCGACAGGAGTATTTATATTGCGCCCGTTACGTGGGCTTCGACTGTAAATC<br><u>AGAAAGGAGAAAACACCT</u> |
| SEQ ID NO: 15 | GTCAGCATAACACCCTGACCTCTCATTAATTGTTCATGCCGGGCGGCACTAT<br>CGTCGTCCGGCCTTTTCCTCTCTTACTCTGCTACGTACATCTATTTCTATAAA<br>TCCGTTCAATTTGTCTGTTTTTTGCACAAACATGAAATATCAGACAATTCCG<br>TGACTTAAGAAAATTTATACAAATCAGCAATATACCCCTTAAGGAGTATAT<br>AAAGGTGAATTTGATTTACATCAATAAGCGGGGTTGCTGAATCGTTAAGGA<br>TCC<u>CTCTAGAAATAATTTTGTTTAACTTTAAGAAGGAGATATACAT</u> |
| SEQ ID NO: 16 | CATTTCCTCTCATCCCATCCGGGGTGAGAGTCTTTTCCCCCGACTTATGGCT<br>CATGCATGCATCAAAAAAGATGTGAGCTTGATCAAAAACAAAAAATATTTC<br>ACTCGACAGGAGTATTTATATTGCGCCCGGATCC<u>CTCTAGAAATAATTTTG<br>TTTAACTTTAAGAAGGAGATATACAT</u> |
| SEQ ID NO: 17 | AGTTGTTCTTATTGGTGGTGTTGCTTTATGGTTGCATCGTAGTAAATGGTTGT<br>AACAAAAGCAATTTTTCCGGCTGTCTGTATACAAAAACGCCGTAAAGTTTG<br>AGCGAAGTCAATAAACTCTCTACCCATTCAGGGCAATATCTCTCTTGGATC<br>C<u>CTCTAGAAATAATTTTGTTTAACTTTAAGAAGGAGATATACAT</u> |

In one embodiment, the FNR responsive promoter comprises SEQ ID NO: 13. In one embodiment, the FNR responsive promoter comprises SEQ ID NO: 14. In another embodiment, the FNR responsive promoter comprises SEQ ID NO: 15. In another embodiment, the FNR responsive promoter comprises SEQ ID NO: 16. In another embodiment, the FNR responsive promoter comprises SEQ ID NO:17. Additional FNR responsive promoters are shown below in Table 6.

TABLE 6

FNR Promoter Sequences

| SEQ ID NO | FNR-responsive regulatory region Sequence |
|---|---|
| SEQ ID NO: 18 | ATCCCCATCACTCTTGATGGAGATCAATTCCCCAAGCTGCTAGAGCGTTA<br>CCTTGCCCTTAAACATTAGCAATGTCGATTTATCAGAGGGCCGACAGGC<br>TCCCACAGGAGAAAACCG |
| SEQ ID NO: 19 | CTCTTGATCGTTATCAATTCCCACGCTGTTTCAGAGCGTTACCTTGCCCTT<br>AAACATTAGCAATGTCGATTTATCAGAGGGCCGACAGGCTCCCACAGGA<br>GAAAACCG |
| nirB1<br>SEQ ID NO: 20 | GTCAGCATAACACCCTGACCTCTCATTAATTGTTCATGCCGGGCGGCACT<br>ATCGTCGTCCGGCCTTTTCCTCTCTTACTCTGCTACGTACATCTATTTCTA<br>TAAATCCGTTCAATTTGTCTGTTTTTTGCACAAACATGAAATATCAGACA<br>ATTCCGTGACTTAAGAAAATTTATACAAATCAGCAATATACCCCTTAAG<br>GAGTATATAAAGGTGAATTTGATTTACATCAATAAGCGGGGTTGCTGAA<br>TCGTTAAGGTAGGCGGTAATAG<u>AAAAGAAATCGAGGCAAAA</u> |
| nirB2<br>SEQ ID NO: 21 | CGGCCCGATCGTTGAACATAGCGGTCCGCAGGCGGCACTGCTTACAGCA<br>AACGGTCTGTACGCTGTCGTCTTTGTGATGTGCTTCCTGTTAGGTTTCGT<br>CAGCCGTCACCGTCAGCATAACACCCTGACCTCTCATTAATTGCTCATGC<br>CGGACGGCACTATCGTCGTCCGGCCTTTTCCTCTCTTCCCCCGCTACGTG<br>CATCTATTTCTATAAACCCGCTCATTTTGTCTATTTTTTGCACAAACATGA<br>AATATCAGACAATTCCGTGACTTAAGAAAATTTATACAAATCAGCAATA<br>TACCCATTAAGGAGTATATAAAGGTGAATTTGATTTACATCAATAAGCG<br>GGGTTGCTGAATCGTTAAGGTAGGCGGTAATAGAAAAGAAATCGAGGC<br>AAAAatgtttgtttaactttaagaaggagatatacat |

TABLE 6-continued

FNR Promoter Sequences

| SEQ ID NO | FNR-responsive regulatory region Sequence |
|---|---|
| nirB3<br>SEQ ID NO:<br>22 | GTCAGCATAACACCCTGACCTCTCATTAATTGCTCATGCCGGACGGCACT<br>ATCGTCGTCCGGCCTTTTCCTCTCTTCCCCCGCTACGTGCATCTATTTCTA<br>TAAACCCGCTCATTTTGTCTATTTTTTGCACAAACATGAAATATCAGACA<br>ATTCCGTGACTTAAGAAAATTTATACAAATCAGCAATATACCCATTAAG<br>GAGTATATAAAGGTGAATTTGATTTACATCAATAAGCGGGGTTGCTGAA<br>TCGTTAAGGTAGGCGGTAATAGAAAAGAAATCGAGGCAAAA |
| ydfZ<br>SEQ ID NO:<br>23 | ATTTCCTCTCATCCCATCCGGGGTGAGAGTCTTTTCCCCCGACTTATGGC<br>TCATGCATGCATCAAAAAAGATGTGAGCTTGATCAAAAACAAAAAATAT<br>TTCACTCGACAGGAGTATTTATATTGCGCCCGTTACGTGGGCTTCGACTG<br>TAAATC<u>AGAAAGGAGAAAACACCT</u> |
| nirB + RBS<br>SEQ ID NO:<br>24 | GTCAGCATAACACCCTGACCTCTCATTAATTGTTCATGCCGGGCGGCACT<br>ATCGTCGTCCGGCCTTTTCCTCTCTTACTCTGCTACGTACATCTATTTCTA<br>TAAATCCGTTCAATTTGTCTGTTTTTTGCACAAACATGAAATATCAGACA<br>ATTCCGTGACTTAAGAAAATTTATACAAATCAGCAATATACCCCTTAAG<br>GAGTATATAAAGGTGAATTTGATTTACATCAATAAGCGGGGTTGCTGAA<br>TCGTTAAGGATCC<u>CTCTAGAAATAATTTTGTTTAACTTTAAGAAGGAGA<br>TATACAT</u> |
| ydfZ + RBS<br>SEQ ID NO:<br>25 | CATTTCCTCTCATCCCATCCGGGGTGAGAGTCTTTTCCCCCGACTTATGG<br>CTCATGCATGCATCAAAAAAGATGTGAGCTTGATCAAAAACAAAAAATA<br>TTTCACTCGACAGGAGTATTTATATTGCGCCCGGATCC<u>CTCTAGAAATA<br>ATTTTGTTTAACTTTAAGAAGGAGATATACAT</u> |
| fnrS1<br>SEQ ID NO:<br>26 | AGTTGTTCTTATTGGTGGTGTTGCTTTATGGTTGCATCGTAGTAAATGGT<br>TGTAACAAAAGCAATTTTTCCGGCTGTCTGTATACAAAAACGCCGTAAA<br>GTTTGAGCGAAGTCAATAAACTCTCTACCCATTCAGGGCAATATCTCTCT<br>TGGATCCCTCTAGAAATAATTTTGTTTAACTTTAAGAAGGAGATATACAT |
| fnrS2<br>SEQ ID NO:<br>27 | AGTTGTTCTTATTGGTGGTGTTGCTTTATGGTTGCATCGTAGTAAATGGT<br>TGTAACAAAAGCAATTTTTCCGGCTGTCTGTATACAAAAACGCCGCAAA<br>GTTTGAGCGAAGTCAATAAACTCTCTACCCATTCAGGGCAATATCTCTCT<br>TGGATCCAAAGTGAACTCTAGAAATAATTTTGTTTAACTTTAAGAAGGA<br>GATATACAT |
| nirB + crp<br>SEQ ID NO:<br>28 | TCGTCTTTGTGATGTGCTTCCTGTTAGGTTTCGTCAGCCGTCACCGTCAG<br>CATAACACCCTGACCTCTCATTAATTGCTCATGCCGGACGGCACTATCGT<br>CGTCCGGCCTTTTCCTCTCTTCCCCCGCTACGTGCATCTATTTCTATAAAC<br>CCGCTCATTTTGTCTATTTTTTGCACAAACATGAAATATCAGACAATTCC<br>GTGACTTAAGAAAATTTATACAAATCAGCAATATACCCATTAAGGAGTA<br>TATAAGGTGAATTTGATTTACATCAATAAGCGGGGTTGCTGAATCGTT<br>AAGGTAGAaatgtgatctagttcacatttGCGGTAATAGAAAAGAAATCGAGGCAAAA<br>*atgtttgtttaactttaagaaggagatatacat* |
| fnrS + crp<br>SEQ ID NO:<br>29 | AGTTGTTCTTATTGGTGGTGTTGCTTTATGGTTGCATCGTAGTAAATGGT<br>TGTAACAAAAGCAATTTTTCCGGCTGTCTGTATACAAAAACGCCGCAAA<br>GTTTGAGCGAAGTCAATAAACTCTCTACCCATTCAGGGCAATATCTCTCa<br>aatgtgatctagttcacattt*ttttgtttaactttaagaaggagatatacat* |

In one embodiment, the FNR responsive promoter comprises SEQ ID NO: 18. In one embodiment, the FNR responsive promoter comprises SEQ ID NO: 19. In another embodiment, the FNR responsive promoter comprises SEQ ID NO: 20. In another embodiment, the FNR responsive promoter comprises SEQ ID NO: 21. In another embodiment, the FNR responsive promoter comprises SEQ ID NO:22. In one embodiment, the FNR responsive promoter comprises SEQ ID NO: 23. In one embodiment, the FNR responsive promoter comprises SEQ ID NO: 24. In another embodiment, the FNR responsive promoter comprises SEQ ID NO: 25. In another embodiment, the FNR responsive promoter comprises SEQ ID NO: 26. In another embodiment, the FNR responsive promoter comprises SEQ ID NO:27. In another embodiment, the FNR responsive promoter comprises SEQ ID NO: 28. In another embodiment, the FNR responsive promoter comprises SEQ ID NO:29.

In some embodiments, multiple distinct FNR nucleic acid sequences are inserted in the genetically engineered bacteria. In alternate embodiments, the genetically engineered bacteria comprise a gene and/or gene cassette(s) encoding one or more oxalate catabolism enzyme(s), e.g., selected from formyl-CoA:oxalate CoA-transferase, e.g., Frc (from O. formigenes), oxalyl-CoA synthetase, e.g., ScAAE3 (from S. cerevisiae), oxalyl-CoA decarboxylase, e.g., Oxc (from O. formigenes), and/or acetyl-CoA:oxalate CoA-transferase, e.g., YfdE (from E. coli) or other enzyme disclosed herein, is expressed under the control of an alternate oxygen level-dependent promoter, e.g., DNR (Trunk et al., 2010) or ANR (Ray et al., 1997). In alternate embodiments, the genetically engineered bacteria comprise a gene and/or gene cassette encoding one or more transporter(s) of oxalate, e.g., OxlT from O. formigenes, which is expressed under the control of an alternate oxygen level-dependent promoter, e.g., DNR (Trunk et al., 2010) or ANR (Ray et al., 1997). In these embodiments, catabolism of oxalate and/or its metabolites, is particularly activated in a low-oxygen or anaerobic environment, such as in the gut. In some embodiments, gene expression is further optimized by methods known in the art, e.g., by optimizing ribosomal binding sites and/or increasing mRNA stability. In one embodiment, the mammalian gut is a human mammalian gut.

In some embodiments, the bacterial cell comprises an oxygen-level dependent transcriptional regulator, e.g., FNR, ANR, or DNR, and corresponding promoter from a different bacterial species. The heterologous oxygen-level dependent transcriptional regulator and promoter increase the transcription of genes operably linked to said promoter, e.g., the gene and/or gene cassette encoding one or more oxalate catabolism enzyme(s), and/or the gene and/or gene cassette encoding one or more transporter(s) of oxalate, e.g., OxlT from *O. formigenes* in a low-oxygen or anaerobic environment, as compared to the native gene(s) and promoter in the bacteria under the same conditions. In certain embodiments, the non-native oxygen-level dependent transcriptional regulator is an FNR protein from *N. gonorrhoeae* (see, e.g., Isabella et al., 2011). In some embodiments, the corresponding wild-type transcriptional regulator is left intact and retains wild-type activity. In alternate embodiments, the corresponding wild-type transcriptional regulator is deleted or mutated to reduce or eliminate wild-type activity.

In some embodiments, the genetically engineered bacteria comprise a wild-type oxygen-level dependent transcriptional regulator, e.g., FNR, ANR, or DNR, and corresponding promoter that is mutated relative to the wild-type promoter from bacteria of the same subtype. The mutated promoter enhances binding to the wild-type transcriptional regulator and increases the transcription of genes operably linked to said promoter, e.g., the gene and/or gene cassette encoding one or more oxalate catabolism enzyme(s), and/or the gene and/or gene cassette encoding one or more transporter(s) of oxalate, e.g., OxlT from *O. formigenes* in a low-oxygen or anaerobic environment, as compared to the wild-type promoter under the same conditions. In some embodiments, the genetically engineered bacteria comprise a wild-type oxygen-level dependent promoter, e.g., FNR, ANR, or DNR promoter, and corresponding transcriptional regulator that is mutated relative to the wild-type transcriptional regulator from bacteria of the same subtype. The mutated transcriptional regulator enhances binding to the wild-type promoter and increases the transcription of genes operably linked to said promoter, e.g., the gene and/or gene cassette encoding one or more oxalate catabolism enzyme(s), and/or the gene and/or gene cassette encoding one or more transporter(s) of oxalate, e.g., OxlT from *O. formigenes* in a low-oxygen or anaerobic environment, as compared to the wild-type transcriptional regulator under the same conditions. In certain embodiments, the mutant oxygen-level dependent transcriptional regulator is an FNR protein comprising amino acid substitutions that enhance dimerization and FNR activity (see, e.g., Moore et al., 2006).

In some embodiments, the bacterial cells disclosed herein comprise multiple copies of the endogenous gene encoding the oxygen level-sensing transcriptional regulator, e.g., the FNR gene. In some embodiments, the gene encoding the oxygen level-sensing transcriptional regulator is present on a plasmid. In some embodiments, the gene encoding the oxygen level-sensing transcriptional regulator and the gene and/or gene cassette encoding one or more oxalate catabolism enzyme(s) are present on different plasmids. In some embodiments, the gene encoding the oxygen level-sensing transcriptional regulator and the gene and/or gene cassette encoding one or more oxalate catabolism enzyme(s) and/or the gene encoding a transporter of an oxalate are present on different plasmids. In some embodiments, the gene encoding the oxygen level-sensing transcriptional regulator and the gene and/or gene cassette encoding one or more oxalate catabolism enzyme(s) and/or the gene and/or gene cassette encoding one or more transporter(s) of oxalate are present on the same plasmid.

In some embodiments, the gene encoding the oxygen level-sensing transcriptional regulator is present on a chromosome. In some embodiments, the gene encoding the oxygen level-sensing transcriptional regulator and the gene and/or gene cassette encoding one or more oxalate catabolism enzyme(s) and/or the gene and/or gene cassette encoding one or more a transporter(s) of oxalate are present on different chromosomes. In some embodiments, the gene encoding the oxygen level-sensing transcriptional regulator and the gene and/or gene cassette encoding one or more oxalate catabolism enzyme(s) and/or the gene and/or gene cassette encoding one or more transporter(s) of oxalate are present on the same chromosome. In some instances, it may be advantageous to express the oxygen level-sensing transcriptional regulator under the control of an inducible promoter in order to enhance expression stability. In some embodiments, expression of the transcriptional regulator is controlled by a different promoter than the promoter that controls expression of the gene and/or gene cassette encoding one or more oxalate catabolism enzyme(s) and/or oxalate transporter. In some embodiments, expression of the transcriptional regulator is controlled by the same promoter that controls expression of the oxalate catabolism enzyme(s) and/or Oxalate transporter(s). In some embodiments, the transcriptional regulator and the oxalate catabolism enzyme(s) are divergently transcribed from a promoter region.

RNS-Dependent Regulation

In some embodiments, the genetically engineered bacteria comprise a gene and/or gene cassette encoding one or more oxalate catabolism enzyme(s) that is expressed under the control of an inducible promoter. In some embodiments, the genetically engineered bacterium that expresses one or more oxalate catabolism enzyme(s) and/or oxalate transporter(s) is under the control of a promoter that is activated by inflammatory conditions. In one embodiment, the gene and/or gene cassette for producing the oxalate catabolism enzyme(s) and/or oxalate transporter is expressed under the control of an inflammatory-dependent promoter that is activated in inflammatory environments, e.g., a reactive nitrogen species or RNS promoter.

As used herein, "reactive nitrogen species" and "RNS" are used interchangeably to refer to highly active molecules, ions, and/or radicals derived from molecular nitrogen. RNS can cause deleterious cellular effects such as nitrosative stress. RNS includes, but is not limited to, nitric oxide (NO.), peroxynitrite or peroxynitrite anion (ONOO—), nitrogen dioxide (.NO2), dinitrogen trioxide (N2O3), peroxynitrous acid (ONOOH), and nitroperoxycarbonate (ONOOCO2-) (unpaired electrons denoted by ●). Bacteria have evolved transcription factors that are capable of sensing RNS levels. Different RNS signaling pathways are triggered by different RNS levels and occur with different kinetics.

As used herein, "RNS-inducible regulatory region" refers to a nucleic acid sequence to which one or more RNS-sensing transcription factors is capable of binding, wherein the binding and/or activation of the corresponding transcription factor activates downstream gene expression; in the presence of RNS, the transcription factor binds to and/or activates the regulatory region. In some embodiments, the RNS-inducible regulatory region comprises a promoter sequence. In some embodiments, the transcription factor senses RNS and subsequently binds to the RNS-inducible regulatory region, thereby activating downstream gene expression. In alternate embodiments, the transcription factor is bound to the RNS-inducible regulatory region in the absence of RNS; in the presence of RNS, the transcription factor undergoes a conformational change, thereby activating downstream gene expression. The RNS-inducible regulatory region may be operatively linked to a gene and/or gene ore gene cassette, e.g., an oxalate catabolism enzyme gene sequence(s), e.g., any of the oxalate catabolism enzymes described herein. For example, in the presence of RNS, a transcription factor senses RNS and activates a corresponding RNS-inducible regulatory region, thereby driving expression of an operatively linked gene sequence. Thus, RNS induces expression of the gene or gene sequences.

As used herein, "RNS-derepressible regulatory region" refers to a nucleic acid sequence to which one or more RNS-sensing transcription factors is capable of binding, wherein the binding of the corresponding transcription factor represses downstream gene expression; in the presence of RNS, the transcription factor does not bind to and does not repress the regulatory region. In some embodiments, the RNS-derepressible regulatory region comprises a promoter sequence. The RNS-derepressible regulatory region may be operatively linked to a gene or gene cassette, e.g., one or more oxalate catabolism enzyme gene sequence(s) and oxalate transporter sequence(s). For example, in the presence of RNS, a transcription factor senses RNS and no longer binds to and/or represses the regulatory region, thereby derepressing an operatively linked gene sequence or gene cassette. Thus, RNS derepresses expression of the gene or gene cassette.

As used herein, "RNS-repressible regulatory region" refers to a nucleic acid sequence to which one or more RNS-sensing transcription factors is capable of binding, wherein the binding of the corresponding transcription factor represses downstream gene expression; in the presence of RNS, the transcription factor binds to and represses the regulatory region. In some embodiments, the RNS-repressible regulatory region comprises a promoter sequence. In some embodiments, the transcription factor that senses RNS is capable of binding to a regulatory region that overlaps with part of the promoter sequence. In alternate embodiments, the transcription factor that senses RNS is capable of binding to a regulatory region that is upstream or downstream of the promoter sequence. The RNS-repressible regulatory region may be operatively linked to a gene sequence or gene cassette. For example, in the presence of RNS, a transcription factor senses RNS and binds to a corresponding RNS-repressible regulatory region, thereby blocking expression of an operatively linked gene sequence or gene sequences. Thus, RNS represses expression of the gene or gene sequences.

As used herein, a "RNS-responsive regulatory region" refers to a RNS-inducible regulatory region, a RNS-repressible regulatory region, and/or a RNS-derepressible regulatory region. In some embodiments, the RNS-responsive regulatory region comprises a promoter sequence. Each regulatory region is capable of binding at least one corresponding RNS-sensing transcription factor. Examples of transcription factors that sense RNS and their corresponding RNS-responsive genes, promoters, and/or regulatory regions include, but are not limited to, those shown in Table 7.

TABLE 7

Examples of RNS-sensing transcription factors and RNS-responsive genes

| RNS-sensing transcription factor: | Primarily capable of sensing: | Examples of responsive genes, promoters, and/or regulatory regions: |
|---|---|---|
| NsrR | NO | norB, aniA, nsrR, hmpA, ytfE, ygbA, hcp, hcr, nrfA, aox |
| NorR | NO | norVW, norR |
| DNR | NO | norCB, nir; nor, nos |

In some embodiments, the genetically engineered bacteria of the invention comprise a tunable regulatory region that is directly or indirectly controlled by a transcription factor that is capable of sensing at least one reactive nitrogen species. The tunable regulatory region is operatively linked to a gene and/or gene cassette capable of directly or indirectly driving the expression of one or more oxalate catabolism enzyme(s), oxalate transporter(s), thus controlling expression of the oxalate catabolism enzyme, oxalate transporter(s), relative to RNS levels. For example, the tunable regulatory region is a RNS-inducible regulatory region, and the payload is one or more oxalate catabolism enzyme(s), oxalate transporter(s), such as any of the oxalate catabolism enzymes, and/or oxalate transporter(s) provided herein; when RNS is present, e.g., in an inflamed tissue, a RNS-sensing transcription factor binds to and/or activates the regulatory region and drives expression of the oxalate catabolism enzyme and/or oxalate transporter gene or gene cassette. Subsequently, when inflammation is ameliorated, RNS levels are reduced, and production of the oxalate catabolism enzyme(s) and oxalate transporter(s) is decreased or eliminated.

In some embodiments, the tunable regulatory region is a RNS-inducible regulatory region; in the presence of RNS, a transcription factor senses RNS and activates the RNS-inducible regulatory region, thereby driving expression of an operatively linked gene or gene cassette. In some embodiments, the transcription factor senses RNS and subsequently binds to the RNS-inducible regulatory region, thereby activating downstream gene expression. In alternate embodiments, the transcription factor is bound to the RNS-inducible regulatory region in the absence of RNS; when the transcription factor senses RNS, it undergoes a conformational change, thereby inducing downstream gene expression.

In some embodiments, the tunable regulatory region is a RNS-inducible regulatory region, and the transcription factor that senses RNS is NorR. NorR "is an NO-responsive transcriptional activator that regulates expression of the norVW genes encoding flavorubredoxin and an associated flavoprotein, which reduce NO to nitrous oxide" (Spiro 2006). The genetically engineered bacteria of the invention may comprise any suitable RNS-responsive regulatory region from a gene that is activated by NorR. Genes that are capable of being activated by NorR are known in the art (see, e.g., Spiro 2006; Vine et al., 2011; Karlinsey et al., 2012; Table 1). In certain embodiments, the genetically engineered bacteria of the invention comprise a RNS-inducible regulatory region from norVW that is operatively linked to a gene and/or gene cassette, e.g., one or more oxalate catabolism enzyme(s) and/or oxalate transporter(s). In the presence of RNS, a NorR transcription factor senses RNS and activates to the norVW regulatory region, thereby driving expression of the operatively linked gene and/or gene cassette and producing the oxalate catabolism enzyme(s) and/or oxalate transporter(s).

In some embodiments, the tunable regulatory region is a RNS-inducible regulatory region, and the transcription factor that senses RNS is DNR. DNR (dissimilatory nitrate respiration regulator) "promotes the expression of the nir, the nor and the nos genes" in the presence of nitric oxide (Castiglione et al., 2009). The genetically engineered bacteria of the invention may comprise any suitable RNS-responsive regulatory region from a gene that is activated by DNR. Genes that are capable of being activated by DNR are known in the art (see, e.g., Castiglione et al., 2009; Giardina et al., 2008; Table 1). In certain embodiments, the genetically engineered bacteria of the invention comprise a RNS-inducible regulatory region from norCB that is operatively linked to a gene or gene cassette, e.g., a butyrogenic gene cassette. In the presence of RNS, a DNR transcription factor senses RNS and activates to the norCB regulatory region, thereby driving expression of the operatively linked gene or gene cassette and producing one or more oxalate catabolism enzymes. In some embodiments, the DNR is Pseudomonas aeruginosa DNR.

In some embodiments, the tunable regulatory region is a RNS-derepressible regulatory region, and binding of a corresponding transcription factor represses downstream gene expression; in the presence of RNS, the transcription factor no longer binds to the regulatory region, thereby derepressing the operatively linked gene or gene cassette.

In some embodiments, the tunable regulatory region is a RNS-derepressible regulatory region, and the transcription factor that senses RNS is NsrR. NsrR is "an Rrf2-type transcriptional repressor [that] can sense NO and control the expression of genes responsible for NO metabolism" (Isabella et al., 2009). The genetically engineered bacteria of the invention may comprise any suitable RNS-responsive regulatory region from a gene that is repressed by NsrR. In some embodiments, the NsrR is Neisseria gonorrhoeae NsrR. Genes that are capable of being repressed by NsrR are known in the art (see, e.g., Isabella et al., 2009; Dunn et al., 2010; Table 1). In certain embodiments, the genetically engineered bacteria of the invention comprise a RNS-derepressible regulatory region from norB that is operatively linked to a gene or gene cassette, e.g., an oxalate catabolism enzyme gene or gene cassette. In the presence of RNS, an NsrR transcription factor senses RNS and no longer binds to the norB regulatory region, thereby derepressing the operatively linked oxalate catabolism enzyme and/or oxalate transporter gene or gene cassette and producing the encoding an oxalate catabolism enzyme(s).

In some embodiments, it is advantageous for the genetically engineered bacteria to express a RNS-sensing transcription factor that does not regulate the expression of a significant number of native genes in the bacteria. In some embodiments, the genetically engineered bacterium of the invention expresses a RNS-sensing transcription factor from a different species, strain, or substrain of bacteria, wherein the transcription factor does not bind to regulatory sequences in the genetically engineered bacterium of the invention. In some embodiments, the genetically engineered bacterium of the invention is *Escherichia coli*, and the RNS-sensing transcription factor is NsrR, e.g., from is Neisseria gonorrhoeae, wherein the *Escherichia coli* does not comprise binding sites for said NsrR. In some embodiments, the heterologous transcription factor minimizes or eliminates off-target effects on endogenous regulatory regions and genes in the genetically engineered bacteria.

In some embodiments, the tunable regulatory region is a RNS-repressible regulatory region, and binding of a corresponding transcription factor represses downstream gene expression; in the presence of RNS, the transcription factor senses RNS and binds to the RNS-repressible regulatory region, thereby repressing expression of the operatively linked gene or gene cassette. In some embodiments, the RNS-sensing transcription factor is capable of binding to a regulatory region that overlaps with part of the promoter sequence. In alternate embodiments, the RNS-sensing transcription factor is capable of binding to a regulatory region that is upstream or downstream of the promoter sequence.

In these embodiments, the genetically engineered bacteria may comprise a two repressor activation regulatory circuit, which is used to express an oxalate catabolism enzyme. The two repressor activation regulatory circuit comprises a first RNS-sensing repressor and a second repressor, which is operatively linked to a gene or gene cassette, e.g., encoding an oxalate catabolism enzyme. In one aspect of these embodiments, the RNS-sensing repressor inhibits transcription of the second repressor, which inhibits the transcription of the gene or gene cassette. Examples of second repressors useful in these embodiments include, but are not limited to, TetR, C1, and LexA. In the absence of binding by the first repressor (which occurs in the absence of RNS), the second repressor is transcribed, which represses expression of the gene or gene cassette. In the presence of binding by the first repressor (which occurs in the presence of RNS), expression of the second repressor is repressed, and the gene(s) or gene cassette(s), e.g., one or more oxalate catabolism enzyme(s) and/or oxalate transporter(s) gene or gene cassette is expressed.

A RNS-responsive transcription factor may induce, derepress, or repress gene expression depending upon the regulatory region sequence used in the genetically engineered bacteria. One or more types of RNS-sensing transcription factors and corresponding regulatory region sequences may be present in genetically engineered bacteria. In some embodiments, the genetically engineered bacteria comprise one type of RNS-sensing transcription factor, e.g., NsrR, and one corresponding regulatory region sequence, e.g., from norB. In some embodiments, the genetically engineered bacteria comprise one type of RNS-sensing transcription factor, e.g., NsrR, and two or more different corresponding regulatory region sequences, e.g., from norB and aniA. In some embodiments, the genetically engineered bacteria comprise two or more types of RNS-sensing transcription factors, e.g., NsrR and NorR, and two or more corresponding regulatory region sequences, e.g., from norB and norR, respectively. One RNS-responsive regulatory region may be capable of binding more than one transcription factor. In some embodiments, the genetically engineered bacteria comprise two or more types of RNS-sensing transcription factors and one corresponding regulatory region sequence. Nucleic acid sequences of several RNS-regulated regulatory regions are known in the art (see, e.g., Spiro 2006; Isabella et al., 2009; Dunn et al., 2010; Vine et al., 2011; Karlinsey et al., 2012).

In some embodiments, the genetically engineered bacteria of the invention comprise a gene encoding a RNS-sensing transcription factor, e.g., the nsrR gene, that is controlled by its native promoter, an inducible promoter, a promoter that is stronger than the native promoter, e.g., the GlnRS promoter or the P(Bla) promoter, or a constitutive promoter. In some instances, it may be advantageous to express the RNS-sensing transcription factor under the control of an inducible promoter in order to enhance expression stability. In some embodiments, expression of the RNS-sensing transcription factor is controlled by a different promoter than the promoter that controls expression of the therapeutic molecule. In some embodiments, expression of the RNS-sensing transcription factor is controlled by the same promoter that controls expression of the therapeutic molecule. In some embodiments, the RNS-sensing transcription factor and therapeutic molecule are divergently transcribed from a promoter region.

In some embodiments, the genetically engineered bacteria of the invention comprise a gene for a RNS-sensing transcription factor from a different species, strain, or substrain of bacteria. In some embodiments, the genetically engineered bacteria comprise a RNS-responsive regulatory region from a different species, strain, or substrain of bacteria. In some embodiments, the genetically engineered bacteria comprise a RNS-sensing transcription factor and corresponding RNS-responsive regulatory region from a different species, strain, or substrain of bacteria. The heterologous RNS-sensing transcription factor and regulatory region may increase the transcription of genes operatively linked to said regulatory region in the presence of RNS, as compared to the native transcription factor and regulatory region from bacteria of the same subtype under the same conditions.

In some embodiments, the genetically engineered bacteria comprise a RNS-sensing transcription factor, NsrR, and corresponding regulatory region, nsrR, from Neisseria gonorrhoeae. In some embodiments, the native RNS-sensing transcription factor, e.g., NsrR, is left intact and retains wild-type activity. In alternate embodiments, the native RNS-sensing transcription factor, e.g., NsrR, is deleted or mutated to reduce or eliminate wild-type activity.

In some embodiments, the genetically engineered bacteria of the invention comprise multiple copies of the endogenous gene encoding the RNS-sensing transcription factor, e.g., the nsrR gene. In some embodiments, the gene encoding the RNS-sensing transcription factor is present on a plasmid. In some embodiments, the gene encoding the RNS-sensing transcription factor and the gene or gene cassette for producing the therapeutic molecule are present on different plasmids. In some embodiments, the gene encoding the RNS-sensing transcription factor and the gene or gene cassette for producing the therapeutic molecule are present on the same plasmid. In some embodiments, the gene encoding the RNS-sensing transcription factor is present on a chromosome. In some embodiments, the gene encoding the RNS-sensing transcription factor and the gene or gene cassette for producing the therapeutic molecule are present on different chromosomes. In some embodiments, the gene encoding the RNS-sensing transcription factor and the gene or gene cassette for producing the therapeutic molecule are present on the same chromosome.

In some embodiments, the genetically engineered bacteria comprise a wild-type gene encoding a RNS-sensing transcription factor, e.g., the NsrR gene, and a corresponding regulatory region, e.g., a norB regulatory region, that is mutated relative to the wild-type regulatory region from bacteria of the same subtype. The mutated regulatory region increases the expression of the oxalate catabolism enzyme in the presence of RNS, as compared to the wild-type regulatory region under the same conditions. In some embodiments, the genetically engineered bacteria comprise a wild-type RNS-responsive regulatory region, e.g., the norB regulatory region, and a corresponding transcription factor, e.g., NsrR, that is mutated relative to the wild-type transcription factor from bacteria of the same subtype. The mutant transcription factor increases the expression of the oxalate catabolism enzyme(s) in the presence of RNS, as compared to the wild-type transcription factor under the same conditions. In some embodiments, both the RNS-sensing transcription factor and corresponding regulatory region are mutated relative to the wild-type sequences from bacteria of the same subtype in order to increase expression of the oxalate catabolism enzyme(s) and/or oxalate transporter(s) in the presence of RNS.

In some embodiments, the gene or gene cassette for producing the anti-inflammation and/or gut barrier function enhancer molecule is present on a plasmid and operably linked to a promoter that is induced by RNS. In some embodiments, expression is further optimized by methods known in the art, e.g., by optimizing ribosomal binding sites, manipulating transcriptional regulators, and/or increasing mRNA stability.

In some embodiments, any of the gene(s) of the present disclosure may be integrated into the bacterial chromosome at one or more integration sites. For example, one or more copies of an oxalate catabolism enzyme and/or oxalate transporter gene(s) may be integrated into the bacterial chromosome. Having multiple copies of the gene or gen(s) integrated into the chromosome allows for greater production of the oxalate catabolism enzyme(s) and also permits fine-tuning of the level of expression. Alternatively, different circuits described herein, such as any of the secretion or exporter circuits, in addition to the therapeutic gene(s) or gene cassette(s) could be integrated into the bacterial chromosome at one or more different integration sites to perform multiple different functions.

ROS-Dependent Regulation

In some embodiments, the genetically engineered bacteria comprise a gene and/or gene cassette for producing one or more oxalate catabolism enzyme(s) and/or oxalate transporter(s) that is expressed under the control of an inducible promoter. In some embodiments, the genetically engineered bacterium that expresses one or more oxalate catabolism enzyme(s) and/or oxalate transporter(s) under the control of a promoter that is activated by conditions of cellular damage. In one embodiment, the gene and/or gene cassette for producing one or more oxalate catabolism enzyme(s) is expressed under the control of a cellular damaged-dependent promoter that is activated in environments in which there is cellular or tissue damage, e.g., a reactive oxygen species or ROS promoter.

As used herein, "reactive oxygen species" and "ROS" are used interchangeably to refer to highly active molecules, ions, and/or radicals derived from molecular oxygen. ROS can be produced as byproducts of aerobic respiration or metal-catalyzed oxidation and may cause deleterious cellular effects such as oxidative damage. ROS includes, but is not limited to, hydrogen peroxide ($H_2O_2$), organic peroxide (ROOH), hydroxyl ion (OH—), hydroxyl radical (.OH), superoxide or superoxide anion (.$O_2$-), singlet oxygen ($1O_2$), ozone ($O_3$), carbonate radical, peroxide or peroxyl radical (.$O_2$-2), hypochlorous acid (HOCl), hypochlorite ion (OCl—), sodium hypochlorite (NaOCl), nitric oxide (NO.), and peroxynitrite or peroxynitrite anion (ONOO—) (unpaired electrons denoted by.). Bacteria have evolved transcription factors that are capable of sensing ROS levels. Different ROS signaling pathways are triggered by different ROS levels and occur with different kinetics (Marinho et al., 2014).

As used herein, "ROS-inducible regulatory region" refers to a nucleic acid sequence to which one or more ROS-sensing transcription factors is capable of binding, wherein the binding and/or activation of the corresponding transcription factor activates downstream gene expression; in the presence of ROS, the transcription factor binds to and/or activates the regulatory region. In some embodiments, the ROS-inducible regulatory region comprises a promoter sequence. In some embodiments, the transcription factor senses ROS and subsequently binds to the ROS-inducible regulatory region, thereby activating downstream gene expression. In alternate embodiments, the transcription factor is bound to the ROS-inducible regulatory region in the absence of ROS; in the presence of ROS, the transcription factor undergoes a conformational change, thereby activating downstream gene expression. The ROS-inducible regulatory region may be operatively linked to a gene sequence or gene sequence, e.g., a sequence or sequences encoding one or more oxalate catabolism enzyme(s). For example, in the presence of ROS, a transcription factor, e.g., OxyR, senses ROS and activates a corresponding ROS-inducible regulatory region, thereby driving expression of an operatively linked gene sequence or gene sequences. Thus, ROS induces expression of the gene or gene cassette.

As used herein, "ROS-derepressible regulatory region" refers to a nucleic acid sequence to which one or more ROS-sensing transcription factors is capable of binding, wherein the binding of the corresponding transcription factor represses downstream gene expression; in the presence of ROS, the transcription factor does not bind to and does not repress the regulatory region. In some embodiments, the ROS-derepressible regulatory region comprises a promoter sequence. The ROS-derepressible regulatory region may be operatively linked to a gene or gene cassette, e.g., one or more genes encoding one or more oxalate catabolism enzyme(s). For example, in the presence of ROS, a transcription factor, e.g., OhrR, senses ROS and no longer binds to and/or represses the regulatory region, thereby derepressing an operatively linked gene sequence or gene cassette. Thus, ROS derepresses expression of the gene or gene cassette.

As used herein, "ROS-repressible regulatory region" refers to a nucleic acid sequence to which one or more ROS-sensing transcription factors is capable of binding, wherein the binding of the corresponding transcription factor represses downstream gene expression; in the presence of ROS, the transcription factor binds to and represses the regulatory region. In some embodiments, the ROS-repressible regulatory region comprises a promoter sequence. In some embodiments, the transcription factor that senses ROS is capable of binding to a regulatory region that overlaps with part of the promoter sequence. In alternate embodiments, the transcription factor that senses ROS is capable of binding to a regulatory region that is upstream or downstream of the promoter sequence. The ROS-repressible regulatory region may be operatively linked to a gene sequence or gene sequences. For example, in the presence of ROS, a transcription factor, e.g., PerR, senses ROS and binds to a corresponding ROS-repressible regulatory region, thereby blocking expression of an operatively linked gene sequence or gene sequences. Thus, ROS represses expression of the gene or gene cassette.

As used herein, a "ROS-responsive regulatory region" refers to a ROS-inducible regulatory region, a ROS-repressible regulatory region, and/or a ROS-derepressible regulatory region. In some embodiments, the ROS-responsive regulatory region comprises a promoter sequence. Each regulatory region is capable of binding at least one corresponding ROS-sensing transcription factor. Examples of transcription factors that sense ROS and their corresponding ROS-responsive genes, promoters, and/or regulatory regions include, but are not limited to, those shown in Table 8.

TABLE 8

Examples of ROS-sensing transcription factors and ROS-responsive genes

| ROS-sensing transcription factor: | Primarily capable of sensing: | Examples of responsive genes, promoters, and/or regulatory regions: |
|---|---|---|
| OxyR | $H_2O_2$ | ahpC; ahpF; dps; dsbG; fhuF; flu; fur; gor; grxA; hemH; katG; oxyS; sufA; sufB; sufC; sufD; sufE; sufS; trxC; uxuA; yaaA; yaeH; yaiA; ybjM; ydcH; ydeN; ygaQ; yljA; ytfK |
| PerR | $H_2O_2$ | katA; ahpCF; mrgA; zoaA; fur; hemAXCDBL; srfA |
| OhrR | Organic peroxides NaOCl | ohrA |
| SoxR | •$O_2$ NO• (also capable of sensing $H_2O_2$) | soxS |
| RosR | $H_2O_2$ | rbtT; tnp16a; rluC1; tnp5a; mscL; tnp2d; phoD; tnp15b; pstA; tnp5b; xylC; gabD1; rluC2; cgtS9; azlC; narKGHJI; rosR |

In some embodiments, the genetically engineered bacteria comprise a tunable regulatory region that is directly or indirectly controlled by a transcription factor that is capable of sensing at least one reactive oxygen species. The tunable regulatory region is operatively linked to a gene or gene cassette capable of directly or indirectly driving the expression of an oxalate catabolism enzyme, thus controlling expression of the oxalate catabolism enzyme(s) relative to ROS levels. For example, the tunable regulatory region is a ROS-inducible regulatory region, and the molecule is an oxalate catabolism enzyme; when ROS is present, e.g., in an inflamed tissue, a ROS-sensing transcription factor binds to and/or activates the regulatory region and drives expression of the gene sequence and/or gene cassette sequence for one or more the oxalate catabolism enzyme(s) and/or oxalate transporter(s) thereby producing the oxalate catabolism enzyme(s) and/or oxalate transporter(s). Subsequently, when inflammation is ameliorated, ROS levels are reduced, and production of the oxalate catabolism enzyme(s) and/or oxalate transporter(s) is decreased or eliminated.

In some embodiments, the tunable regulatory region is a ROS-inducible regulatory region; in the presence of ROS, a transcription factor senses ROS and activates the ROS-inducible regulatory region, thereby driving expression of an operatively linked gene or gene cassette. In some embodiments, the transcription factor senses ROS and subsequently binds to the ROS-inducible regulatory region, thereby activating downstream gene expression. In alternate embodiments, the transcription factor is bound to the ROS-inducible regulatory region in the absence of ROS; when the transcription factor senses ROS, it undergoes a conformational change, thereby inducing downstream gene expression.

In some embodiments, the tunable regulatory region is a ROS-inducible regulatory region, and the transcription factor that senses ROS is OxyR. OxyR "functions primarily as a global regulator of the peroxide stress response" and is capable of regulating dozens of genes, e.g., "genes involved in H2O2 detoxification (katE, ahpCF), heme biosynthesis (hemH), reductant supply (grxA, gor, trxC), thiol-disulfide isomerization (dsbG), Fe—S center repair (sufA-E, sufS), iron binding (yaaA), repression of iron import systems (fur)" and "OxyS, a small regulatory RNA" (Dubbs et al., 2012). The genetically engineered bacteria may comprise any suitable ROS-responsive regulatory region from a gene that is activated by OxyR. Genes that are capable of being activated by OxyR are known in the art (see, e.g., Zheng et al., 2001; Dubbs et al., 2012; Table 1). In certain embodiments, the genetically engineered bacteria of the invention comprise a ROS-inducible regulatory region from oxyS that is operatively linked to a gene and/or gene cassette, e.g., one or more oxalate catabolism enzyme(s) and/or oxalate transporter genes. In the presence of ROS, e.g., H2O2, an OxyR transcription factor senses ROS and activates to the oxyS regulatory region, thereby driving expression of the operatively linked oxalate catabolism enzyme and/or oxalate transporter gene and or gene cassette and producing the oxalate catabolism enzyme(s) and/or oxalate transporter(s). In some embodiments, OxyR is encoded by an *E. coli* oxyR gene. In some embodiments, the oxyS regulatory region is an *E. coli* oxyS regulatory region. In some embodiments, the ROS-inducible regulatory region is selected from the regulatory region of katG, dps, and ahpC.

In alternate embodiments, the tunable regulatory region is a ROS-inducible regulatory region, and the corresponding transcription factor that senses ROS is SoxR. When SoxR is "activated by oxidation of its [2Fe-2S] cluster, it increases the synthesis of SoxS, which then activates its target gene expression" (Koo et al., 2003). "SoxR is known to respond primarily to superoxide and nitric oxide" (Koo et al., 2003), and is also capable of responding to H2O2. The genetically engineered bacteria of the invention may comprise any suitable ROS-responsive regulatory region from a gene that is activated by SoxR. Genes that are capable of being activated by SoxR are known in the art (see, e.g., Koo et al., 2003; Table 1). In certain embodiments, the genetically engineered bacteria of the invention comprise a ROS-inducible regulatory region from soxS that is operatively linked to a gene and/or gene cassette, e.g., an oxalate catabolism enzyme. In the presence of ROS, the SoxR transcription factor senses ROS and activates the soxS regulatory region, thereby driving expression of the operatively linked oxalate catabolism enzyme and/or oxalate transporter gene or gene cassette and producing one or more oxalate catabolism enzyme(s) and/or oxalate transporter(s).

In some embodiments, the tunable regulatory region is a ROS-derepressible regulatory region, and binding of a corresponding transcription factor represses downstream gene expression; in the presence of ROS, the transcription factor no longer binds to the regulatory region, thereby derepressing the operatively linked gene or gene cassette.

In some embodiments, the tunable regulatory region is a ROS-derepressible regulatory region, and the transcription factor that senses ROS is OhrR. OhrR "binds to a pair of inverted repeat DNA sequences overlapping the ohrA promoter site and thereby represses the transcription event," but oxidized OhrR is "unable to bind its DNA target" (Duarte et al., 2010). OhrR is a "transcriptional repressor [that] . . . senses both organic peroxides and NaOCl" (Dubbs et al., 2012) and is "weakly activated by H2O2 but it shows much higher reactivity for organic hydroperoxides" (Duarte et al., 2010). The genetically engineered bacteria of the invention may comprise any suitable ROS-responsive regulatory region from a gene that is repressed by OhrR. Genes that are capable of being repressed by OhrR are known in the art (see, e.g., Dubbs et al., 2012; Table 1). In certain embodiments, the genetically engineered bacteria of the invention comprise a ROS-derepressible regulatory region from ohrA that is operatively linked to a gene or gene cassette, e.g., an oxalate catabolism enzyme and/or oxalate transporter gene. In the presence of ROS, e.g., NaOCl, an OhrR transcription factor senses ROS and no longer binds to the ohrA regulatory region, thereby derepressing the operatively linked oxalate catabolism enzyme and/or oxalate transporter gene and producing the oxalate catabolism enzyme and/or oxalate transporter.

OhrR is a member of the MarR family of ROS-responsive regulators. "Most members of the MarR family are transcriptional repressors and often bind to the −10 or −35 region in the promoter causing a steric inhibition of RNA polymerase binding" (Bussmann et al., 2010). Other members of this family are known in the art and include, but are not limited to, OspR, MgrA, RosR, and SarZ. In some embodiments, the transcription factor that senses ROS is OspR, MgRA, RosR, and/or SarZ, and the genetically engineered bacteria of the invention comprises one or more corresponding regulatory region sequences from a gene that is repressed by OspR, MgRA, RosR, and/or SarZ. Genes that are capable of being repressed by OspR, MgRA, RosR, and/or SarZ are known in the art (see, e.g., Dubbs et al., 2012).

In some embodiments, the tunable regulatory region is a ROS-derepressible regulatory region, and the corresponding transcription factor that senses ROS is RosR. RosR is "a MarR-type transcriptional regulator" that binds to an "18-bp inverted repeat with the consensus sequence TTGTTGAY-RYRTCAACWA" and is "reversibly inhibited by the oxidant H2O2" (Bussmann et al., 2010). RosR is capable of repressing numerous genes and putative genes, including but not limited to "a putative polyisoprenoid-binding protein (cg1322, gene upstream of and divergent from rosR), a sensory histidine kinase (cgtS9), a putative transcriptional regulator of the Crp/FNR family (cg3291), a protein of the glutathione S-transferase family (cg1426), two putative FMN reductases (cg1150 and cg1850), and four putative monooxygenases (cg0823, cg1848, cg2329, and cg3084)" (Bussmann et al., 2010). The genetically engineered bacteria of the invention may comprise any suitable ROS-responsive regulatory region from a gene that is repressed by RosR. Genes that are capable of being repressed by RosR are known in the art (see, e.g., Bussmann et al., 2010; Table 1). In certain embodiments, the genetically engineered bacteria of the invention comprise a ROS-derepressible regulatory region from cgtS9 that is operatively linked to a gene or gene cassette, e.g., an enzyme and/or oxalate transporter. In the presence of ROS, e.g., H2O2, a RosR transcription factor senses ROS and no longer binds to the cgtS9 regulatory region, thereby derepressing the operatively linked oxalate catabolism enzyme and/or oxalate transporter gene and producing the oxalate catabolism enzyme and/or oxalate transporter.

In some embodiments, it is advantageous for the genetically engineered bacteria to express a ROS-sensing transcription factor that does not regulate the expression of a significant number of native genes in the bacteria. In some embodiments, the genetically engineered bacterium of the invention expresses a ROS-sensing transcription factor from a different species, strain, or substrain of bacteria, wherein the transcription factor does not bind to regulatory sequences in the genetically engineered bacterium of the invention. In some embodiments, the genetically engineered bacterium of the invention is *Escherichia coli*, and the ROS-sensing transcription factor is RosR, e.g., from *Corynebacterium glutamicum*, wherein the *Escherichia coli* does not comprise binding sites for said RosR. In some embodiments, the heterologous transcription factor minimizes or eliminates off-target effects on endogenous regulatory regions and genes in the genetically engineered bacteria.

In some embodiments, the tunable regulatory region is a ROS-repressible regulatory region, and binding of a corresponding transcription factor represses downstream gene expression; in the presence of ROS, the transcription factor senses ROS and binds to the ROS-repressible regulatory region, thereby repressing expression of the operatively linked gene or gene cassette. In some embodiments, the ROS-sensing transcription factor is capable of binding to a regulatory region that overlaps with part of the promoter sequence. In alternate embodiments, the ROS-sensing transcription factor is capable of binding to a regulatory region that is upstream or downstream of the promoter sequence.

In some embodiments, the tunable regulatory region is a ROS-repressible regulatory region, and the transcription factor that senses ROS is PerR. In *Bacillus subtilis*, PerR "when bound to DNA, represses the genes coding for proteins involved in the oxidative stress response (katA, ahpC, and mrgA), metal homeostasis (hemAXCDBL, fur, and zoaA) and its own synthesis (perR)" (Marinho et al., 2014). PerR is a "global regulator that responds primarily to H2O2" (Dubbs et al., 2012) and "interacts with DNA at the per box, a specific palindromic consensus sequence (TTATAATNATTATAA) residing within and near the promoter sequences of PerR-controlled genes" (Marinho et al., 2014). PerR is capable of binding a regulatory region that "overlaps part of the promoter or is immediately downstream from it" (Dubbs et al., 2012). The genetically engineered bacteria of the invention may comprise any suitable ROS-responsive regulatory region from a gene that is repressed by PerR. Genes that are capable of being repressed by PerR are known in the art (see, e.g., Dubbs et al., 2012; Table 1).

In these embodiments, the genetically engineered bacteria may comprise a two repressor activation regulatory circuit, which is used to express an oxalate catabolism enzyme. The two repressor activation regulatory circuit comprises a first ROS-sensing repressor, e.g., PerR, and a second repressor, e.g., TetR, which is operatively linked to a gene or gene cassette, e.g., an oxalate catabolism enzyme. In one aspect of these embodiments, the ROS-sensing repressor inhibits transcription of the second repressor, which inhibits the transcription of the gene or gene cassette. Examples of second repressors useful in these embodiments include, but are not limited to, TetR, C1, and LexA. In some embodiments, the ROS-sensing repressor is PerR. In some embodiments, the second repressor is TetR. In this embodiment, a PerR-repressible regulatory region drives expression of TetR, and a TetR-repressible regulatory region drives expression of the gene or gene cassette, e.g., an oxalate catabolism enzyme. In the absence of PerR binding (which occurs in the absence of ROS), tetR is transcribed, and TetR represses expression of the gene or gene cassette, e.g., an oxalate catabolism enzyme. In the presence of PerR binding (which occurs in the presence of ROS), tetR expression is repressed, and the gene or gene cassette, e.g., an oxalate catabolism enzyme and/or oxalate transporter is expressed.

A ROS-responsive transcription factor may induce, derepress, or repress gene expression depending upon the regulatory region sequence used in the genetically engineered bacteria. For example, although "OxyR is primarily thought of as a transcriptional activator under oxidizing conditions . . . . OxyR can function as either a repressor or activator under both oxidizing and reducing conditions" (Dubbs et al., 2012), and OxyR "has been shown to be a repressor of its own expression as well as that of fhuF (encoding a ferric ion reductase) and flu (encoding the antigen 43 outer membrane protein)" (Zheng et al., 2001). The genetically engineered bacteria of the invention may comprise any suitable ROS-responsive regulatory region from a gene that is repressed by OxyR. In some embodiments, OxyR is used in a two repressor activation regulatory circuit, as described above. Genes that are capable of being repressed by OxyR are known in the art (see, e.g., Zheng et al., 2001; Table 1). Or, for example, although RosR is capable of repressing a number of genes, it is also capable of activating certain genes, e.g., the narKGHJI operon. In some embodiments, the genetically engineered bacteria comprise any suitable ROS-responsive regulatory region from a gene that is activated by RosR. In addition, "PerR-mediated positive regulation has also been observed . . . and appears to involve PerR binding to distant upstream sites" (Dubbs et al., 2012). In some embodiments, the genetically engineered bacteria comprise any suitable ROS-responsive regulatory region from a gene that is activated by PerR.

One or more types of ROS-sensing transcription factors and corresponding regulatory region sequences may be present in genetically engineered bacteria. For example, "OhrR is found in both Gram-positive and Gram-negative bacteria and can co-reside with either OxyR or PerR or both" (Dubbs et al., 2012). In some embodiments, the genetically engineered bacteria comprise one type of ROS-sensing transcription factor, e.g., OxyR, and one corresponding regulatory region sequence, e.g., from oxyS. In some embodiments, the genetically engineered bacteria comprise one type of ROS-sensing transcription factor, e.g., OxyR, and two or more different corresponding regulatory region sequences, e.g., from oxyS and katG. In some embodiments, the genetically engineered bacteria comprise two or more types of ROS-sensing transcription factors, e.g., OxyR and PerR, and two or more corresponding regulatory region sequences, e.g., from oxyS and katA, respectively. One ROS-responsive regulatory region may be capable of binding more than one transcription factor. In some embodiments, the genetically engineered bacteria comprise two or more types of ROS-sensing transcription factors and one corresponding regulatory region sequence.

Nucleic acid sequences of several exemplary OxyR-regulated regulatory regions are shown in Table 5. OxyR binding sites are underlined and bolded. In some embodiments, genetically engineered bacteria comprise a nucleic acid sequence that is at least about 80%, at least about 85%, at least about 90%, at least about 95%, or at least about 99% homologous to the DNA sequence of SEQ ID NO: 46, 47, 48, or 49, or a functional fragment thereof.

TABLE 9

Nucleotide sequences of exemplary OxyR-regulated regulatory regions

| Regulatory sequence | 0123456789012345678901234567890123456789012345678 9 |
|---|---|
| katG (SEQ ID NO: 30) | TGTGGCTTTTATGAAAATCACACAGTGATCACAAATTTTAAACAGAGCA CAAAATGCTGCCTCGAAATGAGGGCGGGAAAATAAGGTTATCAGCCTTG TTTTCTCCCTCATTACTTGAAGGATATGAAGCTAAAACCCTTTTTTATAA AGCATTTGTCCGAATTCGGACATAATCAAAAAAGCTTAATTAAGATCAA TTTGATCTACATCTCTTTAACCAACAATATGTAAGATCTCAACTATCGC ATCCGTGGATTAATTCAATTATAACTTCTCTCTAACGCTGTGTATCGTA ACGGTAACACTGTAGAGGGGAGCACATTGATGCGAATTCATTAAAGAGG AGAAAGGTACC |
| dps (SEQ ID NO: 31) | TTCCGAAAATTCCTGGCGAGCAGATAAATAAGAATTGTTCTTATCAATAT ATCTAACTCATTGAATCTTTATTAGTTTTGTTTTTCACGCTTGTTACCAC TATTAGTGTGATAGGAACAGCCAGAATAGCGGAACACATAGCCGGTGC TATACTTAATCTCGTTAATTACTGGGACATAACATCAAGAGGATATGAA ATTCGAATTCATTAAAGAGGAGAAAGGTACC |
| ahpC (SEQ ID NO: 32) | GCTTAGATCAGGTGATTGCCCTTTGTTTATGAGGGTGTTGTAATCCATGT CGTTGTTGCATTTGTAAGGGCAACACCTCAGCCTGCAGGCAGGCACTGA AGATACCAAAGGGTAGTTCAGATTACACGGTCACCTGGAAAGGGGCC ATTTTACTTTTTATCGCCGCTGGCGGTGCAAAGTTCACAAAGTTGTCTTA CGAAGGTTGTAAGGTAAAACTTATCGATTTGATAATGGAAACGCATT AGCCGAATCGGCAAAAATTGGTTACCTTACATCTCATCGAAAACACGGA GGAAGTATAGATGCGAATTCATTAAAGAGGAGAAAGGTACC |
| oxyS (SEQ ID NO: 33) | CTCGAGTTCATTATCCATCCTCCATCGCCACGATAGTTCATGGCGATAG GTAGAATAGCAATGAACGATTATCCCTATCAAGCATTCTGACTGATAAT TGCTCACACGAATTCATTAAAGAGGAGAAAGGTACC |

In some embodiments, the genetically engineered bacteria of the invention comprise a gene encoding a ROS-sensing transcription factor, e.g., the oxyR gene, that is controlled by its native promoter, an inducible promoter, a promoter that is stronger than the native promoter, e.g., the GlnRS promoter or the P(Bla) promoter, or a constitutive promoter. In some instances, it may be advantageous to express the ROS-sensing transcription factor under the control of an inducible promoter in order to enhance expression stability. In some embodiments, expression of the ROS-sensing transcription factor is controlled by a different promoter than the promoter that controls expression of the therapeutic molecule. In some embodiments, expression of the ROS-sensing transcription factor is controlled by the same promoter that controls expression of the therapeutic molecule. In some embodiments, the ROS-sensing transcription factor and therapeutic molecule are divergently transcribed from a promoter region.

In some embodiments, the genetically engineered bacteria of the invention comprise a gene for a ROS-sensing transcription factor from a different species, strain, or substrain of bacteria. In some embodiments, the genetically engineered bacteria comprise a ROS-responsive regulatory region from a different species, strain, or substrain of bacteria. In some embodiments, the genetically engineered bacteria comprise a ROS-sensing transcription factor and corresponding ROS-responsive regulatory region from a different species, strain, or substrain of bacteria. The heterologous ROS-sensing transcription factor and regulatory region may increase the transcription of genes operatively linked to said regulatory region in the presence of ROS, as compared to the native transcription factor and regulatory region from bacteria of the same subtype under the same conditions.

In some embodiments, the genetically engineered bacteria comprise a ROS-sensing transcription factor, OxyR, and corresponding regulatory region, oxyS, from Escherichia coli. In some embodiments, the native ROS-sensing transcription factor, e.g., OxyR, is left intact and retains wild-type activity. In alternate embodiments, the native ROS-sensing transcription factor, e.g., OxyR, is deleted or mutated to reduce or eliminate wild-type activity.

In some embodiments, the genetically engineered bacteria of the invention comprise multiple copies of the endogenous gene encoding the ROS-sensing transcription factor, e.g., the oxyR gene. In some embodiments, the gene encoding the ROS-sensing transcription factor is present on a plasmid. In some embodiments, the gene encoding the ROS-sensing transcription factor and the gene or gene cassette for producing the therapeutic molecule are present on different plasmids. In some embodiments, the gene encoding the ROS-sensing transcription factor and the gene or gene cassette for producing the therapeutic molecule are present on the same. In some embodiments, the gene encoding the ROS-sensing transcription factor is present on a chromosome. In some embodiments, the gene encoding the ROS-sensing transcription factor and the gene or gene cassette for producing the therapeutic molecule are present on different chromosomes. In some embodiments, the gene encoding the ROS-sensing transcription factor and the gene or gene cassette for producing the therapeutic molecule are present on the same chromosome.

In some embodiments, the genetically engineered bacteria comprise a wild-type gene encoding a ROS-sensing transcription factor, e.g., the soxR gene, and a corresponding regulatory region, e.g., a soxS regulatory region, that is mutated relative to the wild-type regulatory region from bacteria of the same subtype. The mutated regulatory region increases the expression of the oxalate catabolism enzyme and/or oxalate transporter in the presence of ROS, as compared to the wild-type regulatory region under the same conditions. In some embodiments, the genetically engineered bacteria comprise a wild-type ROS-responsive regulatory region, e.g., the oxyS regulatory region, and a corresponding transcription factor, e.g., OxyR, that is mutated relative to the wild-type transcription factor from bacteria of the same subtype. The mutant transcription factor increases the expression of the oxalate catabolism enzyme and/or oxalate transporter in the presence of ROS, as compared to the wild-type transcription factor under the same conditions. In some embodiments, both the ROS-sensing transcription factor and corresponding regulatory region are mutated relative to the wild-type sequences from bacteria of the same subtype in order to increase expression of the oxalate catabolism enzyme(s) in the presence of ROS.

In some embodiments, the gene or gene cassette for producing the oxalate catabolism enzyme(s) is present on a plasmid and operably linked to a promoter that is induced by ROS. In some embodiments, the gene or gene cassette for producing the oxalate catabolism enzyme(s) is present in the chromosome and operably linked to a promoter that is induced by ROS. In some embodiments, the gene or gene cassette for producing the oxalate catabolism enzyme(s) is present on a chromosome and operably linked to a promoter that is induced by exposure to tetracycline. In some embodiments, the gene or gene cassette for producing the oxalate catabolism enzyme and/or oxalate transporter is present on a plasmid and operably linked to a promoter that is induced by exposure to tetracycline. In some embodiments, expression is further optimized by methods known in the art, e.g., by optimizing ribosomal binding sites, manipulating transcriptional regulators, and/or increasing mRNA stability.

In some embodiments, the genetically engineered bacteria may comprise multiple copies of the gene(s) capable of producing an oxalate catabolism enzyme(s) and/or oxalate transporter(s). In some embodiments, the gene(s) capable of producing an oxalate catabolism enzyme(s) and/or oxalate transporter(s) is present on a plasmid and operatively linked to a ROS-responsive regulatory region. In some embodiments, the gene(s) capable of producing an oxalate catabolism enzyme and/or oxalate transporter is present in a chromosome and operatively linked to a ROS-responsive regulatory region.

Thus, in some embodiments, the genetically engineered bacteria or genetically engineered virus produce one or more oxalate catabolism enzymes under the control of an oxygen level-dependent promoter, a reactive oxygen species (ROS)-dependent promoter, or a reactive nitrogen species (RNS)-dependent promoter, and a corresponding transcription factor.

In some embodiments, the genetically engineered bacteria comprise a stably maintained plasmid or chromosome carrying a gene for producing an oxalate catabolism enzyme and/or oxalate transporter such that the oxalate catabolism enzyme and/or oxalate transporter can be expressed in the host cell, and the host cell is capable of survival and/or growth in vitro, e.g., in medium, and/or in vivo. In some embodiments, a bacterium may comprise multiple copies of the gene and/or gene cassette encoding one or more oxalate catabolism enzyme(s) and/or oxalate transporter(s). In some embodiments, the gene and/or gene cassette encoding one or more oxalate catabolism enzyme(s) and/or oxalate transporter(s) is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, the gene and/or gene cassette encoding one or more oxalate catabolism enzyme(s) and/or oxalate transporter(s) is expressed on a high-copy plasmid. In some embodiments, the high-copy plasmid may be useful for increasing expression of the oxalate catabolism enzyme(s) and/or oxalate transporter(s). In some embodiments, the gene and/or gene cassette encoding one or more oxalate catabolism enzyme(s) and/or oxalate transporter(s) is expressed on a chromosome.

In some embodiments, the bacteria are genetically engineered to include multiple mechanisms of action (MOAs), e.g., circuits producing multiple copies of the same product (e.g., to enhance copy number) or circuits performing multiple different functions. For example, the genetically engineered bacteria may include four copies of the gene and/or gene cassette encoding one or more particular oxalate catabolism enzyme(s) and/or oxalate transporter(s) inserted at four different insertion sites. Alternatively, the genetically engineered bacteria may include three copies of the gene encoding a particular oxalate catabolism enzyme and/or oxalate transporter inserted at three different insertion sites and three copies of the gene encoding a different oxalate catabolism enzyme and/or oxalate transporter inserted at three different insertion sites.

In some embodiments, under conditions where the oxalate catabolism enzyme(s) and/or oxalate transporter is expressed, the genetically engineered bacteria of the disclosure produce at least about 1.5-fold, at least about 2-fold, at least about 10-fold, at least about 15-fold, at least about 20-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, at least about 1,000-fold, or at least about 1,500-fold more of the oxalate catabolism enzyme(s) and/or oxalate transporter(s) and/or transcript of the gene(s) in the operon as compared to unmodified bacteria of the same subtype under the same conditions.

In some embodiments, quantitative PCR (qPCR) is used to amplify, detect, and/or quantify mRNA expression levels of the oxalate catabolism enzyme(s) and/or oxalate transporter(s) gene(s). Primers specific for oxalate catabolism enzyme and/or oxalate transporter gene(s) may be designed and used to detect mRNA in a sample according to methods known in the art. In some embodiments, a fluorophore is added to a sample reaction mixture that may contain oxalate catabolism enzyme mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the oxalate catabolism enzyme and/or oxalate transporter gene(s).

In some embodiments, quantitative PCR (qPCR) is used to amplify, detect, and/or quantify mRNA expression levels of the oxalate catabolism enzyme(s) and/or oxalate transporter gene(s). Primers specific for oxalate catabolism enzyme and/or oxalate transporter gene(s) may be designed and used to detect mRNA in a sample according to methods known in the art. In some embodiments, a fluorophore is added to a sample reaction mixture that may contain oxalate catabolism enzyme and/or oxalate transporter mRNA, and a thermal cycler is used to illuminate the sample reaction mixture with a specific wavelength of light and detect the subsequent emission by the fluorophore. The reaction mixture is heated and cooled to predetermined temperatures for predetermined time periods. In certain embodiments, the heating and cooling is repeated for a predetermined number of cycles. In some embodiments, the reaction mixture is heated and cooled to 90-100° C., 60-70° C., and 30-50° C. for a predetermined number of cycles. In a certain embodiment, the reaction mixture is heated and cooled to 93-97° C., 55-65° C., and 35-45° C. for a predetermined number of cycles. In some embodiments, the accumulating amplicon is quantified after each cycle of the qPCR. The number of cycles at which fluorescence exceeds the threshold is the threshold cycle (CT). At least one CT result for each sample is generated, and the CT result(s) may be used to determine mRNA expression levels of the oxalate catabolism enzyme and/or oxalate transporter gene(s).

In other embodiments, the inducible promoter is a propionate responsive promoter. For example, the prpR promoter is a propionate responsive promoter. In one embodiment, the propionate responsive promoter comprises SEQ ID NO: 58.

Essential Genes and Auxotrophs

As used herein, the term "essential gene" refers to a gene which is necessary to for cell growth and/or survival. Bacterial essential genes are well known to one of ordinary skill in the art, and can be identified by directed deletion of genes and/or random mutagenesis and screening (see, for example, Zhang and Lin, 2009, DEG 5.0, a database of essential genes in both prokaryotes and eukaryotes, Nucl. Acids Res., 37:D455-D458 and Gerdes et al., Essential genes on metabolic maps, Curr. Opin. Biotechnol., 17(5): 448-456, the entire contents of each of which are expressly incorporated herein by reference).

An "essential gene" may be dependent on the circumstances and environment in which an organism lives. For example, a mutation of, modification of, or excision of an essential gene may result in the recombinant bacteria of the disclosure becoming an auxotroph. An auxotrophic modification is intended to cause bacteria to die in the absence of an exogenously added nutrient essential for survival or growth because they lack the gene(s) necessary to produce that essential nutrient.

An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in one or more gene(s) required for cell survival and/or growth.

In some embodiments, the bacterial cell comprises a genetic mutation in one or more endogenous gene(s) encoding an oxalate biosynthesis gene, wherein the genetic mutation reduces biosynthesis of oxalate in the bacterial cell.

In one embodiment, the essential gene is an oligonucleotide synthesis gene, for example, thyA. In another embodiment, the essential gene is a cell wall synthesis gene, for example, dapA. In yet another embodiment, the essential gene is an amino acid gene, for example, serA or MetA. Any gene required for cell survival and/or growth may be targeted, including but not limited to, cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thiI, as long as the corresponding wild-type gene product is not produced in the bacteria.

Table 10 lists depicts exemplary bacterial genes which may be disrupted or deleted to produce an auxotrophic strain. These include, but are not limited to, genes required for oligonucleotide synthesis, amino acid synthesis, and cell wall synthesis.

TABLE 10

Non-limiting Examples of Bacterial Genes Useful for Generation of an Auxotroph

| Amino Acid | Oligonucleotide | Cell Wall |
|---|---|---|
| cysE | thyA | dapA |
| glnA | uraA | dapB |
| ilvD | | dapD |
| leuB | | dapE |
| lysA | | dapF |
| serA | | |
| metA | | |
| glyA | | |
| hisB | | |
| ilvA | | |
| pheA | | |
| proA | | |
| thrC | | |
| trpC | | |
| tyrA | | |

Table 11 shows the survival of various amino acid auxotrophs in the mouse gut, as detected 24 hrs and 48 hrs post-gavage. These auxotrophs were generated using BW25113, a non-Nissle strain of *E. coli*.

TABLE 11

Survival of amino acid auxotrophs in the mouse gut

| Gene | AA Auxotroph | Pre-Gavage | 24 hours | 48 hours |
|---|---|---|---|---|
| argA | Arginine | Present | Present | Absent |
| cysE | Cysteine | Present | Present | Absent |
| glnA | Glutamine | Present | Present | Absent |
| glyA | Glycine | Present | Present | Absent |
| hisB | Histidine | Present | Present | Present |
| ilvA | Isoleucine | Present | Present | Absent |
| leuB | Leucine | Present | Present | Absent |
| lysA | Lysine | Present | Present | Absent |
| metA | Methionine | Present | Present | Present |
| pheA | Phenylalanine | Present | Present | Present |
| proA | Proline | Present | Present | Absent |
| serA | Serine | Present | Present | Present |
| thrC | Threonine | Present | Present | Present |
| trpC | Tryptophan | Present | Present | Present |
| tyrA | Tyrosine | Present | Present | Present |
| ilvD | Valine/Isoleucine/Leucine | Present | Present | Absent |
| thyA | Thiamine | Present | Absent | Absent |
| uraA | Uracil | Present | Absent | Absent |
| flhD | FlhD | Present | Present | Present |

For example, thymine is a nucleic acid that is required for bacterial cell growth; in its absence, bacteria undergo cell death. The thyA gene encodes thymidylate synthetase, an enzyme that catalyzes the first step in thymine synthesis by converting dUMP to dTMP (Sat et al., 2003). In some embodiments, the bacterial cell of the disclosure is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the bacterial cell of the disclosure is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

Diaminopimelic acid (DAP) is an amino acid synthetized within the lysine biosynthetic pathway and is required for bacterial cell wall growth (Meadow et al., 1959; Clarkson et al., 1971). In some embodiments, any of the genetically engineered bacteria described herein is a dapD auxotroph in which dapD is deleted and/or replaced with an unrelated gene. A dapD auxotroph can grow only when sufficient amounts of DAP are present, e.g., by adding DAP to growth media in vitro. Without sufficient amounts of DAP, the dapD auxotroph dies. In some embodiments, the auxotrophic modification is used to ensure that the bacterial cell does not survive in the absence of the auxotrophic gene product (e.g., outside of the gut).

In other embodiments, the genetically engineered bacterium of the present disclosure is a uraA auxotroph in which uraA is deleted and/or replaced with an unrelated gene. The uraA gene codes for UraA, a membrane-bound transporter that facilitates the uptake and subsequent metabolism of the pyrimidine uracil (Andersen et al., 1995). A uraA auxotroph can grow only when sufficient amounts of uracil are present, e.g., by adding uracil to growth media in vitro. Without sufficient amounts of uracil, the uraA auxotroph dies. In some embodiments, auxotrophic modifications are used to ensure that the bacteria do not survive in the absence of the auxotrophic gene product (e.g., outside of the gut).

In complex communities, it is possible for bacteria to share DNA. In very rare circumstances, an auxotrophic bacterial strain may receive DNA from a non-auxotrophic strain, which repairs the genomic deletion and permanently rescues the auxotroph. Therefore, engineering a bacterial strain with more than one auxotroph may greatly decrease the probability that DNA transfer will occur enough times to rescue the auxotrophy. In some embodiments, the genetically engineered bacteria comprise a deletion or mutation in two or more genes required for cell survival and/or growth.

Other examples of essential genes include, but are not limited to yhbV, yagG, hemB, secD, secF, ribD, ribE, thiL, dxs, ispA, dnaX, adk, hemH, lpxH, cysS, fold, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, mc, ftsB, eno, pyrG, chpR, lgt, fbaA, pgk, yqgD, metK, yqgF, plsC, ygiT, pare, ribB, cca, ygjD, tdcF, yraL, yihA, ftsN, murI, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, dnaC, ribF, lspA, ispH, dapB, folA, imp, yabQ, ftsL, ftsI, murE, murF, mraY, murD, ftsW, murG, murC, ftsQ, ftsA, ftsZ, lpxC, secM, secA, can, folK, hemL, yadR, dapD, map, rpsB, infB, nusA, ftsH, obgE, rpmA, rplU, ispB, murA, yrbB, yrbK, yhbN, rpsI, rplM, degS, mreD, mreC, mreB, accB, accC, yrdC, def, fmt, rplQ, rpoA, rpsD, rpsK, rpsM, entD, mrdB, mrdA, nadD, hlepB, rpoE, pssA, yfiO, rplS, trmD, rpsP, ffh, grpE, yfjB, csrA, ispF, ispD, rplW, rplD, rplC, rpsJ, fusA, rpsG, rpsL, trpS, yrfF, asd, rpoH, ftsX, ftsE, ftsY, frr, dxr, ispU, rfaK, kdtA, coaD, rpmB, dfp, dut, gmk, spot, gyrB, dnaN, dnaA, rpmH, rnpA, yidC, tnaB, glmS, glmU, wzyE, hemp, hemC, yigP, ubiB, ubiD, hemG, secY, rplO, rpmD, rpsE, rplR, rplF, rpsH, rpsN, rplE, rplX, rplN, rpsQ, rpmC, rplP, rpsC, rplV, rpsS, rplB, cdsA, yaeL, yaeT, lpxD, fabZ, lpxA, lpxB, dnaE, accA, tilS, proS, yaff, tsf, pyrH, olA, rlpB, leuS, lnt, glnS, fldA, cydA, infA, cydC, ftsK, lolA, serS, rpsA, msbA, lpxK, kdsB, mukF, mukE, mukB, asnS, fabA, mviN, mc, yceQ, fabD, fabG, acpP, tmk, holB, lolC, lolD, lolE, purB, ymfK, minE, mind, pth, rsA, ispE, lolB, hemA, prfA, prmC, kdsA, topA, ribA, fabI racR, dicA, ydfB, tyrS, ribC, ydiL, pheT, pheS, yhhQ, bcsB, glyQ, yibJ, and gpsA. Other essential genes are known to those of ordinary skill in the art.

In some embodiments, the genetically engineered bacterium of the present disclosure is a synthetic ligand-dependent essential gene (SLiDE) bacterial cell. SLiDE bacterial cells are synthetic auxotrophs with a mutation in one or more essential genes that only grow in the presence of a particular ligand (see Lopez and Anderson "Synthetic Auxotrophs with Ligand-Dependent Essential Genes for a BL21 (DE3) Biosafety Strain," ACS Synthetic Biology (2015) DOI: 10.1021/acssynbio.5b00085, the entire contents of which are expressly incorporated herein by reference).

In some embodiments, the SLiDE bacterial cell comprises a mutation in an essential gene. In some embodiments, the essential gene is selected from the group consisting of pheS, dnaN, tyrS, metG and adk. In some embodiments, the essential gene is dnaN comprising one or more of the following mutations: H191N, R240C, I317S, F319V, L340T, V347I, and S345C. In some embodiments, the essential gene is dnaN comprising the mutations H191N, R240C, I317S, F319V, L340T, V347I, and S345C. In some embodiments, the essential gene is pheS comprising one or more of the following mutations: F125G, P183T, P184A, R186A, and I188L. In some embodiments, the essential gene is pheS comprising the mutations F125G, P183T, P184A, R186A, and I188L. In some embodiments, the essential gene is tyrS comprising one or more of the following mutations: L36V, C38A and F40G. In some embodiments, the essential gene is tyrS comprising the mutations L36V, C38A and F40G. In some embodiments, the essential gene is metG comprising one or more of the following mutations: E45Q, N47R, I49G, and A51C. In some embodiments, the essential gene is metG comprising the mutations E45Q, N47R, I49G, and A51C. In some embodiments, the essential gene is adk comprising one or more of the following mutations: I4L, L5I and L6G. In some embodiments, the essential gene is adk comprising the mutations I4L, L5I and L6G.

In some embodiments, the genetically engineered bacterium is complemented by a ligand. In some embodiments, the ligand is selected from the group consisting of benzothiazole, indole, 2-aminobenzothiazole, indole-3-butyric acid, indole-3-acetic acid, and L-histidine methyl ester. For example, bacterial cells comprising mutations in metG (E45Q, N47R, I49G, and A51C) are complemented by benzothiazole, indole, 2-aminobenzothiazole, indole-3-butyric acid, indole-3-acetic acid or L-histidine methyl ester. Bacterial cells comprising mutations in dnaN (H191N, R240C, I317S, F319V, L340T, V347I, and S345C) are complemented by benzothiazole, indole or 2-aminobenzothiazole. Bacterial cells comprising mutations in pheS (F125G, P183T, P184A, R186A, and I188L) are complemented by benzothiazole or 2-aminobenzothiazole. Bacterial cells comprising mutations in tyrS (L36V, C38A, and F40G) are complemented by benzothiazole or 2-aminobenzothiazole. Bacterial cells comprising mutations in adk (I4L, L5I and L6G) are complemented by benzothiazole or indole.

In some embodiments, the genetically engineered bacterium comprises more than one mutant essential gene that renders it auxotrophic to a ligand. In some embodiments, the bacterial cell comprises mutations in two essential genes. For example, in some embodiments, the bacterial cell comprises mutations in tyrS (L36V, C38A, and F40G) and metG (E45Q, N47R, I49G, and A51C). In other embodiments, the bacterial cell comprises mutations in three essential genes. For example, in some embodiments, the bacterial cell comprises mutations in tyrS (L36V, C38A, and F40G), metG (E45Q, N47R, I49G, and A51C), and pheS (F125G, P183T, P184A, R186A, and I188L).

In some embodiments, the genetically engineered bacterium is a conditional auxotroph whose essential gene(s) is replaced using the arabinose system described herein.

In some embodiments, the genetically engineered bacterium of the disclosure is an auxotroph and also comprises kill-switch circuitry, such as any of the kill-switch components and systems described herein. For example, the recombinant bacteria may comprise a deletion or mutation in an essential gene required for cell survival and/or growth, for example, in a DNA synthesis gene, for example, thyA, cell wall synthesis gene, for example, dapA and/or an amino acid gene, for example, serA or MetA or ilvC, and may also comprise a toxin gene that is regulated by one or more transcriptional activators that are expressed in response to an environmental condition(s) and/or signal(s) (such as the described arabinose system) or regulated by one or more recombinases that are expressed upon sensing an exogenous environmental condition(s) and/or signal(s) (such as the recombinase systems described herein). Other embodiments are described in Wright et al., "GeneGuard: A Modular Plasmid System Designed for Biosafety," ACS Synthetic Biology (2015) 4: 307-16, the entire contents of which are expressly incorporated herein by reference). In some embodiments, the genetically engineered bacterium of the disclosure is an auxotroph and also comprises kill-switch circuitry, such as any of the kill-switch components and systems described herein, as well as another biosecurity system, such a conditional origin of replication (see Wright et al., supra).

Genetic Regulatory Circuits

In some embodiments, the genetically engineered bacteria comprise multi-layered genetic regulatory circuits for expressing the constructs described herein (see, e.g., U.S. Provisional Application No. 62/184,811, incorporated herein by reference in its entirety). The genetic regulatory circuits are useful to screen for mutant bacteria that produce one or more oxalate catabolism enzyme(s) and/or oxalate transporter(s) or rescue an auxotroph. In certain embodiments, the invention provides methods for selecting genetically engineered bacteria that produce one or more genes of interest.

In some embodiments, the invention provides genetically engineered bacteria comprising a gene or gene cassette for producing a payload and a T7 polymerase-regulated genetic regulatory circuit. For example, the genetically engineered bacteria comprise a first gene encoding a T7 polymerase, wherein the first gene is operably linked to a fumarate and nitrate reductase regulator (FNR)-responsive promoter; a second gene or gene cassette for producing a payload, wherein the second gene or gene cassette is operably linked to a T7 promoter that is induced by the T7 polymerase; and a third gene encoding an inhibitory factor, lysY, that is capable of inhibiting the T7 polymerase. In the presence of oxygen, FNR does not bind the FNR-responsive promoter, and the payload is not expressed. LysY is expressed constitutively (P-lac constitutive) and further inhibits T7 polymerase. In the absence of oxygen, FNR dimerizes and binds to the FNR-responsive promoter, T7 polymerase is expressed at a level sufficient to overcome lysY inhibition, and the payload is expressed. In some embodiments, the lysY gene is operably linked to an additional FNR binding site. In the absence of oxygen, FNR dimerizes to activate T7 polymerase expression as described above, and also inhibits lysY expression.

In some embodiments, the invention provides genetically engineered bacteria comprising a gene or gene cassette for producing a payload and a protease-regulated genetic regulatory circuit. For example, the genetically engineered bacteria comprise a first gene encoding an mf-lon protease, wherein the first gene is operably linked to a FNR-responsive promoter; a second gene or gene cassette for producing a payload operably linked to a Tet regulatory region (tetO); and a third gene encoding an mf-lon degradation signal linked to a Tet repressor (tetR), wherein the tetR is capable of binding to the Tet regulatory region and repressing expression of the second gene or gene cassette. The mf-lon protease is capable of recognizing the mf-lon degradation signal and degrading the tetR. In the presence of oxygen, FNR does not bind the FNR-responsive promoter, the repressor is not degraded, and the payload is not expressed. In the absence of oxygen, FNR dimerizes and binds the FNR-responsive promoter, thereby inducing expression of mf-lon protease. The mf-lon protease recognizes the mf-lon degradation signal and degrades the tetR, and the payload is expressed.

In some embodiments, the invention provides genetically engineered bacteria comprising a gene or gene cassette for producing a payload and a repressor-regulated genetic regulatory circuit. For example, the genetically engineered bacteria comprise a first gene encoding a first repressor, wherein the first gene is operably linked to a FNR-responsive promoter; a second gene or gene cassette for producing a payload operably linked to a first regulatory region comprising a constitutive promoter; and a third gene encoding a second repressor, wherein the second repressor is capable of binding to the first regulatory region and repressing expression of the second gene or gene cassette. The third gene is operably linked to a second regulatory region comprising a constitutive promoter, wherein the first repressor is capable of binding to the second regulatory region and inhibiting expression of the second repressor. In the presence of oxygen, FNR does not bind the FNR-responsive promoter, the first repressor is not expressed, the second repressor is expressed, and the payload is not expressed. In the absence of oxygen, FNR dimerizes and binds the FNR-responsive promoter, the first repressor is expressed, the second repressor is not expressed, and the payload is expressed.

Examples of repressors useful in these embodiments include, but are not limited to, ArgR, TetR, ArsR, AscG, LacI, CscR, DeoR, DgoR, FruR, GalR, GatR, CI, LexA, RafR, QacR, and PtxS (US20030166191).

In some embodiments, the invention provides genetically engineered bacteria comprising a gene or gene cassette for producing a payload and a regulatory RNA-regulated genetic regulatory circuit. For example, the genetically engineered bacteria comprise a first gene encoding a regulatory RNA, wherein the first gene is operably linked to a FNR-responsive promoter, and a second gene or gene cassette for producing a payload. The second gene or gene cassette is operably linked to a constitutive promoter and further linked to a nucleotide sequence capable of producing an mRNA hairpin that inhibits translation of the payload. The regulatory RNA is capable of eliminating the mRNA hairpin and inducing payload translation via the ribosomal binding site. In the presence of oxygen, FNR does not bind the FNR-responsive promoter, the regulatory RNA is not expressed, and the mRNA hairpin prevents the payload from being translated. In the absence of oxygen, FNR dimerizes and binds the FNR-responsive promoter, the regulatory RNA is expressed, the mRNA hairpin is eliminated, and the payload is expressed.

In some embodiments, the invention provides genetically engineered bacteria comprising a gene or gene cassette for producing a payload and a CRISPR-regulated genetic regulatory circuit. For example, the genetically engineered bacteria comprise a Cas9 protein; a first gene encoding a CRISPR guide RNA, wherein the first gene is operably linked to a FNR-responsive promoter; a second gene or gene cassette for producing a payload, wherein the second gene or gene cassette is operably linked to a regulatory region comprising a constitutive promoter; and a third gene encoding a repressor operably linked to a constitutive promoter, wherein the repressor is capable of binding to the regulatory region and repressing expression of the second gene or gene cassette. The third gene is further linked to a CRISPR target sequence that is capable of binding to the CRISPR guide RNA, wherein said binding to the CRISPR guide RNA induces cleavage by the Cas9 protein and inhibits expression of the repressor. In the presence of oxygen, FNR does not bind the FNR-responsive promoter, the guide RNA is not expressed, the repressor is expressed, and the payload is not expressed. In the absence of oxygen, FNR dimerizes and binds the FNR-responsive promoter, the guide RNA is expressed, the repressor is not expressed, and the payload is expressed.

In some embodiments, the invention provides genetically engineered bacteria comprising a gene or gene cassette for producing a payload and a recombinase-regulated genetic regulatory circuit. For example, the genetically engineered bacteria comprise a first gene encoding a recombinase, wherein the first gene is operably linked to a FNR-responsive promoter, and a second gene or gene cassette for producing a payload operably linked to a constitutive promoter. The second gene or gene cassette is inverted in orientation (3' to 5') and flanked by recombinase binding sites, and the recombinase is capable of binding to the recombinase binding sites to induce expression of the second gene or gene cassette by reverting its orientation (5' to 3'). In the presence of oxygen, FNR does not bind the FNR-responsive promoter, the recombinase is not expressed, the payload remains in the 3' to 5' orientation, and no functional payload is produced. In the absence of oxygen, FNR dimerizes and binds the FNR-responsive promoter, the recombinase is expressed, the payload is reverted to the 5' to 3' orientation, and functional payload is produced.

In some embodiments, the invention provides genetically engineered bacteria comprising a gene or gene cassette for producing a payload and a polymerase- and recombinase-regulated genetic regulatory circuit. For example, the genetically engineered bacteria comprise a first gene encoding a recombinase, wherein the first gene is operably linked to a FNR-responsive promoter; a second gene or gene cassette for producing a payload operably linked to a T7 promoter; a third gene encoding a T7 polymerase, wherein the T7 polymerase is capable of binding to the T7 promoter and inducing expression of the payload. The third gene encoding the T7 polymerase is inverted in orientation (3' to 5') and flanked by recombinase binding sites, and the recombinase is capable of binding to the recombinase binding sites to induce expression of the T7 polymerase gene by reverting its orientation (5' to 3'). In the presence of oxygen, FNR does not bind the FNR-responsive promoter, the recombinase is not expressed, the T7 polymerase gene remains in the 3' to 5' orientation, and the payload is not expressed. In the absence of oxygen, FNR dimerizes and binds the FNR-responsive promoter, the recombinase is expressed, the T7 polymerase gene is reverted to the 5' to 3' orientation, and the payload is expressed.

Kill Switches

In some embodiments, the genetically engineered bacteria also comprise a kill switch (see, e.g., U.S. Provisional Application Nos. 62/183,935 and 62/263,329, each of which are expressly incorporated herein by reference in their entireties). The kill switch is intended to actively kill engineered microbes in response to external stimuli. As opposed to an auxotrophic mutation where bacteria die because they lack an essential nutrient for survival, the kill switch is triggered by a particular factor in the environment that induces the production of toxic molecules within the microbe that cause cell death.

Bacteria engineered with kill switches have been engineered for in vitro research purposes, e.g., to limit the spread of a biofuel-producing microorganism outside of a laboratory environment. Bacteria engineered for in vivo administration to treat a disease or disorder may also be programmed to die at a specific time after the expression and delivery of a heterologous gene or gene cassette, for example, a therapeutic gene(s) or after the subject has experienced the therapeutic effect. For example, in some embodiments, the kill switch is activated to kill the bacteria after a period of time following expression of an oxalate catabolism enzyme. In some embodiments, the kill switch is activated in a delayed fashion following expression of the oxalate catabolism gene, for example, after the production of the oxalate catabolism enzyme. Alternatively, the bacteria may be engineered to die after the bacteria has spread outside of a disease site. Specifically, it may be useful to prevent long-term colonization of subjects by the microorganism, spread of the microorganism outside the area of interest (for example, outside the gut) within the subject, or spread of the microorganism outside of the subject into the environment (for example, spread to the environment through the stool of the subject).

Examples of such toxins that can be used in kill-switches include, but are not limited to, bacteriocins, lysins, and other molecules that cause cell death by lysing cell membranes, degrading cellular DNA, or other mechanisms. Such toxins can be used individually or in combination. The switches that control their production can be based on, for example, transcriptional activation (toggle switches; see, e.g., Gardner et al., 2000), translation (riboregulators), or DNA recombination (recombinase-based switches), and can sense environmental stimuli such as anaerobiosis or reactive oxygen species. These switches can be activated by a single environmental factor or may require several activators in AND, OR, NAND and NOR logic configurations to induce cell death. For example, an AND riboregulator switch is activated by tetracycline, isopropyl β-D-1-thiogalactopyranoside (IPTG), and arabinose to induce the expression of lysins, which permeabilize the cell membrane and kill the cell. IPTG induces the expression of the endolysin and holin mRNAs, which are then derepressed by the addition of arabinose and tetracycline. All three inducers must be present to cause cell death. Examples of kill switches are known in the art (Callura et al., 2010). In some embodiments, the kill switch is activated to kill the bacteria after a period of time following oxygen level-dependent expression of an oxalate catabolism enzyme. In some embodiments, the kill switch is activated in a delayed fashion following oxygen level-dependent expression of an oxalate catabolism enzyme.

Kill-switches can be designed such that a toxin is produced in response to an environmental condition or external signal (e.g., the bacteria are killed in response to an external cue; i.e., an activation-based kill switch, see FIG. 16-21)) or, alternatively designed such that a toxin is produced once an environmental condition no longer exists or an external signal is ceased (i.e., a repression-based kill switch, see FIG. 17-20).

Thus, in some embodiments, the genetically engineered bacteria of the disclosure are further programmed to die after sensing an exogenous environmental signal, for example, in a low oxygen environment. In some embodiments, the genetically engineered bacteria of the present disclosure, e.g., bacteria expressing an oxalate catabolism enzyme, comprise one or more genes encoding one or more recombinase(s), whose expression is induced in response to an environmental condition or signal and causes one or more recombination events that ultimately leads to the expression of a toxin which kills the cell. In some embodiments, the at least one recombination event is the flipping of an inverted heterologous gene encoding a bacterial toxin which is then constitutively expressed after it is flipped by the first recombinase. In one embodiment, constitutive expression of the bacterial toxin kills the genetically engineered bacterium. In these types of kill-switch systems once the engineered bacterial cell senses the exogenous environmental condition and expresses the heterologous gene of interest, the recombinant bacterial cell is no longer viable.

In another embodiment in which the genetically engineered bacteria of the present disclosure, e.g., bacteria expressing an oxalate catabolism enzyme, express one or more recombinase(s) in response to an environmental condition or signal causing at least one recombination event, the genetically engineered bacterium further expresses a heterologous gene encoding an anti-toxin in response to an exogenous environmental condition or signal. In one embodiment, the at least one recombination event is flipping of an inverted heterologous gene encoding a bacterial toxin by a first recombinase. In one embodiment, the inverted heterologous gene encoding the bacterial toxin is located between a first forward recombinase recognition sequence and a first reverse recombinase recognition sequence. In one embodiment, the heterologous gene encoding the bacterial toxin is constitutively expressed after it is flipped by the first recombinase. In one embodiment, the anti-toxin inhibits the activity of the toxin, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In another embodiment, the at least one recombination event is flipping of an inverted heterologous gene encoding a second recombinase by a first recombinase, followed by the flipping of an inverted heterologous gene encoding a bacterial toxin by the second recombinase. In one embodiment, the inverted heterologous gene encoding the second recombinase is located between a first forward recombinase recognition sequence and a first reverse recombinase recognition sequence. In one embodiment, the inverted heterologous gene encoding the bacterial toxin is located between a second forward recombinase recognition sequence and a second reverse recombinase recognition sequence. In one embodiment, the heterologous gene encoding the second recombinase is constitutively expressed after it is flipped by the first recombinase. In one embodiment, the heterologous gene encoding the bacterial toxin is constitutively expressed after it is flipped by the second recombinase. In one embodiment, the genetically engineered bacterium is killed by the bacterial toxin. In one embodiment, the genetically engineered bacterium further expresses a heterologous gene encoding an anti-toxin in response to the exogenous environmental condition. In one embodiment, the anti-toxin inhibits the activity of the toxin when the exogenous environmental condition is present, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In one embodiment, the at least one recombination event is flipping of an inverted heterologous gene encoding a second recombinase by a first recombinase, followed by flipping of an inverted heterologous gene encoding a third recombinase by the second recombinase, followed by flipping of an inverted heterologous gene encoding a bacterial toxin by the third recombinase. Accordingly, in one embodiment, the disclosure provides at least 1, 2, 3, 4, 5, 6, 7, 8, 9, 10, 11, 12, 13, 14, 15, 16, 17, 18, 19, or 20 recombinases that can be used serially.

In one embodiment, the at least one recombination event is flipping of an inverted heterologous gene encoding a first excision enzyme by a first recombinase. In one embodiment, the inverted heterologous gene encoding the first excision enzyme is located between a first forward recombinase recognition sequence and a first reverse recombinase recognition sequence. In one embodiment, the heterologous gene encoding the first excision enzyme is constitutively expressed after it is flipped by the first recombinase. In one embodiment, the first excision enzyme excises a first essential gene. In one embodiment, the programmed recombinant bacterial cell is not viable after the first essential gene is excised.

In one embodiment, the first recombinase further flips an inverted heterologous gene encoding a second excision enzyme. In one embodiment, the wherein the inverted heterologous gene encoding the second excision enzyme is located between a second forward recombinase recognition sequence and a second reverse recombinase recognition sequence. In one embodiment, the heterologous gene encoding the second excision enzyme is constitutively expressed after it is flipped by the first recombinase. In one embodiment, the genetically engineered bacterium dies or is no longer viable when the first essential gene and the second essential gene are both excised. In one embodiment, the genetically engineered bacterium dies or is no longer viable when either the first essential gene is excised or the second essential gene is excised by the first recombinase.

In one embodiment, the first excision enzyme is Xis1. In one embodiment, the first excision enzyme is Xis2. In one embodiment, the first excision enzyme is Xis1, and the second excision enzyme is Xis 2.

In one embodiment, the genetically engineered bacterium dies after the at least one recombination event occurs. In another embodiment, the genetically engineered bacterium is no longer viable after the at least one recombination event occurs.

In any of these embodiment, the recombinase can be a recombinase selected from the group consisting of: BxbI, PhiC31, TP901, BxbI, PhiC31, TP901, HK022, HP1, R4, Int1, Int2, Int3, Int4, Int5, Int6, Int7, Int8, Int9, Int10, Int11, Int12, Int13, Int14, Int15, Int16, Int17, Int18, Int19, Int20, Int21, Int22, Int23, Int24, Int25, Int26, Int27, Int28, Int29, Int30, Int31, Int32, Int33, and Int34, or a biologically active fragment thereof.

In the above-described kill-switch circuits, a toxin is produced in the presence of an environmental factor or signal. In another aspect of kill-switch circuitry, a toxin may be repressed in the presence of an environmental factor (not produced) and then produced once the environmental condition or external signal is no longer present. Such kill switches are called repression-based kill switches and represent systems in which the bacterial cells are viable only in the presence of an external factor or signal, such as arabinose or other sugar. Exemplary kill switch designs in which the toxin is repressed in the presence of an external factor or signal (and activated once the external signal is removed) are shown in the figures. The disclosure provides recombinant bacterial cells which express one or more heterologous gene(s) upon sensing arabinose or other sugar in the exogenous environment. In this aspect, the recombinant bacterial cells contain the araC gene, which encodes the AraC transcription factor, as well as one or more genes under the control of the araBAD promoter. In the absence of arabinose, the AraC transcription factor adopts a conformation that represses transcription of genes under the control of the araBAD promoter. In the presence of arabinose, the AraC transcription factor undergoes a conformational change that allows it to bind to and activate the araBAD promoter, which induces expression of the desired gene, for example tetR, which represses expression of a toxin gene. In this embodiment, the toxin gene is repressed in the presence of arabinose or other sugar. In an environment where arabinose is not present, the tetR gene is not activated and the toxin is expressed, thereby killing the bacteria. The arabinose system can also be used to express an essential gene, in which the essential gene is only expressed in the presence of arabinose or other sugar and is not expressed when arabinose or other sugar is absent from the environment.

Thus, in some embodiments in which one or more heterologous gene(s) are expressed upon sensing arabinose in the exogenous environment, the one or more heterologous genes are directly or indirectly under the control of the araBAD promoter. In some embodiments, the expressed heterologous gene is selected from one or more of the following: a heterologous therapeutic gene, a heterologous gene encoding an antitoxin, a heterologous gene encoding a repressor protein or polypeptide, for example, a TetR repressor, a heterologous gene encoding an essential protein not found in the bacterial cell, and/or a heterologous encoding a regulatory protein or polypeptide.

Arabinose inducible promoters are known in the art, including $P_{ara}$, $P_{araB}$, $P_{araC}$, and $P_{araBAD}$. In one embodiment, the arabinose inducible promoter is from E. coli. In some embodiments, the $P_{araC}$ promoter and the $P_{araBAD}$ promoter operate as a bidirectional promoter, with the $P_{araBAD}$ promoter controlling expression of a heterologous gene(s) in one direction, and the $P_{araC}$ (in close proximity to, and on the opposite strand from the $P_{araBAD}$ promoter), controlling expression of a heterologous gene(s) in the other direction. In the presence of arabinose, transcription of both heterologous genes from both promoters is induced. However, in the absence of arabinose, transcription of both heterologous genes from both promoters is not induced.

In one exemplary embodiment of the disclosure, the engineered bacteria of the present disclosure contains a kill-switch having at least the following sequences: a $P_{araBAD}$ promoter operably linked to a heterologous gene encoding a Tetracycline Repressor Protein (TetR), a $P_{araC}$ promoter operably linked to a heterologous gene encoding AraC transcription factor, and a heterologous gene encoding a bacterial toxin operably linked to a promoter which is repressed by the Tetracycline Repressor Protein ($P_{TetR}$). In the presence of arabinose, the AraC transcription factor activates the $P_{araBAD}$ promoter, which activates transcription of the TetR protein which, in turn, represses transcription of the toxin. In the absence of arabinose, however, AraC suppresses transcription from the $P_{araBAD}$ promoter and no TetR protein is expressed. In this case, expression of the heterologous toxin gene is activated, and the toxin is expressed. The toxin builds up in the recombinant bacterial cell, and the recombinant bacterial cell is killed. In one embodiment, the araC gene encoding the AraC transcription factor is under the control of a constitutive promoter and is therefore constitutively expressed.

In one embodiment of the disclosure, the recombinant bacterial cell further comprises an antitoxin under the control of a constitutive promoter. In this situation, in the presence of arabinose, the toxin is not expressed due to repression by TetR protein, and the antitoxin protein builds-up in the cell. However, in the absence of arabinose, TetR protein is not expressed, and expression of the toxin is induced. The toxin begins to build-up within the recombinant bacterial cell. The recombinant bacterial cell is no longer viable once the toxin protein is present at either equal or greater amounts than that of the anti-toxin protein in the cell, and the recombinant bacterial cell will be killed by the toxin.

In another embodiment of the disclosure, the recombinant bacterial cell further comprises an antitoxin under the control of the $P_{araBAD}$ promoter. In this situation, in the presence of arabinose, TetR and the anti-toxin are expressed, the anti-toxin builds up in the cell, and the toxin is not expressed due to repression by TetR protein. However, in the absence of arabinose, both the TetR protein and the anti-toxin are not expressed, and expression of the toxin is induced. The toxin begins to build-up within the recombinant bacterial cell. The recombinant bacterial cell is no longer viable once the toxin protein is expressed, and the recombinant bacterial cell will be killed by the toxin.

In another exemplary embodiment of the disclosure, the engineered bacteria of the present disclosure contain a kill-switch having at least the following sequences: A $P_{araBAD}$ promoter operably linked to a heterologous gene encoding an essential polypeptide not found in the recombinant bacterial cell (and required for survival), and a $P_{araC}$ promoter operably linked to a heterologous gene encoding AraC transcription factor. In the presence of arabinose, the AraC transcription factor activates the $P_{araBAD}$ promoter, which activates transcription of the heterologous gene encoding the essential polypeptide, allowing the recombinant bacterial cell to survive. In the absence of arabinose, however, AraC suppresses transcription from the $P_{araBAD}$ promoter and the essential protein required for survival is not expressed. In this case, the recombinant bacterial cell dies in the absence of arabinose. In some embodiments, the sequence of $P_{araBAD}$ promoter operably linked to a heterologous gene encoding an essential polypeptide not found in the recombinant bacterial cell can be present in the bacterial cell in conjunction with the TetR/toxin kill-switch system described directly above. In some embodiments, the sequence of $P_{araBAD}$ promoter operably linked to a heterologous gene encoding an essential polypeptide not found in the recombinant bacterial cell can be present in the bacterial cell in conjunction with the TetR/toxin/anti-toxin kill-switch system described directly above.

In yet other embodiments, the bacteria may comprise a plasmid stability system with a plasmid that produces both a short-lived anti-toxin and a long-lived toxin. In this system, the bacterial cell produces equal amounts of toxin and anti-toxin to neutralize the toxin. However, if/when the cell loses the plasmid, the short-lived anti-toxin begins to decay. When the anti-toxin decays completely the cell dies as a result of the longer-lived toxin killing it.

In some embodiments, the engineered bacteria of the present disclosure, for example, bacteria expressing an oxalate catabolism enzyme further comprise the gene(s) encoding the components of any of the above-described kill-switch circuits.

In any of the above-described embodiments, the bacterial toxin is selected from the group consisting of a lysin, Hok, Fst, TisB, LdrD, Kid, SymE, MazF, FlmA, Ibs, XCV2162, dinJ, CcdB, MazF, ParE, YafO, Zeta, hicB, relB, yhaV, yoeB, chpBK, hipA, microcin B, microcin B17, microcin C, microcin C7-C51, microcin J25, microcin ColV, microcin 24, microcin L, microcin D93, microcin L, microcin E492, microcin H47, microcin 147, microcin M, colicin A, colicin E1, colicin K, colicin N, colicin U, colicin B, colicin Ia, colicin Ib, colicin 5, colicin10, colicin S4, colicin Y, colicin E2, colicin E7, colicin E8, colicin E9, colicin E3, colicin E4, colicin E6; colicin E5, colicin D, colicin M, and cloacin DF13, or a biologically active fragment thereof.

In any of the above-described embodiments, the anti-toxin is selected from the group consisting of an anti-lysin, Sok, RNAII, IstR, RdlD, Kis, SymR, MazE, FlmB, Sib, ptaRNA1, yafQ, CcdA, MazE, ParD, yafN, Epsilon, HicA, relE, prlF, yefM, chpBI, hipB, MccE, MccE$^{CTD}$, MccF, Cai, ImmE1, Cki, Cni, Cui, Cbi, Iia, Imm, Cfi, Im10, Csi, Cyi, Im2, Im7, Im8, Im9, Im3, Im4, ImmE6, cloacin immunity protein (Cim), ImmE5, ImmD, and Cmi, or a biologically active fragment thereof.

In one embodiment, the bacterial toxin is bactericidal to the genetically engineered bacterium. In one embodiment, the bacterial toxin is bacteriostatic to the genetically engineered bacterium.

In one embodiment, the method further comprises administering a second recombinant bacterial cell to the subject, wherein the second recombinant bacterial cell comprises a heterologous reporter gene operably linked to an inducible promoter that is directly or indirectly induced by an exogenous environmental condition. In one embodiment, the heterologous reporter gene is a fluorescence gene. In one embodiment, the fluorescence gene encodes a green fluorescence protein (GFP). In another embodiment, the method further comprises administering a second recombinant bacterial cell to the subject, wherein the second recombinant bacterial cell expresses a lacZ reporter construct that cleaves a substrate to produce a small molecule that can be detected in urine (see, for example, Danio et al., Science Translational Medicine, 7(289):1-12, 2015, the entire contents of which are expressly incorporated herein by reference).

Isolated Plasmids

In other embodiments, the disclosure provides an isolated plasmid comprising a first nucleic acid encoding a first payload operably linked to a first inducible promoter, and a second nucleic acid encoding a second payload operably linked to a second inducible promoter. In other embodiments, the disclosure provides an isolated plasmid further comprising a third nucleic acid encoding a third payload operably linked to a third inducible promoter. In other embodiments, the disclosure provides a plasmid comprising four, five, six, or more nucleic acids encoding four, five, six, or more payloads operably linked to inducible promoters. In any of the embodiments described here, the first, second, third, fourth, fifth, sixth, etc. "payload(s)" can be an oxalate catabolism enzyme, a transporter of oxalate, or other sequence described herein. In one embodiment, the nucleic acid encoding the first payload and the nucleic acid encoding the second payload are operably linked to the first inducible promoter. In one embodiment, the nucleic acid encoding the first payload is operably linked to a first inducible promoter and the nucleic acid encoding the second payload is operably linked to a second inducible promoter. In one embodiment, the first inducible promoter and the second inducible promoter are separate copies of the same inducible promoter. In another embodiment, the first inducible promoter and the second inducible promoter are different inducible promoters. In other embodiments comprising a third nucleic acid, the nucleic acid encoding the third payload and the nucleic acid encoding the first and second payloads are all operably linked to the same inducible promoter. In other embodiments, the nucleic acid encoding the first payload is operably linked to a first inducible promoter, the nucleic acid encoding the second payload is operably linked to a second inducible promoter, and the nucleic acid encoding the third payload is operably linked to a third inducible promoter. In some embodiments, the first, second, and third inducible promoters are separate copies of the same inducible promoter. In other embodiments, the first inducible promoter, the second inducible promoter, and the third inducible promoter are different inducible promoters. In some embodiments, the first promoter, the second promoter, and the optional third promoter, or the first promoter and the second promoter and the optional third promoter, are each directly or indirectly induced by low-oxygen or anaerobic conditions. In other embodiments, the first promoter, the second promoter, and the optional third promoter, or the first promoter and the second promoter and the optional third promoter, are each a fumarate and nitrate reduction regulator (FNR) responsive promoter. In other embodiments, the first promoter, the second promoter, and the optional third promoter, or the first promoter and the second promoter and the optional third promoter are each a ROS-inducible regulatory region. In other embodiments, the first promoter, the second promoter, and the optional third promoter, or the first promoter and the second promoter and the optional third promoter are each a RNS-inducible regulatory region.

In some embodiments, the heterologous gene and/or gene cassette encoding one or more oxalate catabolism enzyme(s) is operably linked to a constitutive promoter. In one embodiment, the constitutive promoter is a lac promoter. In another embodiment, the constitutive promoter is a Tet promoter. In another embodiment, the constitutive promoter is a constitutive *Escherichia coli* σ$^{32}$ promoter. In another embodiment, the constitutive promoter is a constitutive *Escherichia coli* σ$^{70}$ promoter. In another embodiment, the constitutive promoter is a constitutive *Bacillus subtilis* σ$^A$ promoter. In another embodiment, the constitutive promoter is a constitutive *Bacillus subtilis* σ$^B$ promoter. In another embodiment, the constitutive promoter is a *Salmonella* promoter. In other embodiments, the constitutive promoter is a bacteriophage T7 promoter. In other embodiments, the constitutive promoter is and a bacteriophage SP6 promoter. In any of the above-described embodiments, the plasmid further comprises a heterologous gene encoding a transporter oxalate, and/or a kill switch construct, which may be operably linked to a constitutive promoter or an inducible promoter.

In some embodiments, the isolated plasmid comprises at least one heterologous oxalate catabolism enzyme gene operably linked to a first inducible promoter; a heterologous gene encoding a TetR protein operably linked to a $P_{araBAD}$ promoter, a heterologous gene encoding AraC operably linked to a $P_{araC}$ promoter, a heterologous gene encoding an antitoxin operably linked to a constitutive promoter, and a heterologous gene encoding a toxin operably linked to a $P_{TetR}$ promoter. In another embodiment, the isolated plasmid comprises at least one heterologous gene and/or gene cassette encoding one or more oxalate catabolism enzyme(s) operably linked to a first inducible promoter; a heterologous gene encoding a TetR protein and an anti-toxin operably linked to a $P_{araBAD}$ promoter, a heterologous gene encoding AraC operably linked to a $P_{araC}$ promoter, and a heterologous gene encoding a toxin operably linked to a $P_{TetR}$ promoter.

In some embodiments, a first nucleic acid encoding one or more oxalate catabolism enzyme(s) comprises a Formyl CoA:oxalate CoA transferase (e.g., frc) gene. In one embodiment, the frc gene is from O. formigenes. In one embodiment, the frc gene has at least about 90% identity to SEQ ID NO: 1. In another embodiment, the frc gene comprises SEQ ID NO: 1. In other embodiments, a first nucleic acid encoding one or more oxalate catabolism enzyme(s) comprises an Oxalate-CoA ligase (e.g., ScAAE3) gene. In one embodiment, the ScAAE3 gene is from S. cerevisiae. In one embodiment, the ScAAE3 gene has at least about 90% identity to SEQ ID NO: 3. In another embodiment, the ScAAE3 gene comprises SEQ ID NO: 3. In other embodiments, a first nucleic acid encoding one or more oxalate catabolism enzyme(s) comprises an acetyl-CoA:oxalate CoA-transferase (e.g., YfdE) gene. In one embodiment, the YfdE gene is from E. coli. In one embodiment, the YfdE gene has at least about 90% identity to SEQ ID NO: 4. In another embodiment, the YfdE gene comprises SEQ ID NO: 4.

In some embodiments, a first nucleic acid encoding one or more oxalate catabolism enzyme(s) comprises a Oxalyl-CoA Decarboxylase (e.g., oxc) gene. In some embodiments, the frc and/or ScAAE3 and/or YfdE gene(s) are co-expressed with a Oxalyl-CoA Decarboxylase (e.g., oxc) gene. In one embodiment, the oxc gene is from O. formigenes. In one embodiment, the oxc gene has at least about 90% identity to SEQ ID NO: 2. In another embodiment, the oxc gene comprises SEQ ID NO: 2.

In some embodiments, a second nucleic acid encoding a transporter of oxalate comprises OxlT. In one embodiment, the OxlT transporter is from O. formigenes. In another embodiment, the OxlT transporter has at least about 90% identity to SEQ ID NO: 11. In another embodiment, the OxlT transporter comprises SEQ ID NO: 11.

In one embodiment, the plasmid is a high-copy plasmid. In another embodiment, the plasmid is a low-copy plasmid.

In another aspect, the disclosure provides a recombinant bacterial cell comprising an isolated plasmid described herein. In another embodiment, the disclosure provides a pharmaceutical composition comprising the recombinant bacterial cell.

In one embodiment, the bacterial cell further comprises a genetic mutation in an endogenous gene encoding an exporter of oxalate, wherein the genetic mutation reduces export of oxalate from the bacterial cell.

In one embodiment, the bacterial cell further comprises a genetic mutation in an endogenous gene encoding an oxalate biosynthesis gene, wherein the genetic mutation reduces biosynthesis of oxalate in the bacterial cell.

Combinations

In some embodiments, the bacteria are genetically engineered to include multiple mechanisms of action (MOAs), e.g., circuits producing multiple copies of the same product (e.g., to enhance copy number) or circuits performing multiple different functions. Examples of insertion sites include, but are not limited to, malE/K, insB/I, araC/BAD, lacZ, dapA, cea, and other shown in FIG. 8. For example, the genetically engineered bacteria may include four copies of an oxalate catabolism gene or oxalate catabolism gene cassette, or four copies of an oxalate catabolism gene inserted at four different insertion sites, e.g., malE/K, insB/I, araC/BAD, and lacZ. Alternatively, the genetically engineered bacteria may include one or more copies of an oxalate catabolism gene or gene cassette inserted at one or more different insertion sites, e.g., malE/K, insB/I, and lacZ, one or more copies of an oxalate catabolism gene or gene cassette inserted at one or more different insertion sites, e.g., dapA, cea, and araC/BAD and/or one or more copies of an oxalate catabolism gene or gene cassette inserted at one or more different insertion sites.

In some embodiments, the genetically engineered bacteria comprise one or more of: (1) one or more gene(s) and/or gene cassettes encoding one or more oxalate catabolism enzyme(s) described herein, in wild type or in a mutated form (for increased stability or metabolic activity); (2) one or more gene(s) and/or gene cassette(s) encoding one or more transporter(s) for uptake of oxalate, in wild type or in mutated form (for increased stability or metabolic activity), which in some embodiments are coupled to formate export; (3) one or more gene(s) and/or gene cassette(s) encoding one or more exporters(s) for export of formate, in wild type or in mutated form (for increased stability or metabolic activity), which in some embodiments are be coupled to oxalate import; (4) one or more gene(s) and/or gene cassette(s) encoding one or more oxalate:formate antiporters, in wild type or in mutated form (for increased stability or metabolic activity), which in some embodiments are be coupled to oxalate import; (5) one or more gene(s) or gene cassette(s) encoding one or more oxalate catabolism enzyme(s) described herein for secretion and extracellular degradation of oxalate (6) one or more gene(s) or gene cassette(s) encoding one or more components of secretion machinery, as described herein (7) one or more auxotrophies, e.g., deltaThyA; (8) one or more gene(s) or gene cassette(s) encoding one or more antibiotic resistance(s), including but not limited to, kanamycin or chloramphenicol resistance; (9) one or more modifications that increase oxalate import into the bacterial cell (10) one or more modifications that increase formate export from the bacterial cell (11) one or modifications that reduce formate import into the bacterial cell; (12) one or modifications that reduce oxalate export from the bacterial cell; (13) mutations/deletions in genes of the endogenous oxalate synthesis pathway; (14) mutations and/or deletions in formate exporters, which result in increased flux through a oxalate:formate antiporter and increased oxalate import.

In some embodiments, the genetically engineered bacteria comprise two or more different pathway cassettes or operons comprising oxalate catabolism enzymes. In some embodiments, the genetically engineered bacteria comprise one or more oxalate catabolism gene(s) or gene cassette(s) encoding one or more oxalate catabolism enzymes. In some embodiments, the genetically engineered bacteria comprise gene sequence(s) encoding one or more oxalate catabolism enzymes selected formyl-CoA:oxalate CoA-transferase, including but not limited to frc from O. formigenes, oxalyl-CoA synthetase, including but not limited to ScAAE3 from S. cerevisiae, oxalyl-CoA decarboxylase, including but not limited to oxc from *O. formigenes*, and/or acetyl-CoA: oxalate CoA-transferase, including but not limited to YfdE from *E. coli*.

In some embodiments, the genetically engineered bacteria comprise one or more oxalate catabolism gene(s) or gene cassette(s) encoding formyl-CoA:oxalate CoA-transferase, including but not limited to frc from *O. formigenes*. In some embodiments, the genetically engineered bacteria comprise one or more oxalate catabolism gene(s) or gene cassette(s) encoding oxalyl-CoA synthetase, including but not limited to ScAAE3 from *S. cerevisiae*. In some embodiments, the genetically engineered bacteria comprise one or more oxalate catabolism gene(s) or gene cassette(s) encoding oxalyl-CoA decarboxylase, including but not limited to oxc from *O. formigenes*. In some embodiments, the genetically engineered bacteria comprise one or more oxalate catabolism gene(s) or gene cassette(s) encoding acetyl-CoA:oxalate CoA-transferase, including but not limited to YfdE from *E. coli*. In some embodiments, the genetically engineered bacteria comprise one or more oxalate catabolism gene(s) or gene cassette(s) encoding formyl-CoA:oxalate CoA-transferase, including but not limited to frc from *O. formigenes*, and oxalyl-CoA synthetase, including but not limited to ScAAE3 from *S. cerevisiae*. In some embodiments, the genetically engineered bacteria comprise one or more oxalate catabolism gene(s) or gene cassette(s) encoding formyl-CoA:oxalate CoA-transferase, including but not limited to frc from *O. formigenes*, and oxalyl-CoA decarboxylase, including but not limited to oxc from *O. formigenes*. In some embodiments, the genetically engineered bacteria comprise one or more oxalate catabolism gene(s) or gene cassette(s) encoding formyl-CoA:oxalate CoA-transferase, including but not limited to frc from *O. formigenes*, and acetyl-CoA:oxalate CoA-transferase, including but not limited to YfdE from *E. coli*. In some embodiments, the genetically engineered bacteria comprise one or more oxalate catabolism gene(s) or gene cassette(s) encoding oxalyl-CoA synthetase, including but not limited to ScAAE3 from *S. cerevisiae*, and oxalyl-CoA decarboxylase, including but not limited to oxc from *O. formigenes*. In some embodiments, the genetically engineered bacteria comprise one or more oxalate catabolism gene(s) or gene cassette(s) encoding oxalyl-CoA synthetase, including but not limited to ScAAE3 from *S. cerevisiae*, and acetyl-CoA:oxalate CoA-transferase, including but not limited to YfdE from *E. coli*. In some embodiments, the genetically engineered bacteria comprise one or more oxalate catabolism gene(s) or gene cassette(s) encoding oxalyl-CoA decarboxylase, including but not limited to oxc from *O. formigenes*, and acetyl-CoA:oxalate CoA-transferase, including but not limited to YfdE from *E. coli*. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, and oxalyl-CoA decarboxylase, including but not limited to oxc from *O. formigenes*. In some embodiments, the genetically engineered bacteria comprise one or more oxalate catabolism gene(s) or gene cassette(s) encoding formyl-CoA: oxalate CoA-transferase, including but not limited to frc from *O. formigenes*, oxalyl-CoA synthetase, including but not limited to ScAAE3 from *S. cerevisiae*, and acetyl-CoA: oxalate CoA-transferase, including but not limited to YfdE from *E. coli*. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA decarboxylase, including but not limited to oxc from *O. formigenes*, and acetyl-CoA:oxalate CoA-transferase, including but not limited to YfdE from *E. coli*. In some embodiments, the genetically engineered bacteria comprise one or more oxalate catabolism gene(s) or gene cassette(s) encoding oxalyl-CoA synthetase, including but not limited to ScAAE3 from *S. cerevisiae*, oxalyl-CoA decarboxylase, including but not limited to oxc from *O. formigenes*, and acetyl-CoA:oxalate CoA-transferase, including but not limited to YfdE from *E. coli*. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, oxalyl-CoA decarboxylase, including but not limited to oxc from *O. formigenes*, and acetyl-CoA:oxalate CoA-transferase, including but not limited to YfdE from *E. coli*.

In some embodiments, the genetically engineered bacteria further comprise one or more oxalate transporters and/or antiporters, including but not limited to OxlT from *O. formigenenes*. In some embodiments, the genetically engineered bacteria comprise one or more oxalate catabolism gene(s) or gene cassette(s) encoding an oxalate transporter, e.g, the oxalate:formate antiporter OxlT from *O. formigenes*. In some embodiments, the genetically engineered bacteria comprise one or more oxalate catabolism gene(s) or gene cassette(s) encoding formyl-CoA:oxalate CoA-transferase, including but not limited to frc from *O. formigenes*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding oxalyl-CoA synthetase, including but not limited to ScAAE3 from *S. cerevisiae*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding oxalyl-CoA decarboxylase, including but not limited to oxc from *O. formigenes*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding acetyl-CoA:oxalate CoA-transferase, including but not limited to YfdE from *E. coli*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding formyl-CoA: oxalate CoA-transferase, including but not limited to frc from *O. formigenes*, oxalyl-CoA synthetase, including but not limited to ScAAE3 from *S. cerevisiae*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA decarboxylase, including but not limited to oxc from *O. formigenes*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding formyl-CoA:oxalate CoA-transferase, including but not limited to frc from *O. formigenes*, acetyl-CoA:oxalate CoA-transferase, including but not limited to YfdE from *E. coli*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding oxalyl-CoA synthetase, including but not limited to ScAAE3 from *S. cerevisiae*, oxalyl-CoA decarboxylase, including but not limited to oxc from *O. formigenes*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding oxalyl-CoA synthetase, including but not limited to ScAAE3 from *S. cerevisiae*, acetyl-CoA:oxalate CoA-transferase, including but not limited to YfdE from *E. coli*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding oxalyl-CoA decarboxylase, including but not limited to oxc from *O. formigenes*, acetyl-CoA:oxalate CoA-transferase, including but not limited to YfdE from *E. coli*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, oxalyl-CoA decarboxylase, including but not limited to oxc from *O. formigenes*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, acetyl-CoA:oxalate CoA-transferase, including but not limited to YfdE from *E. coli*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA decarboxylase, including but not limited to oxc from *O. formigenes*, acetyl-CoA:oxalate CoA-transferase, including but not limited to YfdE from *E. coli*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding oxalyl-CoA synthetase, including but not limited to ScAAE3 from *S. cerevisiae*, oxalyl-CoA decarboxylase, including but not limited to oxc from *O. formigenes*, acetyl-CoA:oxalate CoA-transferase, including but not limited to YfdE from *E. coli*, and an oxalate transporter, e.g., the oxalate:formate antiporter OxlT from *O. formigenes*. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, oxalyl-CoA decarboxylase, including but not limited to oxc from *O. formigenes*, acetyl-CoA:oxalate CoA-transferase, including but not limited to YfdE from *E. coli*, and an oxalate transporter, e.g., the oxalate:formate antiporter OxlT from *O. formigenes*.

In some embodiments, the genetically engineered bacteria, which comprise one or more oxalate catabolism gene(s) or gene cassette(s) and one or more oxalate transporter(s), encode a formate exporter, e.g., as described herein. In some embodiments, the genetically engineered bacteria comprise one or more oxalate catabolism gene(s) or gene cassette(s) and one or more oxalate transporter(s), which also function(s) as an formate exporter, e.g., OxlT, described herein. In some embodiments, formate export and oxalate import are separate. In some embodiments, the genetically engineered bacteria which comprise one or more oxalate catabolism gene(s) or gene cassette(s), comprise a formate exporter. In some embodiments, the genetically engineered bacteria comprise one or more oxalate catabolism gene(s) or gene cassette(s) encoding formyl-CoA:oxalate CoA-transferase, including but not limited to frc from *O. formigenes*, and a formate exporter, e.g., described herein. In some embodiments, the genetically engineered bacteria comprise one or more oxalate catabolism gene(s) or gene cassette(s) encoding oxalyl-CoA synthetase, including but not limited to ScAAE3 from *S. cerevisiae*, and a formate exporter, e.g., described herein. In some embodiments, the genetically engineered bacteria comprise one or more oxalate catabolism gene(s) or gene cassette(s) encoding oxalyl-CoA decarboxylase, including but not limited to oxc from *O. formigenes*, and a formate exporter, e.g., described herein. In some embodiments, the genetically engineered bacteria comprise one or more oxalate catabolism gene(s) or gene cassette(s) encoding acetyl-CoA:oxalate CoA-transferase, including but not limited to YfdE from *E. coli*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA decarboxylase, including but not limited to oxc from *O. formigenes*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, acetyl-CoA:oxalate CoA-transferase, including but not limited to YfdE from *E. coli*, and a formate exporter, e.g., described herein. In some embodiments, the genetically engineered bacteria comprise one or more oxalate catabolism gene(s) or gene cassette(s) encoding oxalyl-CoA synthetase, including but not limited to ScAAE3 from *S. cerevisiae*, oxalyl-CoA decarboxylase, including but not limited to oxc from *O. formigenes*, and a formate exporter, e.g., described herein. In some embodiments, the genetically engineered bacteria comprise one or more oxalate catabolism gene(s) or gene cassette(s) encoding oxalyl-CoA synthetase, including but not limited to ScAAE3 from *S. cerevisiae*, acetyl-CoA:oxalate CoA-transferase, including but not limited to YfdE from *E. coli*, and a formate exporter, e.g., described herein. In some embodiments, the genetically engineered bacteria comprise one or more oxalate catabolism gene(s) or gene cassette(s) encoding oxalyl-CoA decarboxylase, including but not limited to oxc from *O. formigenes*, acetyl-CoA:oxalate CoA-transferase, including but not limited to YfdE from *E. coli*, and a formate exporter, e.g., described herein.

In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, oxalyl-CoA decarboxylase, including but not limited to oxc from *O. formigenes*, and a formate exporter, e.g., described herein. In some embodiments, the genetically engineered bacteria comprise one or more oxalate catabolism gene(s) or gene cassette(s) encoding formyl-CoA: oxalate CoA-transferase, including but not limited to frc from *O. formigenes*, oxalyl-CoA synthetase, including but not limited to ScAAE3 from *S. cerevisiae*, acetyl-CoA: oxalate CoA-transferase, including but not limited to YfdE from *E. coli*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA decarboxylase, including but not limited to oxc from *O. formigenes*, acetyl-CoA:oxalate CoA-transferase, including but not limited to YfdE from *E. coli*, and a formate exporter, e.g., described herein. In some embodiments, the genetically engineered bacteria comprise one or more oxalate catabolism gene(s) or gene cassette(s) encoding oxalyl-CoA synthetase, including but not limited to ScAAE3 from *S. cerevisiae*, oxalyl-CoA decarboxylase, including but not limited to oxc from *O. formigenes*, acetyl-CoA:oxalate CoA-transferase, including but not limited to YfdE from *E. coli*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, oxalyl-CoA decarboxylase, including but not limited to oxc from *O. formigenes*, acetyl-CoA:oxalate CoA-transferase, including but not limited to YfdE from *E. coli*, and a formate exporter, e.g., described herein. In some embodiments, the genetically engineered bacteria comprise one or more oxalate catabolism gene(s) or gene cassette(s) encoding. In some embodiments, the genetically engineered bacteria comprise one or more oxalate catabolism gene(s) or gene cassette(s) encoding an oxalate transporter, e.g., the oxalate:formate antiporter OxlT from *O. formigenes*, a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, an oxalate transporter, e.g., the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding oxalyl-CoA synthetase, including but not limited to ScAAE3 from *S. cerevisiae*, an oxalate transporter, e.g, the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding oxalyl-CoA decarboxylase, including but not limited to oxc from *O. formigenes*, an oxalate transporter, e.g., the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding acetyl-CoA:oxalate CoA-transferase, including but not limited to YfdE from *E. coli*, an oxalate transporter, e.g., the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, an oxalate transporter, e.g., the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA decarboxylase, including but not limited to oxc from *O. formigenes*, an oxalate transporter, e.g., the oxalate: formate antiporter OxlT from *O. formigenes*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, acetyl-CoA:oxalate CoA-transferase, including but not limited to YfdE from *E. coli*, an oxalate transporter, e.g., the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding oxalyl-CoA synthetase, including but not limited to ScAAE3 from *S. cerevisiae*, oxalyl-CoA decarboxylase, including but not limited to oxc from *O. formigenes*, an oxalate transporter, e.g., the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding oxalyl-CoA synthetase, including but not limited to ScAAE3 from *S. cerevisiae*, acetyl-CoA: oxalate CoA-transferase, including but not limited to YfdE from *E. coli*, an oxalate transporter, e.g., the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding oxalyl-CoA decarboxylase, including but not limited to oxc from *O. formigenes*, acetyl-CoA:oxalate CoA-transferase, including but not limited to YfdE from *E. coli*, an oxalate transporter, e.g., the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, oxalyl-CoA decarboxylase, including but not limited to oxc from *O. formigenes*, an oxalate transporter, e.g., the oxalate: formate antiporter OxlT from *O. formigenes*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, acetyl-CoA:oxalate CoA-transferase, including but not limited to YfdE from *E. coli*, an oxalate transporter, e.g, the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA decarboxylase, including but not limited to oxc from *O. formigenes*, acetyl-CoA:oxalate CoA-transferase, including but not limited to YfdE from *E. coli*, an oxalate transporter, e.g., the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding oxalyl-CoA synthetase, including but not limited to ScAAE3 from *S. cerevisiae*, oxalyl-CoA decarboxylase, including but not limited to oxc from *O. formigenes*, acetyl-CoA:oxalate CoA-transferase, including but not limited to YfdE from *E. coli*, an oxalate transporter, e.g., the oxalate:formate antiporter OxlT from *O. formigenes*, and a formate exporter, e.g., described herein. In some embodiments, the genetically engineered bacteria comprise one or more oxalate catabolism gene(s) or gene cassette(s) encoding formyl-CoA:oxalate CoA-transferase, including but not limited to frc from *O. formigenes*, oxalyl-CoA synthetase, including but not limited to ScAAE3 from *S. cerevisiae*, oxalyl-CoA decarboxylase, including but not limited to oxc from *O. formigenes*, acetyl-CoA:oxalate CoA-transferase, including but not limited to YfdE from *E. coli*, an oxalate transporter, e.g., the oxalate:formate antiporter OxlT from *O. formigenes*, and a formate exporter, e.g., described herein.

In some embodiments, the genetically engineered bacteria further comprise one or more of auxotrophies, e.g., deltaThyA; one or more gene(s) or gene cassette(s) encoding one or more antibiotic resistance(s), including but not limited to, kanamycin or chloramphenicol resistance; one or more modifications that increase formate export from the bacterial cell; one or modifications that reduce formate import into the bacterial cell; mutations/deletions in genes, as described herein, e.g., oxalate exporters; mutations/deletions in genes of the endogenous oxalate synthesis pathway. In some embodiments, the genetically engineered bacteria comprise two or more different pathway cassettes or operons comprising oxalate catabolism enzymes. In one embodiment, the gene sequence(s) encoding the one or more oxalate catabolism enzyme(s) is directly operably linked to a first promoter. In another embodiment, the gene sequence(s) encoding the one or more oxalate catabolism enzyme(s) is indirectly operably linked to a first promoter. In one embodiment, the promoter is not operably linked with the at least one gene encoding the oxalate catabolism enzyme in nature.

In some embodiments, the gene sequence(s) encoding the one or more oxalate catabolism enzyme(s) is expressed under the control of a constitutive promoter. In another embodiment, the gene sequence(s) encoding the one or more oxalate catabolism enzyme(s) is expressed under the control of an inducible promoter. In some embodiments, the gene sequence(s) encoding the one or more oxalate catabolism enzyme(s) is expressed under the control of a promoter that is directly or indirectly induced by exogenous environmental conditions. In one embodiment, the gene sequence(s) encoding the one or more oxalate catabolism enzyme(s) is expressed under the control of a promoter that is directly or indirectly induced by low-oxygen or anaerobic conditions, wherein expression of the gene sequence(s) encoding the one or more oxalate catabolism enzyme(s) is activated under low-oxygen or anaerobic environments, such as the environment of the mammalian gut. In some embodiments, the gene sequence(s) encoding the one or more oxalate catabolism enzyme(s) is expressed under the control of a promoter that is directly or indirectly induced by inflammatory conditions. Exemplary inducible promoters described herein include oxygen level-dependent promoters (e.g., FNR-inducible promoter), promoters induced by inflammation or an inflammatory response (RNS, ROS promoters), and promoters induced by a metabolite that may or may not be naturally present (e.g., can be exogenously added) in the gut, e.g., arabinose and tetracycline. Examples of inducible promoters include, but are not limited to, an FNR responsive promoter, a $P_{araC}$ promoter, a $P_{araBAD}$ promoter, and a $P_{TetR}$ promoter, each of which are described in more detail herein. Inducible promoters are described in more detail infra.

The at least one gene encoding the at least one oxalate catabolism enzyme may be present on a plasmid or chromosome in the bacterial cell. In one embodiment, the gene sequence(s) encoding the one or more oxalate catabolism enzyme(s) is located on a plasmid in the bacterial cell. In another embodiment, the gene sequence(s) encoding the one or more oxalate catabolism enzyme(s) is located in the chromosome of the bacterial cell. In yet another embodiment, a native copy of the gene sequence(s) encoding the one or more oxalate catabolism enzyme(s) is located in the chromosome of the bacterial cell, and at least one gene encoding at least one oxalate catabolism enzyme from a different species of bacteria is located on a plasmid in the bacterial cell. In yet another embodiment, a native copy of the gene sequence(s) encoding the one or more oxalate catabolism enzyme(s) is located on a plasmid in the bacterial cell, and at least one gene encoding the at least one oxalate catabolism enzyme from a different species of bacteria is located on a plasmid in the bacterial cell. In yet another embodiment, a native copy of the gene sequence(s) encoding the one or more oxalate catabolism enzyme(s) is located in the chromosome of the bacterial cell, and at least one gene encoding the at least one oxalate catabolism enzyme from a different species of bacteria is located in the chromosome of the bacterial cell.

In some embodiments, the gene sequence(s) encoding the one or more oxalate catabolism enzyme(s) is expressed on a low-copy plasmid. In some embodiments, the gene sequence(s) encoding the one or more oxalate catabolism enzyme(s) is expressed on a high-copy plasmid. In some embodiments, the high-copy plasmid may be useful for increasing expression of the at least one oxalate catabolism enzyme, thereby increasing the catabolism of oxalate, oxalic acid, and/or oxalyl-CoA.

In some embodiments, a recombinant bacterial cell of the invention comprising at least one gene encoding at least one oxalate catabolism enzyme expressed on a high-copy plasmid does not increase oxalate catabolism or decrease oxalate and/or oxalic acid levels as compared to a recombinant bacterial cell comprising the same gene expressed on a low-copy plasmid in the absence of a heterologous importer of oxalate and additional copies of a native importer of oxalate. Furthermore, in some embodiments that incorporate a transporter (importer) of oxalate into the recombinant bacterial cell, there may be additional advantages to using a low-copy plasmid comprising the gene sequence(s) encoding the one or more oxalate catabolism enzyme(s) in conjunction in order to enhance the stability of expression of the oxalate catabolism enzyme, while maintaining high oxalate catabolism and to reduce negative selection pressure on the transformed bacterium. In alternate embodiments, the importer of oxalate is used in conjunction with a high-copy plasmid.

In some embodiments, the genetically engineered bacteria described above further comprise one or more of the modifications, mutations, and/or deletions in endogenous genes described herein.

Host-Plasmid Mutual Dependency

In some embodiments, the genetically engineered bacteria also comprise a plasmid that has been modified to create a host-plasmid mutual dependency. In certain embodiments, the mutually dependent host-plasmid platform is GeneGuard (Wright et al., 2015). In some embodiments, the GeneGuard plasmid comprises (i) a conditional origin of replication, in which the requisite replication initiator protein is provided in trans; (ii) an auxotrophic modification that is rescued by the host via genomic translocation and is also compatible for use in rich media; and/or (iii) a nucleic acid sequence which encodes a broad-spectrum toxin. The toxin gene may be used to select against plasmid spread by making the plasmid DNA itself disadvantageous for strains not expressing the anti-toxin (e.g., a wild-type bacterium). In some embodiments, the GeneGuard plasmid is stable for at least 100 generations without antibiotic selection. In some embodiments, the GeneGuard plasmid does not disrupt growth of the host. The GeneGuard plasmid is used to greatly reduce unintentional plasmid propagation in the genetically engineered bacteria described herein.

The mutually dependent host-plasmid platform may be used alone or in combination with other biosafety mechanisms, such as those described herein (e.g., kill switches, auxotrophies). In some embodiments, the genetically engineered bacteria comprise a GeneGuard plasmid. In other embodiments, the genetically engineered bacteria comprise a GeneGuard plasmid and/or one or more kill switches. In other embodiments, the genetically engineered bacteria comprise a GeneGuard plasmid and/or one or more auxotrophies. In still other embodiments, the genetically engineered bacteria comprise a GeneGuard plasmid, one or more kill switches, and/or one or more auxotrophies.

In some embodiments, the vector comprises a conditional origin of replication. In some embodiments, the conditional origin of replication is a R6K or ColE2-P9. In embodiments where the plasmid comprises the conditional origin of replication R6K, the host cell expresses the replication initiator protein π. In embodiments where the plasmid comprises the conditional origin or replication ColE2, the host cell expresses the replication initiator protein RepA. It is understood by those of skill in the art that the expression of the replication initiator protein may be regulated so that a desired expression level of the protein is achieved in the host cell to thereby control the replication of the plasmid. For example, in some embodiments, the expression of the gene encoding the replication initiator protein may be placed under the control of a strong, moderate, or weak promoter to regulate the expression of the protein.

In some embodiments, the vector comprises a gene encoding a protein required for complementation of a host cell auxotrophy, preferably a rich-media compatible auxotrophy. In some embodiments, the host cell is auxotrophic for thymidine (ΔthyA), and the vector comprises the thymidylate synthase (thyA) gene. In some embodiments, the host cell is auxotrophic for diaminopimelic acid (ΔdapA) and the vector comprises the 4-hydroxy-tetrahydrodipicolinate synthase (dapA) gene. It is understood by those of skill in the art that the expression of the gene encoding a protein required for complementation of the host cell auxotrophy may be regulated so that a desired expression level of the protein is achieved in the host cell.

In some embodiments, the vector comprises a toxin gene. In some embodiments, the host cell comprises an anti-toxin gene encoding and/or required for the expression of an anti-toxin. In some embodiments, the toxin is Zeta and the anti-toxin is Epsilon. In some embodiments, the toxin is Kid, and the anti-toxin is Kis. In preferred embodiments, the toxin is bacteriostatic. Any of the toxin/antitoxin pairs described herein may be used in the vector systems of the present disclosure. It is understood by those of skill in the art that the expression of the gene encoding the toxin may be regulated using art known methods to prevent the expression levels of the toxin from being deleterious to a host cell that expresses the anti-toxin. For example, in some embodiments, the gene encoding the toxin may be regulated by a moderate promoter. In other embodiments, the gene encoding the toxin may be cloned adjacent to ribosomal binding site of interest to regulate the expression of the gene at desired levels (see, e.g., Wright et al. (2015)).

Integration

In some embodiments, any of the gene(s) or gene cassette(s) of the present disclosure may be integrated into the bacterial chromosome at one or more integration sites. One or more copies of the gene (for example, an oxalate catabolism gene, oxalate transporter gene, and/or oxalate binding protein gene) or gene cassette (for example, a gene cassette comprising an oxalate catabolism gene and/or an oxalate transporter gene may be integrated into the bacterial chromosome. Having multiple copies of the gene or gene cassette integrated into the chromosome allows for greater production of the payload, e.g., one or more oxalate catabolism enzyme(s) and/or oxalate transporter gene(s) and other enzymes of a gene cassette, and also permits fine-tuning of the level of expression. Alternatively, different circuits described herein, such as any of the kill-switch circuits, in addition to the therapeutic gene(s) or gene cassette(s) could be integrated into the bacterial chromosome at one or more different integration sites to perform multiple different functions.

Figure 8:
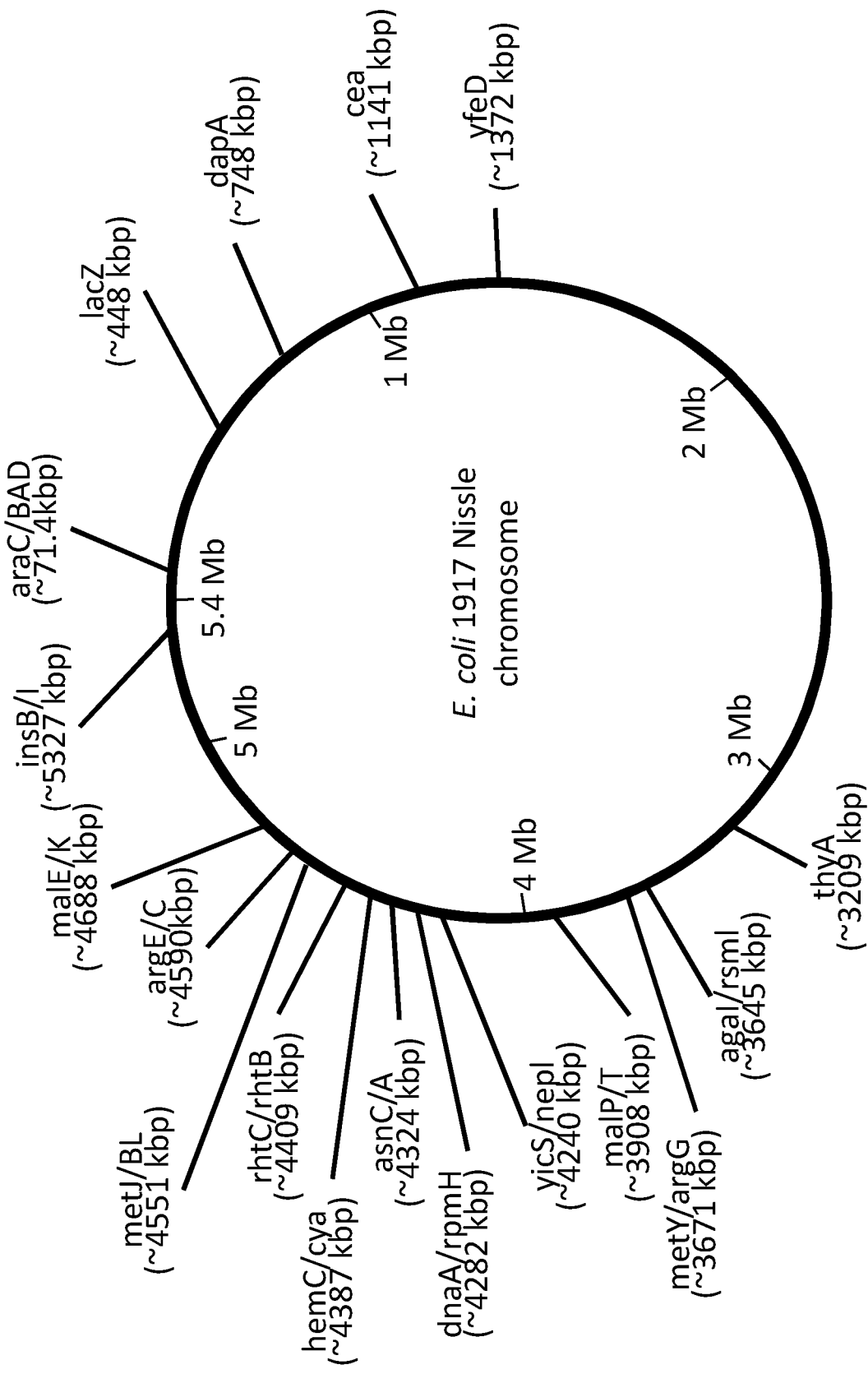
FIG. 8 depicts a map of exemplary integration sites within the *E. coli* 1917 Nissle chromosome. These sites indicate regions where circuit components may be inserted into the chromosome without interfering with essential gene expression. Backslashes (/) are used to show that the insertion will occur between divergently or convergently expressed genes. Insertions within biosynthetic genes, such as thyA, can be useful for creating nutrient auxotrophies. In some embodiments, an individual circuit component is inserted into more than one of the indicated sites. The malE/K site is circled. In some embodiments of the disclosure, FNR-ArgAfbr is inserted at the malEK locus.
Figure 9:
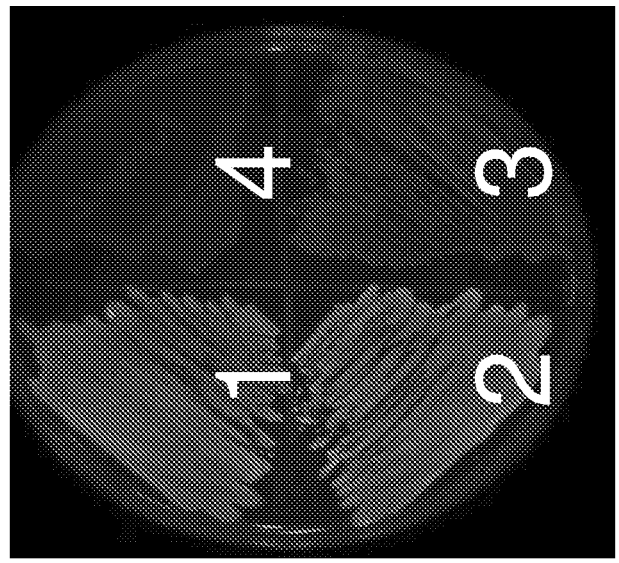
FIG. 9 depicts three bacterial strains which constitutively express red fluorescent protein (RFP). In strains 1-3, the rfp gene has been inserted into different sites within the bacterial chromosome, and results in varying degrees of brightness under fluorescent light. Unmodified *E. coli* Nissle (strain 4) is non-fluorescent.
Figure 10:
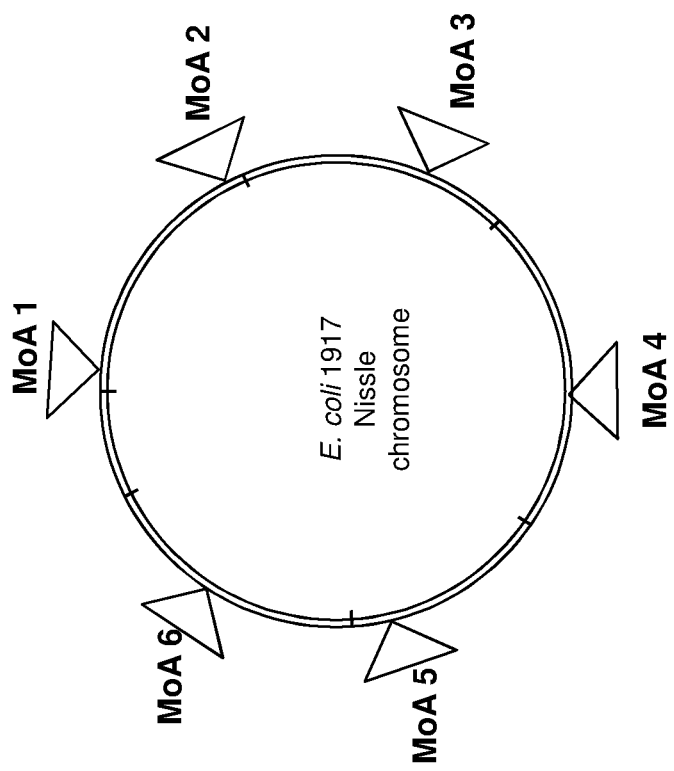
FIG. 10 depicts an exemplary schematic of the E. coli 1917 Nissle chromosome comprising multiple mechanisms of action (MoAs). In a non-limiting example, the genetically engineered bacterium may exogenously produce more than one effector molecules or increase or reduce the level of one or more metabolites. Additionally, in a non-limiting example, one or more of the same or different oxalate catabolic cassettes, oxalate importers and/or formate exporters described herein can be inserted at several different chromosomal insertion sites.
Figure 11:
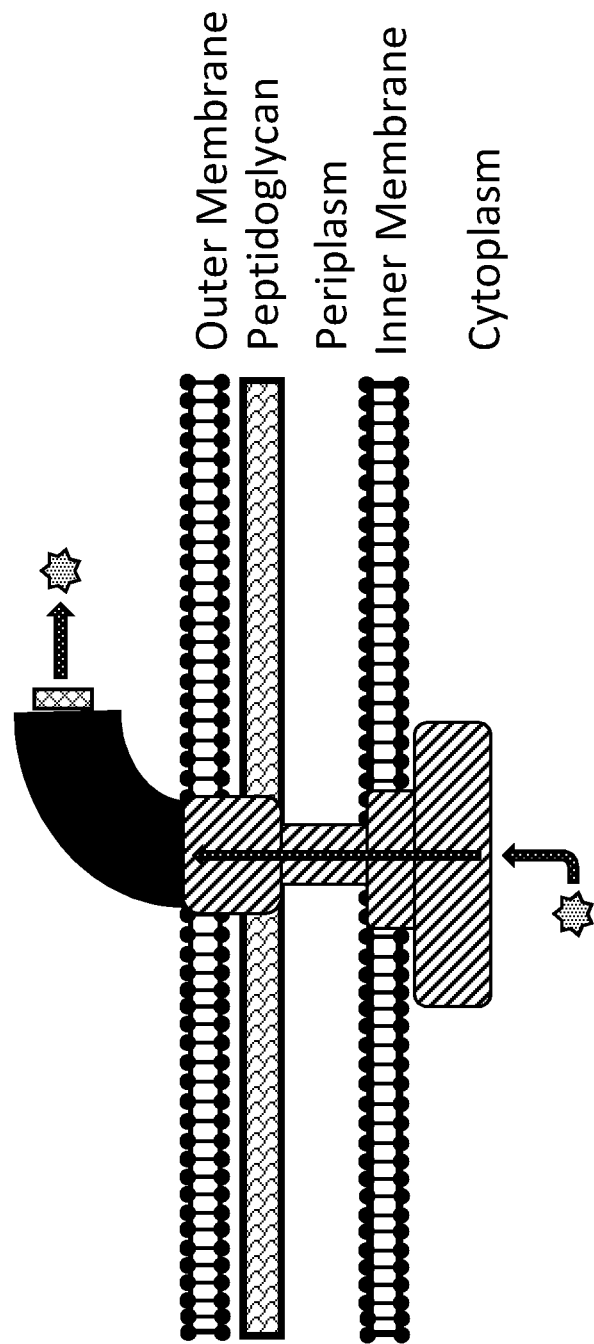
FIG. 11 depicts a schematic of a secretion system based on the flagellar type III secretion in which an incomplete flagellum is used to secrete a therapeutic peptide of interest (star) by recombinantly fusing the peptide to an N-terminal flagellar secretion signal of a native flagellar component so that the intracellularly expressed chimeric peptide can be mobilized across the inner and outer membranes into the surrounding host environment.

For example, FIG. 8 depicts a map of integration sites within the *E. coli* Nissle chromosome. FIG. 8 depicts three bacterial strains wherein the RFP gene has been successfully integrated into the bacterial chromosome at an integration site.

Secretion

In some embodiments, the genetically engineered bacteria further comprise a native secretion mechanism (e.g., gram positive bacteria) or non-native secretion mechanism (e.g., gram negative bacteria) that is capable of secreting the oxalate catabolism enzyme from the bacterial cytoplasm. Many bacteria have evolved sophisticated secretion systems to transport substrates across the bacterial cell envelope. Substrates, such as small molecules, proteins, and DNA, may be released into the extracellular space or periplasm (such as the gut lumen or other space), injected into a target cell, or associated with the bacterial membrane.

In Gram-negative bacteria, secretion machineries may span one or both of the inner and outer membranes. In some embodiments, the genetically engineered bacteria further comprise a non-native double membrane-spanning secretion system. Double membrane-spanning secretion systems include, but are not limited to, the type I secretion system (T1SS), the type II secretion system (T2SS), the type III secretion system (T3SS), the type IV secretion system (T4SS), the type VI secretion system (T6SS), and the resistance-nodulation-division (RND) family of multi-drug efflux pumps (Pugsley 1993; Gerlach et al., 2007; Collinson et al., 2015; Costa et al., 2015; Reeves et al., 2015;

WO2014138324A1, incorporated herein by reference). Examples of such secretion systems are shown in FIG. 11-15. Mycobacteria, which have a Gram-negative-like cell envelope, may also encode a type VII secretion system (T7SS) (Stanley et al., 2003). With the exception of the T2SS, double membrane-spanning secretions generally transport substrates from the bacterial cytoplasm directly into the extracellular space or into the target cell. In contrast, the T2SS and secretion systems that span only the outer membrane may use a two-step mechanism, wherein substrates are first translocated to the periplasm by inner membrane-spanning transporters, and then transferred to the outer membrane or secreted into the extracellular space. Outer membrane-spanning secretion systems include, but are not limited to, the type V secretion or autotransporter system (T5SS), the curli secretion system, and the chaperone-usher pathway for pili assembly (Saier, 2006; Costa et al., 2015).

In some embodiments, the genetically engineered bacteria of the invention further comprise a type III or a type III-like secretion system (T3SS) from Shigella, Salmonella, E. coli, Bivrio, Burkholderia, Yersinia, Chlamydia, or Pseudomonas. The T3SS is capable of transporting a protein from the bacterial cytoplasm to the host cytoplasm through a needle complex. The T3SS may be modified to secrete the molecule from the bacterial cytoplasm, but not inject the molecule into the host cytoplasm. Thus, the molecule is secreted into the gut lumen or other extracellular space. In some embodiments, the genetically engineered bacteria comprise said modified T3SS and are capable of secreting the oxalate catabolism enzyme from the bacterial cytoplasm. In some embodiments, the secreted molecule, such as a heterologous protein or peptide, e.g., an oxalate catabolism enzyme, comprises a type III secretion sequence that allows the oxalate catabolism enzyme to be secreted from the bacteria.

In some embodiments, a flagellar type III secretion pathway is used to secrete the molecule of interest, e.g., an oxalate catabolism enzyme. In some embodiments, an incomplete flagellum is used to secrete a therapeutic peptide of interest by recombinantly fusing the peptide to an N-terminal flagellar secretion signal of a native flagellar component. In this manner, the intracellularly expressed chimeric peptide can be mobilized across the inner and outer membranes into the surrounding host environment.

Figure 12:
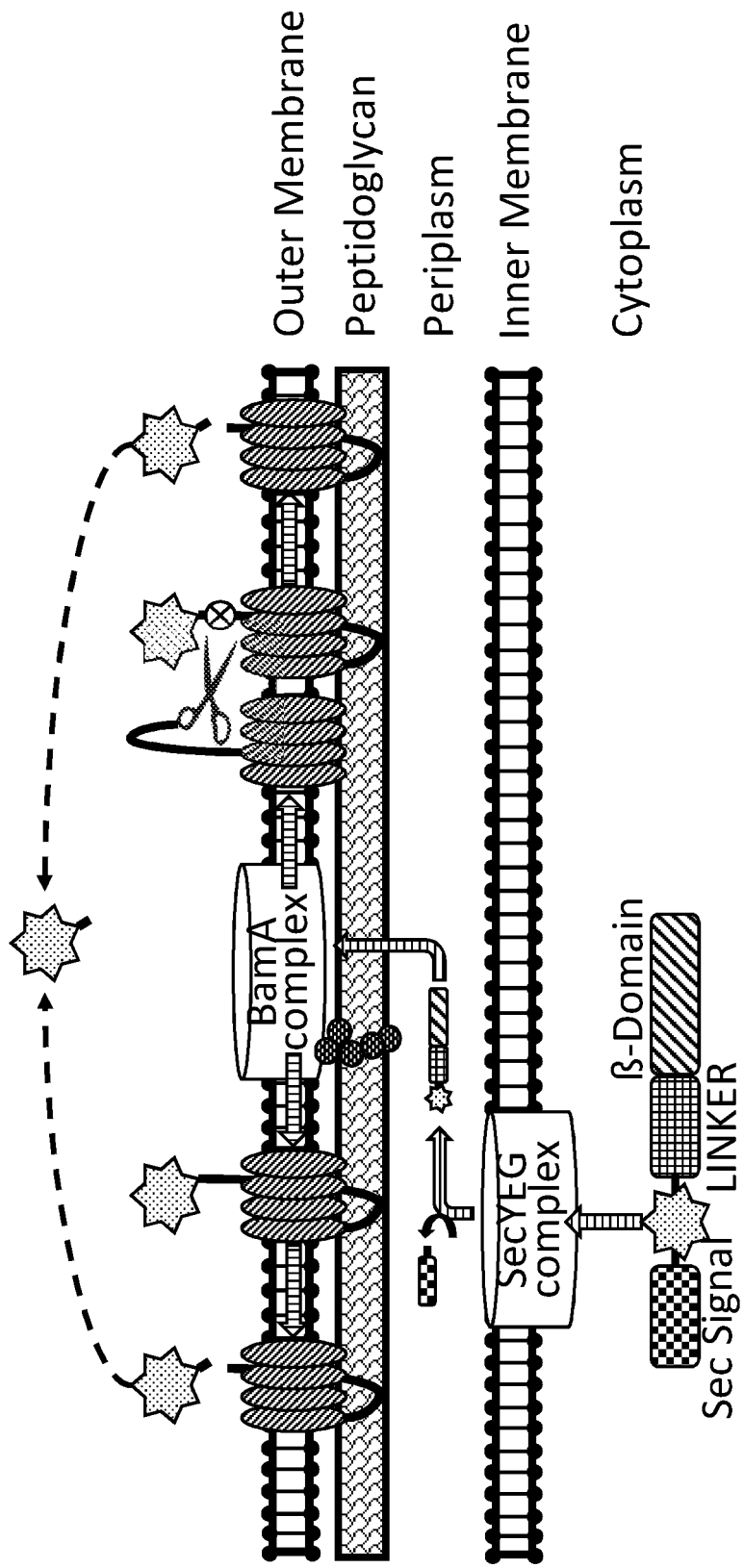
FIG. 12 depicts a schematic of a type V secretion system for the extracellular production of recombinant proteins in which a therapeutic peptide (star) can be fused to an N-terminal secretion signal, a linker and the beta-domain of an autotransporter. In this system, the N-terminal signal sequence directs the protein to the SecA-YEG machinery which moves the protein across the inner membrane into the periplasm, followed by subsequent cleavage of the signal sequence. The beta-domain is recruited to the Bam complex where the beta-domain is folded and inserted into the outer membrane as a beta-barrel structure. The therapeutic peptide is then thread through the hollow pore of the beta-barrel structure ahead of the linker sequence. The therapeutic peptide is freed from the linker system by an autocatalytic cleavage or by targeting of a membrane-associated peptidase (scissors) to a complementary protease cut site in the linker.

In some embodiments, a Type V Autotransporter Secretion System is used to secrete the molecule of interest, e.g., therapeutic peptide. Due to the simplicity of the machinery and capacity to handle relatively large protein fluxes, the Type V secretion system is attractive for the extracellular production of recombinant proteins. As shown in FIG. 12, a therapeutic peptide (star) can be fused to an N-terminal secretion signal, a linker, and the beta-domain of an autotransporter. The N-terminal signal sequence directs the protein to the SecA-YEG machinery which moves the protein across the inner membrane into the periplasm, followed by subsequent cleavage of the signal sequence. The Beta-domain is recruited to the Bam complex ('Beta-barrel assembly machinery') where the beta-domain is folded and inserted into the outer membrane as a beta-barrel structure. The therapeutic peptide is thread through the hollow pore of the beta-barrel structure ahead of the linker sequence. Once exposed to the extracellular environment, the therapeutic peptide can be freed from the linker system by an autocatalytic cleavage (left side of Bam complex) or by targeting of a membrane-associated peptidase (black scissors; right side of Bam complex) to a complimentary protease cut site in the linker. Thus, in some embodiments, the secreted molecule, such as a heterologous protein or peptide, e.g., aanoxalate catabolism enzyme, comprises an N-terminal secretion signal, a linker, and beta-domain of an autotransporter so as to allow the molecule to be secreted from the bacteria.

Figure 13:
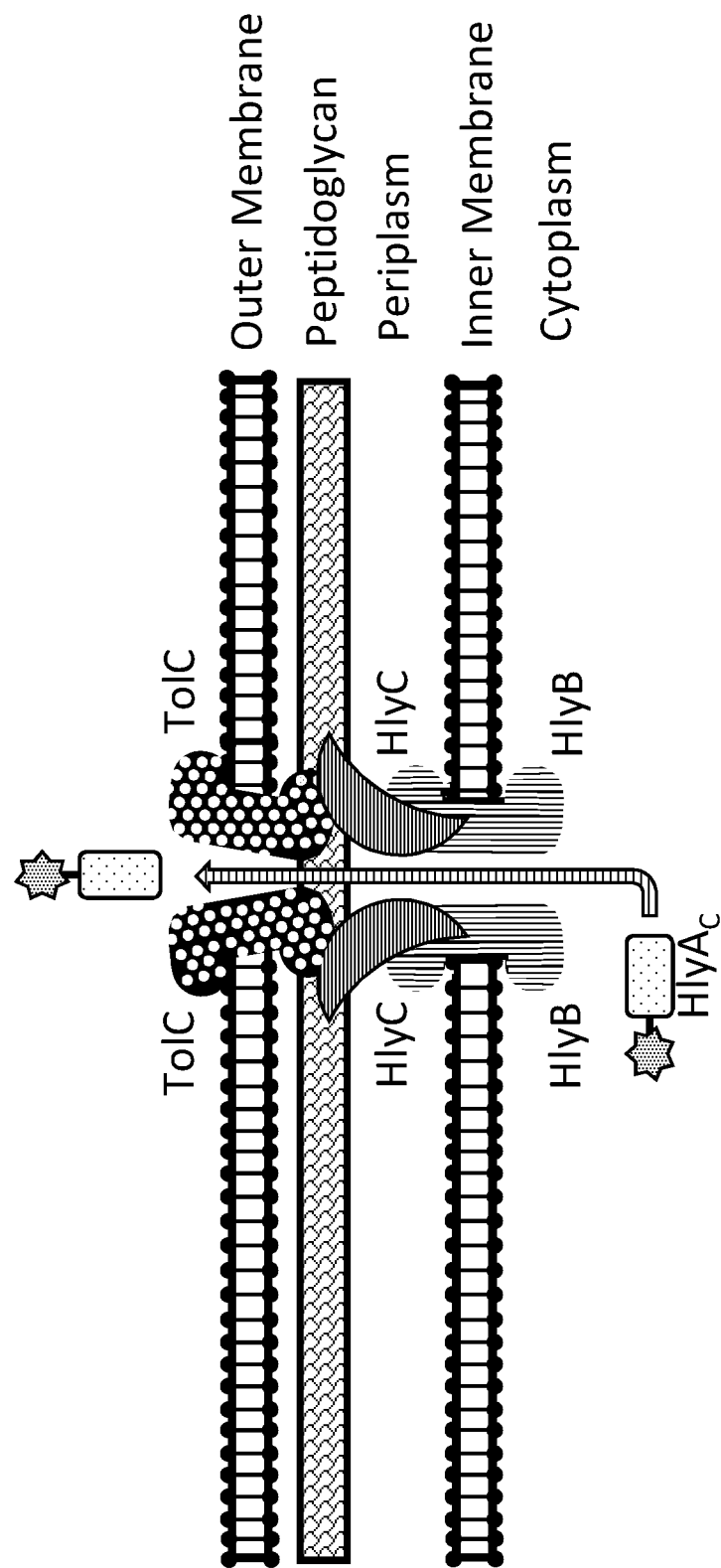
FIG. 13 depicts a schematic of a type I secretion system, which translocates a passenger peptide directly from the cytoplasm to the extracellular space using HlyB (an ATP-binding cassette transporter); HlyD (a membrane fusion protein); and TolC (an outer membrane protein) which form a channel through both the inner and outer membranes. The secretion signal-containing C-terminal portion of HlyA is fused to the C-terminal portion of a therapeutic peptide (star) to mediate secretion of this peptide.
Figure 14:
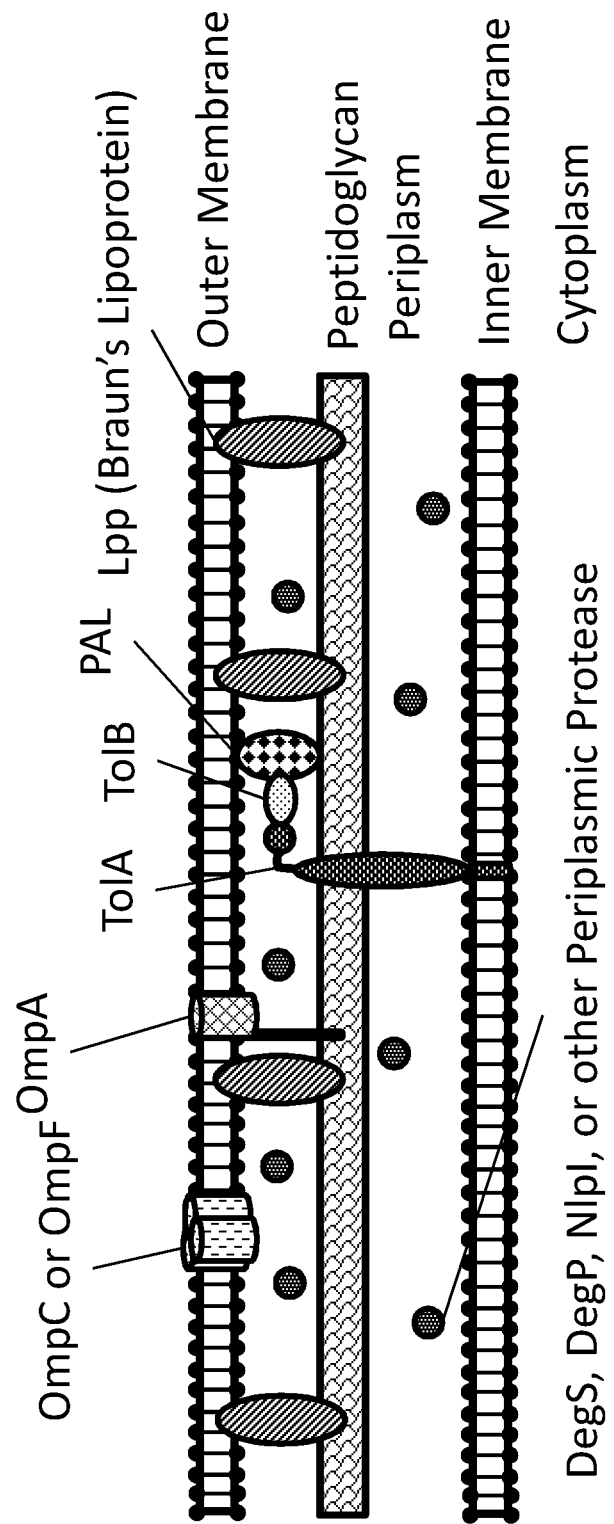
FIG. 14 depicts a schematic of the outer and inner membranes of a gram-negative bacterium, and several deletion targets for generating a leaky or destabilized outer membrane, thereby facilitating the translocation of a therapeutic polypeptides to the extracellular space, e.g., therapeutic polypeptides of eukaryotic origin containing disulphide bonds. Deactivating mutations of one or more genes encoding a protein that tethers the outer membrane to the peptidoglycan skeleton, e.g., lpp, ompC, ompA, ompF, tolA, tolB, pal, and/or one or more genes encoding a periplasmic protease, e.g., degS, degP, nlpl, generates a leaky phenotype. Combinations of mutations may synergistically enhance the leaky phenotype.
Figure 15:
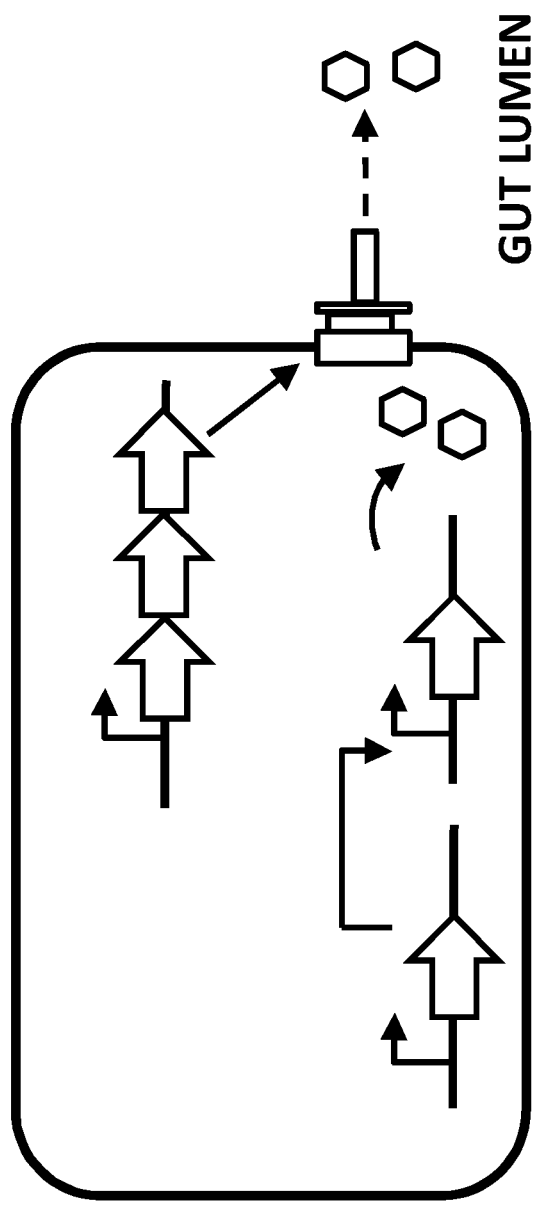
FIG. 15 depicts a modified type 3 secretion system (T3SS) to allow the bacteria to inject secreted therapeutic proteins into the gut lumen. An inducible promoter (small arrow, top), e.g. a FNR-inducible promoter, drives expression of the T3 secretion system gene cassette (3 large arrows, top) that produces the apparatus that secretes tagged peptides out of the cell. An inducible promoter (small arrow, bottom), e.g. a FNR-inducible promoter, drives expression of a regulatory factor, e.g. T7 polymerase, that then activates the expression of the tagged therapeutic peptide (hexagons).
Figure 16A:
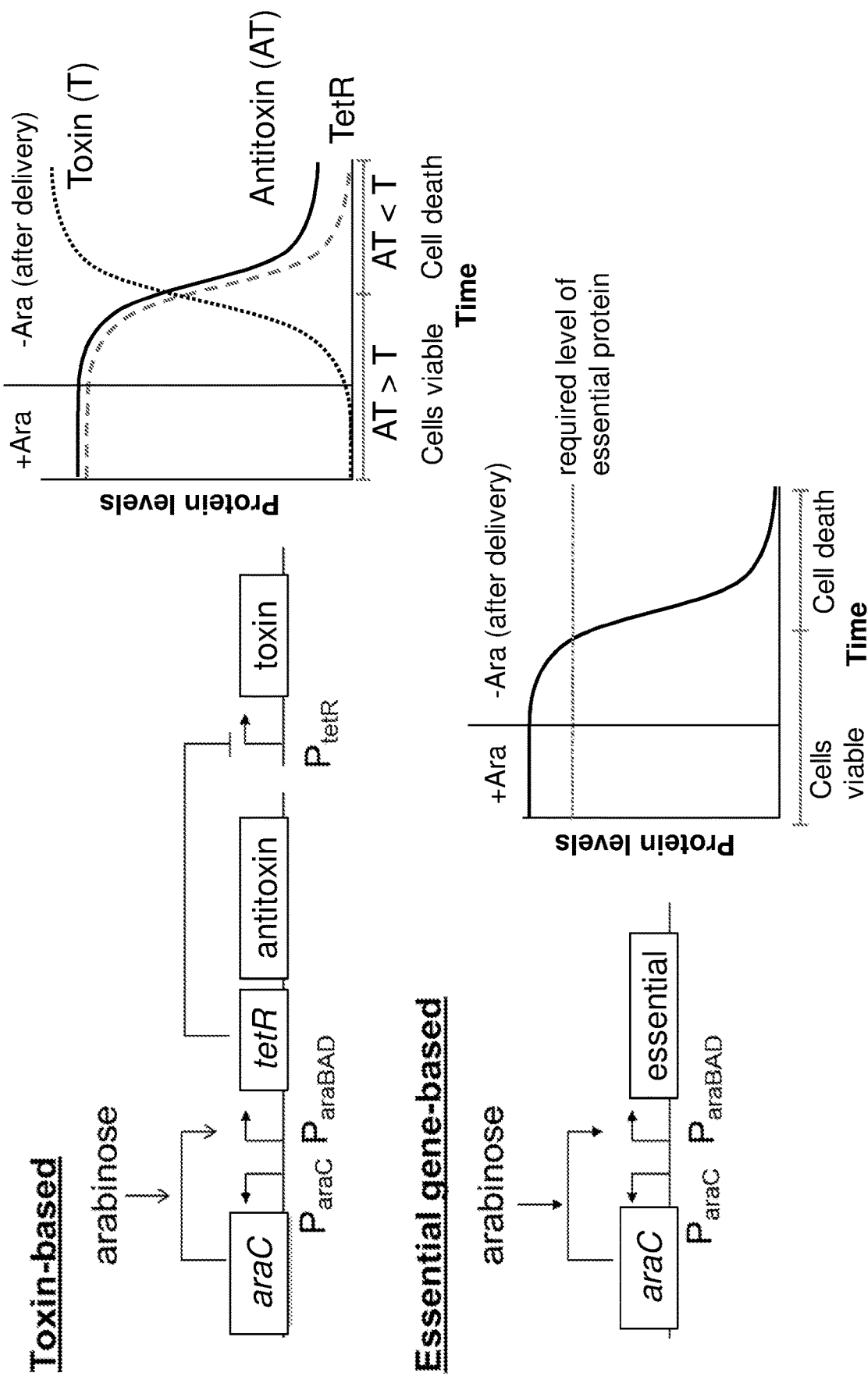
FIG. 16A, FIG. 16B, and FIG. 16C depict schematics of non-limiting embodiments of the disclosure.
Figure 16B:
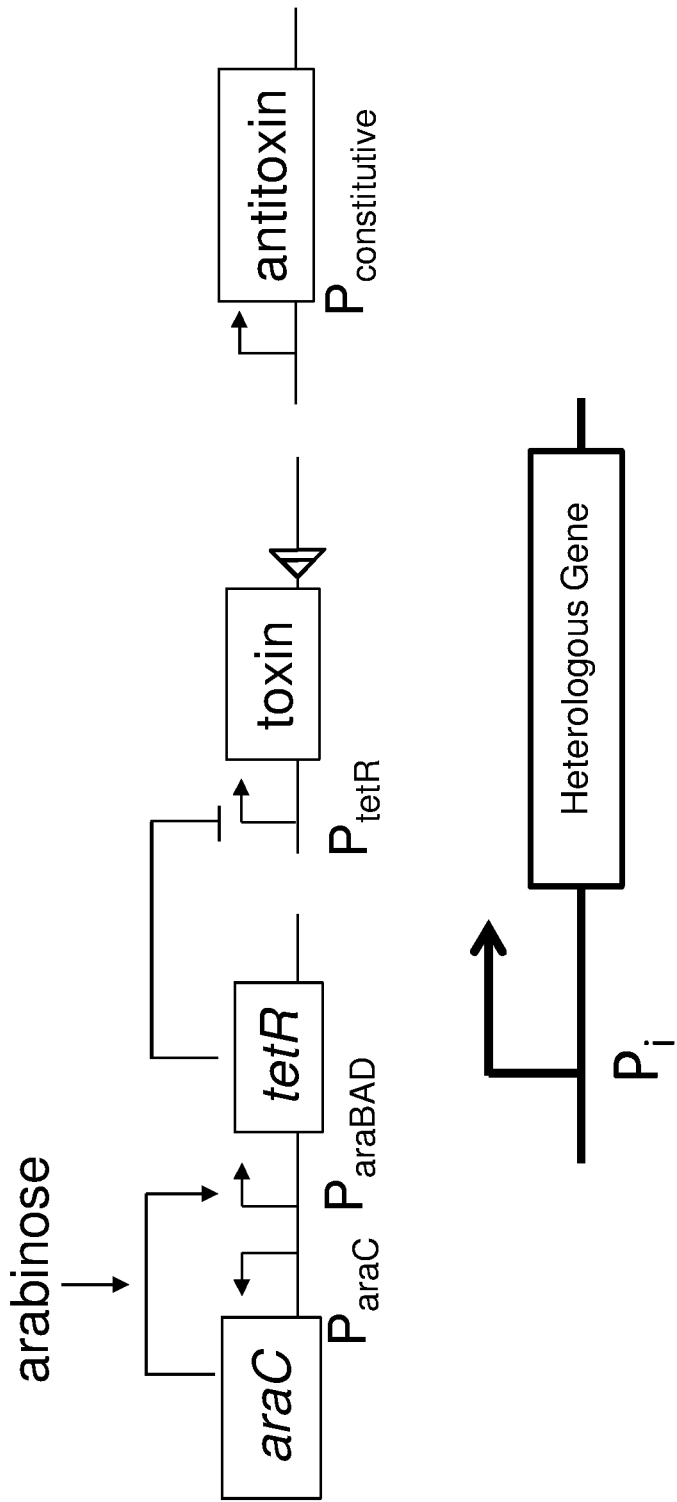
Figure 16C:
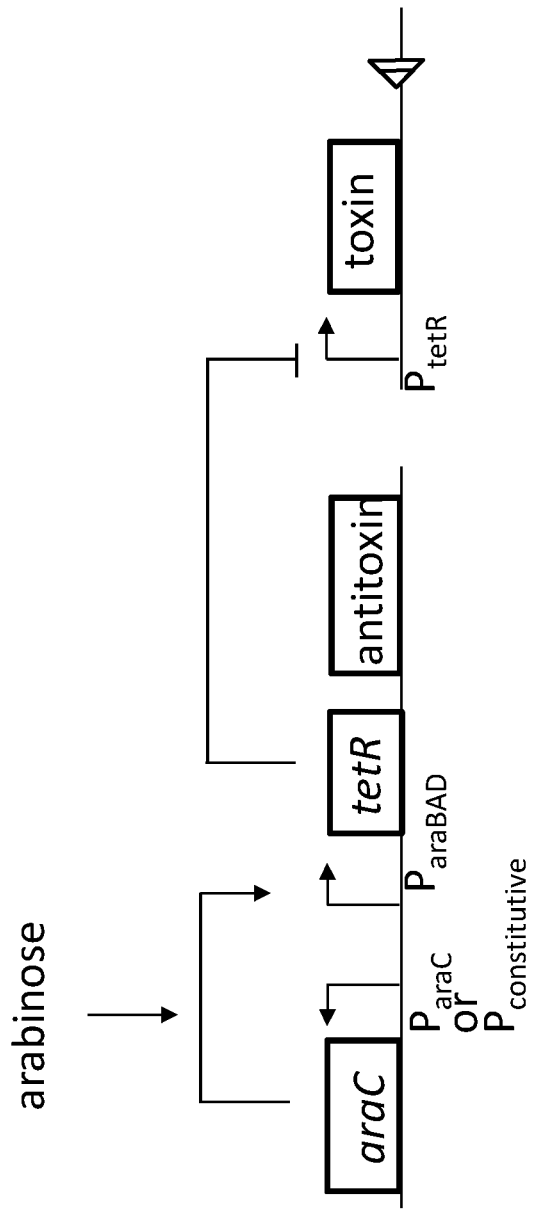
Figure 17:
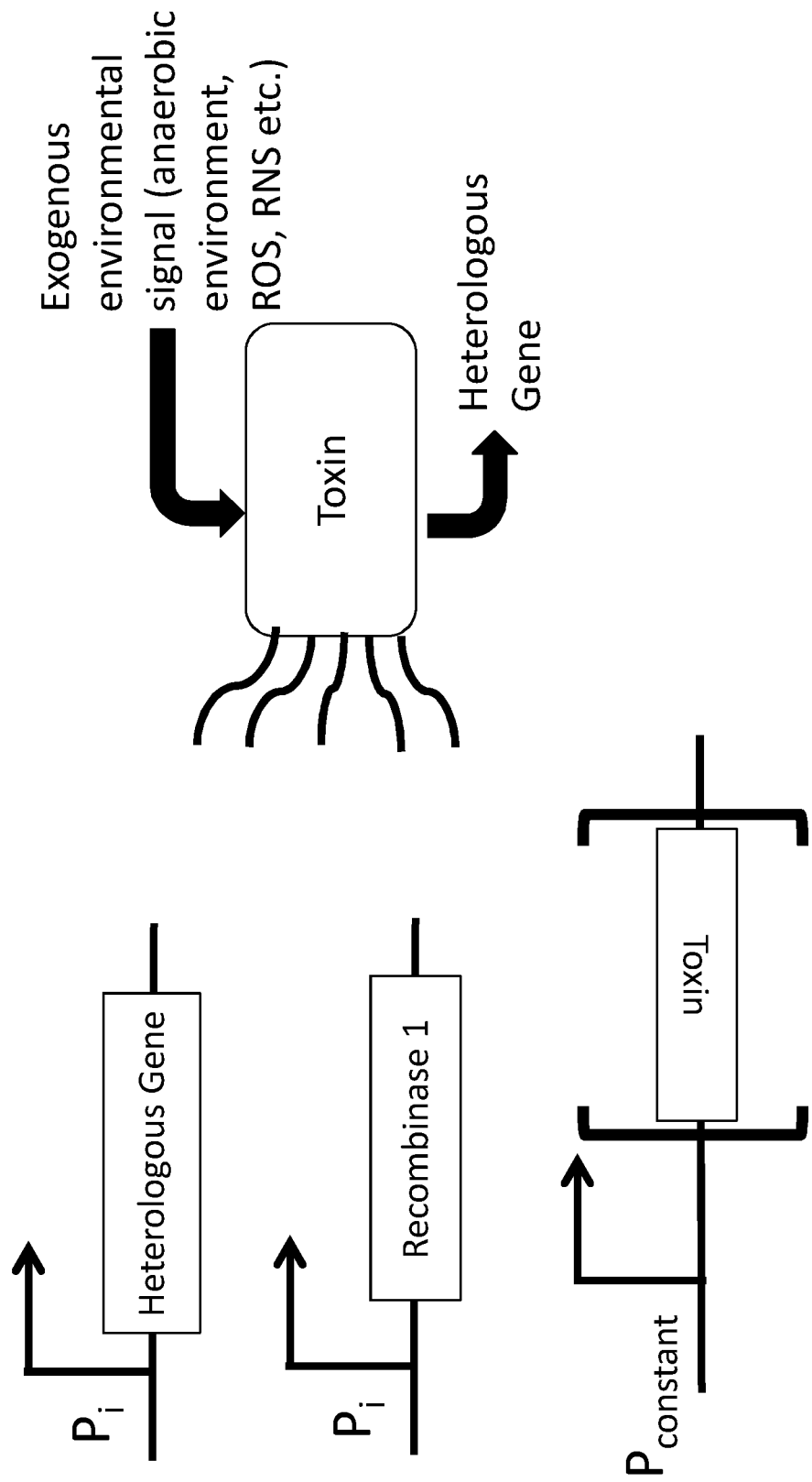
FIG. 17 depicts one non-limiting embodiment of the disclosure, where an exogenous environmental condition or one or more environmental signals activates expression of a heterologous gene and at least one recombinase from an inducible promoter or inducible promoters. The recombinase then flips a toxin gene into an activated conformation, and the natural kinetics of the recombinase create a time delay in expression of the toxin, allowing the heterologous gene to be fully expressed. Once the toxin is expressed, it kills the cell.
Figure 18:
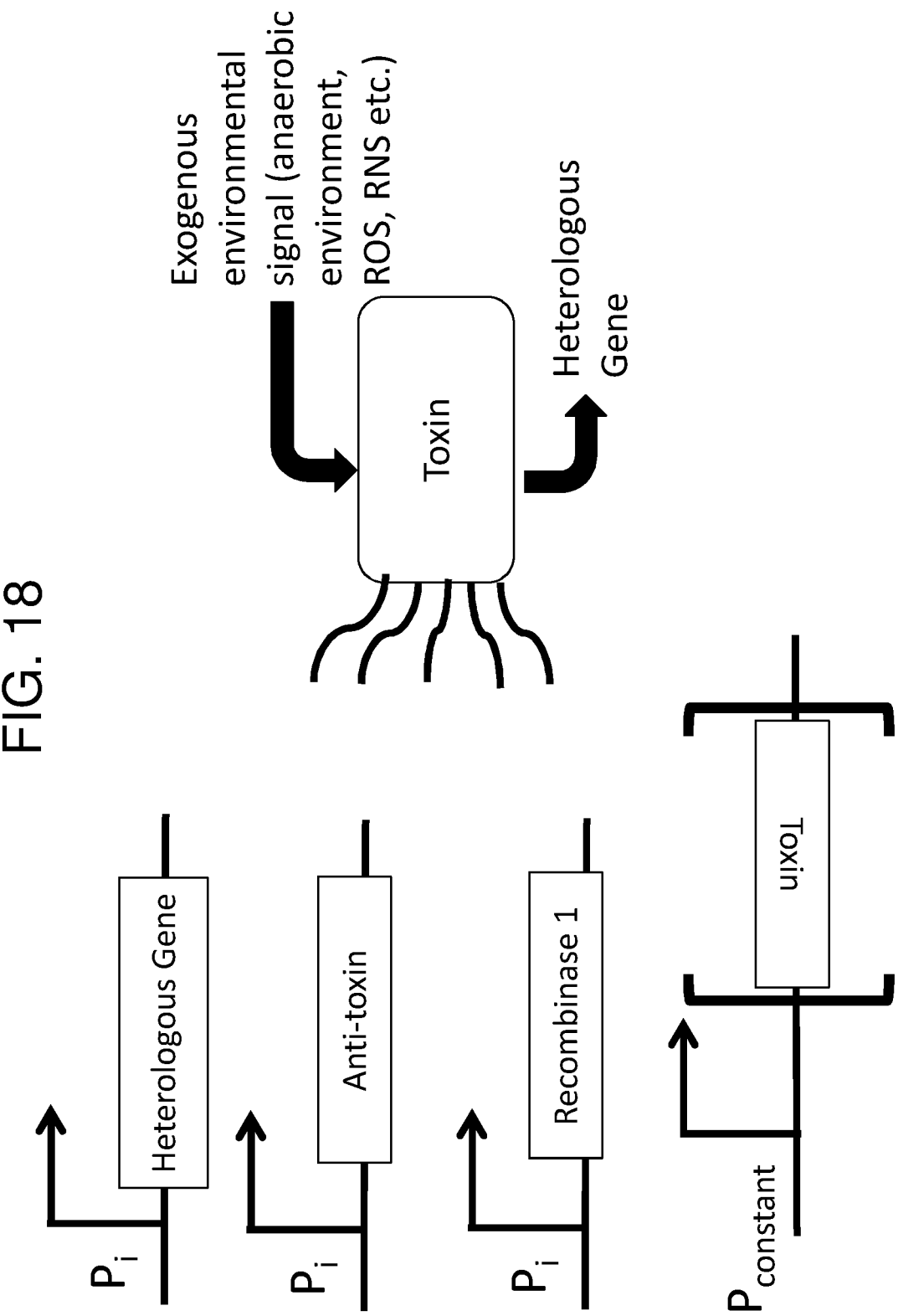
FIG. 18 depicts another non-limiting embodiment of the disclosure, where an exogenous environmental condition or one or more environmental signals activates expression of a heterologous gene, an anti-toxin, and at least one recombinase from an inducible promoter or inducible promoters. The recombinase then flips a toxin gene into an activated conformation, but the presence of the accumulated anti-toxin suppresses the activity of the toxin. Once the exogenous environmental condition or cue(s) is no longer present, expression of the anti-toxin is turned off. The toxin is constitutively expressed, continues to accumulate, and kills the bacterial cell.
Figure 20:
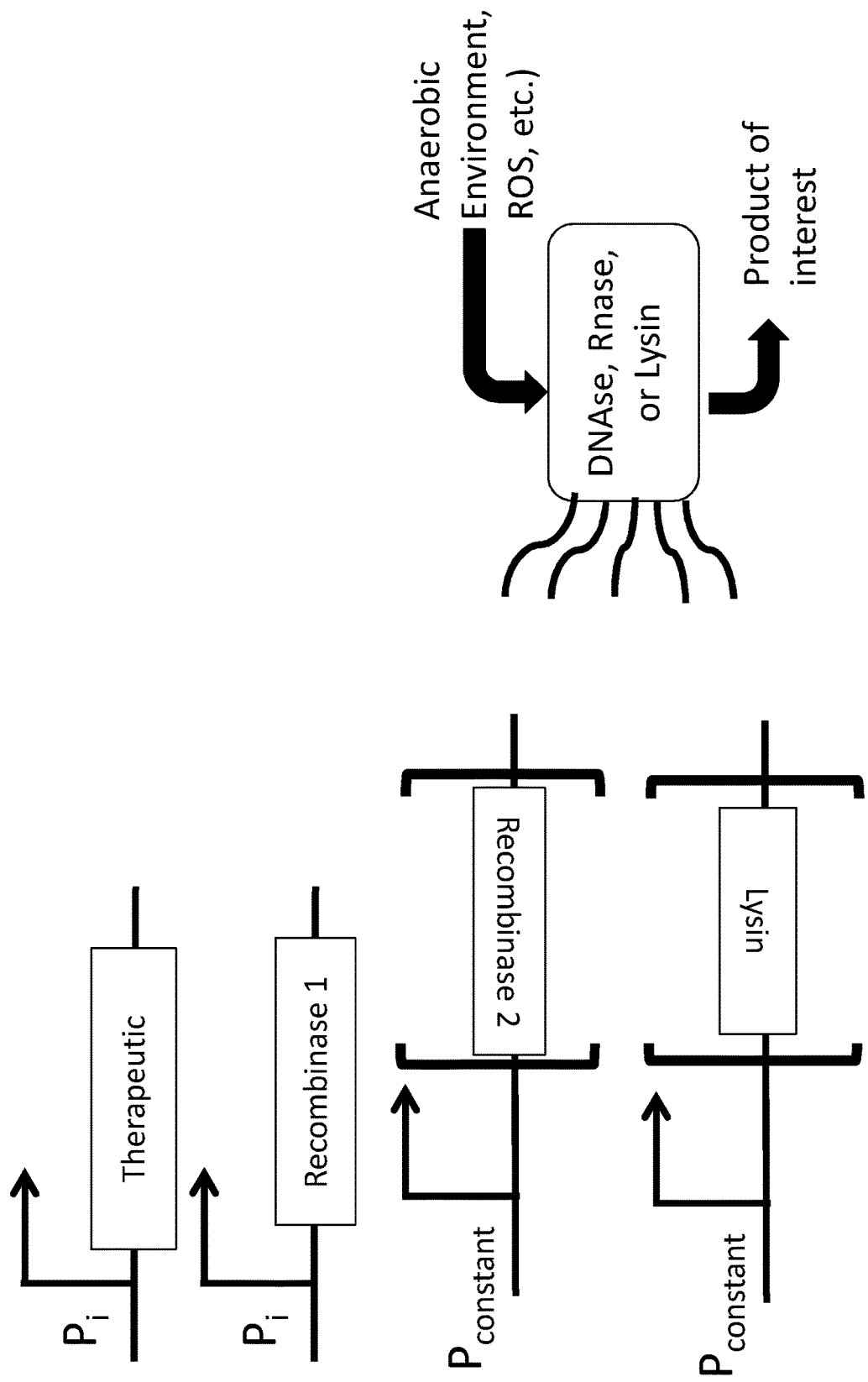
FIG. 20 depicts one non-limiting embodiment of the disclosure, where an exogenous environmental condition or one or more environmental signals activates expression of a heterologous gene and a first recombinase from an inducible promoter or inducible promoters. The recombinase then flips a second recombinase from an inverted orientation to an active conformation. The activated second recombinase flips the toxin gene into an activated conformation, and the natural kinetics of the recombinase create a time delay in expression of the toxin, allowing the heterologous gene to be fully expressed. Once the toxin is expressed, it kills the cell.
Figure 21:
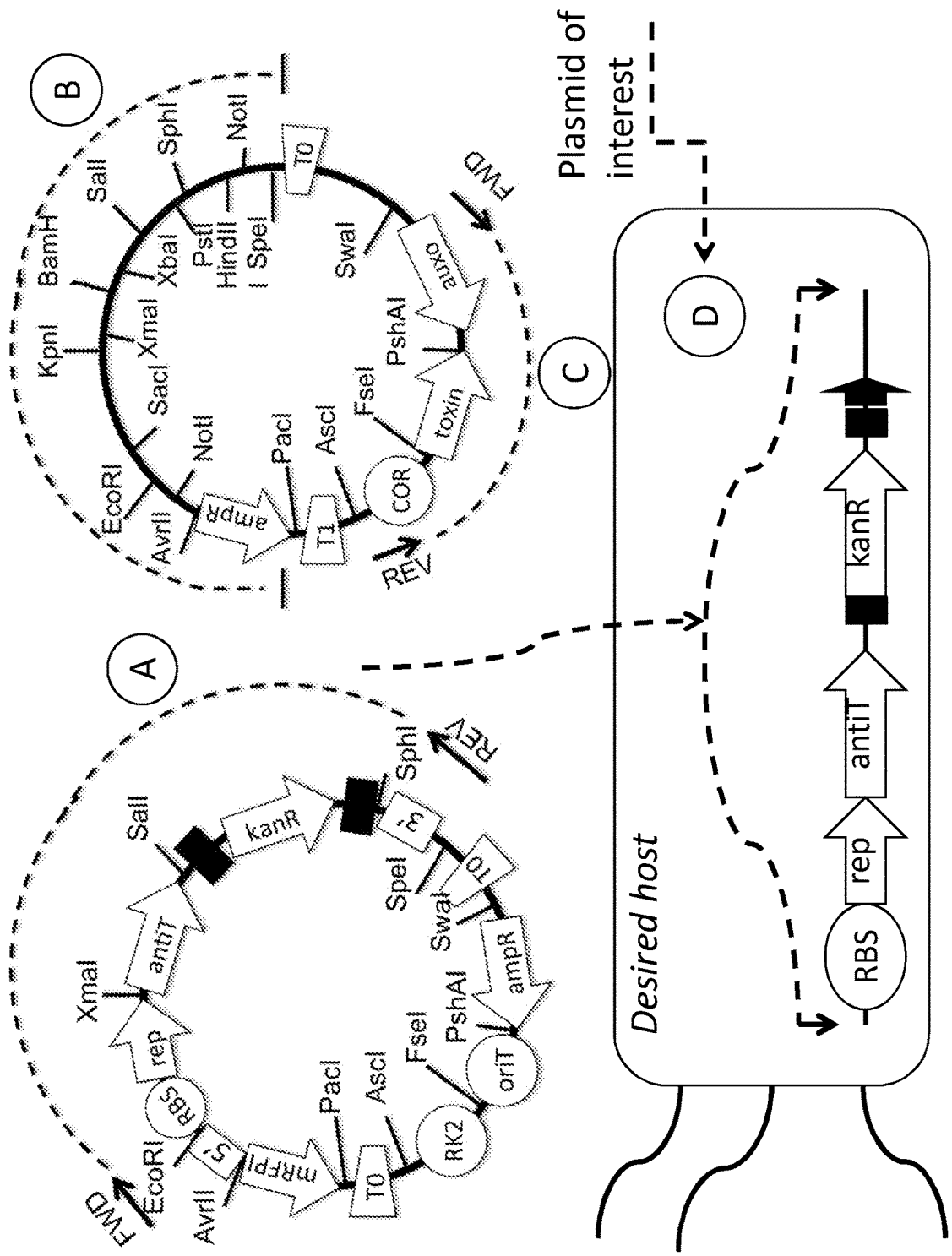
FIG. 21 depicts the use of GeneGuards as an engineered safety component. All engineered DNA is present on a plasmid which can be conditionally destroyed. See, e.g., Wright et al., "GeneGuard: A Modular Plasmid System Designed for Biosafety," ACS Synthetic Biology (2015) 4: 307-316.

In some embodiments, a Hemolysin-based Secretion System is used to secrete the molecule of interest, e.g., therapeutic peptide. Type I Secretion systems offer the advantage of translocating their passenger peptide directly from the cytoplasm to the extracellular space, obviating the two-step process of other secretion types. FIG. 13 shows the alpha-hemolysin (HlyA) of uropathogenic Escherichia coli. This pathway uses HlyB, an ATP-binding cassette transporter; HlyD, a membrane fusion protein; and TolC, an outer membrane protein. The assembly of these three proteins forms a channel through both the inner and outer membranes. Natively, this channel is used to secrete HlyA, however, to secrete the therapeutic peptide of the present disclosure, the secretion signal-containing C-terminal portion of HlyA is fused to the C-terminal portion of a therapeutic peptide (star) to mediate secretion of this peptide.

In alternate embodiments, the genetically engineered bacteria further comprise a non-native single membrane-spanning secretion system. Single membrane-spanning transporters may act as a component of a secretion system, or may export substrates independently. Such transporters include, but are not limited to, ATP-binding cassette translocases, flagellum/virulence-related translocases, conjugation-related translocases, the general secretory system (e.g., the SecYEG complex in E. coli), the accessory secretory system in mycobacteria and several types of Gram-positive bacteria (e.g., Bacillus anthracis, Lactobacillus johnsonii, Corynebacterium glutamicum, Streptococcus gordonii, Staphylococcus aureus), and the twin-arginine translocation (TAT) system (Saier, 2006; Rigel and Braunstein, 2008; Albiniak et al., 2013). It is known that the general secretory and TAT systems can both export substrates with cleavable N-terminal signal peptides into the periplasm, and have been explored in the context of biopharmaceutical production. The TAT system may offer particular advantages, however, in that it is able to transport folded substrates, thus eliminating the potential for premature or incorrect folding. In certain embodiments, the genetically engineered bacteria comprise a TAT or a TAT-like system and are capable of secreting the oxalate catabolism enzyme from the bacterial cytoplasm. One of ordinary skill in the art would appreciate that the secretion systems disclosed herein may be modified to act in different species, strains, and subtypes of bacteria, and/or adapted to deliver different payloads.

In order to translocate a protein, e.g., therapeutic polypeptide, to the extracellular space, the polypeptide must first be translated intracellularly, mobilized across the inner membrane and finally mobilized across the outer membrane. Many effector proteins (e.g., therapeutic polypeptides)—particularly those of eukaryotic origin—contain disulphide bonds to stabilize the tertiary and quaternary structures. While these bonds are capable of correctly forming in the oxidizing periplasmic compartment with the help of periplasmic chaperones, in order to translocate the polypeptide across the outer membrane the disulphide bonds must be reduced and the protein unfolded again.

One way to secrete properly folded proteins in gram-negative bacteria—particularly those requiring disulphide bonds—is to target the periplasm in a bacterium with a destabilized outer membrane. In this manner the protein is mobilized into the oxidizing environment and allowed to fold properly. In contrast to orchestrated extracellular secretion systems, the protein is then able to escape the periplasmic space in a correctly folded form by membrane leakage. These "leaky" gram-negative mutants are therefore capable of secreting bioactive, properly disulphide-bonded polypeptides. In some embodiments, the genetically engineered bacteria have a "leaky" or de-stabilized outer membrane. Destabilizing the bacterial outer membrane to induce leakiness can be accomplished by deleting or mutagenizing genes responsible for tethering the outer membrane to the rigid peptidoglycan skeleton, including for example, lpp, ompC, ompA, ompF, tolA, tolB, pal, degS, degP, and nlpI. Lpp is the most abundant polypeptide in the bacterial cell existing at ~500,000 copies per cell and functions as the primary 'staple' of the bacterial cell wall to the peptidoglycan. (Silhavy, T. J., Kahne, D. & Walker, S. The bacterial cell envelope. *Cold Spring Harb Perspect Biol* 2, a000414 (2010)). TolA-PAL and OmpA complexes function similarly to Lpp and are other deletion targets to generate a leaky phenotype. Additionally, leaky phenotypes have been observed when periplasmic proteases are deactivated. The periplasm is very densely packed with protein and therefore encode several periplasmic proteins to facilitate protein turnover. Removal of periplasmic proteases such as degS, degP or nlpI can induce leaky phenotypes by promoting an excessive build-up of periplasmic protein. Mutation of the proteases can also preserve the effector polypeptide by preventing targeted degradation by these proteases. Moreover, a combination of these mutations may synergistically enhance the leaky phenotype of the cell without major sacrifices in cell viability. Thus, in some embodiments, the engineered bacteria have one or more deleted or mutated membrane genes. In some embodiments, the engineered bacteria have a deleted or mutated lpp gene. In some embodiments, the engineered bacteria have one or more deleted or mutated gene(s), selected from ompA, ompA, and ompF genes. In some embodiments, the engineered bacteria have one or more deleted or mutated gene(s), selected from tolA, tolB, and pal genes. In some embodiments, the engineered bacteria have one or more deleted or mutated periplasmic protease genes. In some embodiments, the engineered bacteria have one or more deleted or mutated periplasmic protease genes selected from degS, degP, and nlpI. In some embodiments, the engineered bacteria have one or more deleted or mutated gene(s), selected from lpp, ompA, ompA, ompF, tolA, tolB, pal, degS, degP, and nlpI genes.

To minimize disturbances to cell viability, the leaky phenotype can be made inducible by placing one or more membrane or periplasmic protease genes, e.g., selected from lpp, ompA, ompA, ompF, tolA, tolB, pal, degS, degP, and nlpI, under the control of an inducible promoter. For example, expression of lpp or other cell wall stability protein or periplasmic protease can be repressed in conditions where the therapeutic polypeptide needs to be delivered (secreted). For instance, under inducing conditions a transcriptional repressor protein or a designed antisense RNA can be expressed which reduces transcription or translation of a target membrane or periplasmic protease gene. Conversely, overexpression of certain peptides can result in a destabilized phenotype, e.g., overexpression of colicins or the third topological domain of TolA, which peptide overexpression can be induced in conditions in which the therapeutic polypeptide needs to be delivered (secreted). These sorts of strategies would decouple the fragile, leaky phenotypes from biomass production. Thus, in some embodiments, the engineered bacteria have one or more membrane and/or periplasmic protease genes under the control of an inducible promoter.

The tables below list secretion systems for Gram positive bacteria and Gram negative bacteria.

TABLE 12

Secretion systems for gram positive bacteria

| Bacterial Strain | Relevant Secretion System |
|---|---|
| C. novyi-NT (Gram+) | Sec pathway |
|  | Twin- arginine (TAT) pathway |
| C. butryicum (Gram+) | Sec pathway |
|  | Twin- arginine (TAT) pathway |
| *Listeria monocytogenes* (Gram+) | Sec pathway |
|  | Twin- arginine (TAT) pathway |

TABLE 13

Secretion Systems for Gram negative bacteria
Protein secretary pathways (SP) in gram-negative bacteria and their descendants

| Type (Abbreviation) | Name | TC[#2] | Bacteria | Archaea | Eukarya | # Proteins/ System | Energy Source |
|---|---|---|---|---|---|---|---|
| IMPS-Gram-negative bacterial inner membrane channel-forming translocases | | | | | | | |
| ABC (SIP) | ATP binding cassette translocase | 3.A.1 | + | + | + | 3-4 | ATP |
| SEC (IISP) | General secretory translocase | 3.A.5 | + | + | + | ~12 | GTP OR ATP + PMF |
| Fla/Path (IIISP) | Flagellum/ virulence-related translocase | 3.A.6 | + | − | − | >10 | ATP |
| Conj (IVSP) | Conjugation-related translocase | 3.A.7 | + | − | − | >10 | ATP |
| Tat (IISP) | Twin-arginine targeting translocase | 2.A.64 | + | + | + (chloroplasts) | 2-4 | PMF |

TABLE 13-continued

Secretion Systems for Gram negative bacteria
Protein secretary pathways (SP) in gram-negative bacteria and their descendants

| Type (Abbreviation) | Name | TC[#2] | Bacteria | Archaea | Eukarya | # Proteins/System | Energy Source |
|---|---|---|---|---|---|---|---|
| Oxa1 (YidC) | Cytochrome oxidase biogenesis family | 2.A.9 | + | + | + (mitochondria chloroplasts) | 1 | None or PMF |
| MscL | Large conductance mechano-sensitive channel family | 1.A.22 | + | + | + | 1 | None |
| Holins | Holin functional superfamily | 1.E.1 • 21 | + | − | − | 1 | None |
| Eukaryotic Organelles | | | | | | | |
| MPT | Mitochondrial protein translocase | 3.A.B | − | − | + (mitochondrial) | >20 | ATP |
| CEPT | Chloroplast envelope protein translocase | 3.A.9 | (+) | − | + (chloroplasts) | ≥3 | GTP |
| Bcl-2 | Eukaryotic Bcl-2 family (programmed cell death) | 1.A.21 | − | − | + | 1? | None |
| Gram-negative bacterial outer membrane channel-forming translocases | | | | | | | |
| MTB (IISP) | Main terminal branch of the general secretory translocase | 3.A.15 | +[b] | − | − | ~14 | ATP; PMF |
| FUP AT-1 | Fimbrial usher protein Autotransporter-1 | 1.B.11 1.B.12 | +[b] +[b] | − | − − | 1 1 | None None |
| AT-2 OMF (ISP) TPS Secretin (IISP and IISP) | Autotransporter-2 | 1.B.40 1.B.17 1.B.20 1.B.22 | +[b] +[b] + +[b] | − − − − | − +(?) + − | 1 1 1 1 | None None None None |
| OmpIP | Outer membrane insertion porin | 1.B.33 | + | − | + (mitochondria; chloroplasts) | ≥4 | None? |

The above tables for gram positive and gram negative bacteria list secretion systems that can be used to secret oxalate catabolism enzyme(s) and other polypeptides from the engineered bacteria, which are reviewed in Milton H. Saier, Jr. Microbe/Volume 1, Number 9, 2006 "Protein Secretion Systems in Gram-Negative Bacteria Gram-negative bacteria possess many protein secretion-membrane insertion systems that apparently evolved independently", the contents of which is herein incorporated by reference in its entirety.

In some embodiments, one or more oxalate catabolic enzymes described herein are secreted. In some embodiments, the one or more oxalate catabolic enzymes described herein are further modified to improve secretion efficiency, decreased susceptibility to proteases, stability, and/or half-life. In some embodiments, formyl-CoA:oxalate CoA-transferase, e.g., Frc (from *O. formigenes*) is secreted, alone or in combination other oxalate catabolic enzymes, e.g., oxalyl-CoA synthetase, e.g., ScAAE3 (from *S. cerevisiae*) and/or oxalyl-CoA decarboxylase, e.g., Oxc (from *O. formigenes*), and/or acetyl-CoA:oxalate CoA-transferase, e.g., YfdE (from *E. coli*). In some embodiments, oxalyl-CoA synthetase, e.g., ScAAE3 (from *S. cerevisiae*) is secreted, alone or in combination other oxalate catabolic enzymes, e.g., formyl-CoA:oxalate CoA-transferase, e.g., Frc (from *O. formigenes*) and/or oxalyl-CoA decarboxylase, e.g., Oxc (from *O. formigenes*), and/or acetyl-CoA:oxalate CoA-transferase, e.g., YfdE (from *E. coli*). In some embodiments, oxalyl-CoA decarboxylase, e.g., Oxc (from *O. formigenes*) is secreted, alone or in combination other oxalate catabolic enzymes, e.g., oxalyl-CoA synthetase, e.g., ScAAE3 (from *S. cerevisiae*) and/or formyl-CoA:oxalate CoA-transferase, e.g., Frc (from *O. formigenes*) and/or, and/or acetyl-CoA:oxalate CoA-transferase, e.g., YfdE (from *E. coli*). In some embodiments, acetyl-CoA:oxalate CoA-transferase, e.g., YfdE (from *E. coli*) is secreted, alone or in combination other oxalate catabolic enzymes, e.g., oxalyl-CoA decarboxylase, e.g., Oxc (from *O. formigenes*) and/or oxalyl-CoA synthetase, e.g., ScAAE3 (from *S. cerevisiae*) and/or formyl-CoA:oxalate CoA-transferase, e.g., Frc (from *O. formigenes*).

In some embodiments, one or more oxalate catabolism enzyme(s) selected from alanine glyoxalate aminotransferase (AGT, encoded by the AGXT gene, e.g. the human form) and/or glyoxylate/hydroxypyruvate reductase (GRHPR; an enzyme having glyoxylate reductase (GR), hydroxypyruvate reductase (HPR), and D-glycerate dehydrogenase (DGDH) activities, e.g., the human form), and/or 4-hydroxy 2-oxoglutarate aldolase (encoded by the HOGA1 gene, e.g. in humans, is secreted alone or in various combinations, or in combination with other oxalate catabolism enzymes described herein.

Pharmaceutical Compositions and Formulations

Pharmaceutical compositions comprising the genetically engineered microorganisms of the invention may be used to treat, manage, ameliorate, and/or prevent diseases or disorders in which oxalate is detrimental in a subject. In another embodiment, the disorder in which oxalate is detrimental is a disorder that results in daily urinary oxalate excretion over 40 mg per 24 hours. Pharmaceutical compositions of the invention comprising one or more genetically engineered bacteria, and/or one or more genetically engineered virus, alone or in combination with prophylactic agents, therapeutic agents, and/or pharmaceutically acceptable carriers are provided.

In certain embodiments, the pharmaceutical composition comprises one species, strain, or subtype of bacteria that are engineered to comprise one or more of the genetic modifications described herein, e.g., selected from expression of at least one oxalate catabolism enzyme, oxalate importer/transporter and/or formate exporter and/or oxalate:formate antiporter, auxotrophy, kill-switch, knock-out, etc. In alternate embodiments, the pharmaceutical composition comprises two or more species, strains, and/or subtypes of bacteria that are each engineered to comprise the genetic modifications described herein, e.g., one oxalate catabolism enzyme, oxalate importer/transporter and/or formate exporter and/or oxalate:formate antiporter, auxotrophy, kill-switch, knock-out, etc.

The pharmaceutical compositions of the disclosure may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered microorganisms may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, intravenous, subcutaneous, immediate-release, pulsatile-release, delayed-release, or sustained release). Suitable dosage amounts for the genetically engineered bacteria may range from about 104 to 1012 bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In on embodiment, the pharmaceutical composition is administered after the subject eats a meal The genetically engineered bacteria or genetically engineered virus may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the invention may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered microorganisms may be administered intravenously, e.g., by infusion or injection.

The genetically engineered microorganisms of the disclosure may be administered intrathecally. In some embodiments, the genetically engineered microorganisms of the invention may be administered orally. The genetically engineered microorganisms disclosed herein may be administered topically and formulated in the form of an ointment, cream, transdermal patch, lotion, gel, shampoo, spray, aerosol, solution, emulsion, or other form well known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The genetically engineered microorganisms disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the genetically engineered microorganisms are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

In some embodiments, enteric coating materials may be used, in one or more coating layers (e.g., outer, inner and/o intermediate coating layers). Enteric coated polymers remain unionized at low pH, and therefore remain insoluble. But as the pH increases in the gastrointestinal tract, the acidic functional groups are capable of ionisation, and the polymer swells or becomes soluble in the intestinal fluid.

Materials used for enteric coatings include Cellulose acetate phthalate (CAP), Poly(methacrylic acid-co-methyl methacrylate), Cellulose acetate trimellitate (CAT), Poly (vinyl acetate phthalate) (PVAP) and Hydroxypropyl methylcellulose phthalate (HPMCP), fatty acids, waxes, Shellac (esters of aleurtic acid), plastics and plant fibers. Additionally, Zein, Aqua-Zein (an aqueous zein formulation containing no alcohol), amylose starch and starch derivatives, and dextrins (e.g., maltodextrin) are also used. Other known enteric coatings include ethylcellulose, methylcellulose, hydroxypropyl methylcellulose, amylose acetate phthalate, cellulose acetate phthalate, hydroxyl propyl methyl cellulose phthalate, an ethylacrylate, and a methylmethacrylate.

Coating polymers also may comprise one or more of, phthalate derivatives, CAT, HPMCAS, polyacrylic acid derivatives, copolymers comprising acrylic acid and at least one acrylic acid ester, Eudragit™ S (poly(methacrylic acid, methyl methacrylate) 1:2); Eudragit L100™ S (poly(methacrylic acid, methyl methacrylate) 1:1); Eudragit L30D™ (poly(methacrylic acid, ethyl acrylate) 1:1); and (Eudragit L100-55) (poly(methacrylic acid, ethyl acrylate) 1:1) (Eudragit™ L is an anionic polymer synthesized from methacrylic acid and methacrylic acid methyl ester), polymethyl methacrylate blended with acrylic acid and acrylic ester copolymers, alginic acid, ammonia alginate, sodium, potassium, magnesium or calcium alginate, vinyl acetate copolymers, polyvinyl acetate 30D (30% dispersion in water), a neutral methacrylic ester comprising poly(dimethylaminoethylacrylate) ("Eudragit E™"), a copolymer of methylmethacrylate and ethylacrylate with trimethylammonioethyl methacrylate chloride, a copolymer of methylmethacrylate and ethylacrylate, Zein, shellac, gums, or polysaccharides, or a combination thereof.

Coating layers may also include polymers which contain Hydroxypropylmethylcellulose (HPMC), Hydroxypropylethylcellulose (HPEC), Hydroxypropylcellulose (HPC), hydroxypropylethylcellulose (HPEC), hydroxymethylpropylcellulose (HMPC), ethylhydroxyethylcellulose (EHEC) (Ethulose), hydroxyethylmethylcellulose (HEMC), hydroxymethylethylcellulose (HMEC), propylhydroxyethylcellulose (PHEC), methylhydroxyethylcellulose (MHEC), hydrophobically modified hydroxyethylcellulose (NEXTON), carboxymethyl hydroxyethylcellulose (CMHEC), Methylcellulose, Ethylcellulose, water soluble vinyl acetate copolymers, gums, polysaccharides such as alginic acid and alginates such as ammonia alginate, sodium alginate, potassium alginate, acid phthalate of carbohydrates, amylose acetate phthalate, cellulose acetate phthalate (CAP), cellulose ester phthalates, cellulose ether phthalates, hydroxypropylcellulose phthalate (HPCP), hydroxypropylethylcellulose phthalate (HPECP), hydroxyproplymethylcellulose phthalate (HPMCP), hydroxyproplymethylcellulose acetate succinate (HPMCAS).

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered microorganisms described herein.

In one embodiment, the genetically engineered microorganisms of the disclosure may be formulated in a composition suitable for administration to pediatric subjects. As is well known in the art, children differ from adults in many aspects, including different rates of gastric emptying, pH, gastrointestinal permeability, etc. (Ivanovska et al., Pediatrics, 134(2):361-372, 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the genetically engineered microorganisms may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. For example, see U.S. 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered microorganisms described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered microorganisms may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

In some embodiments, the invention provides pharmaceutically acceptable compositions that are not in the form of or incorporated into a food or edible product.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, LD50, ED50, EC50, and IC50 may be determined, and the dose ratio between toxic and therapeutic effects (LD50/ED50) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

In some embodiments, the genetically engineered viruses are prepared for delivery, taking into consideration the need for efficient delivery and for overcoming the host antiviral immune response. Approaches to evade antiviral response include the administration of different viral serotypes as par of the treatment regimen (serotype switching), formulation, such as polymer coating to mask the virus from antibody recognition and the use of cells as delivery vehicles.

In another embodiment, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

The genetically engineered bacteria of the invention may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In Vivo Methods

The recombinant bacteria of the invention may be evaluated in vivo, e.g., in an animal model. Any suitable animal model of a disease or condition in which oxalate is detrimental may be used. For example, an alanine glyoxylate aminotransferase-deficient (agxt-1-) mouse model of PHI as described by Salido et al. can be used (see, e.g., Salido et al., *Proc. Natl. Acad. Sci.* 103: 18249-54 (2006)). A glyoxylate reductase/hydroxypyruvate reductase knock-out (GRHPR-/-) mouse model of PHII can also be used (see, e.g., Knight et al., Am. J. Physiol. Renal. Physiol. 302: F688-93 (2012)). Mice deficient in the oxalate transporter protein SLC26A6 (Slc26a6-null mice) which develop hyperoxaluria can also be used (see, e.g., Jiang et al. *Nature Gen.* 38: 474-8 (2006)).

Alternatively, a rat model may be used. For example, Canales et al describe a rat model of Roux-en-Y gastric bypass (RYGB) surgery, in which high fat feeding results in steatorrhea, hyperoxaluria, and low urine pH. RYGB animals on normal fat and no oxalate diets excreted twice as much oxalate as age-matched, sham controls; hyperoxaluria was partially reversible by lowering dietary fat and oxalate content (Canales et al., Steatorrhea And Hyperoxaluria Occur After Gastric Bypass Surgery In Obese Rats Regardless Of Dietary Fat Or Oxalate; J Urol. 2013 September; 190(3): 1102-1109).

The recombinant bacterial cells of the invention may be administered to the animal, e.g., by oral gavage, and treatment efficacy is determined, e.g., by measuring urine levels of oxalic acid before and after treatment. The animal may be sacrificed, and tissue samples may be collected and analyzed.

The following Table 14 includes additional rat models which can be used to assess in vivo activity of the genetically engineered bacteria.

TABLE 14

| | | Rat Models of Calcium Oxalate Nephrolithiasis | |
|---|---|---|---|
| Induction Technique | Crystal Deposition | Renal changes and urinary changes | Strengths |
| Ethylene glycol in drinking water | Intraluminal in renal tubules of both cortex and medulla, crystals deposit in association with cellular degradation products, plaques and stones at papillary tips. | Necrotic and apoptotic renal injury, interstitial inflammation, increased synthesis and urinary excretion of OPN, Bikunin, MCP-1, alpha-1-microglobulin, hyperoxaluria, enzymuria, membranuria, and CaOx crystaluria | Easy to induce consistent hyperoxaluria, crystalluria, and CaOx nephrolithiasis |
| Hydroxy-L-proline in drinking water | No crystals in the renal fornices and pelvis | Kidneys appear normal, hyperoxaluria, enzymuria, and CaOx crystalluria, increased synthesis of OPN by papillary surface epithelial cells | Simple, more physiological than the administration of ethylene glycol or some other oxalate precursors |
| Hydroxy-L-proline mixed with food | Intraluminal in renal tubules of both cortex and medulla, plaques and stones at papillary tips | Hyperoxaluria, CaOx crystalluria, signs of renal injury and inflammation in association with the crystals | Simple, more physiological than the administration of ethylene glycol or some other oxalate precursors |
| Implantation of osmotic mini-pumps filled with oxalate | Intraluminal in renal tubules of both cortex and medulla | Hyperoxaluria, CaOx crystalluria, upregulation of TNF receptor kidney injury marker and OPN | Reliable and consistent hyperoxaluria and CaOx nephrolithiasis |
| Vitamin B-6-deficient diet | CaOx crystals intraluminal in tubules of medulla, plaques at papillary tips, stones in renal fornices, pelvis, ureters, and bladder | Hyperoxaluria, hypercalciuria, enzymuria, hypocitraturia, CaOx crystalluria | |
| Glycolic acid in diet | CaOx crystals in tubules of renal cortex and medulla, stones in renal pelvis | Hyperoxaluria | |
| Ileal resection and feeding of oxalate | CaOx crystals mixed with CaP and Ca carbonate crystals, intraluminal in both cortex and medulla, interstitial in the papilla, plaques on papillary surface | Tubular obstruction and interstitial inflammation, hyperoxaluria, hypocitraturia | Models nephrolithiasis after ileal resection or bypass surgery |

Methods of Screening

In some embodiments of the invention, the efficacy or activity of any of the importers, exporters, antiporters, and oxalate catabolism enzymes can be improved through mutations in any of these genes. Methods for directed mutation and screening are known in the art.

Generation of Bacterial Strains with Enhance Ability to Transport Metabolites of Interest Due to their ease of culture, short generation times, very high population densities and small genomes, microbes can be evolved to unique phenotypes in abbreviated timescales. Adaptive laboratory evolution (ALE) is the process of passaging microbes under selective pressure to evolve a strain with a preferred phenotype. Most commonly, this is applied to increase utilization of carbon/energy sources or adapting a strain to environmental stresses (e.g., temperature, pH), whereby mutant strains more capable of growth on the carbon substrate or under stress will outcompete the less adapted strains in the population and will eventually come to dominate the population.

This same process can be extended to any essential metabolite by creating an auxotroph. An auxotroph is a strain incapable of synthesizing an essential metabolite and must therefore have the metabolite provided in the media to grow. In this scenario, by making an auxotroph and passaging it on decreasing amounts of the metabolite, the resulting dominant strains should be more capable of obtaining and incorporating this essential metabolite.

For example, if the biosynthetic pathway for producing a metabolite of interest is disrupted a strain capable of high-affinity capture of the metabolite of interest can be evolved via ALE. First, the strain is grown in varying concentrations of the auxotrophic metabolite of interest, until a minimum concentration to support growth is established. The strain is then passaged at that concentration, and diluted into lowering concentrations of the metabolite of interest at regular intervals. Over time, cells that are most competitive for the metabolite of interest—at growth-limiting concentrations—will come to dominate the population. These strains will likely have mutations in their metabolite of interest-transporters resulting in increased ability to import the essential and limiting metabolite of interest.

Similarly, by using an auxotroph that cannot use an upstream metabolite to form the metabolite of interest, a strain can be evolved that not only can more efficiently import the upstream metabolite, but also convert the metabolite into the essential downstream metabolite of interest. These strains will also evolve mutations to increase import of the upstream metabolite, but may also contain mutations which increase expression or reaction kinetics of downstream enzymes, or that reduce competitive substrate utilization pathways.

A metabolite innate to the microbe can be made essential via mutational auxotrophy and selection applied with growth-limiting supplementation of the endogenous metabolite. However, phenotypes capable of consuming non-native compounds can be evolved by tying their consumption to the production of an essential compound. For example, if a gene from a different organism is isolated which can produce an essential compound or a precursor to an essential compound this gene can be recombinantly introduced and expressed in the heterologous host. This new host strain will now have the ability to synthesize an essential nutrient from a previously non-metabolizable substrate.

Hereby, a similar ALE process can be applied by creating an auxotroph incapable of converting an immediately downstream metabolite and selecting in growth-limiting amounts of the non-native compound with concurrent expression of the recombinant enzyme. This will result in mutations in the transport of the non-native substrate, expression and activity of the heterologous enzyme and expression and activity of downstream native enzymes. It should be emphasized that the key requirement in this process is the ability to tether the consumption of the non-native metabolite to the production of a metabolite essential to growth.

Once the basis of the selection mechanism is established and minimum levels of supplementation have been established, the actual ALE experimentation can proceed. Throughout this process several parameters must be vigilantly monitored. It is important that the cultures are maintained in an exponential growth phase and not allowed to reach saturation/stationary phase. This means that growth rates must be check during each passaging and subsequent dilutions adjusted accordingly. If growth rate improves to such a degree that dilutions become large, then the concentration of auxotrophic supplementation should be decreased such that growth rate is slowed, selection pressure is increased and dilutions are not so severe as to heavily bias subpopulations during passaging. In addition, at regular intervals cells should be diluted, grown on solid media and individual clones tested to confirm growth rate phenotypes observed in the ALE cultures.

Predicting when to halt the stop the ALE experiment also requires vigilance. As the success of directing evolution is tied directly to the number of mutations "screened" throughout the experiment and mutations are generally a function of errors during DNA replication, the cumulative cell divisions (CCD) acts as a proxy for total mutants which have been screened. Previous studies have shown that beneficial phenotypes for growth on different carbon sources can be isolated in about $10^{11.2}$ CCD$^1$. This rate can be accelerated by the addition of chemical mutagens to the cultures—such as N-methyl-N-nitro-N-nitrosoguanidine (NTG)—which causes increased DNA replication errors. However, when continued passaging leads to marginal or no improvement in growth rate the population has converged to some fitness maximum and the ALE experiment can be halted.

At the conclusion of the ALE experiment, the cells should be diluted, isolated on solid media and assayed for growth phenotypes matching that of the culture flask. Best performers from those selected are then prepped for genomic DNA and sent for whole genome sequencing. Sequencing with reveal mutations occurring around the genome capable of providing improved phenotypes, but will also contain silent mutations (those which provide no benefit but do not detract from desired phenotype). In cultures evolved in the presence of NTG or other chemical mutagen, there will be significantly more silent, background mutations. If satisfied with the best performing strain in its current state, the user can proceed to application with that strain. Otherwise the contributing mutations can be deconvoluted from the evolved strain by reintroducing the mutations to the parent strain by genome engineering techniques. See Lee, D.-H., Feist, A. M., Barrett, C. L. & Palsson, B. O. Cumulative Number of Cell Divisions as a Meaningful Timescale for Adaptive Laboratory Evolution of *Escherichia coli*. *PLoS ONE* 6, e26172 (2011).

Similar methods can be used to generate *E. coli* Nissle mutants that consume or import oxalate.

Methods of Treatment

Another aspect of the invention provides methods of treating a disorder in which oxalate is detrimental in a subject, or symptom(s) associated with the disorder in which oxalate is detrimental in a subject. In one embodiment, the disorder in which oxalate is detrimental is a disorder associated with increased levels of oxalate. In one embodiment, a disorder associated with increased levels of oxalate is a disorder in which daily urinary oxalate excretion is 40 mg or higher per 24 hours. Disorders associated with increased levels of oxalate include PHI, PHII, PHIII, secondary hyperoxaluria, enteric hyperoxaluria, dietary hyperoxaluria, idiopathic hyperoxaluria, syndrome of bacterial overgrowth, Crohn's disease, inflammatory bowel disease, hyperoxaluria following renal transplantation, hyperoxaluria after a jejunoileal bypass for obesity, hyperoxaluria after gastric ulcer surgery, and chronic mesenteric ischemia. In one embodiment, the disorder in which oxalate is detrimental is PHI. In one embodiment, the disorder in which oxalate is detrimental is PHII. In another embodiment, the disorder in which oxalate is detrimental is PHIII. In one embodiment, the disorder in which oxalate is detrimental is secondary hyperoxaluria. In another embodiment, the disorder in which oxalate is detrimental is dietary hyperoxaluria. In one embodiment, the disorder in which oxalate is detrimental is idiopathic hyperoxaluria. In another embodiment, the disorder in which oxalate is detrimental is enteric hyperoxaluria. In one embodiment, the disorder in which oxalate is detrimental is the syndrome of bacterial overgrowth. In another embodiment, the disorder in which oxalate is detrimental is Crohn's disease. In one embodiment, the disorder in which oxalate is detrimental is inflammatory bowel disease. In another embodiment, the disorder in which oxalate is detrimental is hyperoxaluria following renal transplantation. In one embodiment, the disorder in which oxalate is detrimental is hyperoxaluria after a jejunoileal bypass for obesity. In another embodiment, the disorder in which oxalate is detrimental is hyperoxaluria after gastric ulcer surgery. In one embodiment, the disorder in which oxalate is detrimental is chronic mesenteric ischemia.

The present disclosure surprisingly demonstrates that pharmaceutical compositions comprising the recombinant bacterial cells disclosed herein may be used to treat disorders in which oxalate is detrimental, such as PHI and PHI.

In one embodiment, the subject having PHI has a mutation in a AGXT gene. In another embodiment, the subject having PHII has a mutation in a GRHPR gene. In one embodiment, the subject having PHIII has a mutation in a HOGA1 gene. In another aspect, the invention provides methods for decreasing the plasma level of oxalate and/or oxalic acid in a subject by administering a pharmaceutical composition comprising a bacterial cell of the invention to the subject, thereby decreasing the plasma level of the oxalate and/or oxalic acid in the subject. In one embodiment, the subject has a disease or disorder in which oxalate is detrimental. In one embodiment, the disorder in which oxalate is detrimental is PHI.

In one embodiment, the disorder in which oxalate is detrimental is PHII. In another embodiment, the disorder in which oxalate is detrimental is PHIII. In one embodiment, the disorder in which oxalate is detrimental is secondary hyperoxaluria. In another embodiment, the disorder in which oxalate is detrimental is dietary hyperoxaluria. In one embodiment, the disorder in which oxalate is detrimental is idiopathic hyperoxaluria. In another embodiment, the disorder in which oxalate is detrimental is enteric hyperoxaluria. In one embodiment, the disorder in which oxalate is detrimental is the syndrome of bacterial overgrowth. In another embodiment, the disorder in which oxalate is detrimental is Crohn's disease. In one embodiment, the disorder in which oxalate is detrimental is inflammatory bowel disease. In another embodiment, the disorder in which oxalate is detrimental is hyperoxaluria following renal transplantation. In one embodiment, the disorder in which oxalate is detrimental is hyperoxaluria after a jejunoileal bypass for obesity. In another embodiment, the disorder in which oxalate is detrimental is hyperoxaluria after gastric ulcer surgery. In one embodiment, the disorder in which oxalate is detrimental is chronic mesenteric ischemia.

In some embodiments, the disclosure provides methods for reducing, ameliorating, or eliminating one or more symptom(s) associated with these diseases, including but not limited to fever, vomiting, diarrhea, kidney stones, oxalosis, bone disease, erythropoietin refractory anemia, skin ulcers, digital gangrene, cardiac arrhythmias, and cardiomyopathy. In some embodiments, the disease is secondary to other conditions, e.g., liver disease.

In certain embodiments, the bacterial cells disclosed herein are capable of catabolizing oxalate and/or oxalic acid in a subject in order to treat a disorder in which oxalate is detrimental. In these embodiments, a patient suffering from a disorder in which oxalate is detrimental, e.g., PHI or PHII, may be able to resume a substantially normal diet, or a diet that is less restrictive than an oxalate-free or a very low-oxalate diet. In some embodiments, the bacterial cells may be capable of catabolizing oxalate and/or oxalic acid, from additional sources, e.g., the blood, in order to treat a disorder in which oxalate is detrimental.

Figure 3:
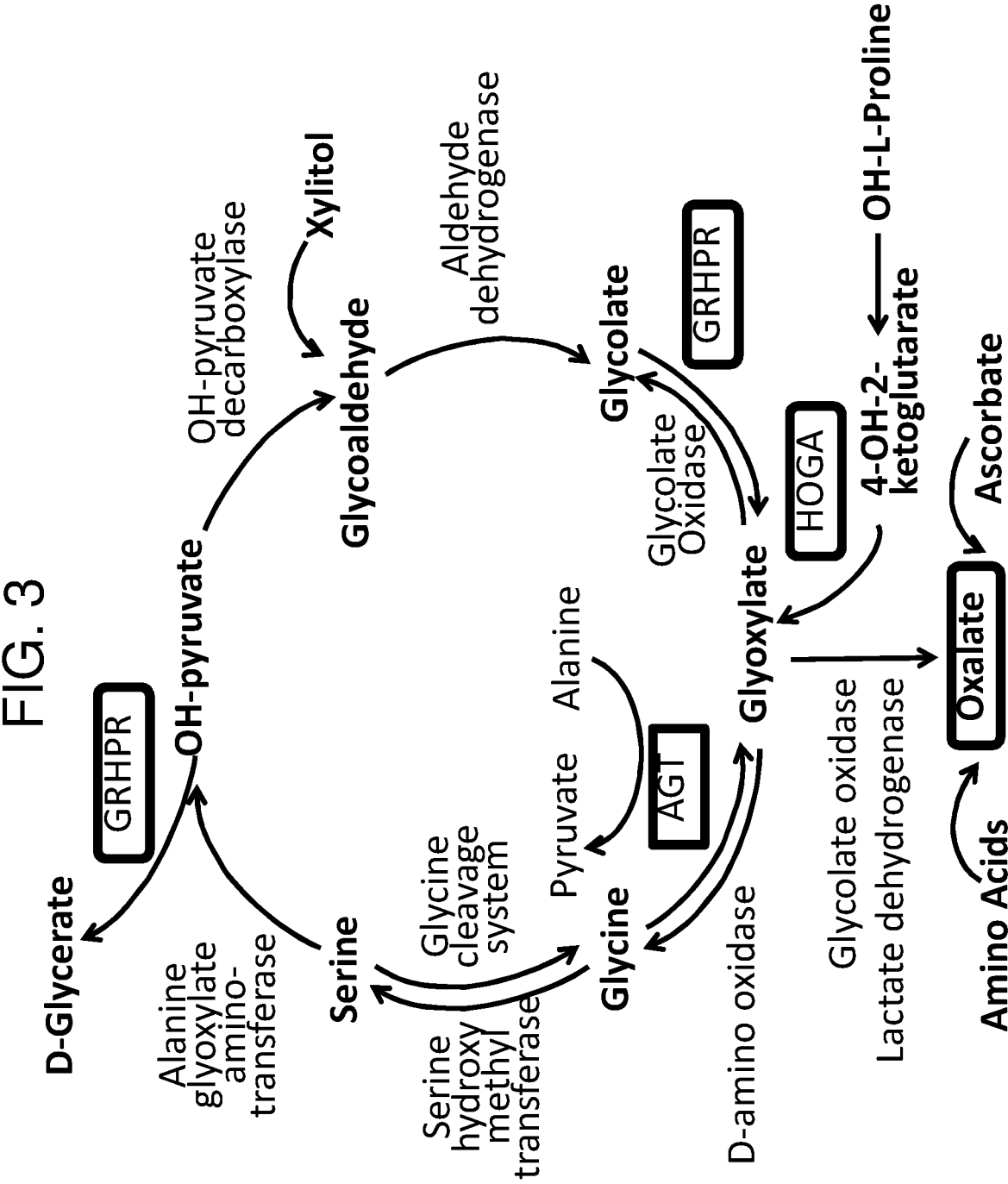
FIG. 3 depicts the oxalate pathway and proteins involved in hyperoxalurias in humans.
Figure 4A:
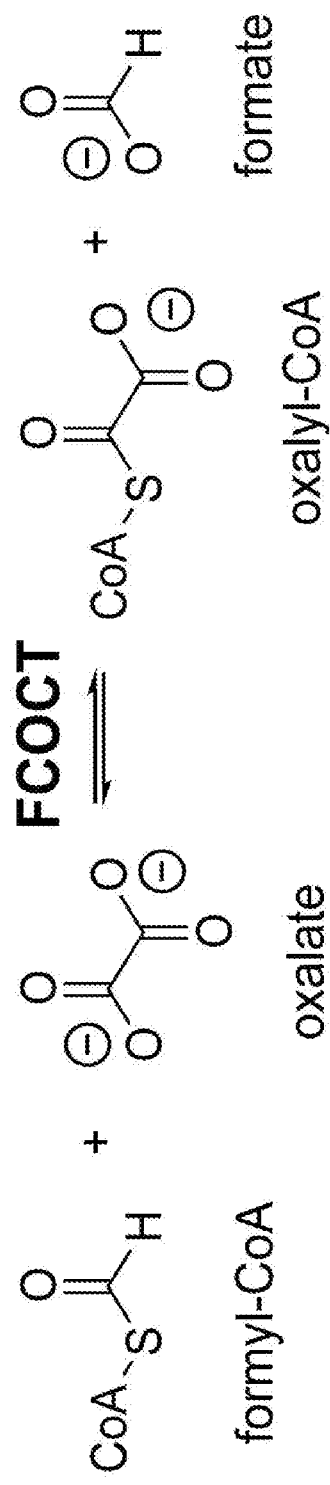
FIG. 4A, FIG. 4B, FIG. 4C, and FIG. 4D depict schematics of three types of oxalate catabolizing enzymes.
Figure 4B:
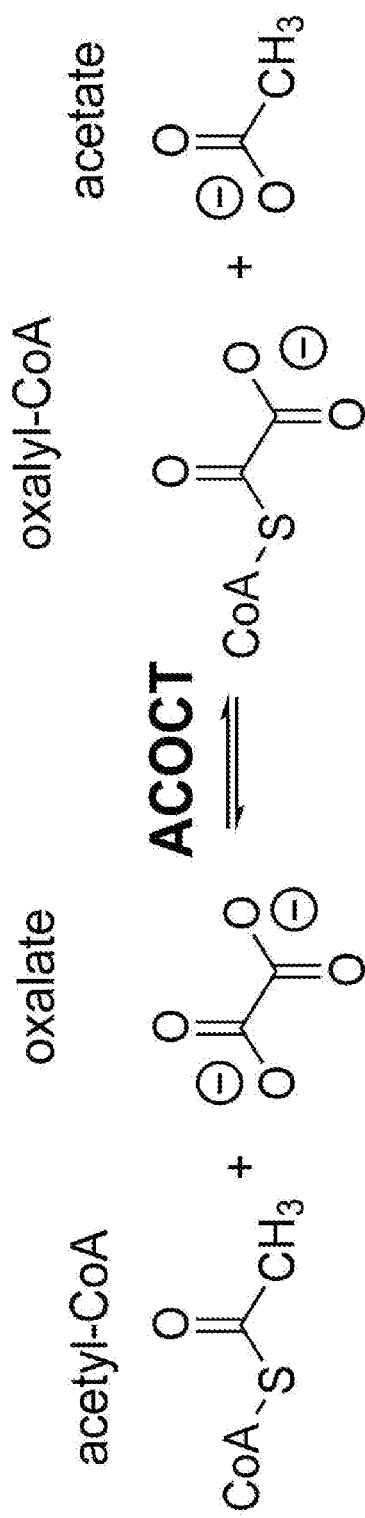
Figure 4C:
Figure 4D:
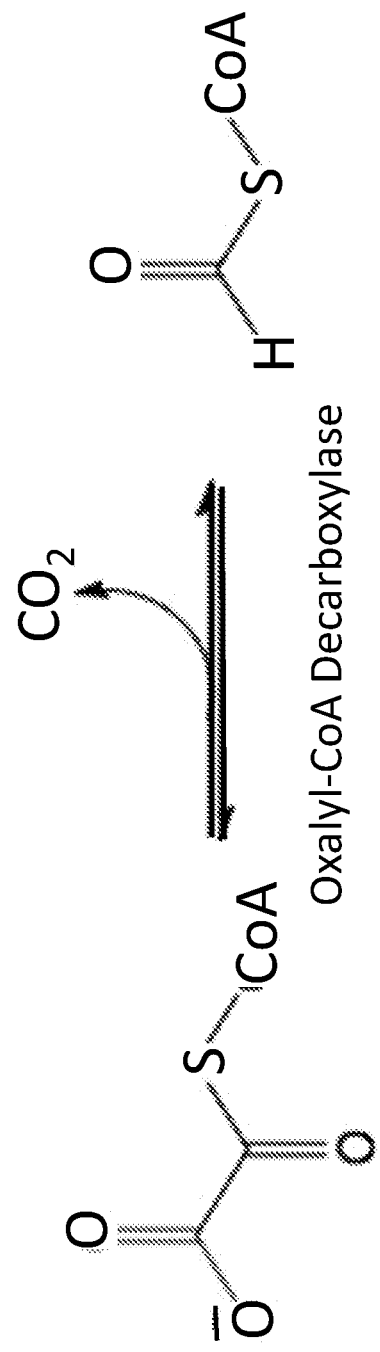
Figure 5A:
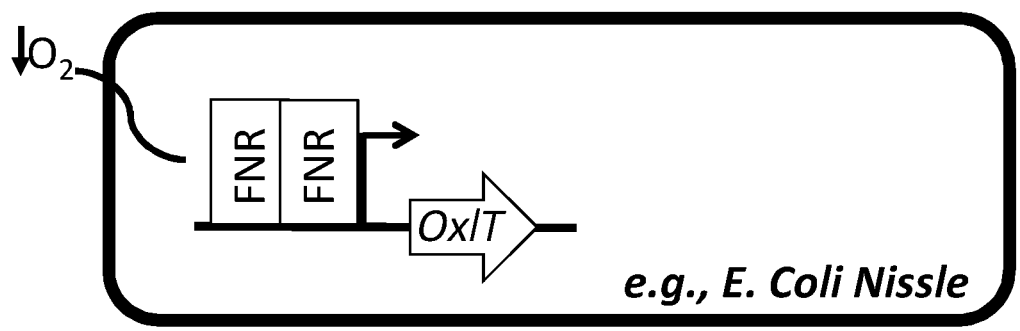
FIG. 5A, FIG. 5B, FIG. 5C, FIG. 5D, FIG. 5E, FIG. 5F, and FIG. 5G depict schematics of exemplary embodiments of the disclosure.
Figure 5B:
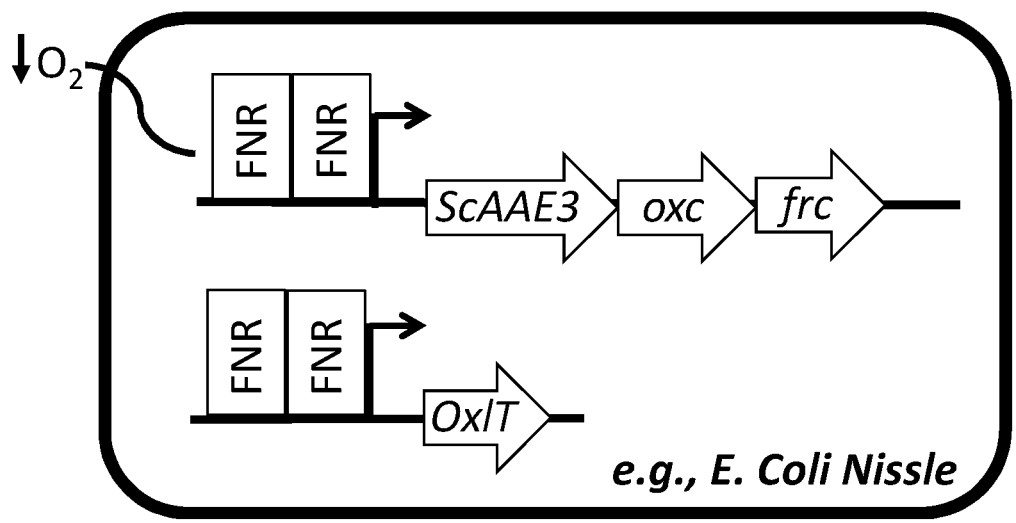
Figure 5C:
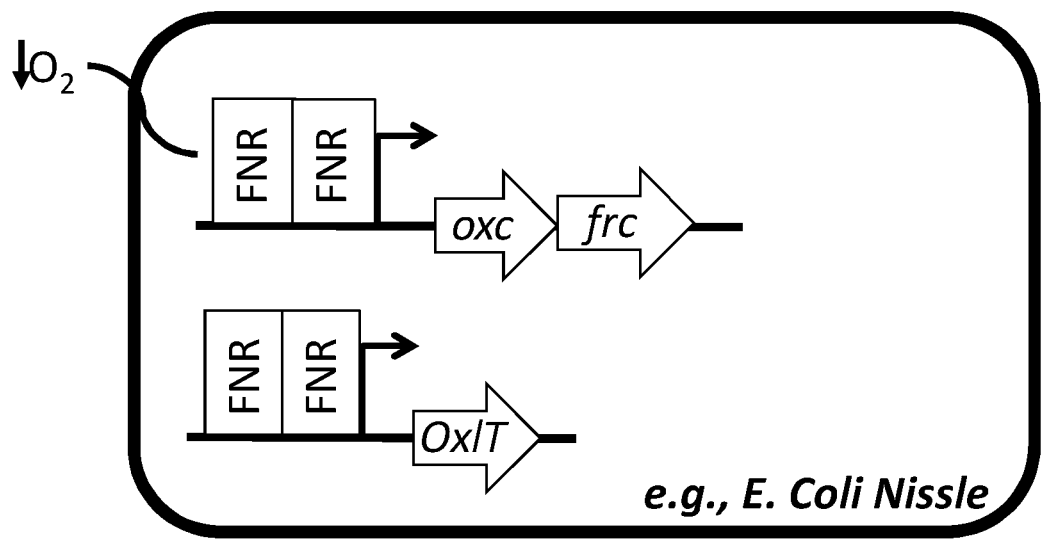
Figure 5D:
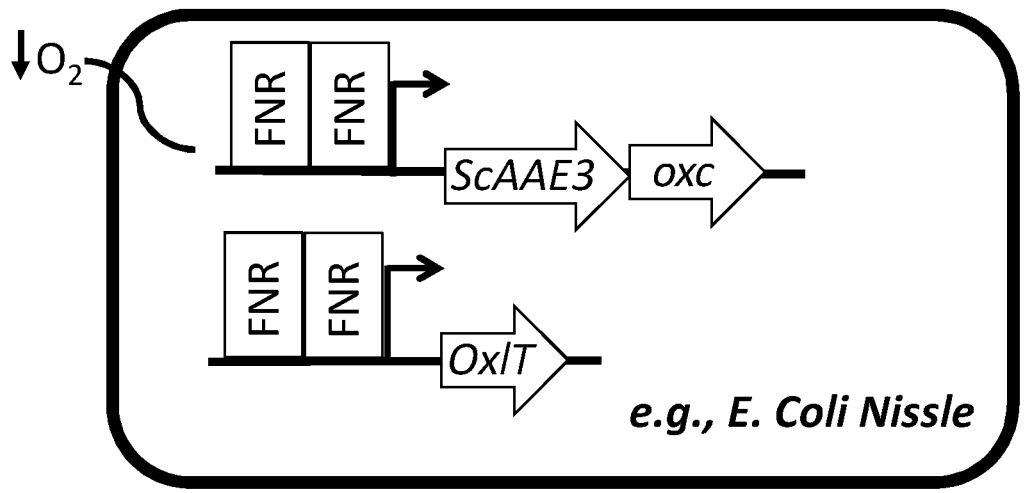
Figure 5E:
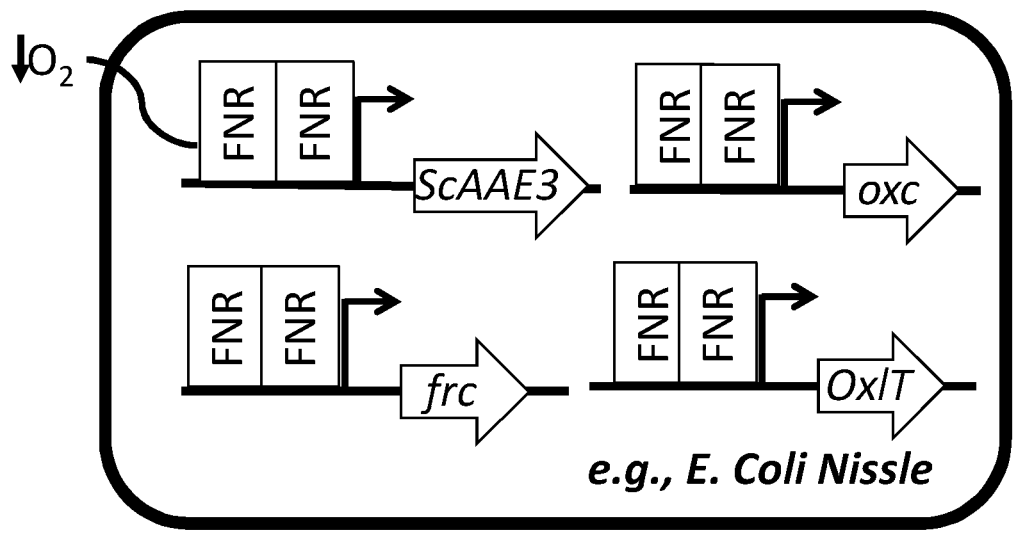
Figure 5F:
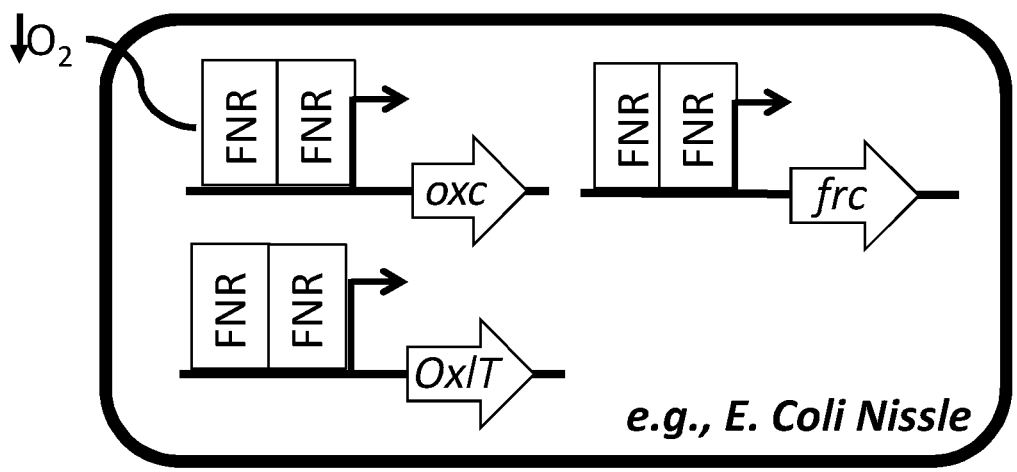
Figure 5G:
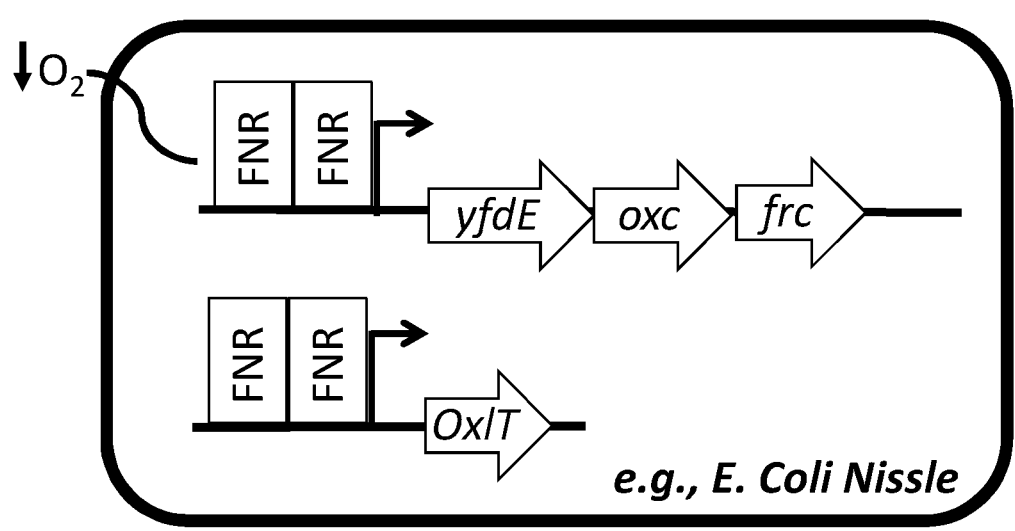

In some embodiments, dietary uptake of oxalate is suppressed by providing the genetically engineered bacteria described herein. In some embodiments, oxalate generated through metabolic pathways, e.g., in a mammal (see, e.g., FIG. 3) is reduced.

The method may comprise preparing a pharmaceutical composition with at least one genetically engineered species, strain, or subtype of bacteria described herein, and administering the pharmaceutical composition to a subject in a therapeutically effective amount. In some embodiments, the method of treating a disease or disorder associated with elevated oxalate comprises administering to a subject in need thereof an engineered bacterium comprising gene sequence(s) encoding one or more oxalate catabolism enzyme(s) or a pharmaceutical composition thereof. In some embodiments, the method of treating a disease or disorder associated with elevated oxalate comprises administering to a subject in need thereof an engineered bacterium comprising gene sequence(s) encoding one or more oxalate transporter(s) or a pharmaceutical composition thereof. In some embodiments, the method of treating a disease or disorder associated with elevated oxalate comprises administering to a subject in need thereof an engineered bacterium comprising gene sequence(s) encoding one or more formate importers(s) or a pharmaceutical composition thereof. In some embodiments, the method of treating a disease or disorder associated with elevated oxalate comprises administering to a subject in need thereof an engineered bacterium comprising gene sequence(s) encoding one or more oxalate:formate antiporter(s) or a pharmaceutical composition thereof. In some embodiments, the method of treating a disease or disorder associated with elevated oxalate comprises administering to a subject in need thereof an engineered bacterium comprising gene sequence(s) encoding one or more oxalate catabolism enzyme(s) and gene sequence(s) encoding one or more of the following: (i) one or more oxalate transporter(s); (ii) one or more formate exporter(s); (iii) one or more oxalate:formate antiporter(s); and (iv) combinations thereof or a pharmaceutical composition thereof. In some embodiments, the bacterial cells disclosed herein are administered orally, e.g., in a liquid suspension. In some embodiments, the bacterial cells disclosed herein are lyophilized in a gel cap and administered orally. In some embodiments, the bacterial cells disclosed herein are administered via a feeding tube or gastric shunt. In some embodiments, the bacterial cells disclosed herein are administered rectally, e.g., by enema. In some embodiments, the genetically engineered bacteria are administered topically, intraintestinally, intrajejunally, intraduodenally, intraileally, and/or intracolically.

In certain embodiments, the administering the pharmaceutical composition described herein is administered to reduce oxalate and/or oxalic acid levels in a subject. In some embodiments, the methods of the present disclosure reduce the oxalate and/or oxalic acid levels in a subject by at least about 10%, 20%, 25%, 30%, 40%, 50%, 60%, 70%, 75%, 80%, 85%, 90%, 95%, or more. In another embodiment, the methods of the present invention reduce the oxalate and/or oxalic acid levels in a subject by at least two-fold, three-fold, four-fold, five-fold, six-fold, seven-fold, eight-fold, nine-fold, or ten-fold. In another embodiment, the methods of the present invention reduce the daily urinary oxalate excretion of a subject to less than 40 mg per 24 hours. In some embodiments, reduction is measured by comparing the oxalate and/or oxalic acid level in a subject before and after administration of the pharmaceutical composition. In one embodiment, the oxalate and/or oxalic acid level is reduced in the gut of the subject. In one embodiment, the oxalate and/or oxalic acid level is reduced in the urine of the subject. In another embodiment, the oxalate and/or oxalic acid level is reduced in the blood of the subject. In another embodiment, the oxalate and/or oxalic acid level is reduced in the plasma of the subject. In another embodiment, the oxalate and/or oxalic acid level is reduced in the fecal matter of the subject. In another embodiment, the oxalate and/or oxalic acid level is reduced in the brain of the subject.

In one embodiment, the pharmaceutical composition described herein is administered to reduce oxalate and/or oxalic acid levels in a subject to normal levels. In another embodiment, the pharmaceutical composition described herein is administered to reduce oxalate and/or oxalic acid levels in a subject to below a normal level. In another embodiment, the pharmaceutical composition described herein is administered to reduce the daily urinary oxalate excretion of a subject to less than 40 mg per 24 hours.

In certain embodiments, the pharmaceutical composition described herein is administered to reduce oxalate levels in a subject. In some embodiments, the methods of the present disclosure reduce the oxalate levels, in a subject by at least about 10%, 20%, 25%, 30%, 40%, 50%, 60%, 70%, 75%, 80%, 85%, 90%, 95%, or more as compared to levels in an untreated or control subject. In another embodiment, the methods of the present disclosure reduce the oxalate levels, in a subject by at least two-fold, three-fold, four-fold, five-fold, six-fold, seven-fold, eight-fold, nine-fold, or ten-fold. In some embodiments, reduction is measured by comparing the oxalate levels in a subject before and after administration of the pharmaceutical composition. In one embodiment, the oxalate level is reduced in the gut of the subject. In another embodiment, the oxalate level is reduced in the blood of the subject. In another embodiment, the oxalate level is reduced in the plasma of the subject. In another embodiment, the oxalate level is reduced in the liver of the subject. In another embodiment, the oxalate level is reduced in the kidney of the subject.

In one embodiment, the pharmaceutical composition described herein is administered to reduce oxalate in a subject to a normal level.

In some embodiments, the method of treating the disorder in which oxalate is detrimental, e.g., PHI or PHII, allows one or more symptoms of the condition or disorder to improve by at least about 10%, 20%, 30%, 40%, 50%, 60%, 70%, 80%, 90%, 95%, or more. In some embodiments, the method of treating the disorder in which oxalate is detrimental, e.g., PHI or PHII, allows one or more symptoms of the condition or disorder to improve by at least about two-fold, three-fold, four-fold, five-fold, six-fold, seven-fold, eight-fold, nine-fold, or ten-fold.

Before, during, and after the administration of the pharmaceutical composition, oxalate and/or oxalic acid levels in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, kidney, liver, duodenum, jejunum, ileum, cecum, colon, rectum, and anal canal. In some embodiments, the methods may include administration of the compositions disclosed herein to reduce levels of the oxalate and/or oxalic acid. In some embodiments, the methods may include administration of the compositions of the invention to reduce the oxalate and/or oxalic acid to undetectable levels in a subject. In some embodiments, the methods may include administration of the compositions of the invention to reduce the oxalate and/or oxalic acid concentrations to undetectable levels, or to less than about 1%, 2%, 5%, 10%, 20%, 25%, 30%, 40%, 50%, 60%, 70%, 75%, 80%, 85%, 90%, or 95% of the subject's oxalate and/or oxalic acid levels prior to treatment.

In some embodiments, the recombinant bacterial cells disclosed herein produce an oxalate catabolism enzyme under exogenous environmental conditions, such as the low-oxygen environment of the mammalian gut, to reduce levels of oxalate and/or oxalic acid in the urine, blood or plasma by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions.

In one embodiment, the bacteria disclosed herein reduce plasma levels of oxalate will be reduced to less than 4 mg/dL. In one embodiment, the bacteria disclosed herein reduce plasma levels of oxalate will be reduced to less than 3.9 mg/dL. In one embodiment, the bacteria disclosed herein reduce plasma levels of oxalate, to less than 3.8 mg/dL, 3.7 mg/dL, 3.6 mg/dL, 3.5 mg/dL, 3.4 mg/dL, 3.3 mg/dL, 3.2 mg/dL, 3.1 mg/dL, 3.0 mg/dL, 2.9 mg/dL, 2.8 mg/dL, 2.7 mg/dL, 2.6 mg/dL, 2.5 mg/dL, 2.0 mg/dL, 1.75 mg/dL, 1.5 mg/dL, 1.0 mg/dL, or 0.5 mg/dL.

In one embodiment, the subject has plasma levels of at least 4 mg/dL oxalate prior to administration of the pharmaceutical composition disclosed herein. In another embodiment, the subject has plasma levels of at least 4.1 mg/dL, 4.2 mg/dL, 4.3 mg/dL, 4.4 mg/dL, 4.5 mg/dL, 4.75 mg/dL, 5.0 mg/dL, 5.5 mg/dL, 6 mg/dL, 7 mg/dL, 8 mg/dL, 9 mg/dL, or 10 mg/dL prior to administration of the pharmaceutical composition disclosed herein.

Certain unmodified bacteria will not have appreciable levels of oxalate or oxalyl-CoA processing. In embodiments using genetically modified forms of these bacteria, processing of oxalate and/or oxalyl-CoA will be appreciable under exogenous environmental conditions.

Oxalate and/or oxalic acid levels may be measured by methods known in the art. For example, plasma oxalate levels can be measured using the spectrophotometric plasma oxalate assay described by Ladwig et al. (Ladwig et. al., Clin. Chem. 51: 2377-80 (2005)). Further, urine oxalate levels can be measured for example, by using a oxalate oxidase colorimetric enzymatic assay (Kasidas and Rose, Ann. Clin. Biochem. 22: 412-9 (1985)). In some embodiments, oxalate catabolism enzyme, e.g., Frc, expression is measured by methods known in the art. In another embodiment, oxalate catabolism enzyme activity is measured by methods known in the art to assess Frc activity (see oxalate catabolism enzyme sections, supra).

In certain embodiments, the recombinant bacteria are *E. coli* Nissle. The recombinant bacteria may be destroyed, e.g., by defense factors in the gut or blood serum (Sonnenborn et al., 2009) or by activation of a kill switch, several hours or days after administration. Thus, the pharmaceutical composition comprising the recombinant bacteria may be re-administered at a therapeutically effective dose and frequency. In alternate embodiments, the recombinant bacteria are not destroyed within hours or days after administration and may propagate and colonize the gut.

In one embodiments, the bacterial cells disclosed herein are administered to a subject once daily. In another embodiment, the bacterial cells disclosed herein are administered to a subject twice daily. In another embodiment, the bacterial cells disclosed herein are administered to a subject in combination with a meal. In another embodiment, the bacterial cells disclosed herein are administered to a subject prior to a meal. In another embodiment, the bacterial cells disclosed herein are administered to a subject after a meal. In another embodiment, the bacterial cells of the invention are not administered in the form of a food or edible product or incorporated into a food or edible product. The dosage of the pharmaceutical composition and the frequency of administration may be selected based on the severity of the symptoms and the progression of the disease. The appropriate therapeutically effective dose and/or frequency of administration can be selected by a treating clinician.

The methods disclosed herein may comprise administration of a composition disclosed herein alone or in combination with one or more additional therapies, e.g., pyridoxine, citrate, orthophosphate, and magnesium, oral calcium supplementation, and bile acid sequestrants, or a low fat and/or low oxalate diet. An important consideration in the selection of the one or more additional therapeutic agents is that the agent(s) should be compatible with the bacteria disclosed herein, e.g., the agent(s) must not interfere with or kill the bacteria. In some embodiments, the genetically engineered bacteria are administered in combination with a low fat and/or low oxalate diet. In some embodiments, administration of the genetically engineered bacteria provides increased tolerance, so that the patient can consume more oxalate and/or fat.

The methods disclosed herein may further comprise isolating a plasma sample from the subject prior to administration of a composition disclosed herein and determining the level of the oxalate and/or oxalic acid in the sample. In some embodiments, the methods disclosed herein may further comprise isolating a plasma sample from the subject after to administration of a composition disclosed herein and determining the level of oxalate and/or oxalic acid in the sample.

The methods of the invention may further comprise isolating a urine sample from the subject prior to administration of a composition of the invention and determining the level of the oxalate and/or oxalic acid in the sample. In some embodiments, the methods of the invention may further comprise isolating a urine sample from the subject after to administration of a composition of the invention and determining the level of oxalate and/or oxalic acid in the sample.

In one embodiment, the methods disclosed herein further comprise comparing the level of the oxalate and/or oxalic acid in the plasma sample from the subject after administration of a composition disclosed herein to the subject to the plasma sample from the subject before administration of a composition disclosed herein to the subject. In one embodiment, a reduced level of the oxalate and/or oxalic acid in the plasma sample from the subject after administration of a composition disclosed herein indicates that the plasma levels of the oxalate and/or oxalic acid are decreased, thereby treating the disorder in which oxalate is detrimental in the subject. In one embodiment, the plasma level of oxalate and/or oxalic acid is decreased at least 10%, 20%, 30%, 40%, 50%, 60%, 70%, 80%, 90%, or 100% in the sample after administration of the pharmaceutical composition as compared to the plasma level in the sample before administration of the pharmaceutical composition. In another embodiment, the plasma level of the oxalate and/or oxalic acid is decreased at least two-fold, three-fold, four-fold, or five-fold in the sample after administration of the pharmaceutical composition as compared to the plasma level in the sample before administration of the pharmaceutical composition.

In one embodiment, the methods of the invention further comprise comparing the level of the oxalate and/or oxalic acid in the urine sample from the subject after administration of a composition of the invention to the subject to the urine sample from the subject before administration of a composition of the invention to the subject. In one embodiment, a reduced level of the oxalate and/or oxalic acid in the urine sample from the subject after administration of a composition of the invention indicates that the urine levels of the oxalate and/or oxalic acid are decreased, thereby treating the disorder in which oxalate is detrimental in the subject. In one embodiment, the urine level of oxalate and/or oxalic acid is decreased at least 10%, 20%, 30%, 40%, 50%, 60%, 70%, 80%, 90%, or 100% in the sample after administration of the pharmaceutical composition as compared to the plasma level in the sample before administration of the pharmaceutical composition. In another embodiment, the urine level of the oxalate and/or oxalic acid is decreased at least two-fold, three-fold, four-fold, or five-fold in the sample after administration of the pharmaceutical composition as compared to the urine level in the sample before administration of the pharmaceutical composition.

In one embodiment, the methods disclosed herein further comprise comparing the level of the oxalate/oxalic acid in the plasma sample from the subject after administration of a composition disclosed herein to a control level of oxalate and/or oxalic acid.

In another embodiment, the methods of the invention further comprise comparing the level of the oxalate/oxalic acid in the urine sample from the subject after administration of a composition of the invention to a control level of oxalate and/or oxalic acid.

EXAMPLES

The present invention is further illustrated by the following examples which should not be construed as limiting in any way. The contents of all cited references, including literature references, issued patents, and published patent applications, as cited throughout this application are hereby expressly incorporated herein by reference. It should further be understood that the contents of all the figures and tables attached hereto are also expressly incorporated herein by reference.

Development of Recombinant Bacterial Cells of the Invention

Example 1

Construction of Plasmids Encoding Oxalate Catabolism Enzymes and Oxalate Importers The frc gene from *Oxalobacter formigenes* (SEQ ID NO:1) and the oxc gene from *O. formigenes* (SEQ ID NO:2) are synthesized (Genewiz), fused to the Tet promoter, cloned into the high-copy plasmid pUC57-Kan by Gibson assembly, and transformed into *E. coli* DH5a as described herein to generate the plasmid pTet-Frc-OXC. The OxlT gene of *O. formigenes* fused to the Tet promoter (SEQ ID NO: 11) is synthesized (Genewiz) and cloned into the high-copy plasmid pUC57-Kan to generate the plasmid pTet-OxlT.

Example 2

Generation of Recombinant Bacteria Comprising an Importer of Oxalate and/or an Oxalate Catabolism Enzyme The pTet-Frc-OXC and pTet-OxlT plasmids described above are transformed into *E. coli* Nissle, DH5α, or PIR1. All tubes, solutions, and cuvettes are pre-chilled to 4° C. An overnight culture of *E. coli* (Nissle, DH5a or PIR1) is diluted 1:100 in 4 mL of LB and grown until it reaches an $OD_{600}$ of 0.4-0.6. 1 mL of the culture is then centrifuged at 13,000 rpm for 1 min in a 1.5 mL microcentrifuge tube and the supernatant is removed. The cells are then washed three times in pre-chilled 10% glycerol and resuspended in 40 uL pre-chilled 10% glycerol. The electroporator is set to 1.8 kV. 1 uL of a pTet-Frc-OXC and/or pTet-OxlT miniprep is added to the cells, mixed by pipetting, and pipetted into a sterile, chilled 1 mm cuvette. The dry cuvette is placed into the sample chamber, and the electric pulse is applied. 500 uL of room-temperature SOC media is immediately added, and the mixture is transferred to a culture tube and incubated at 37° C. for 1 hr. The cells are spread out on an LB plate containing 50 ug/mL Kanamycin for pTet-Frc-OXC and pTet-OxlT.

Example 3

Construction of Vectors for Reducing Oxalate

To facilitate inducible production of oxalate catabolism enzymes in *Escherichia coli* Nissle, an oxalate catabolic gene cassette comprising the genes encoding the ScAAE3 (*S. cerevisiae*), oxc (*O. formigenes*), and frc (*O. formigenes*) as well as transcriptional and translational elements, are synthesized (Gen9, Cambridge, Mass.) and cloned into vector pBR322. A second clone is generated as described above using an oxalate catabolism gene cassette comprising the genes encoding the OxlT oxalate:formate antiporter (*O. formigenes*). Each oxalate catabolic gene cassette is expressed under the control of each of the following regulatory regions: a FNR-inducible regulatory region selected from the sequences listed in Table 5 or Table 6, a tetracycline-inducible promoter, and an arabinose-inducible promoter. In certain constructs, the FNR-responsive promoter is further fused to a strong ribosome binding site sequence. For efficient translation of oxalate catabolism genes, each synthetic gene in the operon is separated by an approximately 15 base pair ribosome binding site (e.g., it can be derived from the T7 promoter/translational start site). Each gene cassette and regulatory region construct is expressed on a high-copy plasmid, a low-copy plasmid, or a chromosome.

In some embodiments, the OxlT oxalate:formate antiporter and/or ScAAE3-oxc-frc construct (or other oxalate catabolism construct) is inserted into the bacterial genome at one or more of the following insertion sites in *E. coli* Nissle: malE/K, araC/BAD, lacZ, thyA, malP/T. Any suitable insertion site may be used (see, e.g., FIG. 8). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. At the site of insertion, DNA primers that are homologous to the site of insertion and to the OxlT oxalate:formate antiporter and/or ScAAE3-oxc-frc construct (or other oxalate catabolism construct) are designed. A linear DNA fragment containing the construct with homology to the target site is generated by PCR, and lambda red recombination is performed as described below. The resulting *E. coli* Nissle bacteria are genetically engineered to express a the OxlT oxalate:formate antiporter and/or ScAAE3-oxc-frc construct (or other oxalate catabolism construct) and produce the OxlT oxalate:formate antiporter and oxalate catabolism enzymes and reduce levels of oxalate.

Example 4

Lambda Red Recombination

Lambda red recombination is used to make chromosomal modifications, e.g., to express OxlT oxalate:formate antiporter and/or ScAAE3-oxc-frc construct (or other oxalate catabolism construct or cassette) in *E. coli* Nissle. Lambda red is a procedure using recombination enzymes from a bacteriophage lambda to insert a piece of custom DNA into the chromosome of *E. coli*. A pKD46 plasmid is transformed into the *E. coli* Nissle host strain. *E. coli* Nissle cells are grown overnight in LB media. The overnight culture is diluted 1:100 in 5 mL of LB media and grown until it reaches an $OD_{600}$ of 0.4-0.6. All tubes, solutions, and cuvettes are pre-chilled to 4° C. The *E. coli* cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 1 ng of pKD46 plasmid DNA is added to the *E. coli* cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 30° C. for 1 hr. The cells are spread out on a selective media plate and incubated overnight at 30° C.

DNA sequences comprising the desired oxalate catabolism genes and transporters, e.g., those shown in Table 2 and Table 4 shown above are ordered from a gene synthesis company. The lambda enzymes are used to insert this construct into the genome of *E. coli* Nissle through homologous recombination. The construct is inserted into a specific site in the genome of *E. coli* Nissle based on its DNA sequence. In one example, the construct is pTet-OxlT in the *E. coli* Nissle genome, which was inserted at the lacZ site. In other embodiments, the constructs are pFNRS-OxlT or various oxalate catabolism gene cassettes described herein, e.g. driven by an inducible promoter, e.g., a FNRS, or a Tet or arabinose inducible promoter, inserted at any suitable chromosomal insertion site, including the sites described in FIG. 8 and elsewhere herein. The construct is inserted into a specific site, the homologous DNA sequence flanking the construct is identified, and includes approximately 50 bases on either side of the sequence. The homologous sequences are ordered as part of the synthesized gene. Alternatively, the homologous sequences may be added by PCR. The construct includes an antibiotic resistance marker that may be removed by recombination. The resulting construct comprises approximately 50 bases of homology upstream, a kanamycin resistance marker that can be removed by recombination, the OxlT oxalate:formate antiporter and/or ScAAE3-oxc-frc construct (or other oxalate catabolism construct), and approximately 50 bases of homology downstream.

Example 5

Transforming *E. coli*

Each of the plasmid-based constructs above is transformed into *E. coli* Nissle comprising pKD46. All tubes, solutions, and cuvettes are pre-chilled to 4° C. An overnight culture is diluted 1:100 in 5 mL of LB media containing ampicillin and grown until it reaches an $OD_{600}$ of 0.1. 0.05 mL of 100× L-arabinose stock solution is added to induce pKD46 lambda red expression. The culture is grown until it reaches an $OD_{600}$ of 0.4-0.6. The *E. coli* cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 0.5 µg of the construct is added to the cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 37° C. for 1 hr. The cells are spread out on an LB plate containing kanamycin and incubated overnight.

In alternate embodiments, the oxalate catabolism cassette or OxlT cassette may be inserted into the Nissle genome through homologous recombination (Genewiz, Cambridge, Mass.). Organization of the constructs and nucleotide sequences are shown in FIGS. 1-5. For example, to create a vector capable of integrating the synthesized pTet-OxlT construct into the chromosome, Gibson assembly was first used to add 1000 bp sequences of DNA homologous to the Nissle lacZ locus into the R6K origin plasmid pKD3. This targets DNA cloned between these homology arms to be integrated into the lacZ locus in the Nissle genome. Gibson assembly was used to clone the fragment between these arms. PCR was used to amplify the region from this plasmid containing the entire sequence of the homology arms, as well as the OxlT cassette between them. This PCR fragment was used to transform electrocompetent Nissle-pKD46, a strain that contains a temperature-sensitive plasmid encoding the lambda red recombinase genes. After transformation, cells were grown out for 2 hours before plating on chloramphenicol at 20 ug/mL at 37 degrees C. Growth at 37 degrees C. also cures the pKD46 plasmid. Transformants containing cassette were chloramphenicol resistant and lac-minus (lac–).

Example 6

Verifying Mutants

The presence of the OxlT and/or oxalate catabolism cassette is verified by colony PCR. Colonies are picked with a pipette tip and resuspended in 20 µL of cold ddH2O by pipetting up and down. 3 µl of the suspension is pipetted onto an index plate with appropriate antibiotic for use later. The index plate is grown at 37° C. overnight. A PCR master mix is made using 5 µl of 10× PCR buffer, 0.6 µl of 10 mM dNTPs, 0.4 µl of 50 mM Mg2SO4, 6.0 µl of 10× enhancer, and 3.0 µl of ddH2O (15 µl of master mix per PCR reaction). A 10 µM primer mix is made by mixing 2 µL of primers unique to the OxlT and/or oxalate catabolism construct (100 µM stock) into 16 µL of ddH2O. For each 20 µl reaction, 15 µL of the PCR master mix, 2.0 µL of the colony suspension (template), 2.0 µL of the primer mix, and 1.0 µL of Pfx Platinum DNA Pol are mixed in a PCR tube. The PCR thermocycler is programmed as follows, with steps 2-4 repeating 34 times: 1) 94° C. at 5:00 min., 2) 94° C. at 0:15 min., 3) 55° C. at 0:30 min., 4) 68° C. at 2:00 min., 5) 68° C. at 7:00 min., and then cooled to 4° C. The PCR products are analyzed by gel electrophoresis using 10 µL of each amplicon and 2.5 µL 5× dye. The PCR product only forms if the heterologous sequence has been inserted.

Example 7

Functional Assay Demonstrating that the Genetically Engineered Bacterial Cells of the Invention Decrease Oxalate Concentration For in vitro studies, all incubations will be performed at 37° C. Cultures of E. coli Nissle containing pTet-Frc-OXC and/or pTet-OxlT are grown overnight in LB and then diluted 1:100 in LB. The cells are grown with shaking (250 rpm) to early log phase with the appropriate antibiotics. Anhydrous tetracycline (ATC) is added to cultures at a concentration of 100 ng/mL to induce expression of Frc, Oxc, and/or OxlT, and bacteria are grown for another 3 hours. Culture broths are then inoculated at 20% in flasks containing fresh LB culture media containing 20, or 40 mmol/L ammonium oxalate and grown for 16 hours with shaking (250 rpm). A "medium blank" for each culture condition broth is also prepared whereby the "medium blank" is not inoculated with bacteria but treated under the same conditions as the inoculated broths. Following the 16-hour incubation period, broth cultures are pasteurized at 90° C. for 15 minutes, centrifuged at 5,000 rpm for 10 minutes, and supernatants filtered with a 0.45-micron filter. Oxalic acid in the supernatants is determined using Bio Vision's Oxalate Colorimetric Assay Kit (Cat. No. K663-100; Bio Vision Inc., Milpita, Calif., USA). Oxalate degradation is calculated by determining the concentration of oxalate in the inoculated media supernatant as compared to the equivalent reference "medium blank."

Example 8

Figure 6A:
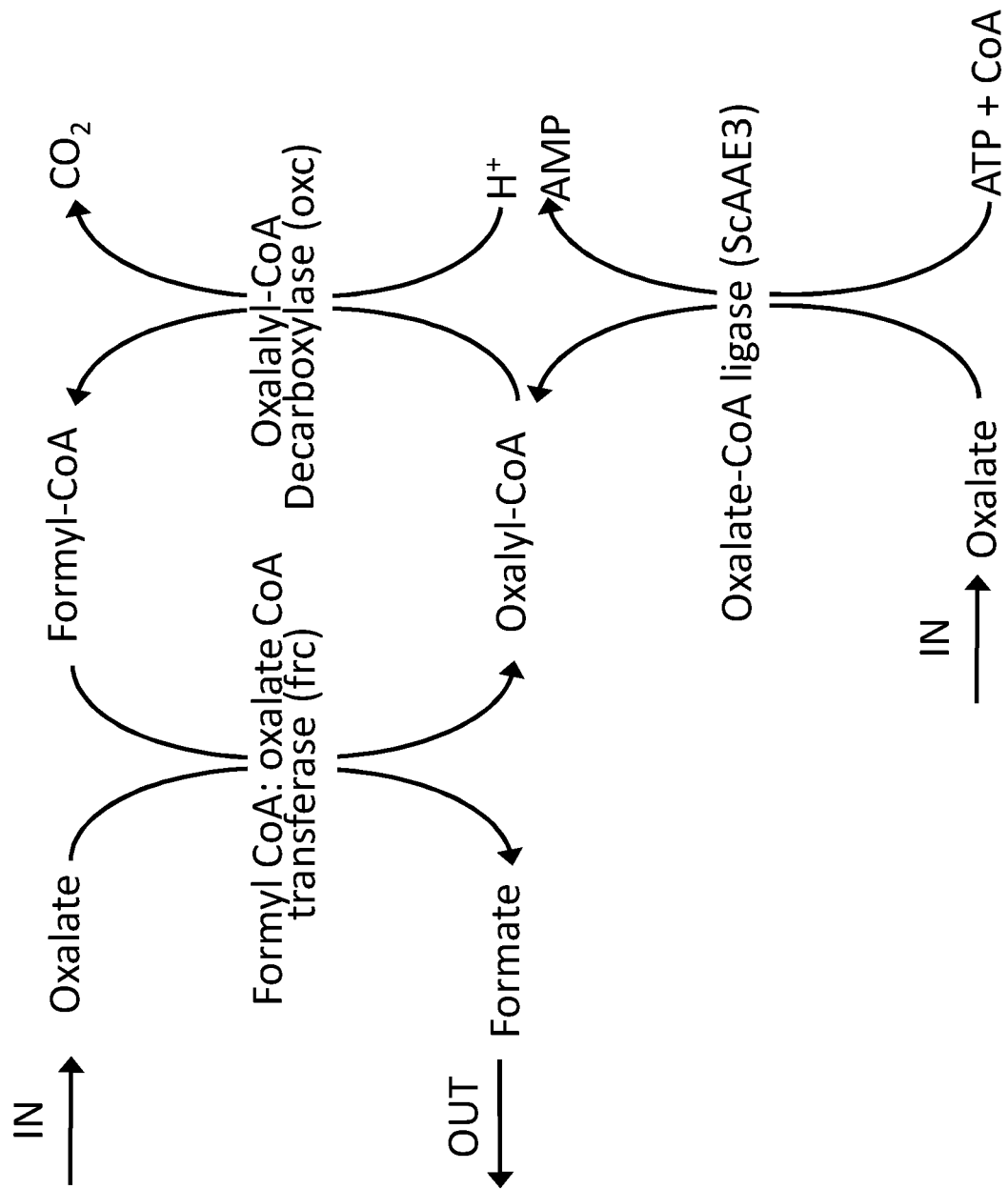
Figure 6B:
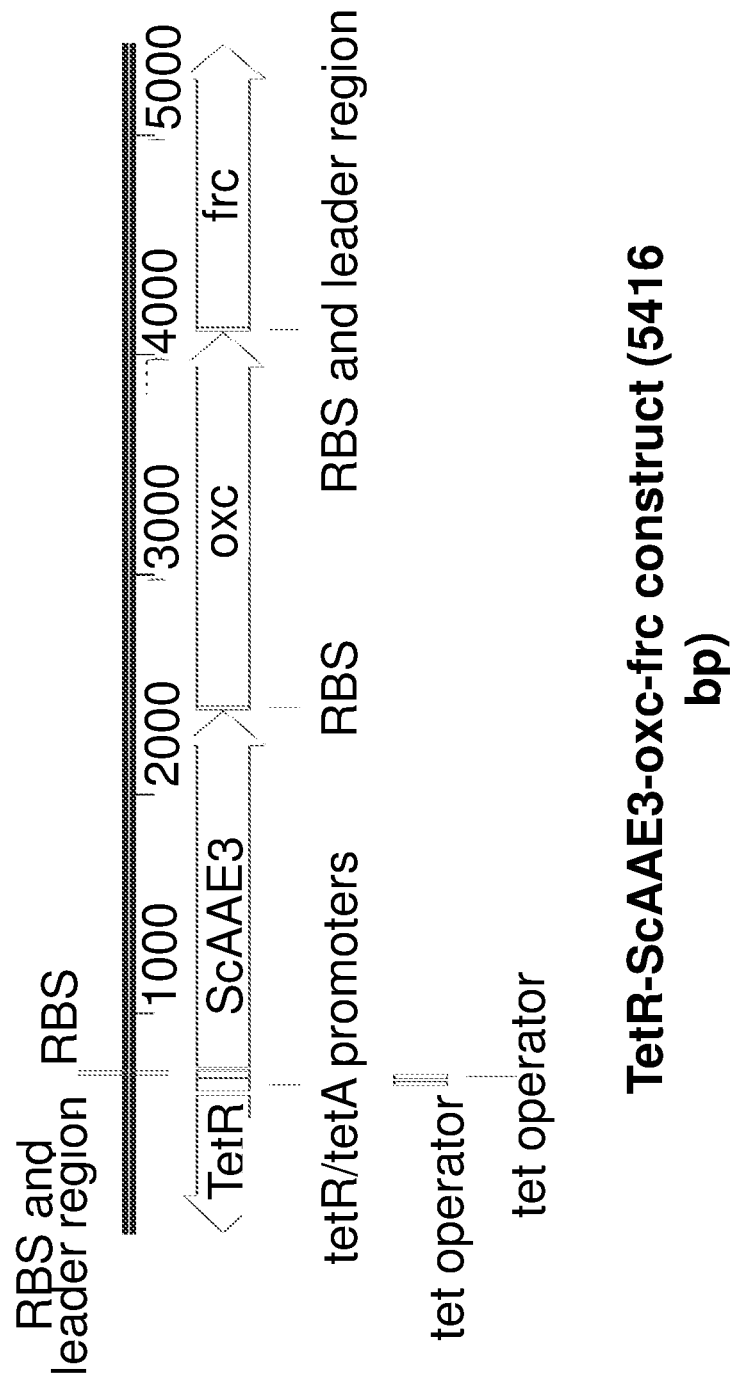
Figure 6C:
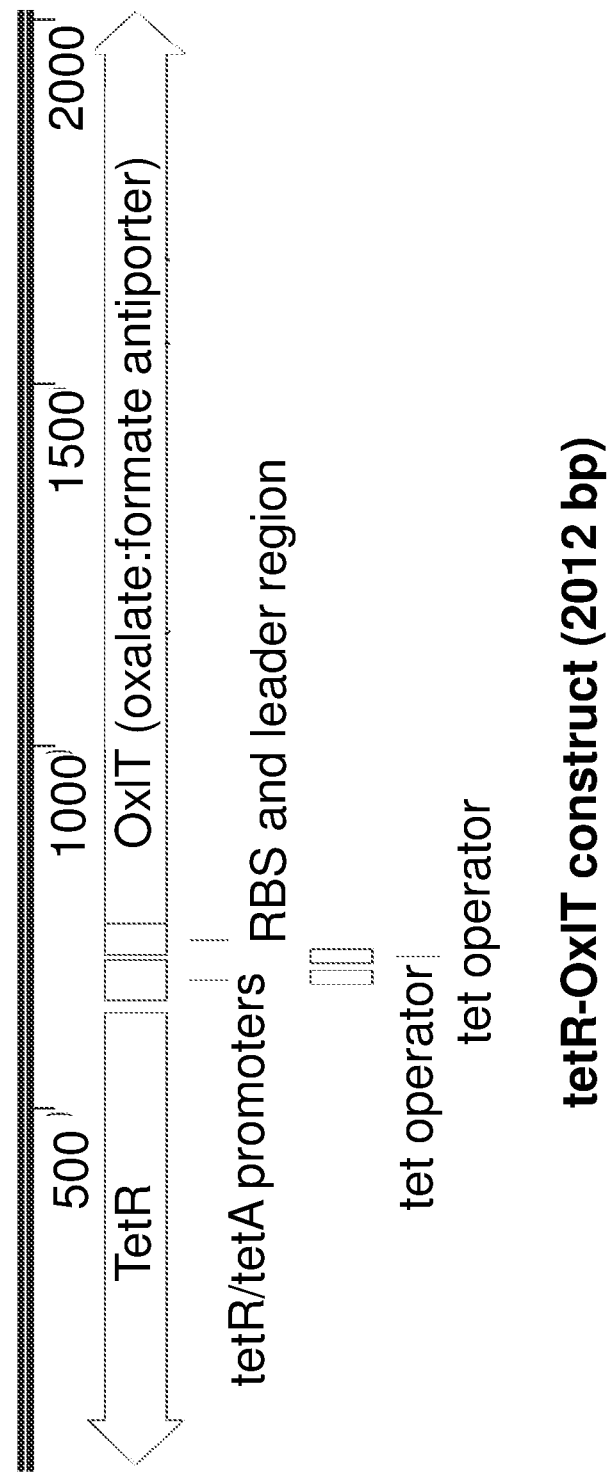

Functional Assay Demonstrating that the Genetically Engineered Bacterial Cells of the Invention Decrease Oxalate Concentration In one in vitro assay, an *Escherichia coli* Nissle strain engineered to have a chromosomal integration of OxlT (oxalate:formate antiporter), and a Puc57-kan plasmid with frc (formyl-CoA transferase from *O. formigenes*), oxc (oxalyl-CoA decarboxylase from *O. formigenes*), and ScAAE3 (oxalate-CoA ligase from *S. cerevisiae*) under control of Tet, was cultured oversight in LB and 50 ug/mL Kanamycin at 37° C. Constructs are depicted in FIG. 6B and FIG. 6C. Subcultures were then diluted 1:100 in 10 mL LB with 50 ug/mL Kanamycin in 125 mL baffled flasks in duplicate, and grown for 1.5 hours shaking at 37° C. The cultures were then induced with 1× ATC, and one flask was then grown anaerobically for 2 hours at 37° C. and one flask was grown aerobically for 2 hours at 37° C. 5 mL of each culture was then spun down, and resuspended in 1 mL of assay buffer containing 1×M9 media salts, 10 mM ammonium oxalate, 0.5% glucose, and 50 mM MOPS in 1.5 mL Eppendorf tubes. A sample from each culture was taken immediately and plated to determine the cfu/mL. Samples from each culture were then taken for testing after 1 hour, 2 hours, 3 hours, 4 hours, and 24 hours of growth. At each time point, 130 mL of sample was spun down at the maximum speed for 30 seconds, and 100 uL of supernatant was pipetted into a conical 96 well sample plate and frozen at –80° C. until processing for liquid chromatography/mass spectrometry (LC/MS) analysis as described in Example 12. FIG. 6D provides the in vitro results for this assay and shows that the recombinant bacteria reduced the amount of oxalate under both aerobic and anaerobic conditions. Table 15 lists the construct sequences used for plasmid-based pTet-ScAAE3-oxc-frc. In alternate embodiments the cassette is chromosomally integrated.

TABLE 15

Construct comprising oxalate catabolism cassette driven by Tet responsive promoter

| Description | Sequence | SEQ ID NO |
|---|---|---|
| Construct comprising TetR in reverse orientation, TetR/TetA promoter, and oxalate catabolism cassette comprising ScAAE3 (oxalate-CoA ligase from *S. cerevisiae*), oxy, oxylyl-coA decarboxylase from *O. formigenes*, and formyl-coA transferase from *O. formigenes*, separated by ribosome binding sites Underline: Tet Repressor in revers orientation Underline italic: tetR/tetA promoters Bold: coding region of oxalate catabolism enzymes Bold underline italics: RBS and leader region or RBS alone | <u>TTAAGACCCACTTTCACATTTAAGTTGTTTTTCTAATCCGCATA<br>TGATCAATTCAAGGCCGAATAAGAAGGCTGGCTCTGCACCTTG<br>GTGATCAAATAATTCGATAGCTTGTCGTAATAATGGCGGCATA<br>CTATCAGTAGTAGGTGTTTCCCTTTCTTCTTTAGCGACTTGATG<br>CTCTTGATCTTCCAATACGCAACCTAAAGTAAAATGCCCCACA<br>GCGCTGAGTGCATATAATGCATTCTCTAGTGAAAAACCTTGTT<br>GGCATAAAAAGGCTAATTGATTTTCGAGAGTTTCATACTGTTTT<br>TCTGTAGGCCGTGTACCTAAATGTACTTTTGCTCCATCGCGATG<br>ACTTAGTAAAGCACATCTAAAACTTTTAGCGTTATTACGTAAA<br>AAATCTTGCCAGCTTTCCCCTTCTAAAGGGCAAAAGTGAGTAT<br>GGTGCCTATCTAACATCTCAATGGCTAAGGCGTCGAGCAAAGC<br>CCGCTTATTTTTTACATGCCAATACAATGTAGGCTGCTCTACAC<br>CTAGCTTCTGGGCGAGTTTACGGGTTGTTAAACCTTCGATTCCG<br>ACCTCATTAAGCAGCTCTAATGCGCTGTTAATCACTTTACTTTT<br>ATCTAATCTAGACAT<br>CATTAATTCCTAATTTTT</u><u>*GTTGACACTCTATCATTGATAGAGTTATT*<br>*TTACCACTCCCTATCAGTGATAGAGAAAGT*</u><br>**<u>*GAACTCTAGAAATAATTTTGT*</u><u>*TTAACTTTAAGAAGGAGA*</u>TATAC<br>AT<br>ATGACCAGTGCAGCTACGGTGACCGCGAGCTTTAATGACA<br>CTTTTTCTGTGAGCGATAATGTCGCGGTAATCGTACCGGAA<br>ACCGATACGCAGGTCACCTACCGTGATCTTTCCCACATGGT<br>AGGACACTTTCAAACAATGTTCACGAACCCGAATAGTCCTC<br>TGTACGGGGCGGTCTTTCGTCAAGACACGGTAGCGATTAG<br>CATGCGTAACGGCCTTGAATTTATTGTGGCTTTCCTTGGAG<br>CCACGATGGATGCGAAAATTGGTGCGCCACTGAATCCCAA<br>TTATAAAGAGAAGGAGTTTAATTTTTACCTGAATGACTTAA<br>AGTCCAAAGCCATCTGCGTGCCGAAAGGCACCACCAAACT<br>GCAAAGTTCAGAAATTCTTAAGAGTGCGTCCACGTTCGGGT<br>GCTTTATTGTGGAACTGGCGTTTGACGCCACCCGTTTTCGT<br>GTTGAATATGACATTTACTCCCCGGAGGACAATTATAAACG<br>TGTGATCTACCGCAGCCTTAACAATGCTAAGTTTGTCAACA<br>CAAACCCTGTCAAGTTCCCGGGTTTCGCCCGCAGCTCGGAT<br>GTTGCACTTATTTTGCATACCTCAGGCACCACTAGTACCCC<br>AAAGACCGTACCCCTCTTGCATCTGAATATTGTCCGTTCAA<br>CCCTGAATATCGCCAACACTTACAAACTTACCCCGCTGGAT<br>CGCTCCTATGTTGTAATGCCGCTGTTTCATGTACATGGATT<br>AATCGGCGTCTTACTGAGTACGTTCCGCACCCAGGGCAGT<br>GTAGTCGTCCCGGACGGCTTTCATCCGAAGCTCTTCTGGGA<br>TCAGTTTGTTAAATATAACTGCAATTGGTTTAGTTGCGTCC<br>CAACGATCTCTATGATTATGTTGAATATGCCCAAACCGAAT<br>CCGTTTCCGCACATTCGCTTTATCCGCTCATGTAGCAGCGC<br>GCTGGCGCCAGCAACGTTTCACAAGCTGGAAAAAGAATTT<br>AATGCCCCAGTTCTGGAAGCGTACGCGATGACAGAACGAT<br>CTCATCAGATGACCAGTAACAATCTGCCTCCCGGTAAACGT<br>AAACCGGGGACCGTGGGCCAACCTCAAGGTGTAACCGTAG<br>TAATCCTGGATGACAACGATAACGTTCTGCCGCCCGGCAAA<br>GTTGGCGAGGTGTCGATCCGTGGGGAGAACGTCACCCTGG<br>GCTACGCTAATAACCCGAAAGCTAACAAAGAAAACTTCACT<br>AAACGTGAAAACTATTTCCGTACCGGGGATCAGGGCTACTT<br>CGACCCGGAGGGCTTTCTCGTGCTGACCGGCCGCATTAAA<br>GAATTGATCAATCGCGGTGGTGAAAAAATTAGTCCTATTGA<br>ACTGGACGGAATCATGCTCTCGCATCCTAAAATCGACGAG<br>GCGGTGGCGTTCGGCGTTCCAGATGATATGTATGGCCAAG<br>TCGTTCAGGCGGCAATCGTGTTGAAAAAGGGGGAAAAGAT<br>GACCTATGAAGAATTAGTGAATTTCCTGAAAAAGCATTTAG<br>CAAGCTTTAAAATCCCAACCAAAGTCTACTTTGTGGATAAG<br>CTGCCTAAAACGGCCACCGGGAAGATTCAACGTCGCGTAA<br>TCGCCGAAACCTTCGCGAAATCTAGTCGCAACAAAAGCAAA<br>CTTTAA<br><u>*AAGAAGGAGATATACAT*</u><br>ATGAGTAACGACGACAATGTAGAGTTGACTGATGGCTTTCA<br>TGTTTTGATCGATGCCCTGAAAATGAATGACATCGATACCA<br>TGTATGGTGTTGTCGGCATTCCTATCACGAACCTGGCTCGT<br>ATGTGGCAAGATGACGGTCAGCGTTTTTACAGCTTCCGTCA<br>CGAACAACACGCAGGTTATGCAGCTTCTATCGCCGGTTACA<br>TCGAAGGAAAACCTGGCGTTTGCTTGACCGTTTCCGCCCCT<br>GGCTTCCTGAACGGCGTGACTTCCCTGGCTCATGCAACCAC<br>CAACTGCTTCCCAATGATCCTGTTGAGCGGTTCCAGTGAAC<br>GTGAAATCGTCGATTTGCAACAGGGCGATTACGAAGAAAT<br>GGATCAGATGAATGTTGCACGTCCACACTGCAAAGCTTCTT<br>TCCGTATCAACAGCATCAAAGACATTCCAATCGGTATCGCT<br>CGTGCAGTTCGCACCGCTGTATCCGGACGTCCAGGTGGTG<br>TTTACGTTGACTTGCCAGCAAAACTGTTCGGTCAGACCATT** | SEQ ID NO: 34 |

TABLE 15-continued

Construct comprising oxalate catabolism cassette driven by Tet responsive promoter

| Description | Sequence | SEQ ID NO |
|---|---|---|
| | TCTGTAGAAGAAGCTAACAAACTGCTCTTCAAACCAATCGA<br>TCCAGCTCCGGCACAGATTCCTGCTGAAGACGCTATCGCTC<br>GCGCTGCTGACCTGATCAAGAACGCCAAACGTCCAGTTATC<br>ATGCTGGGTAAAGGCGCTGCATACGCACAATGCGACGACG<br>AAATCCGCGCACTGGTTGAAGAAACCGGCATCCCATTCCTG<br>CCAATGGGTATGGCTAAAGGCCTGCTGCCTGACAACCATC<br>CACAATCCGCTGCTGCAACCCGTGCTTTCGCACTGGCACAG<br>TGTGACGTTTGCGTACTGATCGGCGCTCGTCTGAACTGGCT<br>GATGCAGCACGGTAAAGGCAAAACCTGGGGCGACGAACTG<br>AAGAAATACGTTCAGATCGACATCCAGGCTAACGAAATGG<br>ACAGCAACCAGCCTATCGCTGCACCAGTTGTTGGTGACATC<br>AAGTCCGCCGTTTCCCTGCTCCGCAAAGCACTGAAAGGCG<br>CTCCAAAAGCTGACGCTGAATGGACCGGCGCTCTGAAAGC<br>CAAAGTTGACGGCAACAAAGCCAAACTGGCTGGCAAGATG<br>ACTGCCGAAACCCCATCCGGAATGATGAACTACTCCAATTC<br>CCTGGGCGTTGTTCGTGACTTCATGCTGGCAAATCCGGATA<br>TTTCCCTGGTTAACGAAGGCGCTAATGCACTCGACAACACT<br>CGTATGATTGTTGACATGCTGAAACCACGCAAACGTCTTGA<br>CTCCGGTACCTGGGGTGTTATGGGTATTGGTATGGGCTACT<br>GCGTTGCTGCAGCTGCTGTTACCGGCAAACCGGTTATCGCT<br>GTTGAAGGCGATAGCGCATTCGGTTTCTCCGGTATGGAACT<br>GGAAACCATCTGCCGTTACAACCTGCCAGTTACCGTTATCA<br>TCATGAACAATGGTGGTATCTATAAAGGTAACGAAGCAGAT<br>CCACAACCAGGCGTTATCTCCTGTACCCGTCTGACCCGTGG<br>TCGTTACGACATGATGATGGAAGCATTTGGCGGTAAAGGTT<br>ATGTTGCCAATACTCCAGCAGAACTGAAAGCTGCTCTGGAA<br>GAAGCTGTTGCTTCCGGCAAACCATGCCTGATCAACGCGAT<br>GATCGATCCAGACGCTGGTGTCGAATCTGGCCGTATCAAG<br>AGCCTGAACGTTGTAAGTAAAGTTGGCAAGAAATAA<br>*TAAGAAGGAGATATACAT*<br>ATGACTAAACCATTAGATGGAATTAATGTGCTTGACTTTAC<br>CCACGTCCAGGCAGGTCCTGCCTGTACACAGATGATGGGT<br>TTCTTGGGCGCAAACGTCATCAAGATTGAAAGACGTGGTTC<br>CGGAGATATGACTCGTGGATGGCTGCAGGACAAACCAAAT<br>GTTGATTCCCTGTATTTCACGATGTTCAACTGTAACAAACG<br>TTCGATTGAACTGGACATGAAAACCCCGGAAGGCAAAGAG<br>CTTCTGGAACAGATGATCAAGAAAGCCGACGTCATGGTCG<br>AAAACTTCGGACCAGGCGCACTGGACCGTATGGGCTTTAC<br>TTGGGAATACATTCAGGAACTGAATCCACGCGTCATTCTGG<br>CTTCCGTTAAAGGCTATGCAGAAGGCCACGCCAACGAACA<br>CCTGAAAGTTTATGAAAACGTTGCACAGTGTTCCGGCGGTG<br>CTGCAGCTACCACCGGTTTCTGGGATGGTCCTCCAACCGTT<br>TCCGGCGCTGCTCTGGGTGACTCCAACTCCGGTATGCACCT<br>GATGATCGGTATTCTGGCCGCTCTGGAAATGCGTCACAAAA<br>CCGGCCGTGGTCAGAAAGTTGCCGTCGCTATGCAGGACGC<br>TGTTCTGAATCTGGTTCGTATCAAACTGCGTGACCAGCAAC<br>GTCTGGAAAGAACCGGCATTCGGCTGAATACCCACAGGC<br>TCAGCCTAACTTTGCCTTCGACAGAGACGGTAACCCACTGT<br>CCTTCGACAACATCACTTCCGTTCCACGTGGTGGTAACGCA<br>GGTGGCGGCGGCCAGCCAGGCTGGATGCTGAAATGTAAAG<br>GTTGGGAAACCGATGCGGACTCCTACGTTTACTTCACCATC<br>GCTGCAAACATGTGGCCACAGATCTGCGACATGATCGACA<br>AGCCAGAATGGAAAGACGACCCAGCCTACAACACATTCGA<br>AGGTCGTGTTGACAAGCTGATGGACATCTTCTCCTTCATCG<br>AAACCAAGTTCGCTGACAAGGACAAATTCGAAGTTACCGAA<br>TGGGCTGCCCAGTACGGCATTCCTTGCGGTCCGGTCATGT<br>CCATGAAAGAACTGGCTCACGATCCTTCCCTGCAGAAAGTT<br>GGTACCGTCGTTGAAGTTGTCGACGAAATTCGTGGTAACCA<br>CCTGACCGTTGGCGCACCGTTCAAATTCTCCGGATTCCAGC<br>CGGAAATTACCCGTGCTCCGCTGTTGGGCGAACATACCGA<br>CGAAGTTCTGAAAGAACTGGGTCTTGACGATGCCAAGATC<br>AAGGAACTGCATGCAAAACAGGTAGTTTGA | |
| Construct comprising TetR/TetA promoter, and oxalate catabolism cassette comprising ScAAE3 (oxalate-CoA ligase from *S. cerevisiae*), | CATTAATTCCTAATTTTT<u>GTTGACACTCTATCATTGATAGAGTTATT</u><br><u>TTACCACTCCCTATCAGTGATAGAGA</u>AAAGT<br>*GAACTCTAGAAATAATTTTGTTTAACTTTAAGAAGGAGA*TATAC<br>AT<br>ATGACCAGTGCAGCTACGGTGACCGCGAGCTTTAATGACA<br>CTTTTTCTGTGAGCGATAATGTCGCGGTAATCGTACCGGAA<br>ACCGATACGCAGGTCACCTACCGTGATCTTTCCCACATGGT<br>AGGACACTTTCAAACAATGTTCACGAACCCGAATAGTCCTC<br>TGTACGGGGCGGTCTTTCGTCAAGACACGGTAGCGATTAG<br>CATGCGTAACGGCCTTGAATTTATTGTGGCTTTCCTTGGAG<br>CCACGATGGATGCGAAAATTGGTGCGCCACTGAATCCCAA | SEQ ID NO: 35 |

TABLE 15-continued

Construct comprising oxalate catabolism cassette driven by Tet responsive promoter

| Description | Sequence | SEQ ID NO |
|---|---|---|
| oxc, oxylyl-CoA decarboxylase from O. formigenes, and frc, formyl-coA transferase from O. formigenes, separated by ribosome binding sites Underline: Tet Repressor in revers orientation Underline italic: tetR/tetA promoters Bold: coding region of oxalate catabolism enzymes Bold underline italics: RBS and leader region or RBS alone | TTATAAAGAGAAGGAGTTTAATTTTTACCTGAATGACTTAA<br>AGTCCAAAGCCATCTGCGTGCCGAAAGGCACCACCAAACT<br>GCAAAGTTCAGAAATTCTTAAGAGTGCGTCCACGTTCGGGT<br>GCTTTATTGTGGAACTGGCGTTTGACGCCACCCGTTTTCGT<br>GTTGAATATGACATTTACTCCCCGGAGGACAATTATAAACG<br>TGTGATCTACCGCAGCCTTAACAATGCTAAGTTTGTCAACA<br>CAAACCCTGTCAAGTTCCCGGGTTTCGCCCGCAGCTCGGAT<br>GTTGCACTTATTTTGCATACCTCAGGCACCACTAGTACCCC<br>AAAGACCGTACCCCTCTTGCATCTGAATATTGTCCGTTCAA<br>CCCTGAATATCGCCAACACTTACAAACTTACCCCGCTGGAT<br>CGCTCCTATGTTGTAATGCCGCTGTTTCATGTACATGGATT<br>AATCGGCGTCTTACTGAGTACGTTCCGCACCCAGGGCAGT<br>GTAGTCGTCCCGGACGGCTTTCATCCGAAGCTCTTCTGGGA<br>TCAGTTTGTTAAATATAACTGCAATTGGTTTAGTTGCGTCC<br>CAACGATCTCTATGATTATGTTGAATATGCCCAAACCGAAT<br>CCGTTTCCGCACATTCGCTTTATCCGCTCATGTAGCAGCGC<br>GCTGGCGCCAGCAACGTTTCACAAGCTGGAAAAAGAATTT<br>AATGCCCCAGTTCTGGAAGCGTACGCGATGACAGAAGCAT<br>CTCATCAGATGACCAGTAACAATCTGCCTCCCGGTAAACGT<br>AAACCGGGGACCGTGGGCCAACCTCAAGGTGTAACCGTAG<br>TAATCCTGGATGACAACGATAACGTTCTGCCGCCCGGCAAA<br>GTTGGCGAGGTGTCGATCCGTGGGGAGAACGTCACCCTGG<br>GCTACGCTAATAACCCGAAAGCTAACAAAGAAAACTTCACT<br>AAACGTGAAAACTATTTCCGTACCGGGGATCAGGGCTACTT<br>CGACCCGGAGGGCTTTCTCGTGCTGACCGGCCGCATTAAA<br>GAATTGATCAATCGCGGTGGTGAAAAAATTAGTCCTATTGA<br>ACTGGACGGAATCATGCTCTCGCATCCTAAAATCGACGAG<br>GCGGTGGCGTTCGGCGTTCCAGATGATATGTATGGCCAAG<br>TCGTTCAGGCGGCAATCGTGTTGAAAAAGGGGGAAAAGAT<br>GACCTATGAAGAATTAGTGAATTTCCTGAAAAAGCATTTAG<br>CAAGCTTTAAAATCCCAACCAAAGTCTACTTTGTGGATAAG<br>CTGCCTAAAACGGCCACCGGGAAGATTCAACGTCGCGTAA<br>TCGCCGAAACCTTCGCGAAATCTAGTCGCAACAAAAGCAAA<br>CTTTAA<br>*AAGAAGGAGATATACAT*<br>ATGAGTAACGACGACAATGTAGAGTTGACTGATGGCTTTCA<br>TGTTTTGATCGATGCCCTGAAAATGAATGACATCGATACCA<br>TGTATGGTGTTGTCGGCATTCCTATCACGAACCTGGCTCGT<br>ATGTGGCAAGATGACGGTCAGCGTTTTTACAGCTTCCGTCA<br>CGAACAACACGCAGGTTATGCAGCTTCTATCGCCGGTTACA<br>TCGAAGGAAAACCTGGCGTTTGCTTGACCGTTTCCGCCCCT<br>GGCTTCCTGAACGGCGTGACTTCCCTGGCTCATGCAACCAC<br>CAACTGCTTCCCAATGATCCTGTTGAGCGGTTCCAGTGAAC<br>GTGAAATCGTCGATTTGCAACAGGGCGATTACGAAGAAAT<br>GGATCAGATGAATGTTGCACGTCCACACTGCAAAGCTTCTT<br>TCCGTATCAACAGCATCAAAGACATTCCAATCGGTATCGCT<br>CGTGCAGTTCGCACCGCTGTATCCGGACGTCCAGGTGGTG<br>TTTACGTTGACTTGCCAGCAAAACTGTTCGGTCAGACCATT<br>TCTGTAGAAGAAGCTAACAAACTGCTCTTCAAACCAATCGA<br>TCCAGCTCCGGCACAGATTCCTGCTGAAGACGCTATCGCTC<br>GCGCTGCTGACCTGATCAAGAACGCCAAACGTCCAGTTATC<br>ATGCTGGGTAAAGGCGCTGCATACGCACAATGCGACGACG<br>AAATCCGCGCACTGGTTGAAGAAACCGGCATCCCATTCCTG<br>CCAATGGGTATGGCTAAAGGCCTGCTGCCTGACAACCATC<br>CACAATCCGCTGCTGCAACCCGTGCTTTCGCACTGGCACAG<br>TGTGACGTTTGCGTACTGATCGGCGCTCGTCTGAACTGGCT<br>GATGCAGCACGGTAAAGGCAAAACCTGGGGCGACGAACTG<br>AAGAAATACGTTCAGATCGACATCCAGGCTAACGAAATGG<br>ACAGCAACCAGCCTATCGCTGCACCAGTTGTTGGTGACATC<br>AAGTCCGCCGTTTCCCTGCTCCGCAAAGCACTGAAAGGCG<br>CTCCAAAAGCTGACGCTGAATGGACCGGCGCTCTGAAAGC<br>CAAAGTTGACGGCAACAAAGCCAAACTGGCTGGCAAGATG<br>ACTGCCGAAACCCCATCCGGAATGATGAACTACTCCAATTC<br>CCTGGGCGTTGTTCGTGACTTCATGCTGGCAAATCCGGATA<br>TTTCCCTGGTTAACGAAGGCGCTAATGCACTCGACAACACT<br>CGTATGATTGTTGACATGCTGAAACCACGCAAACGTCTTGA<br>CTCCGGTACCTGGGGTGTTATGGGTATTGGTATGGGCTACT<br>GCGTTGCTGCAGCTGCTGTTACCGGCAAACCGGTTATCGCT<br>GTTGAAGGCGATAGCGCATTCGGTTTCTCCGGTATGGAACT<br>GGAAACCATCTGCCGTTACAACCTGCCAGTTACCGTTATCA<br>TCATGAACAATGGTGGTATCTATAAAGGTAACGAAGCAGAT<br>CCACAACCAGGCGTTATCTCCTGTACCCGTCTGACCCGTGG<br>TCGTTACGACATGATGATGAAGCATTTGGCGGTAAAGGTT<br>ATGTTGCCAATACTCCAGCAGAACTGAAAGCTGCTCTGGAA | |

TABLE 15-continued

Construct comprising oxalate catabolism cassette driven by Tet responsive promoter

| Description | Sequence | SEQ ID NO |
|---|---|---|
| | GAAGCTGTTGCTTCCGGCAAACCATGCCTGATCAACGCGAT<br>GATCGATCCAGACGCTGGTGTCGAATCTGGCCGTATCAAG<br>AGCCTGAACGTTGTAAGTAAAGTTGGCAAGAAATAA<br>_TAAGAAGGAGATATACAT_<br>ATGACTAAACCATTAGATGGAATTAATGTGCTTGACTTTAC<br>CCACGTCCAGGCAGGTCCTGCCTGTACACAGATGATGGGT<br>TTCTTGGGCGCAAACGTCATCAAGATTGAAAGACGTGGTTC<br>CGGAGATATGACTCGTGGATGGCTGCAGGACAAACCAAAT<br>GTTGATTCCCTGTATTTCACGATGTTCAACTGTAACAAACG<br>TTCGATTGAACTGGACATGAAAACCCCGGAAGGCAAAGAG<br>CTTCTGGAACAGATGATCAAGAAAGCCGACGTCATGGTCG<br>AAAACTTCGGACCAGGCGCACTGGACCGTATGGGCTTTAC<br>TTGGGAATACATTCAGGAACTGAATCCACGCGTCATTCTGG<br>CTTCCGTTAAAGGCTATGCAGAAGGCCACGCCAACGAACA<br>CCTGAAAGTTTATGAAAACGTTGCACAGTGTTCCGGCGGTG<br>CTGCAGCTACCACCGGTTTCTGGGATGGTCCTCCAACCGTT<br>TCCGGCGCTGCTCTGGGTGACTCCAACTCCGGTATGCACCT<br>GATGATCGGTATTCTGGCCGCTCTGGAAATGCGTCACAAAA<br>CCGGCCGTGGTCAGAAAGTTGCCGTCGCTATGCAGGACGC<br>TGTTCTGAATCTGGTTCGTATCAAACTGCGTGACCAGCAAC<br>GTCTGGAAAGAACCGGCATTCTGGCTGAATACCCACAGGC<br>TCAGCCTAACTTTGCCTTCGACAGAGACGGTAACCCACTGT<br>CCTTCGACAACATCACTTCCGTTCCACGTGGTGGTAACGCA<br>GGTGGCGGCGGCCAGCCAGGCTGGATGCTGAAATGTAAAG<br>GTTGGGAAACCGATGCGGACTCCTACGTTTACTTCACCATC<br>GCTGCAAACATGTGGCCACAGATCTGCGACATGATCGACA<br>AGCCAGAATGGAAAGACGACCCAGCCTACAACACATTCGA<br>AGGTCGTGTTGACAAGCTGATGGACATCTTCTCCTTCATCG<br>AAACCAAGTTCGCTGACAAGGACAAATTCGAAGTTACCGAA<br>TGGGCTGCCCAGTACGGCATTCCTTGCGGTCCGGTCATGT<br>CCATGAAAGAACTGGCTCACGATCCTTCCCTGCAGAAAGTT<br>GGTACCGTCGTTGAAGTTGTCGACGAAATTCGTGGTAACCA<br>CCTGACCGTTGGCGCACCGTTCAAATTCTCCGGATTCCAGC<br>CGGAAATTACCCGTGCTCCGCTGTTGGGCGAACATACCGA<br>CGAAGTTCTGAAAGAACTGGGTCTTGACGATGCCAAGATC<br>AAGGAACTGCATGCAAAACAGGTAGTTTGA | |
| Construct comprising oxalate catabolism cassette comprising ScAAE3 (oxalate-CoA ligase from S. cerevisiae), oxy, oxylyl-CoA decarboxylase from O. formigenes, and formyl-CoA transferase from O. formigenes, separated by ribosome binding sites Underline: Tet Repressor in revers orientation Underline italic: tetR/tetA promoters Bold: coding region of oxalate catabolism enzymes Bold underline italics: RBS and leader | ATGACCAGTGCAGCTACGGTGACCGCGAGCTTTAATGACA<br>CTTTTTCTGTGAGCGATAATGTCGCGGTAATCGTACCGAA<br>ACCGATACGCAGCTCACCTACCGTGATCTTTCCCACATGGT<br>AGGACACTTTCAAACAATGTTCACGAACCCGAATAGTCCTC<br>TGTACGGGGCGGTCTTTCGTCAAGACACGGTAGCGATTAG<br>CATGCGTAACGGCCTTGAATTTATTGTGGCTTTCCTTGGAG<br>CCACGATGGATGCGAAAATTGGTGCGCCACTGAATCCCAA<br>TTATAAAGAGAAGGAGTTTAATTTTTACCTGAATGACTTAA<br>AGTCCAAAGCCATCTGCGTGCCGAAAGGCACCACCAAACT<br>GCAAAGTTCAGAAATTCTTAAGAGTGCGTCCACGTTCGGGT<br>GCTTTATTGTGGAACTGGCGTTTGACGCCACCCGTTTTCGT<br>GTTGAATATGACATTTACTCCCCGGAGGACAATTATAAACG<br>TGTGATCTACCGCAGCCTTAACAATGCTAAGTTTGTCAACA<br>CAAACCCTGTCAAGTTCCCGGGTTTCGCCCGCAGCTCGGAT<br>GTTGCACTTATTTTGCATACCTCAGGCACCACTAGTACCCC<br>AAAGACCGTACCCCTCTTGCATCTGAATATTGTCCGTTCAA<br>CCCTGAATATCGCCAACACTTACAAACTTACCCCGCTGGAT<br>CGCTCCTATGTTGTAATGCCGCTGTTTCATGTACATGGATT<br>AATCGGCGTCTTACTGAGTACGTTCCGCACCCAGGGCAGT<br>GTAGTCGTCCCGGACGGCTTTCATCCGAAGCTCTTCTGGGA<br>TCAGTTTGTTAAATATAACTGCAATTGGTTTAGTTGCGTCC<br>CAACGATCTCTATGATTATGTTGAATATGCCCAAACCGAAT<br>CCGTTTCCGCACATTCGCTTTATCCGCTCATGTAGCAGCGC<br>GCTGGCGCCAGCAACGTTTCACAAGCTGGAAAAAGAATTT<br>AATGCCCCAGTTCTGGAAGCGTACGCGATGACAGAAGCAT<br>CTCATCAGATGACCAGTAACAATCTGCCTCCCGGTAAACGT<br>AAACCGGGGACCGTGGGCCAACCTCAAGGTGTAACCGTAG<br>TAATCCTGGATGACAACGATAACGTTCTGCCGCCCGGCAAA<br>GTTGGCGAGGTGTCGATCCGTGGGGAGAACGTCACCCTGG<br>GCTACGCTAATAACCCGAAAGCTAACAAAGAAAACTTCACT<br>AAACGTGAAAACTATTTCCGTACCGGGGATCAGGGCTACTT<br>CGACCCGGAGGGCTTTCTCGTGCTGACCGGCCGCATTAAA<br>GAATTGATCAATCGCGGTGGTGAAAAAATTAGTCCTATTGA<br>ACTGGACGGAATCATGCTCTCGCATCCTAAAATCGACGAG<br>GCGGTGGCGTTCGGCGTTCCAGATGATATGTATGGCCAAG<br>TCGTTCAGGCGGCAATCGTGTTGAAAAAGGGGAAAAGAT<br>GACCTATGAAGAATTAGTGAATTTCCTGAAAAAGCATTTAG | SEQ ID NO: 36 |

TABLE 15-continued

Construct comprising oxalate catabolism cassette driven by Tet responsive promoter

| Description | Sequence | SEQ ID NO |
|---|---|---|
| region or RBS alone | CAAGCTTTAAAATCCCAACCAAAGTCTACTTTGTGGATAAG<br>CTGCCTAAAACGGCCACCGGGAAGATTCAACGTCGCGTAA<br>TCGCCGAAACCTTCGCGAAATCTAGTCGCAACAAAAGCAAA<br>CTTTAA<br>AAGAAGGAGATATACAT<br>ATGAGTAACGACGACAATGTAGAGTTGACTGATGGCTTTCA<br>TGTTTTGATCGATGCCCTGAAAATGAATGACATCGATACCA<br>TGTATGGTGTTGTCGGCATTCCTATCACGAACCTGGCTCGT<br>ATGTGGCAAGATGACGGTCAGCGTTTTTACAGCTTCCGTCA<br>CGAACAACACGCAGGTTATGCAGCTTCTATCGCCGGTTACA<br>TCGAAGGAAAACCTGGCGTTTGCTTGACCGTTTCCGCCCCT<br>GGCTTCCTGAACGGCGTGACTTCCCTGGCTCATGCAACCAC<br>CAACTGCTTCCCAATGATCCTGTTGAGCGGTTCCAGTGAAC<br>GTGAAATCGTCGATTTGCAACAGGGCGATTACGAAGAAAT<br>GGATCAGATGAATGTTGCACGTCCACACTGCAAAGCTTCTT<br>TCCGTATCAACAGCATCAAAGACATTCCAATCGGTATCGCT<br>CGTGCAGTTCGCACCGCTGTATCCGGACGTCCAGGTGGTG<br>TTTACGTTGACTTGCCAGCAAAACTGTTCGGTCAGACCATT<br>TCTGTAGAAGAAGCTAACAAACTGCTCTTCAAACCAATCGA<br>TCCAGCTCCGGCACAGATTCCTGCTGAAGACGCTATCGCTC<br>GCGCTGCTGACCTGATCAAGAACGCCAAACGTCAGTTATC<br>ATGCTGGGTAAAGGCGCTGCATACGCACAATGCGACGACG<br>AAATCCGCGCACTGGTTGAAGAAACCGGCATCCCATTCCTG<br>CCAATGGGTATGGCTAAAGGCCTGCTGCCTGACAACCATC<br>CACAATCCGCTGCTGCAACCCGTGCTTTCGCACTGGCACAG<br>TGTGACGTTTGCGTACTGATCGGCGCTCGTCTGAACTGGCT<br>GATGCAGCACGGTAAAGGCAAAACCTGGGGCGACGAACTG<br>AAGAAATACGTTCAGATCGACATCCAGGCTAACGAAATGG<br>ACAGCAACCAGCCTATCGCTGCACCAGTTGTTGGTGACATC<br>AAGTCCGCCGTTTCCCTGCTCCGCAAAGCACTGAAAGGCG<br>CTCCAAAAGCTGACGCTGAATGGACCGGCGCTCTGAAAGC<br>CAAAGTTGACGGCAACAAAGCCAAACTGGCTGGCAAGATG<br>ACTGCCGAAACCCCATCCGGAATGATGAACTACTCCAATTC<br>CCTGGGCGTTGTTCGTGACTTCATGCTGGCAAATCCGGATA<br>TTTCCCTGGTTAACGAAGGCGCTAATGCACTCGACAACACT<br>CGTATGATTGTTGACATGCTGAAACCACGCAAACGTCTTGA<br>CTCCGGTACCTGGGGTGTTATGGGTATTGGTATGGGCTACT<br>GCGTTGCTGCAGCTGCTGTTACCGGCAAACCGGTTATCGCT<br>GTTGAAGGCGATAGCGCATTCGGTTTCTCCGGTATGGAACT<br>GGAAACCATCTGCCGTTACAACCTGCCAGTTACCGTTATCA<br>TCATGAACAATGGTGGTATCTATAAAGGTAACGAAGCAGAT<br>CCACAACCAGGCGTTATCTCCTGTACCCGTCTGACCCGTGG<br>TCGTTACGACATGATGATGGAAGCATTTGGCGGTAAAGGTT<br>ATGTTGCCAATACTCCAGCAGAACTGAAAGCTGCTCTGGAA<br>GAAGCTGTTGCTTCCGGCAAACCATGCCTGATCAACGCGAT<br>GATCGATCCAGACGCTGGTGTCGAATCTGGCCGTATCAAG<br>AGCCTGAACGTTGTAAGTAAAGTTGGCAAGAAATAA<br>TAAGAAGGAGATATACAT<br>ATGACTAAACCATTAGATGGAATTAATGTGCTTGACTTTAC<br>CCACGTCCAGGCAGGTCCTGCCTGTACACAGATGATGGGT<br>TTCTTGGGCGCAAACGTCATCAAGATTGAAAGACGTGGTTC<br>CGGAGATATGACTCGTGGATGGCTGCAGGACAAACCAAAT<br>GTTGATTCCCTGTATTTCACGATGTTCAACTGTAACAAACG<br>TTCGATTGAACTGGACATGAAAACCCCGGAAGGCAAAGAG<br>CTTCTGGAACAGATGATCAAGAAAGCCGACGTCATGGTCG<br>AAAACTTCGGACCAGGCGCACTGGACCGTATGGGCTTTAC<br>TTGGGAATACATTCAGGAACTGAATCCACGCGTCATTCTGG<br>CTTCCGTTAAAGGCTATGCAGAAGGCCACGCCAACGAACA<br>CCTGAAAGTTTATGAAAACGTTGCACAGTGTTCCGGCGGTG<br>CTGCAGCTACCACCGGTTTCTGGGATGGTCCTCCAACCGTT<br>TCCGGCGCTGCTCTGGGTGACTCCAACTCCGGTATGCACCT<br>GATGATCGGTATTCTGGCCGCTCTGGAAATGCGTCACAAAA<br>CCGGCCGTGGTCAGAAAGTTGCCGTCGCTATGCAGGACGC<br>TGTTCTGAATCTGGTTCGTATCAAACTGCGTGACCAGCAAC<br>GTCTGGAAAGAACCGGCATTCTGGCTGAATACCCACAGGC<br>TCAGCCTAACTTTGCCTTCGACAGAGACGGTAACCCACTGT<br>CCTTCGACAACATCACTTCCGTTCCACGTGGTGGTAACGCA<br>GGTGGCGGCGGCCAGCCAGGCTGGATGCTGAAATGTAAAG<br>GTTGGGAAACCGATGCGGACTCCTACGTTTACTTCACCATC<br>GCTGCAAACATGTGGCCACAGATCTGCGACATGATCGACA<br>AGCAGAATGGAAAGACGACCCAGCCTACAACACATTCGA<br>AGGTCGTGTTGACAAGCTGATGGACATCTTCTCCTTCATCG<br>AAACCAAGTTCGCTGACAAGGACAAATTCGAAGTTACCGAA<br>TGGGCTGCCCAGTACGGCATTCCTTGCGGTTCCGGTCATGT |  |

TABLE 15-continued

Construct comprising oxalate catabolism cassette driven by Tet responsive promoter

| Description | Sequence | SEQ ID NO |
|---|---|---|
| | CCATGAAAGAACTGGCTCACGATCCTTCCCTGCAGAAAGTT GGTACCGTCGTTGAAGTTGTCGACGAAATTCGTGGTAACCA CCTGACCGTTGGCGCACCGTTCAAATTCTCCGGATTCCAGC CGGAAATTACCCGTGCTCCGCTGTTGGGCGAACATACCGA CGAAGTTCTGAAAGAACTGGGTCTTGACGATGCCAAGATC AAGGAACTGCATGCAAAACAGGTAGTTTGA | |

Table 16 lists the construct for the chromosomally integrated OxlT at the lacZ locus.

TABLE 16

Construct comprising OxlT (oxalate:formate antiporter) driven by tet-inducible promoter

| Description | Sequence | SEQ ID NO |
|---|---|---|
| Construct comprising TetR in reverse orientation, TetR/TetA promoter, driving OxlT (oxalate:formate antiporter from *O. formigenes*) Underline: Tet Repressor in reverse orientation Underline italic: tetR/tetA promoters Bold: coding region of OxlT Bold underline italics: RBS and leader region or RBS alone | <u>TTAAGACCCACTTTCACATTTAAGTTGTTTTTCTAATCCGCATA</u><br><u>TGATCAATTCAAGGCCGAATAAGAAGGCTGGCTCTGCACCTTG</u><br><u>GTGATCAAATAATTCGATAGCTTGTCGTAATAATGGCGGCATA</u><br><u>CTATCAGTAGTAGGTGTTTCCCTTTCTTCTTTAGCGACTTGATG</u><br><u>CTCTTGATCTTCCAATACGCAACCTAAAGTAAAATGCCCCACA</u><br><u>GCGCTGAGTGCATATAATGCATTCTCTAGTGAAAAACCTTGTT</u><br><u>GGCATAAAAAGGCTAATTGATTTTCGAGAGTTTCATACTGTTTT</u><br><u>TCTGTAGGCCGTGTACCTAAATGTACTTTTGCTCCATCGCGATG</u><br><u>ACTTAGTAAAGCACATCTAAAACTTTTAGCGTTATTACGTAAA</u><br><u>AAATCTTGCCAGCTTTCCCCTTCTAAAGGGCAAAAGTGAGTAT</u><br><u>GGTGCCTATCTAACATCTCAATGGCTAAGGCGTCGAGCAAAGC</u><br><u>CCGCTTATTTTTTACATGCCAATACAATGTAGGCTGCTCTACAC</u><br><u>CTAGCTTCTGGGCGAGTTTACGGGTTGTTAAACCTTCGATTCCG</u><br><u>ACCTCATTAAGCAGCTCTAATGCGCTGTTAATCACTTTACTTTT</u><br><u>ATCTAATCTAGACAT</u><br>CATTAATTCCTAATTTTT<br>*GTTGACACTCTATCATTGATAGAGTTATTTTACCACTCCCTATCAGT*<br>*GATAGAGAA*<br>AAGTGAA<br>*CTCTAGAAATAATTTTGTTTAACTTTAAGAAGGAGATATACAT*<br>ATGAATAATCCACAAACAGGACAATCAACAGGCCTCTTGGG<br>CAATCGTTGGTTCTACTTGGTATTAGCAGTTTTGCTGATGT<br>GTATGATCTCGGGTGTCCAATATTCCTGGACACTGTACGCT<br>AACCCGGTTAAAGACAACCTTGGCGTTTCTTTGGCTGCGGT<br>TCAGACGGCTTTCACACTCTCTCAGGTCATTCAAGCTGGTT<br>CTCAGCCTGGTGGTGGTTACTTCGTTGATAAATTCGGTCCA<br>AGAATTCCATTGATGTTCGGTGGTGCGATGGTTCTCGCTGG<br>CTGGACCTTCATGGGTATGGTTGACAGTGTTCCTGCTCTGT<br>ATGCTCTTTATACTCTGGCCGGTGCAGGTGTTGGTATCGTT<br>TACGGTATCGCGATGAACACGGCTAACAGATGGTTCCCGG<br>ACAAACGCGGTCTGGCTTCCGGTTTCACCGCTGCCGGTTAC<br>GGTCTGGGTGTTCTGCCGTTCCTGCCACTGATCAGCTCCGT<br>TCTGAAAGTTGAAGGTGTTGGCGCAGCATTCATGTACACCG<br>GTTTGATCATGGGTATCCTGATTATCCTGATCGCTTTCGTT<br>ATCCGTTTCCCTGGCCAGCAAGGCGCCAAAAAACAAATCGT<br>TGTTACCGACAAGGATTTCAATTCTGGCGAAATGCTGAGAA<br>CACCACAATTCTGGGTTCTGTGGACCGCATTCTTTTCCGTT<br>AACTTTGGTGGTTTGCTGCTGGTTGCCAACAGCGTCCCTTA<br>CGGTCGCAGCCTCGGTCTTGCCGCAGGTGTGCTGACGATC<br>GGTGTTTCGATCCAGAACCTGTTCAATGGTGGTTGCCGTCC<br>TTTCTGGGGTTTCGTTTCCGATAAAATCGGCCGTTACAAAA<br>CCATGTCCGTCGTTTTCGGTATCAATGCTGTTGTTCTCGCA<br>CTTTTCCCGACGATTGCTGCCTTGGGCGATGTAGCCTTTAT<br>CGCCATGTTGGCAATCGCATTCTTCACATGGGTGGTAGCT<br>ACGCTCTGTTCCCATCGACCAACAGCGATATTTTCGGTACG<br>GCATACTCTGCCAGAAACTATGGTTTCTTCTGGGCTGCAAA<br>AGCAACTGCCTCGATCTTCGGTGGTGGTCTGGGTGCTGCA<br>ATTGCAACCAACTTCGGATGGAATACCGCTTTCCTGATTAC<br>TGCGATTACTTCTTTCATCGCATTTGCTCTGGCTACCTTCG<br>TTATTCCAAGAATGGGCCGTCCAGTCAAGAAAATGGTCAAA<br>TTGTCTCCAGAAGAAAAAGCTGTACATTAA | SEQ ID NO: 37 |

TABLE 16-continued

Construct comprising OxlT (oxalate:formate antiporter) driven by tet-inducible promoter

| Description | Sequence | SEQ ID NO |
|---|---|---|
| Construct comprising TetR/TetA promoter, driving OxlT (oxalate:formate antiporter from *O. formigenes*) | CATTAATTCCTAATTTTT<br>*GTTGACACTCTATCATTGATAGAGTTATTTTACCACTCCCTATCAGT*<br>*GATAGAGAA*<br>AAGTGAA<br>*CTCTAGAAATAATTTTGTTTAACTTTAAGAAGGAGATATACAT*<br>ATGAATAATCCACAAACAGGACAATCAACAGGCCTCTTGGG<br>CAATCGTTGGTTCTACTTGGTATTAGCAGTTTTGCTGATGT<br>GTATGATCTCGGGTGTCCAATATTCCTGGACACTGTACGCT<br>AACCCGGTTAAAGACAACCTTGGCGTTTCTTTGGCTGCGGT<br>TCAGACGGCTTTCACACTCTCTCAGGTCATTCAAGCTGGTT<br>CTCAGCCTGGTGGTGGTTACTTCGTTGATAAATTCGGTCCA<br>AGAATTCCATTGATGTTCGGTGGTGCGATGGTTCTCGCTGG<br>CTGGACCTTCATGGGTATGGTTGACAGTGTTCCTGCTCTGT<br>ATGCTCTTTATACTCTGGCCGGTGCAGGTGTTGGTATCGTT<br>TACGGTATCGCGATGAACACGGCTAACAGATGGTTCCCGG<br>ACAAACGCGGTCTGGCTTCCGGTTTCACCGCTGCCGGTTAC<br>GGTCTGGGTGTTCTGCCGTTCCTGCCACTGATCAGCTCCGT<br>TCTGAAAGTTGAAGGTGTTGGCGCAGCATTCATGTACACCG<br>GTTTGATCATGGGTATCCTGATTATCCTGATCGCTTTCGTT<br>ATCCGTTTCCCTGGCCAGCAAGGCGCCAAAAAACAAATCGT<br>TGTTACCGACAAGGATTTCAATTCTGGCGAAATGCTGAGAA<br>CACCACAATTCTGGGTTCTGTGGACCGCATTCTTTTCCGTT<br>AACTTTGGTGGTTTGCTGCTGGTTGCCAACAGCGTCCCTTA<br>CGGTCGCAGCCTCGGTCTTGCCGCAGGTGTGCTGACGATC<br>GGTGTTTCGATCCAGAACCTGTTCAATGGTGGTTGCCGTCC<br>TTTCTGGGGTTTCGTTTCCGATAAAATCGGCCGTTACAAAA<br>CCATGTCCGTCGTTTTCGGTATCAATGCTGTTGTTCTCGCA<br>CTTTTCCCGACGATTGCTGCCTTGGGCGATGTAGCCTTTAT<br>CGCCATGTTGGCAATCGCATTCTTCACATGGGGTGGTAGCT<br>ACGCTCTGTTCCCATCGACCAACAGCGATATTTTCGGTACG<br>GCATACTCTGCCAGAAACTATGGTTTCTTCTGGGCTGCAAA<br>AGCAACTGCCTCGATCTTCGGTGGTGGTCTGGGTGCTGCA<br>ATTGCAACCAACTTCGGATGGAATACCGCTTTCCTGATTAC<br>TGCGATTACTTCTTTCATCGCATTTGCTCTGGCTACCTTCG<br>TTATTCCAAGAATGGGCCGTCCAGTCAAGAAAATGGTCAAA<br>TTGTCTCCAGAAGAAAAAGCTGTACATTAA | SEQ ID NO: 38 |
| Construct comprising RBS and leader region driving OxlT (oxalate:formate antiporter from *O. formigenes*) | *CTCTAGAAATAATTTTGTTTAACTTTAAGAAGGAGATATACAT*<br>ATGAATAATCCACAAACAGGACAATCAACAGGCCTCTTGGG<br>CAATCGTTGGTTCTACTTGGTATTAGCAGTTTTGCTGATGT<br>GTATGATCTCGGGTGTCCAATATTCCTGGACACTGTACGCT<br>AACCCGGTTAAAGACAACCTTGGCGTTTCTTTGGCTGCGGT<br>TCAGACGGCTTTCACACTCTCTCAGGTCATTCAAGCTGGTT<br>CTCAGCCTGGTGGTGGTTACTTCGTTGATAAATTCGGTCCA<br>AGAATTCCATTGATGTTCGGTGGTGCGATGGTTCTCGCTGG<br>CTGGACCTTCATGGGTATGGTTGACAGTGTTCCTGCTCTGT<br>ATGCTCTTTATACTCTGGCCGGTGCAGGTGTTGGTATCGTT<br>TACGGTATCGCGATGAACACGGCTAACAGATGGTTCCCGG<br>ACAAACGCGGTCTGGCTTCCGGTTTCACCGCTGCCGGTTAC<br>GGTCTGGGTGTTCTGCCGTTCCTGCCACTGATCAGCTCCGT<br>TCTGAAAGTTGAAGGTGTTGGCGCAGCATTCATGTACACCG<br>GTTTGATCATGGGTATCCTGATTATCCTGATCGCTTTCGTT<br>ATCCGTTTCCCTGGCCAGCAAGGCGCCAAAAAACAAATCGT<br>TGTTACCGACAAGGATTTCAATTCTGGCGAAATGCTGAGAA<br>CACCACAATTCTGGGTTCTGTGGACCGCATTCTTTTCCGTT<br>AACTTTGGTGGTTTGCTGCTGGTTGCCAACAGCGTCCCTTA<br>CGGTCGCAGCCTCGGTCTTGCCGCAGGTGTGCTGACGATC<br>GGTGTTTCGATCCAGAACCTGTTCAATGGTGGTTGCCGTCC<br>TTTCTGGGGTTTCGTTTCCGATAAAATCGGCCGTTACAAAA<br>CCATGTCCGTCGTTTTCGGTATCAATGCTGTTGTTCTCGCA<br>CTTTTCCCGACGATTGCTGCCTTGGGCGATGTAGCCTTTAT<br>CGCCATGTTGGCAATCGCATTCTTCACATGGGGTGGTAGCT<br>ACGCTCTGTTCCCATCGACCAACAGCGATATTTTCGGTACG<br>GCATACTCTGCCAGAAACTATGGTTTCTTCTGGGCTGCAAA<br>AGCAACTGCCTCGATCTTCGGTGGTGGTCTGGGTGCTGCA<br>ATTGCAACCAACTTCGGATGGAATACCGCTTTCCTGATTAC<br>TGCGATTACTTCTTTCATCGCATTTGCTCTGGCTACCTTCG<br>TTATTCCAAGAATGGGCCGTCCAGTCAAGAAAATGGTCAAA<br>TTGTCTCCAGAAGAAAAAGCTGTACATTAA | SEQ ID NO: 39 |

Example 9

Genetically Engineered Bacterial Cells Decrease Oxalate Concentration Under Control of a FNR Promoter In one in vitro assay, an *Escherichia coli* Nissle strain engineered to have a chromosomal integration of OxlT (oxalate:formate antiporter), and a plasmid with frc (formyl-CoA transferase from *O. formigenes*), oxc (oxalyl-CoA decarboxylase from *O. formigenes*), and ScAAE3 (oxalate-CoA ligase from *S. cerevisiae*) under control of FNR, is cultured oversight in LB and 50 ug/mL Kanamycin at 37° C. Subcultures are then diluted 1:100 in 10 mL LB with 50 ug/mL Kanamycin in 125 mL baffled flasks in duplicate, and grown for 1.5 hours shaking at 37° C. After 1.5 hrs of growth, cultures are placed in a Coy anaerobic chamber supplying 90% $N_2$, 5% $CO_2$, and 5% $H_2$. After 4 hrs of induction, bacteria are resuspended in 1 ml of assay buffer containing 1∴M9 media salts, 10 mM ammonium oxalate, 0.5% glucose, and 50 mM MOPS in 1.5 mL Eppendorf tubes. A sample from each culture is taken immediately and plated to determine the cfu/mL. Samples from each culture are then taken for testing after 1 hour, 2 hours, 3 hours, 4 hours, and 24 hours of growth. At each time point, 130 mL of sample is spun down at the maximum speed for 30 seconds, and 100 uL of supernatant is pipetted into a conical 96 well sample plate and frozen at −80° C. until processing for liquid chromatography/mass spectrometry (LC/MS) analysis as described in Example 12. Table 17 lists the construct sequences used for a plasmid-based pFNRS-ScAAE3-oxc-frc. In some embodiments the plasmid is a high copy plasmid. In other embodiments, the plasmid is a low copy plasmid. In alternate embodiments, the FNRS-ScAAE3-oxc-frc construct is chromosomally integrated at one or more positions. Table 18 lists the construct sequence used for pFNRS-OxlT. In some embodiments, FNRS-OxlT is chromosomally integrated at one or more positions, e.g., at the lacZ locus. In other embodiments, the FNRS-OxlT construct is provided on a plasmid, e.g., a low copy or a high copy plasmid.

TABLE 17

Construct comprising oxalate catabolism cassette (pFNRS-ScAAE3-oxc-frc) under control of a FNR promoter

| Description | Sequence | SEQ ID NO |
|---|---|---|
| Construct comprising promoter with FNR binding site driving expression of cassette comprising ScAAE3 (oxalate-CoA ligase from *S. cerevisiae*), oxy, oxylyl-coA decarboxylase from *O. formigenes*, and formyl-coA transferase from *O. formigenes*, separated by ribosome binding sites Underline: FNR promoter Underline italic: FNR binding site Bold: coding region of oxalate catabolism enzymes Bold underline italics: RBS and leader region or RBS alone | GGTACCAGTTGTTCTTATTGGTGGTGTTGCTTTATGGTTGCATCGTAG<br>TAAATGGTTGTAACAAAAGCAATTTTTCCGGCTGTCTGTATACAAAA<br>ACGCCGTAAAGTTTGAGCGAAGTCAATAAACTCTCTACCCATTCAGGG<br>CAATATCTCTCTTGGATCCAAAGTGAA*CTCTAGAAATAATTTTGTTTA*<br>*ACTTTAAGAAGGAGATATACAT*ATGACCAGTGCAGCTACGGTGACC<br>GCGAGCTTTAATGACACTTTTTCTGTGAGCGATAATGTCGCGGTA<br>ATCGTACCGGAAACCGATACGCAGGTCACCTACCGTGATCTTTC<br>CCACATGGTAGGACACTTTCAAACAATGTTCACGAACCCGAATA<br>GTCCTCTGTACGGGCGGTCTTTCGTCAAGCACGGTAGCGATT<br>AGCATGCGTAACGGCCTTGAATTTATTGTGGCTTTCCTTGGAGCC<br>ACGATGGATGCGAAAATTGGTGCGCCACTGAATCCCAATTATAA<br>AGAGAAGGAGTTTAATTTTTACCTGAATGACTTAAAGTCCAAAGC<br>CATCTGCGTGCCGAAAGGCACCACCAAACTGCAAAGTTCAGAAA<br>TTCTTAAGAGTGCGTCCACGTTCGGGTGCTTTATTGTGGAACTG<br>GCGTTTGACGCCACCCGTTTTCGTGTTGAATATGACATTTACTCC<br>CCGGAGGACAATTATAAACGTGTGATCTACCGCAGCCTTAACAA<br>TGCTAAGTTTGTCAACACAAACCCTGTCAAGTTCCCGGGTTTCGC<br>CCGCAGCTCGGATGTTGCACTTATTTTGCATACCTCAGGCACCAC<br>TAGTACCCCAAAGACCGTACCCCTCTTGCATCTGAATATTGTCCG<br>TTCAACCCTGAATATCGCCAACACTTACAAACTTACCCCGCTGGA<br>TCGCTCCTATGTTGTAATGCCGCTGTTTCATGTACATGGATTAAT<br>CGGCGTCTTACTGAGTACGTTCCGCACCCAGGGCAGTGTAGTCG<br>TCCCGGACGGCTTTCATCCGAAGCTCTTCTGGGATCAGTTTGTTA<br>AATATAACTGCAATTGGTTTAGTTGCGTCCCAACGATCTCTATGA<br>TTATGTTGAATATGCCCAAACCGAATCCGTTTCCGCACATTCGCT<br>TTATCCGCTCATGTAGCAGCGCGCTGGCGCCAGCAACGTTTCAC<br>AAGCTGGAAAAAGAATTTAATGCCCCAGTTCTGGAAGCGTACGC<br>GATGACAGAAGCATCTCATCAGATGACCAGTAACAATCTGCCTC<br>CCGGTAAACGTAAACCGGGGACCGTGGGCCAACCTCAAGGTGTA<br>ACCGTAGTAATCCTGGATGACAACGATAACGTTCTGCCGCCCGG<br>CAAAGTTGGCGAGGTGTCGATCCGTGGGGAGAACGTCACCCTGG<br>GCTACGCTAATAACCCGAAAGCTAACAAAGAAAACTTCACTAAA<br>CGTGAAAACTATTTCCGTACCGGGGATCAGGGCTACTTCGACCC<br>GGAGGGCTTTCTCGTGCTGACCGGCCGCATTAAAGAATTGATCA<br>ATCGCGGTGGTGAAAAAATTAGTCCTATTGAACTGGACGGAATC<br>ATGCTCTCGCATCCTAAAATCGACGAGGCGGTGGCGTTCGGCGT<br>TCCAGATGATATGTATGGCCAAGTCGTTCAGGCGGCAATCGTGT<br>TGAAAAAGGGGGAAAAGATGACCTATGAAGAATTAGTGAATTTC<br>CTGAAAAAGCATTTAGCAAGCTTTAAAATCCCAACCAAAGTCTAC<br>TTTGTGGATAAGCTGCCTAAAACGGCCACCGGGAAGATTCAACG<br>TCGCGTAATCGCCGAAACCTTCGCGAAATCTAGTCGCAACAAAA<br>GCAAACTTTAA<br>*AAGAAGGAGATATACAT*<br>ATGAGTAACGACGACAATGTAGAGTTGACTGATGGCTTTCATGT<br>TTTGATCGATGCCCTGAAAATGAATGACATCGATACCATGTATGG<br>TGTTGTCGGCATTCCTATCACGAACCTGGCTCGTATGTGGCAAG<br>ATGACGGTCAGCGTTTTTACAGCTTCCGTCACGAACAACACGCA | SEQ ID NO: 40 |

TABLE 17-continued

Construct comprising oxalate catabolism cassette (pFNRS-ScAAE3-oxc-frc) under control of a FNR promoter

| Description | Sequence | SEQ ID NO |
|---|---|---|
| | GGTTATGCAGCTTCTATCGCCGGTTACATCGAAGGAAAACCTGG<br>CGTTTGCTTGACCGTTTCCGCCCCTGGCTTCCTGAACGGCGTGA<br>CTTCCCTGGCTCATGCAACCACCAACTGCTTCCCAATGATCCTGT<br>TGAGCGGTTCCAGTGAACGTGAAATCGTCGATTTGCAACAGGGC<br>GATTACGAAGAAATGGATCAGATGAATGTTGCACGTCCACACTG<br>CAAAGCTTCTTTCCGTATCAACAGCATCAAAGACATTCCAATCGG<br>TATCGCTCGTGCAGTTCGCACCGCTGTATCCGGACGTCCAGGTG<br>GTGTTTACGTTGACTTGCCAGCAAAACTGTTCGGTCAGACCATTT<br>CTGTAGAAGAAGCTAACAAACTGCTCTTCAAACCAATCGATCCA<br>GCTCCGGCACAGATTCCTGCTGAAGACGCTATCGCTCGCGCTGC<br>TGACCTGATCAAGAACGCCAAACGTCCAGTTATCATGCTGGGTA<br>AAGGCGCTGCATACGCACAATGCGACGACGAAATCCGCGCACTG<br>GTTGAAGAAACCGGCATCCCATTCCTGCCAATGGGTATGGCTAA<br>AGGCCTGCTGCCTGACAACCATCCACAATCCGCTGCTGCAACCC<br>GTGCTTTCGCACTGGCACAGTGTGACGTTTGCGTACTGATCGGC<br>GCTCGTCTGAACTGGCTGATGCAGCACGGTAAAGGCAAAACCTG<br>GGGCGACGAACTGAAGAAATACGTTCAGATCGACATCCAGGCTA<br>ACGAAATGGACAGCAACCAGCCTATCGCTGCACCAGTTGTTGGT<br>GACATCAAGTCCGCCGTTTCCCTGCTCCGCAAAGCACTGAAAGG<br>CGCTCCAAAAGCTGACGCTGAATGGACCGGCGCTCTGAAAGCCA<br>AAGTTGACGGCAACAAAGCCAAACTGGCTGGCAAGATGACTGCC<br>GAAACCCCATCCGGAATGATGAACTACTCCAATTCCCTGGGCGT<br>TGTTCGTGACTTCATGCTGGCAAATCCGGATATTTCCCTGGTTAA<br>CGAAGGCGCTAATGCACTCGACAACACTCGTATGATTGTTGACA<br>TGCTGAAACCACGCAAACGTCTTGACTCCGGTACCTGGGGTGTT<br>ATGGGTATTGGTATGGGCTACTGCGTTGCTGCAGCTGCTGTTAC<br>CGGCAAACCGGTTATCGCTGTTGAAGGCGATAGCGCATTCGGTT<br>TCTCCGGTATGGAACTGGAAACCATCTGCCGTTACAACCTGCCA<br>GTTACCGTTATCATCATGAACAATGGTGGTATCTATAAAGGTAAC<br>GAAGCAGATCCACAACCAGGCGTTATCTCCTGTACCCGTCTGAC<br>CCGTGGTCGTTACGACATGATGATGGAAGCATTTGGCGGTAAAG<br>GTTATGTTGCCAATACTCCAGCAGAACTGAAAGCTGCTCTGGAA<br>GAAGCTGTTGCTTCCGGCAAACCATGCCTGATCAACGCGATGAT<br>CGATCCAGACGCTGGTGTCGAATCTGGCCGTATCAAGAGCCTGA<br>ACGTTGTAAGTAAAGTTGGCAAGAAATAA<br><u>TAAGAAGGAGATATACAT</u><br>ATGACTAAACCATTAGATGGAATTAATGTGCTTGACTTTACCCAC<br>GTCCAGGCAGGTCCTGCCTGTACACAGATGATGGGTTTCTTGGG<br>CGCAAACGTCATCAAGATTGAAAGACGTGGTTCCGGAGATATGA<br>CTCGTGGATGGCTGCAGGACAAACCAAATGTTGATTCCCTGTAT<br>TTCACGATGTTCAACTGTAACAAACGTTCGATTGAACTGGACATG<br>AAAACCCCGGAAGGCAAAGAGCTTCTGGAACAGATGATCAAGAA<br>AGCCGACGTCATGGTCGAAAACTTCGGACCAGGCGCACTGGACC<br>GTATGGGCTTTACTTGGGAATACATTCAGGAACTGAATCCACGC<br>GTCATTCTGGCTTCCGTTAAAGGCTATGCAGAAGGCCACGCCAA<br>CGAACACCTGAAAGTTTATGAAAACGTTGCACAGTGTTCCGGCG<br>GTGCTGCAGCTACCACCGGTTTCTGGGATGGTCCTCCAACCGTT<br>TCCGGCGCTGCTCTGGGTGACTCCAACTCCGGTATGCACCTGAT<br>GATCGGTATTCTGGCCGCTCTGGAAATGCGTCACAAAACCGGCC<br>GTGGTCAGAAAGTTGCCGTCGCTATGCAGGACGCTGTTCTGAAT<br>CTGGTTCGTATCAAACTGCGTGACCAGCAACGTCTGGAAAGAAC<br>CGGCATTCTGGCTGAATACCCACAGGCTCAGCCTAACTTTGCCTT<br>CGACAGAGACGGTAACCCACTGTCCTTCGACAACATCACTTCCG<br>TTCCACGTGGTGGTAACGCAGGTGGCGGCGGCCAGCCAGGCTG<br>GATGCTGAAATGTAAAGGTTGGGAAACCGATGCGGACTCCTACG<br>TTTACTTCACCATCGCTGCAAACATGTGGCCACAGATCTGCGACA<br>TGATCGACAAGCCAGAATGGAAAGACGACCCAGCCTACAACACA<br>TTCGAAGGTCGTGTTGACAAGCTGATGGACATCTTCTCCTTCATC<br>GAAACCAAGTTCGCTGACAAGGACAAATTCGAAGTTACCGAATG<br>GGCTGCCCAGTACGGCATTCCTTGCGGTCCGGTCATGTCCATGA<br>AAGAACTGGCTCACGATCCTTCCCTGCAGAAAGTTGGTACCGTC<br>GTTGAAGTTGTCGACGAAATTCGTGGTAACCACCTGACCGTTGG<br>CGCACCGTTCAAATTCTCCGGATTCCAGCCGGAAATTACCCGTG<br>CTCCGCTGTTGGGCAACATACCGACGAAGTTCTGAAAGAACTG<br>GGTCTTGACGATGCCAAGATCAAGGAACTGCATGCAAAACAGGT<br>AGTTTGA | |
| FNR promoter with RBS and leader region; FNR binding site | GGTACCAGTTGTTCTTATTGGTGGTGTTGCTTTATGGTTGCATCGTAG<br>TAAATGGTTGTAACAAAAGCAATTTTTCCGGCTGTCTGTATACAAAA<br>ACGCCGTAAAGT<u>TTGAGCGAAGTCAA</u>TAAACTCTCTACCCATTCAGGG<br>CAATATCTCTCTTGGATCCAAAGTGAACTCTAGAAATAATTTTGTTT<br>AACTTTAAGAAGGAGATATACAT | SEQ ID NO: 41 |

TABLE 17-continued

Construct comprising oxalate catabolism cassette (pFNRS-ScAAE3-oxc-frc) under control of a FNR promoter

| Description | Sequence | SEQ ID NO |
|---|---|---|
| is italic underlined; RBS and leader region is bold underlined | | |
| FNR promoter without RBS and leader region;; FNR binding site is italic underlined; | GGTACCAGTTGTTCTTATTGGTGGTGTTGCTTTATGGTTGCATCGTAG TAAATGGTTGTAACAAAAGCAATTTTTCCGGCTGTCTGTATACAAAA ACGCCGTAAAGT*TTGAGCGAAGTCAA*TAAACTCTCTACCCATTCAGGG CAATATCTCTCTTGGATCCAAAGTGAA | |

TABLE 18

Construct comprising OxlT (oxalate:formate antiporter) under control of a FNR promoter

| Description | Sequence | SEQ ID NO |
|---|---|---|
| Construct comprising FNR promoter, driving OxlT (oxalate:formate antiporter from *O. formigenes*) Underline: FNR promoter Underline italic: FNR binding site Bold: coding region of OxlT Bold underline italics: RBS and leader region or RBS alone | <u>GGTACCAGTTGTTCTTATTGGTGGTGTTGCTTTATGGTTGCATCGTAG</u><br><u>TAAATGGTTGTAACAAAAGCAATTTTTCCGGCTGTCTGTATACAAAA</u><br><u>ACGCCGTAAAGT*TTGAGCGAAGTCAA*TAAACTCTCTACCCATTCAGGG</u><br><u>CAATATCTCTCTTGGATCCAAAGTGAACTCTAGAAATAATTTTGTTT</u><br><u>AACTTTAAGAAGGAGATATACAT</u><br>ATGAATAATCCACAAACAGGACAATCAACAGGCCTCTTGGGCAA<br>TCGTTGGTTCTACTTGGTATTAGCAGTTTTGCTGATGTGTATGAT<br>CTCGGGTGTCCAATATTCCTGGACACTGTACGCTAACCCGGTTA<br>AAGACAACCTTGGCGTTTCTTTGGCTGCGGTTCAGACGGCTTTC<br>ACACTCTCTCAGGTCATTCAAGCTGGTTCTCAGCCTGGTGGTGG<br>TTACTTCGTTGATAAATTCGGTCCAAGAATTCCATTGATGTTCGG<br>TGGTGCGATGGTTCTCGCTGGCTGGACCTTCATGGGTATGGTTG<br>ACAGTGTTCCTGCTCTGTATGCTCTTTATACTCTGGCCGGTGCA<br>GGTGTTGGTATCGTTTACGGTATCGCGATGAACACGGCTAACAG<br>ATGGTTCCCGGACAAACGCGGTCTGGCTTCCGGTTTCACCGCTG<br>CCGGTTACGGTCTGGGTGTTCTGCCGTTCCTGCCACTGATCAGC<br>TCCGTTCTGAAAGTTGAAGGTGTTGGCGCAGCATTCATGTACAC<br>CGGTTTGATCATGGGTATCCTGATTATCCTGATCGCTTTCGTTAT<br>CCGTTTCCCTGGCCAGCAAGGCGCCAAAAAACAAATCGTTGTTA<br>CCGACAAGGATTTCAATTCTGGCGAAATGCTGAGAACACCACAA<br>TTCTGGGTTCTGTGGACCGCATTCTTTTCCGTTAACTTTGGTGGT<br>TTGCTGCTGGTTGCCAACAGCGTCCCTTACGGTCGCAGCCTCGG<br>TCTTGCCGCAGGTGTGCTGACGATCGGTGTTTCGATCCAGAACC<br>TGTTCAATGGTGGTTGCCGTCCTTTCTGGGGTTTCGTTTCCGAT<br>AAAATCGGCCGTTACAAAACCATGTCCGTCGTTTTCGGTATCAA<br>TGCTGTTGTTCTCGCACTTTTCCCGACGATTGCTGCCTTGGGCG<br>ATGTAGCCTTTATCGCCATGTTGGCAATCGCATTCTTCACATGG<br>GGTGGTAGCTACGCTCTGTTCCCATCGACCAACAGCGATATTTT<br>CGGTACGGCATACTCTGCCAGAAACATGGTTTCTTCTGGGCTG<br>CAAAAGCAACTGCCTCGATCTTCGGTGGTGGTCTGGGTGCTGCA<br>ATTGCAACCAACTTCGGATGGAATACCGCTTTCCTGATTACTGC<br>GATTACTTCTTTCATCGCATTTGCTCTGGCTACCTTCGTTATTCC<br>AAGAATGGGCCGTCCAGTCAAGAAAATGGTCAAATTGTCTCCAG<br>AAGAAAAAGCTGTACATTAA | SEQ ID NO: 42 |

Example 10

Genetically Engineered Bacterial Cells Decrease Oxalate Concentration Under Control of a FNR Promoter Essentially the same assay is conducted as described in Example 5, but with the following constructs: (1) FNRS-OxlT construct and an oxalate catabolism cassette (oxc-frc) driven by FNRS promoter; (2) FNRS-OxlT construct and an oxalate catabolism cassette (yfdE-oxc-frc) driven by FNRS promoter. In some embodiments, the FNRS-OxlT construct is integrated into the chromosome at one or more positions. In some embodiments, the FNRS-OxlT construct is provided on a plasmid e.g., a low copy or a high copy plasmid. In some embodiments, the FNRS-oxc-frc construct is integrated into the chromosome at one or more positions, in other embodiments, the FNRS-oxc-frc construct is provided on a plasmid e.g., a low copy or a high copy plasmid. In some embodiments, the FNRS-yfdE-oxc-frc construct is integrated into the chromosome at one or more positions, in other embodiments, the FNRS-yfdE-oxc-frc construct is provided on a plasmid e.g., a low copy or a high copy plasmid. Sequences for the oxalate catabolism cassettes are shown in Table 19. (FNRS-oxc-frc) and Table 20. (FNRS-yfdE-oxc-frc).

TABLE 19

Oxalate catabolism cassette (oxc-frc) driven by FNRS promoter

| Description | Sequence | SEQ ID NO |
|---|---|---|
| Construct comprising FNR promoter, driving a oxalate catabolism cassette comprising oxc-frc. Underline: FNR promoter Underline italic: FNR binding site Bold: coding region of oxc and frc Bold underline italics: RBS and leader region or RBS alone | <u>GGTACCAGTTGTTCTTATTGGTGGTGTTGCTTTATGGTTGCATCGT<br>AGTAAATGGTTGTAACAAAAGCAATTTTTCCGGCTGTCTGTATAC<br>AAAAACGCCGTAAAGTTT*GAGCGAAGTC*AATAAACTCTCTACCCAT<br>TCAGGGCAATATCTCTCTTGGATCCAAAGTGAA</u><br>*CTCTAGAAATAATTTTGTTTAACTTTAAGAAGGAGATATACAT*<br>ATGAGTAACGACGACAATGTAGAGTTGACTGATGGCTTTCAT<br>GTTTTGATCGATGCCCTGAAAATGAATGACATCGATACCATGT<br>ATGGTGTTGTCGGCATTCCTATCACGAACCTGGCTCGTATGT<br>GGCAAGATGACGGTCAGCGTTTTTACAGCTTCCGTCACGAAC<br>AACACGCAGGTTATGCAGCTTCTATCGCCGGTTACATCGAAG<br>GAAAACCTGGCGTTTGCTTGACCGTTTCCGCCCCTGGCTTCCT<br>GAACGGCGTGACTTCCCTGGCTCATGCAACCACCAACTGCTT<br>CCCAATGATCCTGTTGAGCGGTTCCAGTGAACGTGAAATCGT<br>CGATTTGCAACAGGGCGATTACGAAGAAATGGATCAGATGAA<br>TGTTGCACGTCCACACTGCAAAGCTTCTTTCCGTATCAACAGC<br>ATCAAAGACATTCCAATCGGTATCGCTCGTGCAGTTCGCACC<br>GCTGTATCCGGACGTCCAGGTGGTGTTTACGTTGACTTGCCA<br>GCAAAACTGTTCGGTCAGACCATTTCTGTAGAAGAAGCTAAC<br>AAACTGCTCTTCAAACCAATCGATCCAGCTCCGGCACAGATTC<br>CTGCTGAAGACGCTATCGCTCGCGCTGCTGACCTGATCAAGA<br>ACGCCAAACGTCCAGTTATCATGCTGGGTAAAGGCGCTGCAT<br>ACGCACAATGCGACGACGAAATCCGCGCACTGGTTGAAGAAA<br>CCGGCATCCCATTCCTGCCAATGGGTATGGCTAAAGGCCTGC<br>TGCCTGACAACCATCCACAATCCGCTGCTGCAACCCGTGCTTT<br>CGCACTGGCACAGTGTGACGTTTGCGTACTGATCGGCGCTCG<br>TCTGAACTGGCTGATGCAGCACGGTAAAGGCAAAACCTGGGG<br>CGACGAACTGAAGAAATACGTTCAGATCGACATCCAGGCTAA<br>CGAAATGGACAGCAACCAGCCTATCGCTGCACCAGTTGTTGG<br>TGACATCAAGTCCGCCGTTTCCCTGCTCCGCAAAGCACTGAA<br>AGGCGCTCCAAAAGCTGACGCTGAATGGACCGGCGCTCTGAA<br>AGCCAAAGTTGACGGCAACAAAGCCAAACTGGCTGGCAAGAT<br>GACTGCCGAAACCCCATCCGGAATGATGAACTACTCCAATTC<br>CCTGGGCGTTGTTCGTGACTTCATGCTGGCAAATCCGGATAT<br>TTCCCTGGTTAACGAAGGCGCTAATGCACTCGACAACACTCG<br>TATGATTGTTGACATGCTGAAACCACGCAAACGTCTTGACTCC<br>GGTACCTGGGGTGTTATGGGTATTGGTATGGGCTACTGCGTT<br>GCTGCAGCTGCTGTTACCGGCAAACCGGTTATCGCTGTTGAA<br>GGCGATAGCGCATTCGGTTTCTCCGGTATGGAACTGGAAACC<br>ATCTGCCGTTACAACCTGCCAGTTACCGTTATCATCATGAACA<br>ATGGTGGTATCTATAAAGGTAACGAAGCAGATCCACAACCAG<br>GCGTTATCTCCTGTACCCGTCTGACCCGTGGTCGTTACGACAT<br>GATGATGGAAGCATTTGGCGGTAAAGGTTATGTTGCCAATAC<br>TCCAGCAGAACTGAAAGCTGCTCTGGAAGAAGCTGTTGCTTC<br>CGGCAAACCATGCCTGATCAACGCGATGATCGATCCAGACGC<br>TGGTGTCGAATCTGGCCGTATCAAGAGCCTGAACGTTGTAAG<br>TAAAGTTGGCAAGAAATAA<br>*TAAGAAGGAGATATACAT*<br>ATGACTAAACCATTAGATGGAATTAATGTGCTTGACTTTACCC<br>ACGTCCAGGCAGGTCCTGCCTGTACACAGATGATGGGTTTCT<br>TGGGCGCAAACGTCATCAAGATTGAAAGACGTGGTTCCGGAG<br>ATATGACTCGTGGATGGCTGCAGGACAAACCAAATGTTGATT<br>CCCTGTATTTCACGATGTTCAACTGTAACAAACGTTCGATTGA<br>ACTGGACATGAAAACCCCGGAAGGCAAAGAGCTTCTGGAACA<br>GATGATCAAGAAAGCCGACGTCATGGTCGAAAACTTCGGACC<br>AGGCGCACTGGACCGTATGGGCTTTACTTGGGAATACATTCA<br>GGAACTGAATCCACGCGTCATTCTGGCTTCCGTTAAAGGCTA<br>TGCAGAAGGCCACGCCAACGAACACCTGAAAGTTTATGAAAA<br>CGTTGCACAGTGTTCCGGCGGTGCTGCAGCTACCACCGGTTT | SEQ ID NO: 43 |

TABLE 19-continued

Oxalate catabolism cassette (oxc-frc) driven by FNRS promoter

| Description | Sequence | SEQ ID NO |
|---|---|---|
| | CTGGGATGGTCCTCCAACCGTTTCCGGCGCTGCTCTGGGTGA CTCCAACTCCGGTATGCACCTGATGATCGGTATTCTGGCCGC TCTGGAAATGCGTCACAAAACCGGCCGTGGTCAGAAAGTTGC CGTCGCTATGCAGGACGCTGTTCTGAATCTGGTTCGTATCAA ACTGCGTGACCAGCAACGTCTGGAAAGAACCGGCATTCTGGC TGAATACCCACAGGCTCAGCCTAACTTTGCCTTCGACAGAGA CGGTAACCCACTGTCCTTCGACAACATCACTTCCGTTCCACGT GGTGGTAACGCAGGTGGCGGCGGCCAGCCAGGCTGGATGCT GAAATGTAAAGGTTGGGAAACCGATGCGGACTCCTACGTTTA CTTCACCATCGCTGCAAACATGTGGCCACAGATCTGCGACAT GATCGACAAGCCAGAATGGAAAGACGACCCAGCCTACAACAC ATTCGAAGGTCGTGTTGACAAGCTGATGGACATCTTCTCCTTC ATCGAAACCAAGTTCGCTGACAAGGACAAATTCGAAGTTACC GAATGGGCTGCCCAGTACGGCATTCCTTGCGGTCCGGTCATG TCCATGAAAGAACTGGCTCACGATCCTTCCCTGCAGAAAGTT GGTACCGTCGTTGAAGTTGTCGACGAAATTCGTGGTAACCAC CTGACCGTTGGCGCACCGTTCAAATTCTCCGGATTCCAGCCG GAAATTACCCGTGCTCCGCTGTTGGGCGAACATACCGACGAA GTTCTGAAAGAACTGGGTCTTGACGATGCCAAGATCAAGGAA CTGCATGCAAAACAGGTAGTTTGA | |
| Construct comprising oxalate catabolism cassette comprising oxc-frc with RBS and leader region Underline: FNR promoter Underline italic: FNR binding site Bold: coding region of oxc and frc Bold underline italics: RBS and leader region or RBS alon | *CTCTAGAAATAATTTTGTTTAACTTTTAAGAAGGAGATATACAT* ATGAGTAACGACGACAATGTAGAGTTGACTGATGGCTTTCAT GTTTTGATCGATGCCCTGAAAATGAATGACATCGATACCATGT ATGGTGTTGTCGGCATTCCTATCACGAACCTGGCTCGTATGT GGCAAGATGACGGTCAGCGTTTTTACAGCTTCCGTCACGAAC AACACGCAGGTTATGCAGCTTCTATCGCCGGTTACATCGAAG GAAAACCTGGCGTTTGCTTGACCGTTTCCGCCCCTGGCTTCCT GAACGGCGTGACTTCCCTGGCTCATGCAACCACCAACTGCTT CCCAATGATCCTGTTGAGCGGTTCCAGTGAACGTGAAATCGT CGATTTGCAACAGGGCGATTACGAAGAAATGGATCAGATGAA TGTTGCACGTCCACACTGCAAAGCTTCTTTCCGTATCAACAGC ATCAAAGACATTCCAATCGGTATCGCTCGTCAGTTCGCACC GCTGTATCCGGACGTCCAGGTGGTGTTTACGTTGACTTGCCA GCAAAACTGTTCGGTCAGACCATTTCTGTAGAAGAAGCTAAC AAACTGCTCTTCAAACCAATCGATCCAGCTCCGGCACAGATTC CTGCTGAAGACGCTATCGCTCGCGCTGCTGACCTGATCAAGA ACGCCAAACGTCCAGTTATCATGCTGGGTAAAGGCGCTGCAT ACGCACAATGCGACGACGAAATCCGCGCACTGGTTGAAGAAA CCGGCATCCCATTCCTGCCAATGGGTATGGCTAAAGGCCTGC TGCCTGACAACCATCCACAATCCGCTGCTGCAACCCGTGCTTT CGCACTGGACAGTGTGACGTTTGCGTACTGATCGGCGCTCG TCTGAACTGGCTGATGCAGCACGGTAAAGGCAAACCTGGGG CGACGAACTGAAGAAATACGTTCAGATCGACATCCAGGCTAA CGAAATGGACAGCAACCAGCCTATCGCTGCACCAGTTGTTGG TGACATCAAGTCCGCCGTTTCCCTGCTCCGCAAAGCACTGAA AGGCGCTCCAAAAGCTGACGCTGAATGGACCGGCGCTCTGAA AGCCAAAGTTGACGGCAACAAAGCCAAACTGGCTGGCAAGAT GACTGCCGAAACCCCATCCGGAATGATGAACTACTCCAATTC CCTGGGCGTTGTTCGTGACTTCATGCTGGCAAATCCGGATAT TTCCCTGGTTAACGAAGGCGCTAATGCACTCGACAACACTCG TATGATTGTTGACATGCTGAAACCACGCAAACGTCTTGACTCC GGTACCTGGGGTGTTATGGGTATTGGTATGGGCTACTGCGTT GCTGCAGCTGCTGTTACCGGCAAACCGGTTATCGCTGTTGAA GGCGATAGCGCATTCGGTTTCTCCGGTATGGAACTGGAAACC ATCTGCCGTTACAACCTGCCAGTTACCGTTATCATCATGAACA ATGGTGGTATCTATAAAGGTAACGAAGCAGATCCACAACCAG GCGTTATCTCCTGTACCCGTCTGACCCGTGGTCGTTACGACAT GATGATGGAAGCATTTGGCGGTAAAGGTTATGTTGCCAATAC TCCAGCAGAACTGAAAGCTGCTCTGGAAGAAGCTGTTGCTTC CGGCAAACCATGCCTGATCAACGCGATGATCGATCCAGACGC TGGTGTCGAATCTGGCCGTATCAAGAGCCTGAACGTTGTAAG TAAAGTTGGCAAGAAATAA *TAAGAAGGAGATATACAT* ATGACTAAACCATTAGATGGAATTAATGTGCTTGACTTTACCC ACGTCCAGGCAGGTCCTGCCTGTACACAGATGATGGGTTTCT TGGGCGCAAACGTCATCAAGATTGAAAGACGTGGTTCCGGAG ATATGACTCGTGGATGGCTGCAGGACAAACCAAATGTTGATT CCCTGTATTTCACGATGTTCAACTGTAACAAACGTTCGATTGA ACTGGACATGAAAACCCCGGAAGGCAAAGAGCTTCTGGAACA GATGATCAAGAAGCCGACGTCATGGTCGAAAACTTCGGACC AGGCGCACTGGACCGTATGGGCTTTACTTGGGAATACATTCA GGAACTGAATCCACGCGTCATTCTGGCTTCCGTTAAAGGCTA TGCAGAAGGCCACGCCAACGAACACCTGAAAGTTTATGAAAA CGTTGCACAGTGTTCCGGCGGTGCTGCAGCTACCACCGGTTT | SEQ ID NO: 44 |

TABLE 19-continued

Oxalate catabolism cassette (oxc-frc) driven by FNRS promoter

| Description | Sequence | SEQ ID NO |
|---|---|---|
| | CTGGGATGGTCCTCCAACCGTTTCCGGCGCTGCTCTGGGTGA CTCCAACTCCGGTATGCACCTGATGATCGGTATTCTGGCCGC TCTGGAAATGCGTCACAAAACCGGCCGTGGTCAGAAAGTTGC CGTCGCTATGCAGGACGCTGTTCTGAATCTGGTTCGTATCAA ACTGCGTGACCAGCAACGTCTGGAAAGAACCGGCATTCTGGC TGAATACCCACAGGCTCAGCCTAACTTTGCCTTCGACAGAGA CGGTAACCCACTGTCCTTCGACAACATCACTTCCGTTCCACGT GGTGGTAACGCAGGTGGCGGCGGCCAGCCAGGCTGGATGCT GAAATGTAAAGGTTGGGAAACCGATGCGGACTCCTACGTTTA CTTCACCATCGCTGCAAACATGTGGCCACAGATCTGCGACAT GATCGACAAGCCAGAATGGAAAGACGACCCAGCCTACAACAC ATTCGAAGGTCGTGTTGACAAGCTGATGGACATCTTCTCCTTC ATCGAAACCAAGTTCGCTGACAAGGACAAATTCGAAGTTACC GAATGGGCTGCCCAGTACGGCATTCCTTGCGGTCCGGTCATG TCCATGAAAGAACTGGCTCACGATCCTTCCCTGCAGAAAGTT GGTACCGTCGTTGAAGTTGTCGACGAAATTCGTGGTAACCAC CTGACCGTTGGCGCACCGTTCAAATTCTCCGGATTCCAGCCG GAAATTACCCGTGCTCCGCTGTTGGGCGAACATACCGACGAA GTTCTGAAAGAACTGGGTCTTGACGATGCCAAGATCAAGGAA CTGCATGCAAAACAGGTAGTTTGA | |

TABLE 20

Oxalate catabolism cassette
(yfdE-oxc-frc) driven by FNRS promoter

| Description | Sequence | SEQ ID NO |
|---|---|---|
| Construct comprising FNR promoter, driving a oxalate catabolism cassette comprising yfdE-oxc-frc. Underline: FNR promoter Underline italic: FNR binding site Bold: coding region of oxc and frc Bold underline italics: RBS and leader region or RBS alone | ggtaccAGTTGTTCTTATTGGTGGTGTTGCTTTATGGTTGCATCG TAGTAAATGGTTGTAACAAAAGCAATTTTTCCGGCTGTCTGT ATACAAAAACGCCGTAAAGTTTGAGCGAAGTCAATAAACTCTC TACCCATTCAGGGCAATATCTCTCTTggatccaaagtgaa ctctagaaataatttgtttaactttaagaaggagatatacat atgACAAATAATGAAAGCAAAGGGCCGTTTGAAGGCTTATTAG TTATCGATATGACACATGTCCTTAATGGACCTTTCGGAACTC AACTTCTTTGTAATATGGGCGCAAGGGTAATTAAAGTTGAGC CGCCGGGTCATGGTGATGATACCCGCACATTTGGTCCCTATG TGGATGGACAGTCACTCTATTACAGTTTTATTAATCATGGCA AAGAGAGTGTGGTTCTTGATTTAAAGAATGATCACGATAAAA GTATATTTATAAATATGCTCAAACAAGCTGATGTATTAGCTG AGAATTTTCGCCCAGGTACAATGGAAAAACTGGGGTTTTCAT GGGAAACGCTTCAAGAAATCAACCCGCGCCTCATATATGCTT CATCGTCAGGTTTCGGACATACCGGTCCGCTAAAAGATGCTC CTGCCTACGATACCATCATTCAGGCAATGAGCGGGATAATGA TGGAAACAGGATATCCTGATGCTCCGCCAGTGCGCGTTGGTA CATCTCTTGCGGATCTATGCGGCGGTGTCTATTTATTCAGCG GAATAGTGAGTGCACTTTATGGCCGCGAAAAGAGCCAGAGA GGGGCGCATGTCGATATAGCGATGTTTGATGCCACGCTGAGG TTTTCTGGAGCATGGTCTGATGGCATATATCGCAACTGGGAA GTCACCACAACGTCTGGGAAATCGCCATCCCTACATGGCACC TTTTGATGTTTTCAATACTCAGGATAAGCCGATTACGATTGT TGTGGTAATGACAAGCTTTTTTCTGCGTTATGCCAGGCACTG GAGCTTACGGAACTGGTTAATGATCCCCGATTTAGCAGCAAT ATTTTACGCGTACAAAACCAGGCTATTCTTAAACAATATATT GAGCGGACGTTAAAAACGCAGGCAGCTGAAGTTTGGTTAGC CAGAATACATGAAGTTGGTGTACCCGTCGCGCCGTTATTAAG TGTGGCTGAGGCCATTAAATTGCCACAAACTCAGGCGAGAAA TATGTTGATTGAAGCCGGGGGAATAATGATGCCGGGTAATCC GATAAAAATCAGCGGCTGCGCGGACCCGCATGTTATGCCGG GAGCGGCAACGCTCGACCAGCATGGGGAACAAATTCGCCAG GAGTTCTCATCAtaa aagaaggagatatacatATGAGTAACGACGACAATGTAGAGTTGACTG ATGGCTTTCATGTTTTGATCGATGCCCTGAAAATGAATGACA TCGATACCATGTATGGTGTTGTCGGCATTCCTATCACGAACC TGGCTCGTATGTGGCAAGATGACGGTCAGCGTTTTTACAGCT TCCGTCACGAACAACACGCAGGTTATGCAGCTTCTATCGCCG GTTACATCGAAGGAAAACCTGGCGTTTGCTTGACCGTTTCCG CCCCTGGCTTCCTGAACGGCGTGACTTCCCTGGCTCATGCAA CCACCAACTGCTTCCCAATGATCCTGTTGAGCGGTTCCAGTG AACGTGAAATCGTCGATTTGCAACAGGGCGATTACGAAGAAA TGGATCAGATGAATGTTGCACGTCCACACTGCAAAGCTTCTT | SEQ ID NO: 45 |

TABLE 20-continued

Oxalate catabolism cassette
(yfdE-oxc-frc) driven by FNRS promoter

| Description | Sequence | SEQ ID NO |
|---|---|---|
| | TCCGTATCAACAGCATCAAAGACATTCCAATCGGTATCGCTC<br>GTGCAGTTCGCACCGCTGTATCCGGACGTCCAGGTGGTGTTT<br>ACGTTGACTTGCCAGCAAAACTGTTCGGTCAGACCATTTCTG<br>TAGAAGAAGCTAACAAACTGCTCTTCAAACCAATCGATCCAG<br>CTCCGGCACAGATTCCTGCTGAAGACGCTATCGCTCGCGCTG<br>CTGACCTGATCAAGAACGCCAAACGTCCAGTTATCATGCTGG<br>GTAAAGGCGCTGCATACGCACAATGCGACGACGAAATCCGC<br>GCACTGGTTGAAGAAACCGGCATCCCATTCCTGCCAATGGGT<br>ATGGCTAAAGGCCTGCTGCCTGACAACCATCCACAATCCGCT<br>GCTGCAACCCGTGCTTTCGCACTGGCACAGTGTGACGTTTGC<br>GTACTGATCGGCGCTCGTCTGAACTGGCTGATGCAGCACGG<br>TAAAGGCAAAACCTGGGGCGACGAACTGAAGAAATACGTTC<br>AGATCGACATCCAGGCTAACGAAATGGACAGCAACCAGCCT<br>ATCGCTGCACCAGTTGTTGGTGACATCAAGTCCGCCGTTTCC<br>CTGCTCCGCAAAGCACTGAAAGGCGCTCCAAAAGCTGACGC<br>TGAATGGACCGGCGCTCTGAAAGCCAAAGTTGACGGCAACA<br>AAGCCAAACTGGCTGGCAAGATGACTGCCGAAACCCCATCC<br>GGAATGATGAACTACTCCAATTCCCTGGGCGTTGTTCGTGAC<br>TTCATGCTGGCAAATCCGGATATTTCCCTGGTTAACGAAGGC<br>GCTAATGCACTCGACAACACTCGTATGATTGTTGACATGCTG<br>AAACCACGCAAACGTCTTGACTCCGGTACCTGGGGTGTTATG<br>GGTATTGGTATGGGCTACTGCGTTGCTGCAGCTGCTGTTACC<br>GGCAAACCGGTTATCGCTGTTGAAGGCGATAGCGCATTCGG<br>TTTCTCCGGTATGGAACTGGAAACCATCTGCCGTTACAACCT<br>GCCAGTTACCGTTATCATCATGAACAATGGTGGTATCTATAA<br>AGGTAACGAAGCAGATCCACAACCAGGCGTTATCTCCTGTAC<br>CCGTCTGACCCGTGGTCGTTACGACATGATGATGGAAGCATT<br>TGGCGGTAAAGGTTATGTTGCCAATACTCCAGCAGAACTGAA<br>AGCTGCTCTGGAAGAAGCTGTTGCTTCCGGCAAACCATGCCT<br>GATCAACGCGATGATCGATCCAGACGCTGGTGTCGAATCTG<br>GCCGTATCAAGAGCCTGAACGTTGTAAGTAAAGTTGGCAAGA<br>AATAA<br> <u>taagaaggagatatacat</u><br>ATGACTAAACCATTAGATGGAATTAATGTGCTTGACTTTACC<br>CACGTCCAGGCAGGTCCTGCCTGTACACAGATGATGGGTTTC<br>TTGGGCGCAAACGTCATCAAGATTGAAAGACGTGGTTCCGG<br>AGATATGACTCGTGGATGGCTGCAGGACAAACCAAATGTTGA<br>TTCCCTGTATTTCACGATGTTCAACTGTAACAAACGTTCGATT<br>GAACTGGACATGAAAACCCCGGAAGGCAAAGAGCTTCTGGA<br>ACAGATGATCAAGAAAGCCGACGTCATGGTCGAAAACTTCG<br>GACCAGGCGCACTGGACCGTATGGGCTTTACTTGGGAATAC<br>ATTCAGGAACTGAATCCACGCGTCATTCTGGCTTCCGTTAAA<br>GGCTATGCAGAAGGCCACGCCAACGAACACCTGAAAGTTTAT<br>GAAAACGTTGCACAGTGTTCCGGCGGTGCTGCAGCTACCAC<br>CGGTTTCTGGGATGGTCCTCCAACCGTTTCCGGCGCTGCTCT<br>GGGTGACTCCAACTCCGGTATGCACCTGATGATCGGTATTCT<br>GGCCGCTCTGGAAATGCGTCACAAAACCGGCCGTGGTCAGA<br>AAGTTGCCGTCGCTATGCAGGACGCTGTTCTGAATCTGGTTC<br>GTATCAAACTGCGTGACCAGCAACGTCTGGAAAGAACCGGC<br>ATTCTGGCTGAATACCCACAGGCTCAGCCTAACTTTGCCTTC<br>GACAGAGACGGTAACCCACTGTCCTTCGACAACATCACTTCC<br>GTTCCACGTGGTGGTAACGCAGGTGGCGGCGGCCAGCCAGG<br>CTGGATGCTGAAATGTAAAGGTTGGGAAACCGATGCGGACT<br>CCTACGTTTACTTCACCATCGCTGCAAACATGTGGCCACAGA<br>TCTGCGACATGATCGACAAGCCAGAATGGAAAGACGACCCA<br>GCCTACAACACATTCGAAGGTCGTGTTGACAAGCTGATGGAC<br>ATCTTCTCCTTCATCGAAACCAAGTTCGCTGACAAGGACAAA<br>TTCGAAGTTACCGAATGGGCTGCCCAGTACGGCATTCCTTGC<br>GGTCCGGTCATGTCCATGAAAGAACTGGCTCACGATCCTTCC<br>CTGCAGAAAGTTGGTACCGTCGTTGAAGTTGTCGACGAAATT<br>CGTGGTAACCACCTGACCGTTGGCGCACCGTTCAAATTCTCC<br>GGATTCCAGCCGGAAATTACCCGTGCTCCGCTGTTGGGCGA<br>ACATACCGACGAAGTTCTGAAAGAACTGGGTCTTGACGATGC<br>CAAGATCAAGGAACTGCATGCAAAACAGGTAGTTTGA | |
| Construct comprising oxalate catabolism cassette comprising yfdE-oxc-frc with RBS and leader | <u>ggtacc</u>AGTTGTTCTTATTGGTGGTGTTGCTTTATGGTTGCATCGTAG<br><u>TAAATGGTTGTAACAAAAGCAATTTTTCCGGCTGTCTGTATACAA</u><br><u>AAACGCCGTAAAGTTT</u>GAGCGAAGTCAATAAACTCTCTACCCATT<br>CAGGGCAATATCTCTCTT<u>ggatccaaagtgaa</u><br> <u>ctctagaaataattttgttaacttaagaaggagatatacat</u><br>at<u>g</u>ACAAATAATGAAAGCAAAGGGCCGTTTGAAGGCTTATTAG<br>TTATCGATATGACACATGTCCTTAATGGACCTTTCGGAACTC<br>AACTTCTTTGTAATATGGGCGCAAGGGTAATTAAAGTTGAGC<br>CGCCGGGTCATGGTGATGATACCCGCACATTTGGTCCCTATG | SEQ ID NO: 46 |

TABLE 20-continued

Oxalate catabolism cassette
(yfdE-oxc-frc) driven by FNRS promoter

| Description | Sequence | SEQ ID NO |
|---|---|---|
| region Underline: FNR promoter Underline italic: FNR binding site Bold: coding region of oxc and frc Bold underline italics: RBS and leader region or RBS alon | TGGATGGACAGTCACTCTATTACAGTTTTATTAATCATGGCA<br>AAGAGAGTGTGGTTCTTGATTTAAAGAATGATCACGATAAAA<br>GTATATTTATAAATATGCTCAAACAAGCTGATGTATTAGCTG<br>AGAATTTTCGCCCAGGTACAATGGAAAAACTGGGGTTTTCAT<br>GGGAAACGCTTCAAGAAATCAACCCGCGCCTCATATATGCTT<br>CATCGTCAGGTTTCGGACATACCGGTCCGCTAAAAGATGCTC<br>CTGCCTACGATACCATCATTCAGGCAATGAGCGGGATAATGA<br>TGGAAACAGGATATCCTGATGCTCCGCCAGTGCGCGTTGGTA<br>CATCTCTTGCGGATCTATGCGGCGGTGTCTATTTATTCAGCG<br>GAATAGTGAGTGCACTTTATGGCCGCGAAAAGAGCCAGAGA<br>GGGGCGCATGTCGATATAGCGATGTTTGATGCCACGCTGAG<br>TTTTCTGGAGCATGGTCTGATGGCATATATCGCAACTGGGAA<br>GTCACCACAACGTCTGGGAAATCGCCATCCCTACATGGCACC<br>TTTTGATGTTTTCAATACTCAGGATAAGCCGATTACGATTTGT<br>TGTGGTAATGACAAGCTTTTTTCTGCGTTATGCCAGGCACTG<br>GAGCTTACGGAACTGGTTAATGATCCCCGATTTAGCAGCAAT<br>ATTTTACGCGTACAAAACCAGGCTATTCTTAAACAATATATT<br>GAGCGGACGTTAAAAACGCAGGCAGCTGAAGTTTGGTTAGC<br>CAGAATACATGAAGTTGGTGTACCCGTCGCGCCGTTATTAAG<br>TGTGGCTGAGGCCATTAAATTGCCACAAACTCAGGCGAGAAA<br>TATGTTGATTGAAGCCGGGGGAATAATGATGCCGGGTAATCC<br>GATAAAAATCAGCGGCTGCGCGGACCCGCATGTTATGCCGG<br>GAGCGGCAACGCTCGACCAGCATGGGGAACAAATTCGCCAG<br>GAGTTCTCATCAtaa<br>_aagaaggagatatacat_ATGAGTAACGACGACAATGTAGAGTTGACTG<br>ATGGCTTTCATGTTTTGATCGATGCCCTGAAAATGAATGACA<br>TCGATACCATGTATGGTGTTGTCGGCATTCCTATCACGAACC<br>TGGCTCGTATGTGGCAAGATGACGGTCAGCGTTTTTACAGCT<br>TCCGTCACGAACAACACGCAGGTTATGCAGCTTCTATCGCCG<br>GTTACATCGAAGGAAAACCTGGCGTTTGCTTGACCGTTTCCG<br>CCCCTGGCTTCCTGAACGGCGTGACTTCCCTGGCTCATGCAA<br>CCACCAACTGCTTCCCAATGATCCTGTTGAGCGGTTCCAGTG<br>AACGTGAAATCGTCGATTTGCAACAGGGCGATTACGAAGAAA<br>TGGATCAGATGAATGTTGCACGTCCACACTGCAAAGCTTCTT<br>TCCGTATCAACAGCATCAAAGACATTCCAATCGGTATCGCTC<br>GTGCAGTTCGCACCGCTGTATCCGGACGTCCAGGTGGTGTTT<br>ACGTTGACTTGCCAGCAAAACTGTTCGGTCAGACCATTTCTG<br>TAGAAGAAGCTAACAAACTGCTCTTCAAACCAATCGATCCAG<br>CTCCGGCACAGATTCCTGCTGAAGACGCTATCGCTCGCGCTG<br>CTGACCTGATCAAGAACGCCAAACGTCCAGTTATCATGCTGG<br>GTAAAGGCGCTGCATACGCACAATGCGACGACGAAATCCGC<br>GCACTGGTTGAAGAAACCGGCATCCCATTCCTGCCAATGGGT<br>ATGGCTAAAGGCCTGCTGCCTGACAACCATCCACAATCCGCT<br>GCTGCAACCCGTGCTTTCGCACTGGCACAGTGTGACGTTTGC<br>GTACTGATCGGCGCTCGTCTGAACTGGCTGATGCAGCACGG<br>TAAAGGCAAAACCTGGGGCGACGAACTGAAGAAATACGTTC<br>AGATCGACATCCAGGCTAACGAAATGGACAGCAACCAGCCT<br>ATCGCTGCACCAGTTGTTGGTGACATCAAGTCCGCCGTTTCC<br>CTGCTCCGCAAAGCACTGAAAGGCGCTCCAAAAGCTGACGC<br>TGAATGGACCGGCGCTCTGAAAGCCAAAGTTGACGGCAACA<br>AAGCCAAACTGGCTGGCAAGATGACTGCCGAAACCCCATCC<br>GGAATGATGAACTACTCCAATTCCCTGGGCGTTGTTCGTGAC<br>TTCATGCTGGCAAATCCGGATATTTCCCTGGTTAACGAAGGC<br>GCTAATGCACTCGACAACACTCGTATGATTGTTGACATGCTG<br>AAACCACGCAAACGTCTTGACTCCGGTACCTGGGGTGTTATG<br>GGTATTGGTATGGGCTACTGCGTTGCTGCAGCTGCTGTTACC<br>GGCAAACCGGTTATCGCTGTTGAAGGCGATAGCGCATTCGG<br>TTTCTCCGGTATGGAACTGGAAACCATCTGCCGTTACAACCT<br>GCCAGTTACCGTTATCATCATGAACAATGGTGGTATCTATAA<br>AGGTAACGAAGCAGATCCACAACCAGGCGTTATCTCCTGTAC<br>CCGTCTGACCCGTGGTCGTTACGACATGATGATGGAAGCATT<br>TGGCGGTAAAGGTTATGTTGCCAATACTCCAGCAGAACTGAA<br>AGCTGCTCTGGAAGAAGCTGTTGCTTCCGGCAAACCATGCCT<br>GATCAACGCGATGATCGATCCAGACGCTGGTGTCGAATCTG<br>GCCGTATCAAGAGCCTGAACGTTGTAAGTAAAGTTGGCAAGA<br>AATAA<br>_taagaaggagatatacat_<br>ATGACTAAACCATTAGATGGAATTAATGTGCTTGACTTTACC<br>CACGTCCAGGCAGGTCCTGCCTGTACACAGATGATGGGTTTC<br>TTGGGCGCAAACGTCATCAAGATTGAAAGACGTGGTTCCGG<br>AGATATGACTCGTGGATGGCTGCAGGACAAACCAAATGTTGA<br>TTCCCTGTATTTCACGATGTTCAACTGTAACAAACGTTCGATT<br>GAACTGGACATGAAAACCCCGGAAGGCAAAGAGCTTCTGGA<br>ACAGATGATCAAGAAAGCCGACGTCATGGTCGAAAACTTCG | |

TABLE 20-continued

Oxalate catabolism cassette
(yfdE-oxc-frc) driven by FNRS promoter

| Description | Sequence | SEQ ID NO |
|---|---|---|
| | GACCAGGCGCACTGGACCGTATGGGCTTTACTTGGGAATAC | |
| | ATTCAGGAACTGAATCCACGCGTCATTCTGGCTTCCGTTAAA | |
| | GGCTATGCAGAAGGCCACGCCAACGAACACCTGAAAGTTTAT | |
| | GAAAACGTTGCACAGTGTTCCGGCGGTGCTGCAGCTACCAC | |
| | CGGTTTCTGGGATGGTCCTCCAACCGTTTCCGGCGCTGCTCT | |
| | GGGTGACTCCAACTCCGGTATGCACCTGATGATCGGTATTCT | |
| | GGCCGCTCTGGAAATGCGTCACAAAACCGGCCGTGGTCAGA | |
| | AAGTTGCCGTCGCTATGCAGGACGCTGTTCTGAATCTGGTTC | |
| | GTATCAAACTGCGTGACCAGCAACGTCTGGAAAGAACCGGC | |
| | ATTCTGGCTGAATACCCACAGGCTCAGCCTAACTTTGCCTTC | |
| | GACAGAGACGGTAACCCACTGTCCTTCGACAACATCACTTCC | |
| | GTTCCACGTGGTGGTAACGCAGGTGGCGGCGGCCAGCCAGG | |
| | CTGGATGCTGAAATGTAAAGGTTGGGAAACCGATGCGGACT | |
| | CCTACGTTTACTTCACCATCGCTGCAAACATGTGGCCACAGA | |
| | TCTGCGACATGATCGACAAGCCAGAATGGAAAGACGACCCA | |
| | GCCTACAACACATTCGAAGGTCGTGTTGACAAGCTGATGGAC | |
| | ATCTTCTCCTTCATCGAAACCAAGTTCGCTGACAAGGACAAA | |
| | TTCGAAGTTACCGAATGGGCTGCCCAGTACGGCATTCCTTGC | |
| | GGTCCGGTCATGTCCATGAAAGAACTGGCTCACGATCCTTCC | |
| | CTGCAGAAAGTTGGTACCGTCGTTGAAGTTGTCGACGAAATT | |
| | CGTGGTAACCACCTGACCGTTGGCGCACCGTTCAAATTCTCC | |
| | GGATTCCAGCCGGAAATTACCCGTGCTCCGCTGTTGGGCGA | |
| | ACATACCGACGAAGTTCTGAAAGAACTGGGTCTTGACGATGC | |
| | CAAGATCAAGGAACTGCATGCAAAACAGGTAGTTTGA | |

Example 11

In Vivo Studies Demonstrating that the Genetically Engineered Bacterial Cells of the Invention Decrease Oxalate Concentration For in vivo studies, an alanine glyoxylate aminotransferase-deficient mouse model of PHI, or a glyoxylate reductase/hydroxypyruvate reductase knock-out mouse model is used (see, for example Salido et al., 2006 and Knight et al., 2012). Alternatively, mice deficient in the oxalate transporter protein SLC26A6 which develop hyperoxaluria can be used can be used (see, for example, Jiang et al., 2006). Briefly, levels of oxalate are measured in the urine of the mice prior to administration of the recombinant bacteria of the invention on day 0. On day 1, cultures of *E. coli* Nissle containing pTet-Frc-OXC and/or pTet-Frc-OXC and pTet-OxlT are administered to three wild-type mice and three knock-out mice once daily for a week. In addition, three knock-out mice are administered PBS as a control once daily for a week. Treatment efficacy is determined, for example, by measuring urine levels of oxalate. A decrease in urine levels of oxalate after treatment with the recombinant bacterial cells indicates that the recombinant bacterial cells of the invention are effective for treating disorders in which oxalate is detrimental. Additionally, throughout the study, phenotypes of the mice can also be analyzed. A decrease in the number of symptoms associated with disorders in which oxalate is detrimental, for example, blood in the urine or fever, further indicates the efficacy of the recombinant bacterial cells of the invention for treating disorders in which oxalate is detrimental.

Example 12

Detection of Oxalate by LCMS

Oxalate quantification was performed in bacterial supernatants by LC-MS/MS.

Sample Preparation

Oxalic acid stock 10 mg/mL was prepared in water and aliquoted in 1.5 mL microcentrifuge tubes (100 µL), and stored at −20° C. Standards (1000, 500, 250, 100, 20, 4, and 0.8 µg/mL) are prepared in water. On ice, 20 µL of sample (and standards) were mixed with 180 µL of $H_2O$ containing 10 µg/mL of oxalic acid-d2 in the final solution in a V-bottom 96-well plate. The plate was heat-sealed with a ClearASeal sheet and mix well.

LC-MS/MS method

Oxalate was measured by liquid chromatography coupled to tandem mass spectrometry (LC-MS/MS) using a Thermo TSQ Quantum Max triple quadrupole mass spectrometer. Table 21, Table 22 and Table 23 provide the summary of the LC-MS/MS method.

TABLE 21

| | |
|---|---|
| Column | Synergi Hydro column, 4 µm (75 × 4.6 mm) |
| Mobile Phase A | 5 mM Ammonium acetate |
| Mobile Phase B | Methanol |
| Injection volume | 10 uL |

TABLE 22

HPLC Method:

| Time (min) | Flow Rate (µl/min) | A % | B % |
|---|---|---|---|
| 0.0 | 500 | 100 | 0 |
| 0.5 | 500 | 100 | 0 |
| 1.0 | 500 | 5 | 95 |

TABLE 22-continued

HPLC Method:

| Time (min) | Flow Rate (μl/min) | A % | B % |
|---|---|---|---|
| 2.5 | 500 | 5 | 95 |
| 2.51 | 500 | 100 | 0 |
| 2.75 | 500 | 100 | 0 |

TABLE 23

Tandem Mass Spectrometry

| Ion Source | HESI-II |
|---|---|
| Polarity | Negative |
| SRM transitions | Oxalate: 90.5/61.2 |
| SRM transitions | Oxalate-d2: 92.5/62.2 |

Example 13

In Vivo Studies Demonstrating that the Genetically Engineered Bacterial Cells of the Invention Decrease Oxalate Concentration To evaluate the efficacy of the genetically engineered bacteria with respect to oxalate catalism in vivo a rat model is applied. Canales et al. describe a rat model of Roux-en-Y gastric bypass (RYGB) surgery, in which high fat feeding results in steatorrhea, hyperoxaluria, and low urine pH ((Canales et al., Steatorrhea And Hyperoxaluria Occur After Gastric Bypass Surgery In Obese Rats Regardless Of Dietary Fat Or Oxalate; J Urol. 2013 September; 190(3): 1102-1109)). RYGB animals on normal fat and no oxalate diets excreted twice as much oxalate as age-matched, sham controls. For the study, administration wild type Nissle is compared to a genetically engineered bacterium comprising FNRS-OxlT and FNRS-pFNRS-ScAAE3-oxc-frc, in RYGB animals (and sham operated animals) administered a high fat diet with or without oxalate for five weeks.

Male Sprague-Dawley rats are purchased from Charles River Laboratories (Wilmington, Mass., USA) and housed in individual shoe-box cages at a constant temperature of 21-23° C. with a 12-hour light-dark cycle. To produce diet-induced obesity (DIO), 3 week male pups are given ad lib access to 18 weeks of a 60% fat (casein-based), 20% protein, 20% carbohydrate diet without added oxalate (D12492, Research Diets, New Brunswick, N.J.), providing 5.2 kcal/gm.

Once DIO is established, rats are randomly assigned to RYGB (n=60) or sham procedure (Control, n=60) by random number tables. RYGB is conducted as described in Canales et al, which is incorporated herein by reference in its entirety. Briefly, for RYGB animals, a 4 cm mid-line incision is made below the xyphoid process. The terminal ileum is identified at the ileocecal valve and followed orally 35 cm where a 4 mm enterotomy is made (common channel). Bowel is followed another 10 cm proximally and completely transected (Roux limb). Hand-sewn interrupted end-to-side anastomosis is created by sewing the proximal portion of biliopancreatic limb (25-35 cm) to the enterotomy using 5-0 PDS. The gastric artery and vagal nerves of the stomach are identified and mobilized laterally. A 45 mm ETS Laparoscopic Endo-GIA stapler with 2.5 mm reload (Ethicon Endo-Surgery, Cincinnati, Ohio) is used to transect the stomach 3 mm below the level of the gastro-esophageal junction, creating a small stomach pouch. A 4 mm incision is then made on the anterio-lateral stomach above the staple line and hand-sewn gastrojejunostomy is performed using 5-0 PDS. Fascia is closed using a running 4-0 Vicryl suture, and skin re-approximated. All sham animals received similar incisions, stomach mobilization, operative time, and closure as RYGB animals.

Following their procedure, rats are allowed 2 weeks for return of bowel function and are then randomized to ad lib 0.6% calcium, high fat diet (40% fat, 40% carbohydrate, 20% protein; D11021101, Research Diets, New Brunswick, N.J.) with 1.5% potassium oxalate (Ox; n=40) or without added oxalate (No Ox, n=40), providing 4.6 kcal/gm. Weekly weights and daily food and water intake are recorded.

After five weeks, rats are either switched to ad lib 0.6% calcium, normal fat diet (10% fat, 70% carbohydrate, 20% protein; D11032601, Research Diets, New Brunswick, N.J.) for an additional 2 weeks without changing oxalate content, providing 3.8 kcal/gm (n=10 from each group (RYGB or sham; plus or minus oxalate)), or are continued on high fat diet and treated with the wild type (n=10 from each group (RYGB or sham; plus or minus oxalate)) or genetically engineered bacteria (n=10 from each group (RYGB or sham; plus or minus oxalate)).

To prepare the wild type or genetically engineered cells, cells (comprising a OxlT and a ScAAE3-oxc-frc cassette, both under control of the FNR promoter are diluted 1:100 in LB (2 L), grown for 1.5 h aerobically, then shifted to the anaerobe chamber for 4 hours. Prior to administration, cells are concentrated 200× and frozen (15% glycerol, 2 g/L glucose, in PBS). Cells are thawed on ice, and 4e10 cfu/mL are mixed 9:1 in 1M bicarbonate. Each rat is gavaged 800 uL total, or 2.9e10 cfu/rat once or twice a day for two weeks.

To determine weight distribution at study end, whole body adiposity is assessed. Lean-body mass (LBM) and fat mass (FM) is calculated for each animal by multiplying body weight by % lean body mass or % fat mass respectively, and totals are averaged.

At each study period end (e.g., 2 weeks after surgery, after 5 weeks of high fat diet, and at several time points after discontinuation of the high fat diet and switch to 10% fat diet or treatment with the wild type or genetically engineered bacteria), rats are placed individually in metabolic cages and 24-hour urines are collected under mineral oil into 70 ml vessels containing 30 μl of 2% sodium azide preservative as previously described. Urine pH is determined immediately following collection using a pH meter. In acidified (HCl) samples, urine oxalate is determined using a kit assay (Trinity Biotech, St. Louis, Mo.) at wavelength of 590 nm. Urine calcium concentration is determined using kit assay (Point Scientific, Canton, Mich.) at wavelength of 575 nm. Fecal pellets, collected twice over a 48 hour period from a single animal, are slurried, and three separate slurry aliquots and fatty acids are identified and quantitated as described in Canales et al.

Example 14

Generation of ΔThyA

An auxotrophic mutation causes bacteria to die in the absence of an exogenously added nutrient essential for survival or growth because they lack the gene(s) necessary to produce that essential nutrient. In order to generate genetically engineered bacteria with an auxotrophic modification, the thyA, a gene essential for oligonucleotide synthesis was deleted. Deletion of the thyA gene in E. coli Nissle yields a strain that cannot form a colony on LB plates unless they are supplemented with thymidine.

A thyA::cam PCR fragment was amplified using 3 rounds of PCR as follows. Sequences of the primers used at a 100 um concentration are found in Table 24.

containing pKD46 grown for recombineering. Following electroporation, 1 ml SOC medium containing 3 mM thymidine was added, and cells were allowed to recover at 37 C for 2 h with shaking. Cells were then pelleted at 10,000×g for 1 minute, the supernatant was discarded, and the cell pellet was resuspended in 100 ul LB containing 3 mM thymidine and spread on LB agar plates containing 3 mM

TABLE 24

Primer Sequences

| Name | Sequence | Description | SEQ ID NO |
|---|---|---|---|
| SR36 | tagaactgatgcaaaaagtgctcgacgaaggcacacagaTGTGTAGG CTGGAGCTGCTTC | Round 1: binds on pKD3 | SEQ ID NO: 47 |
| SR38 | gtttcgtaattagatagccaccggcgctttaatgcccggaCATATGAAT ATCCTCCTTAG | Round 1: binds on pKD3 | SEQ ID NO: 48 |
| SR33 | caacacgtttcctgaggaaccatgaaacagtatttagaactgatgcaaaaag | Round 2: binds to round 1 PCR product | SEQ ID NO: 49 |
| SR34 | cgcacactggcgtcggctctggcaggatgtttcgtaattagatagc | Round 2: binds to round 1 PCR product | SEQ ID NO: 50 |
| SR43 | atatcgtcgcagcccacagcaacacgtttcctgagg | Round 3: binds to round 2 PCR product | SEQ ID NO: 51 |
| SR44 | aagaatttaacggagggcaaaaaaaaccgacgcacactggcgtcggc | Round 3: binds to round 2 PCR product | SEQ ID NO: 52 |

For the first PCR round, 4×50 ul PCR reactions containing 1 ng pKD3 as template, 25 ul 2×phusion, 0.2 ul primer SR36 and SR38, and either 0, 0.2, 0.4 or 0.6 ul DMSO were brought up to 50 ul volume with nuclease free water and amplified under the following cycle conditions:
  step 1: 98 c for 30 s
  step 2: 98 c for 10 s
  step 3: 55 c for 15 s
  step 4: 72 c for 20 s
  repeat step 2-4 for 30 cycles
  step 5: 72 c for 5 min
Subsequently, 5 ul of each PCR reaction was run on an agarose gel to confirm PCR product of the appropriate size. The PCR product was purified from the remaining PCR reaction using a Zymoclean gel DNA recovery kit according to the manufacturer's instructions and eluted in 30 ul nuclease free water.

For the second round of PCR, 1 ul purified PCR product from round 1 was used as template, in 4×50 ul PCR reactions as described above except with 0.2 ul of primers SR33 and SR34. Cycle conditions were the same as noted above for the first PCR reaction. The PCR product run on an agarose gel to verify amplification, purified, and eluted in 30 ul as described above.

For the third round of PCR, 1 ul of purified PCR product from round 2 was used as template in 4×50 ul PCR reactions as described except with primer SR43 and SR44. Cycle conditions were the same as described for rounds 1 and 2. Amplification was verified, the PCR product purified, and eluted as described above. The concentration and purity was measured using a spectrophotometer. The resulting linear DNA fragment, which contains 92 bp homologous to upstream of thyA, the chloramphenicol cassette flanked by frt sites, and 98 bp homologous to downstream of the thyA gene, was transformed into a E. coli Nissle 1917 strain thy and 20 ug/ml chloramphenicol. Cells were incubated at 37 C overnight. Colonies that appeared on LB plates were restreaked. +cam 20 ug/ml + or − thy 3 mM. (thyA auxotrophs will only grow in media supplemented with thy 3 mM).

Next, the antibiotic resistance was removed with pCP20 transformation. pCP20 has the yeast Flp recombinase gene, FLP, chloramphenicol and ampicillin resistant genes, and temperature sensitive replication. Bacteria were grown in LB media containing the selecting antibiotic at 37° C. until OD600=0.4-0.6. 1 mL of cells were washed as follows: cells were pelleted at 16,000×g for 1 minute. The supernatant was discarded and the pellet was resuspended in 1 mL ice-cold 10% glycerol. This wash step was repeated 3× times. The final pellet was resuspended in 70 ul ice-cold 10% glycerol. Next, cells were electroporated with 1 ng pCP20 plasmid DNA, and 1 mL SOC supplemented with 3 mM thymidine was immediately added to the cuvette. Cells were resuspended and transferred to a culture tube and grown at 30° C. for 1 hours. Cells were then pelleted at 10,000×g for 1 minute, the supernatant was discarded, and the cell pellet was resuspended in 100 ul LB containing 3 mM thymidine and spread on LB agar plates containing 3 mM thy and 100 ug/ml carbenicillin and grown at 30° C. for 16-24 hours. Next, transformants were colony purified non-selectively (no antibiotics) at 42° C.

To test the colony-purified transformants, a colony was picked from the 42° C. plate with a pipette tip and resuspended in 10 μL LB. 3 μL of the cell suspension was pipetted onto a set of 3 plates: Cam, (37° C.; tests for the presence/absence of CamR gene in the genome of the host strain), Amp, (30° C., tests for the presence/absence of AmpR from the pCP20 plasmid) and LB only (desired cells that have lost the chloramphenicol cassette and the pCP20 plasmid), 37° C. Colonies were considered cured if there is no growth in neither the Cam or Amp plate, picked, and re-streaked on an LB plate to get single colonies, and grown overnight at 37° C.

Example 15

Nitric Oxide-Inducible Reporter Constructs

Figure 24C:
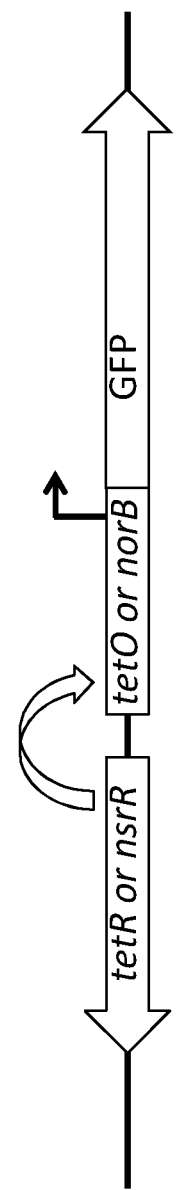

ATC and nitric oxide-inducible reporter constructs were synthesized (Genewiz, Cambridge, Mass.). When induced by their cognate inducers, these constructs express GFP, which is detected by monitoring fluorescence in a plate reader at an excitation/emission of 395/509 nm, respectively. Nissle cells harboring plasmids with either the control, ATC-inducible Ptet-GFP reporter construct, or the nitric oxide inducible PnsrR-GFP reporter construct were first grown to early log phase (OD600 of about 0.4-0.6), at which point they were transferred to 96-well microtiter plates containing LB and two-fold decreased inducer (ATC or the long half-life NO donor, DETA-NO (Sigma)). Both ATC and NO were able to induce the expression of GFP in their respective constructs across a range of concentrations (FIG. 24A and FIG. 24B) promoter activity is expressed as relative florescence units. An exemplary sequence of a nitric oxide-inducible reporter construct is shown. The bsrR sequence is bolded. The gfp sequence is underlined. The PnsrR (NO regulated promoter and RBS) is italicized. The constitutive promoter and RBS are boxed boxed These constructs, when induced by their cognate inducer, lead to high level expression of GFP, which is detected by monitoring fluorescence in a plate reader at an excitation/emission of 395/509 nm, respectively. Nissle cells harboring plasmids with either the ATC-inducible Ptet-GFP reporter construct or the nitric oxide inducible PnsrR-GFP reporter construct were first grown to early log phase (OD600=~0.4-0.6), at which point they were transferred to 96-well microtiter plates containing LB and 2-fold decreases in inducer (ATC or the long half-life NO donor, DETA-NO (Sigma)). It was observed that both the ATC and NO were able to induce the expression of GFP in their respective construct across a wide range of concentrations. Promoter activity is expressed as relative florescence units.

Figure 24D:
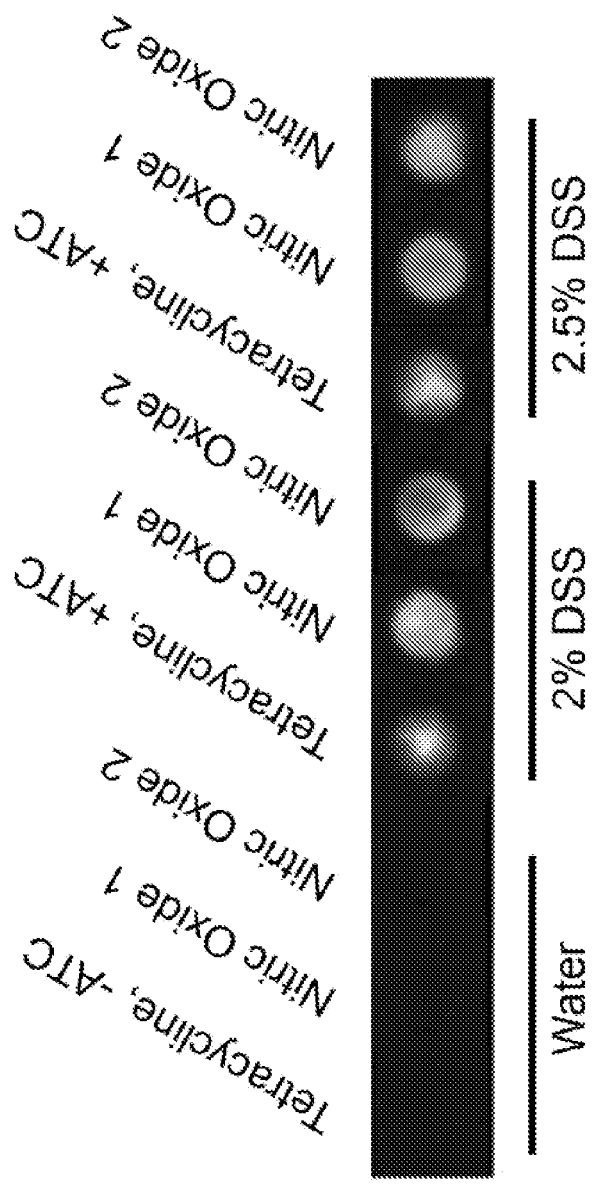
Figure 25:
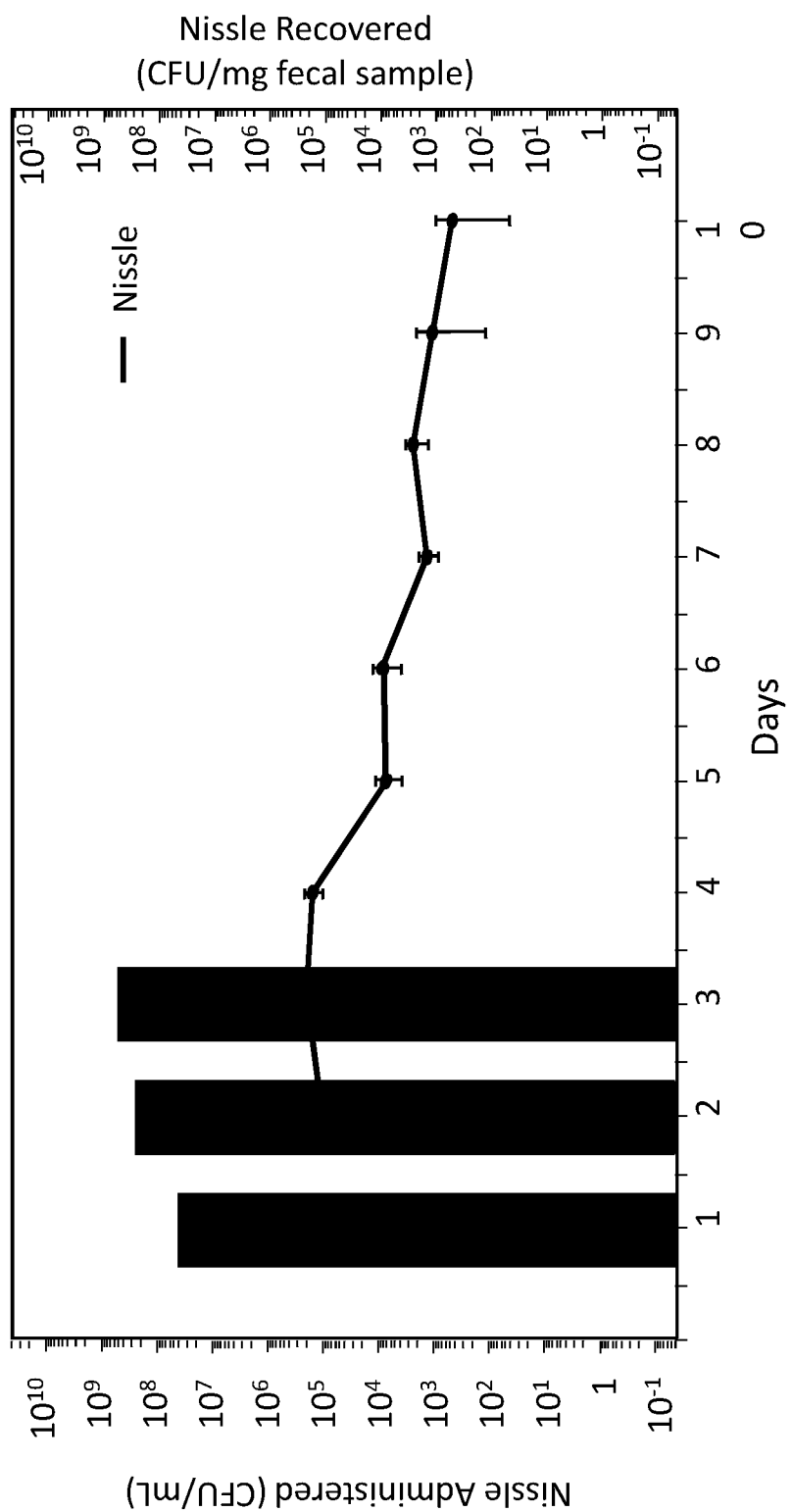
FIG. 25 depicts a graph of Nissle residence in vivo. Streptomycin-resistant Nissle was administered to mice via oral gavage without antibiotic pre-treatment. Fecal pellets from 6 total mice were monitored post-administration to determine the amount of administered Nissle still residing within the mouse gastrointestinal tract. The bars represent the number of bacteria administered to the mice. The line represents the number of Nissle recovered from the fecal samples each day for 10 consecutive days.
Figure 26:
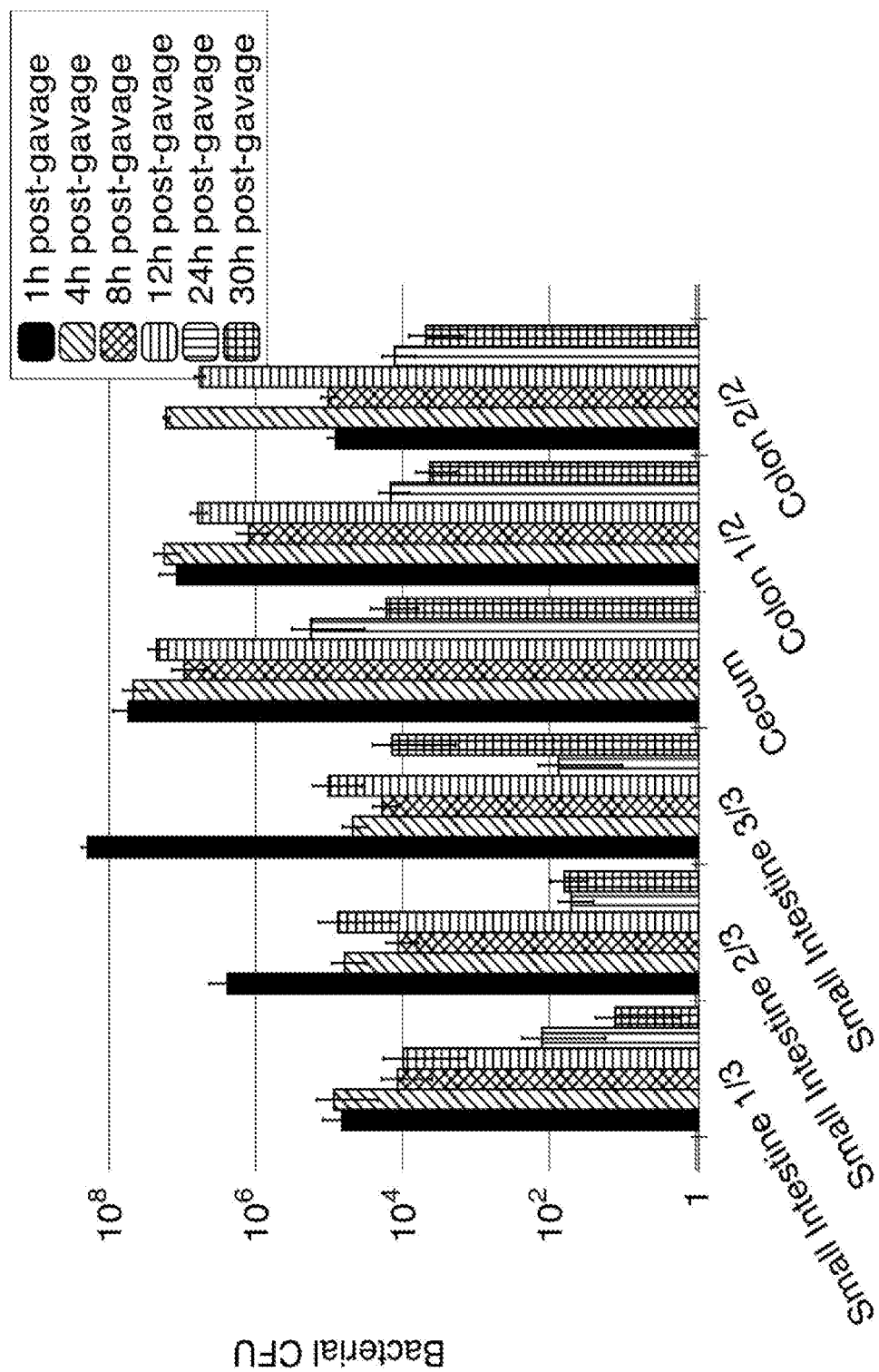
FIG. 26 depicts a bar graph of residence over time for streptomycin resistant Nissle in various compartments of the intestinal tract at 1, 4, 8, 12, 24, and 30 hours post gavage. Mice were treated with approximately 109 CFU, and at each time point, animals (n=4) were euthanized, and intestine, cecum, and colon were removed. The small intestine was cut into three sections, and the large intestine and colon each into two sections. Intestinal effluents gathered and CFUs in each compartment were determined by serial dilution plating.
Figure 28:
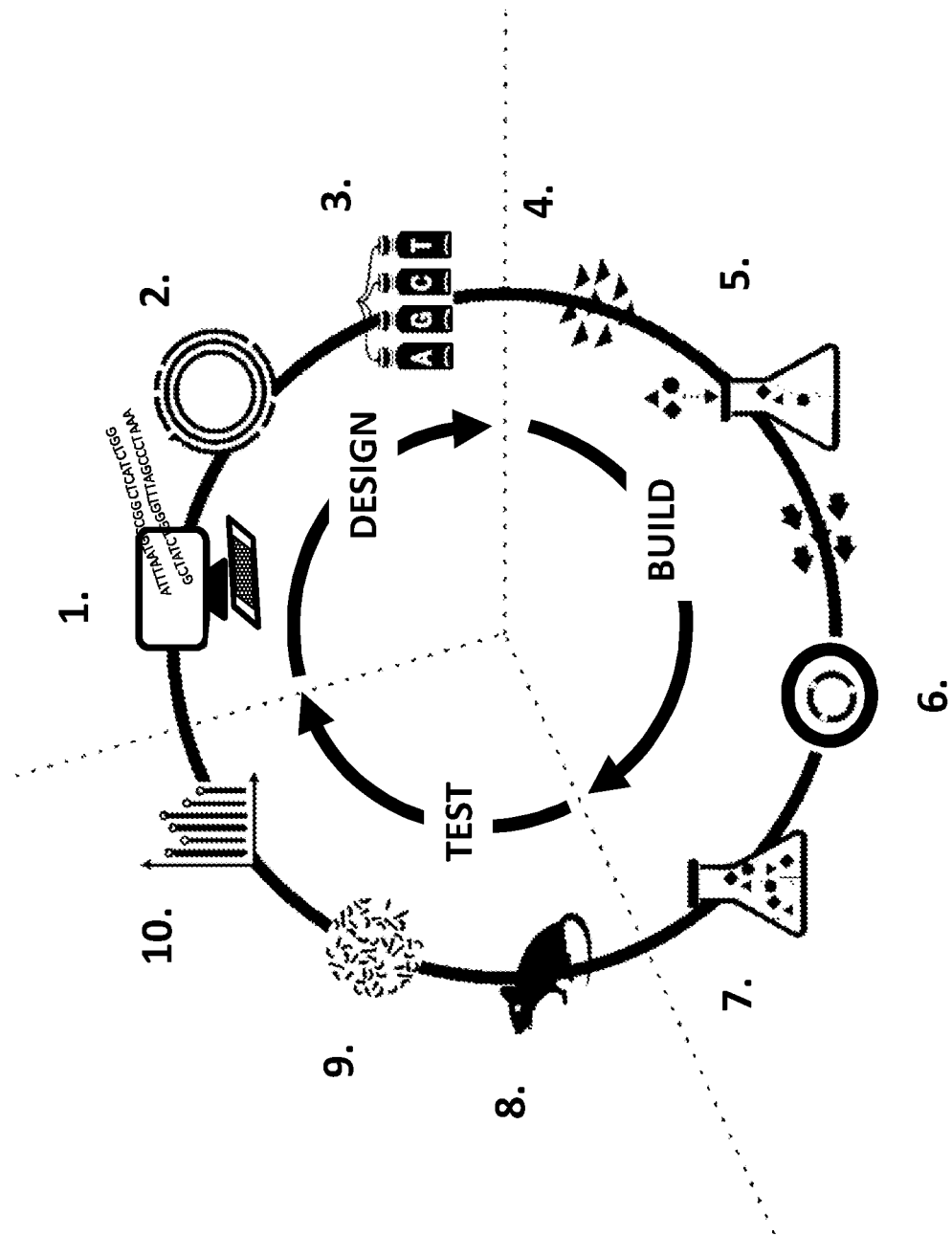
FIG. 28 depicts a simple, robust, and rapid platform for generating and characterizing synthetic biotics, comprising steps 1 through 10. Step 1 comprises designing one or more disease pathway(s); Step 2 comprises identifying one or more target metabolite(s); Step 3 comprises designing on e or more gene circuit(s); Step 4 comprises building the synthetic biotic; Step 5 comprises activating the one or more circuit(s) in vitro; Step 6 comprises characterizing circuit activation kinetics; Step 7 comprises optimizing in vitro productivity to the disease threshold; Step 8 comprises testing the optimized circuit(s) in animal disease model(s); Step 9 comprises assimilation into the microbiome; Step 10 comprises developing understanding of the in vivo PK and dosing regimen.
Figure 29:
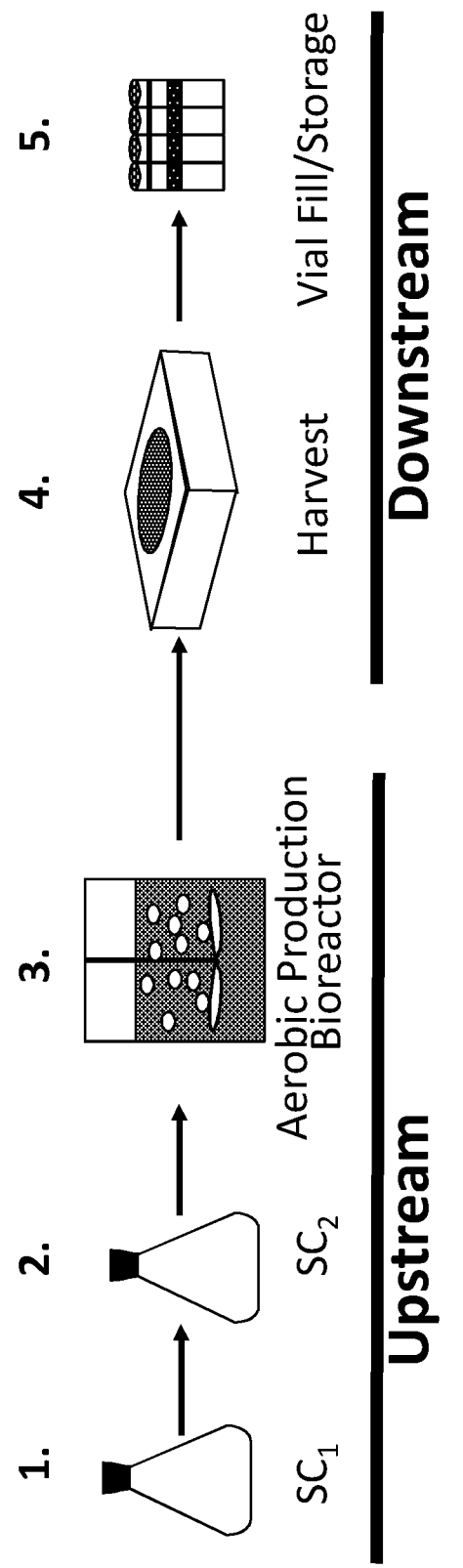
FIG. 29 depict a schematic of non-limiting manufacturing processes for upstream and downstream production of the genetically engineered bacteria of the present disclosure. (1) depicts the parameters for starter culture 1 (SC1): loop full—glycerol stock, duration overnight, temperature 37° C., shaking at 250 rpm. (2) depicts the parameters for starter culture 2 (SC2): 1/100 dilution from SC1, duration 1.5 hours, temperature 37° C., shaking at 250 rpm. (3) depicts the parameters for the production bioreactor: inoculum—SC2, temperature 37° C., pH set point 7.00, pH dead band 0.05, dissolved oxygen set point 50%, dissolved oxygen cascade agitation/gas FLO, agitation limits 300-1200 rpm, gas FLO limits 0.5-20 standard liters per minute, duration 24 hours. (4) depicts the parameters for harvest: centrifugation at speed 4000 rpm and duration 30 minutes, wash 1× 10% glycerol/PBS, centrifugation, re-suspension 10% glycerol/PBS. (5) depicts the parameters for vial fill/storage: 1-2 mL aliquots, −80° C.

FIG. 24D shows NO-GFP constructs (the dot blot) *E. coli* Nissle harboring the nitric oxide inducible NsrR-GFP reporter fusion were grown overnight in LB supplemented with kanamycin. Bacteria were then diluted 1:100 into LB containing kanamycin and grown to an optical density of 0.4-0.5 and then pelleted by centrifugation. Bacteria were resuspended in phosphate buffered saline and 100 microliters were administered by oral gavage to mice. IBD is induced in mice by supplementing drinking water with 2-3% dextran sodium sulfate for 7 days prior to bacterial gavage. At 4 hours post-gavage, mice were sacrificed and bacteria were recovered from colonic samples. Colonic contents were boiled in SDS, and the soluble fractions were used to perform a dot blot for GFP detection (induction of NsrR-regulated promoters). Detection of GFP was performed by binding of anti-GFP antibody conjugated to HRP (horse radish peroxidase). Detection was visualized using Pierce chemiluminescent detection kit. It is shown in the figure that NsrR-regulated promoters are induced in DSS-treated mice, but are not shown to be induced in untreated mice. This is consistent with the role of NsrR in response to NO, and thus inflammation.

Bacteria harboring a plasmid expressing NsrR under control of a constitutive promoter and the reporter gene gfp (green fluorescent protein) under control of an NsrR-inducible promoter were grown overnight in LB supplemented with kanamycin. Bacteria are then diluted 1:100 into LB containing kanamycin and grown to an optical density of about 0.4-0.5 and then pelleted by centrifugation. Bacteria are resuspended in phosphate buffered saline and 100 microliters were administered by oral gavage to mice. IBD is induced in mice by supplementing drinking water with 2-3% dextran sodium sulfate for 7 days prior to bacterial gavage. At 4 hours post-gavage, mice were sacrificed and bacteria were recovered from colonic samples. Colonic contents were boiled in SDS, and the soluble fractions were used to perform a dot blot for GFP detection (induction of NsrR-regulated promoters) Detection of GFP was performed by binding of anti-GFP antibody conjugated to to HRP (horse radish peroxidase). Detection was visualized using Pierce chemiluminescent detection kit. FIG. 24D shows NsrR-regulated promoters are induced in DSS-treated mice, but not in untreated mice.

Example 16

FNR Promoter Activity

Figure 22:
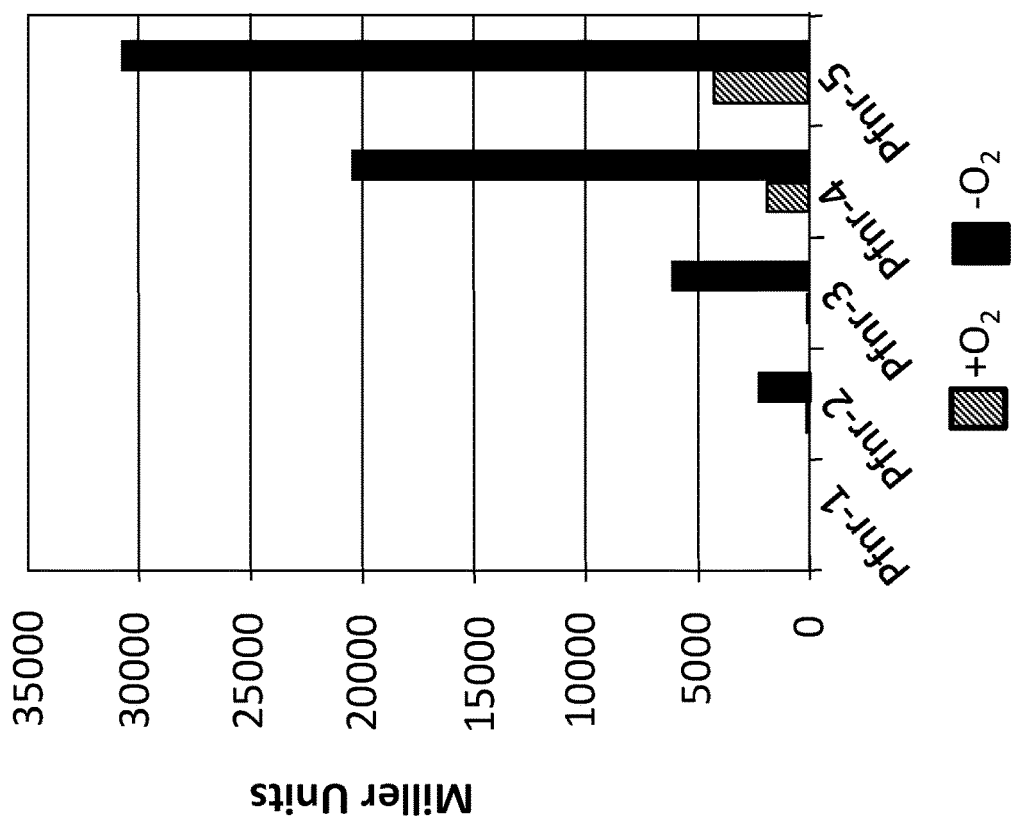
FIG. 22 depicts a bar graph of β-galactosidase levels in samples comprising bacteria harboring a low-copy plasmid expressing lacZ from an FNR-responsive promoter selected from the exemplary FNR promoters shown in Table 5 (Pfnr1-5). Different FNR-responsive promoters were used to create a library of anaerobic-inducible reporters with a variety of expression levels and dynamic ranges. These promoters included strong ribosome binding sites. Bacterial cultures were grown in either aerobic ($+O_2$) or anaerobic conditions ($-O_2$). Samples were removed at 4 hrs and the promoter activity based on β-galactosidase levels was analyzed by performing standard β-galactosidase colorimetric assays.
Figure 23A:
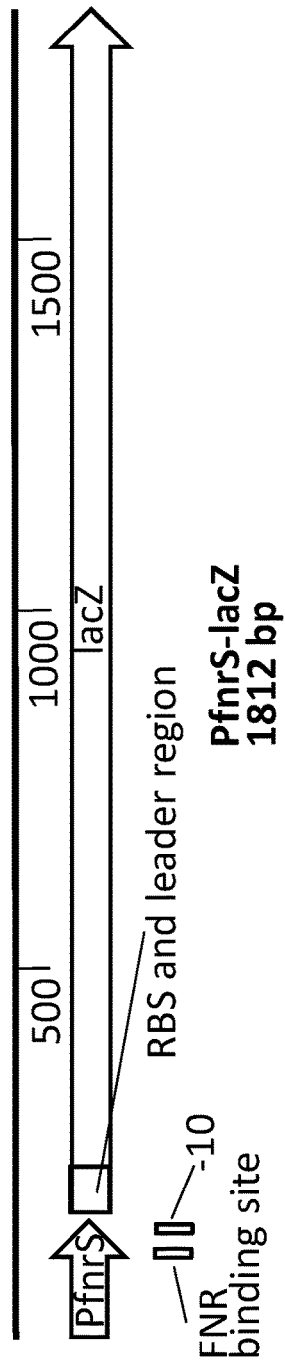
FIG. 23A, FIG. 23B, and FIG. 23C depicts a schematic representation of the lacZ gene under the control of an exemplary FNR promoter ($P_{fnrS}$). LacZ encodes the β-galactosidase enzyme and is a common reporter gene in bacteria.
Figure 23B:
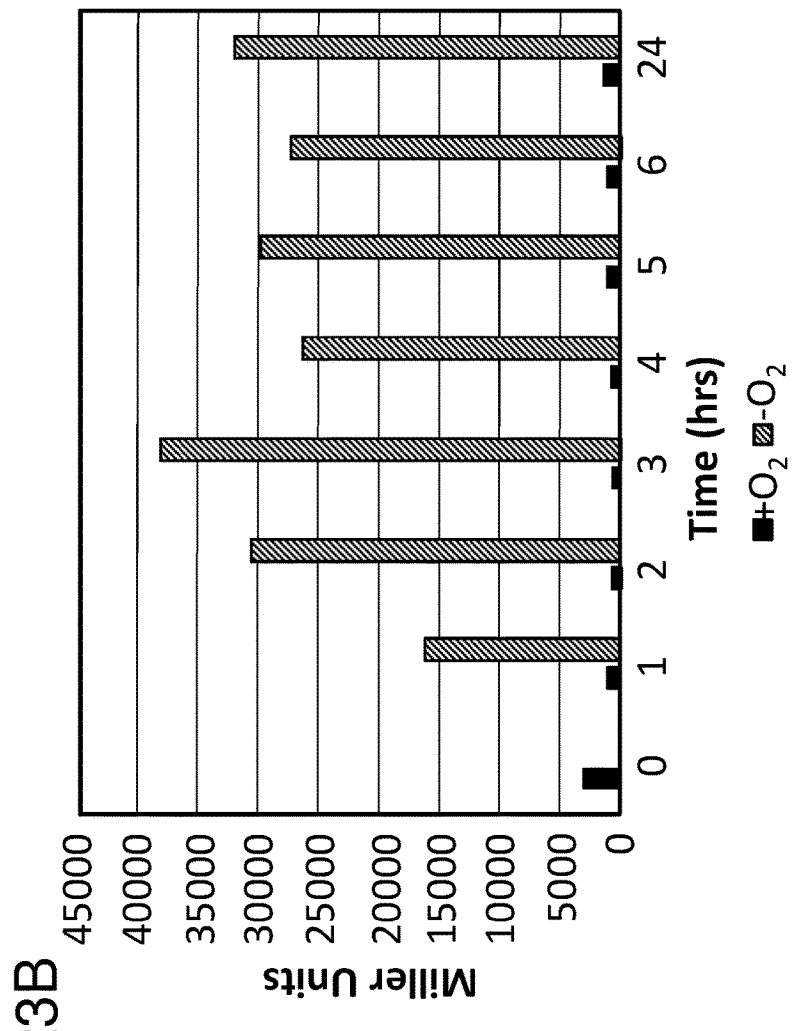
Figure 23C:
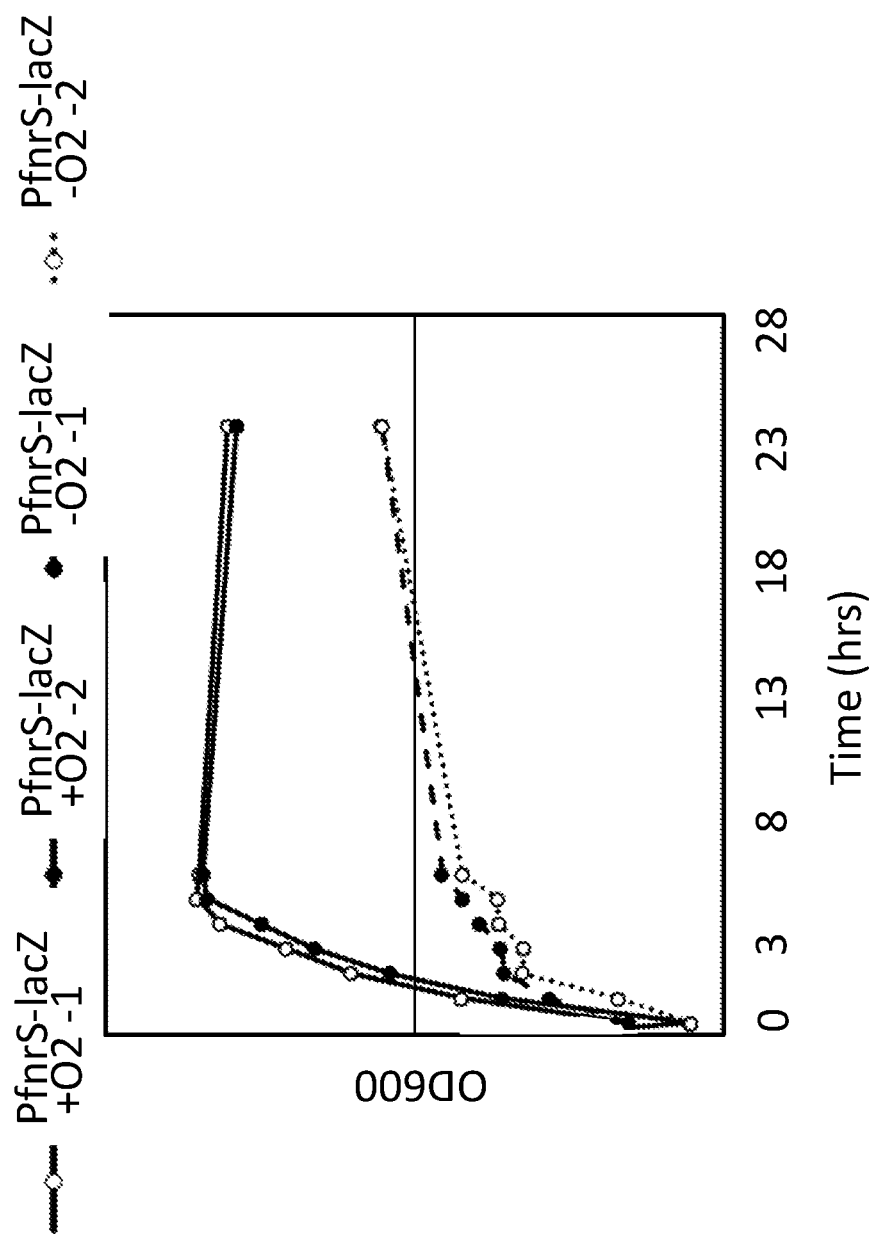

In order to measure the promoter activity of different FNR promoters, the lacZ gene, as well as transcriptional and translational elements, were synthesized (Gen9, Cambridge, Mass.) and cloned into vector pBR322. The lacZ gene was placed under the control of any of the exemplary FNR promoter sequences disclosed in Table 5 and Table 6. The nucleotide sequences of these constructs are shown in Table 25-29 (SEQ ID NO: 53-57). Exemplary results are shown in FIG. 22. However, as noted above, the lacZ gene may be driven by other inducible promoters in order to analyze activities of those promoters, and other genes may be used in place of the lacZ gene as a readout for promoter activity.

Table 25 shows the nucleotide sequence of an exemplary construct comprising a gene encoding lacZ, and an exemplary FNR promoter, $P_{fnr1}$ (SEQ ID NO: 53). The construct comprises a translational fusion of the Nissle nirB1 gene and the lacZ gene, in which the translational fusions are fused in frame to the $8^{th}$ codon of the lacZ coding region. The $P_{fnr1}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 26 shows the nucleotide sequence of an exemplary construct comprising a gene encoding lacZ, and an exemplary FNR promoter, $P_{fnr2}$ (SEQ ID NO: 54). The construct comprises a translational fusion of the Nissle ydfZ gene and the lacZ gene, in which the translational fusions are fused in frame to the $8^{th}$ codon of the lacZ coding region. The $P_{fnr2}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 27 shows the nucleotide sequence of an exemplary construct comprising a gene encoding lacZ, and an exemplary FNR promoter, $P_{fnr3}$ ((SEQ ID NO: 55). The construct comprises a transcriptional fusion of the Nissle nirB gene and the lacZ gene, in which the transcriptional fusions use only the promoter region fused to a strong ribosomal binding site. The $P_{fnr3}$ sequence is bolded lower case, and the predicted ribosome binding site within the promoter is underlined. The lacZ sequence is underlined upper case.

ATG site is bolded upper case, and the cloning sites used to synthesize the construct are shown in regular upper case.

Table 28 shows the nucleotide sequence of an exemplary construct comprising a gene encoding lacZ, and an exemplary FNR promoter, P$_{fnr4}$ ((SEQ ID NO: 56). The construct comprises a transcriptional fusion of the Nissle ydfZ gene and the lacZ gene. The P$_{fnr4}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 29 shows the nucleotide sequence of an exemplary construct comprising a gene encoding lacZ, and an exemplary FNR promoter, PfnrS ((SEQ ID NO: 57). The construct comprises a transcriptional fusion of the anaerobically induced small RNA gene, fnrS1, fused to lacZ. The P$_{fnrs}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

TABLE 25

Pfnr1-lacZ construct Sequences
Nucleotide sequences of Pfnr1-lacZ construct,
low-copy (SEQ ID NO: 53)

GGTACCgtcagcataacaccctgacctctcattaattgttcatgccgggc
ggcactatcgtcgtccggccttttcctctcttactctgctacgtacatct
atttctataaatccgttcaatttgtctgttttttgcacaaacatgaaata
tcagacaattccgtgacttaagaaaatttatacaaatcagcaatataccc
cttaaggagtatataaaggtgaatttgatttacatcaataagcgggttg
ctgaatcgttaaggtaggcggtaatagaaaag<u>aaatcgagg</u>caaaa**ATGa
gcaaagtcagactcgcaatta**tGGATCCTCTGGCCGTCGTATTACAACGT
CGTGACTGGGAAAACCCTGGCGTTACCCAACTTAATCGCCTTGCGGCACA
TCCCCCTTTCGCCAGCTGGCGTAATAGCGAAGAGGCCCGCACCGATCGCC
CTTCCCAACAGTTGCGCAGCCTGAATGGCGAATGGCGCTTTGCCTGGTTT
CCGGCACCAGAAGCGGTGCCGGAAAGCTGGCTGGAGTGCGATCTTCCTGA
CGCCGATACTGTCGTCGTCCCCTCAAACTGGCAGATGCACGGTTACGATG
CGCCTATCTACACCAACGTGACCTATCCCATTACGGTCAATCCGCCGTTT
GTTCCCGCGGAGAATCCGACAGGTTGTTACTCGCTCACATTTAATATTGA
TGAAAGCTGGCTACAGGAAGGCCAGACGCGAATTATTTTTGATGGCGTTA
ACTCGGCGTTTCATCTGTGGTGCAACGGGCGCTGGGTCGGTTACGGCCAG
GACAGCCGTTTGCCGTCTGAATTTGACCTGAGCGCATTTTTACGCGCCGG
AGAAAACCGCCTCGCGGTGATGGTGCTGCGCTGGAGTGACGGCAGTTATC
TGGAAGATCAGGATATGTGGCGGATGAGCGGCATTTTCCGTGACGTCTCG
TTGCTGCATAAACCGACCACGCAAATCAGCGATTTCCAAGTTACCACTCT
CTTTAATGATGATTTCAGCCGCGCGGTACTGGAGGCAGAAGTTCAGATGT
ACGGCGAGCTGCGCGATGAACTGCGGGTGACGGTTTCTTTGTGGCAGGGT
GAAACGCAGGTCGCCAGCGGCACCGCGCCTTTCGGCGGTGAAATTATCGA
TGAGCGTGGCGGTTATGCCGATCGCGTCACACTACGCCTGAACGTTGAAA
ATCCGGAACTGTGGAGCGCCGAAATCCCGAATCTCTATCGTGCAGTGGTT
GAACTGCACACCGCCGACGGCACGCTGATTGAAGCAGAAGCCTGCGACGT
CGGTTTCCGCGAGGTGCGGATTGAAAATGGTCTGCTGCTGCTGAACGGCA
AGCCGTTGCTGATTCGCGGCGTTAACCGTCACGAGCATCATCCTCTGCAT
GGTCAGGTCATGGATGAGCAGACGATGGTGCAGGATATCCTGCTGATGAA
GCAGAACAACTTTAACGCCGTGCGCTGTTCGCATTATCCGAACCATCCGC
TGTGGTACACGCTGTGCGACCGCTACGGCCTGTATGTGGTGGATGAAGCC
AATATTGAAACCCACGGCATGGTGCCAATGAATCGTCTGACCGATGATCC
GCGCTGGCTACCCGCGATGAGCGAACGCGTAACGCGATGGTGCAGCGCG
ATCGTAATCACCCGAGTGTGATCATCTGGTCGCTGGGGAATGAATCAGGC
CACGGCGCTAATCACGACGCGCTGTATCGCTGGATCAAATCTGTCGATCC
TTCCCGCCCGGTACAGTATGAAGGCGGCGGAGCCGACACCACGGCCACCG
ATATTATTTGCCCGATGTACGCGCGCGTGGATGAAGACCAGCCCTTCCCG
GCGGTGCCGAAATGGTCCATCAAAAAATGGCTTTCGCTACCTGGAGAAAT
GCGCCCGCTGATCCTTTGCGAATATGCCCACGCGATGGGTAACAGTCTTG
GCGGCTTCGCTAAATACTGGCAGGCGTTTCGTCAGTACCCCCGTTTACAG
GGCGGCTTCGTCTGGGACTGGGTGGATCAGTCGCTGATTAAATATGATGA
AAACGGCAACCCGTGGTCGGCTTACGGCGGTGATTTTGGCGATACGCCGA
ACGATCGCCAGTTCTGTATGAACGGTCTGGTCTTTGCCGACCGCACGCCG
CATCCGGCGCTGACGGAAGCAAAACACCAACAGCAGTATTTCCAGTTCCG
TTTATCCGGCGAACCATCGAAGTGACCAGCGAATACCTGTTCCGTCATA
GCGATAACGAGTTCCTGCACTGGATGGTGGCACTGGATGGCAAGCCGCTG
GCAAGCGGTGAAGTGCCTCTGGATGTTGCCCGCAAGGTAAGCAGTTGAT
TGAACTGCCTGAACTGCCGCAGCCGGAGAGCGCCGGACAACTCTGGCTAA TABLE 25-continued Pfnr1-lacZ construct Sequences
Nucleotide sequences of Pfnr1-lacZ construct,
low-copy (SEQ ID NO: 53)

CGGTACGCGTAGTGCAACCAAACGCGACCGCATGGTCAGAAGCCGGACAC
ATCAGCGCCTGGCAGCAATGGCGTCTGGCGGAAAACCTCAGCGTGACACT
CCCCTCCGCGTCCCACGCCATCCCTCAACTGACCACCAGCGGAACGGATT
TTTGCATCGAGCTGGGTAATAAGCGTTGGCAATTTAACCGCCAGTCAGGC
TTTCTTTCACAGATGTGGATTGGCGATGAAAAACAACTGCTGACCCCGCT
GCGCGATCAGTTCACCCGTGCGCCGCTGGATAACGACATTGGCGTAAGTG
AAGCGACCCGCATTGACCCTAACGCCTGGGTCGAACGCTGGAAGGCGGCG
GGCCATTACCAGGCCGAAGCGGCGTTGTTGCAGTGCACGGCAGATACACT
TGCCGACGCGGTGCTGATTACAACCGCCCACGCGTGGCAGCATCAGGGGA
AAACCTTATTTATCAGCCGGAAAACCTACCGGATTGATGGGCACGGTGAG
ATGGTCATCAATGTGGATGTTGCGGTGGCAAGCGATACACCGCATCCGGC
GCGGATTGGCCTGACCTGCCAGCTGGCGCAGGTCTCAGAGCGGGTAAACT
GGCTCGGCCTGGGGCCGCAAGAAAACTATCCCGACCGCCTTACTGCAGCC
TGTTTTGACCGCTGGGATCTGCCATTGTCAGACATGTATACCCCGTACGT
CTTCCCGAGCGAAAACGGTCTGCGCTGCGGGACGCGCGAATTGAATTATG
GCCCACACCAGTGGCGCGGCGACTTCCAGTTCAACATCAGCCGCTACAGC
CAACAACAACTGATGGAAACCAGCCATCGCCATCTGCTGCACGCGGAAGA
AGGCACATGGCTGAATATCGACGGTTTCCATATGGGGATTGGTGGCGACG
ACTCCTGGAGCCCGTCAGTATCGGCGGAATTCCAGCTGAGCGCCGGTCGC
TACCATTACCAGTTGGTCTGGTGTCAAAAATAA

TABLE 26

Pfnr2-lacZ construct sequences
Nucleotide sequences of Pfnr2-lacZ construct,
low-copy (SEQ ID NO: 54)

GGTACCcatttcctctcatcccatccggggtgagagtcttttccccgac
ttatggctcatgcatgcatcaaaaaagatgtgagcttgatcaaaaacaaa
aaatatttcactcgacaggagtatttatattgcgcccgttacgtgggctt
cgactgtaaatcagaaaggagaaaacacctATGacgacctacgatcgGGA
TCCTCTGGCCGTCGTATTACAACGTCGTGACTGGGAAAACCCTGGCGTTA
CCCAACTTAATCGCCTTGCGGCACATCCCCCTTTCGCCAGCTGGCGTAAT
AGCGAAGAGGCCCGCACCGATCGCCCTTCCCAACAGTTGCGCAGCCTGAA
TGGCGAATGGCGCTTTGCCTGGTTTCCGGCACCAGAAGCGGTGCCGGAAA
GCTGGCTGGAGTGCGATCTTCCTGACGCCGATACTGTCGTCGTCCCCTCA
AACTGGCAGATGCACGGTTACGATGCGCCTATCTACACCAACGTGACCTA
TCCCATTACGGTCAATCCGCCGTTTGTTCCCGCGGAGAATCCGACAGGTT
GTTACTCGCTCACATTTAATATTGATGAAAGCTGGCTACAGGAAGGCCAG
ACGCGAATTATTTTTGATGGCGTTAACTCGGCGTTTCATCTGTGGTGCAA
CGGGCGCTGGGTCGGTTACGGCCAGGACAGCCGTTTGCCGTCTGAATTTG
ACCTGAGCGCATTTTTACGCGCCGGAGAAAACCGCCTCGCGGTGATGGTG
CTGCGCTGGAGTGACGGCAGTTATCTGGAAGATCAGGATATGTGGCGGAT
GAGCGGCATTTTCCGTGACGTCTCGTTGCTGCATAAACCGACCACGCAAA
TCAGCGATTTCCAAGTTACCACTCTCTTTAATGATGATTTCAGCCGCGCG
GTACTGGAGGCAGAAGTTCAGATGTACGGCGAGCTGCGCGATGAACTGCG
GGTGACGGTTTCTTTGTGGCAGGGTGAAACGCAGGTCGCCAGCGGCACCG
CGCCTTTCGGCGGTGAAATTATCGATGAGCGTGGCGGTTATGCCGATCGC
GTCACACTACGCCTGAACGTTGAAAATCCGGAACTGTGGAGCGCCGAAAT
CCCGAATCTCTATCGTGCAGTGGTTGAACTGCACACCGCCGACGGCACGC
TGATTGAAGCAGAAGCCTGCGACGTCGGTTTCCGCGAGGTGCGGATTGAA
AATGGTCTGCTGCTGCTGAACGGCAAGCCGTTGCTGATTCGCGGCGTTAA
CCGTCACGAGCATCATCCTCTGCATGGTCAGGTCATGGATGAGCAGACGA
TGGTGCAGGATATCCTGCTGATGAAGCAGAACAACTTTAACGCCGTGCGC
TGTTCGCATTATCCGAACCATCCGCTGTGGTACACGCTGTGCGACCGCTA
CGGCCTGTATGTGGTGGATGAAGCCAATATTGAAACCCACGGCATGGTGC
CAATGAATCGTCTGACCGATGATCCGCGCTGGCTACCGGCGATGAGCGAA
CGCGTAACGCGGATGGTGCAGCGCGATCGTAATCACCCGAGTGTGATCAT
CTGGTCGCTGGGGAATGAATCAGGCCACGGCGCTAATCACGACGCGCTGT
ATCGCTGGATCAAATCTGTCGATCCTTCCCGCCCGGTACAGTATGAAGGC
GGCGGAGCCGACACCACGGCCACCGATATTATTTGCCCGATGTACGCGCG
CGTGGATGAAGACCAGCCCTTCCCGGCGGTGCCGAAATGGTCCATCAAAA
AATGGCTTTCGCTACCTGGAGAAATGCGCCCGCTGATCCTTTGCGAATAT
GCCCACGCGATGGGTAACAGTCTTGGCGGCTTCGCTAAATACTGGCAGGC
GTTTCGTCAGTACCCCCGTTTACAGGGCGGCTTCGTCTGGGACTGGGTGG
ATCAGTCGCTGATTAAATATGATGAAAACGGCAACCCGTGGTCGGCTTAC
GGCGGTGATTTTGGCGATACGCCGAACGATCGCCAGTTCTGTATGAACGG
TCTGGTCTTTGCCGACCGCACGCCGCATCCGGCGCTGACGGAAGCAAAAC
ACCAACAGCAGTATTTCCAGTTCCGTTTATCCGGCGAACCATCGAAGTG
ACCAGCGAATACCTGTTCCGTCATAGCGATAACGAGTTCCTGCACTGGAT
GGTGGCACTGGATGGCAAGCCGCTGGCAAGCGGTGAAGTGCCTCTGGATG
TTGCCCGCAAGGTAAGCAGTTGATTGAACTGCCTGAACTGCCGCAGCCG
GAGAGCGCCGGACAACTCTGGCTAACGGTACGCGTAGTGCAACCAAACGC

TABLE 26-continued

Pfnr2-lacZ construct sequences
Nucleotide sequences of Pfnr2-lacZ construct,
low-copy (SEQ ID NO: 54)

GACCGCATGGTCAGAAGCCGGACACATCAGCGCCTGGCAGCAATGGCGTC
TGGCGGAAAACCTCAGCGTGACACTCCCCTCCGCGTCCCACGCCATCCCT
CAACTGACCACCAGCGGAACGGATTTTTGCATCGAGCTGGGTAATAAGCG
TTGGCAATTTAACCGCCAGTCAGGCTTTCTTTCACAGATGTGGATTGGCG
ATGAAAAACAACTGCTGACCCCGCTGCGCGATCAGTTCACCCGTGCGCCG
CTGGATAACGACATTGGCGTAAGTGAAGCGACCCGCATTGACCCTAACGC
CTGGGTCGAACGCTGGAAGGCGGCGGGCCATTACCAGGCCGAAGCGGCGT
TGTTGCAGTGCACGGCAGATACACTTGCCGACGCGGTGCTGATTACAACC
GCCCACGCGTGGCAGCATCAGGGGAAAACCTTATTTATCAGCCGGAAAAC
CTACCGGATTGATGGGCACGGTGAGATGGTCATCAATGTGGATGTTGCGG
TGGCAAGCGATACACCGCATCCGGCGCGGATTGGCCTGACCTGCCAGCTG
GCGCAGGTCTCAGAGCGGGTAAACTGGCTCGGCCTGGGGCCGCAAGAAAA
CTATCCCGACCGCCTTACTGCAGCCTGTTTTGACCGCTGGGATCTGCCAT
TGTCAGACATGTATACCCCGTACGTCTTCCCGAGCGAAAACGGTCTGCGC
TGCGGGACGCGCGAATTGAATTATGGCCCACACCAGTGGCGCGGCGACTT
CCAGTTCAACATCAGCCGCTACAGCCAACAACAACTGATGGAAACCAGCC
ATCGCCATCTGCTGCACGCGGAAGAAGGCACATGGCTGAATATCGACGGT
TTCCATATGGGGATTGGTGGCGACGACTCCTGGAGCCCGTCAGTATCGGC
GGAATTCCAGCTGAGCGCCGGTCGCTACCATTACCAGTTGGTCTGGTGTC
AAAAATAA

TABLE 27

Pfnr3-lacZ construct Sequences
Nucleotide sequences of Pfnr3-lacZ construct,
low-copy (SEQ ID NO: 55)

GGTACCgtcagcataacaccctgacctctcattaattgttcatgccgggc
ggcactatcgtcgtccggccttttcctctcttactctgctacgtacatct
atttctataaatccgttcaatttgtctgtttttgcacaaacatgaaata
tcagacaattccgtgacttaagaaaatttatacaaatcagcaatataccc
cttaaggagtatataaaggtgaatttgatttacatcaataagcggggttg
ctgaatcgttaaGGATCCctctagaaataattttgtttaactttaagaag
gagatatacatATGACTATGATTACGGATTCTCTGGCCGTCGTATTACAA
CGTCGTGACTGGGAAAACCCTGGCGTTACCCAACTTAATCGCCTTGCGC
ACATCCCCCTTTCGCCAGCTGGCGTAATAGCGAAGAGGCCCGCACCGATC
GCCCTTCCAACAGTTGCGCAGCCTGAATGGCGAATGGCGCTTTGCCTGG
TTTCCGGCACCAGAAGCGGTGCCGGAAAGCTGGCTGGAGTGCGATCTTCC
TGACGCCGATACTGTCGTCGTCCCCTCAAACTGGCAGATGCACGGTTACG
ATGCGCCTATCTACACCAACGTGACCTATCCCATTACGGTCAATCCGCCG
TTTGTTCCCGCGGAGAATCCGACAGGTTGTTACTCGCTCACATTTAATAT
TGATGAAAGCTGGCTACAGGAAGGCCAGACGCGAATTATTTTTGATGGCG
TTAACTCGGCGTTTCATCTGTGGTGCAACGGGCGCTGGGTCGGTTACGGC
CAGGACGCCGTTTGCCGTCTGAATTTGACCTGAGCGCATTTTTACGCGC
CGGAGAAAACCGCCTCGCGGTGATGGTGCTGCGCTGGAGTGACGGCAGTT
ATCTGGAAGATCAGGATATGTGGCGGATGAGCGGCATTTTCCGTGACGTC
TCGTTGCTGCATAAACCGACCACGCAAATCAGCGATTTCCAAGTTACCAC
TCTCTTTAATGATGTTTCAGCCGCCGCGGTACTGGAGGCAGAAGTTCAGA
TGTACGGCGAGCTGCGCGATGAACTCGGGTGACGGTTTCTTTGTGGCAG
GGTGAAACGCAGGTCGCCAGCGGCACCGCGCCTTTCGGCGGTGAAATTAT
CGATGAGCGTGGCGGTTATGCCGATCGCGTCACACTACGCCTGAACGTTG
AAAATCCGGAACTGTGGAGCGCCGAAATCTCTATCGTGCAGTG
GTTGAACTGCACACCGCCGACGGCACGCTGATTGAAGCAGAAGCCTGCGA
CGTCGGTTTCCGCGAGGTGCGGATTGAAAATGGTCTGCTGCTGCTGAACG
GCAAGCCGTTGCTGATTCGCGGCGTTAACCGTCACGAGCATCATCCTCTG
CATGGTCAGGTCATGGATGAGCAGACAGATGGTCAGGAGCAAAACTTTAACGCCGTG
GAAGCAGAACAACTTTAACGCCGTGCGCTGTTCGCATTATCCGAACCATC
CGCTGTGGTACACGCTGTGCGACCGCTACGGCCTGTATGTGGTGGATGAA
GCCAATATTGAAACCCACGGCATGGTGCCAATGAATCGTCTGACCGATGA
TCCGCGCTGGCTACCCGCGATGAGCGAACGCGTAACGCGGTAACGCGATGGTGCAC
GCGATCGTAATCACCCGAGTGTGATCATCTGGTCGCTGGGGAATGAATCA
GGCCACGGCGCTAATCACGACGCGCTGTATCGCTGGATCAAATCTGTCGA
TCCTTCCCGCCCGGTACAGTATGAAGGCGGCGGAGCCGACACCACGGCCA
CCGATATTATTTGCCCGATGTACGCGCGCTGGCGAGACAGCCCTTCCCGGCGGTGCCGAAATGGC
CCGGCGGTGCCGAAATGTCCATCAAAAAATGGCTTTCGCTGCCTGGAGA
AATGCGCCGCTGATCCTTTGCGAATATGCCCACGCGATGGGTAACAGTC
TTGGCGGCTTCGCTAAATACTGGCAGGCGTTTCGTCAGTACCCCCGTTTA
CAGGGCGGCTTCGTCTGGGACTGGGTTGGATCAGTCGCTGATTAAATATGA
TGAAAACGCAACCGTGGTCGGCT
TGAAAACGCAACCGTGGTCGGCTTACGGCGGTGATTTTGGCGATATTGGC
CGAACGATCGCCAGTTCGTATGAACGGTCTGGTCTTTGCCGACCGCACG
CCGCATCCGGCGCTGACGGAAGCAAAACACCAACAGCAGTATTTCCAGTT
CCGTTTATCCGGGCGAACCATCGAAGTGACCAGCGAATACCTGTTCCGTC
ATAGCGATAACGAGTTCCTGCACTGGATGGTGGCACTGGATGGCAAGCCG

TABLE 27-continued

Pfnr3-lacZ construct Sequences
Nucleotide sequences of Pfnr3-lacZ construct,
low-copy (SEQ ID NO: 55)

CTGGCAAGCGGTGAAGTGCCTCTGGATGTTGGCCCGCAAGGTAAGCAGTT
GATTGAACTGCCTGAACTGCCGCAGCCGGAGAGCGCCGGACAACTCTGGC
TAACGGTACGCGTAGTGCAACCAAACGCGACCGCATGGTCAGAAGCCGGA
CACATCAGCGCCTGGCAGCAATGGCGTCTGGCGGAAAACCTCAGCGTGAC
ACTCCCCTCCGCGTCCCACGCCATCCCTCAACTGACCACCAGCGGAACGG
ATTTTTGCATCGAGCTGGGTAATAAGCGTTGGCAATTTAACCGCCAGTCA
GGCTTTCTTTCACAGATGTGGATTGGCGATGAAAAACAACTGCTGACCCC
GCTGCGCGATCAGTTCACCCGTGCGCCGCTGGATAACGACATTGGCGTAA
GTGAAGCGACCCGCATTGACCCTAACGCCTGGGTCGAACGCTGGAAGGCG
GCGGGCCATTACCAGGCCGAAGCGGCGTTGTTGCAGTGCACGGCAGATAC
ACTTGCCGACGCGGTGCTGATTACAACCGCCCACGCGTGGCAGCATCAGG
GGAAAACCTTATTTATCAGCCGGAAAACCTACCGGATTGATGGGCACGGT
GAGATGGTCATCAATGTGGATGTTGCGGTGGCAAGCGATACACCGCATCC
GGCGCGGATTGGCCTGACCTGCCAGCTGGCGCAGGTCTCAGAGCGGGTAA
ACTGGCTCGGCCTGGGGCCGCAAGAAAACTATCCCGACCGCCTTACTGCA
GCCTGTTTTGACCGCTGGGATCTGCCATTGTCAGACATGTATACCCCGTA
CGTCTTCCCGAGCGAAAACGGTCTGCGCTGCGGGACGCGCGAATTGAATT
ATGGCCCACACCAGTGGCGCGGCGACTTCCAGTTCAACATCAGCCGCTAC
AGCCAACAACAACTGATGGAAACCAGCCATCGCCATCTGCTGCACGCGGA
AGAAGGCACATGGCTGAATATCGACGGTTTCCATATGGGGATTGGTGGCG
ACGACTCCTGGAGCCCGTCAGTATCGGCGGAATTCCAGCTGAGCGCCGGT
CGCTACCATTACCAGTTGGTCTGGTGTCAAAAATAA

TABLE 28

Pfnr4-lacZ construct Sequences
Nucleotide sequences of Pfnr4-lacZ construct,
low-copy (SEQ ID NO: 56)

GGTACCcatttcctctcatcccatccggggtgagagtcttttcccccgac
ttatggctcatgcatgcatcaaaaaagatgtgagcttgatcaaaaacaaa
aaatatttcactcgacaggagtatttatattgcgcccGGATCCctctaga
aataattttgtttaactttaagaaggagatatacatATGACTATGATTAC
GGATTCTCTGGCCGTCGTATTACAACGTCGTGACTGGGAAAACCCTGGCG
TTACCCAACTTAATCGCCTTGCGCACATCCCCCTTTCGCCAGCTGGCGT
AATAGCGAAGAGGCCCGCACCGATCGCCCTTCCCAACAGTTGCGCAGCCT
GAATGGCGAATGGCGCTTTGCCTGGTTTCCGGCACCAGAAGCGGTGCCGG
AAAGCTGGCTGGAGTGCGATCTTCCTGACGCCGATACTGTCGTCGTCCCC
TCAAACTGGCAGATGCACGGTTACGATGCGCCTATCTACACCAACGTGAC
CTATCCCATTACGGTCAATCCGCCGTTTGTTCCCGCGGAGAATCCGACAG
GTTGTTACTCGCTCACATTTAATATTGATGAAAGCTGGCTACAGGAAGGC
CAGACGCGAATTATTTTTGATGGCGTTAACTCGGCGTTTCATCTGTGGTG
CAACGGGCGCTGGGTCGGTTACGGCCAGGACAGCCGTTTGCCGTCTGAAT
TTGACCTGAGCGCATTTTTACGCGCCGGAGAAAACCGCCTCGCGGTGATG
GTGCTGCGCTGGAGTGACGGCAGTTATCTGGAAGATCAGGATATGTGGCG
GATGAGCGGCATTTTCCGTGACGTCTCGTTGCTGCATAAACCGACCACGC
AAATCAGCGATTTCCAAGTTACCACTCTCTTTAATGATGATTTCAGCCGC
GCGGTACTGGAGGCAGAAGTTCAGATGTACGGCGAGCTGCGCGATGAACT
GCGGGTGACGGTTTCTTTGTGGCAGGGTGAAACGCAGGTCGCCAGCGGCA
CCGCGCCTTTCGGCGGTGAAATTATCGATGAGCGTGGCGGTTATGCCGAT
CGCGTCACACTACGCCTGAACGTTGAAAATCCGGAACTGTGGAGCGCCGA
AATCTCTATCGTGCAGGTTGAACTGCACACCGCCGACGGCA
CGCTGATTGAAGCAGAAGCCTGCGACGTCGGTTTCCGCGAGGTGCGGATT
GAAAATGGTCTGCTGCTGCTGAACGGCAAGCCGTTGCTGATTCGCGGCGT
TAACCGTCACGAGCATCATCCTCTGCATGGTCAGGTCATGGATGAGCAGA
CGATGGTCAGGATATCCTGCTGATGAAGCAGAACAACTTTAACGCCGTG
CGCTGTTCGCATTATCCGAACCATCCGCTGTGGTACACGCTGTGCGACCG
CTACGGCCTGTATGTGGTGGATGAAGCCAATATTGAAACCCACGGCATGG
TGCCAATGAATCGTCTGACCGATGATCCGCGCTGGCTACCCGCGATGAGC
GAACGCGTAACGCGAATGGTGCAGCGCGATCGTAATCACCCGAGTGTGAT
CATCTGGTCGCTGGGGAATGAATCAGGCCACGGCGCTAATCACGACGCGC
TGTATCGCTGGATCAAATCTGTCGATCCTTCCCGCCCGGTACAGTATGAA
GGCGGCGGAGCCGACACCACGGCCACCGATATTATTTGCCCGATGTACGC
GCGCGTGGATGAAGACCAGCCCTTCCCGGCGGTGCCGAAATGGTCCATCA
AAAAATGGCTTTCGCTGCCTGGAGAAATGCGCCGCTGATCCTTTGCGAA
TATGCCCACGCGATGGGTAACAGTCTTGGCGGCTTCGCTAAATACTGGCA
GGCGTTTCGTCAGTACCCCCGTTTACAGGGCGGCTTCGTCTGGGACTGGG
TGGATCAGTCGCTGATTAAATATGATGAAAACGGCAACCGTGGTCGGCT
TACGGCGGTGATTTTGGCGATACGCAACGATCGCCAGTTCGTATGAA
CGGTCTGGTCTTTGCCGACCGCACGCCGCATCCGGCGCTGACGGAAGCAA
AACACCAACAGCAGTATTTCCAGTTCCGTTTATCCGGGCGAACCATCGAA
GTGACCAGCGAATACCTGTTCCGTCATAGCGATAACGAGTTCCTGCACTG
GATGGTGGCACTGGATGGCAAGCCGCTGGCAAGCGGTGAAGTGCCTCTGG

TABLE 28-continued

Pfnr4-lacZ construct Sequences
Nucleotide sequences of Pfnr4-lacZ construct,
low-copy (SEQ ID NO: 56)

ATGTTGGCCCGCAAGGTAAGCAGTTGATTGAACTGCCTGAACTGCCGCAG
CCGGAGAGCGCCGGACAACTCTGGCTAACGGTACGCGTAGTGCAACCAAA
CGCGACCGCATGGTCAGAAGCCGGACACATCAGCGCCTGGCAGCAATGGC
GTCTGGCGGAAAACCTCAGCGTGACACTCCCCTCCGCGTCCCACGCCGGT
CCTCAACTGACCACCACGCGGAACGGATTTTTGCATCGAGCTGGGTAATAA
GCGTTGGCAATTTAACCGCCAGTCAGGCTTTCTTTCACAGATGTGGATTG
GCGATGAAAAACAACTGCTGACCCCGCTGCGCGATCAGTTCACCCGTGCG
CCGCTGGATAACGACATTGGCGTAAGTGAAGCGACCCGCATTGACCCTAA
CGCCTGGGTCGAACGCTGGAAGGCGGCGGGCCATTACCAGGCCGAAGCGG
CGTTGTTGCAGTGCACGGCAGATACCATTGCCGACGCGGTGCTGATTACA
ACCGCCCACGCGTGGCAGCATCAGGGGAAAACCTTATTTATCAGCCGGAA
AACCTACCGGATTGATGGGCACGGTGAGATGGTCATCAATGTGGATGTTG
CGGTGGCAAGCGATACACCGCATCCGGCGCGGATTGGCCTGACCTGCCAG
CTGGCGCAGGTCTCAGACGGGTAAACTGGCTCGGCCTGGGGCCGCAAGA
AAACTATCCCGACCGCCTTACTGCAGCCTGTTTTGACCGCTGGGATCTGC
CATTGTCAGACATGTATACCCCGTACGTCTTCCCGAGCGAAAACGGTCTG
CGCTGCGGGACGCGCGAATTGAATTATGGCCCACACCAGTGGCCGCGGCGA
CTTCCAGTTCAACATCAGCCGCTACAGCCAACAACAACGATGGGAAACCA
GCCATCGCCATCTGCTGCACGCGGAAGAAGGCACATGGCTGAATATCGAC
GGTTTCCATATGGGGATTGGTGGCGACGACTCCTGGAGCCCGTCAGTATC
GGCGGAATTCCAGCTGAGCGCCGGTCGCTACCATTACCAGTTGGTCTGGT
GTCAAAAATAA

TABLE 29

Pfnrs-lacZ construct Sequences
Nucleotide sequences of Pfnrs-lacZ construct,
low-copy (SEQ ID NO: 57)

GGTACCagttgttcttattggtggtgttgctttatggttgcatcgtagta
aatggttgtaacaaaagcaatttttccggctgtctgtatacaaaaacgcc
gtaaagtttgagcgaagtcaataaactctctacccattcagggcaatatc
tctcttGGATCCctctagaaataattttgtttaacttttaagaaggagata
tacatATGCTATGATTACGGATTCTCTGGCCGTCGTATTACAACGTCGTG
ACTGGGAAAACCCTGGCGTTACCCAACTTAATCGCCTTGCGGCACATCCC
CCTTTCGCCAGCTGGCGTAATAGCGAAGAGGCCCGCACCGATCGCCCTTC
CCAACAGTTGCGCAGCCTGAATGGCGAATGGCGCTTTGCCTGGTTTCCGG
CACCAGAAGCGGTGCCGGAAAGCTGGCTGGAGTGCGATCTTCCTGACGCC
GATACTGTCGTCGTCCCCTCAAACTGGCAGATGCACGGTTACGATGCGCC
TATCTACACCAACGTGACCTATCCCATTACGGTCAATCCGCCGTTTGTTC
CCGCGGAGAATCCGACAGGTTGTTACTCGCTCACATTTAATATTGATGAA
AGCTGGCTACAGGAAGGCCAGACGCGAATTATTTTTGATGGCGTTAACTC
GGCGTTTCATCTGTGGTGCAACGGGCGCTGGGTCGGTTACGGCCAGGACA
GCCGTTTGCCGTCTGAATTTGACCTGAGCGCATTTTTACGCGCCGGAGAA
AACCGCCTCGCGGTGATGGTGCTGCGCTGGAGTGACGGCAGTTATCTGGA
AGATCAGGATATGTGGCGGATGAGCGGCATTTTCCGTGACGTCTCGTTGC
TGCATAAACCGACCACGCAAATCAGCGATTTCCAAGTTACCACTCTCTTT
AATGATGATTTCAGCCGCGCGGTACTGGAGGCAGAAGTTCAGATGTACGG
CGAGCTGCGCGATGAACTGCGGGTGACGGTTTCTTTGTGGCAGGGTGAAA

TABLE 29-continued

Pfnrs-lacZ construct Sequences
Nucleotide sequences of Pfnrs-lacZ construct,
low-copy (SEQ ID NO: 57)

CGCAGGTCGCCAGCGGCACCGCGCCTTTCGGCGGTGAAATTATCGATGAG
CGTGGCGGTTATGCCGATCGCGTCACACTACGCCTGAACGTTGAAAATCC
GGAACTGTGGAGCGCCGAAATCCCGAATCTCTATCGTGCAGTGGTTGAAC
TGCACACCGCCGACGGCACGCTGATTGAAGCAGAAGCCTGCGACGTCGGT
TTCCGCGAGGTGCGGATTGAAAATGGTCTGCTGCTGCTGAACGGCAAGCC
GTTGCTGATTCGCGGCGTTAACCGTCACGAGCATCATCCTCTGCATGGTC
AGGTCATGGATGAGCAGACGATGGTGCAGGATATCCTGCTGATGAAGCAG
AACAACTTTAACGCCGTGCGCTGTTCGCATTATCCGAACCATCCGCTGTG
GTACACGCTGTGCGACCGCTACGGCCTGTATGTGGTGGATGAAGCCAATA
TTGAAACCCACGGCATGGTGCCAATGAATCGTCTGACCGATGATCCGCGC
TGGCTACCCGCGATGAGCGAACGCGTAACGCGGATGGTGCAGCGCGATCG
TAATCACCCGAGTGTGATCATCTGGTCGCTGGGGAATGAATCAGGCCACG
GCGCTAATCACGACGCGCTGTATCGCTGGATCAAATCTGTCGATCCTTCC
CGCCCGGTACAGTATGAAGGCGGCGGAGCCGACACCACGGCCACCGATAT
TATTTGCCCGATGTACGCGCGCGTGGATGAAGACCAGCCCTTCCCGGCGG
TGCCGAAATGGTCCATCAAAAAATGGCTTTCGCTGCCTGGAGAAATGCGC
CCGCTGATCCTTTGCGAATATGCCCACGCGATGGGTAACAGTCTTGGCGG
CTTCGCTAAATACTGGCAGGCGTTTCGTCAGTACCCCCGTTTACAGGGCG
GCTTCGTCTGGGACTGGGTGGATCAGTCGCTGATTAAATATGATGAAAAC
GGCAACCCGTGGTCGGCTTACGGCGGTGATTTTGGCGATACGCCGAACGA
TCGCCAGTTCTGTATGAACGGTCTGGTCTTTGCCGACCGCACGCCGCATC
CGGCGCTGACGGAAGCAAAACACCAACAGCAGTATTTCCAGTTCCGTTTA
TCCGGGCGAACCATCGAAGTGACCAGCGAATACCTGTTCCGTCATAGCGA
TAACGAGTTCCTGCACTGGATGGTGGCACTGGATGGCAAGCCGCTGGCAA
GCGGTGAAGTGCCTCTGGATTGCGCCCCGCAAGGTAAGCAGTTGATTGAA
CTGCCTGAACTGCCGCAGCCGGAGAGCGCCGGACAACTCTGGCTAACGGT
ACGCGTAGTGCAACCAAACGCGACCGCATGGTCAGAAGCCGGACACATCA
GCGCCTGGCAGCAATGGCGTCTGGCGGAAAACCTCAGCGTGACACTCCCC
TCCGCGTCCCACGCCATCCCCTCAACTGACCACCACGCGGAACGGATTTTTG
CATCGAGCTGGGTAATAAGCGTTGGCAATTTAACCGCCAGTCAGGCTTTC
TTTCACAGATGTGGATTGGCGATGAAAAACAACTGCTGACCCCGCTGCGC
GATCAGTTCACCCGTGCGCCGCTGGATAACGACATTGGCGTAAGTGAAGC
GACCCGCATTGACCCTAACGCCTGGGTCGAACGCTGGAAGGCGGCGGGCC
ATTACCAGGCCGAAGCGGCGTTGTTGCAGTGCACGGCAGATACCATTGCC
GACGCGGTGCTGATTACAACCGCCCACGCGTGGCAGCATCAGGGGAAAAC
CTTATTTATCAGCCGGAAAACCTACCGGATTGATGGGCACGGTGAGATGG
TCATCAATGTGGATGTTGCGGTGGCAAGCGATACACCGCATCCGGCGCGG
ATTGGCCTGACCTGCCAGCTGGCGCAGGTCTCAGACGGGTAAACTGGCT
CGGCCTGGGGCCGCAAGAAAACTATCCCGACCGCCTTACTGCAGCCTGTT
TTGACCGCTGGGATCTGCCATTGTCAGACATGTATACCCCGTACGTCTTC
CCGAGCGAAAACGGTCTGCGCTGCGGGACGCGCGAATTGAATTATGGCCC
ACACCAGTGGCCGCGGCGACTTCCAGTTCAACATCAGCCGCTACAGCCAA
CAACAACTGATGGAAACCAGCCATCGCCATCTGCTGCACGCGGAAGAAGGC
ACATGGCTGAATATCGACGGTTTCCATATGGGGATTGGTGGCGACGACTC
CTGGAGCCCGTCAGTATCGGCGGAATTCCAGCTGAGCGCCGGTCGCTACC
ATTACCAGTTGGTCTGGTGTCAAAAATAA

Example 17

Other Sequences of Interest

TABLE 30

| prpR Propionate-Responsive Promoter Sequence | | |
|---|---|---|
| Description | Sequence | SEQ ID NO |
| Prp promoter-Highlight: prpR, lower case:Ribosome binding site, underlined atg: start of | TTACCCGTCTGGATTTTCAGTACGCGCTTTTAAACGACGCC ACAGCGTGGTACGGCTGATCCCCAAATAACGTGCGGCGGC GCGCTTATCGCCATTAAAGCGTGCGAGCACCTCCTGCAATG GAAGCGCTTCTGCTGACGAGGGCGTGATTTCTGCTGTGGTC CCCACCAGTTCAGGTAATAATTGCCGCATAAATTGTCTGTC CAGTGTTGGTGCGGGATCGACGCTTAAAAAAAGCGCCAGG CGTTCCATCATATTCCGCAGTTCGCGAATATTACCGGGCCA ATGATAGTTCAGTAGAAGCGGCTGACACTGCGTCAGCCCAT GACGCACCGATTCGGTAAAAGGGATCTCCATCGCGGCCAG | SEQ ID NO: 58 |

TABLE 30-continued prpR Propionate-Responsive Promoter Sequence

| Description | Sequence | SEQ ID NO |
|---|---|---|
| gene of interest | CGATTGTTTTAAAAAGTTTTCCGCCAGAGGCAGAATATCAG<br>GCTGTCGCTCGCGCAAGGGGGAAGCGGCAGACGCAGAAT<br>GCTCAAACGGTAAAACAGATCGGTACGAAAACGTCCTTGC<br>GTTATCTCCCGATCCAGATCGCAATGCGTGGCGCTGATCAC<br>CCGGACATCTACCGGGATCGGCTGATGCCCGCCAACGCGG<br>GTGACGGCTTTTTCCTCCAGTACGCGTAGAAGGCGGGTTTG<br>TAACGGCAGCGGCATTTCGCCAATTTCGTCAAGAAACAGC<br>GTGCCGCCGTGGGCGACCTCAAACAGCCCCGCACGTCCAC<br>CTCGTCTTGAGCCGGTAAACGCTCCCTCCTCATAGCCAAAC<br>AGTTCAGCCTCCAGCAACGACTCGGTAATCGCGCCGCAATT<br>AACGGCGACAAAGGGCGGAGAAGGCTTGTTCTGACGGTGG<br>GGCTGACGGTTAAACAACGCCTGATGAATCGCTTGCGCCGC<br>CAGCTCTTTCCCGGTCCCTGTTTCCCCCTGAATCAGCACTGC<br>CGCGCGGGAACGGGCATAGAGTGTAATCGTATGGCGAACC<br>TGCTCCATTTGTGGTGAATCGCCGAGGATATCGCTCAGCGC<br>ATAACGGGTCTGTAATCCCTTGCTGGAGGTATGCTGGCTAT<br>ACTGACGCCGTGTCAGGCGGGTCATATCCAGCGCATCATGG<br>AAAGCCTGACGTACGGTGGCCGCTGAATAAATAAAGATGG<br>CGGTCATTCCTGCCTCTTCCGCCAGGTCGGTAATTAGTCCT<br>GCCCCAATTACAGCCTCAATGCCGTTAGCTTTGAGCTCGTT<br>AATTTGCCCGCGAGCATCCTCTTCAGTGATATAGCTTCGCT<br>GTTCAAGACGGAGGTGAAACGTTTTCTGAAAGGCGACCAG<br>AGCCGGAATGGTCTCCTGATAGGTCACGATTCCCATTGAGG<br>AAGTCAGCTTTCCCGCTTTTGCCAGAGCCTGTAATACATCG<br>AATCCGCTGGGTTTGATGAGGATGACAGGTACCGACAGTC<br>GGCTTTTTAAATAAGCGCCGTTGGAACCTGCCGCGATAATC<br>GCGTCGCAGCGTTCGGTTGCCAGTTTTTTGCAATGTAGGC<br>TACTGCCTTTTCAAAACCGAGCTGAATAGGCGTGATCGTCG<br>CCAGATGATCAAACTCCAGGCTGATATCCCGAAATAGTTCG<br>AACAGGCGCGTTACCGAGACCGTCCAGATCACCGGTTTATC<br>GCTATTATCGCGCGAAGCGCTATGCACAGTAACCATCGTCG<br>TAGATTCATGTTTAAGGAACGAATTCTTGTTTTATAGATGTT<br>TCGTTAATGTTGCAATGAAACACAGGCCTCCGTTTCATGAA<br>ACGTTAGCTGACTCGTTTTTCTTGTGACTCGTCTGTCAGTAT<br>TAAAAAAGATTTTTCATTTAACTGATTGTTTTAAATTGAAT<br>TTTATTTAATGGTTTCTCGGTTTTTGGGTCTGGCATATCCCT<br>TGCTTTAATGAGTGCATCTTAATTAACAATTCAATAACAAG<br>AGGGCTGAATagtaatttcaacaaaataacgagcattcgaatg | |

TABLE 31

Wild-type clbA and clbA knock-out

```
Wild-type   caaatatcacataatcttaacatatcaataaacacagtaaagtttcatgtgaaaaacatcaaacataaaatacaag
clbA        ctcggaatacgaatcacgctatacacattgctaacaggaatgagattatctaaatgaggattgatatattaattgga
(SEQ ID     catactagttttttttcatcaaaccagtagagataacttccttcactatctcaatgaggaagaaataaaacgctatgat
NO: 59)     cagtttcattttgtgagtgataaagaactctatattttaagccgtatcctgctcaaaacagcactaaaaagatatcaa
```

TABLE 31-continued

Wild-type clbA and clbA knock-out

|  |  |
|---|---|
|  | cctgatgtctcattacaatcatggcaatttagtacgtgcaaatatggcaaaccatttatagttttttcctcagttggcaa<br>aaaagatttttttttaacctttcccatactatagatacagtagccgttgctattagttctcactgcgagcttggtgtcgat<br>attgaacaaataagagatttagacaactcttatctgaatatcagtcagcattttttactccacaggaagctactaac<br>atagtttcacttcctcgttatgaaggtcaattacttttttggaaaatgtggacgctcaaagaagcttacatcaaatatc<br>gaggtaaaggcctatcttttaggactggattgtattgaatttcatttaacaaataaaaaactaacttcaaaatatagag<br>gttcacctgttttatttctctcaatggaaaatatgtaactcatttctcgcattagcctctccactcatcacccctaaaata<br>actattgagctatttcctatgcagtcccaactttatcaccacgactatcagctaattcattcgtcaaatgggcagaat<br>tgaatcgccacggataatctagacacttctgagccgtcgataatattgattttcatattccgtcggtggtgtaagtat<br>cccgcataatcgtgccattcacatttag |
| clbA<br>knock-out<br>(SEQ ID<br>NO: 60) | ggatggggggaaacatggataagttcaaagaaaaaaacccgttatctctgcgtgaaagacaagtattgcgcatgc<br>tggcacaaggtgatgagtactctcaaatatcacataatcttaacatatcaataaacacagtaaagtttcatgtgaaaa<br>acatcaaacataaaatacaagctcggaatacgaatcacgctatacacattgctaacaggaatgagattatctaaatg<br>aggattgaTGTGTAGGCTGGAGCTGCTTCGAAGTTCCTATACTTTCTAGAG<br>AATAGGAACTTCGGAATAGGAACTTCGGAATAGGAACTAAGGAGGAT<br>ATTCATATGtcgtcaaatgggcagaattgaatcgccacggataatctagacacttctgagccgtcgataata<br>ttgattttcatattccgtcggtgg |

The invention claimed is:

1. A bacterium comprising gene sequence(s) encoding one or more oxalate catabolism enzyme(s) operably linked to a directly or indirectly first inducible promoter that is not associated with the oxalate catabolism enzyme gene in nature, wherein the gene sequence(s) encoding the one or more oxalate catabolism enzyme(s) are present in a cassette and encode:

(1) ScAAE3, Oxc, and Frc; or
(2) ScAAE3, Oxc, Frc, and YfdE; or
(3) Oxc, Frc, and YfdE.

2. The bacterium of claim 1, wherein the bacterium further comprises gene sequence(s) encoding one or more transporter(s) of oxalate operably linked to a second promoter that is not associated with the oxalate transporter gene in nature.

3. The bacterium of claim 2, wherein the bacterium further comprises gene sequence(s) encoding one or more exporter(s) of formate operably linked to a third promoter that is not associated with the formate exporter gene in nature.

4. The bacterium of claim 3, wherein the first inducible promoter operably linked to the gene sequence(s) encoding the oxalate catabolism enzyme is directly or indirectly induced by exogenous environmental conditions found in the mammalian gut; wherein the second promoter operably linked to the gene sequence(s) encoding the transporter of oxalate is directly or indirectly induced by exogenous environmental conditions found in the mammalian gut; and/or wherein the third promoter operably linked to the gene sequence(s) encoding the exporter of formate is directly or indirectly induced by exogenous environmental conditions found in the mammalian gut.

5. The bacterium of claim 4, wherein the first inducible promoter operably linked to the gene sequence(s) encoding the oxalate catabolism enzyme is directly or indirectly induced under low-oxygen or anaerobic conditions; wherein the second promoter operably linked to the gene sequence(s) encoding the oxalate transporter is directly or indirectly induced under low-oxygen or anaerobic conditions; and/or wherein the third promoter operably linked to the gene sequence(s) encoding the formate exporter is directly or indirectly induced under low-oxygen or anaerobic conditions.

6. The bacterium of claim 5, wherein the first inducible promoter operably linked to the gene sequence(s) encoding the oxalate catabolism enzyme is selected from the group consisting of an FNR-responsive promoter, an ANR-responsive promoter, and a DNR-responsive promoter; wherein the second promoter operably linked to the gene sequence(s) encoding the oxalate transporter is selected from the group consisting of an FNR-responsive promoter, an ANR-responsive promoter, and a DNR-responsive promoter; and/or wherein the third promoter operably linked to the gene sequence(s) encoding the formate exporter is selected from the group consisting of an FNR-responsive promoter, an ANR-responsive promoter, and a DNR-responsive promoter.

7. The bacterium of claim 1, wherein the one or more oxalate catabolism enzyme(s) convert oxalate to formate; convert oxalate to oxalyl-CoA; or convert oxalyl-CoA to formate.

8. The bacterium of claim 1, wherein the gene sequence(s) encoding the one or more oxalate catabolism enzyme(s) are present in a cassette and encode ScAAE3, Oxc, and Frc.

9. The bacterium of claim 1, wherein the gene sequence(s) encoding the one or more oxalate catabolism enzyme(s) are present in a cassette and encode ScAAE3, Oxc, Frc, and YfdE.

10. The bacterium of claim 1, wherein the gene sequence(s) encoding the one or more oxalate catabolism enzyme(s) are present in a cassette and encode Oxc, Frc, and YfdE.

11. The bacterium of claim 1, wherein the bacterium is a probiotic bacterial cell.

12. The bacterium of claim 11, wherein the bacterium is a member of a genus selected from the group consisting of Bacteroides, Bifidobacterium, Clostridium, Escherichia, Lactobacillus and Lactococcus.

13. The bacterium of claim 1, wherein the engineered bacterial cell is an auxotroph in a gene that is complemented when the engineered bacterial cell is present in a mammalian gut.

14. The bacterium of claim 13, wherein the engineered bacterial cell is an auxotroph in diaminopimelic acid or an enzyme in the thymine biosynthetic pathway.

15. The bacterium of claim 1, wherein the engineered bacterial cell is further engineered to harbor a gene encoding a substance that is toxic to the bacterium, wherein the gene is under the control of a promoter that is directly or indirectly induced by an environmental condition not naturally present in the mammalian gut.

16. A pharmaceutical composition comprising the bacterium of claim 1, and a pharmaceutically acceptable carrier.

17. A method for reducing the levels of oxalate in a subject, the method comprising administering a pharmaceutical composition of claim 16 to the subject.

18. A method for treating a disease or disorder in which oxalate is detrimental in a subject, the method comprising administering a pharmaceutical composition of claim 16.

19. The method of claim 18, wherein the disorder in which oxalate is detrimental is a hyperoxaluria.

20. The bacterium of claim 1, wherein the bacterium further comprises a knockout of a clbA gene.

* * * * *